US012747283B2

(12) United States Patent
Wang et al.

(10) Patent No.: US 12,747,283 B2
(45) Date of Patent: Sep. 29, 2026

(54) COMPOSITIONS AND METHODS RELATED TO HUMAN NEUTRALIZING ANTIBODIES TO HEPATITIS B

(71) Applicant: The Rockefeller University, New York, NY (US)

(72) Inventors: Qiao Wang, New York, NY (US); Michel Nussenzweig, New York, NY (US)

(73) Assignee: The Rockefeller University, New York, NY (US)

( * ) Notice: Subject to any disclaimer, the term of this patent is extended or adjusted under 35 U.S.C. 154(b) by 1190 days.

(21) Appl. No.: 17/641,396

(22) PCT Filed: Sep. 11, 2020

(86) PCT No.: PCT/US2020/050509
§ 371 (c)(1),
(2) Date: Mar. 8, 2022

(87) PCT Pub. No.: WO2021/050954
PCT Pub. Date: Mar. 18, 2021

(65) Prior Publication Data

US 2022/0315645 A1 Oct. 6, 2022

Related U.S. Application Data

(60) Provisional application No. 62/982,276, filed on Feb. 27, 2020, provisional application No. 62/898,735, filed on Sep. 11, 2019.

(51) Int. Cl.
*C07K 16/082* (2026.01)
*A61P 31/20* (2006.01)

(52) U.S. Cl.
CPC ............ *C07K 16/082* (2013.01); *A61P 31/20* (2018.01); *C07K 2317/33* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,180,370 | B1 * | 1/2001 | Queen | A61P 19/02 435/69.6 |
| 10,683,344 | B2 * | 6/2020 | Corti | A61P 31/20 |
| 2007/0087374 | A1 | 4/2007 | Punnonen et al. | |
| 2011/0097270 | A1 | 4/2011 | Schofield et al. | |
| 2015/0166637 | A1 * | 6/2015 | Kim | A61K 38/21 424/85.4 |
| 2016/0034639 | A1 | 2/2016 | Reddy et al. | |
| 2016/0326233 | A1 | 11/2016 | Mondelli | |
| 2019/0119384 | A1 | 4/2019 | Korman et al. | |
| 2019/0225673 | A1 | 7/2019 | Kruse et al. | |

FOREIGN PATENT DOCUMENTS

| | | | |
|---|---|---|---|
| EP | 0250253 | A2 | 12/1987 |
| WO | 2014048910 | A1 | 4/2014 |
| WO | 2015107126 | A1 | 7/2015 |
| WO | 2016085284 | A1 | 6/2016 |
| WO | 2017060504 | A1 | 4/2017 |

OTHER PUBLICATIONS

Janeway, A. C., et al. "Immunobiology: the immune system in health and disease. London." Current Biology (1997): 3:1-3:11. (Year: 1997).*
Kipriyanov, Sergey M., and Fabrice Le Gall. "Generation and production of engineered antibodies." Molecular biotechnology 26.1 (2004): 39-60. (Year: 2004).*
Galun et al., "Clinical Evaluation (Phase I) of a Combination of Two Human Monoclonal Antibodies to HBV: Safety and Antiviral Properties," Hepatology, Mar. 2002, pp. 673-679, vol. 35, No. 3.
Wang et al., "A Combination of Human Broadly Neutralizing Antibodies against Hepatitis B Virus HBsAg with Distinct Epitopes Suppresses Escape Mutations," Cell Host Microbe, Aug. 12, 2020, pp. 1-39, vol. 28, No. 2.
Cerino, A., et al., A Human Monoclonal Antibody against Hepatitis B Surface Antigen with Potent Neutralizing Activity, PLoS One, Apr. 29, 2015, No. e0125704, pp. 1-10.
Eren, R., et al., Preclinical Evaluation of Two Human Anti-Hepatitis B Virus (HBV) Monoclonal Antibodies in the HBV-Trimera Mouse Model and in HBV Chronic Carrier Chimpanzees, Hepatology, Sep. 2000, vol. 32, No. 3, pp. 588-596.
Shin, Y., et al., Human monoclonal antibody against Hepatitis B virus surface antigen (HBsAg), Antiviral Research, May 3, 2007, vol. 75, No. 2, pp. 113-120.

* cited by examiner

*Primary Examiner* — Misook Yu
*Assistant Examiner* — Lia E Taylor
(74) *Attorney, Agent, or Firm* — Hodgson Russ LLP

(57) ABSTRACT

Provided are broadly neutralizing antibodies (bNAbs) and antigen binding fragments thereof that bind with specificity to epitopes expressed by Hepatitis B vims (HBV). The bNAbs target non-overlapping epitopes on the HBV S antigen (HBsAg). Pharmaceutical compositions that contain the bNAbs, or modified bNAbs, are provided. Combinations of the bNAbs are included, and are useful for prophylaxis and therapy of HBV infection, and for inhibiting development of HBV escape mutations in infected individuals. Expression vectors encoding the bNAbs and antigenic fragments of them are included, as are methods of making the bNAbs and antigenic fragments of them. HBV peptides for use as vaccines are provided, and include at least two non-overlapping epitopes from the HBsAg. Diagnostic reagents comprising the bNAbs or antigenic fragments thereof are provided, as are methods of detecting HBV and diagnosing HBV infection.

12 Claims, 49 Drawing Sheets

Specification includes a Sequence Listing.

A

| Antibody | Donor ID | Heavy chain V gene | Light chain V gene | | adr CHO cell | |
|---|---|---|---|---|---|---|
| H001 | 146 | IGHV1-3*01 | IGKV1-39*01 | | 27.1 | |
| H002 | 146 | IGHV2-70D*04 | | IGLV3-21*02 | 30.78 | Red |
| H003 | 60 | IGHV3-23*01 | | IGLV3-21*02 | 33.76 | |
| H004 | 146 | IGHV3-23*04 | | IGLV3-21*02 | 24.65 | |
| H005 | 60 | IGHV3-30*18 | | IGLV3-21*02 | 69.82 | Orange |
| H006 | 60 | IGHV3-30*18 | | IGLV3-21*02 | 49.56 | Red |
| H007 | 146 | IGHV3-30*18 | IGKV3-20*01 | | 46.77 | |
| H008 | 146 | IGHV3-30*18 | | IGLV3-21*02 | 48.27 | |
| H009 | 60 | IGHV3-30*18 | | IGLV3-21*02 | 38.02 | |
| H010 | 60 | IGHV3-30*18 | | IGLV3-21*03 | 35.17 | |
| H011 | 13 | IGHV3-33*01 | IGKV3-11*01 | | 18.66 | |
| H012 | 13 | IGHV3-33*01 | | IGLV3-21*02 | 170.9 | Yellow |
| H013 | 146 | IGHV3-33*01 | | IGLV3-21*02 | 351.2 | |
| H014 | 146 | IGHV3-33*01 | | IGLV3-21*02 | 111.1 | |
| H015 | 60 | IGHV3-33*01 | IGKV1-39*01 | | 74.87 | |
| H016 | 69 | IGHV3-48*02 | IGKV3-15*01 | | 33.58 | |
| H017 | 55 | IGHV3-74*01 | | IGLV2-14*01 | 40.87 | |
| H018 | 60 | IGHV3-9*01 | | IGLV1-51*01 | b.d. | White |
| H019 | 69 | IGHV4-30-4*01 | IGKV1-39*01 | | 34.9 | |
| H020 | 55 | IGHV4-59*08 | IGKV1-12*01 | | 29.58 | |
| libivirumab | (positive control) | | | | 105 | |
| 10-1074 | (negative control) | | | | not binding | |

Fig. 3

C

| adr Yeast | adw Yeast | ad Human blood | ayw Yeast | ay Human blood | |
|---|---|---|---|---|---|
| 26.89 | 30.36 | 42.84 | 18.76 | 63.09 | |
| 24.01 | 40.77 | 53.6 | b.d. | 167.4 | |
| 21.99 | 25.27 | 40.17 | 159.5 | 42.75 | |
| 16.07 | 23 | 25.51 | 27.75 | 13.39 | ← Red |
| 25 | 27.83 | 40.43 | 17.38 | 130.6 | |
| 50.61 | 40.2 | 28.98 | 17.57 | 115.5 | |
| 47.33 | 40.63 | 43.26 | 16.57 | 197.1 | |
| 46.62 | 36.83 | 49.28 | 18.1 | 115.3 | |
| 40.41 | 41.26 | 25.49 | 20.82 | 40.49 | |
| 44.93 | 42.59 | 22.69 | 232 | 38.76 | |
| 21.95 | 19.41 | 609.4 | 29.52 | b.d. | |
| 111.5 | 45.47 | 82.29 | 57.74 | 78.01 | ← Orange |
| 133.1 | 82.14 | 52.14 | 72.54 | 120.2 | ← Yellow |
| 167.2 | 50 | 61.45 | 70.64 | b.d. | |
| 23.07 | b.d. | 103.6 | 34.08 | 129.4 | |
| 25.68 | 68.46 | 46.89 | 23.83 | 102.6 | |
| 28.61 | 74.08 | 66.17 | 25.15 | 207.1 | ← White |
| b.d. | b.d. | 135.1 | b.d. | b.d. | |
| 33.31 | 37.55 | 36.77 | 35.85 | 38.18 | |
| 35.14 | 40.37 | 30.72 | 34.95 | 34.66 | |
| 116.8 | 123.2 | 112.6 | 40.34 | 119.5 | |
| not binding | not binding | not binding | not binding | not binding | |

Fig. 3 (continued)

A

Un-biotinylated antibody (1st)

Group-I | Group-III | Group-II

| Biotinylated antibody (2nd) | H020 | H004 | H005 | H006 | H009 | H008 | H010 | H003 | H019 | H017 | H007 | H016 | H015 | H001 | H011 | 10-1074 | PBS |
|---|---|---|---|---|---|---|---|---|---|---|---|---|---|---|---|---|---|
| H020 | 3 | 39 | 14 | 10 | 13 | 9 | 63 | 30 | 47 | 100 | 96 | 99 | 102 | 101 | 97 | 101 | 100 |
| H004 | 15 | 3 | 5 | 7 | 12 | 8 | 31 | 41 | 67 | 107 | 98 | 101 | 99 | 92 | 101 | 98 | 100 |
| H005 | 11 | 5 | 3 | 5 | 9 | 4 | 28 | 44 | 74 | 94 | 96 | 90 | 96 | 93 | 91 | 100 | 100 |
| H006 | 12 | 4 | 3 | 3 | 6 | 3 | 26 | 38 | 82 | 99 | 96 | 108 | 103 | 93 | 101 | 96 | 100 |
| H009 | 7 | 3 | 3 | 5 | 3 | 3 | 16 | 22 | 67 | 104 | 100 | 100 | 96 | 100 | 99 | 100 | 100 |
| H008 | 6 | 3 | 3 | 3 | 4 | 3 | 16 | 28 | 65 | 86 | 104 | 95 | 97 | 95 | 96 | 103 | 100 |
| H010 | 3 | 3 | 2 | 2 | 3 | 3 | 3 | 5 | 32 | 97 | 99 | 101 | 102 | 100 | 94 | 100 | 100 |
| H003 | 2 | 3 | 2 | 2 | 3 | 2 | 3 | 3 | 22 | 89 | 96 | 94 | 92 | 97 | 103 | 98 | 100 |
| H019 | 3 | 2 | 2 | 3 | 2 | 2 | 3 | 3 | 3 | 96 | 95 | 105 | 105 | 100 | 99 | 100 | 100 |
| H017 | 81 | 88 | 92 | 102 | 92 | 108 | 84 | 86 | 83 | 7 | 99 | 83 | 74 | 86 | 91 | 95 | 100 |
| H007 | 103 | 94 | 99 | 105 | 100 | 97 | 113 | 101 | 101 | 102 | 4 | 3 | 25 | 95 | 103 | 98 | 100 |
| H016 | 74 | 95 | 102 | 103 | 107 | 91 | 99 | 104 | 114 | 58 | 40 | 5 | 20 | 56 | 55 | 101 | 100 |
| H015 | 71 | 82 | 86 | 84 | 104 | 83 | 103 | 100 | 81 | 58 | 25 | 5 | 4 | 62 | 79 | 89 | 100 |
| H001 | 71 | 108 | 113 | 133 | 95 | 94 | 89 | 109 | 98 | 66 | 20 | 11 | 11 | 11 | 86 | 95 | 100 |
| H011 | 98 | 96 | 94 | 99 | 105 | 95 | 103 | 99 | 99 | 93 | 71 | 3 | 4 | 68 | 3 | 85 | 100 |

White; Red; Blue; Light grey; Black; Yellow; Dark grey; Red; Yellow

Fig. 4

B

Dark grey

White

|  | 101 Q | 103 M | 105 P | V | 110 I | 120 P | K | 123 T | 141 K | 142 P | 143 T | 144 D | 145 G | 148 T | 161 Y |  |
|---|---|---|---|---|---|---|---|---|---|---|---|---|---|---|---|---|
| H020 | 123 | 128 | 98 | 133 | 42 | 95 | 111 | 102 | 68 | 86 | 109 | 42 | 62 | 31 | 93 | Group-I |
| H004 | 96 | 96 | 79 | 105 | 71 | 72 | 97 | 108 | 76 | 108 | 105 | 55 | 59 | 59 | 95 | Group-I |
| H006 | 97 | 87 | 79 | 106 | 65 | 96 | 102 | 99 | 68 | 104 | 104 | 102 | 101 | 58 | 105 | Group-I |
| H019 | 112 | 115 | 100 | 122 | 54 | 48 | 75 | 98 | 17 | 70 | 102 | 98 | 99 | 59 | 107 | Group-I |
|  |  |  |  |  |  |  |  |  |  |  |  |  |  |  |  |  |
| H017 | 57 | 69 | 68 | 60 | 106 | 104 | 98 | 82 | 145 | 128 | 124 | 141 | 127 | 81 | 80 | Group-III |
| H007 | 99 | 86 | 129 | 85 | 90 | 76 | 97 | 31 | 96 | 78 | 85 | 40 | 48 | 99 | 80 | Group-II |
| H016 | 98 | 109 | 116 | 81 | 110 | 95 | 61 | 25 | 104 | 102 | 95 | 63 | 17 | 99 | 64 | Group-II |
| H015 | 75 | 79 | 99 | 68 | 78 | 114 | 93 | 94 | 11 | 48 | 11 | 15 | 26 | 102 | 70 | Group-II |

Black

Light grey

Fig. 4 (continued)

C

Dark grey White Light grey Black

| | Q101R | Q101K | M103I | L109I | L109R | I110L | S113N | T114R | T115N | T116N | T118K | P120T | P120S | P120A | K122I | T123A | T123N | C124R | T125M | T126S | T126A | A128V | Q129H | |
|---|---|---|---|---|---|---|---|---|---|---|---|---|---|---|---|---|---|---|---|---|---|---|---|---|
| H020 | 31 | 108 | 121 | 86 | 78 | 92 | 100 | 84 | 69 | 81 | 73 | 111 | 16 | 106 | 100 | 114 | 104 | 17 | 53 | 98 | 110 | 114 | 111 | Group-I |
| H006 | 48 | 145 | 157 | 123 | 92 | 93 | 126 | 108 | 87 | 94 | 85 | 89 | 29 | 97 | 96 | 95 | 103 | 47 | 86 | 98 | 96 | 106 | 114 | Group-I |
| H019 | 77 | 123 | 147 | 115 | 111 | 84 | 138 | 142 | 101 | 110 | 159 | 21 | 86 | 55 | 108 | 100 | 137 | 67 | 100 | 89 | 109 | 116 | 106 | Group-I |
| H017 | 21 | 108 | 120 | 122 | 73 | 97 | 93 | 82 | 90 | 76 | 86 | 124 | 11 | 129 | 93 | 111 | 80 | 94 | 76 | 100 | 113 | 74 | 122 | Group-III |
| H007 | 32 | 106 | 110 | 108 | 77 | 86 | 95 | 92 | 72 | 69 | 131 | 68 | 44 | 96 | 101 | 30 | 33 | 25 | 73 | 92 | 98 | 120 | 116 | Group-II |
| H016 | 41 | 122 | 119 | 110 | 80 | 103 | 96 | 89 | 82 | 77 | 109 | 81 | 41 | 96 | 51 | 27 | 27 | 29 | 82 | 92 | 103 | 111 | 113 | Group-II |
| H015 | 52 | 93 | 95 | 108 | 75 | 98 | 82 | 83 | 69 | 63 | 110 | 104 | 20 | 129 | 101 | 106 | 46 | 62 | 60 | 92 | 110 | 66 | 110 | Group-II |

| | G130R | G130N | M133T | F134L | C137Y | K141E | P142S | T143L | D144E | D144A | G145A | G145E | G145R | N146S | S154V | Y161F | K122R-G145R | T123N-T143S | C137Y-D144V | P142L-G145R | D144E-G145R | Wildtype HBsAg | Empty vector | |
|---|---|---|---|---|---|---|---|---|---|---|---|---|---|---|---|---|---|---|---|---|---|---|---|---|
| H020 | 90 | 96 | 48 | 77 | 15 | 31 | 80 | 125 | 23 | 32 | 65 | 29 | 10 | 37 | 89 | 77 | 12 | 71 | 13 | 9 | 9 | 100 | 11 | Group-I |
| H006 | 90 | 99 | 59 | 91 | 26 | 55 | 105 | 119 | 83 | 78 | 83 | 27 | 24 | 65 | 100 | 89 | 30 | 77 | 14 | 20 | 15 | 100 | 13 | Group-I |
| H019 | 105 | 80 | 38 | 84 | 37 | 35 | 81 | 127 | 84 | 84 | 97 | 93 | 73 | 80 | 107 | 92 | 90 | 70 | 30 | 121 | 46 | 100 | 17 | Group-I |
| H017 | 78 | 108 | 76 | 82 | 103 | 78 | 98 | 126 | 97 | 108 | 104 | 68 | 79 | 57 | 94 | 77 | 77 | 65 | 83 | 126 | 73 | 100 | 11 | Group-III |
| H007 | 79 | 89 | 45 | 82 | 11 | 79 | 51 | 131 | 39 | 36 | 49 | 27 | 11 | 49 | 92 | 76 | 11 | 10 | 11 | 10 | 11 | 100 | 14 | Group-II |
| H016 | 82 | 92 | 53 | 86 | 28 | 85 | 80 | 114 | 71 | 55 | 12 | 23 | 10 | 70 | 98 | 83 | 34 | 12 | 12 | 11 | 11 | 100 | 13 | Group-II |
| H015 | 58 | 81 | 47 | 76 | 20 | 17 | 41 | 13 | 13 | 12 | 24 | 23 | 15 | 49 | 101 | 78 | 20 | 38 | 19 | 12 | 11 | 100 | 13 | Group-II |

Fig. 4 (continued)

| | $IC_{50}$ (ng/ml) HBsAg | HBcAg | HBeAg |
|---|---|---|---|
| H001 | b.d. | b.d. | n.d. |
| H002 | b.d. | b.d. | n.d. |
| H003 | [illegible] | 130 | n.d. |
| H004 | 8.4 | [illegible] | 11 |
| H005 | 6.2 | [illegible] | n.d. |
| H006 | 6.0 | 14 | 2.6 |
| H007 | 9.5 | [illegible] | 8.2 |
| H008 | 6.8 | 11 | n.d. |
| H009 | 5.8 | 15 | n.d. |
| H010 | 81 | 290 | n.d. |
| H011 | b.d. | b.d. | n.d. |
| H012 | >500 | >500 | n.d. |
| H013 | 18 | >500 | n.d. |
| H014 | >500 | b.d. | n.d. |
| H015 | [illegible] | 64 | n.d. |
| H016 | [illegible] | 51 | 4.0 |
| H017 | [illegible] | 130 | n.d. |
| H018 | b.d. | b.d. | n.d. |
| H019 | 5.1 | [illegible] | n.d. |
| H020 | [illegible] | [illegible] | [illegible] |
| libivumab | [illegible] | 130 | n.d. |
| 10-1074 | not neutralizing | | |

I

| Red arrow | Escape mutation |
|---|---|
| 1 | G145R |
| 2 | G145R |
| 3 | G145R |
| 4 | G145E |
| 5 | G145R |
| 6 | G145R |
| 7 | G145R |
| 8 | K122R / G145R |
| 9 | C137Y |
| 10 | C137Y / D144V |

Fig. 7 (continued)

A

| Group | | 101 Q | G | M | L | P | V | C | P | L | 110 I | P | G | S | T | T | T | S | T | G | 120 P | C | K | 123 T | C | T |
|---|---|---|---|---|---|---|---|---|---|---|---|---|---|---|---|---|---|---|---|---|---|---|---|---|---|---|
| Group-I | H020 | 123 | | 128 | | 98 | 133 | | 121 | 107 | [illegible] | 95 | 110 | 108 | 106 | 98 | 105 | 102 | 93 | 93 | 95 | | 111 | 102 | | 103 |
| Group-I | H004 | 96 | | 96 | | 79 | 105 | | 100 | 96 | 71 | 113 | 101 | 103 | 103 | 101 | 100 | 100 | 101 | 92 | 72 | | 97 | 108 | | 112 |
| Group-I | H006 | 97 | | 87 | | 79 | 106 | | 92 | 110 | 65 | 114 | 102 | 97 | 97 | 98 | 96 | 98 | 95 | 92 | 96 | | 102 | 99 | | 103 |
| Group-I | H019 | 112 | | 115 | | 100 | 122 | | 105 | 106 | 54 | 112 | 99 | 92 | 92 | 99 | 91 | 99 | 95 | 114 | [illegible] | | 75 | 98 | | 83 |
| Group-III | H017 | 57 | | 69 | | 68 | 60 | | 87 | 85 | 106 | 100 | 80 | 91 | 90 | 91 | 88 | 98 | 89 | 84 | 104 | | 98 | 82 | | 78 |
| Group-II | H007 | 99 | | 86 | | 129 | 85 | | 108 | 85 | 90 | 99 | 105 | 103 | 104 | 107 | 105 | 99 | 107 | 102 | 76 | | 97 | [illegible] | | 97 |
| Group-II | H016 | 98 | | 109 | | 116 | 81 | | 94 | 96 | 110 | 86 | 97 | 103 | 102 | 104 | 103 | 106 | 109 | 113 | 95 | | 61 | 23 | | 95 |
| Group-II | H015 | 75 | | 79 | | 99 | 68 | | 80 | 100 | 78 | 80 | 85 | 94 | 95 | 94 | 100 | 96 | 100 | 94 | 114 | | 93 | 94 | | 108 |

Dark grey

White

Black

Light grey

Fig. 11

A (continued)

| | 151 P | I | P | S | S | W | A | F | A | K | 161 Y | L | W | E | W | A | S | V | R | F | 171 S | W | | Emp | WT | |
|---|---|---|---|---|---|---|---|---|---|---|---|---|---|---|---|---|---|---|---|---|---|---|---|---|---|---|
| H020 | 103 | | 104 | 98 | 115 | | | 99 | | 99 | 93 | 110 | 107 | 100 | 99 | | 104 | 105 | | 96 | 93 | 100 | | 19 | 100 | Group-I |
| H004 | 103 | | 108 | 97 | 108 | | | 103 | | 99 | 95 | 102 | 96 | 91 | 99 | | 97 | 96 | | 94 | 100 | 99 | | 27 | 100 | Group-I |
| H006 | 100 | | 108 | 102 | 111 | | | 109 | | 106 | 105 | 102 | 94 | 93 | 99 | | 98 | 102 | | 106 | 101 | 105 | | 17 | 100 | Group-I |
| H019 | 98 | | 100 | 93 | 101 | | | 99 | | 94 | 107 | 110 | 100 | 105 | 104 | | 99 | 96 | | 99 | 103 | 89 | | 28 | 100 | Group-I |
| | | | | | | | | | | | | | | | | | | | | | | | | | | |
| H017 | 109 | | 145 | 113 | 117 | | | 117 | | 106 | 80 | 94 | 101 | 99 | 92 | | 110 | 104 | | 106 | 102 | 96 | | 16 | 100 | Group-III |
| H007 | 99 | | 100 | 108 | 93 | | | 98 | | 107 | 80 | 97 | 101 | 102 | 101 | | 99 | 100 | | 100 | 99 | 101 | | 21 | 100 | Group-II |
| H016 | 98 | | 90 | 99 | 85 | | | 95 | | 97 | 64 | 94 | 102 | 104 | 103 | | 104 | 101 | | 107 | 106 | 105 | | 20 | 100 | Group-II |
| H015 | 99 | | 91 | 103 | 87 | | | 97 | | 97 | 70 | 85 | 100 | 105 | 95 | | 99 | 99 | | 97 | 97 | 100 | | 17 | 100 | Group-II |

White

Dark grey

Light grey

Black

Fig. 11 (continued)

B

| | |
|---|---|
| Wavelength (Å) | 0.979 |
| Resolution range | 67.35-1.78 (1.82-1.78) |
| Space group | $P2_12_12_1$ |
| Unit cell | 49.9 71.2 134.7 |
| Total reflections | 615,285 (56,022) |
| Unique reflections | 46,432 (4,386) |
| Multiplicity | 12.9 (12.1) |
| Completeness (%) | 99.5 (91.0) |
| Mean I/sigma (I) | 17.2 (1.26) |
| Wilson B-factor | 33 |
| Anisotropy | 0.449 |
| R-merge | 0.084 (1.26) |
| R-meas | 0.090 (1.309) |
| R-pim | 0.034 (0.505) |
| $CC_{1/2}$ | 0.999 (0.793) |
| Reflections used in refinement | 46432 (4380) |
| Reflections used for R-free | 1999 (188) |
| R-work | 0.182 (0.276) |
| R-free | 0.227 (0.293) |

| | |
|---|---|
| Number of non-hydrogen atoms | 3752 |
| Macromolecules | 3391 |
| Solvent | 361 |
| Protein residues | 451 |
| RMSZ (bonds) | 0.37 |
| RMSZ (angles) | 0.55 |
| Ramachandran favored (%) | 98 |
| Ramachandran allowed (%) | 2 |
| Ramachandran outliers (%) | 0.00 |
| Rotamer outliers (%) | 0.00 |
| Clashscore | 1.00 |
| Average B-factor | 39 |
| Average B of H/L | 39 |
| Average B of the peptide | 49 |
| Macromolecules | 38 |
| Solvent | 43 |
| Fo,Fc correlation | 0.97 |
| Bulk solvent $k_{sol}$ (e/Å$^3$), $B_{sol}$ (Å$^2$) | 0.32, 42.8 |

Fig. 13 (continued)

D

| |
|---|
| H-bonds within the peptide |
| Ser139(O) – Thr 148(N, OG1) |
| Lys141(N) – ASN146(O) |
| Lys141(O) – Gly145(N) |
| Asp144(OD2) – Asp146(N, ND2) |
| Asp144(OD1) – Asp146(N) |
| |
| Salt bridge within the peptide |
| Lys141(NZ) – Asp144(OD2) |
| |
| H-bonds between Fab and peptide |
| Lys141(NZ) – Asp H100(O) |
| Lys141(NZ) – Leu103(O) |
| Pro142(O) – Trp H52(NE1) |
| Ser143(O) – Tyr H59(OH) |
| Ser143(OG) – Glu H99(OE2) |
| Asp144(O) – Phe H53(N) |
| |
| Salt Bridge between Fab and peptide |
| Lys141(NZ) – Glu H99(OE2) |
| |
| Hydrophobic between Fab and peptide |
| Pro142 – Leu L29 |
| Gly145 – Trp H52 |

Fig. 13 (continued)

COMPOSITIONS AND METHODS RELATED TO HUMAN NEUTRALIZING ANTIBODIES TO HEPATITIS B

CROSS REFERENCE TO RELATED APPLICATIONS

This application claims priority to U.S. provisional patent application No. 62/898,735, filed Sep. 11, 2019, and to U.S. provisional patent application no. 62/982,276, filed Feb. 27, 2020, the entire disclosures of each of which are incorporated herein by reference in their entireties.

STATEMENT REGARDING FEDERALLY SPONSORED RESEARCH OR DEVELOPMENT

This invention was made with government support under grant no. UL1TR001866 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 9, 2020, is named 076091_00092_SL.txt and is 307,317 bytes in size.

BACKGROUND

Despite the existence of effective vaccines, hepatitis B virus (HBV) infection remains a major global health problem with an estimated 257 million people living with the infection. Whereas 95% of adults and 50-75% of children between the ages of 1 and 5 years spontaneously control HBV, only 10% of infants recover naturally. The remainder develop a chronic infection that can lead to liver cirrhosis and hepatocellular carcinoma. Although chronic infection can be suppressed with antiviral medications, there is no effective curative therapy (Dienstag, 2008; Revill et al., 2016; Thomas, 2019).

HBV is an enveloped double-stranded DNA virus of the Hepadnaviridae family. Its genome is the smallest genome among pathogenic human DNA viruses, with only four open reading frames. Infected liver cells produce both infectious HBV virions (Dane particles) and non-infectious subviral particles (Australia antigen) (Dane et al., 1970; Hu and Liu, 2017). The virion is a 42 nm-diameter particle containing the viral genome and HBV core antigen (HBcAg) encapsidated by a lipid membrane containing the hepatitis B surface antigen (HBsAg) (Blumberg, 1964; Venkatakrishnan and Zlotnick, 2016). Subviral particles lack the viral genome.

HBV strains were originally grouped into four HBsAg serotypes (adr, adw, ayw, and ayr). Genetic analysis revealed several highly conserved domains and defined eight genotypes A-H, which are highly correlated with the 4 serotypes (Norder et al., 2004). The HBV surface protein, HBsAg, has 4 putative transmembrane domains and can be subdivided into PreS1-, PreS2- and S-regions. The S domain is a cysteine-rich protein consisting of 226 amino acids that contain all 4 of the transmembrane domains (Abou-Jaoude and Sureau, 2007). In addition, the S-protein can be glycosylated at asparagine residue 146 (Julithe et al., 2014).

Antibodies to HBsAg (anti-HBs) are associated with successful vaccination and recovery from acute infection, while antibodies to HBcAg (anti-HBc) are indicative of past or current HBV infection (Ganem, 1982). Indeed, the most significant difference between chronically infected and naturally recovered individuals is a robust antibody response to HBsAg (Ganem, 1982). Conversely, the inability to produce these antibodies during acute infection is associated with chronicity (Trepo et al., 2014). Whether these associations reflect an etiologic role for anti-HBs antibodies in protecting from or clearing established infection is not known. However, depletion of antibody-producing B lymphocytes in exposed humans by anti-CD20 therapies (e.g. rituximab) is associated with HBV reactivation, indicating that B cells and/or their antibody products play a significant role in controlling the infection (Loomba and Liang, 2017).

Several human antibodies against HBsAg have been obtained using a variety of methods including: phage display (Kim and Park, 2002; Li et al., 2017; Sankhyan et al., 2016; Wang et al., 2016); humanized mice (Eren et al., 1998); Epstein-Barr virus-induced B cell transformation (Heijtink et al., 2002; Heijtink et al., 1995; Sa'adu et al., 1992); hybridoma technology (Colucci et al., 1986); human B cell cultures (Cerino et al., 2015); and microwell array chips (Jin et al., 2009; Tajiri et al., 2010). However, the donors in these studies were not selected for serum neutralizing activity. Thus, there remains a need for improved approaches and compositions of combatting HBV infection. The present disclosure is pertinent to this need.

BRIEF SUMMARY

The disclosure provides in part a description of the human humoral immune response to HBsAg in immunized and spontaneously recovered individuals that had been selected for high levels of serum neutralizing activity. The disclosure demonstrates that these individuals develop closely related bNAbs that target shared non-overlapping epitopes in HBsAg. The crystal structure of one of the antibodies with its peptide target reveals a loop that helps to explain why certain amino acid residues are frequently mutated in escape viruses and why combinations of bNAbs may be needed to control infection. In vivo experiments in humanized mice demonstrate that the bNAbs are protective and can be therapeutic when used in combination.

Any antibody described herein can comprise at least one modification of its constant region. The modification may be made for any one or more amino acids. The modification can have any of a number of desirable effects. In certain approaches, the modification increases in vivo half-life of the antibody, or alters the ability of the antibody to bind to Fc receptors, or alters the ability of the antibody to cross placenta or to cross a blood-brain barrier or to cross a blood-testes barrier, or inhibits aggregation of the antibodies, or a combination of said modifications, or wherein the antibody is attached to a label or a substrate. In embodiments, the modification improves the manufacturability of the antibody. In embodiments, any antibody or combination thereof described herein can be present in an immunological assay, such as an enzyme-linked immunosorbent assay (ELISA) assay, or an ELISA assay control. The ELISA assay can be any of a direct ELISA assay, an indirect ELISA assay, a sandwich ELISA assay, or a competition ELISA assay.

In another aspect the disclosure provides a method for prophylaxis or therapy of a hepatitis viral infection comprising administering to an individual in need thereof an effective amount of at least one antibody described herein, or an antigen binding fragment thereof. The antibody may comprise at least one modification of the constant region. In embodiments, the composition is administered to an individual who is infected with or is at risk of being infected with a hepatitis B virus. In one approach, at least two antibodies are administered, wherein optionally the two antibodies recognize distinct HBV epitopes. In an embodiment, administering at least two distinct antibodies suppresses formation of viruses that are resistant to the antibodies.

In another aspect the disclosure provides vaccine formulations. In an embodiment a vaccine formulation comprises an isolated or recombinant peptide or a polynucleotide encoding the peptide, wherein the peptide is derived from an epitope that is frequently targeted by HepB immune resistance, and which is located in a loop anchored by oppositely charged residues, as further described herein.

In another aspect the disclosure provides one or more recombinant expression vectors, and kits comprising the expression vectors. The expression vectors encode at least the heavy chain and the light chain CDRs of any of the antibodies of described herein. Cells comprising the recombinant expression vectors are included, as are methods of making antibodies by culturing cells that comprise expression vectors that express the antibodies, and separating antibodies from the cells. Cell culture media containing such cells and/or antibodies is also included.

BRIEF DESCRIPTION OF THE FIGURES

FIG. 4. HBsAg epitopes. (A) Competition ELISA defines 3 groups of antibodies. Results of competition ELISA shown as percent of binding by biotinylated antibodies and illustrated by colors: black, 0-25%; dark grey, 26-50%; light grey, 51-75%; white, >76%. Weak binders (H002, H012, H013, H014, H018) were excluded. Representative of two experiments. (B) Results of ELISA on alanine scanning mutants of S-protein. Only the amino acids vital for antibody binding are shown. Binding to mutants relative to wild-type S-protein: black, 0-25%; dark grey, 26-50%; light grey, 51-75%; white, >75%. Additional details are provided in FIG. 11. (C) Results of ELISA on human escape mutations of S-protein. Wild-type S-protein and empty vector serve as a positive and negative controls, respectively. Binding to mutants relative to wild-type S-protein: black, 0-25%; dark grey, 26-50%; light grey, 51-75%; white, >75%. Amino acid mutations in bold represent frequently observed mutations in humans (Ma and Wang, 2012). The antibodies tested in (B and C) were selected from Group-I, -II, -III based on their neutralizing activity (FIG. 5A-5C). All experiments were performed at least two times. See also FIG. 11.

DETAILED DESCRIPTION OF THE DISCLOSURE

Figure 1:
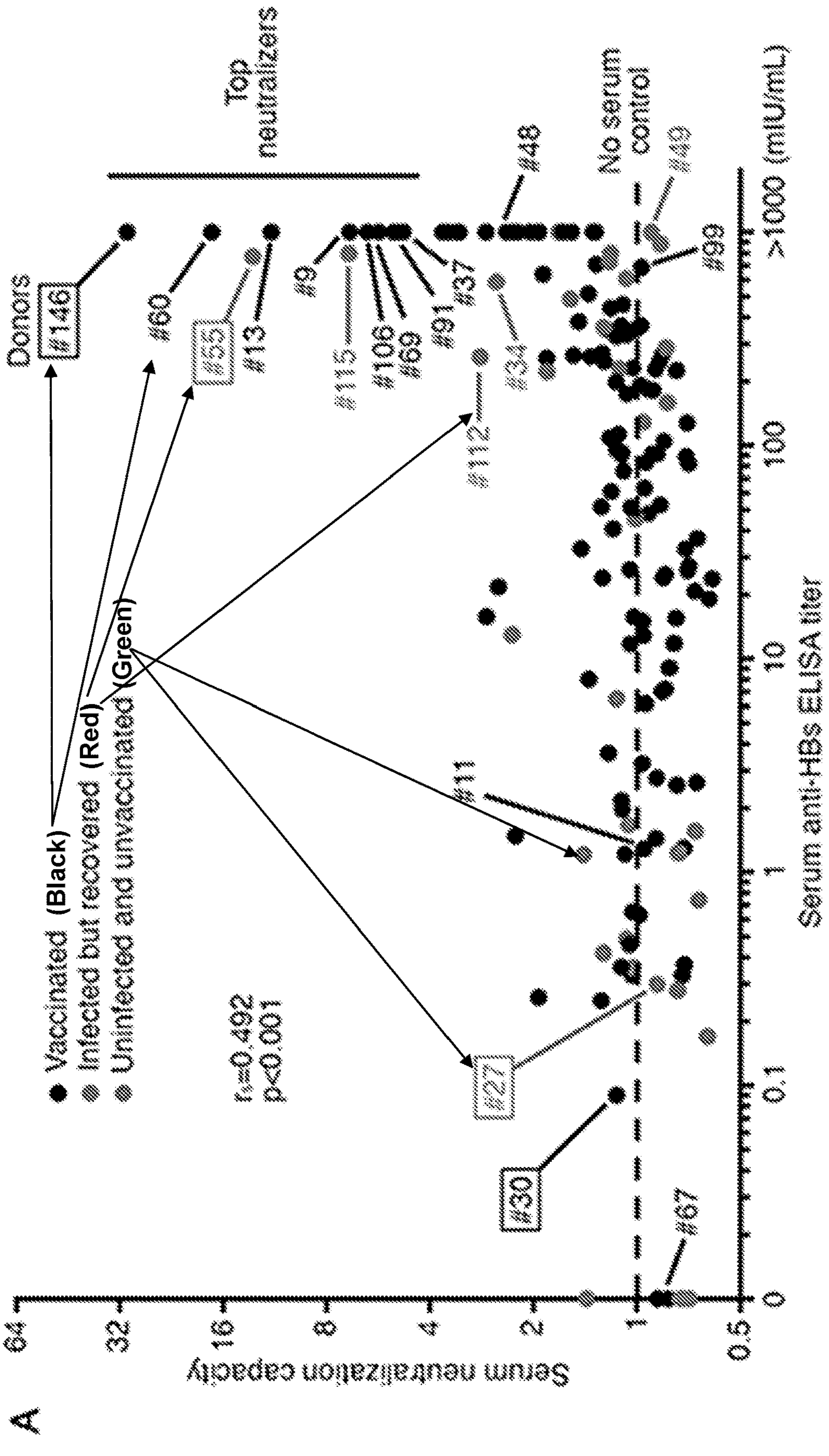
FIG. 1. Antibody responses in HBV vaccinated and recovered individuals. (A) Donor screen. Sera from 159 volunteers were evaluated for anti-HBs binding by ELISA (x-axis) and HBV serum neutralization capacity using HepG2-NTCP cells (y-axis). Serum neutralization capacity on the y-axis was calculated as the reciprocal of the relative percentage of infected HepG2-NTCP cells. The values for unexposed naïve donors are Neutralization tests were performed at 1:5 serum dilution in the final assay volume. Each dot represents an individual donor. Green indicates unvaccinated and unexposed, black indicates vaccinated, and red indicates spontaneously recovered. The dashed line indicates the no serum control. Top neutralizers (serum neutralization capacity higher than 4) are indicated (top right). Boxed are representative samples shown in FIG. 2A. Spearman's rank correlation coefficient ($r_s$) and significance value (p). (B and C) Dose-dependent HBV neutralization by serum (B) or by purified IgG (C). Two assays were used to measure percent infection: ELISA to measure HBsAg protein in the medium (upper panels) and immunofluorescent staining for HBcAg in HepG2-NTCP cells (lower panels). Dashed line indicates virus-only control. (D) Schematic representation illustrating the three forms of the HBV surface protein: L-, M- and S-protein. These three forms of envelope protein all share the same S-region, with PreS1/PreS2 and PreS2 alone as the N-terminal extensions for L- and M-protein, respectively. (E)S-protein produced in Chinese hamster ovary (CHO) cells blocks serum neutralizing activity. Graphs show infection efficiency as a function of the amount of S-protein added. The concentration of polyclonal IgG antibodies (pAb) is indicated. Upper and lower panels are as in (B) and (C). A representative of at least two experiments is shown. See also FIG. 8 and Table S1.
Figure 1:
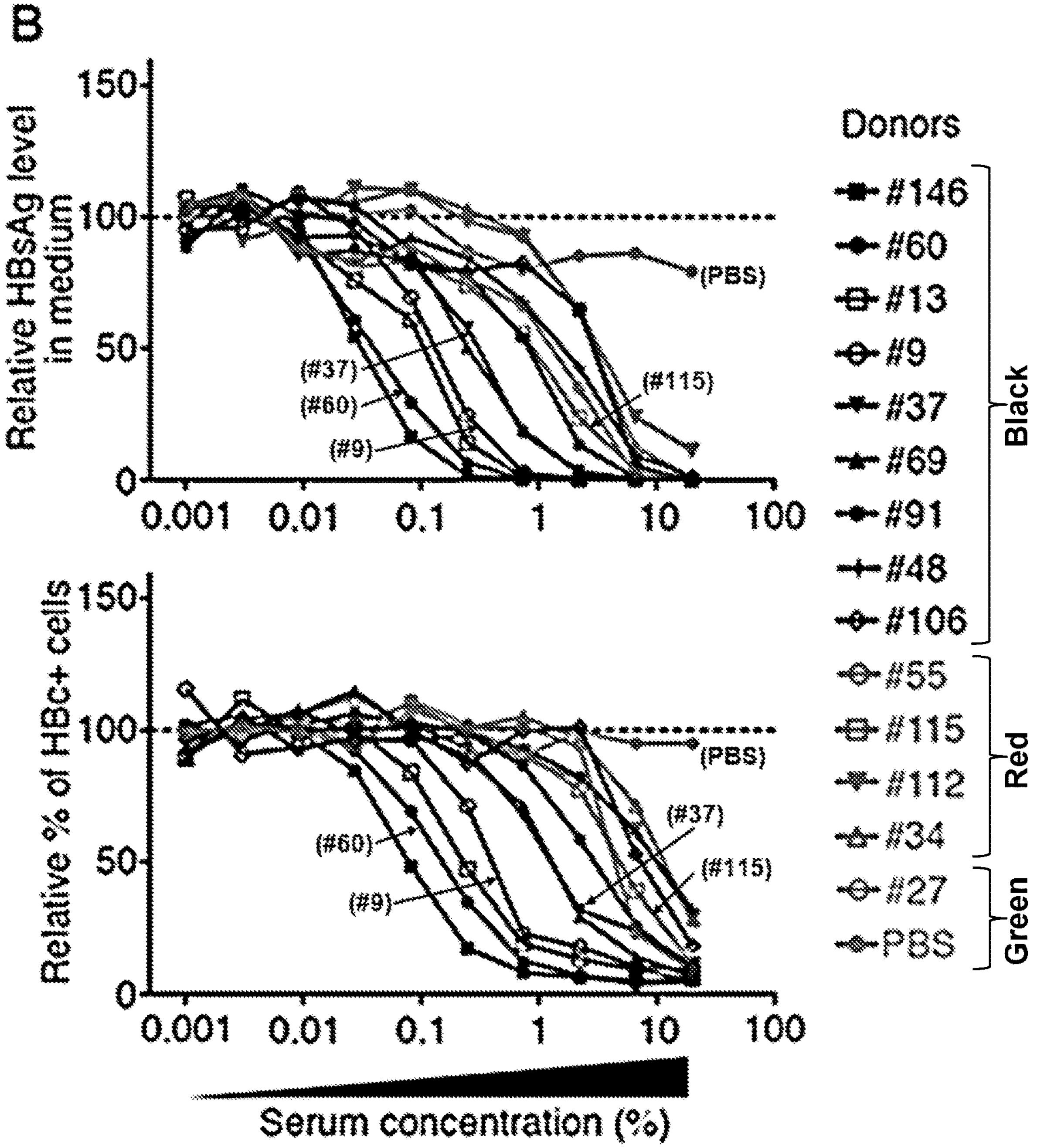
Figure 1:
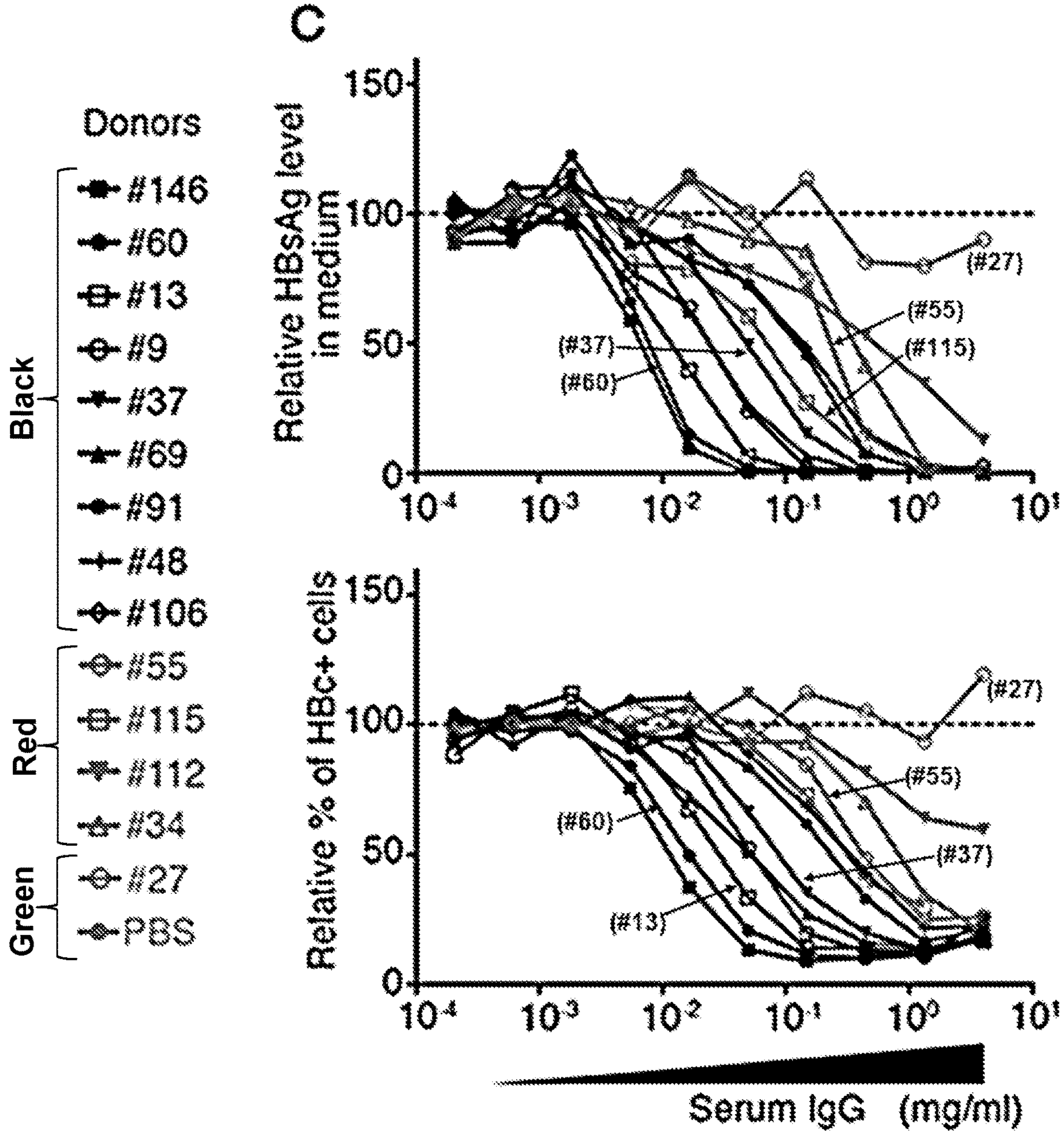
Figure 1:
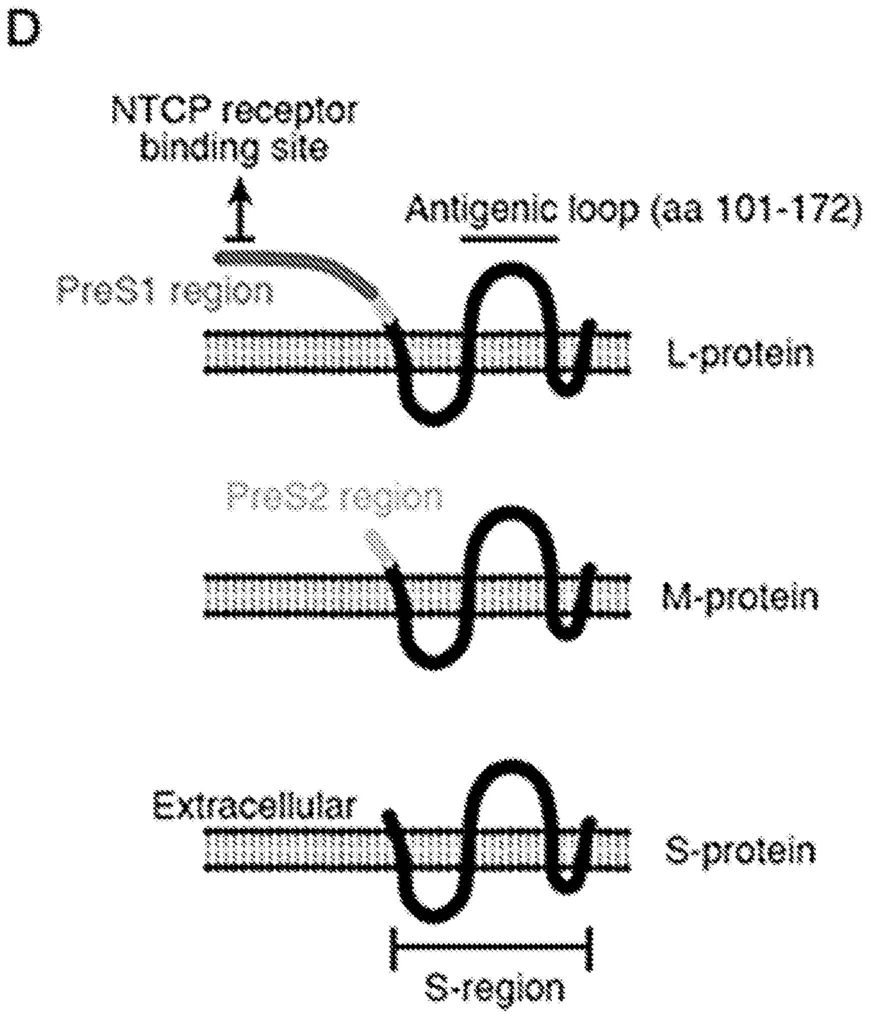
Figure 1:
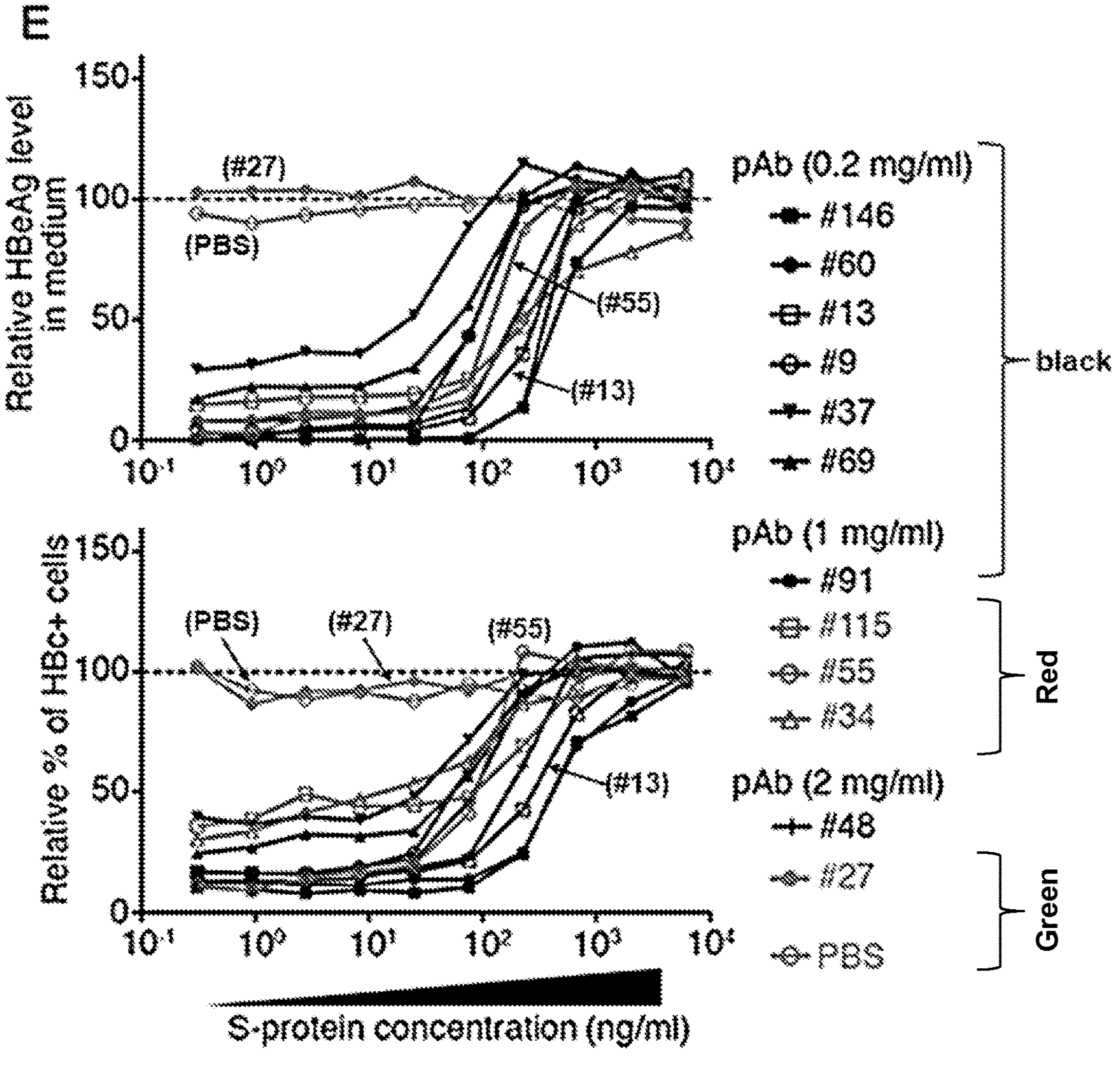

Unless defined otherwise, all technical and scientific terms used herein have the same meaning as commonly understood by one of ordinary skill in the art to which this invention belongs.

Every numerical range given throughout this specification includes its upper and lower values, as well as every narrower numerical range that falls within it, as if such narrower numerical ranges were all expressly written herein.

This disclosure includes every nucleotide sequence described herein, and in the tables and figures, and all sequences that are complementary to them, RNA equivalents of DNA sequences, all amino acid sequences described herein, and all polynucleotide sequences encoding the amino acid sequences. Every antibody sequence and functional fragments of them are included. Polynucleotide and amino acid sequences having from 80-99% similarity, inclusive, and including ranges of numbers there between, with the sequences provided here are included in the invention. All of the amino acid sequences described herein can include amino acid substitutions, such as conservative substitutions, that do not adversely affect the function of the protein or polypeptide that comprises the amino acid sequences. It will be recognized that when reference herein is made to an "antibody" it does not necessarily mean a single antibody molecule. For example, "administering an antibody" includes administering a plurality of the same antibodies. Likewise, a composition comprising an "antibody" can comprise a plurality of the same antibodies.

For amino acid and polynucleotide sequences of this disclosure, contiguous segments of the sequences are included, and can range from 2 amino acids, up to full-length protein sequences. Polynucleotide sequences encoding such segments are also included.

The disclosure includes DNA and RNA sequences encoding the antibodies and antigen fragments thereof, and any virus peptides described herein for use in prophylactic and therapeutic approaches as protein or DNA and/or RNA vaccines, which may be formulated and/or delivered according to known approaches, given the benefit of this disclosure. The disclosure includes a cDNA sequences encoding the antibodies, antigen binding fragments thereof, and any viral proteins or peptides described herein. Expression vectors that contain cDNAs are also included, and encode said antibodies, antigen binding fragments thereof, and viral proteins and peptides.

All sequences from the figures, text, and tables of this application or patent include every amino acid sequence associated with every Donor ID, and all possible combinations of the amino acid sequences given for all complementarity determining regions (CDRs), e.g., all combinations of heavy chain CDR1, CDR2, CDR3 sequences, and all combinations of light chain CDR1, CDR2, and CDR3 sequences, including heavy chain sequences, and light chain sequences that are either lambda or kappa light chain sequences. The disclosure includes all combinations of antibodies described herein. One or more antibodies may also be excluded from any combination of antibodies.

The disclosure includes antibodies described herein, which are present in an in vitro complex with one or more hepatitis B proteins.

In embodiments, the disclosure provides an isolated or recombinant antibody that binds with specificity to a hepatitis B virus epitope, and wherein the antibody optionally comprises a modification of its amino acid sequence, including but not limited to a modification of its constant region.

In embodiments, one or more antibodies described herein bind with specificity to an epitope present in the HBsAg protein or the S-protein in the unmutated, or mutated form.

In embodiments, the antibodies described herein bind to a hepatitis B protein that comprises one or more HepB escape mutations. In embodiments, the antibodies bind to a hepatitis B virus protein that comprises a mutation that is a substitution of a large positively charged residue for a small neutral residue. In embodiments, the mutation is present in the so-called "a" determinant area, which is known in the art. In embodiments, the epitope is present in the major hydrophilic region of the HBsAg protein. In embodiments, the epitope to which the antibodies bind is present in the S-protein, including but not necessarily limited to the predicted or actual extracellular domain of the S-protein.

In embodiments, the epitope to which the described antibodies bind is common to HBsAg L-protein, M-protein, or S-protein. In embodiments, the antibodies bind to an epitope present in the L-protein version of HBsAg, which comprises the amino acid sequence that is accessible via Accession number: AAL66340.1 as that amino acid sequence exists in the database as of the filing date of this application or patent. In an embodiment, this amino acid sequence is:

```
                                        (SEQ ID NO: 2)
MGGWSSKPRQGMGTNLSVPNPLGFFPDHQLDPAFGANSNNPDWDFNPNKD
HWPEANQVGAGAFGPGFTPPHGGLLGWSPQAQGILTTVPVAPPPASTNRQ
SGRQPTPISPPLRDSHPQAMQWNSTTFHQALLDPRVRGLYFPAGGSSSGT
VNPVPTTASPISSIFSRTGDPAPNMESTTSGFLGPLLVLQAGFFLLTRIL
TIPQSLDSWWTSLNFLGGAPTCPGQNSQSPTSNHSPTSCPPICPGYRWMC
LRRFIIFLFILLLCLIFLLVLLDYQGMLPVCPLLPGTSTTSTGPCKTCTS
PAQGTSMFPSCCCTKPSDGNCTCIPIPSSWAFARFLWEWASVRFSWLSLL
VPFVQWFVGLSPTVWLSVIWMMWYWGPCLYNILSPFLPLLPIFFCLW
VYI.
```

In embodiments, the disclosure includes use of only two proteins, or at least two proteins. In an embodiment, the S proteins may be used as bait to sort B cells purified from Chinese hamster ovary (CHO) cells, or any other suitable cell type, including but not limited to human cell cultures. In embodiments, the S protein comprises or consists of the amino acid sequence available under Uniprot ID P30019, the amino acid sequence of which is incorporated herein as it exists in the database at the filing date of this application or patent. In an embodiment, the S protein comprises the sequence:

(SEQ ID NO: 3)
MENTASGFLGPLLVLQAGFFLLTRILTIPQSLDSWWTSLNFLGGAPTCPG
QNSQSPTSNHSPTSCPPICPGYRWMCLRRFIIFLFILLLCLIFLLVLLDY
HGMLPVCPLLPGTSTTSTGPCKTCTIPAQGTSMFPSCCCTKPSDGNCTCI
PIPSSWAFARFLWEWASVRFSWLSLLVPFVQWFVGLSPTVWLSVIWMMWY
WGPSLYNILSPFLPLLPIFFCLWVYI.

In non-limiting embodiments, the S polynucleotide sequence used for alanine scanning comprises:

(SEQ ID NO: 4)
ATGGAGAACATCACATCAGGATTCCTAGGACCCCTGCTCGTGTTACAGGC
GGGGTTTTTCTTGTTGACAAGAATCCTCACAATACCGCAGAGTCTAGACT
CGTGGTGGACTTCTCTCAATTTTCTAGGGGGATCTCCCGTGTGTCTTGGC
CAAAATTCGCAGTCCCCAACCTCCAATCACTCACCAACCTCCTGTCCTCC
AATTTGTCCTGGTTATCGCTGGATGTGTCTGCGGCGTTTTATCATATTCC
TCTTCATCCTGCTGCTATGCCTCATCTTCTTATTGGTTCTTCTGGATTAT
CAAGGTATGTTGCCCGTTTGTCCTCTAATTCCAGGATCAACAACAACCAG
TACGGGACCATGCAAAACCTGCACGACTCCTGCTCAAGGCAACTCTATGT
TTCCCTCATGTTGCTGTACAAAACCTACGGATGGAAATTGCACCTGTATT
CCCATCCCATCGTCCTGGGCTTTCGCAAAATACCTATGGGAGTGGGCCTC
AGTCCGTTTCTCTTGGCTCAGTTTACTAGTGCCATTTGTTCAGTGGTTCG
TAGGGCTTTCCCCCACTGTTTGGCTTTCAGCTATATGGATGATGTGGTAT
TGGGGGCCAAGTCTGTACAGCATCGTGAGTCCCTTTATACCGCTGTTACC
AATTTTCTTTTGTCTCTGGGTATACATTTAA.

The amino acid sequence encoded by the DNA sequence immediately above is:

(SEQ ID NO: 5)
MENITSGFLGPLLVLQAGFFLLTRILTIPQSLDSWWTSLNFLGGSPVCLG
QNSQSPTSNHSPTSCPPICPGYRWMCLRRFIIFLFILLLCLIFLLVLLDY
QGMLPVCPLIPGSTTTSTGPCKTCTTPAQGNSMFPSCCCTKPTDGNCTCI
PIPSSWAFAKYLWEWASVRFSWLSLLVPFVQWFVGLSPTVWLSAIWMMWY
WGPSLYSIVSPFIPLLPIFFCLWVYI.

In embodiments, antibodies of this disclosure bind to an epitope present in any of the foregoing amino sequences, including linear and confirmation epitopes that may be formed by proteins comprising or consisting of said sequences.

Figure 6:
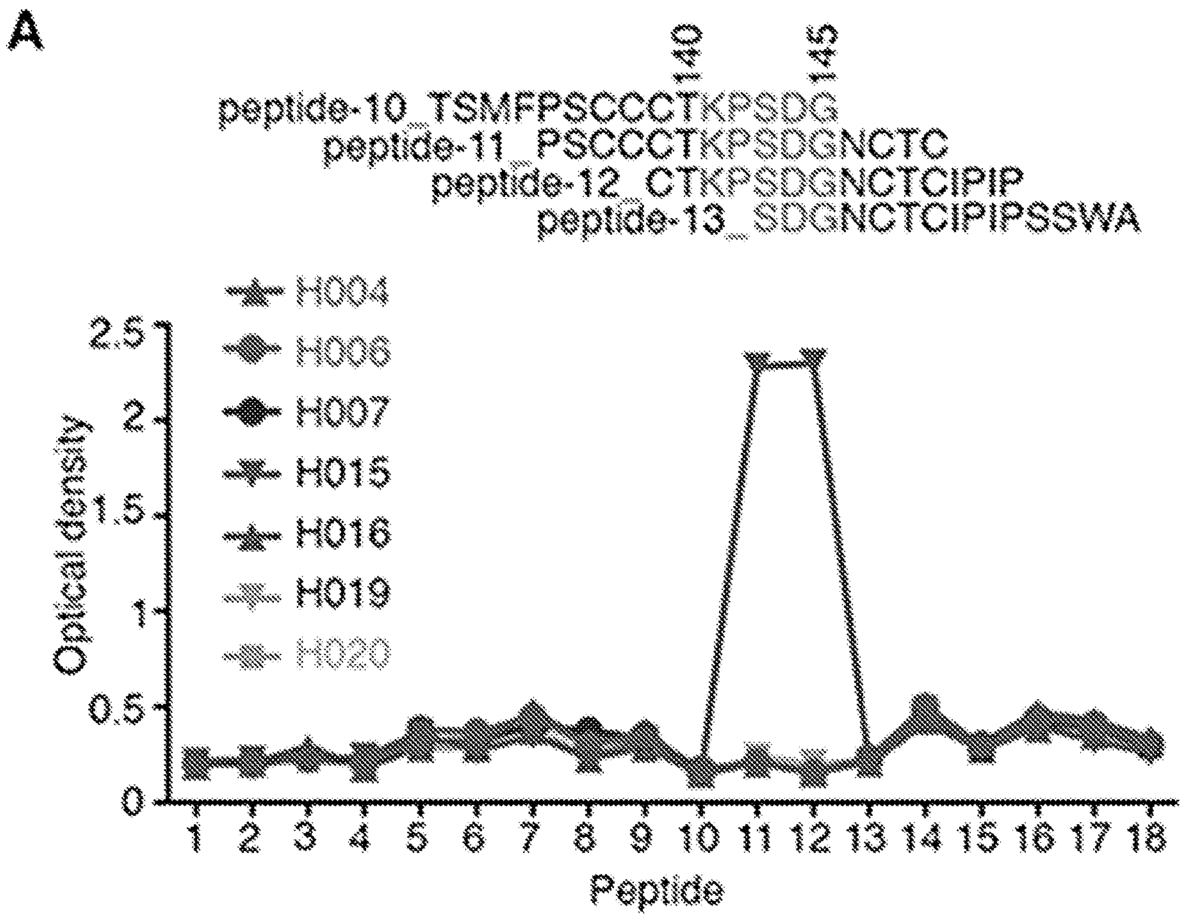
FIG. 6. Crystal structure of H015 bound to its recognition motif. A single crystal was used to obtain a high resolution (1.78 Å) structure. (A) Synthetic peptides (SEQ ID NOS 1452-1455, respectively, in order of appearance) spanning the antigenic loop region were subjected to ELISA for antibody binding. Among the tested antibodies, only H015 binds peptides-11 and -12. Experiments were performed three times and details are in FIG. 13A. (B and C) The peptide binds to CDR1 (R31), CDR2 (W52 and F53) and CDR3 (E99, P101, L103, and L104) of H015 heavy chain (green) and CDR3 (P95) of the light chain (cyan) (B). The interacting residues (C) on the heavy chain (green) are R31 (main chain), W52, F53 (main chain), E99, P101 (main chain), L103 (main chain), L104 (hydrophobic). One contact with the light chain (cyan) is with P95. (D) Electron density map of the bound peptide as seen in the 2Fo-Fc map contoured at 1 RMSD indicating high occupancy (92%). (E) The recognition motif, KPSDGN (SEQ ID NO: 1), adopts a sharp hairpin conformation due to the salt-bridge between K141 and D144 and is facilitated by kinks at P142 and G145. Glycine 145 (G145, circled) is the residue that escapes the immune system when mutated to an arginine. See also FIG. 13.
Figure 6:
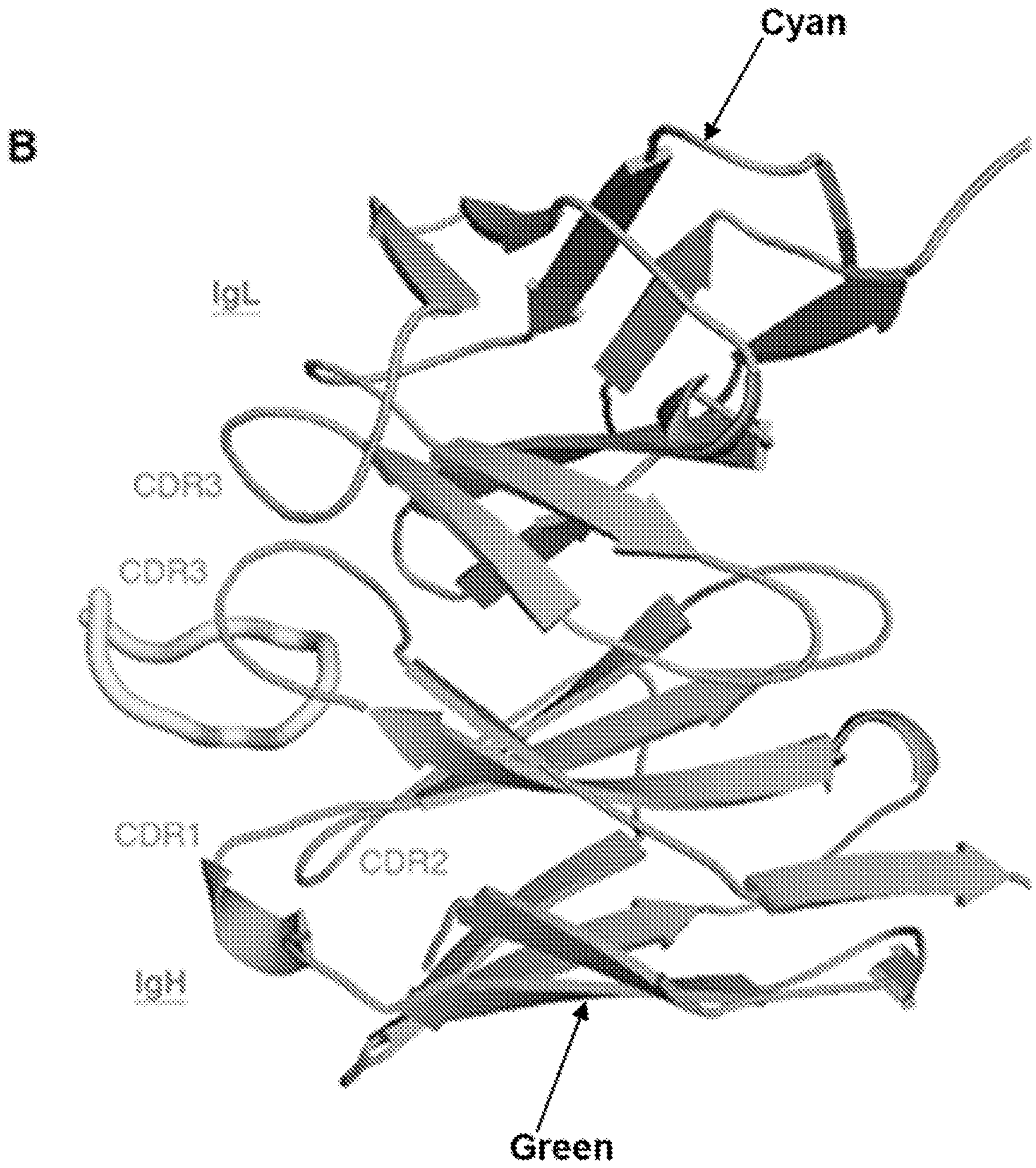
Figure 6:
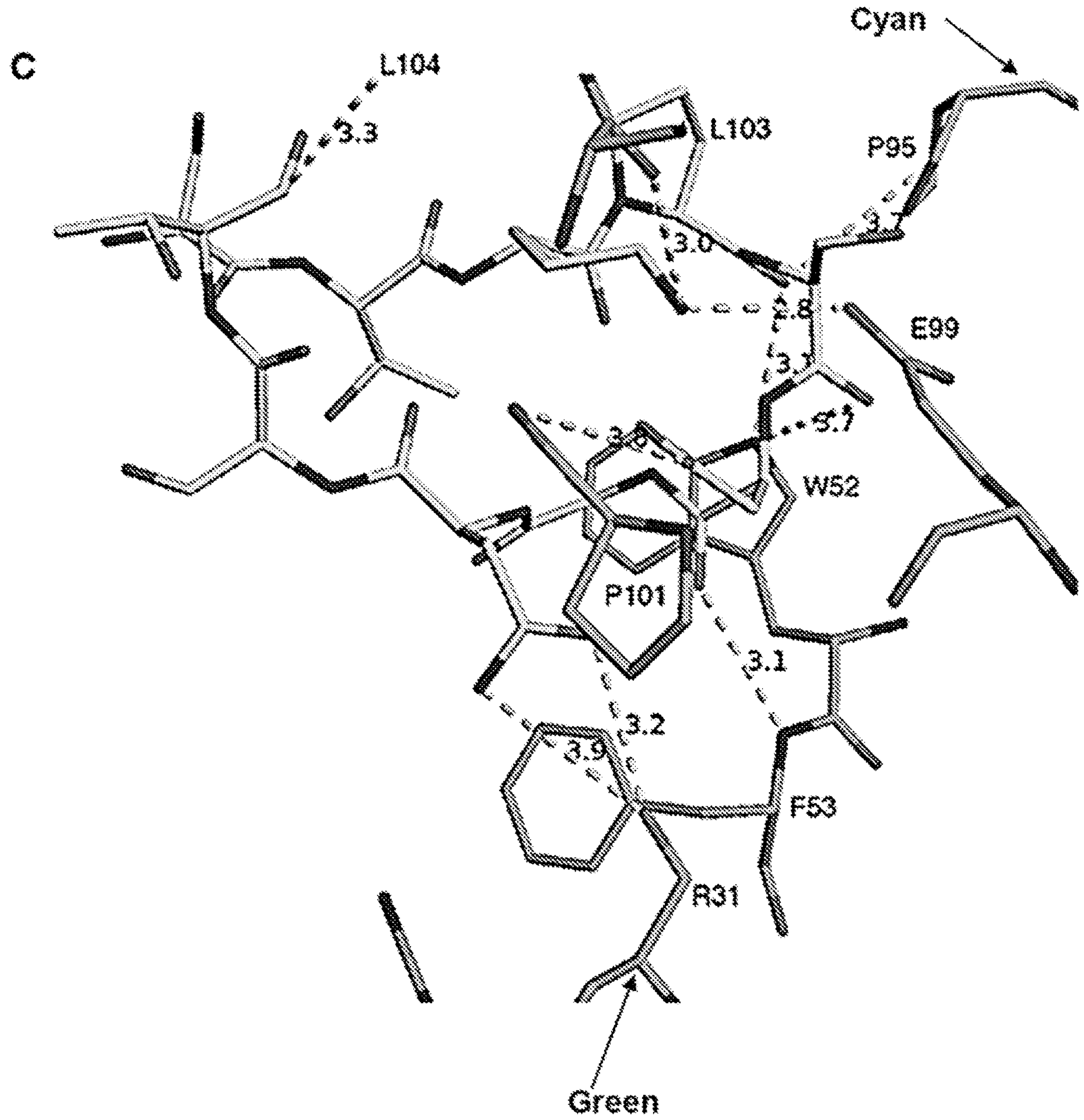
Figure 6:
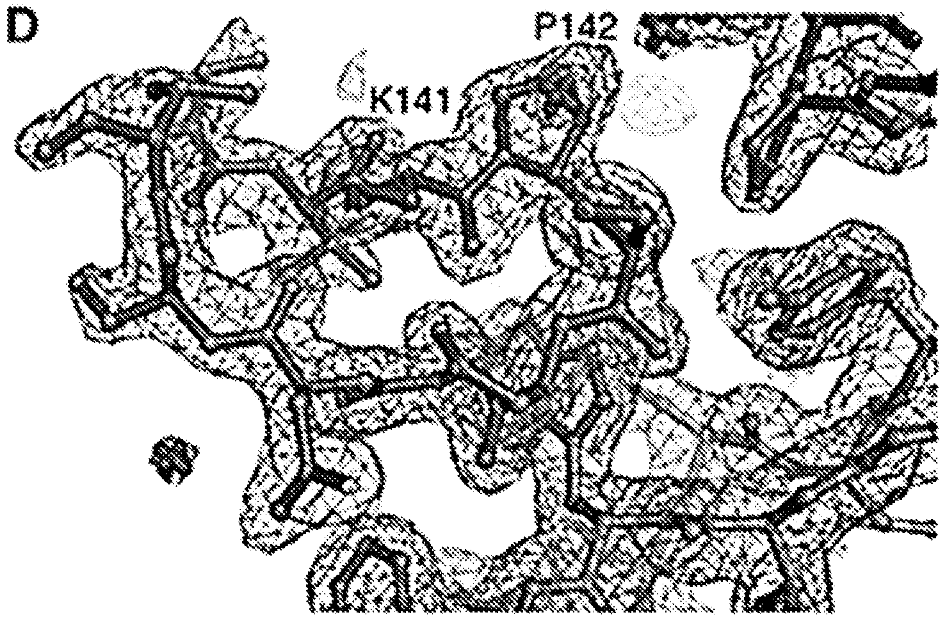
Figure 6:
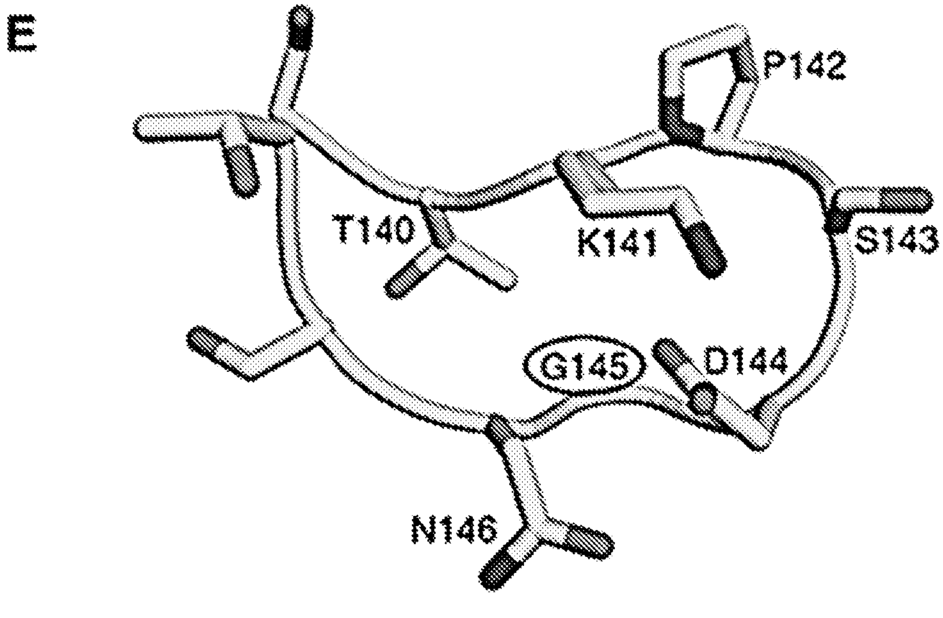

In an embodiment, the isolated or recombinant antibody or antigen binding fragment thereof binds with specificity to an epitope comprised by a structurally defined peptide loop, as further described herein. In embodiments, the loop is as generally depicted in FIG. 6, which comprises a partial structure of HepB surface protein, and demonstrates the existence of a loop that includes the most frequently targeted residue found in human escapes G145. Without intending to be bound by any particular theory, it is considered that this structure explains why this mutant can escape, and also why additional commonly found escape mutants exist. Further, the structure and the antibody peptide complex represents a new and previously undiscovered target for drug discovery. Thus, in embodiments, the disclosure provides for screening drug candidates that can interfere with formation of this structure, and thus which may also interfere with the viability of the virus. Those skilled in the art will recognize from the present disclosure how to design an assay to determine whether or not drug candidates could interfere with the complex, and how antibodies described in herein may be used in such an assay.

In embodiments, antibodies described herein bind with specificity to an amino acid sequence comprised by any peptide sequence described herein. In embodiments, the peptide comprises the sequence KPSDG (SEQ ID NO: 6), or mutants thereof. In embodiments, antibodies described herein bind with specificity to an epitope in an amino acid sequence that comprises the sequence PSSSSTKPSDGNSTS (SEQ ID NO: 7), or mutants thereof. Additional and non-limiting examples of peptides of this disclosure include those shown on FIG. 6, e.g., peptide-11 and peptide-12.

In embodiments, the disclosure comprises compositions and methods that involve use of more than one distinct antibody or antigen binding fragment thereof. In embodiments, the methods of this disclosure comprise administering a combination of antibodies or antigen binding fragment thereof which bind distinct hepatitis B epitopes. In embodiments, distinct antibodies recognize epitopes present in two dominant non-overlapping antigenic sites on the HBsAg, or epitopes present on the S-protein. In embodiments, the disclosure provides for use of a combination of the Group-I and Group-II antibodies described herein. Thus, the disclosure comprises co-administration or sequential administration of a combination of antibodies. In an embodiment, administration of a combination of distinct antibodies suppresses formation of viruses that are resistant to the effects of any one of the antibodies alone. In embodiments, the disclosure includes administering a combination comprising at least one Group I antibody and at least one Group II antibody, wherein at least one of the antibodies is G145R mutation resistant. In non-limiting embodiments, antibodies that are provided by the present disclosure, and which can be administered to an individual in need thereof, comprise at least one of H006, H007, H0017, H0019, or H020. Further, H005, H008 and H009 are similar to H006, and therefore may be used as alternatives to H006.

All combinations of H and L chains described herein are included, including all kappa and lambda light chains. In embodiments, a single antibody of this disclosure may comprise an H+L chain from one antibody, and an H+L chain from another antibody. In embodiments, the antibodies comprise modifications that are not coded for in any B cells obtained from an individual, and/or the antibodies are not produced by immune cells in an individual from which a biological sample from the individual is used at least in part to identify and/or generate and/or characterize the antibodies of this disclosure. In embodiments, antibodies provided by this disclosure can be made recombinantly, and can be expressed with a constant region of choice, which may be different from a constant region that was coded for in any sample from which the amino acid sequences of the antibodies were deduced.

As discussed above, in embodiments, the disclosure includes a combination of antibodies or antigen binding fragments thereof, or a composition comprising or consisting of said antibodies or antigen binding fragments thereof. In embodiments, a combination of antibodies of this disclosure are effective in preventing viral escape by mutation. In this regard, the disclosure includes data demonstrating that not all antibody combinations are effective in preventing escape by mutation, such as the combination of H006 and H007, which are ineffective. Thus, in embodiments, a combinations of antibodies or antigen binding fragments collectively target more than one commonly occurring escape mutation, examples of which escape mutations are known in the art and are described herein. Accordingly, combinations of antibodies and antigen binding fragments thereof of this disclosure may target non-overlapping groups of common escape mutations. In embodiments, the disclosure thus includes a proviso that excludes any combination of antibodies that collectively only target separate epitopes but have overlapping sensitivity to commonly occurring escape mutations.

In embodiments, at least one antibody or antigen binding fragment thereof included in this disclosure, and in the combinations and methods of this disclosure, has greater virus neutralizing activity than a control neutralizing activity value, such as the neutralizing capability of libivirumab. In embodiments, at least one antibody or antigen binding fragment of this disclosure exhibits a viral neutralizing activity with an $IC_{50}$ values that is less than 128 ng/ml, or less than 35 ng/ml, or less than 5 ng/ml, and including all integers and ranges of integers between 128 and 5 ng/ml. Such neutralizing activity can be determined using known approaches, such as by ELISA or immunofluorescence assays, and as further described in Example 5 of this disclosure. In embodiments, an antibody or antigen binding fragment thereof that is encompassed by this disclosure includes but is not limited to antibodies or antigen binding fragments selected from the H016, H017 and H019 antibodies, as defined by their CDRs. In an embodiment, the disclosure includes combinations of these antibodies, and can include antigen binding fragments thereof. In embodiments, the combination of antibodies comprises the H017 and H019 antibodies, and/or antigen binding fragments thereof. In an embodiment, the combination optionally further comprises the H016 antibody or an antigen binding fragment thereof. In embodiments, a combination of the disclosure comprises a combination that consists of only the H017 and H019 antibodies or antigen binding fragments thereof. In embodiments, a combination of the disclosure comprises a combination that consists of only the H016, H017, and H019 antibodies or antigen binding fragments thereof. Methods of administration of the described antibody combinations, and all other antibodies and antigen binding fragments thereof described herein, sequentially and concurrently are included within the scope of this disclosure. Thus, the disclosure includes administering to an individual in need concurrently or sequentially a combination of antibodies or antigen binding fragments thereof, which in certain embodiments comprise or consist of H017 and H019, or H016, H017, and H019 and antigen binding fragments thereof. Additional antibodies and antibody combinations, including antigen binding fragments thereof, include but are not limited to antibodies and antigen binding fragments thereof that comprise the heavy and light chain CDRs of H004, H005, and H009, and H020.

With respect to the H016, H017, and H019 antibodies, as can been seen from Table S2, the H016 antibody comprises a heavy chain CDR1 with the amino acid sequence GFTFPSHT (SEQ ID NO: 8), a heavy chain CDR2 with the amino acid sequence ISTTSEAI (SEQ ID NO: 9), and a heavy chain CDR3 with the amino acid sequence ARVGLALTISGYWYFDL (SEQ ID NO: 10). The H016 antibody comprises a kappa light chain CDR1 with the amino acid sequence QSISSN (SEQ ID NO: 11), a kappa light chain with the CDR2 amino acid sequence RAS, and a kappa light chain with the CDR3 amino acid sequence QQYDHWPLT (SEQ ID NO: 12).

As can be seen from Table S2, the H017 antibody comprises a heavy chain CDR1 with the amino acid sequence GFTFSNYW (SEQ ID NO: 13), a heavy chain CDR2 with the amino acid sequence ISTDGSST (SEQ ID NO: 14), and a heavy chain CDR3 with the amino acid sequence ARGSTYYFGSGSVDY (SEQ ID NO: 15). The H017 antibody comprises a lambda light chain with the CDR1 sequence SSDIGVYNY (SEQ ID NO: 16), a lambda light chain with the CDR2 sequence DVT, and a lambda light chain with the CDR3 sequence SSYRGSSTPYV (SEQ ID NO: 17).

As can be seen from Table S2, the H019 antibody comprises a heavy chain CDR1 with the amino acid sequence GGSITTGDYY (SEQ ID NO: 18), a heavy chain CDR2 with the amino acid sequence IYYSGST (SEQ ID NO: 19), and a heavy chain CDR3 with the amino acid sequence AIYMDEAWAFE (SEQ ID NO: 20). The H019 antibody comprises a lambda light chain CDR1 with the amino acid sequence QSIGNY (SEQ ID NO: 21), a lambda light chain with the CDR2 amino acid sequence AVS, and a lambda light chain with the CDR3 amino acid sequence QQSYTISLFT (SEQ ID NO: 22).

In certain embodiments, the antibodies contain one or more modifications, such as non-naturally occurring mutations. As non-limiting examples, in certain approaches the Fc region of the antibodies can be changed, and may be of any isotype, including but not limited to any IgG type, or an IgA type, etc. Antibodies of this disclosure can be modified to improve certain biological properties of the antibody, e.g., to improve stability, to modify effector functions, to improve or prevent interaction with cell-mediated immunity and transfer across tissues (placenta, blood-brain barrier, blood-testes barrier), and for improved recycling, half-life and other effects, such as manufacturability and delivery.

In embodiments, an antibody of this disclosure can be modified by using techniques known in the art, such as those described in Buchanan, et al., Engineering a therapeutic IgG molecule to address cysteinylation, aggregation and enhance thermal stability and expression mAbs 5:2, 255-262; March/April 2013, and in Zalevsky J. et al., (2010) Nature Biotechnology, Vol. 28, No. 2, p 157-159, and Ko, S-Y, et al., (2014) Nature, Vol. 514, p 642-647, and Horton, H. et al., Cancer Res 2008; 68: (19), Oct. 1, 2008, from which the descriptions are incorporated herein by reference. In certain embodiments an antibody modification increases in vivo half-life of the antibody (e.g. LS mutations), or alters the ability of the antibody to bind to Fc receptors (e.g. GRLR mutations), or alters the ability to cross the placenta or to cross the blood-brain barrier or to cross the blood-testes barrier. Thus, in certain embodiments an antibody modification comprises a change of G to R, L to R, M to L, or N to S, or any combination thereof.

In embodiments bi-specific antibodies are provided by modifying and/or combining segments of antibodies as described herein, such as by combining heavy and light chain pairs from distinct antibodies into a single antibody. Suitable methods of making bispecific antibodies are known in the art, such as in Kontermann, E. et al., Bispecific antibodies, Drug Discovery Today, Volume 20, Issue 7, July 2015, Pages 838-847, the description of which is incorporated herein by reference.

In embodiments, any antibody described herein comprises a modified heavy chain, a modified light chain, a modified constant region, or a combination thereof, thus rendering them distinct from antibodies produced by humans. In embodiments, the modification is made in a hypervariable region, and/or in a framework region (FR).

In embodiments, mutations to an antibody described herein, including but not limited to the antibodies described, comprise modifications relative to the antibodies originally produced in humans. Such modifications include but are not necessarily limited to the heavy chain to increase the antibody half-life.

In embodiments, antibodies of this disclosure have variable regions that are described herein, and may comprise or consist of any of these sequences, and may include sequences that have from 80-99% similarity, inclusive, and including ranges of numbers there between, with the sequences expressly disclosed herein, provided antibodies that have differing sequences retain the same or similar binding affinity as an antibody with an unmodified sequence. In embodiments, the sequences are at least 95%, 96%, 97%, 98% or 99% similar to an expressly disclosed sequence herein.

Antibodies comprising the sequences described in Table S2 have been isolated and characterized for at least binding affinity, and as otherwise described herein, such as for virus neutralizing activity. Thus, in embodiments the disclosure provides neutralizing antibodies. The term "neutralizing antibody" refers to an antibody or a plurality of antibodies that inhibits, reduces or completely prevents viral infection. Whether any particular antibody is a neutralizing antibody can be determined by in vitro assays described in the examples below, and as is otherwise known in the art. The term "broadly neutralizing" antibody refers to an antibody that can neutralize more than one strain or serotype of a virus.

Antibodies of this disclosure can be provided as intact immunoglobulins, or as antigen binding fragments of immunoglobulins, including but not necessarily limited to antigen-binding (Fab) fragments, Fab' fragments, $(Fab')_2$ fragments, Fd (N-terminal part of the heavy chain) fragments, Fv fragments (the two variable domains), dAb fragments, single domain fragments or single monomeric variable antibody domains, isolated CDR regions, single-chain variable fragment (scFv), and other antibody fragments that retain virus-binding capability and preferably virus neutralizing activity as further described below. In embodiments, the variable regions, including but not necessarily limited to the described CDRs, may be used as a component of a Bispecific T-cell engager (BiTE), bispecific killer cell engager (BiKE), or a chimeric antigen receptor (CAR), such as for producing chimeric antigen receptor T cells (e.g. CAR T cells). In embodiments, the disclosure includes tri-valent antibodies, which can bind with specificity to three different epitopes.

Antibodies and antigens of this disclosure can be provided in pharmaceutical formulations. It is considered that administering a DNA or RNA polynucleotide encoding any protein described herein (including peptides and polypeptides), such as antibodies and antigens described herein, is also a method of delivering such proteins to an individual, provided the protein is expressed in the individual. Methods of delivering DNA and RNAs encoding proteins are known in the art and can be adapted to deliver the protein, particularly the described antigens, given the benefit of the present disclosure. Similarly, the antibodies of this disclosure can be administered as DNA molecules encoding for such antibodies using any suitable expression vector(s), or as RNA molecules encoding the antibodies.

Pharmaceutical formulations containing antibodies or viral antigens or polynucleotides encoding them can be prepared by mixing them with pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, liposomes, antioxidants, chelating agents such as EDTA; salt forming counter-ions such as sodium; non-ionic surfactants such as TWEEN, PLURONICS or polyethylene glycol (PEG), or combinations thereof. In embodiments, a pharmaceutical/vaccine formulation exhibits an improved activity relative to a control, such as antibodies that are delivered without adding additional agents, or a particular added agent improves the activity of the antibodies.

The formulation can contain more than one antibody type or antigen, and thus mixtures of antibodies, and mixtures of antigens, and combinations thereof as described herein can be included. These components can be combined with a carrier in any suitable manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

The antibodies and vaccine components of this disclosure are employed for the treatment and/or prevention of hepatitis B virus infection in a subject, as well as for inhibition and/or prevention of their transmission from one individual to another.

The term "treatment" of viral infection refers to effective inhibition of the viral infection so as to delay the onset, slow down the progression, reduce viral load, and/or ameliorate the symptoms caused by the infection.

The term "prevention" of viral infection means the onset of the infection is delayed, and/or the incidence or likelihood of contracting the infection is reduced or eliminated.

In embodiments, to treat and/or prevent viral infection, a therapeutic amount of an antibody or antigen vaccine disclosed herein is administered to a subject in need thereof. The term "therapeutically effective amount" means the dose required to effect an inhibition of infection so as to treat and/or prevent the infection.

The dosage of an antibody or antigen vaccine depends on the disease state and other clinical factors, such as weight and condition of the subject, the subject's response to the therapy, the type of formulations and the route of administration. The precise dosage to be therapeutically effective and non-detrimental can be determined by those skilled in the art. As a general rule, a suitable dose of an antibody for the administration to adult humans parenterally is in the range of about 0.1 to 20 mg/kg of patient body weight per day, once a week, or even once a month, with the typical initial range used being in the range of about 2 to 10 mg/kg. Since the antibodies will eventually be cleared from the bloodstream, re-administration may be required. Alternatively, implantation or injection of the antibodies provided in a controlled release matrix can be employed.

The antibodies can be administered to the subject by standard routes, including oral, transdermal, and parenteral (e.g., intravenous, intraperitoneal, intradermal, subcutaneous or intramuscular). In addition, the antibodies and/or the antigen vaccines can be introduced into the body, by injection or by surgical implantation or attachment such that a significant amount of an antibody or the vaccine is able to enter blood stream in a controlled release fashion. In certain embodiments antibodies described herein are incorporated into one or more prophylactic compositions or devices to, for instance, neutralize a virus before it enters cells of the recipient's body. For example, in certain embodiments a composition and/or device comprises a polymeric matrix that may be formed as a gel, and comprises at least one of hydrophilic polymers, hydrophobic polymers, poly(acrylic acids) (PAA), poly(lactic acids) (PLA), carageenans, polystyrene sulfonate, polyamides, polyethylene oxides, cellulose, poly(vinylpyrrolidone) (PVP), poly(vinyl alcohol) (PVA), chitosan, poly(ethylacrylate), methylmethacrylate, chlorotrimethyl ammonium methylmethacrylate, hydroxyapatite, pectin, porcine gastric mucin, poly(sebacic acid) (PSA), hydroxypropyl methylcellulose (HPMC), cellulose acetate phthalate (CAP), magnesium stearate (MS), polyethylene glycol, gum-based polymers and variants thereof, poly (D,L)-lactide (PDLL), polyvinyl acetate and povidone, carboxypolymethylene, and derivatives thereof. In certain aspects the disclosure comprises including antibodies in micro- or nano-particles formed from any suitable biocompatible material, including but not necessarily limited to poly(lactic-co-glycolic acid) (PLGA). Liposomal and microsomal compositions are also included. In certain aspects a gel of this disclosure comprises a carbomer, methylparaben, propylparaben, propylene glycol, sodium carboxymethylcellulose, sorbic acid, dimethicone, a sorbitol solution, or a combination thereof. In embodiments a gel of this disclosure comprises one or a combination of benzoic acid, BHA, mineral oil, peglicol 5 oleate, pegoxol 7 stearate, and purified water, and can include any combination of these compositions.

Antibodies of this disclosure can be produced by utilizing techniques available to those skilled in the art. For example, one or distinct DNA molecules encoding one or both of the H and L chains of the antibodies can be constructed based on the coding sequence using standard molecular cloning techniques. The resulting DNAs can be placed into a variety of suitable expression vectors known in the art, which are then transfected into host cells, which are preferably human cells cultured in vitro, but may include *E. coli* or yeast cells, simian COS cells, Chinese Hamster Ovary (CHO) cells, and human embryonic kidney 293 cells, etc. Antibodies can be produced from a single, or separate expression vectors, including but not limited to separate vectors for heavy and light chains, and may include separate vectors for kappa and lambda light chains as appropriate.

In embodiments, the antibodies may be isolated from cells. In embodiments, the antibodies are recombinant antibodies. "Recombinant" antibodies mean the antibodies are produced by expression within cells from one or more expression vectors.

In certain approaches the disclosure includes neutralizing antibodies as discussed above, and methods of stimulating the production of such antibodies.

In certain approaches the disclosure includes vaccinating an individual using a composition described herein, and determining the presence, absence, and/or an amount of neutralizing antibodies produced in response to the vaccination. Thus, methods of determining and monitoring efficacy of a vaccination at least in terms of neutralizing antibody production are included. In an embodiment, subsequent to determining an absence of neutralizing antibodies, and/or an amount of neutralizing antibodies below a suitable reference value, the invention includes administering a composition disclosed herein to the individual. Subsequent administrations and measurements can be made to track the treatment efficacy and make further adjustments to treatment accordingly.

Antibodies and proteins of this disclosure can be detectably labeled and/or attached to a substrate. Any substrate and detectable label conventionally used in immunological assays and/or devices is included. In embodiments the substrate comprises biotin, or a similar agent that binds specifically with another binding partner to facilitate immobilization and/or detection and/or quantification of antibodies and/or viral proteins.

In embodiments any type of enzyme-linked immunosorbent (ELISA) assay can be used, and can be performed using polypeptides and/or antibodies of this disclosure for diagnostic purposes, and can include direct, indirect, and competitive ELISA assays, and adaptations thereof that will be apparent to those skilled in the art given the benefit of this disclosure.

Any diagnostic result described herein can be compared to any suitable control. Further, any diagnostic result can be fixed in a tangible medium of expression and communicated to a health care provider, or any other recipient. In one aspect the disclosure comprises diagnosing an individual as infected with hepatitis B virus and administering a composition of this invention to the individual.

In certain embodiments the disclosure includes one or more recombinant expression vectors encoding at least H and L chains of an antibody or antigen binding fragment of this disclosure, cells and cell cultures comprising the expression vectors, methods comprising culturing such cells and separating antibodies from the cell culture, the cell culture media that comprises the antibodies, antibodies that are separated from the cell culture, and kits comprising the expression vectors encoding an antibody and/or a polypeptide of this disclosure. Products containing the antibodies and/or the polypeptides are provided, wherein the antibodies and/or the polypeptides are provided as a pharmaceutical formulation contained in one or more sealed containers, which may be sterile and arranged in any manner by which such agents would be suitable for administration to a human or non-human subject. The products/kits may further comprise one or more articles for use in administering the compositions.

The following Examples are intended to illustrate but not limit the invention.

Example 1

Serologic Responses Against HBV

To select individuals with outstanding antibody responses to HBsAg, we performed ELISA assays on serum obtained from 159 volunteers. These included 15 uninfected and unvaccinated controls (HBsAg$^-$, anti-HBs$^-$, anti-HBc$^-$), 20 infected and spontaneously recovered (HBsAg$^-$, anti-HBs$^{+/-}$, anti-HBO, and 124 vaccinated (HBsAg$^-$, anti-HBs$^{+/-}$, anti-HBc$^-$) volunteers. These individuals displayed a broad spectrum of anti-HBs titers (x-axis in FIG. 1A and FIG. 8B; Table S1). To determine their neutralizing activity, we tested their ability to block HBV infection in sodium taurocholate co-transporting polypeptide (NTCP)-overexpressing HepG2 cells (Michailidis et al., 2017; Yan et al., 2012) (y-axis in FIG. 1A and FIGS. 8B and 8C; Table S1). Sera or antibodies purified from individuals with high levels of neutralizing activity were then compared across a wide range of dilutions (FIGS. 1B and 1C). Although anti-HBs ELISA titers positively correlated with neutralizing activity ($r_s$=0.492, p<0.001, Spearman's rank correlation), there were notable exceptions as exemplified by volunteers #99 and #49, whose sera failed to neutralize HBV despite high anti-HBs ELISA titers (FIG. 1A). Thus, ELISA titers against HBsAg are not entirely predictive of neutralizing activity in vitro.

The HBV surface protein, HBsAg can be subdivided into PreS1-, PreS2- and S-regions (FIG. 1D). To determine which of these regions is the dominant target of the neutralizing response in the selected top neutralizers, we used S-protein to block neutralizing activity in vitro. The neutralizing activity in volunteers that received the HBV vaccine, which is composed of S-protein, was completely blocked by S-protein (black lines in FIG. 1E). The same was true for the spontaneously recovered individuals in our cohort despite a reported ability of this population to produce anti-PreS1 or anti-PreS2 antibodies (Coursaget et al., 1988; Li et al., 2017; Sankhyan et al., 2016) (red lines in FIG. 1E). These results suggest that the neutralizing antibody response in the selected individuals is directed primarily against the S-protein irrespective of immunization or infection.

Example 2

Human Monoclonal Antibodies to HBV

Figure 9:
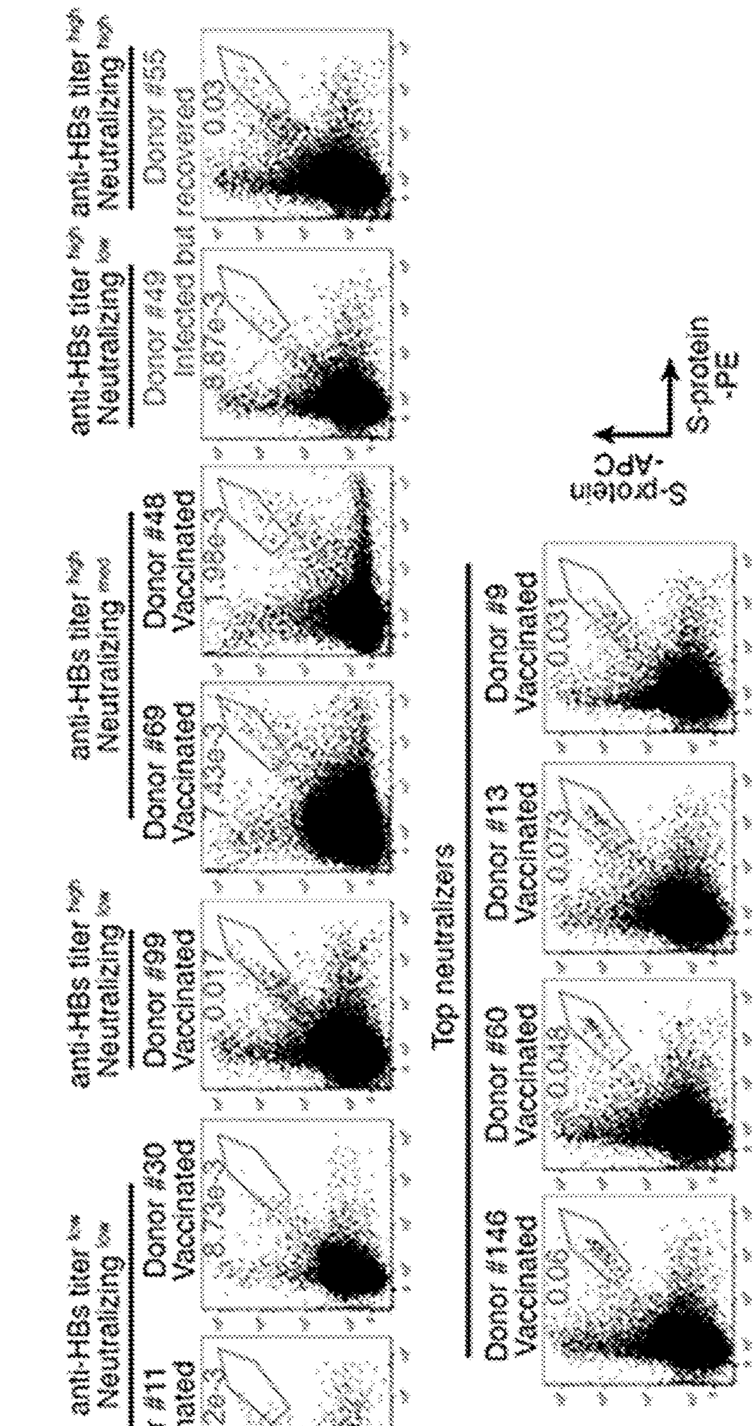
FIG. 9. Antibody Cloning and Sequence Analysis of Anti-HBs, Related to FIG. 2. (A) Frequency of S-protein-specific memory B cells in peripheral blood mononuclear cells of all twelve donors. Details are similar to FIG. 2A. (B) Pie charts show the distribution of anti-HBs antibodies. Figure legends are similar to FIG. 2C. VH and VL genes for each slice are shown and the 20 chosen anti-HBs antibodies are labeled. (C) Phylogenetic tree of all cloned anti-HBs antibodies based on IGH Fab region. IGH Fab regions from 244 memory B cells sorted with HBsAg were aligned followed by tree construction.
Figure 9:
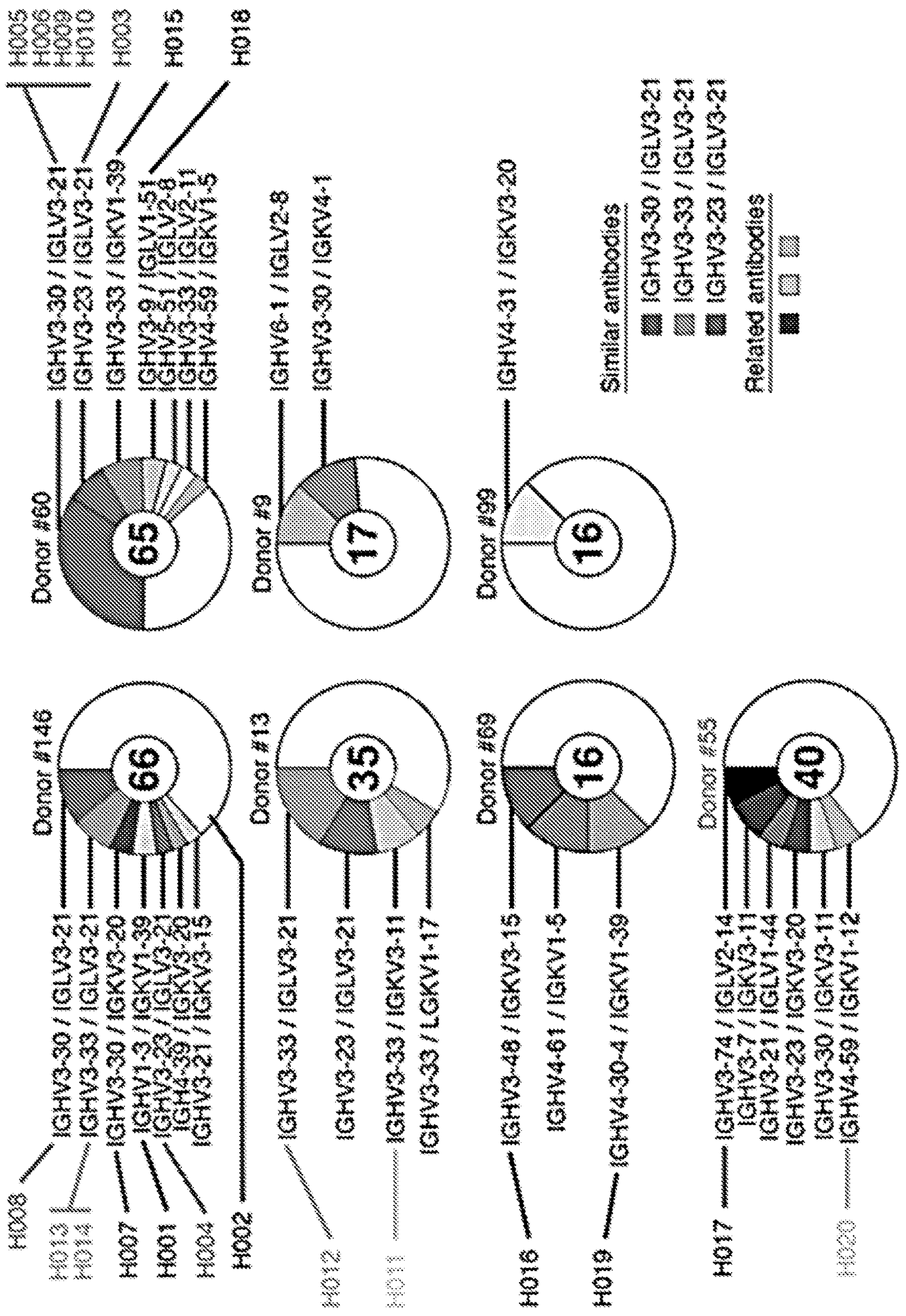
Figure 9:
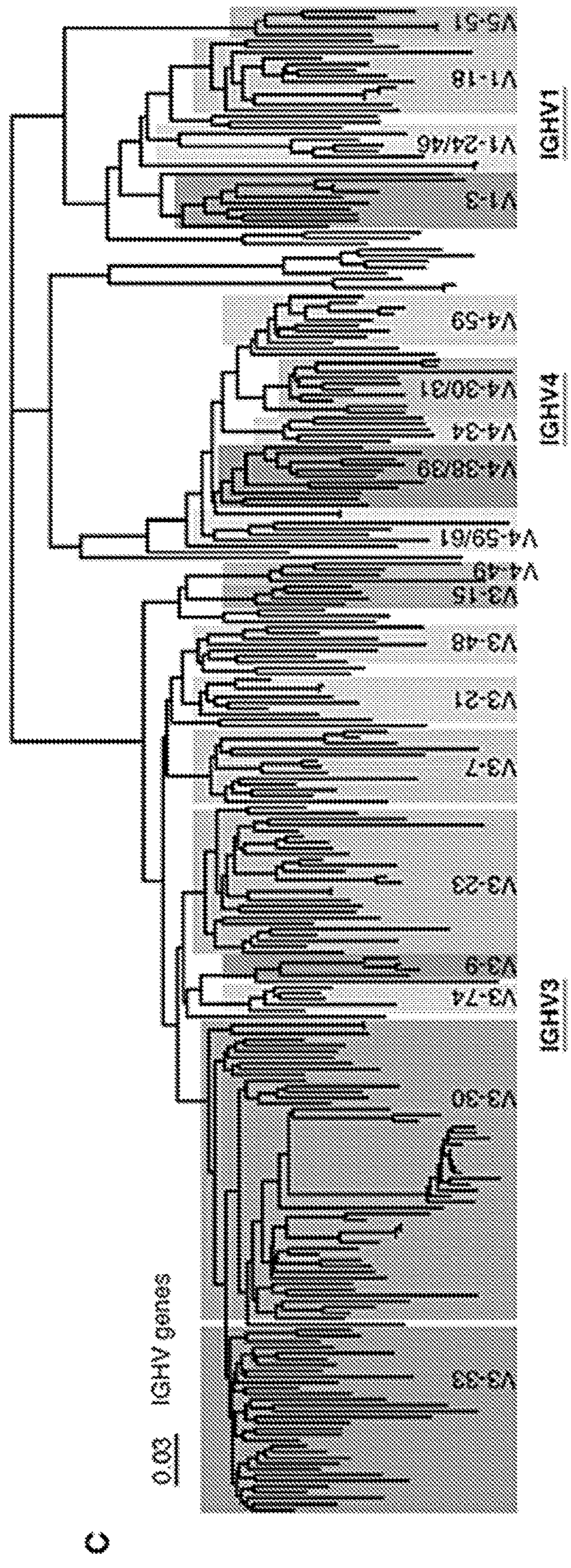

To characterize the antibodies responsible for neutralizing activity in the selected individuals, we purified S-protein binding class-switched memory B cells (Escolano et al., 2019; Scheid et al., 2009a). Unexposed naïve controls and vaccinated individuals with low anti-HBs ELISA titers showed background levels of S-protein specific memory B cells (FIGS. 2A and 9A). In contrast, individuals with high neutralizing activity displayed a distinct population of S-antigen binding B cells constituting 0.03-0.07% of the IgG$^+$ memory compartment (CD19-MicroBeads$^+$ CD20-PECy7$^+$ IgG-Bv421$^+$ S-protein-PE$^+$ S-protein-APC$^+$ ovalbumin-Alexa Fluor 488$^-$) (FIGS. 2A and 9A). Consistent with the findings in elite HIV-1 neutralizers (Rouers et al., 2017), the fraction of S-protein specific cells was directly correlated to the neutralization titer of the individual ($r_s$=0.699, p=0.0145, Spearman's rank correlation) (FIG. 2B).

Immunoglobulin heavy (IGH) and light (IGL or IGK) chain genes were amplified from single memory B cells by PCR (Robbiani et al., 2017; Scheid et al., 2009b; von Boehmer et al., 2016). Overall, we obtained 244 paired heavy and light chain variable regions from S-protein-binding memory B cells from eight volunteers with high anti-HBs ELISA titers (FIGS. 9B and 9C; Table S2). Expanded clones composed of cells producing antibodies encoded by the same Ig variable gene segments with closely related CDR3s were found in each of the top neutralizers #146, #60 and #13 (FIG. 2C). Moreover, IGHV3-30/IGLV3-21 was present in #146 and #60; IGHV3-33/IGLV3-21 in #146 and #13; and IGHV3-23/IGLV3-21 in #146, #60 and #13. The variable diversity and joining (V(D)J) region of these antibodies was approximately 80% identical at the amino acid level (FIG. 2D). Antibodies with related Ig heavy and light chains were also identified between volunteer #55 (HBV infected but recovered) and vaccinated individuals (FIGS. 2C and 9B). We conclude that top HBV neutralizers produce clones of antigen-binding B cells that express related Ig heavy and light chains.

Example 3

Breadth of Reactivity

Figure 3:
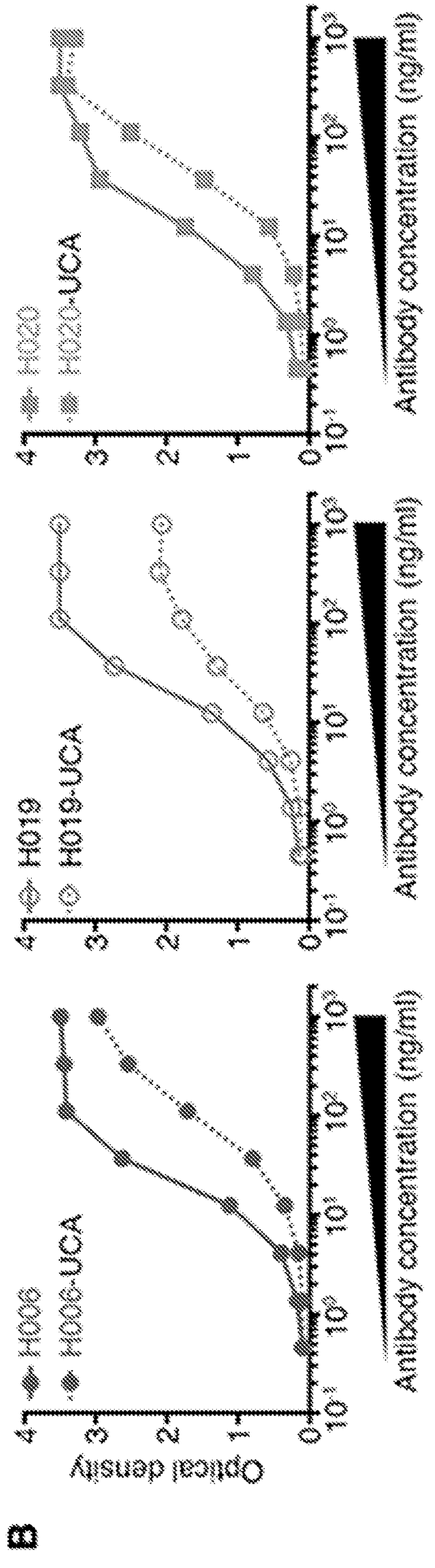
FIG. 3. Broad cross-reactivity. (A) Binding to S-protein (adr serotype). 50% effective concentration ($EC_{50}$ in ng/ml) required for binding of the indicated human monoclonal antibodies to the S-protein. Libivirumab (Eren et al., 2000; Eren et al., 1998) and anti-HIV antibody 10-1074 (Mouquet et al., 2012) were used as positive and negative controls, respectively. All antibodies were tested. (B) Comparative binding of the mature and unmutated common ancestor (UCA) of antibodies H006, H019, and H020 to S-protein by ELISA. (C) Anti-HBs antibody binding to 5 different serotypes of HBsAg. Similar to panel (A), $EC_{50}$ values are color-coded: red, ≤50 ng/ml; orange, 50 to 100 ng/ml; yellow, 100 to 200 ng/ml; and white, >200 ng/ml. The abbreviation b.d. indicates below detection. All antibodies were tested. All experiments were performed at least two times. See also FIG. 10.

Twenty representative antibodies from 5 individuals, designated as H001 to H020, were selected for expression and further testing (FIG. 9B). All 20 antibodies showed reactivity to the S-protein antigen used for B cell selection (HBsAg adr CHO) by ELISA with 50% effective concentration ($EC_{50}$) values ranging from 18-350 ng/ml (FIG. 3A). These antibodies carried somatic mutations that enhanced antigen binding as determined by reversion to the inferred unmutated common ancestor (UCA) (FIG. 3B). Thus, affinity maturation was essential for their high binding activity.

Figure 10:
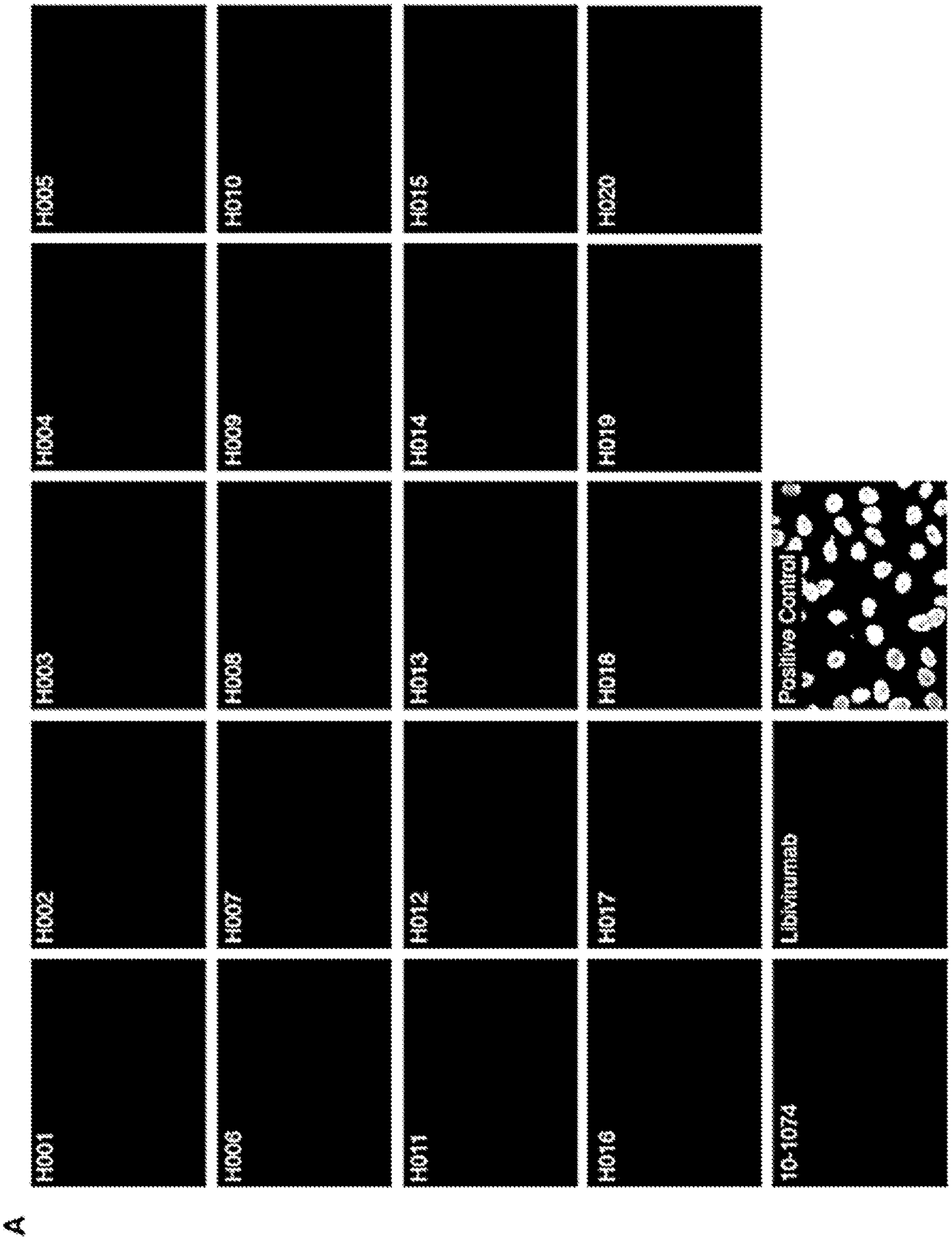
FIG. 10. Autoreactivity of 20 anti-HBs antibodies, Related to FIG. 3. (A) Autoreactivity of monoclonal antibodies. Positive control antibody efficiently stained the nucleus of HEp-2 cells. Twenty anti-HBs antibodies, as well as anti-HBs antibody libivirumab and anti-HIV antibody 10-1074, were also tested. (B) Polyreactivity profiles of 20 anti-HBs antibodies. ELISA measures antibody binding to the following antigens: double-stranded DNA (dsDNA), insulin, keyhole limpet hemocyanin (KLH), lipopolysaccharides (LPS), and single-stranded DNA (ssDNA). Red and green lines represent positive control antibody ED38 and negative control antibody mGO53 respectively, while dashed lines show cut-off values for positive reactivity (Gitlin et al., 2016).
Figure 10:
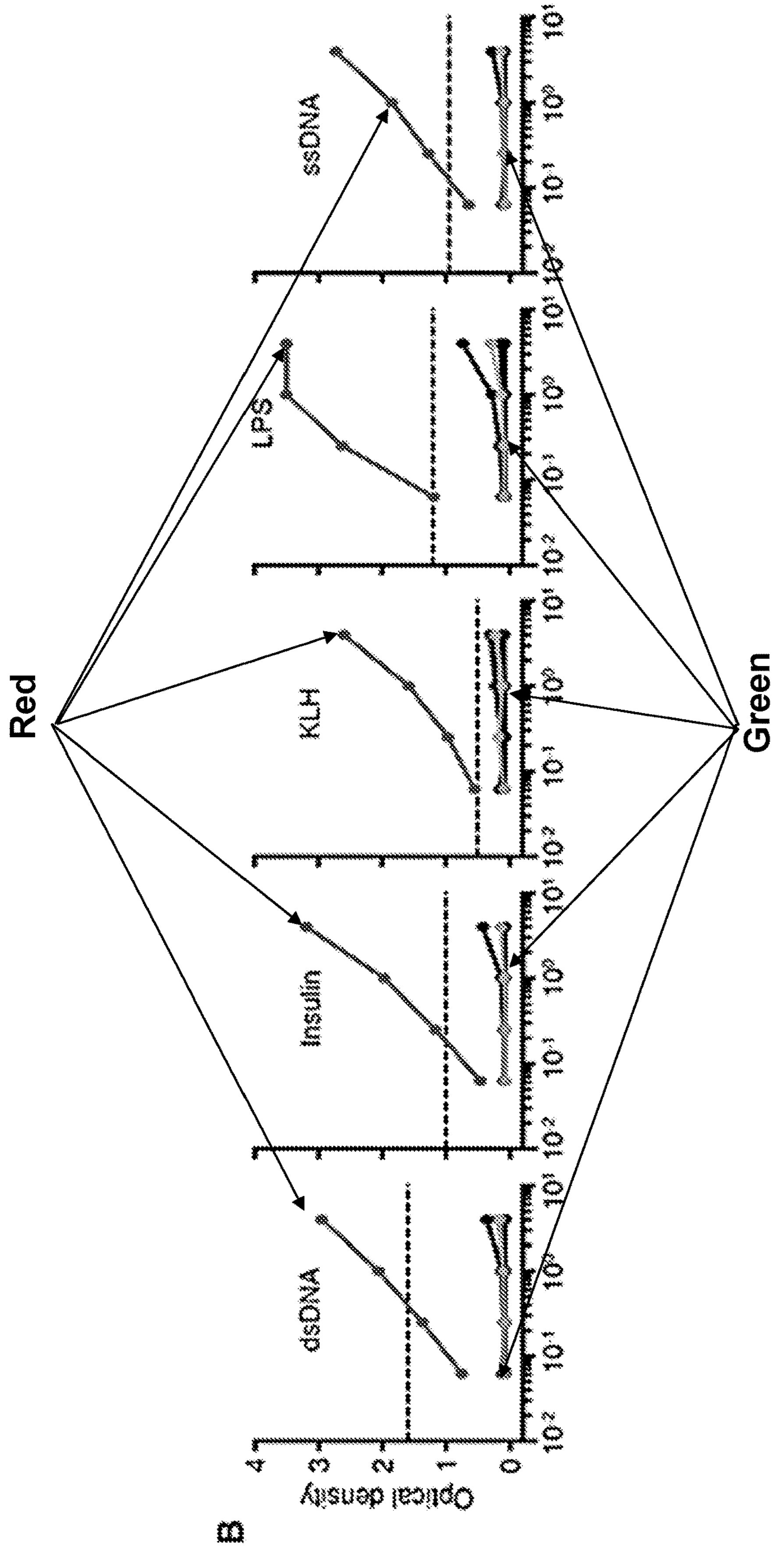

Four major serotypes of HBV exist as defined by a constant "a" determinant and two variable and mutually exclusive determinants "d/y" and "w/r" (Bancroft et al., 1972; Le Bouvier, 1971) with a highly statistically significant association between serotypes and genotypes (Kramvis et al., 2008; Norder et al., 2004). To determine whether our antibodies cross-react to different HBsAg serotypes, we performed ELISAs with 5 additional HBsAg antigens: yeast-expressed serotype "adr", "adw", and "ayw", as well as "ad" and "ay" antigen purified from human blood (FIG. 3C). Many of the antibodies tested displayed broad cross-reactivity and $EC_{50}$ values lower than libivirumab, a human anti-HBs monoclonal antibody that was isolated from HBV-immunized humanized mice and then tested clinically (Eren et al., 2000; Eren et al., 1998; Galun et al., 2002). These antibodies were not polyreactive or autoreactive when tested in polyreactivity ELISA and HEp-2 immunofluorescence assays respectively (FIGS. 10A and 10B). We conclude that the antibodies tested are broadly cross-reactive with different HBV serotypes.

Example 4

Antigenic Epitopes on S-Protein

To determine whether the selected antibodies bind to overlapping or non-overlapping epitopes, we performed competition ELISA assays, in which the S-protein was pre-incubated with a selected antibody followed by a second biotinylated antibody. Antibodies that showed weak levels of binding in ELISA (H002, H012, H013, H014, H018) were excluded. As expected, all of the antibodies tested blocked the binding of the autologous biotinylated monoclonal (yellow boxes in FIG. 4A), while control human anti-HIV antibody 10-1074 failed to block any of the anti-HBs antibodies. The competition ELISA identified three mutually exclusive groups of monoclonal antibodies, suggesting that there are at least three dominant non-overlapping antigenic sites on HBsAg (red box for Group-I, blue box for Group-II, and H017 in Group-III, FIG. 4A). Each of the individuals that had 2 or more antibodies tested in the competition ELISA expressed monoclonal antibodies that targeted 2 of the 3 non-overlapping epitopes (FIGS. 4A and 9B).

Figure 11:
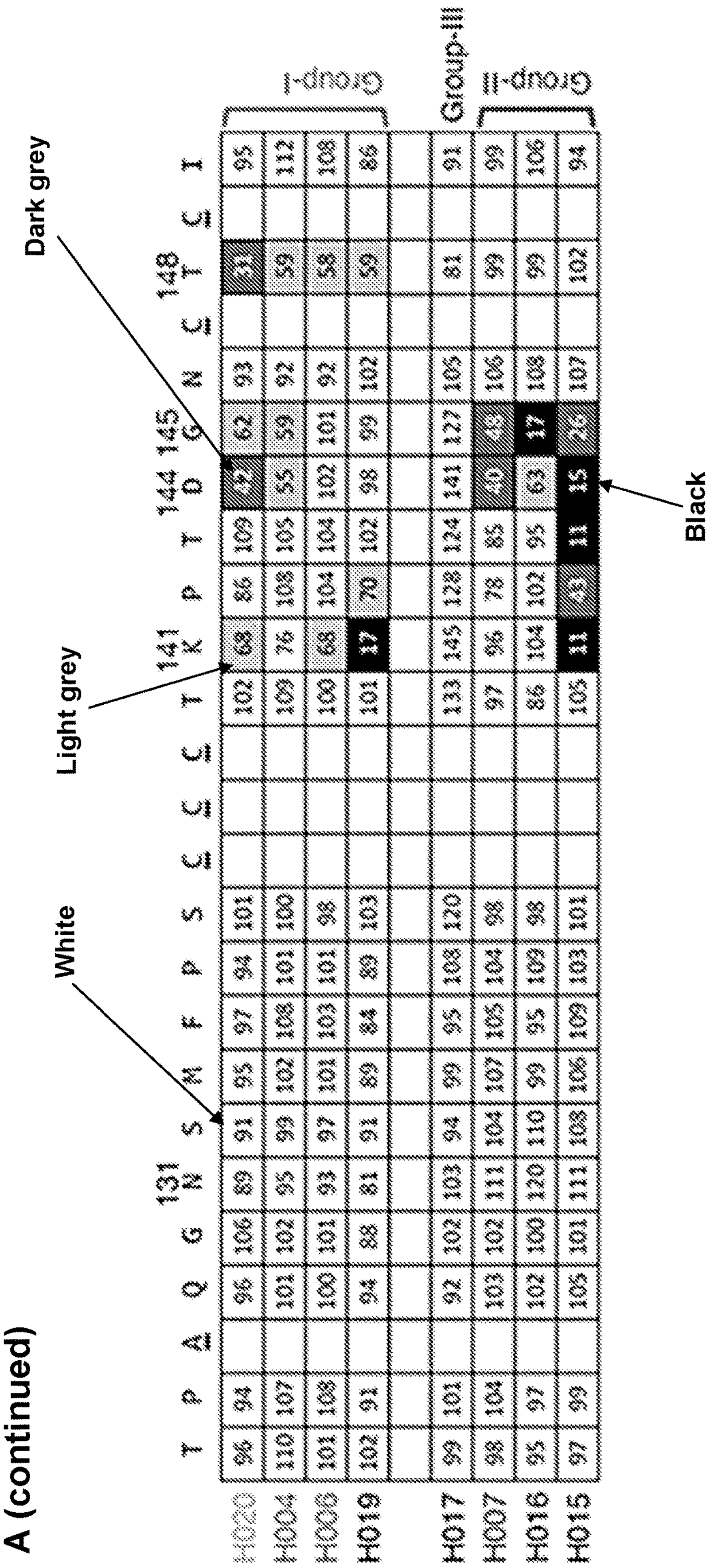
FIG. 11. Alanine Scanning and Peptide Screening, Related to FIG. 4. (A) Results of ELISA on alanine scanning mutants of HBsAg. Binding to mutants was normalized to wild-type S-protein: black, 0-25%; dark grey, 26-50%; light grey, 51-75%; white, >76%. Experiments were performed three times. Underlined cysteines, alanines, and amino acids known to be critical for S-protein production were not mutated (Salisse and Sureau, 2009). Figure discloses SEQ ID NO: 1456. (B) Schematic diagram of alanine scanning results. Figure discloses the primary amino acid sequence as SEQ ID NO: 1456 and the sequence containing alanine mutations as SEQ ID NO: 1457.
Figure 11:
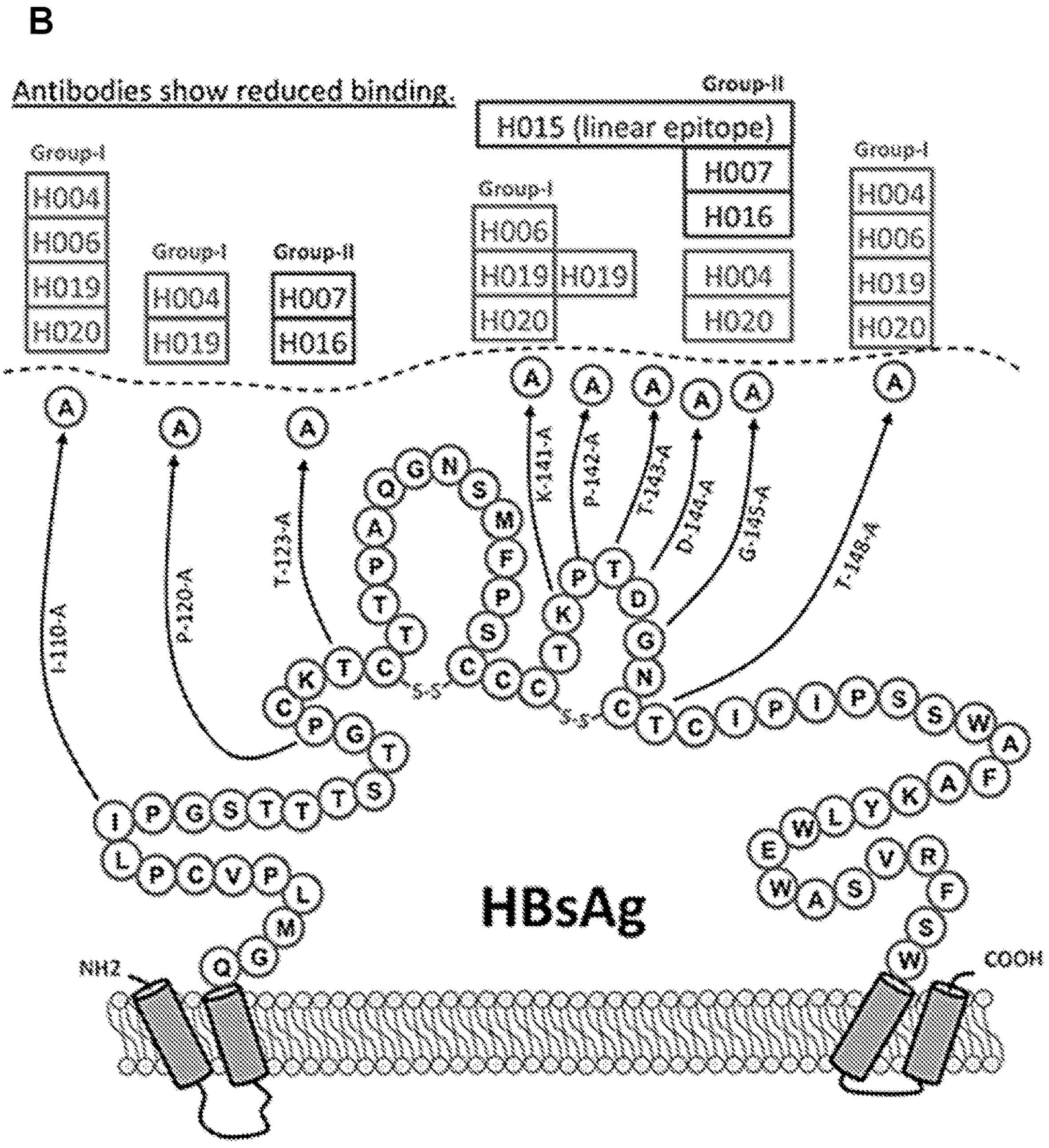

To further define these epitopes, we produced a series of alanine mutants spanning most of the predicted extracellular domain of the S-protein with the exception of cysteines, alanines, and amino acid residues critical for S-protein production (Salisse and Sureau, 2009) (FIG. 1D). ELISA assays with the representative antibodies from each antibody group and the mutant proteins revealed a series of binding patterns partially corresponding to the three groups defined in the competition assays (FIGS. 4B and 11). For example, mutations I110A and T148A interfered with binding by Group-I antibodies exemplified by H004, H006, H019, and H020, but had little measurable effect on Group-II antibodies exemplified by H007, H015, and H016 or Group-III antibody H017 (FIGS. 4B and 11).

However alanine scanning suggested that some residues such as D144 and G145 are critical for binding of monoclonals in both Group-I and Group-II despite their inability to compete with each other for binding to the native antigen (FIGS. 4B and 11). Without intending to be constrained by any particular theory, it is considered that D144A and G145A mutations alter the overall structure of HBsAg thereby interfering with binding of antibodies that normally target independent sites on the protein.

In addition to alanine scanning, we also produced 44 common naturally occurring escape variants found in chronically infected individuals (Hsu et al., 2015; Ijaz et al., 2012; Ma and Wang, 2012; Salpini et al., 2015). Whereas alanine scanning showed that some of the antibodies in Group-I and -II were resistant to G145A, the corresponding naturally occurring mutations at the same position, G145E and G145R, revealed decreased binding by most antibodies (FIG. 4C). Among the antibodies tested, H017 and H019, in Groups-I and -III respectively, showed the greatest resistance to G145 mutations and the greatest breadth and complementarity (FIG. 4C). We conclude that human anti-HBs monoclonals obtained from the selected individuals recognize distinct epitopes on HBsAg, most of which appear to be non-linear conformational epitopes spanning different regions of the protein.

Example 5

In Vitro Neutralizing Activity

Figure 5:
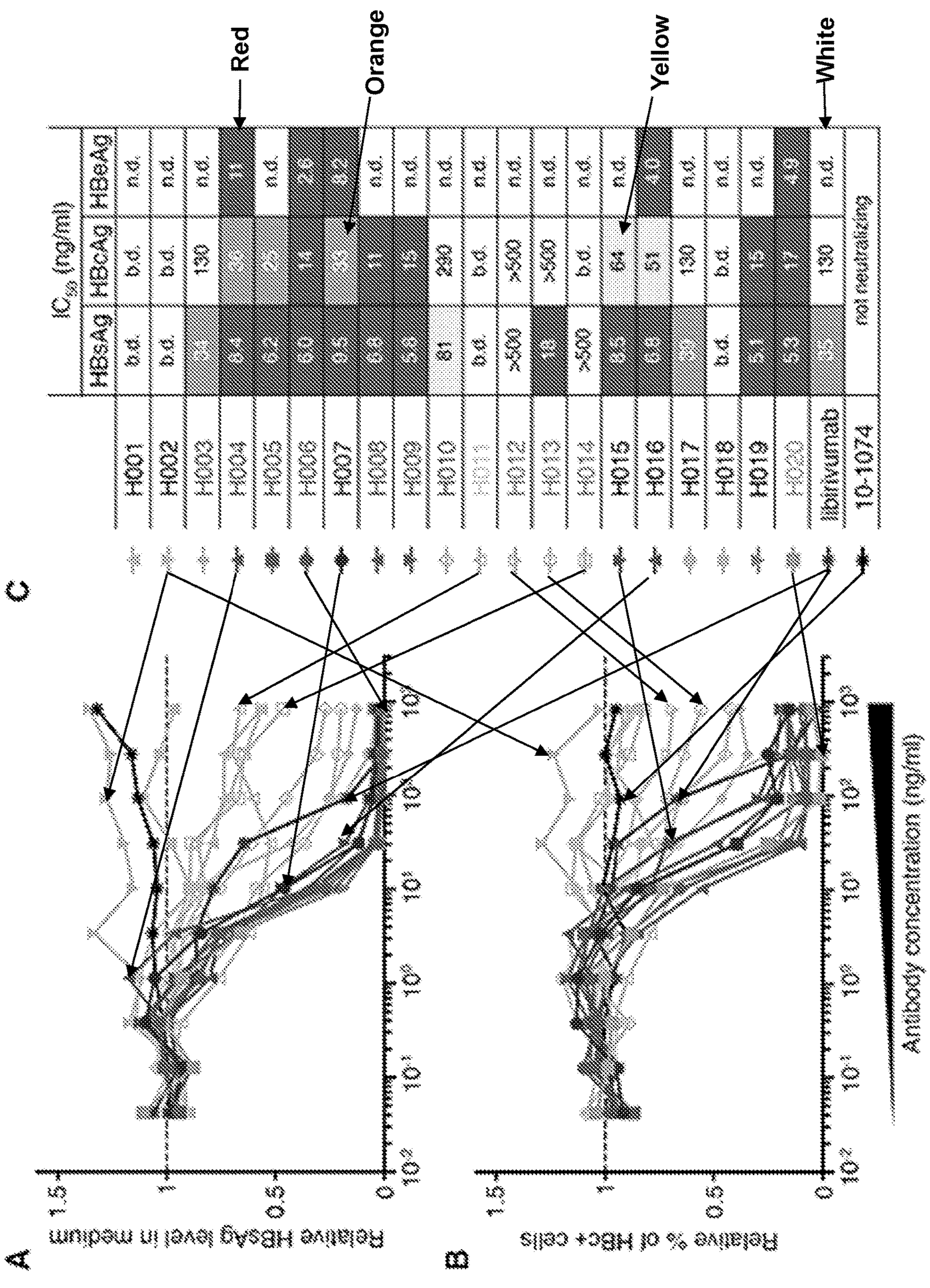
FIG. 5. In vitro neutralization by the monoclonal antibodies. (A and B) In vitro neutralization assays using HepG2-NTCP cells. Percent infection in the presence of the indicated concentrations of bNAbs measured by ELISA of HBsAg in medium (A) and anti-HBcAg immunofluorescence (B). Anti-HIV antibody 10-1074 (Mouquet et al., 2012) and libivirumab (Eren et al., 2000; Eren et al., 1998) were used as negative and positive controls respectively. The corresponding $IC_{50s}$ are shown in the left and middle column of panel (C). All experiments were repeated a minimum of two times. (C) bNAb 50% maximal inhibitory concentration ($IC_{50}$) calculated based on HBsAg ELISA (left column) and HBcAg immunofluorescence (middle column) for the in vitro neutralization assays using HepG2-NTCP cells, or HBeAg ELISA (right column) for in vitro neutralization using primary human hepatocytes. The abbreviation b.d. and n.d. indicate below detection and not done respectively. (D) In vitro neutralization using primary human hepatocytes. The levels of HBeAg in medium were measured by ELISA. The calculated $IC_{50}$ values are shown in the right column of panel (C). Experiments were repeated three times. (E) In vitro neutralization assay using HepG2-NTCP cells. IgG antibodies were compared to their corresponding Fab fragments. Concentrations of Fab fragments were adjusted to correspond to IgG. Experiment was performed two times. See also FIG. 12.
Figure 5:
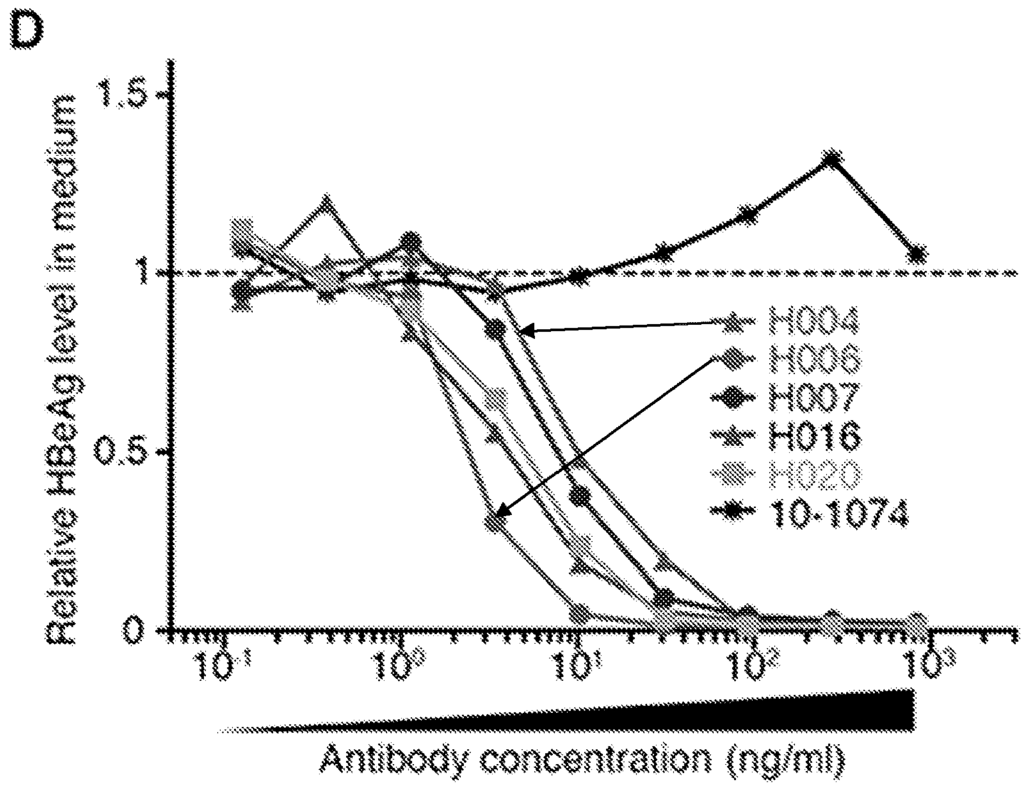
Figure 5:
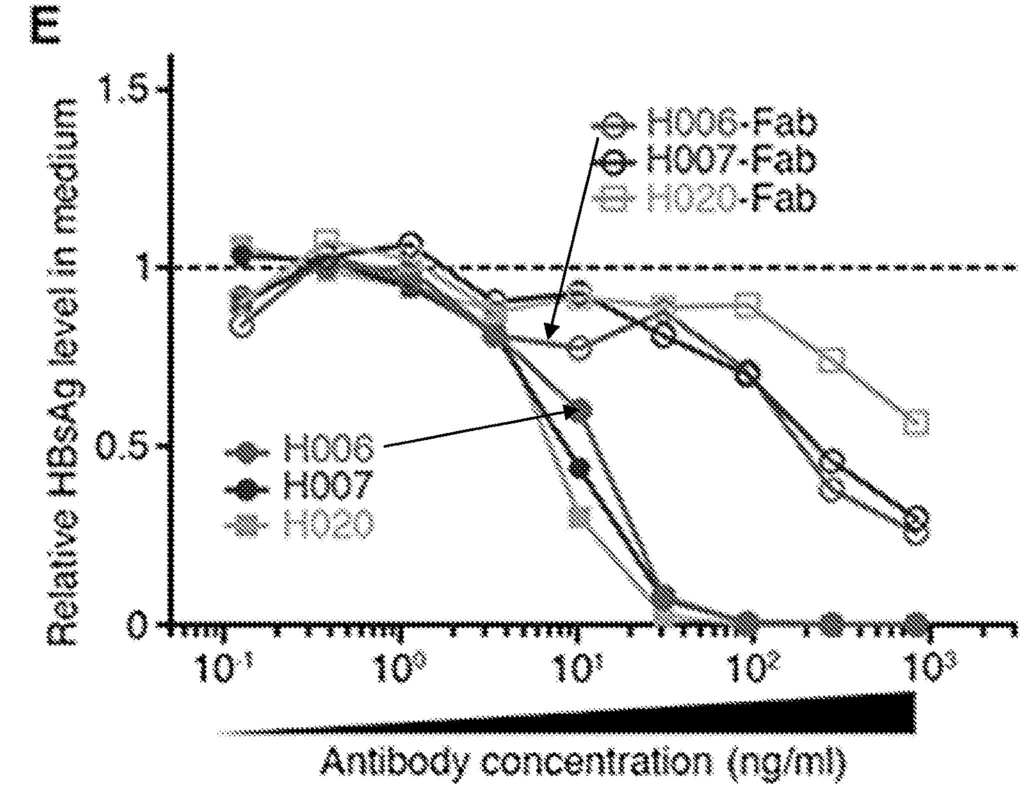
Figure 12:
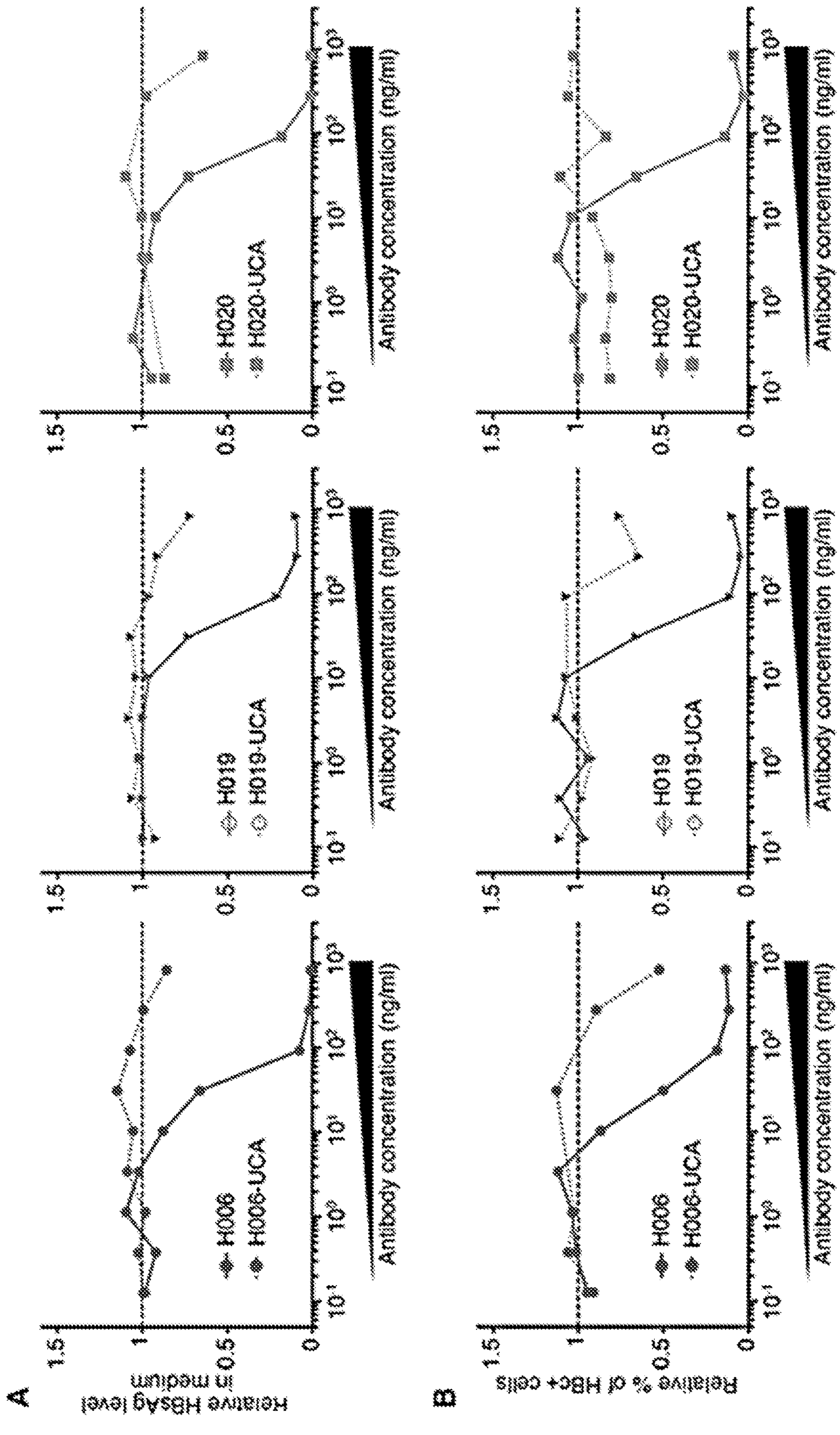
FIG. 12. In Vitro Neutralization Assay of anti-HBs bNAb Unmutated Common Ancestor Antibodies or Combinations, Related to FIG. 5. (A-B) In vitro neutralization assay of anti-HBs bNAbs and their corresponding unmutated common ancestor (UCA) antibodies. The relative infection rates were calculated based on either HBsAg protein level in culture medium (A) or HBcAg staining intracellularly (B). (C) In vitro neutralization assay of anti-HBs bNAbs recognizing different epitopes and the same total amount of antibody combination at 1:1 or 1:1:1 ratio.
Figure 12:
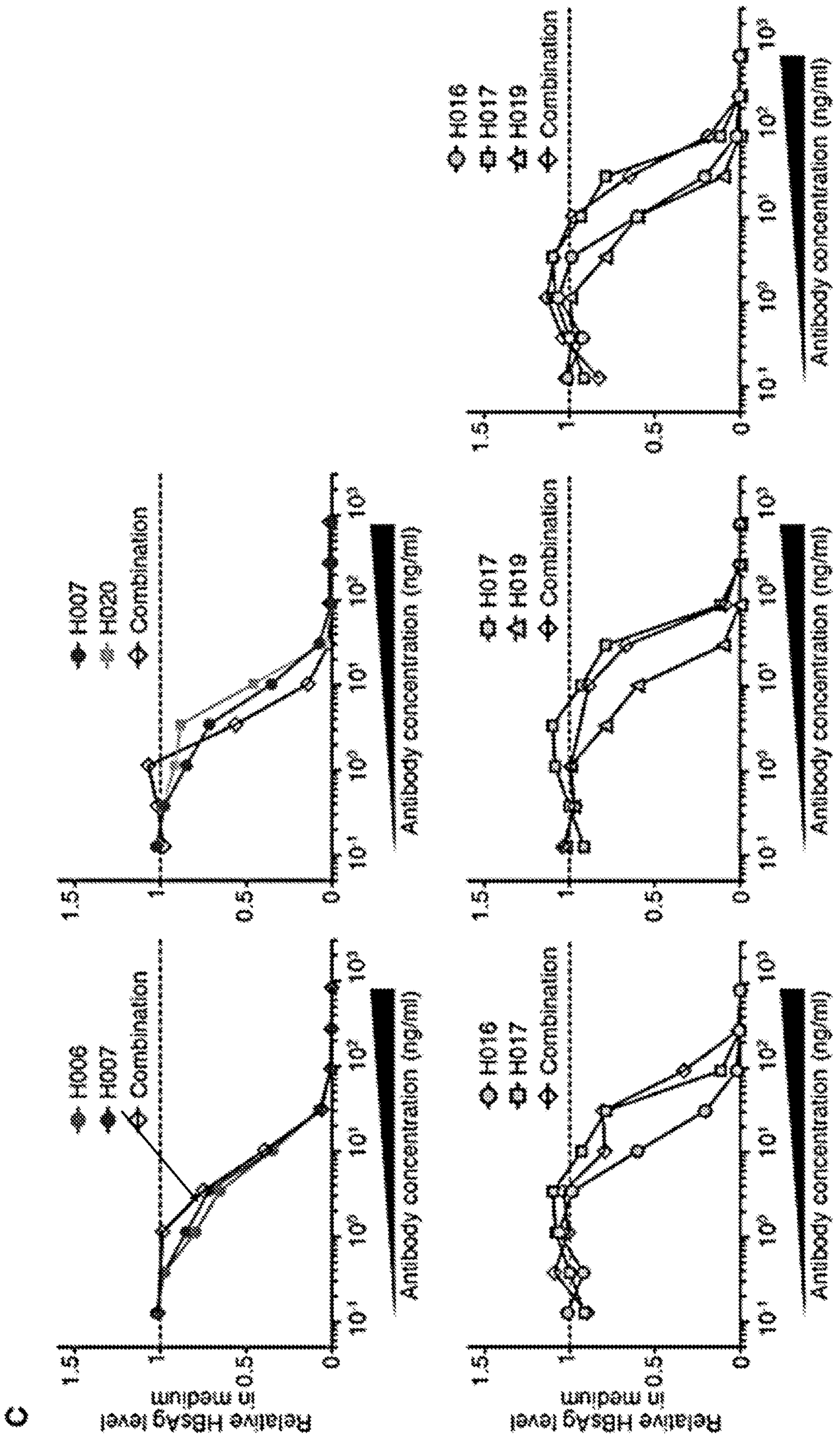

To determine whether the new monoclonals neutralize HBV in vitro, we performed neutralization assays using HepG2-NTCP cells (FIGS. 5A and 5B). The 50% inhibitory concentration ($IC_{50}$) values were calculated based on HBsAg/HBeAg ELISA or immunofluorescence staining for HBcAg expression (Michailidis et al., 2017) (FIG. 5C). Neutralizing activity was further verified by in vitro neutralization assays using primary human hepatocytes (Michailidis et al., 2020) (FIGS. 5C and 5D). Fourteen of the 20 antibodies tested showed neutralizing activity with $IC_{50}$ values as low as 5 ng/ml (FIG. 5C). By comparison, libivirumab had an $IC_{50}$ of 35 and 128 ng/ml in the neutralization assays based on ELISA and immunofluorescence assays respectively (FIG. 5C). Somatic mutations were essential for potent neutralizing activity as illustrated by the reduced activity of the inferred UCAs (FIGS. 12A and 12B). In addition, optimal activity required bivalent binding since the $IC_{50}$ values for Fab fragments were 2 orders of magnitude higher than intact antibodies (FIG. 5E). Finally, there was no overt synergy when Group-I, -II, and -III antibodies were combined (FIG. 12C). We conclude that half of the new monoclonals were significantly more potent than libivirumab including Group-I H004, H005, H006, H008, H009, H019, and H020 and Group-II H007, H015, and H016 (FIG. 5C).

Example 6

Structure of the H015 Antibody/Peptide Complex

Figure 13:
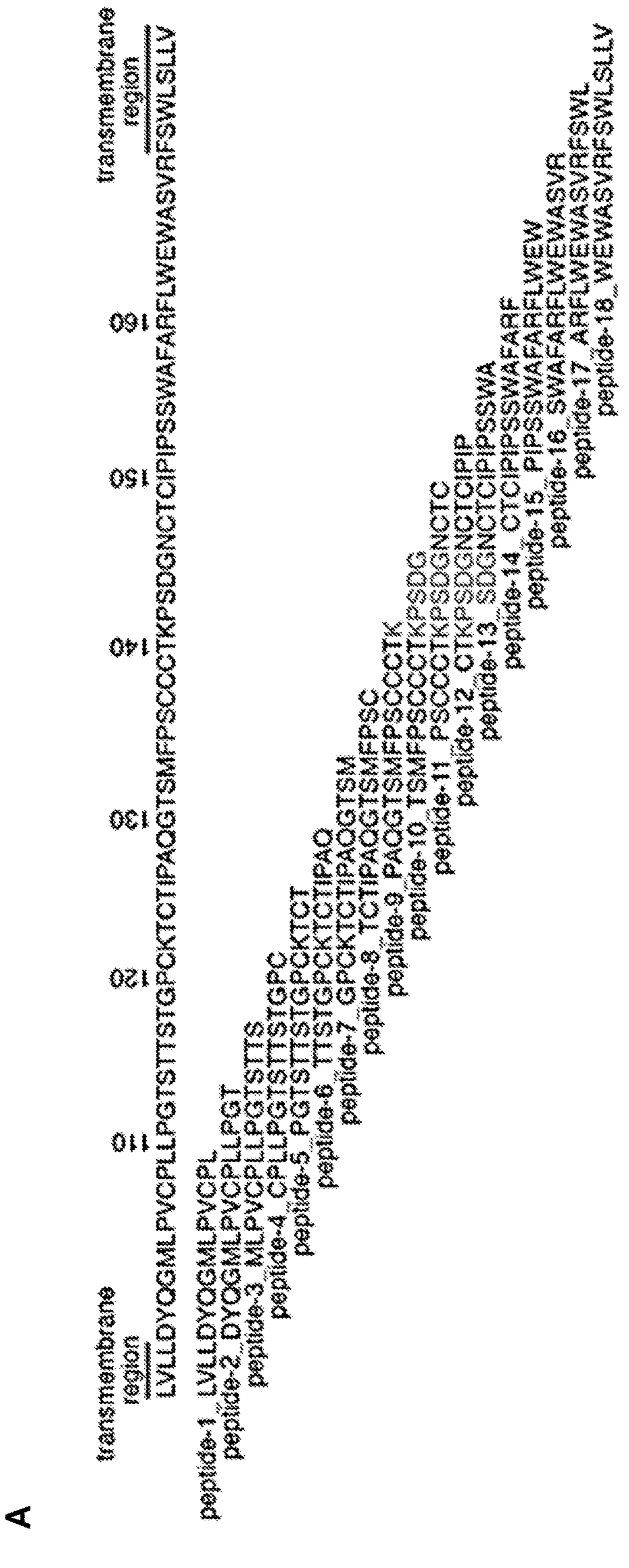
FIG. 13. Detailed Information of Crystal Structure of H015 and Its Linear Epitope, Related to FIG. 6. (A) Synthesized peptides (SEQ ID NOS 1458-1476, respectively, in order of appearance) for antigenic loop region were subjected to ELISA for antibody binding. Among the tested antibodies, only H015 binds peptide-11 and -12. (B) Data collection and refinement statistics for H015 Fab are summarized. Statistics for the highest-resolution shell are shown in parentheses. Refinement program PHENIX 1.16. (C) The green/red density is the unbiased omit map. Red is negative density equated to noise. (D) Table of contacts within the peptide and between Fab fragment and peptide.
Figure 13:
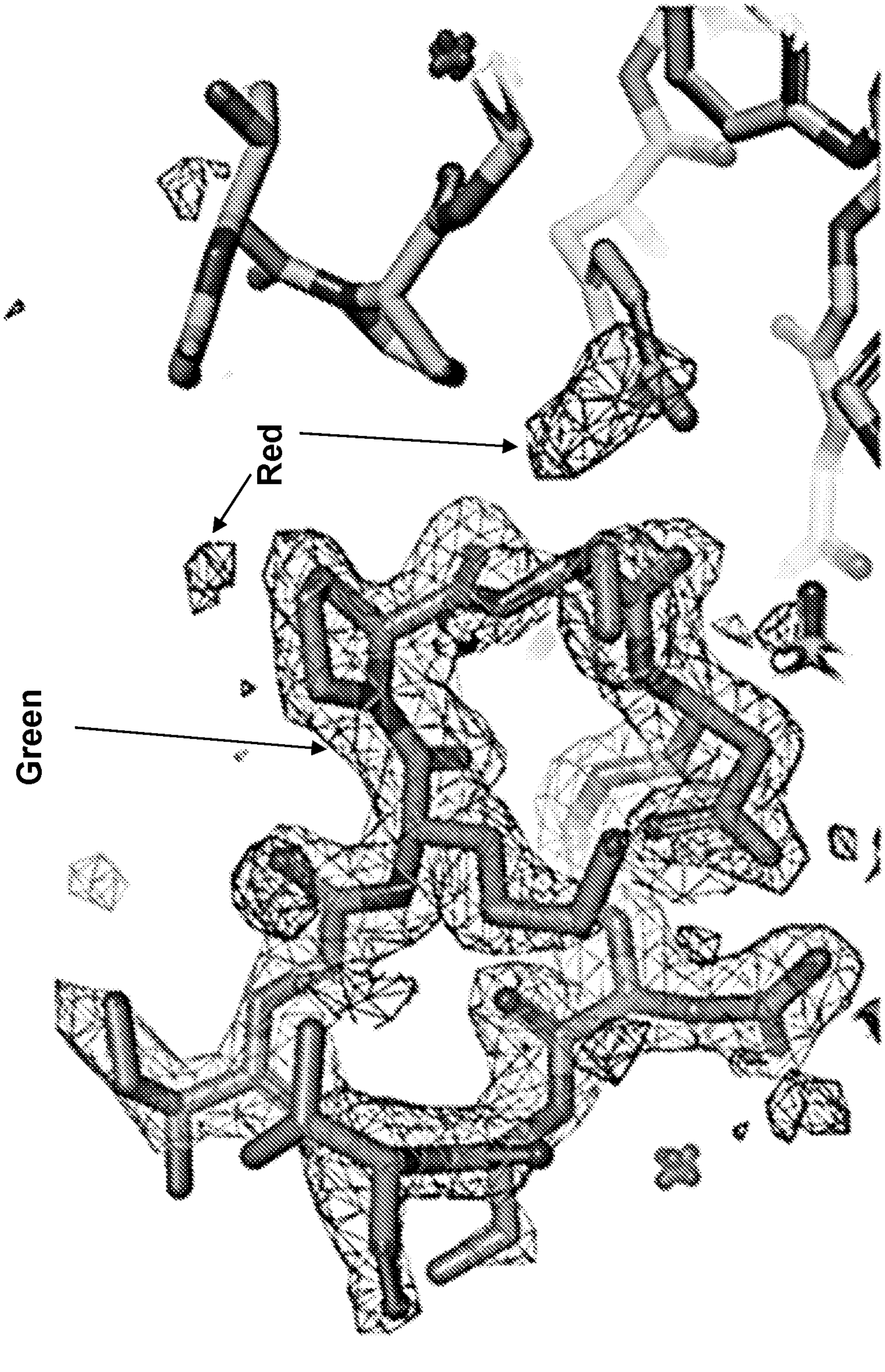

H015 differed from other antibodies in that its binding was inhibited by 5 consecutive alanine mutations spanning positions K141-G145 indicating the existence of a linear epitope. This idea was verified by ELISA against a series of overlapping peptides comprising the predicted extracellular domain of S-protein (FIGS. 6A and 13A). The data showed that H015 binds to KPSDGN (SEQ ID NO: 23), which is near the center of the putative extracellular domain and contains some of the most frequently mutated amino acids during natural infection.

To examine the molecular basis for H015 binding, its Fab fragment was co-crystallized with the target peptide epitope PSSSSTKPSDGNSTS (SEQ ID NO: 24), where all cysteine residues that flank the recognition sequence were substituted with serine to avoid non-physiological cross-linking. The 1.78 Å structure (FIGS. 6B and 13B) revealed that the peptide is primarily bound to the immunoglobulin heavy chain (FIGS. 6B and 6C), interacting with residues from CDR1 (R31), CDR2 (W52, F53) and CDR3 (E99, P101, L103, L104) of IgH with only one contact with CDR3 (P95) of IgL. The peptide adopts a three-residue beta hairpin (class 3) of the 3:5 type involving residues K141 through G145 as only one hydrogen bond is seen, between K141 and G145 (Milner-White and Poet, 1986), and they are not part of a beta sheet. The peptide is further stabilized by a salt-bridge formed between K141 and D144 (FIGS. 6D and 13C). Interestingly, the distance between the Cαs of the two residues (C139 and C147) flanking the recognition residues is 6.4 Å and are poised to form a disulfide bond between C139 and C147 found in the native HBsAg structure (Ito et al., 2010). The H015 Fab appears to stabilize the conformation of the peptide via the Fab-peptide contacts (FIG. 13D) including a large binding surface (866 $Å^2$; antibody-antigen buried surface of 600-900 $Å^2$ (Braden and Poljak, 1995)) comprised primarily of a single salt-bridge (lysine to aspartate; 0.9±0.3 Kcal/mol) (White et al., 2013) and five hydrogen bonds (1-2 Kcal/mol/bond) (Sheu et al., 2003). Moreover, the peptide further restricts loop through intra-peptide contacts (FIG. 13D) even in the absence of the disulfides.

The residues that form the hairpin are important for anti-HBs antibody recognition as determined by alanine scanning (FIGS. 4B and 11). In addition, each of these residues has been identified as important for immune recognition during natural infection (Ma and Wang, 2012). G145R, the most common naturally occurring S-protein escape mutation substitutes a large positively charged residue for a small neutral residue (circled residue in FIG. 6E) potentially altering the antigenic binding surface. G145 adopts a positive phi angle of 77.9 and by doing so introduces a kink in the beta-strand, a structure that would be disrupted with the substitution to arginine.

HBsAg can be glycosylated at N146 and this site is also strictly conserved. However, some studies have suggested that this glycosylation site is never fully occupied, resulting in a nearly 1:1 ratio of glycosylated and non-glycosylated isoforms on the surface of viral envelope (Julithe et al., 2014). The glycosylation may be either NAG-NAG-MAN or NAG-(FUC)-NAG-MAN (Hyakumura et al., 2015). We have modeled both fucosylated and non-fucosylated options by grafting a 7mer and 11mer glycan conjugated at N146 of peptide in the presence of the Fab. We found that both glycosylation forms are tolerated at that location with only minimal torsional adaptations without clashes with the Fab, though the fucosylated (branched) glycan required some additional torsional angle changes to the Fab, as well.

Example 7

Protection and Therapy in Humanized Mice

Figure 7:
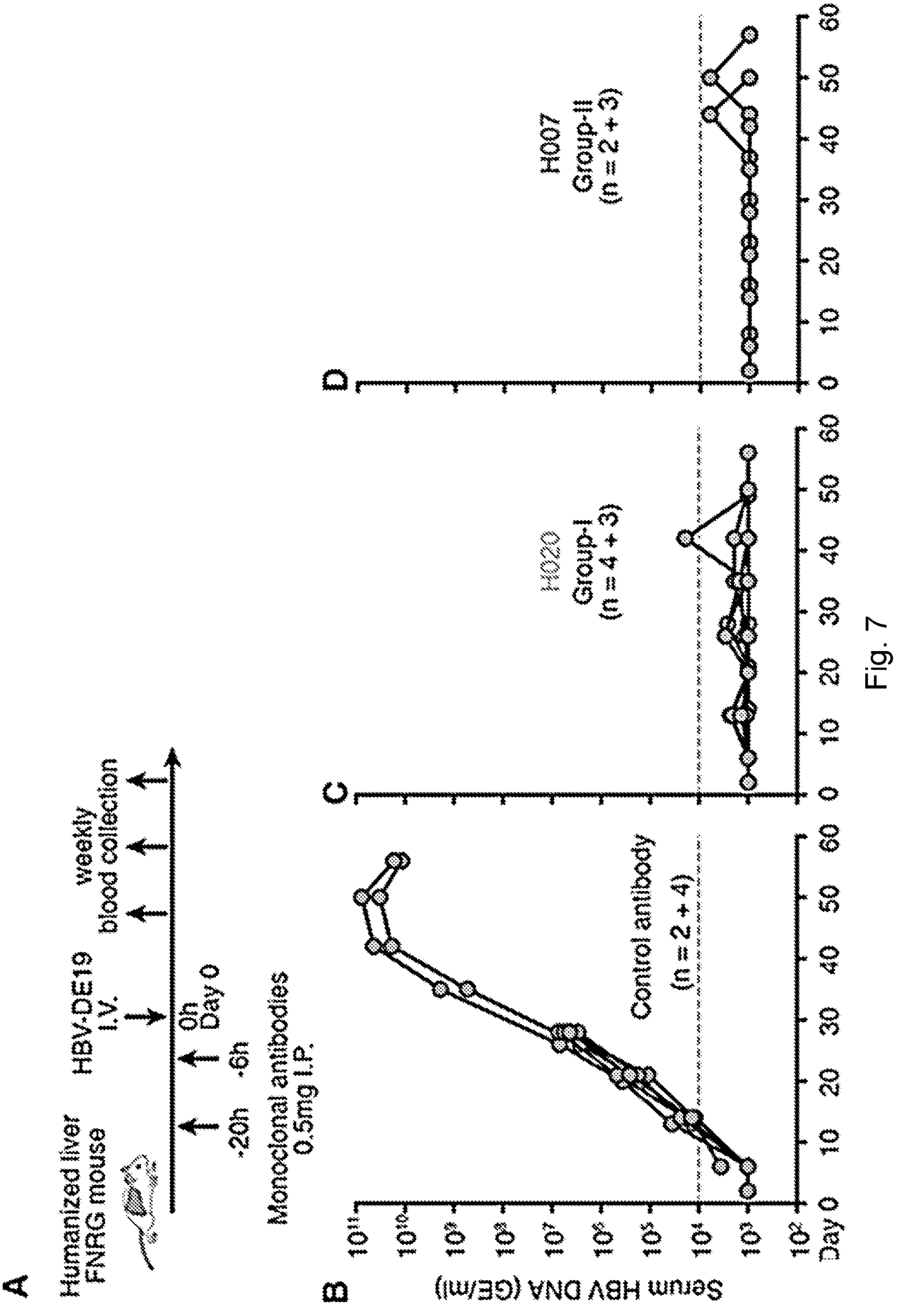
FIG. 7. Anti-HBs bNAbs are protective and therapeutic in vivo. (A and E) Diagram of the prophylaxis and treatment protocols, respectively. (B) Prophylaxis with isotype control antibody 10-1074 (Mouquet et al., 2012). (C and D) Prophylaxis with H020 and H007 respectively. The dashed line in (B-D) indicates the detection limit. (F) Treatment of viremic huFNRG mice with control antibody 10-1074. (G and H) Treatment of viremic huFNRG mice with H020 alone or H007 alone, respectively. HBV DNA levels in serum were monitored on a weekly basis. Two independent experiments comprising a total of 5 to 8 mice were combined and displayed. (I) Mutations in the S-protein sequence from the indicated mice (red arrows) in (G), (H) and (J). S-protein sequence chromotograms are shown in FIG. 14. (J-L) Treatment of viremic huFNRG mice with combination of anti-HBs bNAb H006+H007 (J), or H017+H019 (K), or H016+H017+H019 (L), respectively. Sequencing showed that none of the mice in (K) and (J) carried viruses with escape mutations in the S-protein. See also FIG. 14.
Figure 7:
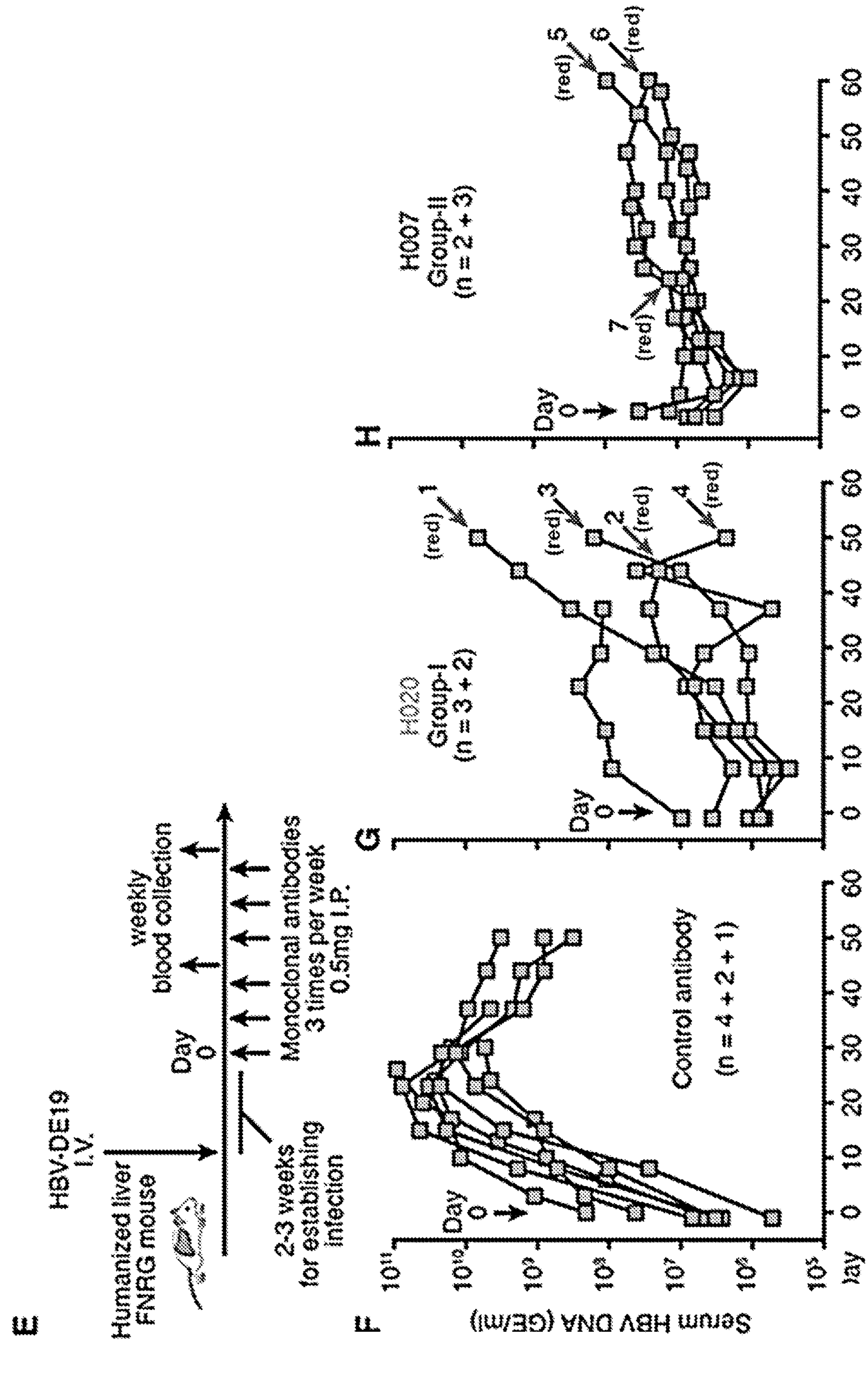
Figure 7:
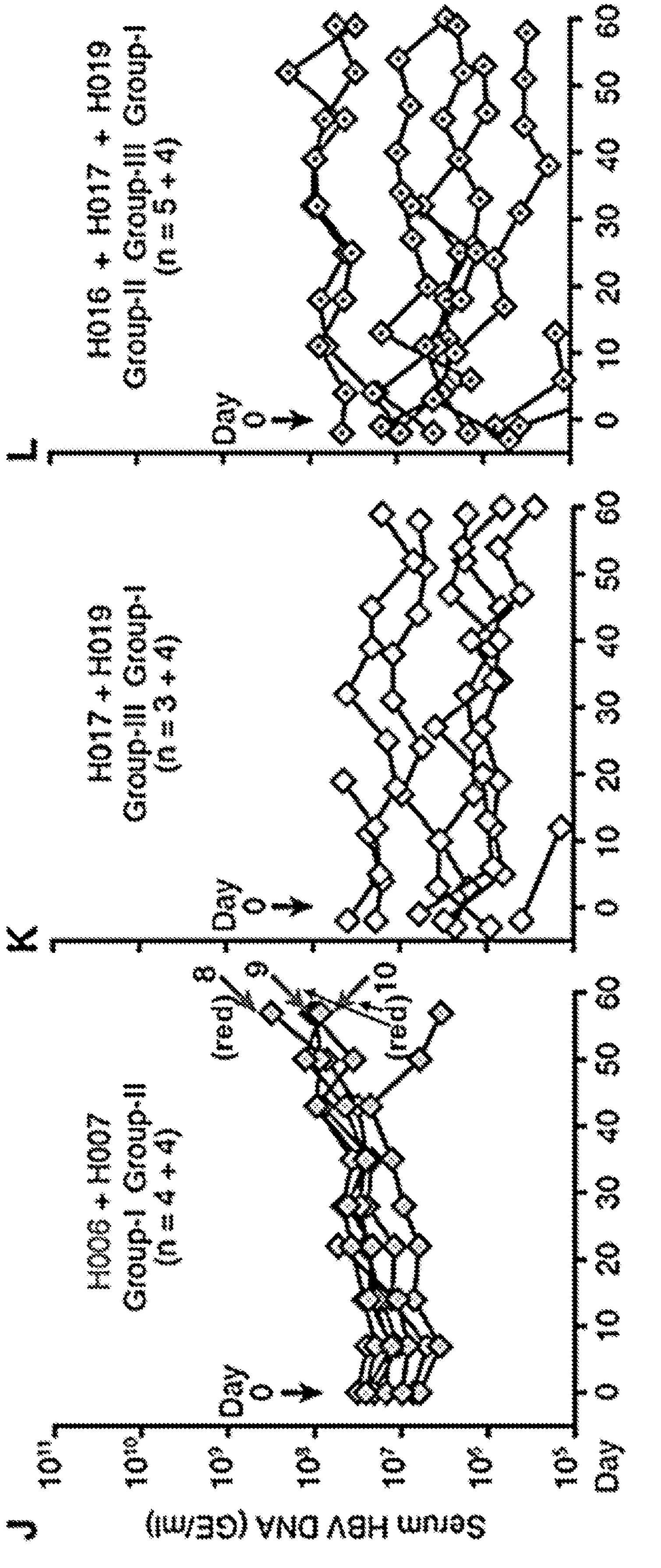

HBV infection is limited to humans, chimpanzees, tree shrews, and human liver chimeric mice (Sun and Li, 2017). To determine whether our anti-HBs bNAbs prevent infection in vivo we produced human liver chimeric $Fah^{-/-}$ $NODRag1^{-/-}$ $IL2rg^{null}$ (huFNRG) mice (de Jong et al., 2014) and injected them with control or H020 (Group-I) or H007 (Group-II) antibodies before infection with HBV (FIG. 7A-7D). These two antibodies were chosen because they bind to non-overlapping sites, and have broad and potent neutralizing activity. Whereas all six control animals in two independent experiments were infected, pre-exposure prophylaxis with either H007 or H020 was fully protective (FIG. 7B-7D). We conclude that single anti-HBs bNAbs targeting different epitopes on the major virus surface antigen can prevent infection in vivo.

To determine whether bNAbs can also control established infections, we infused control antibody or bNAb H020 (Group-I) or H007 (Group-II) into huFNRG mice with HBV viral loads of $10^6$-$10^8$ copies/ml of serum (FIG. 7E-7H and FIG. 14A). $Fah^{-/-}$ $NODRag1^{-/-}$ $IL2rg^{null}$ mice are highly immunodeficient and unable to mount adaptive immune responses due to absence of T and B lymphocytes. In addition, the $IL2rg^{null}$ mutation prevents cytokine signaling through multiple receptors, leading to a deficiency in innate immune function including antibody-dependent cellular cytotoxicity. Thus, elimination of viremia of $10^6$-$10^8$ DNA copies/ml in huFNRG mice by antibody therapy alone would not be expected.

Animals that received the control antibodies further increased viremia to as high as ~$10^{11}$ DNA copies/ml (FIG. 7F). In contrast, the 5 mice that received H020 maintained stable levels of viremia for around 30 days (FIG. 7G), after which time 2 mice showed increased viremia (arrow-1/3 in FIG. 7G). A similar result was observed in the 5 mice that received H007 (FIG. 7H), where only one showed a slight increase viremia at around day 50 (arrow-5 in FIG. 7H).

Figure 14:
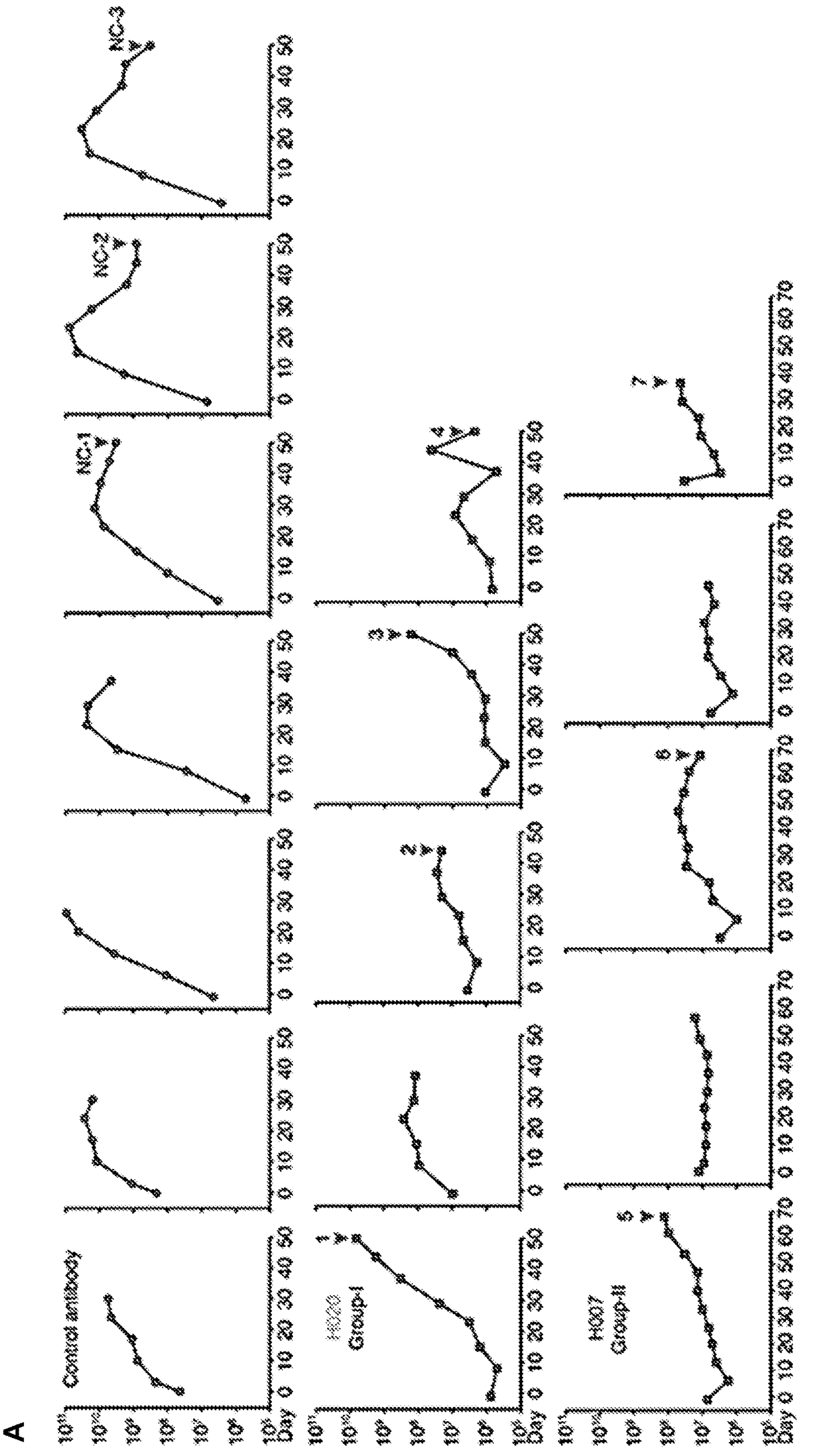
FIG. 14. HBV DNA levels and S-protein Sequences in Antibody-Treated huFNRG Mice, Related to FIG. 7. (A) HBV DNA levels in representative individual huFNRG mice treated by control antibody 10-1074, anti-HBs bNAb H020, anti-HBs bNAb H007, combination of anti-HBs bNAb (H006+H007), (H017+H019), and (H016+H017+H019). HBV DNA levels in mouse sera were monitored on a weekly basis. The mice without arrows bear no escape mutations at the last time point. (B) Part of the S-protein sequences from the indicated mice (arrows and numbers) are shown below as chromatograms, with mutations marked by arrowheads. (B) discloses the S-protein amino acid and nucleotide sequences as SEQ ID NOS 1477 and 1478, respectively. The sequences represented by the subsequent chromatograms that disclose amino acid residues and nucleotides are SEQ ID NOS 1479, 1480, 1480, 1480-1482, 1479, 1478, 1480, 1480, 1478, 1480, and 1483-1488, respectively, in order of columns. (C-D) HBsAg levels in mouse sera before and after antibody infusion. Mice were treated by anti-HBs combination H017+H019 (C) (see FIG. 7K) and H016+H017+H019 (D) (see FIG. 7L). Each line represents a mouse with concentrations of serum HBsAg level expressed in NCU/ml (national clinical units per milliliter).
Figure 14:
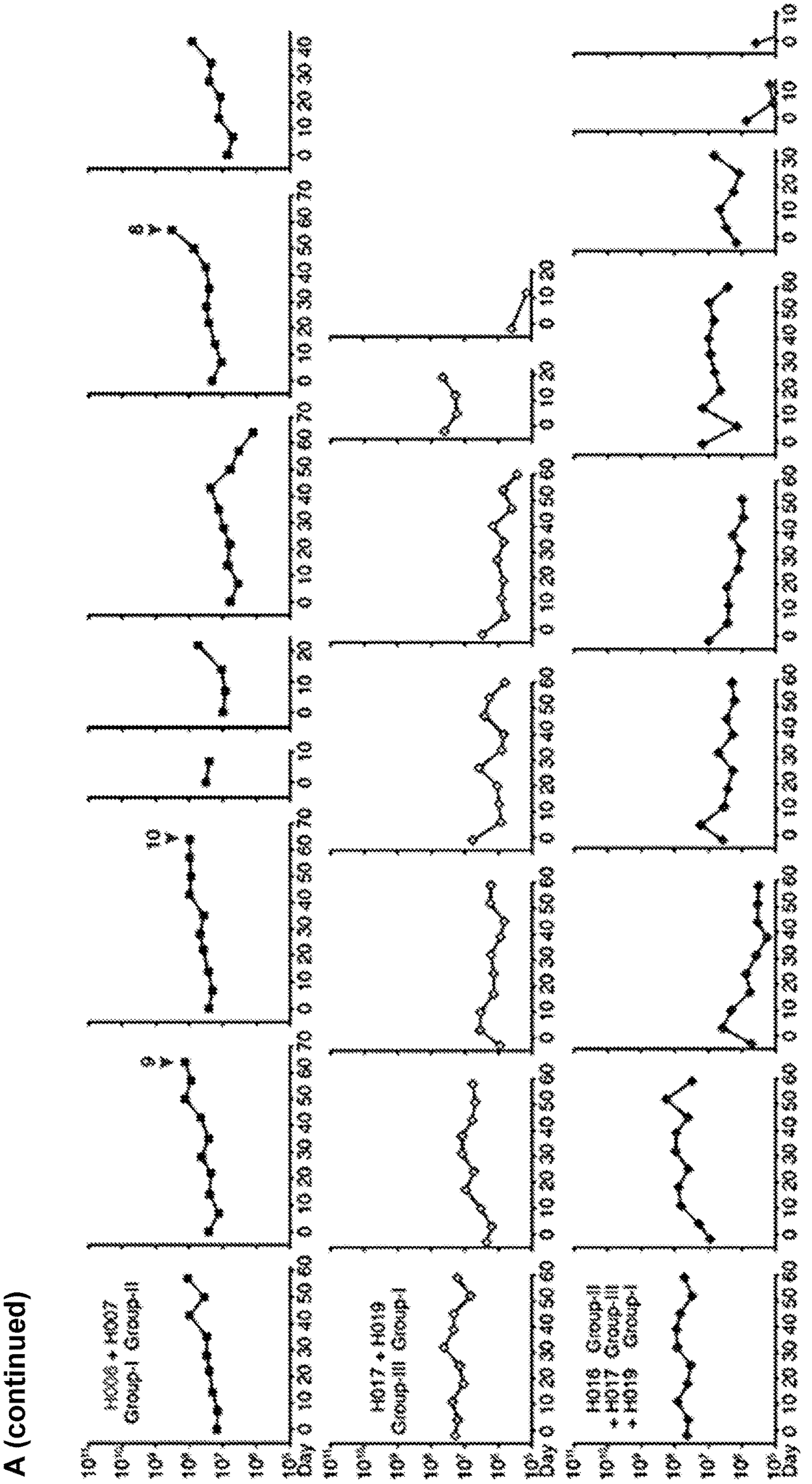
Figure 14:
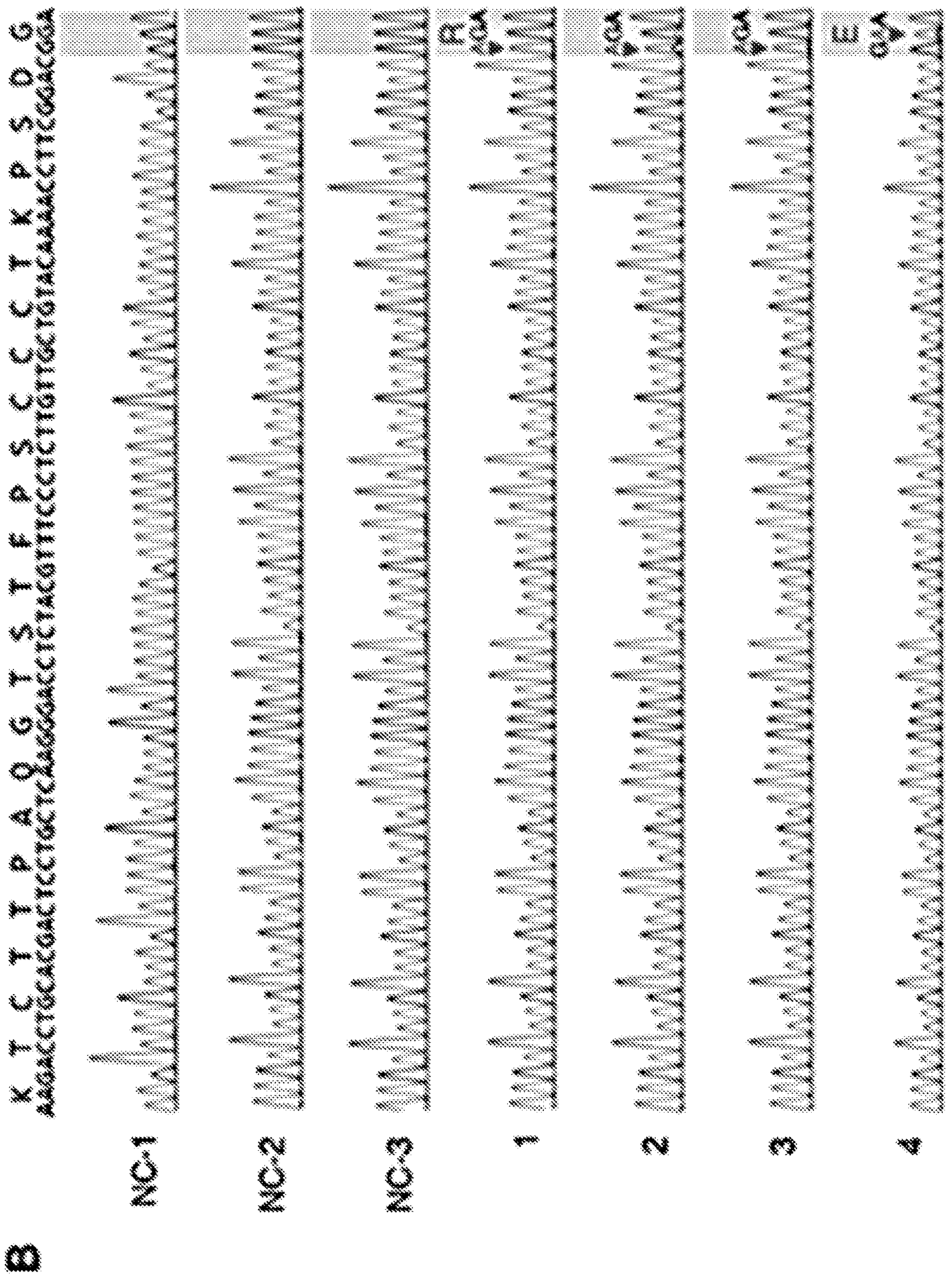
Figure 14:
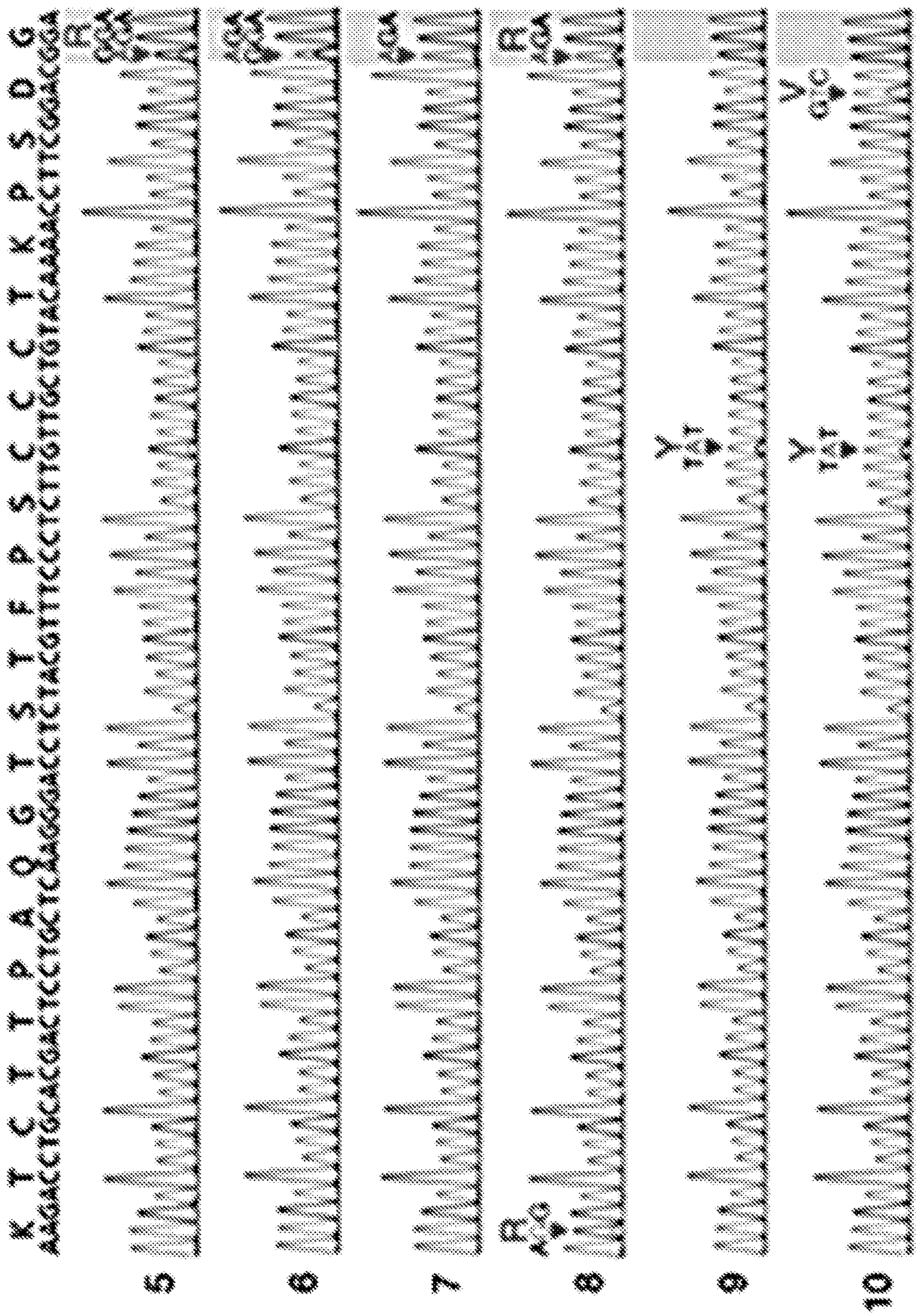
Figure 14:
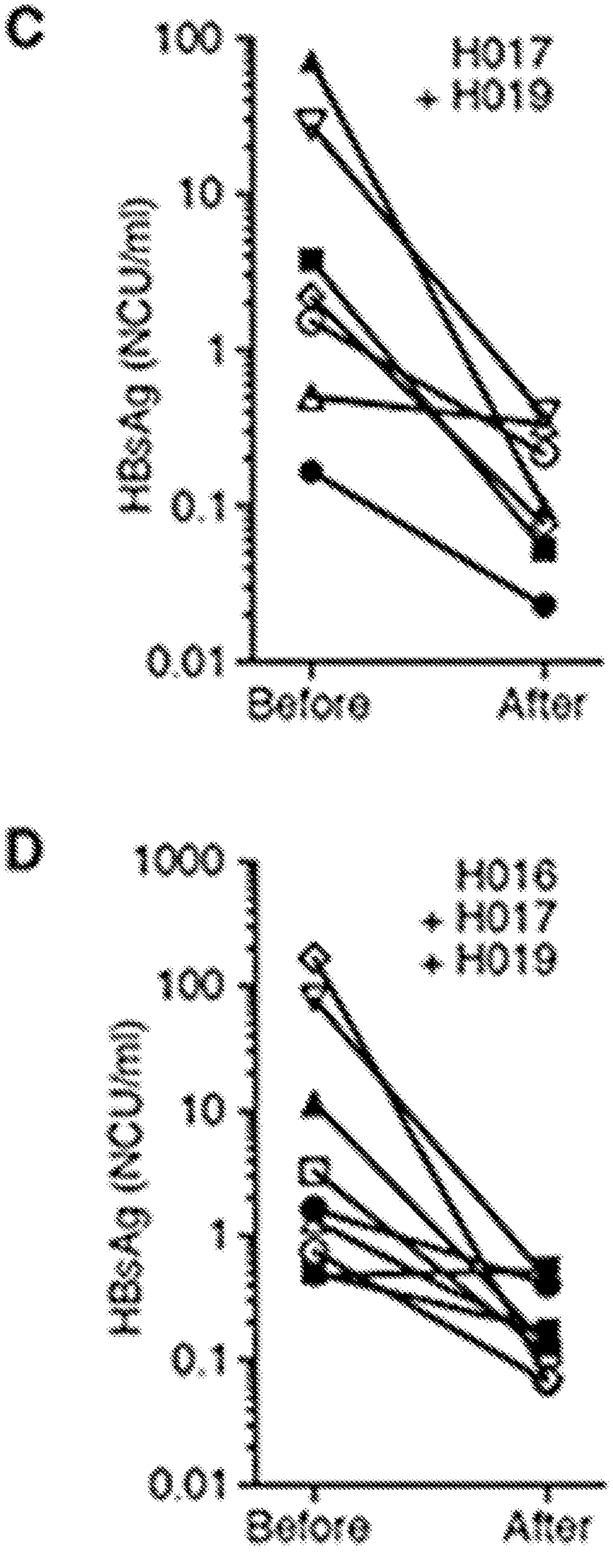

To determine whether the animals that showed increased HBV DNA levels during antibody monotherapy developed escape mutations, we sequenced the viral DNA recovered from mouse blood. All three mice that escaped H020 (Group-I) or H007 (Group-II) monotherapy developed viruses that carried a G145R mutation in the S-protein (arrow-1/3 in FIG. 7G, arrow-5 in FIG. 7H, FIG. 7I, and FIG. 14). This mutation represents a major immune escape mutation in humans (Zanetti et al., 1988). Furthermore, mutations at the same position in the S-protein were also identified in mice that maintained low level viremia (arrow-2/4 in FIG. 7G, arrow-6/7 in FIG. 7H, FIG. 7I, and FIG. 14), but not in control animals (FIG. 14). These results show that anti-HBs bNAb monotherapy leads to the emergence of escape mutations that are consistent with bNAb binding properties in vitro (FIG. 4C).

To determine whether a combination of bNAbs targeting 2 separate epitopes would interfere with the emergence of resistant strains, we co-administered H006+H007 (Group-I and -II, respectively) to 8 HBV-infected huFNRG mice (FIG. 7J). H006 (Group-I) was chosen for this purpose because of its resistance to D144A and G145A mutation (FIG. 4B). Similar to H007 monotherapy, there was only a slight increase in viremia in animals treated with the H006+H007 anti-HBs bNAb combination during the 60-day observation period (FIGS. 7J and 14A). However, sequence analysis revealed that 3 of the mice developed resistance mutations including K122R/G145R, C137Y, and C137Y/D144V (arrow-8/9/10 in FIG. 7J, FIG. 7I, and FIG. 14). These mutations confer loss of binding to both H006 (Group-I) and H007 (Group-II) (FIG. 4C). Thus, the combination of 2 anti-HBs bNAbs targeting separate epitopes but susceptible to the same clinical escape variants is not sufficient to inhibit emergence of escape mutations.

To attempt to block the emergence of escape mutations, we combined H017+H019 (Group-III and -I, respectively) bNAbs because they displayed complementary sensitivity to commonly occurring natural mutations (FIG. 4C). None of 7 mice treated with the combination of showed increased viremia or escape mutations as assessed by sequence analysis (FIGS. 7K and 14A). Similar effects were also observed in the 9 animals treated with the H016, H017 and H019 (Group-II, -III, -I, respectively) triple antibody combination (FIGS. 7L and 14A). Moreover, both these combinations dramatically reduced the HBsAg levels in serum (FIGS. 14C and 14D). Altogether, these findings suggest that control of HBV infection by bNAbs requires a combination of antibodies targeting non-overlapping groups of common escape mutations.

RESOURCES TABLE

| REAGENT or RESOURCE | SOURCE | IDENTIFIER |
|---|---|---|
| Experimental Models: Cell Lines | | |
| Human Hepatocytes, Cryopreserved, Plateable and Interaction Qualified | Lonza Bioscience | Cat#HUCPI |
| Hepatocyte Defined Medium | Corning | Cat#05449 |
| HepG2-NTCP | (Michailidis et al., 2017) | N/A |
| HEK293-6E | National Research Council of Canada | NRCfile 11565 |
| HepDE19 cells | (Cai et al., 2012) | N/A |
| Huh-7.5 | (Robbiani et al., 2017) | N/A |
| Experimental Models: Mouse Strains | | |
| $Fah^{-/-}NODRag1^{-/-}IL2rg^{-/-}$ mouse (huFNRG) | (de Jong et al., 2014) | N/A |

-continued

RESOURCES TABLE

| REAGENT or RESOURCE | SOURCE | IDENTIFIER |
|---|---|---|
| Bacteria and Viruses | | |
| Subcloning Efficiency ™ DH5α ™ Competent Cells | Thermo Fisher Scientific | Cat#18265017 |
| HBV viruses | (Cai et al., 2012) | N |
| Antibodies | | |
| Human recombinant 10-1074 | (Mouquet et al., 2012) | N/A |
| Human recombinant ED38 | (Wardemann et al., 2003) | N/A |
| Human recombinant mG053 | (Yurasov et al., 2005) | N/A |
| Goat anti-Human IgG (H + L) Secondary Antibody, HRP | Thermo Fisher Scientific | Cat#31410 |
| Alexa Fluor 488 Mouse anti-Human CD19 | BD Biosciences | Cat#557697 |
| BV421 Mouse Anti-Human CD 19 | BD Biosciences | Cat#562440 |
| anti-CD20-PECy7 | BD Biosciences | Cat#335811 |
| Anti-CD27-PE | BD Biosciences | Cat#555441 |
| APC Mouse Anti-Human IgG | BD Pharmingen | Cat#550931 |
| Bv421 Mouse Anti-Human IgG | BD Biosciences | Cat#562581 |
| Anti-Hepatitis B virus core antigen IgG | AUSTRAL Biologicals | Cat#HBP-023-9 |
| Alexa Fluor ® 488 AffiniPure Goat Anti-Human IgG, F(ab')2 fragment specific | Jackson ImmunoResearch | Cat#109-545-006 |
| Goat anti-Rabbit IgG (H + L) Alexa Fluor 594 | Thermo Fisher Scientific | Cat#A11037 |
| Chemicals and Proteins | | |
| Streptavidin HRP | BD Biosciences | Cat#554066 |
| APC Streptavidin | BD Biosciences | Cat#554067 |
| Strep-PE | eBioscience | Cat# 12-4317-87 |
| Streptavidin, Alexa Fluor ™ 488 | Thermo Fisher Scientific | Cat#S32354 |
| Human BD Fc Block ™ | BD Biosciences | Cat#564220 |
| Ovalbumin (257-264) chicken | Sigma-Aldrich | Cat#S7951 |
| HBsAg adr CHO | ProSpec | Cat#HBS-875 |
| HBsAg adw | ProSpec | Cat#HBS-872 |
| HBsAg protein adr | Fitzgerald | Cat#30-AH37 |
| HBsAg protein ay | Fitzgerald | Cat#30-1816 |
| HBsAg protein ad | Fitzgerald | Cat#30-AH15 |
| HBsAg protein ayw | Fitzgerald | Cat#30R-AH018 |
| RNAsin Plus RNAse inhibitor | Promega | Cat#N2615 |
| Random Primers | Thermo Fisher Scientific | Cat#48190011 |
| Lipopolysaccharides from *E. coli* O55:B5 | Sigma-Aldrich | Cat#L2637 |
| Insulin solution human | Sigma-Aldrich | Cat#I1927 |
| Deoxyribonucleic acid from calf thymus | Sigma-Aldrich | Cat#4522 |
| Hemocyanin from *Megathura crenulata* (keyhole limpet) | Sigma-Aldrich | Cat#H8283 |
| Poly(ethylene glycol) | Sigma-Aldrich | Cat#81268 |
| Normal Goat Serum | Jackson ImmunoResearch | Cat#005-000-121 |
| DAPI, FluoroPure ™ grade | Thermo Fisher Scientific | Cat#D21490 |
| Paraformaldehyde 4% Aqueous Solution | Electron Microscopy Sciences | Cat#157-4 |
| Phusion High-Fidelity DNA Polymerase | Thermo Fisher Scientific | Cat#F-530L |
| Commercial Assays | | |
| ARCHITECT Anti-HBs | Abbott Laboratories | Cat#B7C180 |
| ARCHITECT HBsAg Qualitative | Abbott Laboratories | Cat#BlP970 |
| ARCHITECT Anti-HBc II | Abbott Laboratories | Cat#B8L440 |
| HBsAg CLIA kit | Autobio Diagnostics Co. | Cat#CL0310-2 |
| HBeAg CLIA kit | Autobio Diagnostics Co. | Cat#CL0312-2 |
| Anti-HBs CLIA kit | Autobio Diagnostics Co. | Cat#CL0311-2 |
| LS magnetic columns | Miltenyi Biotech | Cat#130-042-401 |
| CD 19 MicroBeads, human | Miltenyi Biotech | Cat#130-097-05 5 |
| EZ-Link ™ Micro NHS-PEG4-Biotinylation Kit | Thermo Fisher Scientific | Cat#21955 |
| Superscript III Reverse Transcriptase | Thermo Fisher Scientific | Cat# 18080044 |
| QIAamp DNA blood mini kit | Qiagen | Cat#51104 |
| TaqMan Universal PCR Master Mix | Applied Biosystems | Cat#4304437 |

-continued

| RESOURCES TABLE | | |
|---|---|---|
| REAGENT or RESOURCE | SOURCE | IDENTIFIER |
| Antinuclear antibodies (HEp-2) Kit | MBL International | Cat#ANK-120 |
| Centricon Plus-70 Ultracel PL-100 | Millipore Sigma | Cat#UFC710008 |
| X-tremeGENE 9 DNA Transfection Reagent | Sigma-Aldrich | Cat#6365787001 |
| Plasmids | | |
| IGγ1 expression vector | (von Boehmer et al., 2016) | N/A |
| IGκ expression vector | (von Boehmer et al., 2016) | N/A |
| IGλ expression vector | (von Boehmer et al., 2016) | N/A |
| p1.3xHBV-WT | Laboratory of Charles M. Rice | N/A |
| Softwares and Websites | | |
| PRISM | GraphPad | www.graphpad.com |
| IgBlast | (Ye et al., 2013) | www.ncbi.nlm.nih.gov/igblast/ |
| IMGT/V-QUEST | (Lefranc et al., 2015) | www.imgt.org/IMGT_vquest/vquest |
| Geneious Prime | Geneious | www.geneious.com/ |

Example 8

This Example provides a description of materials, methods, and subjects used to obtain the foregoing results.

Experimental Models and Subjects

Human Subjects

Volunteer recruitment and blood draws were performed at the Rockefeller University Hospital under a protocol approved by the institutional review board (IRB QWA-0947). Study participants ranged in age from 22-65 with a mean of 43, the female:male ratio was 81:78 (FIGS. 8D and 8E; Table 51).

Animals $Fah^{-/-}$ $NODRag1^{-/-}$ $IL2rg^{null}$ (FNRG) female mice were produced as reported (de Jong et al., 2014) and maintained in the AAALAC-certified facility of the Rockefeller University. Animal protocols were in accordance with NIH guidelines and approved by the Rockefeller University Institutional Animal Care and Use Committee under protocol #18063. Female littermates were randomly assigned to experimental groups.

Cell Lines

HepG2-NTCP cells (Michailidis et al., 2017) and HepDE19 cells (Cai et al., 2012) were maintained in collagen-coated flasks in Dulbecco's Modified Eagle Medium (DMEM) supplemented with 10% or 3% fetal bovine serum (FBS) and 0.1 mM non-essential amino acids (NEAA). Huh7.5-NTCP cells were maintained in DMEM supplemented with 10% FBS and 0.1 mM NEAA. All liver cell lines were cultured at 37° C. in 5% $CO_2$. Human embryonic kidney HEK293-6E suspension cells were cultured at 37° C. in 8% $CO_2$ with shaking at 120 rpm.

Viruses

HBV-containing supernatant from HepDE19 cells was collected and concentrated as previously described (Michailidis et al., 2017). The concentrated virus stock was aliquoted and stored at −80° C. For in vivo experiments one aliquot of mouse-passaged genotype C HBV virus, originally launched from patient serum (Billerbeck et al., 2016), was stored at −80° C. and thawed for mouse infection experiments. For protection and treatment experiments, animals were challenged intravenously using $1\times10^4$ DNA copies per mouse.

Bacteria

*E. coli* DH5-alpha were cultured at 37° C. with shaking at 230 rpm.

Methods

Collection of Human Samples

Samples of peripheral blood were collected from volunteers at the Rockefeller University Hospital. Serum was isolated by centrifugation of coagulated whole blood, and aliquoted for storage at −80° C. PBMCs were isolated using a cell separation tube with frit barrier and cryopreserved in liquid nitrogen in 90% heat-inactivated FBS supplemented with 10% dimethylsulfoxide (DMSO).

HBV Stock

HepDE19 cells (Cai et al., 2012) were cultured in the absence of tetracycline to induce HBV replication. After seven days, supernatant was collected every other day for two weeks and fresh medium was added. After each collection, medium was spun down to remove cell debris, passed through a 0.22 μm filter, and kept at 4° C. Collected medium was concentrated 100-fold via centrifugation using Centricon Plus-70 centrifugal filter devices (Millipore-Sigma, Billerica, MA). Mouse-passaged genotype C HBV virus (Billerbeck et al., 2016) was used for in vivo mouse experiment.

In Vitro HBV Neutralization Assay

In vitro HBV infection was performed as previously described (Michailidis et al., 2017). Briefly, HepG2-NTCP cells were seeded in 96-well collagen-coated plates in DMEM supplemented with 10% FBS and 0.1 mM NEAA. The medium was changed to DMEM with 3% FBS, 0.1 mM NEAA, and 2% DMSO the next day and cultured for an additional 24 hours before infection. The inoculation was in DMEM supplemented with 3% FBS and 0.1 mM NEAA 4% PEG and 2% DMSO. Antibodies or serum samples were incubated with the virus in the inoculation medium for one hour at 37° C. before adding to cells. Serum neutralization capacity (y-axis in FIGS. 1A and 8B) was calculated as the reciprocal of the relative percentage of infected HepG2-NTCP cells immunostained by rabbit anti-HBV core antibody (AUSTRAL Biologicals). For example, if the relative percentage of infected cells were 100% (no serum added or the sera from unexposed naïve control donors), the serum neutralization capacity would be calculated as 1; but if the relative percentage of infected cells were 50% or 10%, the serum neutralization capacity would be 2 or 10. For the blocking neutralization assay, S-protein antigen at different concentration was incubated with purified polyclonal antibodies for one hour at 37° C. before incubation with HBV virus. The cells were then spinoculated for one hour by centrifugation at 1,000 g at 37° C. After a 24-hour incubation, supernatant was removed, cells were washed five times with PBS, and 100 μl of fresh DMEM supplemented with 3% FBS, 0.1 mM NEAA, and 2% DMSO. Both supernatant and cells were harvested 7 days after infection for analysis. Neutralization assays in primary human hepatocytes were performed as above using hepatocytes from livers of highly humanized mice that were harvested and seeded on collagen-coated plates in hepatocyte defined medium (Corning) (Michailidis et al., 2020).

Chemiluminescence Immunoassay

For quantitative analysis of secreted antigen HBsAg or HBeAg, 50 μl of the collected supernatant was loaded into 96-well plates of a chemiluminescence immunoassay (CLIA) kit (Autobio Diagnostics Co., Zhengzhou, China) according to the manufacturer's instructions. Plates were read using a FLUOstar Omega luminometer (BMG Labtech). The absolute concentrations were measured and the relative values were calculated by normalizing to the virus-only control well in the same lane. For example, the absolute HBsAg/HBeAg level in virus-only control well (considered as reference) was 20 NCU/ml (national clinical units per milliliter), while adding one neutralizing serum sample might reduce this to 5 NCU/ml. Therefore, after normalization, the relative HBsAg/HBeAg level were calculated as 100% in control and 25% for this neutralizing serum. Since many factors (virus concentration, cell concentration, immunofluorescence reading, etc.) vary between different plates or different rounds of experiments, normalization is necessary for combining data for comparison.

Immunofluorescence

Cells were fixed in 4% paraformaldehyde for 20 minutes at room temperature, washed with PBS and permeabilized with 0.1% Triton X-100 in PBS. After blocking with 5% goat serum, the cells were incubated with rabbit anti-HBV core antibody (AUSTRAL Biologicals) overnight at 4° C. and visualized with goat anti-rabbit Alexa Fluor 594 (Thermo Fisher Scientific). Nuclei were stained with DAPI. Cells were imaged using a Nikon Eclipse TE300 fluorescent microscope and processed with ImageJ. For high-content imaging analysis ImageXpress Micro XLS (Molecular Devices, Sunnyvale, CA) was used. The absolute $HBc^+$ percentages were obtained and the relative percentage of $HBc^+$ cells was calculated by normalizing to the virus-only control well in the same lane. For example, the absolute $HBc^+$ cell percentage in virus-only control well (considered as reference) was 40%, while adding one neutralizing serum sample might reduce this to 10%. Therefore, after normalization, the relative percentages of $HBc^+$ cells were calculated as 100% in control well and 25% for this neutralizing serum sample. Since many factors (virus concentration, cell concentration, immunofluorescence reading, etc.) vary between different plates or different rounds of experiments, normalization is necessary for combining data for comparison.

ELISA Assays

Blood samples were submitted to Memorial Sloan Kettering Cancer Center for clinical testing. The presence of HBsAg protein and anti-HBc antibody, as well as anti-HBs titers, were determined by ELISA (Abbott Laboratories) as per the manufacturer's instructions.

The binding of serum or recombinant IgG antibodies to HBsAg proteins (see KEY RESOURCES TABLE) was measured by coating ELISA plates with 10 μg/ml of antigen in PBS. Plates were blocked with 2% BSA in PBS and incubated with antibody for one hour at room temperature. Visualization was with HRP-conjugated goat anti-human IgG (Thermo Fisher Scientific). The 50% effective concentration ($EC_{50}$) needed for maximal binding was determined by non-linear regression analysis in software PRISM.

For competition ELISAs plates were coated with 0.12 μg/m1HBsAg (adr CHO) and incubated with 16.7 μg/ml primary antibody for two hours, followed by directly adding 0.25 μg/ml biotinylated secondary antibody and incubation for 30 minutes all at room temperature. Detection was with streptavidin-HRP (BD Biosciences).

Autoreactivity and Polyreactivity

Autoreactivity and polyreactivity assays were performed as described (Gitlin et al., 2016; Mayer et al., 2017; Robbiani et al., 2017). For the autoreactivity assays, monoclonal antibodies were tested with the Antinuclear antibodies (HEp-2) Kit (MBL International). Antibodies were incubated at 100 μg/ml and were detected with Alexa Fluor 488 AffiniPure $F(ab')_2$ Fragment Goat Anti-Human IgG (H+L) (Jackson ImmunoResearch) at 10 μg/ml. Fluorescence images were taken with a wide-field fluorescence microscope (Axioplan 2, Zeiss), a 40× dry objective and a Hamamatsu Orca ER B/W digital camera. Images were analyzed with Image J. Human serum containing antinuclear antibodies (MBL International) was used as a positive control. For the polyreactivity ELISA assays, antibody binding to five different antigens, double-stranded DNA (dsDNA), insulin, keyhole limpet hemocyanin (KLH), lipopolysaccharides (LPS), and single-stranded DNA (ssDNA), were measured. ED38 (Wardemann et al., 2003) and mG053 (Yurasov et al., 2005) antibodies were used as positive and negative controls, respectively.

Synthetic Peptides

Eighteen peptides spanning the antigenic loop region of S-protein antigen were synthesized at the Proteomics Resource Center of The Rockefeller University. For peptide ELISAs plates were coated with 10 μg/ml peptide in PBS.

HBsAg-Binding Memory B Cells

S-protein (adr serotype) expressed and purified from Chinese hamster ovary (CHO) cells (ProSpec) and ovalbumin (Sigma-Aldrich) were biotinylated using EZ-Link™ Micro NHS-PEG4-Biotinylation kit (Thermo Fisher Scientific). S-protein-PE and S-protein-APC were prepared by incubating 2-3 μg of biotin-S-protein with streptavidin-PE (eBioscience) or streptavidin-APC (BD Biosciences) in PBS respectively overnight at 4° C. in the dark. Ovalbumin-Alexa Fluor 488 was generated by incubating biotin-ovalbumin with streptavidin-Alexa Fluor 488 (Thermo Fisher Scientific).

B cell purification, labeling, and sorting were as previously described (Escolano et al., 2019; Robbiani et al., 2017; Tiller et al., 2008; von Boehmer et al., 2016). Briefly, PBMCs were thawed and washed with RPMI medium at 37° C. B lymphocytes were positively selected using CD19 MicroBeads (Miltenyi Biotec) followed by incubation with human Fc block (BD Biosciences) and anti-CD20-PECy7 (BD Biosciences), anti-IgG-Bv421 (BD Biosciences), S-protein-PE at 10 μg/ml, S-protein-APC at 10 μg/ml, and ovalbumin-Alexa Fluor 488 at 10 μg/ml at 4° C. for 20 minutes. Single $CD20^+$ $IgG^+$ S-protein-$PE^+$ S-protein-$APC^+$ Ova-Alexa Fluor $488^-$ memory B cells were sorted into 96-well plates using a FACSAriaII (Becton Dickinson) and stored at −80° C.

Antibody Cloning, Sequencing and Production

Antibody cloning, sequencing and production were done as previously reported (Robbiani et al., 2017; Tiller et al., 2008; von Boehmer et al., 2016). Primers are listed in Table S3. Unmutated common ancestor (UCA) antibody sequences of H006, H019 and H020 were synthesized by gBlock IDT (Table S3) and were inserted into antibody vectors for expression. V(D)J gene segment and CDR3 sequences were determined by IgBlast (Ye et al., 2013) and/or IMGT/V-QUEST (Brochet et al., 2008).

S-Protein Mutagenesis

Oligonucleotides fragments with the target point mutations were synthesized by gBlock IDT (Table S3), and were substituted into the antigenic loop region in plasmid p1.3× HBV-WT by Sequence and Ligation-Independent Cloning (SLIC) (Jeong et al., 2012). Mutant plasmids were transfected into Huh-7.5-NTCP cells using X-tremeGENE 9 DNA Transfection Reagent (Sigma-Aldrich) and the culture medium was changed to serum-free DMEM after 24 hours. Supernatants were collected 2 days later and stored at −80° C. Serum-free medium (50 μl) was directly used to coat ELISA plates.

Crystallization, X-Ray Data Collection, Structure Determination and Refinement

Antibody Fab (25 mg/ml) in 50 mM Tris 8.0, 50 mM NaCl was mixed with peptide (5 mg/ml) in the same buffer at 5:1 v/v. Molar ratio of Fab:peptide is around 1:2. Crystals were obtained upon substitution of all peptide-11 cysteine residues with serine in the peptide synthesis (Proteomics Resource Center, RU). The crystallization condition for Fab15/peptide-11Ser was identified from a commercial screen (Morpheus by Molecular Dimensions) by the sitting-drop vapor-diffusion method at room temperature. The crystal used for data collection was obtained directly from the initial setup (position E1) in a precipitant solution consisting of 0.12 M Ethylene glycols (Di, Tri, Tetra and Penta-ethylene glycol), 0.1 M Buffer Mix 1 (Imidazole/MES) at pH 6.5 and 30% Precipitant Mix 1 (20% v/v PEG 500* MME; 10% w/v PEG 20000). The crystals were flash-cooled in liquid nitrogen directly from the mother liquor without additional cryoprotectant. X-ray diffraction data were collected from a single crystal on the Advanced Photon Source (APS) beamline 24-ID-E to 1.78 Å resolution. The data were integrated and scaled with the program XDS (Kabsch, 2010a, b) and other data processing utilities from the CCP4 suite (Collaborative Computational Project, 1994) using RAPD, the software available at the beam-line. Initial phase estimates and electron-density maps were obtained by molecular replacement with Phaser (McCoy et al., 2007) using a single FAB molecule from (PDB: SGGU) as an initial search model in Phenix (Adams et al., 2010). Iterative model building and structural refinement were manually performed using COOT (Emsley et al., 2010) and Phenix, respectively. The peptide density was well defined, and refined to 90% occupancy, for residues STKPSDGNST (SEQ ID NO: 25). All other residues were not visible and the area where they would be is fully solvent, with no crystal contacts involving any of the peptide atoms. The quality of the final model was good as noted in a Ramachandran of 96% of the observed residues within the allowable region. Data-collection and refinement statistics are summarized (FIG. 13B). All molecular graphics were prepared with PyMOL (Version 2.0 Schrödinger, LLC). Atomic coordinates and experimental structure factors have been deposited in the PDB under accession code 6VJT.

Humanized Mice and In Vivo Studies

Six to eight week old $Fah^{-/-}$ $NODRag1^{-/-}$ $IL2rg^{null}$ (FNRG) female mice were transplanted with one million human hepatocytes from a pediatric female donor HUM4188 (Lonza Bioscience) as previously described (de Jong et al., 2014). Briefly, during isoflurane anesthesia mice underwent skin and peritoneal incision, exposing the spleen. One million hepatocytes were injected in the spleen using a 28-gauge needle. The peritoneum was then approximated using 4.0 VICRYL sutures (Johnson & Johnson), and skin was closed using MikRon Autoclip surgical clips (Becton Dickinson). Mice were cycled off the drug nitisinone (Yecuris) on the basis of weight loss and overall health. Humanization was monitored by human albumin quantification in mouse serum using a human-specific ELISA (Bethyl Labs). Humanized FNRG mice with human albumin values greater than 1 mg/ml were used for infection experiments. The human liver chimeric (huFNRG) mice are extremely immunodeficient. The $Rag1^{-/-}$ renders the mice B and T cell deficient and the $IL2rg^{null}$ mutation prevents cytokine signaling through multiple receptors, leading to a deficiency in functional NK cells. Moreover, the genetic background is NOD background, with suboptimal antigen presentation, defects in T and NK cell function, reduced macrophage cytokine production, suppressed wound healing, and C5 complement deficiency. Thus the mice would be unable to produce antibody-dependent effector functions, including antibody-dependent cell-mediated cytotoxicity (ADCC), or passive antibody-enhanced adaptive immunity.

Mice were challenged intravenously with $1\times10^4$ genome equivalent (GE) of mouse-passaged genotype C HBV viruses diluted in PBS. For prophylaxis experiments, 500 μg of monoclonal antibody was administered intraperitoneally at 20 and again at 6 hours before infection. For therapy experiments, huFNRG mice with established HBV infections ($<10^8$ DNA copies/ml of serum) were injected with 500 μg of each monoclonal antibody intraperitoneally 3 times per week.

DNA in mouse serum collected weekly was extracted using a QIAamp DNA Blood Mini Kit (Qiagen). Total HBV DNA was determined by quantitative PCR (Michailidis et al., 2017). PCR was performed using a TaqMan Universal PCR Master Mix (Applied Biosystems), primers and probe (Table S3).

To obtain HBV DNA from serum for sequence analysis the S domain was amplified using primers (Table S3), and Phusion DNA polymerase (Thermo Fisher Scientific). Initial denaturation was at 98° C. for 30 s, followed by 40 amplification cycles (98° C. for 10 s, 60° C. for 30 s, and 72° C. for 30 s), followed by one cycle at 72° C. for 5 min. A ~700 bp fragment was gel extracted for Sanger sequencing. Sequence alignments were performed using MacVector.

Quantification and Statistical Analysis

Figure 8:
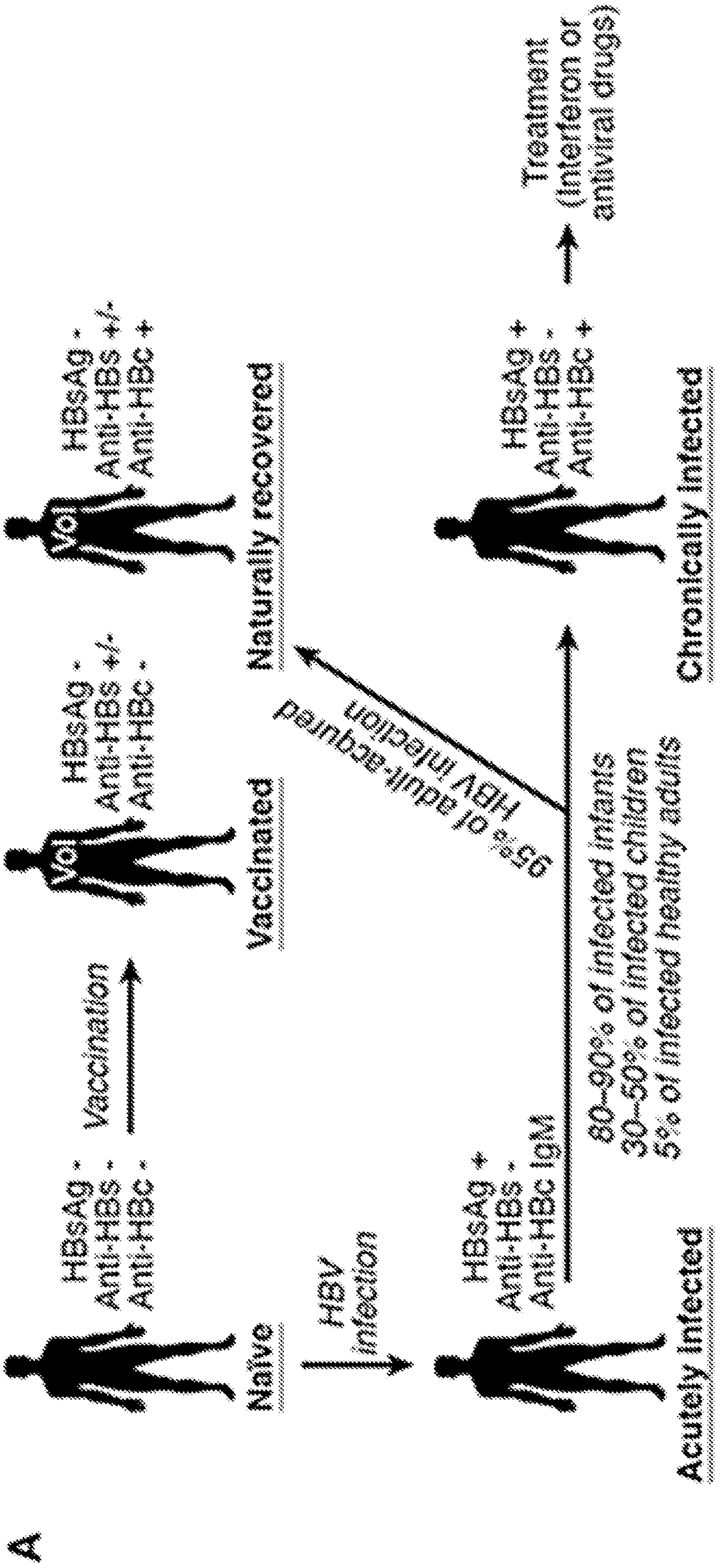
FIG. 8. Characterization of Antibody Immune Response Against HBV, Related to FIG. 1. (A) Schematic representation of different stages of HBV infection. Vaccinated or infected naturally recovered individuals were recruited for this study. (B) Sera (1:50 dilution in the final assay volume) from 159 volunteers were screened, see also FIG. 1A. (C-E) Comparison of anti-HBs ELISA titers (upper panel) and their serum neutralization capacity (lower panel) between different groups of individuals. Vaccinated or recovered individuals show statistically higher anti-HBs titers (upper panel, C) and more potent neutralizing activity (lower panel, C) than the uninfected unvaccinated individuals. Younger individuals (≤45 years old) showed slightly higher antibody immune response against HBsAg (D). No difference was found between genders (E).
Figure 8:
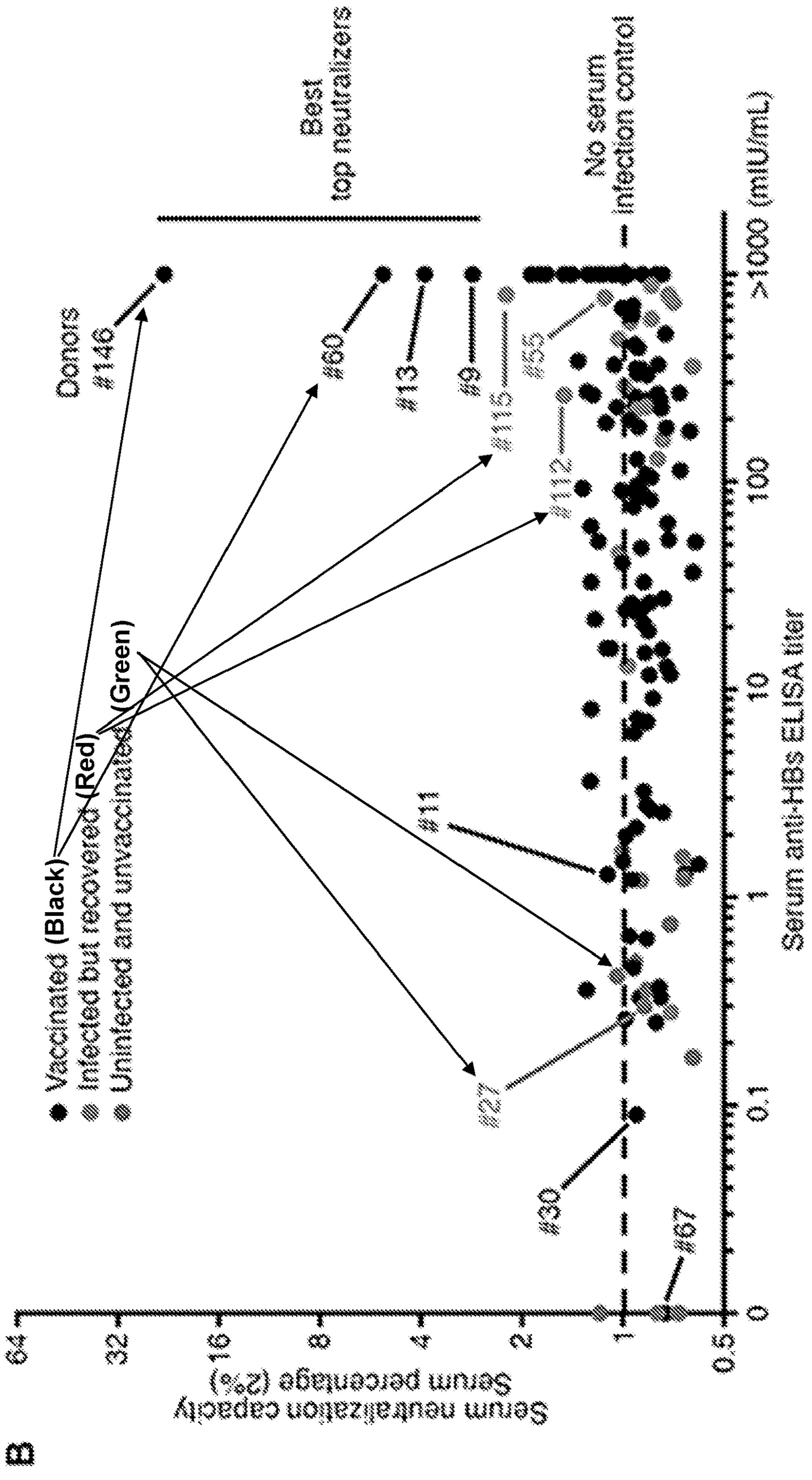
Figure 8:
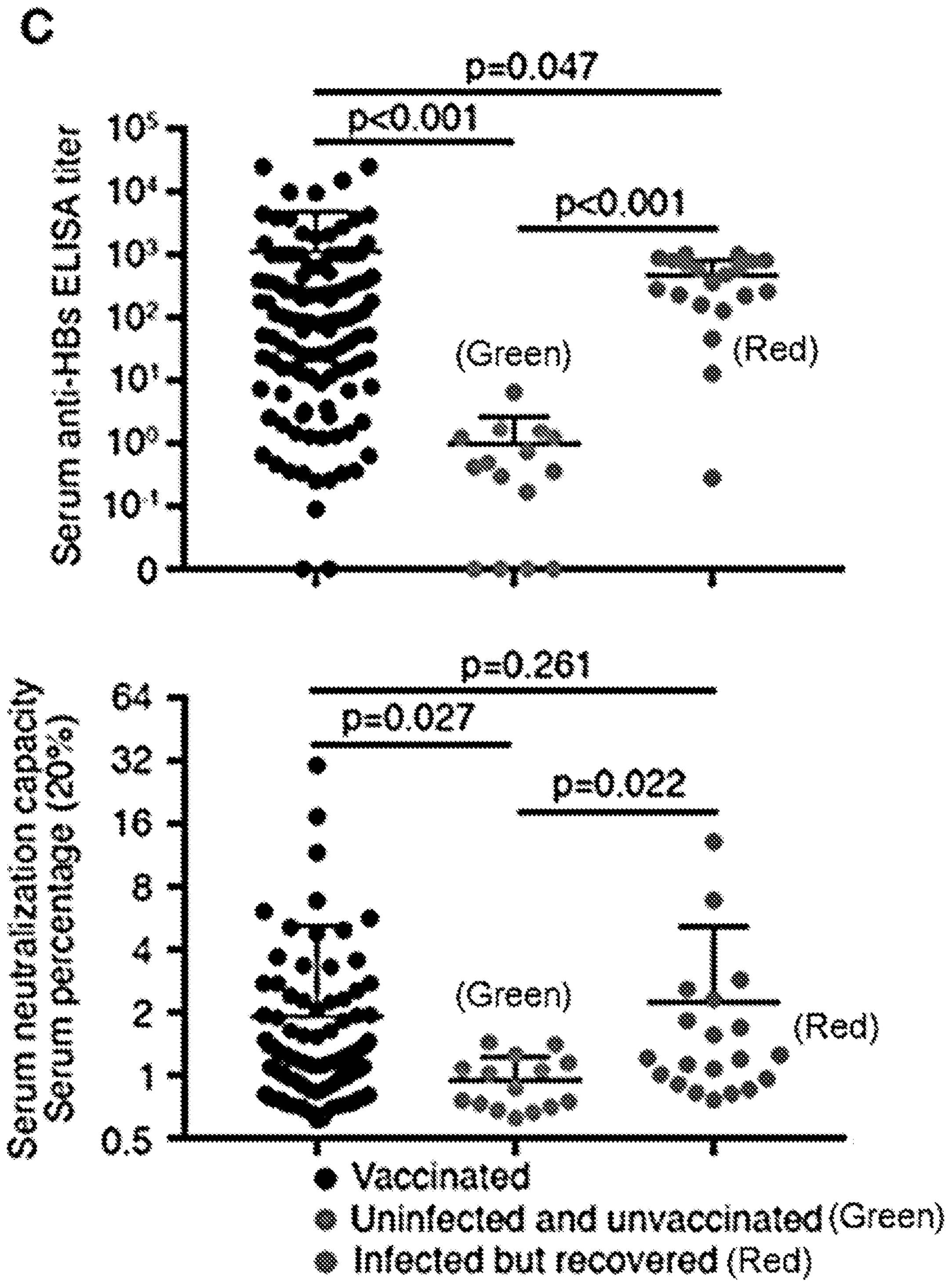
Figure 8:
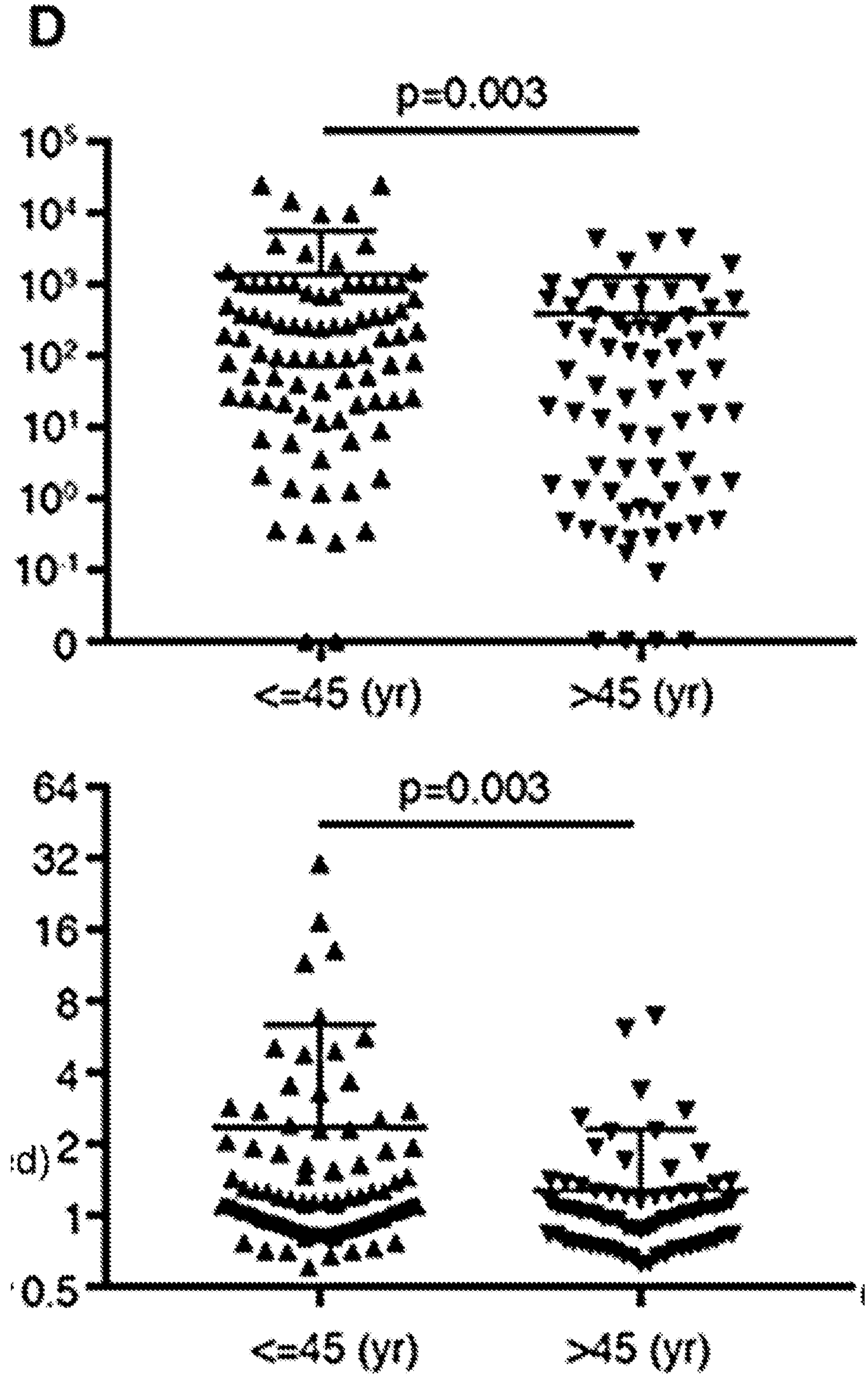
Figure 8:
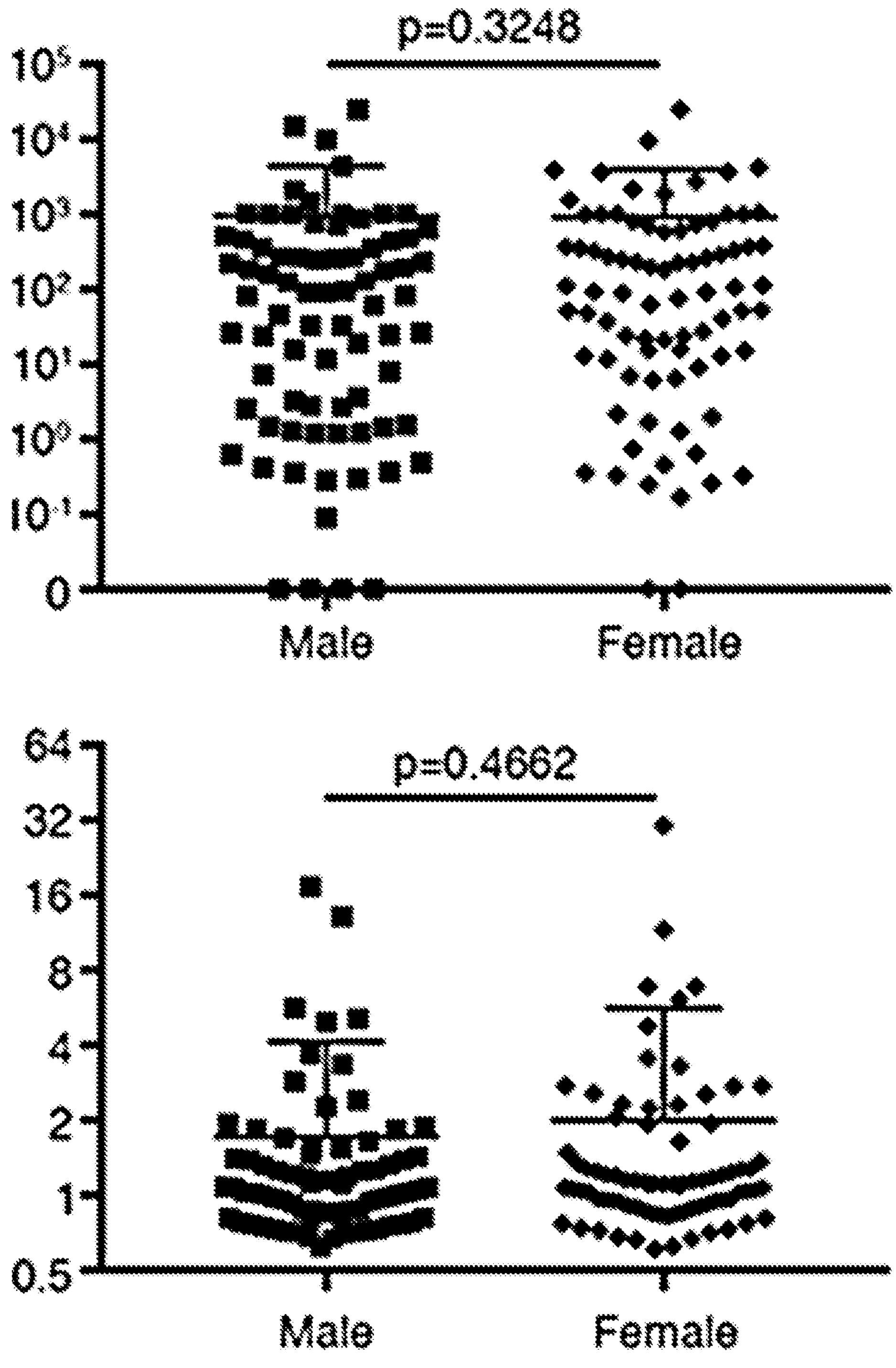

The detailed information of statistical analysis could be found in the Result and Figure Legends. Correlation was evaluated by Spearman's rank correlation method (FIGS. 1A and 2B). Statistical significance was calculated by Dunn's Kruskal-Wallis multiple comparisons with p values corrected with the Benjamini-Hochberg procedure (FIG. 8C). The 50% effective concentration ($EC_{50}$) values by ELISA assays (FIGS. 3A and 3C) and 50% inhibitory concentration ($IC_{50}$) values by neutralization assays (FIG. 5C) were calculated by nonlinear regression analysis in PRISM software.

DISCUSSION OF EXAMPLES

Previous studies have identified several anti-HBs neutralizing antibodies from a small number of otherwise unselected spontaneously recovered or vaccinated individuals (Cerino et al., 2015; Colucci et al., 1986; Eren et al., 1998; Heijtink et al., 2002; Heijtink et al., 1995; Jin et al., 2009; Kim and Park, 2002; Li et al., 2017; Sa'adu et al., 1992; Sankhyan et al., 2016; Tajiri et al., 2007; Tokimitsu et al., 2007; Wang et al., 2016). In contrast, in the present disclosure, sera from 144 exposed volunteers was screened to identify elite neutralizers. Serologic activity varied greatly among the donors with a small number of individuals demonstrating high levels of neutralizing activity. To understand this activity, we isolated 244 anti-HBs antibodies from single B cells obtained from the top donors. Each of the elite donors tested showed expanded clones of memory B cells expressing bNAbs that targeted 3 non-overlapping sites on the S-protein. Moreover, the amino acid sequence of several of the bNAbs was highly similar in different individuals. These closely related antibodies target the same epitope.

The near identity of clones of HBV bNAbs in unrelated elite individuals is akin to reports for elite responders to HIV-1 (Scheid et al., 2011; West et al., 2012), influenza (Laursen and Wilson, 2013; Pappas et al., 2014; Wrammert et al., 2011), Zika (Robbiani et al., 2017), and malaria (Tan et al., 2018). However, none of the elite anti-HBs bNAbs shares both IgH and IgL with previously reported HBV neutralizing antibodies, the best of which have been tested in the clinic but are less potent than some of the bNAbs of this disclosure (libivirumab $IC_{50}$: 35 ng/ml, tuvirumab $IC_{50}$: ~100 ng/ml) (Galun et al., 2002; Heijtink et al., 2001; van Nunen et al., 2001).

The described alanine scanning and competition binding analyses are consistent with the existence of at least 3 domains that can be recognized concomitantly by bNAbs (Gao et al., 2017; Tajiri et al., 2010; Zhang et al., 2016). However, the domains do not appear to be limited to either of two previously defined circular peptide epitopes, 123-137 and 139-148 (Tajiri et al., 2010; Zhang et al., 2016). Instead, residues spanning most of the external domain can contribute to binding by both Group-I and -II antibodies. For example, alanine scanning indicates that Group-I H020 binding is dependent on I110, K141, D144, G145 and T148, while Group-II H016 binding depends on T123, D144, and G145. Thus, despite having non-overlapping binding sites some of the essential residues are shared by Group-I and II suggesting that the epitopes are conformational. Moreover, the antibody epitopes on S-protein identified using mouse and human antibodies may be distinct (Chen et al., 1996; Ijaz et al., 2003; Paulij et al., 1999; Zhang et al., 2019; Zhang et al., 2016). Finally, G145, a residue that is frequently mutated in infected humans (Ma and Wang, 2012; Tong et al., 2013), is believed to be essential for binding by all the Group-II but not all Group-I or -III antibodies tested.

Crystallization of the Group-II bNAb H015 and its linear epitope revealed a loop that includes P142, S/T143, D144, and G145, all of which are frequently mutated during natural infection to produce well-documented immune escape variants (Hsu et al., 2015; Ijaz et al., 2012; Ma and Wang, 2012; Salpini et al., 2015). In addition to immune escape, the residues that form this structure are also essential for infectivity, possibly by facilitating virus interactions with cell surface glycosaminoglycans (Sureau and Salisse, 2013). Mutations in K141, P142 as well as C139 and C147, all of which contribute to the stability of the structure, decrease viral infectivity (Salisse and Sureau, 2009). Without intending to be bound by any particular theory, it is considered that drugs that destabilize the newly elucidated H015-peptide loop structure may also interfere with infectivity.

The G145R mutation, which is among the most frequent immune escape variants, replaces a small neutral residue with a bulky charged residue that would likely interfere with antigenicity by destroying the salt bridge between K141 and D144 that anchors the peptide loop. However, this drastic structural change does not alter infectivity (Salisse and Sureau, 2009), possibly because the additional charge compensates for otherwise altered interactions between HBV and cell surface glycosaminoglycans (Sureau and Salisse, 2013). Thus, the additional charge may allow G145R to function as a dominant immune escape variant while preserving infectivity.

The present disclosure describes antibodies directed at S-protein antigen in part because this is the antigen used in the currently FDA-approved vaccines, and because purified S-protein blocked nearly all of the neutralizing activity in the serum of the elite neutralizers irrespective of whether they were vaccinated or spontaneously recovered. Nevertheless, individuals who recover from infection also produce antibodies to the PreS1 domain of HBsAg (Li et al., 2017; Sankhyan et al., 2016). The PreS1 domain is essential for the virus to interact with the entry factor NCTP on hepatocytes and potent neutralizing antibodies to PreS1 have been described (Li et al., 2017). However, these are not naturally occurring antibodies but rather randomly paired IgH and IgL chains derived from phage libraries obtained from unexposed or vaccinated healthy donors (Li et al., 2017). Moreover, the phage antibodies required further engineering to enhance their neutralizing activity (Li et al., 2017). Thus, whether the human immune system also produces potent anti-PreS1 bNAbs has not been determined.

Chronic HBV infection remains a major global public health problem in need of an effective curative strategy (Graber-Stiehl, 2018; Lazarus et al., 2018; Revill et al., 2016). Chronically infected individuals produce an overwhelming amount of HBsAg that is postulated to incapacitate the immune system. Consequently, immune cells, which might normally clear the virus, are unable to react to antigen, a phenomenon referred to as exhaustion or anergy (Ye et al., 2015). The appearance of anti-HBs antibodies is associated with spontaneous recovery from the disease, perhaps because they can clear the antigen and facilitate the emergence of a productive immune response (Celis and Chang, 1984; Zhang et al., 2016; Zhu et al., 2016). These findings led to the hypothesis that passively administered antibodies might be used in conjunction with antiviral drugs to further decrease the antigenic burden while enhancing immune responses that maintain long-term control of the disease. The presently described results in huFNRG mice infected with HBV indicate that antibody monotherapy with a potent bNAb can lead to the emergence of the very same escape mutations commonly found in chronically infected individuals. Moreover, not all bNAb combinations are effective in preventing escape by mutation. Combinations that target separate epitopes but have overlapping sensitivity to commonly occurring escape mutations such as H006 and H007 are ineffective. In contrast, combinations with complementary sensitivity to common escape mutations prevent the emergence of escape mutations in huFNRG mice infected with HBV. Thus, as described above, the present disclosure provides immunotherapy for HBV infection with combinations of antibodies with complementary activity to avert this potential problem.

The following reference listing is not an indication that any particular reference(s) is material to patentability.

Abou-Jaoude, G., and Sureau, C. (2007). Entry of hepatitis delta virus requires the conserved cysteine residues of the hepatitis B virus envelope protein antigenic loop and is blocked by inhibitors of thiol-disulfide exchange. J Virol. 81(23), 13057-13066. DOI: 10.1128/JVI.01495-07.

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D Biol Crystallogr. 66(Pt 2), 213-221. DOI: 10.1107/S0907444909052925.

Bancroft, W. H., Mundon, F. K., and Russell, P. K. (1972). Detection of additional antigenic determinants of hepatitis B antigen. J Immunol. 109(4), 842-848.

Billerbeck, E., Mommersteeg, M. C., Shlomai, A., Xiao, J. W., Andrus, L., Bhatta, A., Vercauteren, K., Michailidis, E., Dorner, M., Krishnan, A., et al. (2016). Humanized mice efficiently engrafted with fetal hepatoblasts and syngeneic immune cells develop human monocytes and NK cells. J Hepatol. 65(2), 334-343. DOI: 10.1016/j.jhep.2016.04.022.

Blumberg, B. S. (1964). Polymorphisms of the Serum Proteins and the Development of Iso-Precipitins in Transfused Patients. Bull N Y Acad Med. 40, 377-386.

Braden, B. C., and Poljak, R. J. (1995). Structural features of the reactions between antibodies and protein antigens. FASEB J. 9(1), 9-16. DOI: 10.1096/fasebj.9.1.7821765.

Brochet, X., Lefranc, M. P., and Giudicelli, V. (2008). IMGT/V-QUEST: the highly customized and integrated system for IG and TR standardized V-J and V-D-J sequence analysis. Nucleic Acids Res. 36 (Web Server issue), W503-508. DOI: 10.1093/nar/gkn316.

Cai, D., Mills, C., Yu, W., Yan, R., Aldrich, C. E., Saputelli, J. R., Mason, W. S., Xu, X., Guo, J. T., Block, T. M., et al. (2012). Identification of disubstituted sulfonamide compounds as specific inhibitors of hepatitis B virus covalently closed circular DNA formation. Antimicrob Agents Chemother. 56(8), 4277-4288. DOI: 10.1128/AAC.00473-12.

Celis, E., and Chang, T. W. (1984). Antibodies to hepatitis B surface antigen potentiate the response of human T lymphocyte clones to the same antigen. Science. 224(4646), 297-299. DOI: 10.1126/science.6231724.

Cerino, A., Bremer, C. M., Glebe, D., and Mondelli, M. U. (2015). A Human Monoclonal Antibody against Hepatitis B Surface Antigen with Potent Neutralizing Activity. PLoS One. 10(4), e0125704. DOI: 10.1371/journal-.pone.0125704.

Chen, Y. C., Delbrook, K., Dealwis, C., Mimms, L., Mushahwar, I. K., and Mandecki, W. (1996). Discontinuous epitopes of hepatitis B surface antigen derived from a filamentous phage peptide library. Proc Natl Acad Sci USA. 93(5), 1997-2001. DOI: 10.1073/pnas.93.5.1997.

Collaborative Computational Project, N. (1994). The CCP4 suite: programs for protein crystallography. Acta Crystallogr D Biol Crystallogr. 50(Pt 5), 760-763. DOI: 10.1107/S0907444994003112.

Colucci, G., Kohtz, D. S., and Waksal, S. D. (1986). Preparation and characterization of human monoclonal antibodies directed against the hepatitis B virus surface antigen. Liver. 6(3), 145-152.

Coursaget, P., Adamowicz, P., Bourdil, C., Yvonnet, B., Buisson, Y., Barres, J. L., Saliou, P., Chiron, J. P., and Mar, I. D. (1988). Anti-pre-S2 antibodies in natural hepatitis B virus infection and after immunization. Vaccine. 6(4), 357-361.

Dane, D. S., Cameron, C. H., and Briggs, M. (1970). Virus-like particles in serum of patients with Australia-antigen-associated hepatitis. Lancet. 1(7649), 695-698.

de Jong, Y. P., Dorner, M., Mommersteeg, M. C., Xiao, J. W., Balazs, A. B., Robbins, J. B., Winer, B. Y., Gerges, S., Vega, K., Labitt, R. N., et al. (2014). Broadly neutralizing antibodies abrogate established hepatitis C virus infection. Sci Transl Med. 6(254), 254ra129. DOI: 10.1126/scitranslmed.3009512.

Dienstag, J. L. (2008). Hepatitis B virus infection. N Engl J Med. 359(14), 1486-1500. DOI: 10.1056/NEJMra0801644.

Emsley, P., Lohkamp, B., Scott, W. G., and Cowtan, K. (2010). Features and development of Coot. Acta Crystallogr D Biol Crystallogr. 66(Pt 4), 486-501. DOI: 10.1107/S0907444910007493.

Eren, R., Ilan, E., Nussbaum, O., Lubin, I., Terkieltaub, D., Arazi, Y., Ben-Moshe, O., Kitchinzky, A., Ben, S., Gopher, J., et al. (2000). Preclinical evaluation of two human anti-hepatitis B virus (HBV) monoclonal antibodies in the HBV-trimera mouse model and in HBV chronic carrier chimpanzees. Hepatology. 32(3), 588-596. DOI: 10.1053/jhep.2000.9632.

Eren, R., Lubin, I., Terkieltaub, D., Ben-Moshe, O., Zauberman, A., Uhlmann, R., Tzahor, T., Moss, S., Ilan, E., Shouval, D., et al. (1998). Human monoclonal antibodies specific to hepatitis B virus generated in a human/mouse radiation chimera: the Trimera system. Immunology. 93(2), 154-161. DOI: 10.1046/j.1365-2567.1998.00426.x.

Escolano, A., Gristick, H. B., Abernathy, M. E., Merkenschlager, J., Gautam, R., Oliveira, T. Y., Pai, J., West, A. P., Jr., Barnes, C. O., Cohen, A. A., et al. (2019). Immunization expands B cells specific to HIV-1 V3 glycan in mice and macaques. Nature. 570(7762), 468-473. DOI: 10.1038/s41586-019-1250-z.

Galun, E., Eren, R., Safadi, R., Ashour, Y., Terrault, N., Keeffe, E. B., Matot, E., Mizrachi, S., Terkieltaub, D., Zohar, M., et al. (2002). Clinical evaluation (phase I) of a combination of two human monoclonal antibodies to HBV: safety and antiviral properties. Hepatology. 35(3), 673-679. DOI: 10.1053/jhep.2002.31867.

Ganem, D. (1982). Persistent infection of humans with hepatitis B virus: mechanisms and consequences. Rev Infect Dis. 4(5), 1026-1047.

Gao, Y., Zhang, T. Y., Yuan, Q., and Xia, N. S. (2017). Antibody-mediated immunotherapy against chronic hepatitis B virus infection. Hum Vaccin Immunother. 13(8), 1768-1773. DOI: 10.1080/21645515.2017.1319021.

Gilchuk, P., Kuzmina, N., Ilinykh, P. A., Huang, K., Gunn, B. M., Bryan, A., Davidson, E., Doranz, B. J., Turner, H. L., Fusco, M. L., et al. (2018). Multifunctional Pan-ebolavirus Antibody Recognizes a Site of Broad Vulnerability on the Ebolavirus Glycoprotein. Immunity. 49(2), 363-374 e310. DOI: 10.1016/j.immuni.2018.06.018.

Gitlin, A. D., von Boehmer, L., Gazumyan, A., Shulman, Z., Oliveira, T. Y., and Nussenzweig, M. C. (2016). Independent Roles of Switching and Hypermutation in the Development and Persistence of B Lymphocyte Memory. Immunity. 44(4), 769-781. DOI: 10.1016/j.immuni.2016.01.011.

Graber-Stiehl, I. (2018). The silent epidemic killing more people than HIV, malaria or TB. Nature. 564(7734), 24-26. DOI: 10.1038/d41586-018-07592-7.

Heijtink, R. A., Kruining, J., van Bergen, P., de Rave, S., van Hattum, J., Schutten, M., and Osterhaus, A. D. (2002). Characterization of a human monoclonal antibody obtained after immunization with plasma vaccine and a booster with recombinant-DNA hepatitis B vaccine. J Med Virol. 66(3), 304-311.

Heijtink, R. A., Kruining, J., Weber, Y. A., de Man, R. A., and Schalm, S. W. (1995). Anti-hepatitis B virus activity of a mixture of two monoclonal antibodies in an "inhibition in solution" assay. Hepatology. 22 (4 Pt 1), 1078-1083.

Heijtink, R. A., van Nunen, A. B., van Bergen, P., Ostberg, L., Osterhaus, A. D., and de Man, R. A. (2001). Administration of a human monoclonal antibody (TUVIRUMAB) to chronic hepatitis B patients pre-treated with lamivudine: monitoring of serum TUVIRUMAB in immune complexes. J Med Virol. 64(4), 427-434.

Hsu, H. Y., Chang, M. H., Ni, Y. H., Chiang, C. L., Wu, J. F., and Chen, H. L. (2015). Universal infant immunization and occult hepatitis B virus infection in children and adolescents: a population-based study. Hepatology. 61(4), 1183-1191. DOI: 10.1002/hep.27650.

Hu, J., and Liu, K. (2017). Complete and Incomplete Hepatitis B Virus Particles: Formation, Function, and Application. Viruses. 9(3), E56. DOI: 10.3390/v9030056.

Hyakumura, M., Walsh, R., Thaysen-Andersen, M., Kingston, N. J., La, M., Lu, L., Lovrecz, G., Packer, N. H., Locarnini, S., and Netter, H. J. (2015). Modification of Asparagine-Linked Glycan Density for the Design of Hepatitis B Virus Virus-Like Particles with Enhanced Immunogenicity. J Virol. 89(22), 11312-11322. DOI: 10.1128/JVI.01123-15.

Ijaz, S., Ferns, R. B., and Tedder, R. S. (2003). A 'first loop' linear epitope accessible on native hepatitis B surface antigen that persists in the face of 'second loop' immune escape. J Gen Virol. 84(Pt 2), 269-275. DOI: 10.1099/vir.0.18667-0.

Ijaz, S., Szypulska, R., Andrews, N., and Tedder, R. S. (2012). Investigating the impact of hepatitis B virus surface gene polymorphism on antigenicity using ex vivo phenotyping. J Gen Virol. 93(Pt 11), 2473-2479. DOI: 10.1099/vir.0.044305-0.

Ito, K., Qin, Y., Guarnieri, M., Garcia, T., Kwei, K., Mizokami, M., Zhang, J., Li, J., Wands, J. R., and Tong, S. (2010). Impairment of hepatitis B virus virion secretion by single-amino-acid substitutions in the small envelope protein and rescue by a novel glycosylation site. J Virol. 84(24), 12850-12861. DOI: 10.1128/JVI.01499-10.

Jeong, J. Y., Yim, H. S., Ryu, J. Y., Lee, H. S., Lee, J. H., Seen, D. S., and Kang, S. G. (2012). One-step sequence- and ligation-independent cloning as a rapid and versatile cloning method for functional genomics studies. Appl Environ Microbiol. 78(15), 5440-5443. DOI: 10.1128/AEM.00844-12.

Jin, A., Ozawa, T., Tajiri, K., Obata, T., Kondo, S., Kinoshita, K., Kadowaki, S., Takahashi, K., Sugiyama, T., Kishi, H., et al. (2009). A rapid and efficient single-cell manipulation method for screening antigen-specific antibody-secreting cells from human peripheral blood. Nat Med. 15(9), 1088-1092. DOI: 10.1038/nm.1966.

Julithe, R., Abou-Jaoude, G., and Sureau, C. (2014). Modification of the hepatitis B virus envelope protein glycosylation pattern interferes with secretion of viral particles, infectivity, and susceptibility to neutralizing antibodies. J Virol. 88(16), 9049-9059. DOI: 10.1128/JVI.01161-14.

Kabsch, W. (2010a). Integration, scaling, space-group assignment and post-refinement. Acta Crystallogr D Biol Crystallogr. 66(Pt 2), 133-144. DOI: 10.1107/S0907444909047374.

Kabsch, W. (2010b). Xds. Acta Crystallogr D Biol Crystallogr. 66(Pt 2), 125-132. DOI: 10.1107/S0907444909047337.

Kim, S. H., and Park, S. Y. (2002). Selection and characterization of human antibodies against hepatitis B virus surface antigen (HBsAg) by phage-display. Hybrid Hybridomics. 21(5), 385-392. DOI: 10.1089/153685902761022742.

Kramvis, A., Arakawa, K., Yu, M. C., Nogueira, R., Stram, D. O., and Kew, M. C. (2008). Relationship of serological subtype, basic core promoter and precore mutations to genotypes/subgenotypes of hepatitis B virus. J Med Virol. 80(1), 27-46. DOI: 10.1002/jmv.21049.

Laursen, N. S., and Wilson, I. A. (2013). Broadly neutralizing antibodies against influenza viruses. Antiviral Res. 98(3), 476-483. DOI: 10.1016/j.antiviral.2013.03.021.

Lazarus, J. V., Block, T., Brechot, C., Kramvis, A., Miller, V., Ninburg, M., Penicaud, C., Protzer, U., Razavi, H., Thomas, L. A., et al. (2018). The hepatitis B epidemic and the urgent need for cure preparedness. Nat Rev Gastroenterol Hepatol. 15(9), 517-518. DOI: 10.1038/s41575-018-0041-6.

Le Bouvier, G. L. (1971). The heterogeneity of Australia antigen. J Infect Dis. 123(6), 671-675. DOI: 10.1093/infdis/123.6.671.

Li, D., He, W., Liu, X., Zheng, S., Qi, Y., Li, H., Mao, F., Liu, J., Sun, Y., Pan, L., et al. (2017). A potent human neutralizing antibody Fc-dependently reduces established HBV infections. Elife. 6, e26738. DOI: 10.7554/eLife.26738.

Loomba, R., and Liang, T. J. (2017). Hepatitis B Reactivation Associated With Immune Suppressive and Biological Modifier Therapies: Current Concepts, Management Strategies, and Future Directions. Gastroenterology. 152 (6), 1297-1309. DOI: 10.1053/j.gastro.2017.02.009.

Ma, Q., and Wang, Y. (2012). Comprehensive analysis of the prevalence of hepatitis B virus escape mutations in the major hydrophilic region of surface antigen. J Med Virol. 84(2), 198-206. DOI: 10.1002/jmv.23183.

Mayer, C. T., Gazumyan, A., Kara, E. E., Gitlin, A. D., Golijanin, J., Viant, C., Pai, J., Oliveira, T. Y., Wang, Q., Escolano, A., et al. (2017). The microanatomic segregation of selection by apoptosis in the germinal center. Science. 358(6360), eaao2602. DOI: 10.1126/science.aao2602.

McCoy, A. J., Grosse-Kunstleve, R. W., Adams, P. D., Winn, M. D., Storoni, L. C., and Read, R. J. (2007). Phaser crystallographic software. J Appl Crystallogr. 40(Pt 4), 658-674. DOI: 10.1107/S0021889807021206.

Michailidis, E., Pabon, J., Xiang, K., Park, P., Ramanan, V., Hoffmann, H. H., Schneider, W. M., Bhatia, S. N., de Jong, Y. P., Shlomai, A., et al. (2017). A robust cell culture system supporting the complete life cycle of hepatitis B virus. Sci Rep. 7(1), 16616. DOI: 10.1038/s41598-017-16882-5.

Michailidis, E., Vercauteren, K., Mancio-Silva, L., Andrus, L., Jahan, C., Ricardo-Lax, I., Zou, C., Kabbani, M., Park, P., Quirk, C., et al. (2020). Expansion, in vivo-ex vivo cycling, and genetic manipulation of primary human hepatocytes. Proc Natl Acad Sci USA. 117(3), 1678-1688. DOI: 10.1073/pnas.1919035117.

Milner-White, E. J., and Poet, R. (1986). Four classes of beta-hairpins in proteins. Biochem J. 240(1), 289-292. DOI: 10.1042/bj2400289.

Mouquet, H., Scharf, L., Euler, Z., Liu, Y., Eden, C., Scheid, J. F., Halper-Stromberg, A., Gnanapragasam, P. N., Spencer, D. I., Seaman, M. S., et al. (2012). Complex-type N-glycan recognition by potent broadly neutralizing HIV antibodies. Proc Natl Acad Sci USA. 109(47), E3268-3277. DOI: 10.1073/pnas.1217207109.
Norder, H., Courouce, A. M., Coursaget, P., Echevarria, J. M., Lee, S. D., Mushahwar, I. K., Robertson, B. H., Locarnini, S., and Magnius, L. O. (2004). Genetic diversity of hepatitis B virus strains derived worldwide: genotypes, subgenotypes, and HBsAg subtypes. Intervirology. 47(6), 289-309. DOI: 10.1159/000080872.
Pappas, L., Foglierini, M., Piccoli, L., Kallewaard, N. L., Turrini, F., Silacci, C., Fernandez-Rodriguez, B., Agatic, G., Giacchetto-Sasselli, I., Pellicciotta, G., et al. (2014). Rapid development of broadly influenza neutralizing antibodies through redundant mutations. Nature. 516(7531), 418-422. DOI: 10.1038/nature13764.
Paulij, W. P., de Wit, P. L., Sunnen, C. M., van Roosmalen, M. H., Petersen-van Ettekoven, A., Cooreman, M. P., and Heijtink, R. A. (1999). Localization of a unique hepatitis B virus epitope sheds new light on the structure of hepatitis B virus surface antigen. J Gen Virol. 80 (Pt 8), 2121-2126. DOI: 10.1099/0022-1317-80-8-2121.
Revill, P., Testoni, B., Locarnini, S., and Zoulim, F. (2016). Global strategies are required to cure and eliminate HBV infection. Nat Rev Gastroenterol Hepatol. 13(4), 239-248. DOI: 10.1038/nrgastro.2016.7.
Robbiani, D. F., Bozzacco, L., Keeffe, J. R., Khouri, R., Olsen, P. C., Gazumyan, A., Schaefer-Babajew, D., Avila-Rios, S., Nogueira, L., Patel, R., et al. (2017). Recurrent Potent Human Neutralizing Antibodies to Zika Virus in Brazil and Mexico. Cell. 169(4), 597-609 e511. DOI: 10.1016/j.cell.2017.04.024.
Rouers, A., Klingler, J., Su, B., Samri, A., Laumond, G., Even, S., Avettand-Fenoel, V., Richetta, C., Paul, N., Boufassa, F., et al. (2017). HIV-Specific B Cell Frequency Correlates with Neutralization Breadth in Patients Naturally Controlling HIV-Infection. EBioMedicine. 21, 158-169. DOI: 10.1016/j.ebiom.2017.05.029.
Sa'adu, A., Locniskar, M., Bidwell, D., Howard, C., McAdam, K. P., and Voller, A. (1992). Development and characterization of human anti-HBs antibodies. J Virol Methods. 36(1), 25-34.
Salisse, J., and Sureau, C. (2009). A function essential to viral entry underlies the hepatitis B virus "a" determinant. J Virol. 83(18), 9321-9328. DOI: 10.1128/JVI.00678-09.
Salpini, R., Colagrossi, L., Bellocchi, M. C., Surdo, M., Becker, C., Alteri, C., Aragri, M., Ricciardi, A., Armenia, D., Pollicita, M., et al. (2015). Hepatitis B surface antigen genetic elements critical for immune escape correlate with hepatitis B virus reactivation upon immunosuppression. Hepatology. 61(3), 823-833. DOI: 10.1002/hep.27604.
Sankhyan, A., Sharma, C., Dutta, D., Sharma, T., Chosdol, K., Wakita, T., Watashi, K., Awasthi, A., Acharya, S. K., Khanna, N., et al. (2016). Inhibition of preS1-hepatocyte interaction by an array of recombinant human antibodies from naturally recovered individuals. Sci Rep. 6, 21240. DOI: 10.1038/srep21240.
Scheid, J. F., Mouquet, H., Feldhahn, N., Seaman, M. S., Velinzon, K., Pietzsch, J., Ott, R. G., Anthony, R. M., Zebroski, H., Hurley, A., et al. (2009a). Broad diversity of neutralizing antibodies isolated from memory B cells in HIV-infected individuals. Nature. 458(7238), 636-640. DOI: 10.1038/nature07930.
Scheid, J. F., Mouquet, H., Feldhahn, N., Walker, B. D., Pereyra, F., Cutrell, E., Seaman, M. S., Mascola, J. R., Wyatt, R. T., Wardemann, H., et al. (2009b). A method for identification of HIV gp140 binding memory B cells in human blood. J Immunol Methods. 343(2), 65-67. DOI: 10.1016/j.jim.2008.11.012.
Scheid, J. F., Mouquet, H., Ueberheide, B., Diskin, R., Klein, F., Oliveira, T. Y., Pietzsch, J., Fenyo, D., Abadir, A., Velinzon, K., et al. (2011). Sequence and structural convergence of broad and potent HIV antibodies that mimic CD4 binding. Science. 333(6049), 1633-1637. DOI: 10.1126/science.1207227.
Schommers, P., Gruell, H., Abernathy, M. E., Tran, M. K., Dingens, A. S., Gristick, H. B., Barnes, C. O., Schoofs, T., Schlotz, M., Vanshylla, K., et al. (2020). Restriction of HIV-1 Escape by a Highly Broad and Potent Neutralizing Antibody. Cell. 180(3), 471-489 e422. DOI: 10.1016/j.cell.2020.01.010.
Sheu, S. Y., Yang, D. Y., Selzle, H. L., and Schlag, E. W. (2003). Energetics of hydrogen bonds in peptides. Proc Natl Acad Sci USA. 100(22), 12683-12687. DOI: 10.1073/pnas.2133366100.
Sun, S., and Li, J. (2017). Humanized chimeric mouse models of hepatitis B virus infection. Int J Infect Dis. 59, 131-136. DOI: 10.1016/j.ijid.2017.04.002.
Sureau, C., and Salisse, J. (2013). A conformational heparan sulfate binding site essential to infectivity overlaps with the conserved hepatitis B virus a-determinant. Hepatology. 57(3), 985-994. DOI: 10.1002/hep.26125.
Tajiri, K., Kishi, H., Tokimitsu, Y., Kondo, S., Ozawa, T., Kinoshita, K., Jin, A., Kadowaki, S., Sugiyama, T., and Muraguchi, A. (2007). Cell-microarray analysis of antigen-specific B-cells: single cell analysis of antigen receptor expression and specificity. Cytometry A. 71(11), 961-967. DOI: 10.1002/cyto.a.20471.
Tajiri, K., Ozawa, T., Jin, A., Tokimitsu, Y., Minemura, M., Kishi, H., Sugiyama, T., and Muraguchi, A. (2010). Analysis of the epitope and neutralizing capacity of human monoclonal antibodies induced by hepatitis B vaccine. Antiviral Res. 87(1), 40-49. DOI: 10.1016/j.antiviral.2010.04.006.
Tan, J., Pieper, K., Piccoli, L., Abdi, A., Perez, M. F., Geiger, R., Tully, C. M., Jarrossay, D., Maina Ndungu, F., Wambua, J., et al. (2016). A LAIR1 insertion generates broadly reactive antibodies against malaria variant antigens. Nature. 529(7584), 105-109. DOI: 10.1038/nature16450.
Tan, J., Sack, B. K., Oyen, D., Zenklusen, I., Piccoli, L., Barbieri, S., Foglierini, M., Fregni, C. S., Marcandalli, J., Jongo, S., et al. (2018). A public antibody lineage that potently inhibits malaria infection through dual binding to the circumsporozoite protein. Nat Med. 24(4), 401-407. DOI: 10.1038/nm.4513.
Thomas, D. L. (2019). Global Elimination of Chronic Hepatitis. N Engl J Med. 380(21), 2041-2050. DOI: 10.1056/NEJMra1810477.
Tiller, T., Meffre, E., Yurasov, S., Tsuiji, M., Nussenzweig, M. C., and Wardemann, H. (2008). Efficient generation of monoclonal antibodies from single human B cells by single cell RT-PCR and expression vector cloning. J Immunol Methods. 329(1-2), 112-124. DOI: 10.1016/j.jim.2007.09.017.
Tokimitsu, Y., Kishi, H., Kondo, S., Honda, R., Tajiri, K., Motoki, K., Ozawa, T., Kadowaki, S., Obata, T., Fujiki, S., et al. (2007). Single lymphocyte analysis with a microwell array chip. Cytometry A. 71(12), 1003-1010. DOI: 10.1002/cyto.a.20478.
Tong, S., Li, J., Wands, J. R., and Wen, Y. M. (2013). Hepatitis B virus genetic variants: biological properties and clinical implications. Emerg Microbes Infect. 2(3), e10. DOI: 10.1038/emi.2013.10.
Trepo, C., Chan, H. L., and Lok, A. (2014). Hepatitis B virus infection. Lancet. 384(9959), 2053-2063. DOI: 10.1016/S0140-6736(14)60220-8.

van Nunen, A. B., Baumann, M., Manns, M. P., Reichen, J., Spengler, U., Marschner, J. P., de Man, R. A., and International Study, G. (2001). Efficacy and safety of an intravenous monoclonal anti-HBs in chronic hepatitis B patients. Liver. 21(3), 207-212.

Venkatakrishnan, B., and Zlotnick, A. (2016). The Structural Biology of Hepatitis B Virus: Form and Function. Annu Rev Virol. 3(1), 429-451. DOI: 10.1146/annurev-virology-110615-042238.

von Boehmer, L., Liu, C., Ackerman, S., Gitlin, A. D., Wang, Q., Gazumyan, A., and Nussenzweig, M. C. (2016). Sequencing and cloning of antigen-specific antibodies from mouse memory B cells. Nat Protoc. 11(10), 1908-1923. DOI: 10.1038/nprot.2016.102.

Walker, L. M., Huber, M., Doores, K. J., Falkowska, E., Pejchal, R., Julien, J. P., Wang, S. K., Ramos, A., Chan-Hui, P. Y., Moyle, M., et al. (2011). Broad neutralization coverage of HIV by multiple highly potent antibodies. Nature. 477(7365), 466-470. DOI: 10.1038/nature10373.

Wang, W., Sun, L., Li, T., Ma, Y., Li, J., Liu, Y., Li, M., Wang, L., Li, C., Xie, Y., et al. (2016). A human monoclonal antibody against small envelope protein of hepatitis B virus with potent neutralization effect. MAbs. 8(3), 468-477. DOI: 10.1080/19420862.2015.1134409.

Wardemann, H., Yurasov, S., Schaefer, A., Young, J. W., Meffre, E., and Nussenzweig, M. C. (2003). Predominant autoantibody production by early human B cell precursors. Science. 301(5638), 1374-1377. DOI: 10.1126/science.1086907.

West, A. P., Jr., Diskin, R., Nussenzweig, M. C., and Bjorkman, P. J. (2012). Structural basis for germ-line gene usage of a potent class of antibodies targeting the CD4-binding site of HIV-1 gp120. Proc Natl Acad Sci USA. 109(30), E2083-2090. DOI: 10.1073/pnas.1208984109.

White, A. D., Keefe, A. J., Ella-Menye, J. R., Nowinski, A. K., Shao, Q., Pfaendtner, J., and Jiang, S. (2013). Free energy of solvated salt bridges: a simulation and experimental study. J Phys Chem B. 117(24), 7254-7259. DOI: 10.1021/jp4024469.

Wrammert, J., Koutsonanos, D., Li, G. M., Edupuganti, S., Sui, J., Morrissey, M., McCausland, M., Skountzou, I., Hornig, M., Lipkin, W. I., et al. (2011). Broadly cross-reactive antibodies dominate the human B cell response against 2009 pandemic H1N1 influenza virus infection. J Exp Med. 208(1), 181-193. DOI: 10.1084/jem.20101352.

Wu, X., Yang, Z. Y., Li, Y., Hogerkorp, C. M., Schief, W. R., Seaman, M. S., Zhou, T., Schmidt, S. D., Wu, L., Xu, L., et al. (2010). Rational design of envelope identifies broadly neutralizing human monoclonal antibodies to HIV-1. Science. 329(5993), 856-861. DOI: 10.1126/science.1187659.

Yan, H., Zhong, G., Xu, G., He, W., Jing, Z., Gao, Z., Huang, Y., Qi, Y., Peng, B., Wang, H., et al. (2012). Sodium taurocholate cotransporting polypeptide is a functional receptor for human hepatitis B and D virus. Elife. 1, e00049. DOI: 10.7554/eLife.00049.

Ye, B., Liu, X., Li, X., Kong, H., Tian, L., and Chen, Y. (2015). T-cell exhaustion in chronic hepatitis B infection: current knowledge and clinical significance. Cell Death Dis. 6, e1694. DOI: 10.1038/cddis.2015.42.

Ye, J., Ma, N., Madden, T. L., and Ostell, J. M. (2013). IgBLAST: an immunoglobulin variable domain sequence analysis tool. Nucleic Acids Res. 41 (Web Server issue), W34-40. DOI: 10.1093/nar/gkt382.

Yurasov, S., Wardemann, H., Hammersen, J., Tsuiji, M., Meffre, E., Pascual, V., and Nussenzweig, M. C. (2005). Defective B cell tolerance checkpoints in systemic lupus erythematosus. J Exp Med. 201(5), 703-711. DOI: 10.1084/jem.20042251.

Zanetti, A. R., Tanzi, E., Manzillo, G., Maio, G., Sbreglia, C., Caporaso, N., Thomas, H., and Zuckerman, A. J. (1988). Hepatitis B variant in Europe. Lancet. 2(8620), 1132-1133. DOI: 10.1016/s0140-6736(88)90541-7.

Zhang, T. Y., Guo, X. R., Wu, Y. T., Kang, X. Z., Zheng, Q. B., Qi, R. Y., Chen, B. B., Lan, Y., Wei, M., Wang, S. J., et al. (2019). A unique B cell epitope-based particulate vaccine shows effective suppression of hepatitis B surface antigen in mice. Gut. 69(2), 343-354. DOI: 10.1136/gutjnl-2018-317725.

Zhang, T. Y., Yuan, Q., Zhao, J. H., Zhang, Y. L., Yuan, L. Z., Lan, Y., Lo, Y. C., Sun, C. P., Wu, C. R., Zhang, J. F., et al. (2016). Prolonged suppression of HBV in mice by a novel antibody that targets a unique epitope on hepatitis B surface antigen. Gut. 65(4), 658-671. DOI: 10.1136/gutjnl-2014-308964.

Zhu, D., Liu, L., Yang, D., Fu, S., Bian, Y., Sun, Z., He, J., Su, L., Zhang, L., Peng, H., et al. (2016). Clearing Persistent Extracellular Antigen of Hepatitis B Virus: An Immunomodulatory Strategy To Reverse Tolerance for an Effective Therapeutic Vaccination. J Immunol. 196(7), 3079-3087. DOI: 10.4049/jimmunol.1502061.

SUPPLEMENTAL TABLE S1

Detailed information of donors, Related to FIG. 1.
The anti-HBs ELISA titer (x-axis in FIGS. 1A and 8B) and relative infection rate (y-axis in FIGS. 1A and 8B) of each donor's serum sample were determined by ELISA assay and in vitro neutralization assay, respectively.

| DONOR ID | ANTI-HBs ELISA TITER | STATUE | BIG BLOOD DRAW | INFECTION RATE (1:5 SERUM) PERCENTAGE OF HBcAg + CELLS | | | AVERAGE | NEUTRA CAPACITY | INFECTION RATE (1:50 SERUM) PERCENTAGE OF HBcAg + CELLS | | | AVERAGE | NEUTRA CAPACITY |
|---|---|---|---|---|---|---|---|---|---|---|---|---|---|
| QWA-0947-001 | 9.08 | Vaccinated | | 114.00 | 127.12 | 133.64 | 124.92 | 0.80 | 118.06 | 128.90 | 122.19 | 123.05 | 0.81 |
| QWA-0947-002 | 516.12 | Vaccinated | | 65.28 | 77.58 | 75.13 | 72.66 | 1.38 | 131.60 | 137.04 | 133.44 | 134.03 | 0.75 |
| QWA-0947-003 | 0 | Vaccinated | | 108.59 | 118.31 | 118.53 | 115.14 | 0.87 | 132.81 | 136.65 | 132.22 | 133.89 | 0.75 |

SUPPLEMENTAL TABLE S1-continued

Detailed information of donors, Related to FIG. 1.
The anti-HBs ELISA titer (x-axis in FIGS. 1A and 8B) and relative infection rate (y-axis in FIGS. 1A and 8B) of each donor's serum sample were determined by ELISA assay and in vitro neutralization assay, respectively.

| DONOR ID | ANTI-HBs ELISA TITER | STATUE | BIG BLOOD DRAW | INFECTION RATE (1:5 SERUM) PERCENTAGE OF HBcAg + CELLS | | | AVERAGE | NEUTRA CAPACITY | INFECTION RATE (1:50 SERUM) PERCENTAGE OF HBcAg + CELLS | | | AVERAGE | NEUTRA CAPACITY |
|---|---|---|---|---|---|---|---|---|---|---|---|---|---|
| QWA-0947-004 | 267.1 | Vaccinated | | 113.39 | 121.91 | 121.67 | 118.99 | 0.84 | 142.69 | 146.69 | 153.24 | 147.54 | 0.68 |
| QWA-0947-005 | 113.01 | Vaccinated | | 82.91 | 87.48 | 95.39 | 88.59 | 1.13 | 148.24 | 149.36 | 146.75 | 148.12 | 0.68 |
| QWA-0947-006 | 325.77 | Vaccinated | | 81.19 | 85.97 | 96.43 | 87.86 | 1.14 | 117.48 | 116.83 | 119.74 | 118.02 | 0.85 |
| QWA-0947-007 | 63.54 | Vaccinated | | 100.37 | 105.53 | 110.73 | 105.54 | 0.95 | 134.11 | 135.15 | 138.51 | 135.92 | 0.74 |
| QWA-0947-008 | 21.8 | Vaccinated | | 40.86 | 35.60 | 42.82 | 39.76 | 2.52 | 78.64 | 84.09 | 84.79 | 82.51 | 1.21 |
| QWA-0947-009 | >1000 | Vaccinated | BIG BLOOD DRAW | 12.84 | 14.39 | 17.20 | 14.81 | 6.75 | 34.66 | 38.81 | 33.48 | 35.65 | 2.81 |
| QWA-0947-010 | 0.33 | Vaccinated | | 93.33 | 93.42 | 104.91 | 97.22 | 1.03 | 105.41 | 116.72 | 115.58 | 112.57 | 0.89 |
| QWA-0947-011 | 1.29 | Vaccinated | BIG BLOOD DRAW | 109.40 | 113.87 | 94.10 | 105.79 | 0.95 | 95.79 | 93.25 | 81.95 | 90.33 | 1.11 |
| QWA-0947-012 | 12.87 | Vaccinated | | 102.04 | 102.94 | 108.81 | 104.60 | 0.96 | 142.95 | 137.95 | 125.12 | 135.34 | 0.74 |
| QWA-0947-013 | >1000 | Vaccinated | BIG BLOOD DRAW | 9.24 | 8.31 | 8.33 | 8.63 | 11.59 | 19.95 | 20.81 | 17.29 | 19.35 | 5.17 |
| QWA-0947-014 | 248.31 | Vaccinated | | 80.90 | 80.65 | 79.88 | 80.48 | 1.24 | 117.58 | 120.17 | 115.37 | 117.71 | 0.85 |
| QWA-0947-015 | 76.1 | Vaccinated | | 97.26 | 91.48 | 86.95 | 91.90 | 1.09 | 112.79 | 109.82 | 101.19 | 107.93 | 0.93 |
| QWA-0947-016 | 0.36 | Non-Vaccinated | | 100.22 | 96.77 | 95.84 | 97.61 | 1.02 | 118.04 | 120.05 | 117.34 | 118.48 | 0.84 |
| QWA-0947-017 | 0.63 | Vaccinated | | 100.30 | 102.98 | 101.55 | 101.61 | 0.98 | 122.27 | 119.42 | 110.93 | 117.54 | 0.85 |
| QWA-0947-018 | 3.24 | Vaccinated | | 101.65 | 113.38 | 96.98 | 104.00 | 0.96 | 118.18 | 121.26 | 107.05 | 115.50 | 0.87 |
| QWA-0947-019 | >1000 | Vaccinated | | 47.62 | 43.35 | 40.11 | 43.69 | 2.29 | 105.86 | 100.46 | 89.54 | 98.62 | 1.01 |
| QWA-0947-020 | 1.21 | Non-Vaccinated | | 77.13 | 75.25 | 60.04 | 70.81 | 1.41 | 116.28 | 113.72 | 108.65 | 112.88 | 0.89 |
| QWA-0947-021 | 15.81 | Vaccinated | | 33.85 | 41.39 | 34.98 | 36.74 | 2.72 | 89.74 | 89.87 | 88.60 | 89.40 | 1.12 |
| QWA-0947-022 | 2.17 | Vaccinated | | 83.52 | 94.22 | 93.88 | 90.54 | 1.10 | 100.08 | 119.88 | 110.19 | 110.05 | 0.91 |
| QWA-0947-023 | 183.37 | Vaccinated | | 93.15 | 119.57 | 116.08 | 109.60 | 0.91 | 113.43 | 117.91 | 103.45 | 111.60 | 0.90 |
| QWA-0947-024 | 256.85 | Vaccinated | | 55.70 | 60.03 | 49.13 | 54.95 | 1.82 | 104.68 | 116.21 | 105.17 | 108.69 | 0.92 |
| QWA-0947-025 | 709.29 | Vaccinated | | 76.18 | 77.38 | 75.01 | 76.19 | 1.31 | 100.58 | 105.57 | 116.82 | 107.66 | 0.93 |
| QWA-0947-026 | 0.49 | Non-Vaccinated | | 83.02 | 102.42 | 96.98 | 94.14 | 1.06 | 104.24 | 117.09 | 105.73 | 109.02 | 0.92 |

SUPPLEMENTAL TABLE S1-continued

Detailed information of donors, Related to FIG. 1.
The anti-HBs ELISA titer (x-axis in FIGS. 1A and 8B) and relative infection rate (y-axis in FIGS. 1A and 8B) of each donor's serum sample were determined by ELISA assay and in vitro neutralization assay, respectively.

| DONOR ID | ANTI-HBs ELISA TITER | STATUE | BIG BLOOD DRAW | INFECTION RATE (1:5 SERUM) PERCENTAGE OF HBcAg + CELLS | | | AVERAGE | NEUTRA CAPACITY | INFECTION RATE (1:50 SERUM) PERCENTAGE OF HBcAg + CELLS | | | AVERAGE | NEUTRA CAPACITY |
|---|---|---|---|---|---|---|---|---|---|---|---|---|---|
| QWA-0947-027 | 0.3 | Non-Vaccinated | BIG BLOOD DRAW | 103.51 | 128.79 | 114.82 | 115.71 | 0.86 | 105.91 | 126.68 | 117.03 | 116.54 | 0.86 |
| QWA-0947-028 | 6.51 | Non-Vaccinated | | 84.03 | 90.88 | 87.77 | 87.56 | 1.14 | 107.23 | 117.89 | 108.21 | 111.11 | 0.90 |
| QWA-0947-029 | 1.67 | Non-Vaccinated | | 103.72 | 98.68 | 83.74 | 95.38 | 1.05 | 96.06 | 102.25 | 100.20 | 99.50 | 1.00 |
| QWA-0947-030 | 0.09 | Vaccinated | BIG BLOOD DRAW | 86.06 | 84.44 | 91.73 | 87.41 | 1.14 | 111.74 | 115.73 | 102.26 | 109.91 | 0.91 |
| QWA-0947-031 | 488.3 | Core Ab + | | 71.30 | 66.21 | 56.71 | 64.74 | 1.54 | 94.99 | 102.87 | 94.27 | 97.38 | 1.03 |
| QWA-0947-032 | >1000 | Vaccinated | | 71.12 | 67.87 | 56.53 | 65.17 | 1.53 | 97.45 | 107.81 | 106.59 | 103.95 | 0.96 |
| QWA-0947-033 | 330.93 | Vaccinated | | 99.61 | 93.60 | 87.25 | 93.49 | 1.07 | 106.28 | 116.65 | 108.45 | 110.46 | 0.91 |
| QWA-0947-034 | 588.26 | Core Ab + | | 40.92 | 41.19 | 35.30 | 39.14 | 2.56 | 99.54 | 111.16 | 105.28 | 105.32 | 0.95 |
| QWA-0947-035 | 365.7 | Vaccinated | | 101.52 | 113.83 | 94.76 | 103.37 | 0.97 | 129.77 | 131.60 | 121.19 | 127.52 | 0.78 |
| QWA-0947-036 | 108.83 | Vaccinated | | 87.55 | 85.69 | 77.65 | 83.63 | 1.20 | 122.28 | 122.03 | 107.69 | 117.33 | 0.85 |
| QWA-0947-037 | >1000 | Vaccinated | | 23.79 | 21.09 | 18.46 | 21.11 | 4.74 | 66.02 | 59.97 | 52.64 | 59.54 | 1.68 |
| QWA-0947-038 | 11.76 | Vaccinated | | 94.89 | 95.53 | 96.87 | 95.76 | 1.04 | 119.79 | 125.09 | 115.27 | 120.05 | 0.83 |
| QWA-0947-039 | 230.99 | Vaccinated | | 102.08 | 99.23 | 91.54 | 97.62 | 1.02 | 113.01 | 115.04 | 98.95 | 109.00 | 0.92 |
| QWA-0947-040 | 0.26 | Vaccinated | | 54.12 | 57.38 | 45.32 | 52.27 | 1.91 | 102.43 | 107.89 | 95.37 | 101.90 | 0.98 |
| QWA-0947-041 | 0.42 | Non-Vaccinated | | 77.09 | 78.29 | 84.91 | 80.09 | 1.25 | 87.59 | 101.25 | 101.19 | 96.68 | 1.03 |
| QWA-0947-042 | 128.75 | Core Ab + | | 97.03 | 106.51 | 110.26 | 104.60 | 0.96 | 114.07 | 149.01 | 121.98 | 128.35 | 0.78 |
| QWA-0947-043 | 229.75 | Core Ab + | | 78.56 | 94.35 | 95.71 | 89.54 | 1.12 | 95.18 | 144.23 | 123.82 | 121.08 | 0.83 |
| QWA-0947-044 | 222.48 | Core Ab + | | 45.85 | 56.61 | 65.34 | 55.93 | 1.79 | 94.00 | 133.96 | 109.86 | 112.60 | 0.89 |
| QWA-0947-045 | >1000 | Core Ab + | | 51.82 | 66.02 | 61.55 | 59.80 | 1.67 | 104.36 | 122.03 | 120.96 | 115.78 | 0.86 |
| QWA-0947-046 | 350.93 | Vaccinated | | 89.57 | 99.40 | 111.55 | 100.17 | 1.00 | 100.98 | 129.50 | 111.79 | 114.09 | 0.88 |
| QWA-0947-047 | 0.33 | Vaccinated | | 126.88 | 138.30 | 142.37 | 135.85 | 0.74 | 112.35 | 156.77 | 127.72 | 132.28 | 0.76 |
| QWA-0947-048 | >1000 | Vaccinated | BIG BLOOD DRAW | 35.94 | 44.44 | 46.02 | 42.14 | 2.37 | 83.08 | 109.89 | 94.60 | 95.86 | 1.04 |
| QWA-0947-049 | >1000 | Core Ab + | BIG BLOOD DRAW | 94.21 | 120.65 | 119.57 | 111.48 | 0.90 | 113.33 | 139.10 | 126.43 | 126.28 | 0.79 |

SUPPLEMENTAL TABLE S1-continued

Detailed information of donors, Related to FIG. 1. The anti-HBs ELISA titer (x-axis in FIGS. 1A and 8B) and relative infection rate (y-axis in FIGS. 1A and 8B) of each donor's serum sample were determined by ELISA assay and in vitro neutralization assay, respectively.

| DONOR ID | ANTI-HBs ELISA TITER | STATUE | BIG BLOOD DRAW | INFECTION RATE (1:5 SERUM) PERCENTAGE OF HBcAg + CELLS | | | AVERAGE | NEUTRA CAPACITY | INFECTION RATE (1:50 SERUM) PERCENTAGE OF HBcAg + CELLS | | | AVERAGE | NEUTRA CAPACITY |
|---|---|---|---|---|---|---|---|---|---|---|---|---|---|
| QWA-0947-050 | 6.2 | Vaccinated | | 93.10 | 114.26 | 113.58 | 106.98 | 0.93 | 93.34 | 121.07 | 112.91 | 109.10 | 0.92 |
| QWA-0947-051 | 228.35 | Vaccinated | | 111.78 | 112.69 | 115.97 | 113.48 | 0.88 | 104.71 | 102.64 | 83.60 | 96.98 | 1.03 |
| QWA-0947-052 | 2.77 | Vaccinated | | 116.53 | 115.59 | 110.83 | 114.32 | 0.87 | 113.48 | 114.25 | 125.60 | 117.78 | 0.85 |
| QWA-0947-053 | 48.25 | Vaccinated | | 114.90 | 112.78 | 98.40 | 108.69 | 0.92 | 105.04 | 116.61 | 119.01 | 113.55 | 0.88 |
| QWA-0947-054 | 24.06 | Vaccinated | | 121.56 | 125.13 | 111.71 | 119.47 | 0.84 | 99.64 | 118.99 | 122.11 | 113.58 | 0.88 |
| QWA-0947-055 | 772.43 | Core Ab + | BIG BLOOD DRAW | 8.79 | 9.33 | 5.78 | 7.97 | 12.55 | 82.33 | 95.93 | 87.80 | 88.69 | 1.13 |
| QWA-0947-056 | 441.12 | Vaccinated | | 86.57 | 86.67 | 79.10 | 84.12 | 1.19 | 98.81 | 120.31 | 116.13 | 111.75 | 0.89 |
| QWA-0947-057 | 91.37 | Vaccinated | | 120.46 | 113.18 | 110.80 | 114.82 | 0.87 | 111.45 | 107.08 | 116.80 | 111.78 | 0.89 |
| QWA-0947-058 | >1000 | Vaccinated | | 27.66 | 27.74 | 26.37 | 27.26 | 3.67 | 82.86 | 83.73 | 74.74 | 80.44 | 1.24 |
| QWA-0947-059 | 83.28 | Vaccinated | | 110.69 | 109.95 | 99.34 | 106.66 | 0.94 | 115.21 | 115.69 | 99.96 | 110.29 | 0.91 |
| QWA-0947-060 | >1000 | Vaccinated | BIG BLOOD DRAW | 5.68 | 6.72 | 5.17 | 5.86 | 17.08 | 25.39 | 26.65 | 24.93 | 25.66 | 3.90 |
| QWA-0947-061 | 104.78 | Vaccinated | | 109.98 | 120.25 | 131.62 | 120.61 | 0.83 | 107.59 | 134.01 | 124.63 | 122.08 | 0.82 |
| QWA-0947-062 | 2.56 | Vaccinated | | 113.16 | 140.19 | 143.78 | 132.38 | 0.76 | 120.58 | 139.98 | 135.32 | 131.96 | 0.76 |
| QWA-0947-063 | 246.16 | Vaccinated | | 101.93 | 112.01 | 141.39 | 118.44 | 0.84 | 114.71 | 134.13 | 143.18 | 130.67 | 0.77 |
| QWA-0947-064 | Not Available | Vaccinated | | 128.17 | 114.29 | 147.09 | 129.85 | 0.77 | 133.50 | 133.31 | 133.23 | 133.35 | 0.75 |
| QWA-0947-065 | 0.28 | Core Ab + | | 112.39 | 133.12 | 155.43 | 133.65 | 0.75 | 131.76 | 134.78 | 150.74 | 139.09 | 0.72 |
| QWA-0947-066 | 265.6 | Vaccinated | | 50.87 | 68.37 | 86.59 | 68.61 | 1.46 | 129.24 | 133.43 | 119.16 | 127.28 | 0.79 |
| QWA-0947-067 | 0 | Vaccinated | | 106.36 | 120.57 | 150.56 | 125.83 | 0.79 | 122.57 | 142.42 | 139.51 | 134.84 | 0.74 |
| QWA-0947-068 | 0.25 | Vaccinated | | 58.26 | 87.26 | 105.25 | 83.59 | 1.20 | 123.65 | 128.77 | 124.58 | 125.67 | 0.80 |
| QWA-0947-069 | >1000 | Vaccinated | BIG BLOOD DRAW | 11.42 | 27.20 | 22.32 | 20.31 | 4.92 | 50.80 | 55.44 | 64.27 | 56.84 | 1.76 |
| QWA-0947-070 | 7.01 | Vaccinated | | 107.39 | 113.96 | 138.16 | 119.84 | 0.83 | 118.06 | 116.97 | 118.95 | 117.99 | 0.85 |
| QWA-0947-071 | 638.24 | Vaccinated | | 56.39 | 48.55 | 55.42 | 53.45 | 1.87 | 94.83 | 111.19 | 117.23 | 107.75 | 0.93 |
| QWA-0947-072 | 15.55 | Vaccinated | | 128.74 | 135.08 | 126.34 | 130.05 | 0.77 | 137.00 | 132.93 | 122.94 | 130.96 | 0.76 |

SUPPLEMENTAL TABLE S1-continued

Detailed information of donors, Related to FIG. 1.
The anti-HBs ELISA titer (x-axis in FIGS. 1A and 8B) and relative infection rate (y-axis in FIGS. 1A and 8B) of each donor's serum sample were determined by ELISA assay and in vitro neutralization assay, respectively.

| DONOR ID | ANTI-HBs ELISA TITER | STATUE | BIG BLOOD DRAW | INFECTION RATE (1:5 SERUM) PERCENTAGE OF HBcAg + CELLS | | | AVERAGE | NEUTRA CAPACITY | INFECTION RATE (1:50 SERUM) PERCENTAGE OF HBcAg + CELLS | | | AVERAGE | NEUTRA CAPACITY |
|---|---|---|---|---|---|---|---|---|---|---|---|---|---|
| QWA-0947-073 | 225.34 | Vaccinated | | 131.87 | 122.33 | 137.50 | 130.57 | 0.77 | 137.43 | 128.35 | 124.59 | 130.12 | 0.77 |
| QWA-0947-074 | 159.52 | Core Ab + | | 120.51 | 119.04 | 128.75 | 122.76 | 0.81 | 140.98 | 130.18 | 124.00 | 131.72 | 0.76 |
| QWA-0947-075 | 0.37 | Vaccinated | | 131.78 | 125.05 | 159.51 | 138.78 | 0.72 | 133.08 | 135.29 | 117.74 | 128.70 | 0.78 |
| QWA-0947-076 | 27.37 | Vaccinated | | 137.32 | 145.89 | | 141.60 | 0.71 | 132.06 | | | 132.06 | 0.76 |
| QWA-0947-077 | 52.77 | Vaccinated | | 112.72 | 121.48 | | 117.10 | 0.85 | 137.12 | | | 137.12 | 0.73 |
| QWA-0947-078 | 181.6 | Vaccinated | | 116.16 | 107.29 | | 111.72 | 0.90 | 138.30 | 131.27 | | 134.79 | 0.74 |
| QWA-0947-079 | >1000 | Vaccinated | | 54.73 | 59.28 | 71.14 | 61.72 | 1.62 | 130.53 | 128.66 | 118.32 | 125.84 | 0.79 |
| QWA-0947-080 | >1000 | Vaccinated | | 62.38 | 53.55 | 69.34 | 61.76 | 1.62 | 122.37 | 106.42 | | 114.40 | 0.87 |
| QWA-0947-081 | 7.23 | Vaccinated | | 113.81 | 111.55 | 142.59 | 122.65 | 0.82 | 109.38 | 105.63 | 116.78 | 110.60 | 0.90 |
| QWA-0947-082 | 24.98 | Vaccinated | | 120.69 | 124.58 | 118.10 | 121.12 | 0.83 | 106.45 | 118.55 | 117.79 | 114.26 | 0.88 |
| QWA-0947-083 | 90.5 | Vaccinated | | 84.79 | 87.62 | 99.65 | 90.69 | 1.10 | 91.86 | 99.93 | 105.67 | 99.15 | 1.01 |
| QWA-0947-084 | 880.92 | Core Ab + | | 112.81 | 125.10 | 114.29 | 117.40 | 0.85 | 106.78 | 7.78 | 147.46 | 124.01 | 0.81 |
| QWA-0947-085 | 82.25 | Vaccinated | | 120.45 | 148.83 | 159.96 | 143.08 | 0.70 | 114.14 | 114.33 | 136.45 | 121.64 | 0.82 |
| QWA-0947-086 | 19.16 | Vaccinated | | 147.29 | 173.59 | 166.75 | 162.55 | 0.62 | 110.03 | 128.28 | 120.46 | 119.59 | 0.84 |
| QWA-0947-087 | 88.6 | Vaccinated | | 126.58 | 146.46 | 145.74 | 139.59 | 0.72 | 105.86 | 119.12 | 119.22 | 114.74 | 0.87 |
| QWA-0947-088 | 288.42 | Core Ab + | | 108.25 | 120.39 | 140.09 | 122.91 | 0.81 | 90.55 | 101.28 | 115.15 | 102.33 | 0.98 |
| QWA-0947-089 | 15.74 | Vaccinated | | 101.12 | 94.87 | 98.43 | 98.14 | 1.02 | 75.70 | 96.65 | 111.21 | 94.52 | 1.06 |
| QWA-0947-090 | >1000 | Vaccinated | | 54.59 | 47.73 | 53.63 | 51.99 | 1.92 | 71.09 | 87.31 | 99.22 | 85.87 | 1.16 |
| QWA-0947-091 | >1000 | Vaccinated | | 18.28 | 23.05 | 19.85 | 20.39 | 4.90 | 48.17 | 59.50 | 53.15 | 53.61 | 1.87 |
| QWA-0947-093 | 2.64 | Vaccinated | | 155.82 | 147.87 | 143.25 | 148.98 | 0.67 | 126.83 | 113.67 | 124.04 | 121.51 | 0.82 |
| QWA-0947-094 | 127.58 | Vaccinated | | 160.76 | 145.63 | 119.61 | 142.00 | 0.70 | 105.84 | 110.91 | 114.14 | 110.30 | 0.91 |
| QWA-0947-095 | 23.74 | Vaccinated | | 176.74 | 160.65 | 159.27 | 165.55 | 0.60 | 110.83 | 103.36 | 112.17 | 108.78 | 0.92 |
| QWA-0947-096 | >1000 | Vaccinated | | 51.24 | 50.60 | 36.36 | 46.07 | 2.17 | 109.95 | 99.89 | 100.76 | 103.54 | 0.97 |

SUPPLEMENTAL TABLE S1-continued

Detailed information of donors, Related to FIG. 1.
The anti-HBs ELISA titer (x-axis in FIGS. 1A and 8B) and relative infection rate (y-axis in FIGS. 1A and 8B) of each donor's serum sample were determined by ELISA assay and in vitro neutralization assay, respectively.

| DONOR ID | ANTI-HBs ELISA TITER | STATUE | BIG BLOOD DRAW | INFECTION RATE (1:5 SERUM) PERCENTAGE OF HBcAg + CELLS | | | AVERAGE | NEUTRA CAPACITY | INFECTION RATE (1:50 SERUM) PERCENTAGE OF HBcAg + CELLS | | | AVERAGE | NEUTRA CAPACITY |
|---|---|---|---|---|---|---|---|---|---|---|---|---|---|
| QWA-0947-097 | 25.97 | Vaccinated | | 151.86 | 144.37 | 127.26 | 141.16 | 0.71 | 109.63 | 109.86 | 98.50 | 106.00 | 0.94 |
| QWA-0947-098 | >1000 | Vaccinated | | 73.82 | 83.70 | 70.82 | 76.11 | 1.31 | 88.55 | 95.98 | 100.28 | 94.94 | 1.05 |
| QWA-0947-099 | 688.28 | Vaccinated | BIG BLOOD DRAW | 110.48 | 112.47 | 90.05 | 104.33 | 0.96 | 100.29 | 103.59 | 94.65 | 99.51 | 1.00 |
| QWA-0947-100 | 366.05 | Vaccinated | | 85.68 | 99.38 | 86.23 | 90.43 | 1.11 | 97.85 | 101.09 | 85.62 | 94.85 | 1.05 |
| QWA-0947-101 | 1.22 | Vaccinated | | 88.54 | 96.48 | 92.77 | 92.60 | 1.08 | 107.51 | 104.47 | 106.69 | 106.22 | 0.94 |
| QWA-0947-102 | 0.65 | Vaccinated | | 96.90 | 94.97 | 99.88 | 97.25 | 1.03 | 109.63 | 101.73 | 102.43 | 104.60 | 0.96 |
| QWA-0947-103 | 45.53 | Core Ab + | | 100.38 | 104.13 | 93.37 | 99.29 | 1.01 | 103.40 | 95.77 | 93.83 | 97.67 | 1.02 |
| QWA-0947-104 | 95.76 | Vaccinated | | 95.99 | 87.67 | 79.38 | 87.68 | 1.14 | 111.24 | 105.95 | 113.01 | 110.07 | 0.91 |
| QWA-0947-105 | 1.48 | Vaccinated | | 42.47 | 43.05 | 47.61 | 44.38 | 2.25 | 102.15 | 99.45 | 98.24 | 99.95 | 1.00 |
| QWA-0947-106 | >1000 | Vaccinated | | 16.40 | 16.66 | 16.15 | 16.40 | 6.10 | 64.77 | 68.47 | 66.59 | 66.61 | 1.50 |
| QWA-0947-107 | 32.84 | Vaccinated | | 148.16 | 141.65 | 127.35 | 139.05 | 0.72 | 123.79 | 119.06 | 104.81 | 115.89 | 0.86 |
| QWA-0947-108 | 352.99 | Vaccinated | | 78.23 | 81.50 | 84.50 | 81.41 | 1.23 | 109.31 | 116.46 | 103.38 | 109.72 | 0.91 |
| QWA-0947-109 | 15.04 | Vaccinated | | 112.45 | 103.15 | 97.70 | 104.43 | 0.96 | 110.85 | 121.08 | 117.28 | 116.40 | 0.86 |
| QWA-0947-110 | 26.27 | Vaccinated | | 86.31 | 102.24 | 99.68 | 96.08 | 1.04 | 115.57 | 130.13 | 116.61 | 120.77 | 0.83 |
| QWA-0947-111 | 40.79 | Vaccinated | | 81.44 | 86.98 | 87.80 | 85.40 | 1.17 | 109.93 | 98.54 | 91.77 | 100.08 | 1.00 |
| QWA-0947-112 | 260.82 | Core Ab + | | 35.62 | 36.63 | 32.67 | 34.97 | 2.86 | 69.44 | 65.66 | 65.06 | 66.72 | 1.50 |
| QWA-0947-113 | 1.97 | Vaccinated | | 93.25 | 98.77 | 81.76 | 91.26 | 1.10 | 101.75 | 104.27 | 100.12 | 102.05 | 0.98 |
| QWA-0947-114 | >1000 | Vaccinated | | 32.49 | 27.64 | 25.33 | 28.49 | 3.51 | 80.93 | 61.56 | 71.59 | 71.36 | 1.40 |
| QWA-0947-115 | 798.12 | Core Ab + | | 13.86 | 14.67 | 15.02 | 14.52 | 6.89 | 45.62 | 46.82 | 42.16 | 44.87 | 2.23 |
| QWA-0947-116 | 459.84 | Vaccinated | | 99.96 | 93.67 | 81.32 | 91.65 | 1.09 | 107.55 | 108.08 | 109.31 | 108.31 | 0.92 |
| QWA-0947-117 | 0.46 | Vaccinated | | 98.06 | 92.72 | 95.42 | 95.40 | 1.05 | 106.12 | 104.66 | 111.74 | 107.51 | 0.93 |
| QWA-0947-118 | 20.87 | Vaccinated | | 151.82 | 146.04 | 144.65 | 147.50 | 0.68 | 112.36 | 109.15 | 124.29 | 115.26 | 0.87 |
| QWA-0947-119 | 91.47 | Vaccinated | | 114.36 | 109.63 | 108.87 | 110.96 | 0.90 | 108.91 | 112.79 | 104.89 | 108.86 | 0.92 |

SUPPLEMENTAL TABLE S1-continued

Detailed information of donors, Related to FIG. 1.
The anti-HBs ELISA titer (x-axis in FIGS. 1A and 8B) and relative infection rate (y-axis in FIGS. 1A and 8B) of each donor's serum sample were determined by ELISA assay and in vitro neutralization assay, respectively.

| DONOR ID | ANTI-HBs ELISA TITER | STATUE | BIG BLOOD DRAW | INFECTION RATE (1:5 SERUM) PERCENTAGE OF HBcAg + CELLS | | | AVERAGE | NEUTRA CAPACITY | INFECTION RATE (1:50 SERUM) PERCENTAGE OF HBcAg + CELLS | | | AVERAGE | NEUTRA CAPACITY |
|---|---|---|---|---|---|---|---|---|---|---|---|---|---|
| QWA-0947-120 | 13 | Core Ab + | | 44.97 | 45.06 | 40.30 | 43.44 | 2.30 | 102.35 | 110.61 | 97.70 | 103.55 | 0.97 |
| QWA-0947-121 | 175.21 | Vaccinated | | 91.44 | 91.91 | 96.95 | 93.43 | 1.07 | 166.31 | 164.27 | 144.97 | 158.52 | 0.63 |
| QWA-0947-122 | 51.51 | Vaccinated | | 95.47 | 92.45 | 100.97 | 96.30 | 1.04 | 180.79 | 174.92 | 143.73 | 166.48 | 0.60 |
| QWA-0947-123 | 36.81 | Vaccinated | | 145.77 | 156.75 | 146.88 | 149.80 | 0.67 | 180.84 | 176.71 | 135.18 | 164.24 | 0.61 |
| QWA-0947-124 | 1.3 | Vaccinated | | 147.11 | 133.31 | 131.87 | 137.43 | 0.73 | 170.89 | 169.84 | 127.57 | 156.10 | 0.64 |
| QWA-0947-125 | 1.44 | Vaccinated | | 110.99 | 111.85 | 118.19 | 113.68 | 0.88 | 178.09 | 178.48 | 149.45 | 168.67 | 0.59 |
| QWA-0947-126 | 359.06 | Core Ab + | | 79.16 | 76.31 | 85.67 | 80.83 | 1.24 | 167.98 | 161.85 | 154.57 | 161.47 | 0.62 |
| QWA-0947-127 | 1.23 | Non-Vaccinated | | 128.75 | 125.40 | 143.54 | 132.56 | 0.75 | 162.01 | 157.22 | 139.08 | 152.77 | 0.65 |
| QWA-0947-128 | >1000 | Vaccinated | | 30.63 | 25.86 | 36.31 | 30.94 | 3.23 | 69.73 | 82.09 | 84.44 | 78.76 | 1.27 |
| QWA-0947-129 | 0.17 | Non-Vaccinated | | 166.56 | 156.86 | 157.89 | 160.44 | 0.62 | 162.24 | 168.18 | 154.52 | 161.65 | 0.62 |
| QWA-0947-131 | 11.81 | Vaccinated | | 143.14 | 129.67 | 114.98 | 129.26 | 0.77 | 156.94 | 144.37 | 119.26 | 140.19 | 0.71 |
| QWA-0947-132 | 0 | Non-Vaccinated | | 143.37 | 148.51 | 134.41 | 142.09 | 0.70 | 170.72 | 146.03 | 126.56 | 147.77 | 0.68 |
| QWA-0947-133 | 731.27 | Core Ab + | | 86.48 | 85.37 | 78.16 | 83.34 | 1.20 | 157.64 | 137.87 | 131.07 | 142.20 | 0.70 |
| QWA-0947-134 | >1000 | Vaccinated | | 31.62 | 30.52 | 27.60 | 29.92 | 3.34 | 144.36 | 137.82 | 115.14 | 132.44 | 0.76 |
| QWA-0947-135 | 796.93 | Core Ab + | | 81.56 | 81.84 | 88.25 | 83.88 | 1.19 | 157.58 | 142.42 | 116.84 | 138.95 | 0.72 |
| QWA-0947-136 | 0 | Non-Vaccinated | | 128.19 | 132.95 | 139.91 | 133.68 | 0.75 | 165.85 | 140.56 | 137.58 | 148.00 | 0.68 |
| QWA-0947-137 | 1.56 | Non-Vaccinated | | 155.09 | 151.93 | 137.05 | 148.02 | 0.68 | 175.51 | 155.22 | 128.75 | 153.16 | 0.65 |
| QWA-0947-138 | 0.74 | Non-Vaccinated | | 160.76 | 159.87 | 135.61 | 152.08 | 0.66 | 165.30 | 137.96 | 119.52 | 140.93 | 0.71 |
| QWA-0947-139 | 0 | Non-Vaccinated | | 143.96 | 145.71 | 123.98 | 137.88 | 0.73 | 143.82 | 125.60 | 114.22 | 127.88 | 0.78 |
| QWA-0947-140 | 609.46 | Core Ab + | | 93.61 | 96.21 | 89.99 | 93.27 | 1.07 | 125.42 | 135.92 | 106.58 | 122.64 | 0.82 |
| QWA-0947-141 | >1000 | Vaccinated | | 35.14 | 37.74 | 36.31 | 36.40 | 2.75 | 90.32 | 87.71 | 83.80 | 87.28 | 1.15 |
| QWA-0947-142 | 0.01 | Non-Vaccinated | | 72.39 | 72.79 | 69.24 | 71.47 | 1.40 | 85.86 | 89.49 | 80.98 | 85.44 | 1.17 |
| QWA-0947-143 | 51.9 | Vaccinated | | 83.85 | 74.96 | 78.42 | 79.07 | 1.26 | 89.70 | 83.02 | 81.24 | 84.65 | 1.18 |

SUPPLEMENTAL TABLE S1-continued

Detailed information of donors, Related to FIG. 1.
The anti-HBs ELISA titer (x-axis in FIGS. 1A and 8B) and relative infection rate (y-axis in FIGS. 1A and 8B) of each donor's serum sample were determined by ELISA assay and in vitro neutralization assay, respectively.

| DONOR ID | ANTI-HBs ELISA TITER | STATUE | BIG BLOOD DRAW | INFECTION RATE (1:5 SERUM) PERCENTAGE OF HBcAg + CELLS | | | AVERAGE | NEUTRA CAPACITY | INFECTION RATE (1:50 SERUM) PERCENTAGE OF HBcAg + CELLS | | | AVERAGE | NEUTRA CAPACITY |
|---|---|---|---|---|---|---|---|---|---|---|---|---|---|
| QWA-0947-144 | 192.41 | Vaccinated | | 99.03 | 103.75 | 104.69 | 102.49 | 0.98 | 88.00 | 80.96 | 100.21 | 89.73 | 1.11 |
| QWA-0947-145 | >1000 | Vaccinated | | 35.23 | 36.75 | 36.99 | 36.32 | 2.75 | 91.40 | 83.04 | 84.37 | 86.27 | 1.16 |
| QWA-0947-146 | >1000 | Vaccinated | BIG BLOOD DRAW | 3.21 | 3.17 | 3.47 | 3.28 | 30.45 | 4.66 | 4.45 | 3.82 | 4.31 | 23.18 |
| QWA-0947-147 | >1000 | Vaccinated | | 74.42 | 79.63 | 70.02 | 74.69 | 1.34 | 96.43 | 89.82 | 90.93 | 92.39 | 1.08 |
| QWA-0947-149 | >1000 | Vaccinated | | 48.09 | 53.38 | 53.47 | 51.65 | 1.94 | 85.58 | 89.74 | 84.49 | 86.60 | 1.15 |
| QWA-0947-150 | >1000 | Vaccinated | | 45.84 | 50.91 | 49.78 | 48.84 | 2.05 | 97.27 | 93.55 | 92.90 | 94.57 | 1.06 |
| QWA-0947-151 | 24.03 | Vaccinated | | 76.16 | 78.93 | 83.53 | 79.54 | 1.26 | 104.49 | 103.12 | 97.68 | 101.76 | 0.98 |
| QWA-0947-152 | 32.89 | Vaccinated | | 76.50 | 74.31 | 58.42 | 69.75 | 1.43 | 80.82 | 81.72 | 78.43 | 80.33 | 1.24 |
| QWA-0947-153 | 0.36 | Vaccinated | | 92.38 | 95.06 | 83.56 | 90.33 | 1.11 | 81.13 | 82.29 | 70.79 | 78.07 | 1.28 |
| QWA-0947-154 | 8.02 | Vaccinated | | 81.20 | 78.04 | 61.49 | 73.58 | 1.36 | 89.89 | 80.29 | 72.54 | 80.90 | 1.24 |
| QWA-0947-155 | 271.68 | Vaccinated | | 83.98 | 86.99 | 69.06 | 80.01 | 1.25 | 79.14 | 80.93 | 74.47 | 78.18 | 1.28 |
| QWA-0947-156 | >1000 | Vaccinated | | 23.65 | 20.82 | 15.97 | 20.15 | 4.96 | 78.25 | 75.10 | 58.66 | 70.67 | 1.42 |
| QWA-0947-157 | 93.05 | Vaccinated | | 93.75 | 95.02 | 83.23 | 90.67 | 1.10 | 77.02 | 80.62 | 70.27 | 75.97 | 1.32 |
| QWA-0947-158 | 261.09 | Vaccinated | | 78.75 | 78.50 | 64.50 | 73.92 | 1.35 | 88.22 | 86.79 | 71.09 | 82.03 | 1.22 |
| QWA-0947-159 | 61.12 | Vaccinated | | 87.14 | 91.02 | 76.00 | 84.72 | 1.18 | 80.77 | 86.19 | 74.40 | 80.45 | 1.24 |
| QWA-0947-160 | 381.69 | Vaccinated | | 72.70 | 68.79 | 62.46 | 67.98 | 1.47 | 81.13 | 74.64 | 66.11 | 73.96 | 1.35 |
| QWA-0947-161 | 3.62 | Vaccinated | | 91.93 | 85.42 | 72.87 | 83.40 | 1.20 | 85.76 | 80.35 | 74.62 | 80.24 | 1.25 |
| QWA-0947-162 | 198.58 | Vaccinated | | 91.35 | 92.25 | 79.20 | 87.60 | 1.14 | 112.63 | 106.14 | 95.29 | 104.69 | 0.96 |

SUPPLEMENTAL TABLE S2

Figure 2:
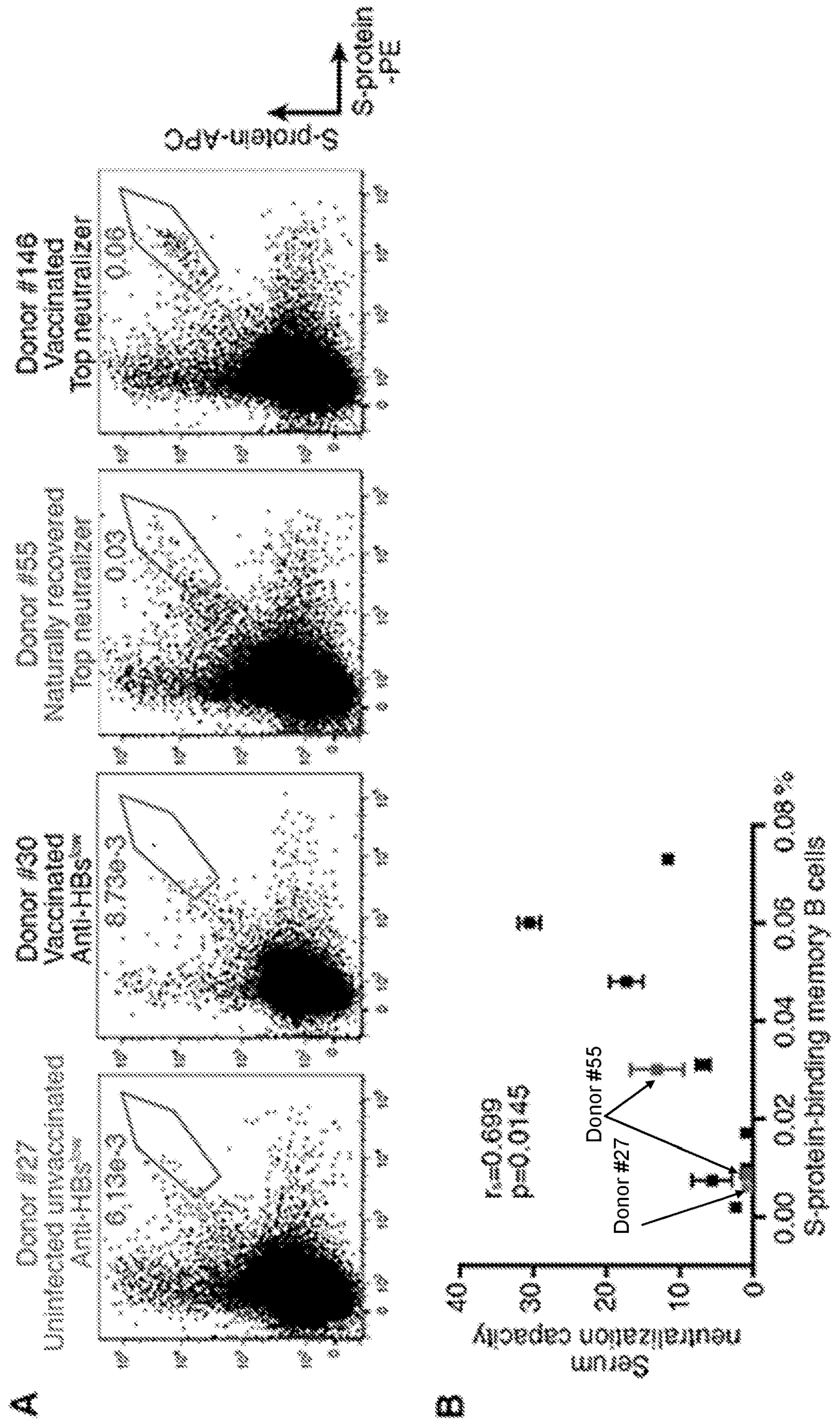
FIG. 2. S-protein-specific antibodies. (A) Frequency of S-protein-specific memory B cells. Representative flow cytometry plots displaying the percentage of all $IgG^+$ memory B cells that bind to both allophycocyanin- and phycoerythrin-tagged S-protein (S-protein-APC and S-protein-PE). Flow cytometry plots from other individuals are shown in FIG. 9A. Experiments were repeated two times. (B) Dot plot showing the correlation between the frequency of S-protein-binding $IgG^+$ memory B cells and the serum neutralizing activity. Spearman's rank correlation coefficient ($r_s$) and significance value (p). (C) Each pie chart represents the antibodies from an individual donor, and the total number of sequenced antibodies with paired heavy and light chains is indicated in the center. Antibodies with the same combination of IGH and IGL variable gene sequences and closely related CDR3s in each individual are shown. The slices with the same color indicate shared antibodies with the same or similar combination of IGH and IGL variable genes between individuals (FIG. 9B). Grey slices indicate antibodies with closely related sequences that are unique to a single donor. In white are singlets. (D) V(D)J alignments for representative IGHV3-30/IGLV3-21, IGHV3-33/IGLV3-21 and IGHV3-23/IGLV3-21 antibodies from donors #60/#146 (H006 and H008), #146/#13 (H014 and H012), and #13/#60/#146 (H021, H003 and H004) respectively. Boxed grey residues are shared between antibodies. See also FIG. 9 and Table S2. Figure discloses SEQ ID NOS 1438-1451, respectively, in order of appearance.
Figure 2:
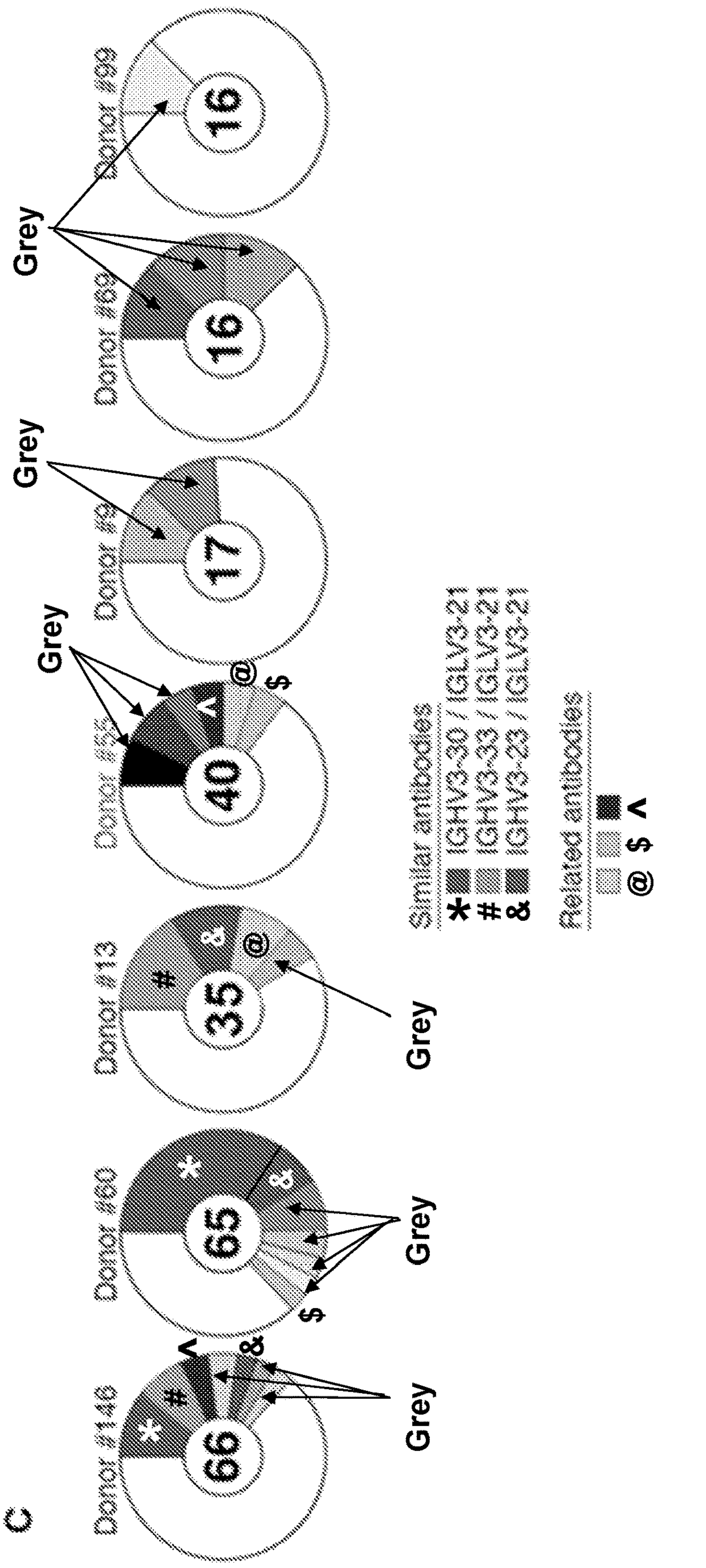
Figure 2:
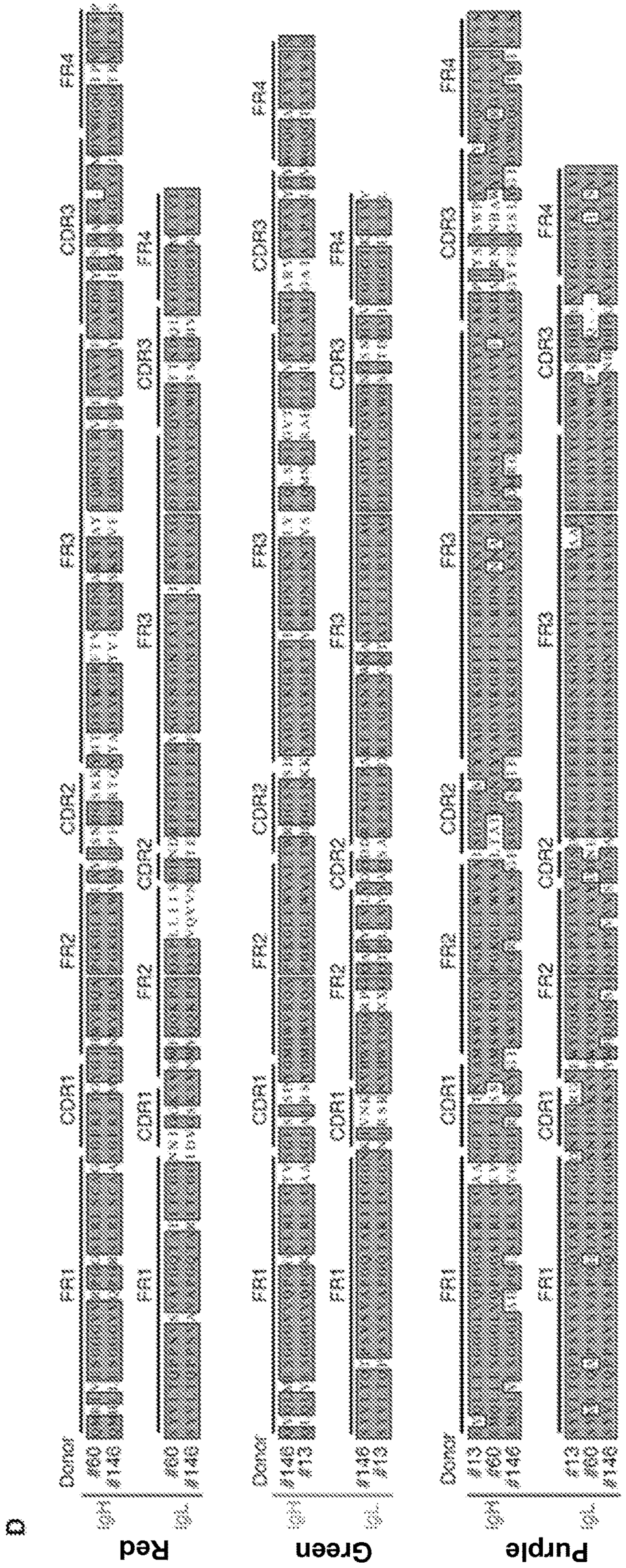

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 9 | IGH V1- 18* 01 | IGH D6- 13* 01 | IGHJ 6*02 | GYT FTT YG | 26 | ISTY NRNT | 27 | ARN GYS SSW HGG THY YYY ALD F | 28 | IGKV 1-5* 03 | IGKJ 1*01 | QSI TNW | 29 | KAS | QQY YSY PWT | 30 | | | | | | | | |
| 55 | IGH V1- 18* 01 | IGH D2- 15* 01 | IGHJ 4*02 | GYS FNT YG | 31 | ISTY NGKT | 32 | ARD SVS WWN LLF KSL EKL TLD Y | 33 | | | | | | | | IGL V2- 23* 01 | IGL J3* 02 | SSD VGS YDL | 34 | EAS | | CSY SGS TTC V | 35 |
| 55 | IGH V1- 18* 01 | IGH D2- 15* 01 | IGHJ 4*02 | GYS FNT YG | 36 | ISTY NGKT | 37 | ARD SVS WWN LLF KSL EKL TLD Y | 38 | IGKV 3-20 *01 | IGKJ 4*01 | QSV SNS Y | 39 | GAS | QQF GSS PLT | 40 | IGL V2- 8*0 1 | IGL J1* 01 | SSD IGG YNY | 41 | EVN | | NSY AGN NNF V | 42 |
| 55 | IGH V1- 18* 01 | IGH D2- 15* 01 | IGHJ 4*02 | GYS ENT YG | 43 | ISTY NGKT | 44 | ARD SVS WWN LLF KSL EKL TLD Y | 45 | IGKV 3-11 *01 | IGKJ 1*01 | QSV SSY | 46 | DAS | QHR SNS WT | 47 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 55 | IGHV1-18*01 | IGHD4-17*01 | IGHJ4*02 | GYTFSSYG | 48 | ISAHSGNT | 49 | ARDPDFGDYGSDIVDY | 50 | | | | | | | | IGLV3-25*02 | IGLJ3*02 | ALPVQF | 51 | KDS | | QSADSTATYWV | 52 |
| 99 | IGHV1-18*01 | IGHD3-16*01 | IGHJ6*03 | GYSFSSYG | 53 | ISAYNGDT | 54 | ARWGVGMTFSYHYHYMDV | 55 | | | | | | | | IGLV3-19*01 | IGLJ3*02 | SLRTYY | 56 | GKN | | GSRDNSGYS | 57 |
| 99 | IGHV1-18*01 | IGHD6-13*01 | IGHJ4*02 | GYTFGSFG | 58 | ISGYSGKT | 59 | ARGRGDSSTWYSLY | 60 | IGKV3-11*01 | IGKJ4*01 | QSVGSY | 61 | DAS | QQYNDWLT | 62 | | | | | | | | |
| 146 | IGHV1-18*01 | IGHD1-1*01 | IGHJ1*01 | DYRSINSG | 63 | ISPFNGNT | 64 | AGDTTSSAALTF | 65 | IGKV4-1*01 | IGKJ3*01 | ESVFFSPHNRNY | 66 | WAS | QQYYTTPS | 67 | | | | | | | | |
| 146 | IGHV1-18*01 | IGHD1-26*01 | IGHJ6*02 | GYNFISYA | 68 | ISPYNGKK | 69 | ARFFGGATMTVYFYGLDV | 70 | IGKV1-5*01 | IGKJ1*01 | QSIKTW | 71 | DAS | QQYNSYSGWT | 72 | | | | | | | | |
| 146 | IGHV1-18*01 | IGHD6-19*01 | IGHJ4*02 | GYKFTNYG | 73 | INAYNGHT | 74 | TRSEQWRSRGEY | 75 | | | | | | | | IGLV1-44*01 | IGLJ3*02 | NSNVGNNV | 76 | ANS | | ASWDDSLSGSWV | 77 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 146 | IGHV1-18*01 | IGHD1-26*01 | IGHJ5*02 | GYTFSNYG | 78 | ISASSGNT | 79 | GRDDSGSYPMSP | 80 | IGKV3-20*01 | IGKJ4*01 | QSVSGSY | 81 | GAS | QQYXSSPLA | 82 | | | | | | | | |
| 146 | IGHV1-18*01 | IGHD1-20*01 | IGHJ4*02 | GYTFRNYG | 83 | INAHNGDT | 84 | VRDINFIFDY | 85 | | | | | | | | IGLV7-43*01 | IGLJ3*02 | TGAVTSSYY | 86 | RTN | | LLYXWSSSALG | 87 |
| 69 | IGHV1-18*04 | IGHD3-10*01 | IGHJ6*03 | GYSFTSYG | 88 | INVYNANT | 89 | AREGWFGEFRRNYNYNYYMDV | 90 | IGKV3-15*01 | IGKJ1*01 | LSVSSN | 91 | DAS | QQYHEWPRT | 92 | | | | | | | | |
| 49 | IGHV1-24*01 | IGHD4-11*01 | IGHJ3*01 | GYTLTELS | 93 | FDPDEGEV | 94 | TLVTRVDAFDV | 95 | IGKV1-39*01 | IGKJ2*01 | QSVRTY | 96 | AAS | QQSYFAPYT | 97 | | | | | | | | |
| 49 | IGHV1-24*01 | IGHD4-11*01 | IGHJ3*01 | GYSHTELP | 98 | FDPDEGET | 99 | TLVTRVDAFEV | 100 | IGKV1-39*01 | IGKJ2*01 | QNIRNY | 101 | AAS | QQSYFAPYT | 102 | | | | | | | | |
| 49 | IGHV1-24*01 | IGHD2-21*02 | IGHJ3*01 | GYTLTELP | 103 | FDPDEGET | 104 | TLVTGVDAFAV | 105 | IGKV1-39*01 | IGKJ2*01 | QNIRTY | 106 | TAS | QQSYFAPYT | 107 | | | | | | | | |
| 49 | IGHV1-24*01 | IGHD3-16*01 | IGHJ3*01 | GYIFSELS | 108 | FDPDEGET | 109 | TSVIKADAFEV | 110 | IGKV1-39*01 | IGKJ2*01 | QNIRTY | 111 | VAS | QQSYFAPYT | 112 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 13 | IGH<br>V1-<br>3*<br>01 | IGH<br>D2-<br>21*<br>01 | IGHJ<br>6*02 | GYT<br>FTH<br>YA | 113 | LNGG<br>NDDR | 114 | ARG<br>GWI<br>IQN<br>GGA<br>RYY<br>HGM<br>DV | 115 | IGKV<br>3-20<br>*01 | IGKJ<br>4*01 | QSV<br>SSS<br>Q | 116 | GAS | QHY<br>NNP<br>VA | 117 | IGL<br>V3-<br>21*<br>02 | IGL<br>J2*<br>01 | NIR<br>NKN | 118 | ADS | | QVW<br>DGG<br>SYH<br>VI | 119 |
| | 13 | IGH<br>V1-<br>3*<br>01 | IGH<br>D3-<br>10*<br>01 | IGHJ<br>4*02 | GYT<br>FTR<br>YP | 120 | INAA<br>NGDT | 121 | ARK<br>DYY<br>GSG<br>SYE<br>FDN | 122 | | | | | | | | IGL<br>V2-<br>11*<br>01 | IGL<br>J2*<br>01 | SSD<br>VGG<br>YNY | 123 | DVN | | CSY<br>AGN<br>YIL<br>V | 124 |
| | 69 | IGH<br>V1-<br>3*<br>01 | IGH<br>D2-<br>2*<br>01 | IGHJ<br>3*01 | GYN<br>FQR<br>SA | 125 | INVG<br>NGNT | 126 | AKG<br>RSS<br>HDL<br>YDP<br>FDF | 127 | IGKV<br>1-5*<br>03 | IGKJ<br>2*01 | ENI<br>GGW | 128 | KAS | QQY<br>NSY<br>SRY<br>T | 129 | | | | | | | | |
| | 99 | IGH<br>V1-<br>3*<br>01 | IGH<br>D3-<br>10*<br>01 | IGHJ<br>4*02 | GYT<br>FTS<br>YP | 130 | INPA<br>NGDT | 131 | ARK<br>NYY<br>ASG<br>SYH<br>FDL | 132 | | | | | | | | IGL<br>V2-<br>11*<br>01 | IGL<br>J3*<br>02 | NSD<br>VGG<br>YNY | 133 | DVT | | SSY<br>AGK<br>YTL<br>V | 134 |
| | 146 | IGH<br>V1-<br>3*<br>01 | IGH<br>D1-<br>1*<br>01 | IGHJ<br>3*02 | GYT<br>LTS<br>YA | 135 | INAG<br>SGLT | 136 | ARV<br>GIP<br>LRG<br>AGG<br>SPF<br>DI | 137 | IGKV<br>1-39<br>*01 | IGKJ<br>4*01 | QSV<br>STY | 138 | TAS | QQS<br>SSV<br>PLT | 139 | | | | | | | | |
| H001 | 146 | IGH<br>V1-<br>3*<br>01 | IGH<br>D3-<br>16*<br>01 | IGHJ<br>3*02 | GYT<br>FTT<br>YA | 140 | INAG<br>NGIT | 141 | ARV<br>GIL<br>VRG<br>AGG<br>SPF<br>DI | 142 | IGKV<br>1-39<br>*01 | IGKJ<br>4*01 | QSI<br>STY | 143 | SAS | QQS<br>YST<br>PLT | 144 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 146 | IGHV1-3*01 | IGHD3-16*01 | IGHJ3*02 | GYTFTTYA | 145 | INAGNGIT | 146 | ARVGILVRGAGGSPFDI | 147 | IGKV1-39*01 | IGKJ4*01 | QSISTY | 148 | TAS | QQSYSTPLT | 149 | | | | | | | | |
| 146 | IGHV1-3*01 | IGHD4-11*01 | IGHJ3*01 | GYTFSRHA | 150 | INIGNGNT | 151 | AREDYTGNYYDAFDF | 152 | IGKV1-5*03 | IGKJ4*01 | QSVSTW | 153 | KAS | QLYNSYSGTT | 154 | | | | | | | | |
| 146 | IGHV1-3*01 | IGHD6-13*01 | IGHJ6*02 | GYSFSNYA | 155 | INAAYGNT | 156 | ARDGVKEQLVYYYFGMDV | 157 | | | | | | | | IGLV1-40*01 | IGLJ2*01 | SSNIGKNYD | 158 | GDT | | QSYDSNLSGSVV | 159 |
| 146 | IGHV1-3*01 | IGHD3-10*01 | IGHJ4*02 | TYVFTAYA | 160 | INAGNGDT | 161 | ARGALLWFRDDFDF | 162 | IGKV1-27*01 | IGKJ3*01 | QGISNY | 163 | AAS | QKYDSAPYT | 164 | IGLV1-51*01 | IGLJ1*01 | SSNIGNTY | 165 | DNN | | GSWDSSLYSFYV | 166 |
| 99 | IGHV1-46*01 | IGHD2-2*01 | IGHJ1*01 | GYTFSNYH | 167 | INPSGDST | 168 | ASRLDAIPFQV | 169 | IGKV3-20*01 | IGKJ2*01 | PNANSGS | 170 | GAS | QQYGGLPFT | 171 | | | | | | | | |
| 99 | IGHV1-46*01 | IGHD4-23*01 | IGHJ6*04 | GYIVTSYR | 172 | IDPSDTYT | 173 | ARKGNYGSRYDWYFDV | 174 | | | | | | | | IGLV2-14*01 | IGLJ3*02 | SSDVGDYSY | 175 | DVN | | SSYTSSSTGV | 176 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 55 | IGH V1- 46* 03 | IGH D3- 9- 01 | IGHJ 3*01 | GYT FTN FN | 177 | INPG AGTT | 178 | TRD PIL RFY DWQ SRD AFD V | 179 | IGKV 1-17 *01 | IGKJ 3*01 | QGI RND | 180 | AAS | LQH NGY PIT | 181 | | | | | | | | |
| 60 | IGH V1- 69* 01 | IGH D3- 3* 01 | IGHJ 6*01 | GGT FSS YS | 182 | IVPI FGIP | 183 | ARV PSV ATC NFG CYS AMD V | 184 | IGKV 1-39 *01 | IGKJ 3*01 | QSI SNY | 185 | GAS | QQS YST LFS | 186 | IGL V2* 14* 01 | IGL J1* 01 | SSD VGG YKY | 187 | EVT | | SSY TGS STR YV | 188 |
| 146 | IGH V1- 69* 06 | IGH D3- 3* 01 | IGHJ 4*02 | GGK FIA YG | 189 | TIPI YGTA | 190 | ARA SFG DLW SGY PNQ FFD H | 191 | IGKV 1-17 *03 | IGKJ 1*01 | QGI SNS | 192 | GAS | LQH NTY PWT | 193 | | | | | | | | |
| 13 | IGH V2- 5* 02 | IGH D3- 9* 01 | IGHJ 5*02 | GFS FST GGV G | 194 | IYGD GDE | 195 | AHR LLT AYY DH | 196 | IGKV 1-5* 03 | IGKJ 1*01 | QSI SRW | 197 | KAS | QQY NSY SWA | 198 | | | | | | | | |
| 55 | IGH V2- 5* 02 | IGH D6- 13* 01 | IGHJ 5*02 | GFS LST FGV G | 199 | IYWD DDK | 200 | AHT VAA AAT FWF DP | 201 | | | | | | | | IGL V1- 44* 01 | IGL J2* 01 | SSN IGS NT | 202 | STN | | ATW DDS LNG LV | 203 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 69 | IGHV2-5*02 | IGHD2-21*02 | IGHJ3*02 | GFSLSTTAVG | 204 | IYGDDK | 205 | AHSSYFDCGGDCSDVAFDI | 206 | | | | | | | | IGLV3-10*01 | IGLJ3*02 | ALPRKY | 207 | EDN | | YSTDSSGDPV | 208 |
| | 146 | IGHV2-5*02 | IGHD2-15*01 | IGHJ3*01 | GFSLTTNGMG | 209 | IYWDDK | 210 | ARSYCRGGNCYSTAFNV | 211 | | | | | | | | IGLV2-11*01 | IGLJ2*01 | SSDVGGYDY | 212 | GVN | | CSYAGAYTYVA | 213 |
| H002 | 146 | IGHV2-70D*04 | IGHD7-27*01 | IGHJ4*02 | GFSLSTNTMR | 214 | IDWDDEK | 215 | ARSNHWGSHFDY | 216 | | | | | | | | IGLV3-21*02 | IGLJ1*01 | NIGGKT | 217 | DNS | | QVWDTSGDHLYV | 218 |
| | 55 | IGHV3-11*01 | IGHD2-21*01 | IGHJ3*01 | GFTFSDYY | 219 | IRGSHSSV | 220 | ARDLPGDEYLDAFDL | 221 | IGKV4-1*01 | IGKJ4*01 | QSLLYSSNNKNY | 222 | WAS | QQFYTAPLT | 223 | | | | | | | | |
| | 60 | IGHV3-11*01 | IGHD6-13*01 | IGHJ6*02 | GLTLSDYY | 224 | ISHDGSTI | 225 | ASGAAVPYFYYGVDV | 226 | | | | | | | | IGLV3-1*01 | IGLJ2*01 | KLGDAY | 227 | QDT | | QAWGSSPAKV | 228 |
| | 99 | IGHV3-13*01 | IGHD3-22*01 | IGHJ4*02 | GFTFSSYD | 229 | IGAATDT | 230 | ARAVHYYDSSGHYSGYYFDY | 231 | | | | | | | | IGLV1-44*01 | IGLJ2*01 | SSNIGSNT | 232 | SNN | | ATWDASLKGVV | 233 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 55 | IGH V3- 15* 01 | IGH D1- 1* 01 | IGHJ 4*02 | GFT FSN AW | 234 | IRSK TDGG TA | 235 | TTQ NAF ES | 236 | | | | | | | | IGL V3- 21* 01 | IGL J1* 01 | NIG SKS | 237 | YDS | | QVW DSS SDH YV | 238 |
| 55 | IGH V3- 15* 01 | IGH D2/ OR1 5- 2a* 01 | IGHJ 6*02 | GFT FSN AY | 239 | IKSI TDGG TI | 240 | HTL STT HYY GMD V | 241 | IGKV 3-20 *01 | IGKJ 4*01 | QSV TSN Y | 242 | GAS | QQY INS PLT | 243 | | | | | | | | |
| 146 | IGH V3- 15* 01 | IGH D6- 25* 01 | IGHJ 4*02 | GFT FSN TY | 244 | IQRK TDGG TA | 245 | AAH NRA AY | 246 | IGKV 1-5* 01 | IGKJ 2*01 | QSI SNW | 247 | DAS | QQY YSY SPL T | 248 | | | | | | | | |
| 9 | IGH V3- 21* 01 | IGH D3- 3* 02 | IGHJ 4*02 | GLT FST HS | 249 | ISGS SDYI | 250 | ARA RPP GTA FGF DH | 251 | | | | | | | | IGL V1* 40* 01 | IGL J2* 01 | SSN IGA GYD | 252 | DNN | | QSY DSS LSG AL | 253 |
| 13 | IGH V3- 21* 01 | IGH D3- 16* 01 | IGHJ 4*02 | GFT FSS YV | 254 | VSSS SYSI | 255 | VRT FYF DY | 256 | IGKV 3-15 *01 | IGKJ 1*01 | QSV RTN | 257 | SAS | QQY DIW PPR T | 258 | | | | | | | | |
| 55 | IGH V3- 21* 01 | IGH D4- 17* 01 | IGHJ 1*01 | GFT FSS FS | 259 | ISSS SRYI | 260 | VRD MTT VTT CXX QH | 261 | | | | | | | | IGL V1- 44* 01 | IGL J2* 01 | SSN IGS HT | 262 | TNS | | AAW DDS LNG LV | 263 |
| 146 | IGH V3- 21* 01 | IGH D4- 17* 01 | IGHJ 1*01 | GFT FSS FS | 264 | ISSS SRYI | 265 | VRD MTT VTT CYL QH | 266 | | | | | | | | IGL V1- 44* 01 | IGL J2* 01 | SSN IGS HT | 267 | TNS | | AAW DDS LNG LV | 268 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 146 | IGH V3- 21* 01 | IGH D3- 3* 01 | IGHJ 4*02 | GFS FNA YS | 274 | ISSS SSYI | 275 | ARV PIL LAQ GVP TFD L | 276 | IGKV 3-15 *01 | IGKJ 2*01 | QSV NSN | 277 | SAS | QQY SDW PRY T | 278 | | | | | | | | |
| | 9 | IGH V3- 23* 01 | IGH D2- 2* 02 | IGHJ 6*03 | GFT FTR YT | 279 | VSGS GSST | 280 | AKA AIL GNY NYY MD V | 281 | | | | | | | | IGL V3- 21* 02 | IGL J2* 01 | NIA SKS | 282 | DDN | | QVW DSS ADH LVV | 283 |
| | 13 | IGH V3- 23* 01 | IGH D1- 1* 01 | IGHJ 4*01 | EFR FGS YA | 284 | IIAT GAKT | 285 | VKD AIY MSN WPW YFD Y | 286 | | | | | | | | IGL V3- 21* 02 | IGL J2* 01 | NIG SKS | 287 | DDN | | | |
| | 13 | IGH V3- 23* 01 | IGH D6- 13* 01 | IGHJ 4*02 | GFT FTN YA | 288 | ISGS GGST | 289 | AKD PIY SSS WPY YFD Y | 290 | | | | | | | | IGL V3- 21* 02 | IGL J2* 01 | NIG SRG | 291 | EDS | | QVW DSS SDH PEV V | 292 |
| H021 | 13 | IGH V3- 23* 01 | IGH D6- 13* 01 | IGHJ 4*02 | GFR FSS YA | 293 | ISGS GGST | 294 | AKD PIY TSR WPY YFD Y | 295 | IGKV 1-39 *01 | IGKJ 2*03 | QSI SSY | 296 | AAS | QQS YSL YS | 297 | IGL V3- 21* 02 | IGL J2* 01 | NIG SKS | 298 | DDS | | QVW DSS SDH SEV I | 299 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 13 | IGHV3-23*01 | IGHD3-10*01 | IGHJ4*02 | GFRFSSYA | 300 | ISGRDAST | 301 | AKDGVLGSYHQYYFQY | 302 | | | | | | | | IGLV3-21*02 | IGLJ2*01 | NIGSKS | 303 | DDT | | QVWDNSSDHPGVV | 304 |
| 13 | IGHV3-23*01 | IGHDS-12*01 | IGHJ4*02 | GFTFSSYA | 305 | ISGSGGST | 306 | AKGSRNGPYIVATLHFDY | 307 | IGKV3-15*01 | IGKJ4*01 | QSVSSN | 308 | GAF | QHYNHWSLT | 309 | | | | | | | | |
| 55 | IGHV3-23*01 | IGHD6-13*01 | IGHJ4*02 | GFTFNNYA | 310 | VSGNGGST | 311 | VLSSSWMDNPFDF | 312 | | | | | | | | IGLV5-45*02 | IGLJ3*02 | SGINVGTYR | 313 | YKSDSDK | 314 | MIWHSSAWV | 315 |
| 55 | IGHV3-23*01 | IGHD1-26*01 | IGHJ4*02 | GFTFSSYA | 316 | ASASGRNT | 317 | AGFPSGTHFFDY | 318 | IGKV3-11*01 | IGKJ1*01 | QSVSNH | 319 | DAS | QQRSNWWT | 320 | | | | | | | | |
| 55 | IGHV3-23*01 | IGHD1-26*01 | IGHJ4*02 | GFTFSSYA | 321 | ASASGRNT | 322 | AGFPSGTHFFDY | 323 | IGKV3-20*01 | IGKJ4*01 | QSVSNSY | 324 | GAS | QQFGSSPLT | 325 | IGLV2-8*01 | IGLJ1*01 | SSDIGGYNY | 326 | EVN | | NSYAGNNNFV | 327 |
| 55 | IGHV3-23*01 | IGHD2-2*01 | IGHJ6*02 | EFTFSSYA | 328 | ISGSGDTT | 329 | ARPDALHCSSITSCSLYGLAYYYGMDV | 330 | | | | | | | | IGLV1-44*01 | IGLJ3*02 | SSNIGTNT | 331 | SNN | | AAWDDRLIGWV | 332 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 55 | IGHV3-23*01 | IGHD1-26*01 | IGHJ4*02 | GFTFSSHG | 333 | ISGNGGFT | 334 | AKRMVEATNRYFDY | 335 | IGKV3-20*01 | IGKJ2*01 | QSVSNSY | 336 | GVS | QQYGSSPPYT | 337 | | | | | | | | |
| | 55 | IGHV3-23*01 | IGHD1-26*01 | IGHJ4*02 | GFTFINYA | 338 | ISANGIYT | 339 | ARDSSEWVLGIDF | 340 | | | | | | | | IGLV2-11*01 | IGLJ2*01 | SSDVGGYNY | 341 | DVN | | CSYAGSYTVV | 342 |
| | 60 | IGHV3-23*01 | IGHD4/OR15-4a*01 | IGHJ2*01 | GFTFSSYA | 343 | ITGSGGST | 344 | AKDAVRSANHAWYFDF | 345 | | | | | | | | IGLV3-21*02 | IGLJ2*01 | NIGIKS | 346 | DDT | | QVWDSNSDHPKVV | 347 |
| | 60 | IGHV3-23*01 | IGHD5-12*01 | IGHJ4*02 | GFTFSSTA | 348 | ISSNGAGT | 349 | AKGYGLFDS | 350 | IGKV3-15*01 | IGKJ1*01 | QSLVTN | 351 | GAS | QQYINWPPWS | 352 | | | | | | | | |
| H003 | 60 | IGHV3-23*01 | IGHD2-21*01 | IGHJ2*01 | GFTFSSYA | 353 | LTATGGNT | 354 | AKDAIRNSNHAWYFDV | 355 | | | | | | | | IGLV3-21*02 | IGLJ2*01 | NIGSKS | 356 | DDN | | QVWDPTSDQV | 357 |
| | 60 | IGHV3-23*01 | IGHD2-8*01 | IGHJ4*02 | GFTFSSYG | 358 | ISGRGDET | 359 | AKSRVTNSGSIDH | 360 | IGKV1-39*01 | IGKJ5*01 | QTIGTY | 361 | AAS | QQSYSTSIT | 362 | | | | | | | | |
| | 60 | IGHV3-23* | IGHD4/OR | IGHJ2*01 | GFRFNNYA | 363 | ISGGDGYT | 364 | AKDAILSAN | 365 | IGKV4-1*01 | IGKJ4*01 | QSVLYSSNN | 366 | WAS | QQYYSTPLT | 367 | IGLV3-21*02 | IGLJ3*02 | NIGTNS | 368 | EDS | | QVWDSSSDH | 369 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | | 01 | 15-4a*01 | | | | | | HPWYFDF | | | | KNY | | | | | 02 | | | | | | PKVV | |
| | 60 | IGHV3-23*01 | IGHD2-21*01 | IGHJ2*01 | GFTFSSYA | 370 | IVNSGGST | 371 | AKDAIRSSNHPWYFHV | 372 | | | | | | | | IGLV3-21*02 | IGLJ2*01 | NIGSES | 373 | DDS | | QVWDGSSDHPKVL | 374 |
| | 60 | IGHV3-23*01 | IGHD4/OR15-4a*01 | IGHJ2*01 | GFRFNNYA | 375 | ITGGEGYT | 376 | AKDAILSANHPWYFDF | 377 | | | | | | | | IGLV3-21*02 | IGLJ3*02 | NIGTNS | 378 | EDS | | QVWDRSSDQSKVV | 379 |
| | 146 | IGHV3-23*01 | IGHD3/OR15-3a*01 | IGHJ4*02 | GFTFSTHA | 380 | ISGGSEWS | 381 | AKGYGLFDF | 382 | IGKV3-15*01 | IGKJ1*01 | QSVSSN | 383 | GPS | QQYINRPPWT | 384 | | | | | | | | |
| | 9 | IGHV3-23*03 | IGHD1-1*01 | IGHJ4*02 | GFTFSNYA | 385 | IYTGGSKT | 386 | AKVLLGGWNGVFDH | 387 | IGKV3-11*01 | IGKJ4*01 | QSVDSY | 388 | DAS | QQRSTWPPS | 389 | | | | | | | | |
| H004 | 146 | IGHV3-23*04 | IGHD3-10*01 | IGHJ6*02 | GFRFNNYG | 390 | FSGSGSNI | 391 | AKDGYFGSGSLYGIDV | 392 | | | | | | | | IGLV3-21*02 | IGLJ2*01 | NIGSKS | 393 | EDS | | QVWDSNHDHPGVV | 394 |
| | 146 | IGHV3- | IGHD3- | IGHJ6*02 | GFTFTS | 395 | ISGSGGST | 396 | AKDGYY | 397 | | | | | | | | IGLV3- | IGLJ2* | NIGSKS | 398 | DDS | | QVWD | 399 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 23* 04 | 10* 01 | | YA | | | | GSG SLY GMD V | | | | | | | | | 21* 02 | 01 | | | | | STS DHP GVV | |
| 146 | IGH V3- 23* 04 | IGH D3- 9* 01 | IGHJ 6*02 | GFT FSS YA | 400 | FSG SGS ST | 401 | AKV IQY PRG FWF YGM DV | 402 | | | | | | | | IGL V1- 51* 01 | IGL J3* 02 | SSN IGN NY | 403 | DNN | | GTW DSS LNN CV | 404 |
| 60 | IGH V3- 30- 3* 01 | IGH D3- 10* 01 | IGHJ 6*02 | GFT FTS YA | 405 | ISYD GSTH | 406 | ARD PGV PYY HYA MDV | 407 | | | | | | | | IGL V2- 8* 01 | IGL J2* 01 | SSD VGG YHY | 408 | EVS | | SSY AGS NNY IL | 409 |
| 146 | IGH V3- 30- 3* 01 | IGH D3- 3* 01 | IGHJ 4*02 | EFT FST YA | 410 | ISAD GNNR | 411 | VRD ETD WEI GVV VAT PEF DY | 412 | IGKV 1-17 *01 | IGKJ 2*01 | QGI RND | 413 | AAS | LQH NSY PRT | 414 | IGL V1- 44* 01 | IGL J2* 01 | GSN VGG NT | 415 | SND | | STW DDS LNG VV | 416 |
| 146 | IGH V3- 30- 3* 02 | IGH D4- 23* 01 | IGHJ 4*02 | GFP FSS HA | 417 | LSFN GDYI | 418 | VTG IRA RDY GGS TFD L | 419 | | | | | | | | IGL V 10- 54* 01 | IGL J2* 01 | NKN VGN EG | 420 | RND | | AAW DSS LSA MI | 421 |
| 9 | IGH V3- 30* 02 | IGH D3- 10* 01 | IGHJ 3*01 | GFR FTN YG | 422 | IRYD GSKK | 423 | AKD GRW FGE SGG FDV | 424 | | | | | | | | IGL V3- 21* 02 | IGL J2* 01 | NIG NTV | 425 | DDN | | QVW ESS TDP VV | 426 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 9 | IGHV3-30*03 | IGHD2-2*01 | IGHJ2*01 | GFTFTSYS | 427 | MSYDGSYE | 428 | ARDYCSRTNCINWIFDL | 429 | IGKV3-20*01 | IGKJ4*01 | PSVSSSY | 430 | GVS | QQYGSSPLT | 431 | | | | | | | | |
| 60 | IGHV3-30*03 | IGHD2-8*02 | IGHJ6*02 | GFRFTGYG | 432 | ISNDGSKK | 433 | AKDGYLSAARGYGMDV | 434 | | | | | | | | IGLV3-21*02 | IGLJ2*01 | NIGGKS | 435 | DDR | | QVWETTSDQLV | 436 |
| 146 | IGHV3-30*03 | IGHD4-17*01 | IGHJ4*02 | GFTFSNYD | 437 | ISYDGSNK | 438 | ARDTFGDYYFDY | 439 | | | | | | | | IGLV1-40*01 | IGLJ1*01 | NSNIGAGYD | 440 | GNH | | QSYDSRLSVPYV | 441 |
| 9 | IGHV3-30*04 | IGHD5-18*01 | IGHJ6*02 | KFTFSKYA | 442 | TSYNGGSK | 443 | ARGGGYTYGSYYYSMDV | 444 | IGKV4-1*01 | IGKJ3*01 | QSVLYSSNNKNY | 445 | WAS | QQYYSTPFT | 446 | | | | | | | | |
| 9 | IGHV3-30*04 | IGHD5-18*01 | IGHJ6*02 | RFTFSKYA | 447 | ISYDGSSK | 448 | ARGGGYTYGSYYYAMDV | 449 | IGKV4-1*01 | IGKJ3*01 | QSLLYSSNNKNY | 450 | WAS | QQYYSTPFT | 451 | | | | | | | | |
| 55 | IGHV3-30*04 | IGHD1-26*01 | IGHJ4*02 | GFTFSSYS | 452 | MSNTGSTK | 453 | ARALLSVVGSKSYYFDF | 454 | IGKV3-11*01 | IGKJ1*01 | QSVSSY | 455 | DAS | QHRSNSWT | 456 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | | LAMBDA LIGHT CHAIN | | | | | | | |
|---|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 55 | IGHV3-30*04 | IGHD1-26*01 | IGHJ4*02 | GFTFSSYS | 457 | MSNTGSTK | 458 | ARALLSVVGSKSYYFDF | 459 | IGKV3-11*01 | IGKJ1*01 | QSVSSY | 460 | DAS | QHRSNSWT | 461 | | | | | | | | |
| 55 | IGHV3-30*04 | IGHD1-26*01 | IGHJ6*02 | GFNFNVYA | 462 | ISYDGSKK | 463 | ARDEKYSGLYSGRTGDYYYGMDV | 464 | | | | | | | | IGLV1-51*01 | IGLJ2*01 | NSNIGNNF | 465 | NSD | | GTWDSSLSLGV | 466 |
| 55 | IGHV3-30*04 | IGHD3-22*01 | IGHJ6*02 | GFTFSAYS | 467 | ISYDGSNR | 468 | ARDGKLGRTYHDSRQSYFYIMDV | 469 | | | | | | | | IGLV2-14*01 | IGLJ2*01 | SSDVGGYNY | 470 | DVN | | SSYTSSTSLV | 471 |
| 13 | IGHV3-30*18 | IGHD3-10*01 | IGHJ6*02 | GFRFSSYG | 472 | TSFDGSKT | 473 | AKDAYYFASGSFFGMDV | 474 | | | | | | | | IGLV3-21*02 | IGLJ2*01 | NIGSKS | 475 | DDN | | QVWGSGGVI | 476 |
| 13 | IGHV3-30*18 | IGHD3-10*01 | IGHJ6*02 | GFTFSRYG | 477 | ISYDGSNK | 478 | AKDAYYYGSGYGMDV | 479 | IGKV1-5*03 | IGKJ4*01 | QSISVW | 480 | KAS | QQYTSFST | 481 | IGLV1-47*01 | IGLJ1*01 | SSNIGSDY | 482 | RNN | | AAWDDRLSGYV | 483 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 60 | IGHV3-30*18 | IGHD3-10*01 | IGHJ6*02 | GFTFRSYG | 484 | ISSDGSKK | 485 | AKDGYVVSGSGYGMDV | 486 | | | | | | | | IGLV3-21*02 | IGLJ2*01 | NIGSKS | 487 | DDS | | QVWDSSSDHVV | 488 |
| H009 | 60 | IGHV3-30*18 | IGHD1-26*01 | IGHJ6*02 | RFSFNTYG | 489 | ISYDGSHE | 490 | AKTDIKWGATNYGMDV | 491 | | | | | | | | IGLV3-21*02 | IGLJ2*01 | NIGRKS | 492 | DDN | | QVWDGTRDHLVV | 493 |
| | 60 | IGHV3-30*18 | IGHD5-12*01 | IGHJ4*02 | GFTFSNYA | 494 | TLYDGSHS | 495 | AKDSAGYGLHY | 496 | IGKV1-17*01 | IGKJ1*01 | QGIRTD | 497 | AAS | LQHNSYPWT | 498 | IGLV3-19*01 | IGLJ2*01 | SLRSFY | 499 | NKD | | NSRDSIGNHVV | 500 |
| | 60 | IGHV3-30*18 | IGHD3-22*01 | IGHJ6*02 | GFRFTGYG | 501 | ISNDGSKK | 502 | AKDGYLSAARGYGMDV | 503 | | | | | | | | IGLV3-21*02 | IGLJ2*01 | NVGSKS | 504 | DDS | | QVWDTTTDQLV | 505 |
| | 60 | IGHV3-30*18 | IGHD3-22*01 | IGHJ6*02 | GFRFTGYG | 506 | ISNDGSKT | 507 | AKDGYLSAARGYGMDV | 508 | | | | | | | | IGLV3-21*02 | IGLJ2*01 | NIGGKS | 509 | DDS | | QVWDTTSDQLV | 510 |
| | 60 | IGHV3-30*18 | IGHD3-22*01 | IGHJ6*02 | GFRFTGYG | 511 | ISNDGSKK | 512 | AKDGYLSAARGYGMDV | 513 | | | | | | | | IGLV3-21*02 | IGLJ2*01 | NIGALS | 514 | DDN | | QVWDTSSDQLV | 515 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| H005 | 60 | IGHV3-30*18 | IGHD3-16*01 | IGHJ6*02 | GFRFTGYG | 516 | ISNDGSKK | 517 | AKDAYLSAARGYGMHV | 518 | | | | | | | | IGLV3-21*02 | IGLJ2*01 | NIGGKS | 519 | DDS | | QVWDTASDQLV | 520 |
| | 60 | IGHV3-30*18 | IGHD3-22*01 | IGHJ6*02 | GFRFTGYG | 521 | ISNDGSKK | 522 | AKDGYLSAARGYGMDV | 523 | | | | | | | | IGLV3-21*02 | IGLJ2*01 | NIGGKS | 524 | DDR | | QVWDTTSDQLV | 525 |
| | 60 | IGHV3-30*18 | IGHD3-22*01 | IGHJ6*02 | GFRFTGYG | 526 | ISNDGSKK | 527 | AKDGYLSAARGYGMDV | 528 | | | | | | | | IGLV3-21*02 | IGLJ2*01 | NIGGKS | 529 | DDT | | QVWDTTSDQLV | 530 |
| | 60 | IGHV3-30*18 | IGHD3-22*01 | IGHJ6*02 | GFRFTGYG | 531 | ISNDGSKK | 532 | AKDGYLSAARGYGMDV | 533 | | | | | | | | IGLV3-21*02 | IGLJ2*01 | NIGGKS | 534 | DDS | | QVWDTTSDQLV | 535 |
| | 60 | IGHV3-30*18 | IGHD1-26*01 | IGHJ6*02 | GFTFNTYA | 536 | ISYDGSNK | 537 | AKTDIRWGATNYGMDV | 538 | | | | | | | | IGLV3-21*02 | IGLJ2*01 | NIGSKS | 539 | DDN | | QVWDGSSDHLVV | 540 |
| H010 | 60 | IGHV3-30*18 | IGHD3-3*01 | IGHJ4*02 | GFSFSTYG | 541 | ISYDGMIK | 542 | AKGPLFGLFSFDQ | 543 | | | | | | | | IGLV3-21*03 | IGLJ2*01 | NIGDMS | 544 | DDS | | QVWDNSRNRGI | 545 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 60 | IGHV3-30*18 | IGHD3-22*01 | IGHJ6*02 | GFRFTGYG | 546 | ISNDGSKK | 547 | AKDGYLSAARGYGMDV | 548 | | | | | | | | IGLV3-21*02 | IGLJ2*01 | NIGGKS | 549 | DDR | | QVWDTTSDQLV | 550 |
| | 60 | IGHV3-30*18 | IGHD3-22*01 | IGHJ6*02 | GFRFTGYS | 551 | ISNDGSKR | 552 | AKDGYLSAARGYGMDV | 553 | IGKV2-30*01 | IGKJ1*01 | QSLVYSDGNTY | 554 | KVS | TQVTLWPPWT | 555 | | | | | | | | |
| H006 | 60 | IGHV3-30*18 | IGHD3-22*01 | IGHJ6*02 | GFRFTGYG | 556 | ISNDGSKK | 557 | AKDGYLSAARGYGMDV | 558 | | | | | | | | IGLV3-21*02 | IGLJ2*01 | NIGGKS | 559 | DDN | | QVWDTTSDQLV | 560 |
| | 60 | IGHV3-30*18 | IGHD3-22*01 | IGHJ6*02 | GFRFTGYG | 561 | ISNDGSKK | 562 | AKDGYLSAARGYGMDV | 563 | | | | | | | | IGLV2-18*02 | IGLJ2*01 | SSDVGSYNR | 564 | EVS | | SSYTSSSTLV | 565 |
| | 60 | IGHV3-30*18 | IGHD2-21*02 | IGHJ4*02 | GFTFRSYG | 566 | ISSDGSKK | 567 | AKDPIKVSANGWGFDY | 568 | | | | | | | | IGLV3-21*03 | IGLJ2*01 | NIGSKS | 569 | DDT | | QVWDSNSDHVV | 570 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 60 | IGHV3-30*18 | IGHD3-22*01 | IGHJ6*02 | GFRFTGYG | 571 | ISNDGSRK | 572 | AKDGYLSAARGFGMDV | 573 | | | | | | | | IGLV3-21*02 | IGLJ2*01 | NIGGKS | 574 | DDS | | QVWDTTSDQLV | 575 |
| 60 | IGHV3-30*18 | IGHD2-15*01 | IGHJ6*02 | RFSFSTYG | 576 | ISYDGSEK | 577 | AKTDIMWRAVNYGMDV | 578 | | | | | | | | IGLV3-21*02 | IGLJ2*01 | NIGSKS | 579 | DDN | | QVWDDSRDHLVI | 580 |
| 60 | IGHV3-30*18 | IGHD2-15*01 | IGHJ6*02 | RFSFSTYG | 581 | ISYDGSEK | 582 | AKTDIMWRAVNYGMDV | 583 | | | | | | | | IGLV3-21*02 | IGLJ2*01 | NIGSKS | 584 | DDN | | QVWDDSRDHLVI | 585 |
| 60 | IGHV3-30*18 | IGHD2-21*01 | IGHJ6*02 | GFSFSTYG | 586 | ISYDGSSK | 587 | AKTDIMWQAVNYGMDV | 588 | | | | | | | | IGLV3-21*02 | IGLJ2*01 | NIGSKS | 589 | DDN | | QVWDDSRDHLVI | 590 |
| 60 | IGHV3-30*18 | IGHD3-22*01 | IGHJ6*02 | GFRFTGYG | 591 | ISNDGSKK | 592 | AKDGYLSAARGYGMDV | 593 | | | | | | | | IGLV3-21*02 | IGLJ2*01 | NIGGKS | 594 | DDR | | QVWDTTSDQLV | 595 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 60 | IGHV3-30*18 | IGHD2-15*01 | IGHJ6*02 | RFSFSTYG | 596 | ISYDGSEK | 597 | AKTDIMWRAVNYGMDV | 598 | | | | | | | | IGLV3-21*02 | IGLJ2*01 | NIGSKS | 599 | DDN | | QVWDESRDHLVI | 600 |
| | 60 | IGHV3-30*18 | IGHD3-22*01 | IGHJ6*02 | GFRFTGYG | 601 | ISNDGSKK | 602 | AKDGYLSAARGYGMDV | 603 | | | | | | | | IGLV3-21*02 | IGLJ2*01 | NIGGKS | 604 | DDR | | QVWDTTSDQLV | 605 |
| H008 | 146 | IGHV3-30*18 | IGHD1-26*01 | IGHJ6*02 | GFRFTMYG | 606 | IPFDGRTQ | 607 | AKDGILGARRGLYGIDV | 608 | | | | | | | | IGLV3-21*02 | IGLJ2*01 | DVGSKS | 609 | DDT | | QVWDSSSDHVV | 610 |
| H007 | 146 | IGHV3-30*18 | IGHD3-3*01 | IGHJ6*02 | GFTFNNYA | 611 | ISYDGSNK | 612 | AKEIGGFDFRSGSQRSYYYYGVDV | 613 | IGKV3-20*01 | IGKJ2*01 | QTIYTTY | 614 | GAS | QQYSSSPPGYT | 615 | | | | | | | | |
| | 146 | IGHV3-30*18 | IGHD3-3*01 | IGHJ6*02 | GFTFSRHG | 616 | ISYDGGNK | 617 | AKEIGGFDFRSGDQLTYYYYGMDV | 618 | IGKV3-20*01 | IGKJ2*01 | QSVYSTY | 619 | GAS | HQYVTSPPGYT | 620 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 146 | IGHV3-30*18 | IGHD5-18*01 | IGHJ6*02 | GFSFSNYG | 621 | ISYDGSNK | 622 | AKDAYIYARGSYYGMDV | 623 | | | | | | | | IGLV3-21*02 | IGLJ2*01 | NIASKS | 624 | DDT | | QVWDSSSNDPVV | 625 |
| 146 | IGHV3-30*18 | IGHD1-26*01 | IGHJ6*02 | GFRFTKYG | 626 | ISFDGSTQ | 627 | AKDGILGARRGXYGIDV | 628 | | | | | | | | IGLV3-21*02 | IGLJ2*01 | NIRSKN | 629 | DDN | | QVWDSYSDHVV | 630 |
| 146 | IGHV3-30*18 | IGHD3-3*01 | IGHJ6*02 | GFTFSNYA | 631 | ISFDGSNK | 632 | AKEIGGFDFRSGKQRSYYYYGVDV | 633 | IGKV3-20*01 | IGKJ2*01 | QTVYNTY | 634 | GAS | QQYGNSPPGYT | 635 | | | | | | | | |
| 146 | IGHV3-30*18 | IGHD3-10*01 | IGHJ4*02 | GFRFTIYG | 636 | VSYDGSKQ | 637 | AKDAYYYGSGSHNNPDY | 638 | | | | | | | | IGLV3-21*02 | IGLJ3*02 | NIGSQS | 639 | DDS | | QVWDSSSMGV | 640 |
| 146 | IGHV3-30*18 | IGHD3-16*02 | IGHJ4*02 | GFTFSNYG | 641 | ISYDGRDK | 642 | AKGYDYIWGTYRPRPDLDS | 643 | | | | | | | | IGLV1-44*01 | IGLJ3*02 | NSNVGNNV | 644 | ANS | | ASWDDSLSGSWV | 645 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 146 | IGH V3-30*18 | IGH D6-13*01 | IGHJ 4*02 | GFT FSD YG | 646 | VSYD GTSE | 647 | AKD PVQ RSN WYY FDY | 648 | | | | | | | | IGL V3-21*02 | IGL J2*01 | NIG SKT | 649 | DDR | | QVW HST TEP VV | 650 |
| | 146 | IGH V3-30*18 | IGH D1-20*01 | IGHJ 4*02 | GFT FSN YG | 651 | TSYD GINK | 652 | AKD PVH RSN WFY FDH | 653 | | | | | | | | IGL V3-21*02 | IGL J2*01 | YIG SKT | 654 | DDR | | QVW YSN SEP VV | 655 |
| | 146 | IGH V3-30*18 | IGH D3-3*01 | IGHJ 6*02 | GTS FST SG | 656 | ISPN AFDK | 657 | AKG SPI IRF LMM DV | 658 | IGKV 1-5*03 | IGKJ 1*01 | QSI DTW | 659 | KAS | QYY SVY ST | 660 | IGL V3-21*02 | IGL J3*02 | NIG SKN | 661 | DDN | | QVW DNN SDH VV | 662 |
| | 13 | IGH V3-33*01 | IGH D6-13*01 | IGHJ 4*02 | GFT FSS YG | 663 | IWSD GSNK | 664 | ARE AGI AAP ASL DF | 665 | | | | | | | | IGL V3-21*02 | IGL J2*01 | NIR GKS | 666 | ADS | | QVW DSS SDH VV | 667 |
| | 13 | IGH V3-33*01 | IGH D6-13*01 | IGHJ 4*02 | GFT FSN YG | 668 | IWSD GTNK | 669 | TRE AGI AAP AAL DY | 670 | | | | | | | | IGL V3-21*02 | IGL J2*01 | NIG NKN | 671 | DDN | | QVW DSS SYH VV | 672 |
| H011 | 13 | IGH V3-33*01 | IGH D1-7*01 | IGHJ 3*01 | GFT FSN YG | 673 | VWYD GSYK | 674 | VRD NWS YNA FDV | 675 | IGKV 3-11*01 | IGKJ 2*03 | QSI SSY | 676 | GTS | QHR NSW PYS | 677 | | | | | | | | |
| | 13 | IGH V3-33*01 | IGH D6-19*01 | IGHJ 4*02 | GFI FSD YG | 678 | IWKD GSNK | 679 | VRE NSG WYY FDY | 680 | IGKV 1-17*01 | IGKJ 4*01 | QGI RNN | 681 | TAS | LQH DSY PFT | 682 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| H012 | 13 | IGHV3-33*01 | IGHD6-13*01 | IGHJ4*02 | GFAFRSYG | 683 | IWHDGSNK | 684 | AREGAIAAPASLDV | 685 | | | | | | | | IGLV3-21*02 | IGLJ2*01 | NIRSRN | 686 | ADS | | QVWDSGTDHVI | 687 |
| | 13 | IGHV3-33*01 | IGHD6-13*01 | IGHJ4*02 | GFTFSSFG | 688 | IWSDGSNQ | 689 | AREGGIAAPAALDF | 690 | | | | | | | | IGLV3-21*02 | IGLJ2*01 | NIRNKN | 691 | ADS | | QVWDGGSYHVI | 692 |
| | 13 | IGHV3-33*01 | | IGHJ4*02 | GVTFNSYG | 693 | IWYDGTNK | 694 | ARESKAYPYYFDY | 695 | IGKV1-39*01 | IGKJ2*03 | QNISIF | 696 | DAS | QHSSFPPQDS | 697 | | | | | | | | |
| | 13 | IGHV3-33*01 | IGHD1-1*01 | IGHJ4*02 | GFTFSNYA | 698 | IWYDGTYK | 699 | ARESNGFGSDF | 700 | IGKV1-17*01 | IGKJ1*01 | QGIRNN | 701 | AAS | LQHNSFPRT | 702 | | | | | | | | |
| | 13 | IGHV3-33*01 | IGHD3-10*01 | IGHJ3*02 | GFVFSSYG | 703 | VWYDGSYK | 704 | VRDNWSYNAFDI | 705 | IGKV3-11*01 | IGKJ2*03 | QSISSY | 706 | ATS | QHRNSWPYS | 707 | | | | | | | | |
| | 13 | IGHV3-33*01 | IGHD1-20*01 | IGHJ3*02 | GFTFSNYG | 708 | IWYDGSYK | 709 | ARDNWKYNAFDI | 710 | IGKV3-11*01 | IGKJ2*03 | QSVSSY | 711 | DAS | QHRSNWPYS | 712 | | | | | | | | |
| | 13 | IGHV3-33*01 | IGHD6-19*01 | IGHJ4*02 | GFTFSRYG | 713 | IWSDGSNQ | 714 | ARESSGWYYFDY | 715 | | | | | | | | IGLV2-23*01 | IGLJ1*01 | SSDVGNYNF | 716 | EGS | | CLYAGSSISYV | 717 |
| | 13 | IGHV3- | IGHD6- | IGHJ5*02 | GFTFSS | 718 | IWYDGSNE | 719 | AREERI | 720 | | | | | | | | IGLV3- | IGLJ2* | NIGRKN | 721 | ADS | | QVWDSS | 722 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | | 33*<br>01 | 13*<br>01 | | FG | | | | AAP<br>ASL<br>DL | | | | | | | | | 21*<br>02 | 01 | | | | | TYH<br>VV | |
| | 13 | IGH<br>V3-<br>33*<br>01 | IGH<br>D6-<br>25*<br>01 | IGHJ<br>4*02 | GFT<br>FSS<br>YG | 723 | IWHD<br>GTNQ | 724 | ARE<br>LRI<br>AAP<br>AAL<br>DY | 725 | | | | | | | | IGL<br>V3-<br>21*<br>02 | IGL<br>J2*<br>01 | NIA<br>NKN | 726 | ADS | | QVW<br>DSG<br>SDH<br>VL | 727 |
| | 49 | IGH<br>V3-<br>33*<br>01 | IGH<br>D3-<br>16*<br>01 | IGHJ<br>4*02 | GFT<br>FSS<br>FN | 728 | IWYD<br>GSHK | 729 | ARQ<br>MFT<br>GHF<br>DY | 730 | IGKV<br>3-15<br>*01 | IGKJ<br>1*01 | QGV<br>SSN | 731 | DAS | QHY<br>NNW<br>PRT | 732 | | | | | | | | |
| | 60 | IGH<br>V3-<br>33*<br>01 | IGH<br>D2-<br>2*<br>01 | IGHJ<br>6*02 | GFT<br>FSG<br>YG | 733 | IWND<br>GSFK | 734 | ARE<br>GRG<br>QLL<br>FHG<br>MDV | 735 | IGKV<br>3-20<br>*01 | IGKJ<br>3*01 | QSV<br>SSS<br>Y | 736 | GAS | QQY<br>GRS<br>QGF<br>T | 737 | | | | | | | | |
| | 60 | IGH<br>V3-<br>33*<br>01 | IGH<br>D2-<br>21*<br>02 | IGHJ<br>4*02 | GFT<br>FSG<br>HG | 738 | IWSS<br>GSKT | 739 | ARD<br>GHC<br>DGG<br>CYS<br>ALY<br>DY | 740 | | | | | | | | IGL<br>V2-<br>23*<br>01 | IGL<br>J3*<br>02 | SSD<br>VGN<br>YNL | 741 | EGT | | CSF<br>AGS<br>RWV | 742 |
| H015 | 60 | IGH<br>V3-<br>33*<br>01 | IGH<br>D6-<br>6*<br>01 | IGHJ<br>4*02 | GFS<br>FSR<br>HG | 743 | IWFD<br>GTND | 744 | ARE<br>DPH<br>LLI<br>ATL<br>DL | 745 | IGKV<br>1-39<br>*01 | IGKJ<br>4*01 | QGL<br>TSF | 746 | SAS | QQS<br>YGT<br>PAL<br>A | 747 | | | | | | | | |
| | 60 | IGH<br>V3-<br>33*<br>01 | IGH<br>D4-<br>11*<br>01 | IGHJ<br>2*01 | GFT<br>FRS<br>YG | 748 | IWAD<br>GTKQ | 749 | ARE<br>TTI<br>FNW<br>YFD<br>L | 750 | IGKV<br>1-39<br>*01 | IGKJ<br>4*01 | QSI<br>NKY | 751 | TAS | QQS<br>FSI<br>PPT | 752 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 60 | IGHV3-33*01 | IGHDS-18*01 | IGHJ4*02 | GFTFSDYG | 753 | IWSDGSNK | 754 | ARERRGFSYGLDDN | 755 | | | | | | | | IGLV2-11*01 | IGLJ2*01 | SSDVGGYNS | 756 | DVS | | CSYAGRYTFVV | 757 |
| 60 | IGHV3-33*01 | IGHD6-19*01 | IGHJ3*01 | GFTFSRYG | 758 | IWKDGTND | 759 | AREQAEIAVASFDF | 760 | IGKV1-39*01 | IGKJ4*01 | QRIGDF | 761 | AAS | QQAYNAPPLT | 762 | | | | | | | | |
| 60 | IGHV3-33*01 | IGHD6-19*01 | IGHJ4*02 | GFTFSNYG | 763 | IWKDGTNK | 764 | ARESHYSAWYVLDY | 765 | | | | | | | | IGLV1-51*01 | IGLJ3*02 | RSNIGSNY | 766 | GND | | GSWDGSLSVGV | 767 |
| 60 | IGHV3-33*01 | IGHD2-8*01 | IGHJ4*02 | GFTFSRHG | 768 | IWYDGSNK | 769 | AREDPNVFIATLDL | 770 | IGKV1-39*01 | IGKJ4*01 | QTITRS | 771 | ATS | QQSDSTPALA | 772 | | | | | | | | |
| 60 | IGHV3-33*01 | IGHD3-16*01 | IGHJ4*02 | GFTFSRYG | 773 | IWNDGSTK | 774 | AREDPYVFMATLDS | 775 | | | | | | | | IGLV2-11*01 | IGLJ3*02 | SSDVGGYNY | 776 | DVS | | CSYAGSYTWV | 777 |
| 60 | IGHV3-33*01 | IGHD2-21*01 | IGHJ2*01 | GFTFRNYG | 778 | IWADGTNQ | 779 | ARETTIFQWYFDL | 780 | IGKV1-39*01 | IGKJ4*01 | QSINNY | 781 | GAS | QQSFSIPPT | 782 | | | | | | | | |
| 69 | IGHV3-33*01 | IGHD2-15*01 | IGHJ6*02 | GFTFSSYG | 783 | IWYDGSLK | 784 | ARETTFGRFCSG | 785 | IGKV2-24*01 | IGKJ1*01 | QSLVHSDGNTY | 786 | QIS | MQAAQFPWT | 787 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | | | | | | | | | GSCYSDYYYGMDV | | | | | | | | | | | | | | | | |
| | 69 | IGHV3-33*01 | IGHD6-13*01 | IGHJ4*02 | GFVFSNYG | 788 | IWADGTNS | 789 | AREGGIVAADK | 790 | | | | | | | | IGLV1-51*01 | IGLJ1*01 | SSNIGNNY | 791 | DNN | | | |
| H014 | 146 | IGHV3-33*01 | IGHD4/OR15-4a*01 | IGHJ4*02 | GFSFSDYG | 792 | IWRDGSNS | 793 | AREARVAAPASYDY | 794 | | | | | | | | IGLV3-21*02 | IGLJ3*02 | KIVNKN | 795 | DDD | | QVWDNGSNHVV | 796 |
| | 146 | IGHV3-33*01 | IGHD6-13*01 | IGHJ4*02 | GFTFSSCG | 797 | IWADGTNK | 798 | AREALIAAPATFDY | 799 | | | | | | | | IGLV3-21*02 | IGLJ2*01 | NIRSKN | 800 | DDD | | QVWDNNSRHVV | 801 |
| | 146 | IGHV3-33*01 | IGHD6-13*01 | IGHJ5*02 | GFTFRNYG | 802 | IWADGSNK | 803 | AREGHIAAPAALDL | 804 | | | | | | | | IGLV3-21*02 | IGLJ2*01 | NIRNKN | 805 | DDD | | QVWDSSSEHVV | 806 |
| H013 | 146 | IGHV3-33*01 | IGHD6-13*01 | IGHJ4*02 | GFTFSGNG | 807 | IWSDGSNK | 808 | AREANIAAPAIYDH | 809 | | | | | | | | IGLV3-21*02 | IGLJ2*01 | NIRSKN | 810 | DDN | | QVWDSYSDHVV | 811 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 146 | IGH V3-33*01 | IGH D2-15*01 | IGHJ 5*02 | GFT FTT YG | 812 | IWAD GSNQ | 813 | ARE GHV ATP ILD L | 814 | IGKV 1-39 *01 | IGKJ 4*01 | QSI ANY | 815 | VAS | QQS YSM PTL T | 816 | | | | | | | | |
| 146 | IGH V3-33*01 | IGH D3-10*01 | IGHJ 3*01 | GFT FSS YG | 817 | IWYD GSIK | 818 | VRD NFG LNA FDV | 819 | IGKV 3-11 *01 | IGKJ 2*01 | QSV TRY | 820 | EAT | QHR SNW PYT | 821 | | | | | | | | |
| 146 | IGH V3-33*01 | IGH D6-13*01 | IGHJ 4*02 | GFT FSN YG | 822 | IWHD GSNQ | 823 | ATE RRI AAP GCL DY | 824 | | | | | | | | IGL V5-48*02 | IGL J2*01 | SGI SVD RSR | 825 | SXS DK | 826 | MIX HSS AMW | 827 |
| 146 | IGH V3-33*01 | IGH D6-13*01 | IGHJ 4*02 | GFT FSS HG | 828 | IWYD GSTK | 829 | ARE ALI AAP ATF DY | 830 | IGKV 1-5*03 | IGKJ 1*01 | QSI DTW | 831 | KAS | QYY SVY ST | 832 | IGL V3-21*02 | IGL J3*02 | NIG SKN | 833 | DDN | | QVW DNN SDH VV | 834 |
| 60 | IGH V3-33*02 | IGH D5-12*01 | IGHJ 6*02 | GFS FSR YG | 835 | IWYD GSTR | 836 | AGG GYS SRG YYN YGL DV | 837 | IGKV 1-33 *01 | IGKJ 4*01 | QDI SNY | 838 | DAS | QQY DNL PPL T | 839 | IGL V3-10*01 | IGL J2*01 | | | EDN | | YST DRS GDQ RV | 840 |
| 99 | IGH V3-33*06 | IGH D2-15*01 | IGHJ 4*02 | GFT FSR YG | 841 | IWSD GSNK | 842 | AKA TCG DGS CGL YYF DY | 843 | | | | | | | | IGL V1-40*01 | IGL J3*02 | SSN IGA GYD | 844 | GNS | | QSY DSN LSG WV | 845 |
| 55 | IGH V3-43* | IGHD 2-21 *01 | IGHJ 5*02 | | | INGN GRDT | 846 | AKD IWI FDG | 847 | IGKV 2-30 *01 | IGKJ 1*01 | QSL VYS DGN | 848 | KVS | MQQ THW PWA | 849 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | | 02 | | | | | | | RRW<br>IAG<br>SPD<br>A | | | | TY | | | | | | | | | | | | |
| | 49 | IGH<br>V3-<br>48*<br>01 | IGH<br>D1-<br>1*<br>01 | IGHJ<br>6*02 | GFS<br>FSS<br>YS | 850 | ITSN<br>SATI | 851 | ARA<br>GPP<br>SPP<br>NYG<br>MDV | 852 | IGKV<br>4-1*<br>01 | IGKJ<br>4*01 | QSL<br>LYR<br>SNN<br>KNY | 853 | WAS | QQY<br>YTA<br>PLL | 854 | | | | | | | | |
| H016 | 69 | IGH<br>V3-<br>48*<br>02 | IGH<br>D3/<br>OR<br>15-<br>3a*<br>01 | IGHJ<br>2*01 | GFT<br>FPS<br>HT | 855 | ISTT<br>SEAI | 856 | ASV<br>GLD<br>SKI<br>SGY<br>WYF<br>DL | 857 | IGKV<br>3-15<br>*01 | IGKJ<br>4*01 | QSI<br>SSN | 858 | RAS | QQY<br>DHW<br>PLT | 859 | | | | | | | | |
| | 69 | IGH<br>V3-<br>48*<br>02 | IGH<br>D3/<br>OR<br>15-<br>3a*<br>01 | IGHJ<br>2*01 | GFT<br>FST<br>YT | 860 | ISSS<br>GDTI | 861 | ARV<br>GLA<br>LTI<br>SGY<br>WYF<br>DL | 862 | IGKV<br>3-15<br>*01 | IGKJ<br>4*01 | QSV<br>SSN | 863 | GAS | QQY<br>NDW<br>PLT | 864 | | | | | | | | |
| | 146 | IGH<br>V3-<br>48*<br>02 | IGH<br>D7-<br>27*<br>01 | IGHJ<br>2*01 | GFT<br>FSS<br>SV | 865 | ISTT<br>SAAI | 866 | ARA<br>KLG<br>SGS<br>YWY<br>FDL | 867 | IGKV<br>3-15<br>*01 | IGKJ<br>4*01 | QSV<br>GSN | 868 | AAS | QQY<br>NNW<br>PLT | 869 | | | | | | | | |
| | 13 | IGH<br>V3-<br>48*<br>03 | IGH<br>D1-<br>1*<br>01 | IGHJ<br>3*02 | GIT<br>LRT<br>YK | 870 | ISSD<br>DKTI | 871 | ARD<br>TGI<br>WNG<br>AYD<br>AFD<br>I | 872 | | | | | | | | IGL<br>V5-<br>45*<br>02 | IGL<br>J1*<br>01 | SGI<br>NVG<br>TYR | 873 | YRS<br>DSD<br>M | 874 | MIW<br>HST<br>AYV | 875 |
| | 13 | IGH<br>V3- | | IGHJ<br>4*02 | GFT<br>FSS | 876 | ISNS<br>GNTI | 877 | VGF<br>DH | 878 | IGKV<br>4-1* | IGKJ<br>5*01 | RSL<br>LYT | 879 | WAS | QQY<br>YSP | 880 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 48* 03 | | | YE | | | | | | 01 | | SVN KNH | | | PIT | | | | | | | | | |
| 55 | IGH V3-48* 03 | IGH D2-2* 02 | IGHJ 4*02 | GFT FSN NE | 881 | ISSS GSVM | 882 | AGH CSS NKC YKY | 883 | | | | | | | | IGL V1-40* 01 | IGL J2* 01 | SSN IGA GYD | 884 | RNS | | QSY DSS LSG SI | 885 |
| 69 | IGH V3-49* 03 | IGH D3-22* 01 | IGHJ 4*02 | GFT FGD YG | 886 | IKPK AYGG AT | 887 | ARD LTI NKI IVA NDF | 888 | IGKV 4-1* 01 | IGKJ 5*01 | QSL LYS SNN KNY | 889 | WAS | QQY YST PIT | 890 | | | | | | | | |
| 146 | IGH V3-49* 03 | IGH D6-13* 01 | IGHJ 4*02 | GFT FGD YA | 891 | IRSK GYGG TR | 892 | ARV PYS SSW YVA WAD Y | 893 | IGKV 4-1* 01 | IGKJ 4*01 | QSV LYS FNN KNY | 894 | WAS | QQY YST PLT | 895 | | | | | | | | |
| 99 | IGH V3-49* 04 | IGH D3-10* 01 | IGHJ 4*02 | GFT FGD YG | 896 | IRRK ANRG TT | 897 | TRG DYY GSR NSY FWL FDY | 898 | IGKV 2D-29* 01 | IGKJ 1*01 | QSL LYS DGK TY | 899 | ELS | MQS IQL RT | 900 | | | | | | | | |
| 69 | IGH V3-53* 01 | IGH D6-19* 01 | IGHJ 4*02 | GFT VIS NY | 901 | IYSG VNT | 902 | ARV IAV AGT NRG GPR WRS TYY FDY | 903 | | | | | | | | IGL V7-43* 01 | IGL J3* 02 | SGT VTT ANY | 904 | STT | | LLY CSG VRV | 905 |
| 9 | IGH V3-7* | IGH D3-3* | IGHJ 4*02 | GLT FSR YW | 906 | INEE GSHS | 907 | ASE LWT AFN | 908 | | | | | | | | IGL V1-51* 02 | IGL J3* | SSN VGK NY | 909 | DSY | | GTW DSS LKV | 910 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 01 | 01 | | | | | | KDW<br>SGY<br>NDY | | | | | | | | | 01 | | | | | | VV | |
| 9 | IGH<br>V3-<br>7*<br>01 | IGH<br>D1-<br>26*<br>01 | IGHJ<br>4*02 | GFT<br>FTN<br>FK | 911 | IKQD<br>GSEK | 912 | TRD<br>TWV<br>DS | 913 | IGKV<br>1-17<br>*03 | IGKJ<br>3*01 | QGI<br>SKY | 914 | ASS | LQH<br>QSY<br>PFT | 915 | | | | | | | | |
| 13 | IGH<br>V3-<br>7*<br>01 | IGH<br>D2-<br>21*<br>01 | IGHJ<br>4*02 | GFS<br>FSN<br>YW | 916 | IKED<br>GSEK | 917 | ASS<br>HYS<br>AGD<br>VSY<br>NFD<br>Y | 918 | | | | | | | | IG<br>LV<br>10-<br>54*<br>01 | IGL<br>J3*<br>02 | NKN<br>VGN<br>KG | 919 | RHN | | SAW<br>DFS<br>LRA<br>WV | 920 |
| 55 | IGH<br>V3-<br>7*<br>03 | IGH<br>D6-<br>13*<br>01 | IGHJ<br>5*02 | GFI<br>FSS<br>SW | 921 | IKQD<br>GSDK | 922 | ARS<br>HVA<br>AGV<br>TRW<br>FDP | 923 | IGKV<br>3-11<br>*01 | IGKJ<br>2*01 | QSV<br>SSY | 924 | DAS | QHR<br>SK | 925 | | | | | | | | |
| 55 | IGH<br>V3-<br>7*<br>03 | IGH<br>D6-<br>13*<br>01 | IGHJ<br>5*01 | SFT<br>FST<br>SW | 926 | INQD<br>GSER | 927 | ARS<br>HVA<br>AGG<br>TRW<br>IDS | 928 | IGKV<br>3-11<br>*01 | IGKJ<br>2*01 | QNI<br>NSQ | 929 | DAS | HHR<br>IN | 930 | | | | | | | | |
| 55 | IGH<br>V3-<br>7*<br>03 | IGH<br>D3-<br>16*<br>02 | IGHJ<br>3*01 | GFT<br>FSD<br>YVV | 931 | INQD<br>GSEY | 932 | ARL<br>DRG<br>TGE<br>SGY<br>RSS<br>DV | 933 | | | | | | | | IGL<br>V1-<br>44*<br>01 | IGL<br>J2*<br>01 | SSN<br>IGS<br>RS | 934 | INN | | AAW<br>DDS<br>LNG<br>VV | 935 |
| 55 | IGH<br>V3-<br>7*<br>03 | IGH<br>D1-<br>7*<br>01 | IGHJ<br>5*02 | GFI<br>FSS<br>NW | 936 | INQD<br>GSDI | 937 | ARS<br>HVA<br>ASG<br>TRW<br>FDP | 938 | IGKV<br>3-11<br>*01 | IGKJ<br>2*01 | QSV<br>SSY | 939 | DAS | QHR<br>SY | 940 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 55 | IGH V3- 72* 01 | IGH D3- 9* 01 | IGHJ 4*02 | GFT FSD HF | 941 | TRNK ANSY TT | 942 | ARD GYD ILN HFV RFD F | 943 | IGKV 3-11 *01 | IGKJ 2*01 | QSV SSY | 944 | DAS | QHR SY | 945 | | | | | | | | |
| | 60 | IGH V3- 72* 01 | IGH D3- 16* 01 | IGHJ 3*02 | GFT FSD HY | 946 | IRNK AKSY TT | 947 | ARE GLG SPT SDA FDI | 948 | | | | | | | | IGL V2- 14* 01 | IGL J3* 02 | SSD VGG YNY | 949 | EVT | | SSY TTS STL V | 950 |
| | 60 | IGH V3- 73* 02 | IGH D4- 17* 01 | IGHJ 6*02 | GFT LSG SA | 951 | IRSK ANNY AT | 952 | TSQ YGD GYY YAM DV | 953 | IGKV 3-15 *01 | IGKJ 3*01 | QNI RNN | 954 | GAS | QHY NNW PLF T | 955 | | | | | | | | |
| | 9 | IGH V3- 74* 01 | | IGHJ 6*02 | | | ISDD ERST | 956 | VRG LNH AMD V | 957 | | | | | | | | IGL V2- 14* 01 | IGL J3* 02 | NSD VGG YNF | 958 | DVT | | CSF TTR NTW V | 959 |
| | 13 | IGH V3- 74* 01 | IGH D3- 22* 01 | IGHJ 4*02 | GFT FST YR | 960 | IKYD GSST | 961 | ARV YRD SRD GSD FRH FDS | 962 | IGKV 4-1* 01 | IGKJ 4*01 | QSL LYS SNK KNY | 963 | WAS | QQY YDI PYT | 964 | | | | | | | | |
| H017 | 55 | IGH V3- 74* 01 | IGH D3- 10* 01 | IGHJ 4*02 | GFT FSN YW | 965 | ISTD GSST | 966 | ARG STY YFG SGS VDY | 967 | | | | | | | | IGL V2- 14* 01 | IGL J1* 01 | SSD IGV YNY | 968 | DVT | | SSY RGS STP YV | 969 |
| | 55 | IGH V3- | IGH D1- | IGHJ 4*02 | GFT FSD | 970 | IESD GSGT | 971 | ARG SLD | 972 | | | | | | | | IGL V2- | IGL J2* | RSD VGA | 973 | DVS | | YSY TTS | 974 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | | 74*01 | 26*01 | | YW | | | | F | | | | | | | | | 14*01 | 01 | YNY | | | | NTLV | |
| | 55 | IGHV3-74*01 | IGHD1-26*01 | IGHJ4*02 | GFTFSDYW | 975 | IDDGGSAT | 976 | SRGSLDY | 977 | | | | | | | | IGLV2-14*01 | IGLJ2*01 | RSDVGAYNY | 978 | DVS | | YSYTTSNTLV | 979 |
| | 99 | IGHV3-74*01 | IGHD4/OR15-4a*01 | IGHJ4*02 | GFTFSNYW | 980 | INSDGTNT | 981 | ACLRVPDRN | 982 | | | | | | | | IGLV7-46*01 | IGLJ2*01 | TGAVTSGHY | 983 | DAS | | LLSYSGAQV | 984 |
| | 13 | IGHV3-9*01 | IGHD2-2*01 | IGHJ4*02 | GFIFDDYS | 985 | ISWNSEFM | 986 | VKANVKKGSTSCFDY | 987 | IGKV3-20*01 | IGKJ1*01 | QSVSSSY | 988 | DAS | QQYSGSSPRT | 989 | | | | | | | | |
| | 60 | IGHV3-9*01 | IGHD6-19*01 | IGHJ4*01 | GFNFNMYA | 990 | ISYNGGAR | 991 | VKDKSQGIPVAGLEY | 992 | | | | | | | | IGLV1-51*01 | IGLJ2*01 | NSNIGNNY | 993 | DDS | | GTWDSSLSAA | 994 |
| | 60 | IGHV3-9*01 | IGHD6-19*01 | IGHJ4*02 | GFTFNMYA | 995 | ISFNGGAR | 996 | VKDKSQGIPLAGLEY | 997 | | | | | | | | IGLV1-51*01 | IGLJ2*01 | SSNIGNNY | 998 | DDS | | ATWDSSLTAA | 999 |
| H018 | 60 | IGHV3-9*01 | IGHD6-19*01 | IGHJ4*01 | GFNFNMYA | 1000 | ISYNGGAR | 1001 | VKDKSQGIPVAGLEY | 1002 | | | | | | | | IGLV1-51*01 | IGLJ2*01 | NSNIGNNF | 1003 | DDS | | GTWDSSLSAA | 1004 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 69 | IGHV4-30-4*01 | IGHD2-2*03 | IGHJ3*02 | GGSITTGDYY | 1005 | IYYSGST | 1006 | AIYMDEAWAFEI | 1007 | IGKV1-39*01 | IGKJ2*01 | QSIGNY | 1008 | AVS | QQSYTISLFT | 1009 | | | | | | | | |
| H019 | 69 | IGHV4-30-4*01 | IGHD2-2*03 | IGHJ3*02 | GGSITTGDYY | 1010 | IYYSGST | 1011 | AIYMDEAWAFEI | 1012 | IGKV1-39*01 | IGKJ2*01 | QSVGNY | 1013 | AVS | QQSYTISLFT | 1014 | | | | | | | | |
| | 146 | IGHV4-30-4*01 | IGHD3-10*01 | IGHJ4*02 | GGSISGGDYY | 1015 | IYYSGNT | 1016 | VRENYITSPLSR | 1017 | | | | | | | | IGLV2-8*01 | IGLJ3*02 | SSDVGGYNY | 1018 | EVT | | SSYAGSNDVV | 1019 |
| | 146 | IGHV4-30-4*01 | IGHD4-17*01 | IGHJ4*02 | GGSINSGDYY | 1020 | VYSSGST | 1021 | ASYTVTTWGGFDY | 1022 | | | | | | | | IGLV3-10*01 | IGLJ3*02 | ALPKKY | 1023 | EDH | | YSTDSSGNYRV | 1024 |
| | 99 | IGHV4-31*02 | IGHD4/OR15-4a*01 | IGHJ4*02 | GGSISSGNYY | 1025 | IHYSGST | 1026 | ARGVLH | 1027 | IGKV3-20*01 | IGKJ2*01 | QSVSSSY | 1028 | GVS | QQYGSSPYT | 1029 | | | | | | | | |
| | 13 | IGHV4-31*03 | IGHD3-22*01 | IGHJ4*02 | GGSISSGGYY | 1030 | IYYSDTTYYSGST | 1031 | ARVVSSGHRHYYFDY | 1032 | IGKV1-27*01 | IGKJ1*01 | QGISNY | 1033 | SAS | QKYWT | 1034 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 60 | IGHV4-31*03 | IGHD1-1*01 | IGHJ5*02 | RGSVGWGENF | 1035 | ILNTGID | 1036 | AQSRRLVGPFVS | 1037 | IGKV3-15*01 | IGKJ2*03 | SININ | 1038 | DAS | QQYDKWPRS | 1039 | IGLV6-57*01 | IGLJ3*02 | SGSIASNY | 1040 | EDN | | QSYDSSNHGV | 1041 |
| 99 | IGHV4-31*03 | IGHD2-8*02 | IGHJ4*02 | GGSISSGGYY | 1042 | ISYSGST | 1043 | ARGVLV | 1044 | IGKV3-20*01 | IGKJ2*01 | QSVSRAY | 1045 | GAS | QQYDSSPYT | 1046 | | | | | | | | |
| 146 | IGHV4-31*03 | IGHD3-10*01 | IGHJ3*01 | GGSINSDDYY | 1047 | IYYDGSA | 1048 | ARVVHASANAFDV | 1049 | IGKV1-6*01 | IGKJ4*01 | QGIRND | 1050 | AAS | LQDYNYPLT | 1051 | IGLV1-51*01 | IGLJ3*02 | SSNIGNTF | 1052 | DNY | | GTWDSSLNGWV | 1053 |
| 146 | IGHV4-31*03 | IGHD3-10*01 | IGHJ3*01 | GGSISNDNYY | 1054 | IYYDGSA | 1055 | ARVVHASANAFDV | 1056 | IGKV1-39*01 | IGKJ5*01 | QSINKF | 1057 | DAS | QQTYSTPT | 1058 | | | | | | | | |
| 146 | IGHV4-31*03 | IGHD4-11*01 | IGHJ3*02 | GVPINNAGFY | 1059 | IHASGAT | 1060 | ARVPLRDFYSNYSPSAFDI | 1061 | IGKV3-15*01 | IGKJ4*01 | QSVSSD | 1062 | GAS | QQYKNWPPLT | 1063 | | | | | | | | |
| 9 | IGHV4-34*01 | IGHD3-16*02 | IGHJ5*02 | RGSFSDYY | 1064 | INHSGST | 1065 | AGGRFTNDFVWGSYRYES | 1066 | IGKV2-28*01 | IGKJ4*01 | QSLLHSNGYNY | 1067 | LGS | MQALQTLLLT | 1068 | | | | | | | | |
| 60 | IGHV4-34* | IGHD6-19* | IGHJ4*02 | GGSFIGHY | 1069 | ISHSGSA | 1070 | VRGGYSSAP | 1071 | | | | | | | | IGLV1-44* | IGLJ3*02 | SSNIGSNT | 1072 | SNN | | AAWDDSLNG | 1073 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 01 | 01 | | | | | | YPR EWR Y | | | | | | | | | 01 | | | | | | WV | |
| 69 | IGH V4- 34* 01 | IGH D5- 24* 01 | IGHJ 6*03 | GGS FSG DF | 1074 | INQS GST | 1075 | ARG RDG YNY VGY YYY YYM DV | 1076 | IGKV 3-11 *01 | IGKJ 1*01 | QSV TNY | 1077 | DGS | QQR SNW QWT | 1078 | | | | | | | | |
| 146 | IGH V4- 34* 01 | IGH D3- 3* 01 | IGHJ 6*02 | GGT FSG YY | 1079 | IDHS GGT | 1080 | ARG IFE VVI IPY YSY RVD V | 1081 | IGKV 3-15 *01 | IGKJ 3*01 | QTI SNN | 1082 | GAS | QQY NNW PPF T | 1083 | IGL V3- 19* 01 | IGL J2* 01 | SLR SYY | 1084 | GRN | | SSR SGN RLV | 1085 |
| 9 | IGH V4- 34* 02 | IGH D6- 13* 01 | IGHJ 5*02 | GGP FSG YY | 1086 | INHS GST | 1087 | GRG LGR EYS SSW YGG RRF DP | 1088 | | | | | | | | IGL V2- 14* 01 | IGL J3* 02 | SRQ DGR YX | 1089 | EVN | | RSY ISN NXX WV | 1090 |
| 9 | IGH V4- 38- 2* 02 | IGH D3- 22* 01 | IGHJ 3*02 | GYS IRN RYY | 1091 | MYHS GST | 1092 | ARD RSG YVF FYD AFD I | 1093 | IGKV 3-20 *01 | IGKJ 4*01 | QSV SSS Y | 1094 | GAS | QQY GSS PLT | 1095 | | | | | | | | |
| 146 | IGH V4- 38- 2* 02 | IGH D2- 21* 02 | IGHJ 4*02 | GYS ISR DYY | 1096 | FSHS GTT | 1097 | GGG VTR ADY | 1098 | | | | | | | | IGL V1- 47* 02 | IGL J3* 02 | SSN IGK NY | 1099 | TND | | AVW DDN LSA WE | 1100 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 60 | IGHV4-39*01 | IGHD2-8*01 | IGHJ4*02 | GGSISSSSYY | 1101 | IDYYGST | 1102 | ARRIQLMVFDF | 1103 | IGKV1-5*03 | IGKJ1*01 | QSISSW | 1104 | KAS | HQYNTYPWT | 1105 | | | | | | | | |
| 60 | IGHV4-39*01 | IGHD3-3*01 | IGHJ2*01 | GGSISNSNYY | 1106 | IYYSGST | 1107 | ARHPYYNFWIYWYFDL | 1108 | | | | | | | | IGLV1-44*01 | IGLJ2*01 | SSTIGSNT | 1109 | LNN | | ASWDDSLNGLVV | 1110 |
| 99 | IGHV4-39*01 | IGHD3-10*01 | IGHJ3*01 | GGSIRSSGYF | 1111 | VSSKGKT | 1112 | TRHWLGGDKWSQSPFLAV | 1113 | | | | | | | | IGLV1-44*01 | IGLJ3*02 | SSNIGVNT | 1114 | ANN | | AVWDDSLNTWV | 1115 |
| 99 | IGHV4-39*01 | IGHD5-12*01 | IGHJ3*02 | GGSISTSNYY | 1116 | IYYGGST | 1117 | AKGRYSGYNDYNAFDI | 1118 | | | | | | | | IGLV1-47*02 | IGLJ3*02 | | | SNN | | AAWDDSPEWLG | 1119 |
| 146 | IGHV4-39*01 | IGHD3-10*01 | IGHJ3*01 | GGSISSMSYY | 1120 | IYYSGTT | 1121 | TRPASGAHDYVSRSYYPGQGAFGV | 1122 | IGKV3-20*01 | IGKJ5*01 | QSVSSSY | 1123 | GAS | QQYGSSSIT | 1124 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 146 | IGHV4-39*01 | IGHD6-13*01 | IGHJ4*02 | GGSIISYTYY | 1125 | LYYTGIT | 1126 | ARLLGIAATGHFDS | 1127 | | | | | | | | IGLV10-54*01 | IGLJ3*02 | SNNIDNQG | 1128 | RNN | | STWDSSLSTWL | 1129 |
| 146 | IGHV4-39*01 | IGHD3-10*01 | IGHJ3*02 | GGSISSISYY | 1130 | IYYSGTP | 1131 | TRPASGAHDYASRSYYPGLGAFGI | 1132 | IGKV3-20*01 | IGKJ5*01 | QSVSTTY | 1133 | GAS | QQYGSSSTT | 1134 | | | | | | | | |
| 146 | IGH-V4-39*01 | IGHD3-3*01 | IGHJ3*02 | GGSITSLSYW | 1135 | IYYSGTT | 1136 | ARPLLNPMTLYGVTPGIGPFEI | 1137 | IGKV3-20*01 | IGKJ4*01 | QSVSSKC | 1138 | GAS | QQHDNSLS | 1139 | | | | | | | | |
| 146 | IGHV4-39*01 | IGHD6-6*01 | IGHJ4*02 | GDSMSRNSFY | 1140 | INYNGIT | 1141 | AAHRVSSSYPADY | 1142 | IGKV1-39*01 | IGKJ1*01 | QNIDDY | 1143 | AAS | QQSYNTPT | 1144 | | | | | | | | |
| 146 | IGHV4-39*01 | IGHD3-3*01 | IGHJ3*02 | GGSSISLSYY | 1145 | IYYSGTA | 1146 | ARPLLNPSTIYGVTPGIGPFEM | 1147 | IGKV3D-15*01 | IGKJ1*01 | QSIRSN | 1148 | GAS | QQYINWPPWT | 1149 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 146 | IGHV4-4*02 | IGHD3-16*02 | IGHJ6*02 | GYSVSTSNW | 1150 | IYHIGST | 1151 | ARGNYDYVWGSYRSDQGYGLDV | 1152 | IGKV1-39*01 | IGKJ2*01 | QSIDNY | 1153 | LAS | QRSYSTPYT | 1154 | | | | | | | | |
| 49 | IGHV4-4*07 | IGHD6-13*01 | IGHJ6*03 | GASIRSHY | 1155 | VHSSGGT | 1156 | AREGGSSYYYYYYMDV | 1157 | | | | | | | | IGLV2-8*01 | IGLJ2*01 | SSDVGSYNY | 1158 | DVT | | SSYAGINSYVI | 1159 |
| 13 | IGHV4-59*01 | IGHD2-2*01 | IGHJ5*02 | GGSISTYF | 1160 | IYYNGGT | 1161 | ARSKNQLLLFDP | 1162 | IGKV3-15*01 | IGKJ4*01 | QSVGSD | 1163 | GAS | QQYNDWPPLT | 1164 | | | | | | | | |
| 13 | IGHV4-59*01 | IGHD4-23*01 | IGHJ5*01 | GDSIGTYF | 1165 | VYHTGGT | 1166 | ARSKNQLLLFEF | 1167 | IGKV1-33*01 | IGKJ4*01 | QDISNY | 1168 | DAS | QQYDNLPLT | 1169 | | | | | | | | |
| 55 | IGHV4-59*01 | IGHD7-27*01 | IGHJ3*01 | GASISSNY | 1170 | MYSSGSV | 1171 | ARTNWAYDPFNV | 1172 | IGKV1-5*03 | IGKJ1*01 | QNINSW | 1173 | KAS | QQYYSYST | 1174 | IGLV1-36*01 | IGLJ2*01 | NNNIGRSA | 1175 | ED | | SAWDFSLSVQV | 1176 |
| 60 | IGHV4-59*01 | IGHD2-15*01 | IGHJ6*02 | GGSISSYY | 1177 | IYDSGST | 1178 | ARDRGYCSGGSCLGGMDV | 1179 | IGKV1-5*03 | IGKJ4*01 | QSISRW | 1180 | KAS | QQYNSYFPLT | 1181 | | | | | | | | |
| 60 | IGHV4- | IGHD2- | IGHJ6*02 | GGSISG | 1182 | IYDSGNT | 1183 | VRDRGF | 1184 | IGKV1-5* | IGKJ1*01 | QSISSW | 1185 | KAS | QQYNSY | 1186 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|---|
| | DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | | 59*<br>01 | 8*<br>02 | | SY | | | | CTG<br>KSC<br>LGG<br>MDV | | 03 | | | | | RT | | | | | | | | | |
| | 60 | IGH<br>V4-<br>59*<br>01 | IGH<br>D2-<br>8*<br>02 | IGHJ<br>4*02 | GGS<br>ISN<br>YF | 1187 | VYSS<br>GTT | 1188 | ARL<br>RRR<br>GLT<br>GTD<br>FDY | 1189 | | | | | | | | IGL<br>V1-<br>44*<br>01 | IGL<br>J2*<br>01 | TSN<br>IGD<br>NN | 1190 | INN | | AAW<br>DDS<br>LNG<br>PNV<br>V | 1191 |
| | 69 | IGH<br>V4-<br>59*<br>01 | IGH<br>D3-<br>22*<br>01 | IGHJ<br>6*03 | GGS<br>IRS<br>YY | 1192 | IYYS<br>GST | 1193 | ARS<br>YYY<br>DSS<br>GYR<br>PSF<br>YYY<br>YMD<br>V | 1194 | | | | | | | | IGL<br>V3-<br>1*<br>01 | IGL<br>J2*<br>01 | KLG<br>DKY | 1195 | QDT | | QAW<br>DSS<br>VV | 1196 |
| | 146 | IGH<br>V4-<br>59*<br>01 | IGH<br>D1-<br>26*<br>01 | IGHJ<br>6*02 | GGS<br>ISG<br>YY | 1197 | IYYS<br>GTT | 1198 | ARG<br>ILG<br>STW<br>YYY<br>YGL<br>DV | 1199 | IGKV<br>1-39<br>*01 | IGKJ<br>2*01 | QSI<br>SSY | 1200 | ATS | HQS<br>YSS<br>PYT | 1201 | | | | | | | | |
| | 55 | IGH<br>V4-<br>59*<br>08 | IGH<br>D5-<br>18*<br>01 | IGHJ<br>4*02 | GGS<br>ISN<br>DY | 1202 | IHSK<br>GDT | 1203 | ARH<br>LYR<br>YGY<br>RNY<br>FDY | 1204 | IGKV<br>1-12<br>*01 | IGKJ<br>4*01 | QGI<br>SSG | 1205 | AAS | QQA<br>NSF<br>PLT | 1206 | | | | | | | | |
| H020 | 55 | IGH<br>V4-<br>59*<br>08 | IGH<br>D5-<br>18*<br>01 | IGHJ<br>4*02 | GGS<br>ISN<br>DY | 1207 | IHSK<br>GDT | 1208 | ARH<br>LYR<br>YGY<br>RNY<br>FDY | 1209 | IGKV<br>1-12<br>*01 | IGKJ<br>4*01 | QGI<br>SSG | 1210 | AAS | QQA<br>NSF<br>PLT | 1211 | | | | | | | | |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 69 | IGHV4-61*08 | IGHD6-13*01 | IGHJ3*02 | GGSVRSTGYF | 1212 | IYTGGAT | 1213 | ARMTSFKQSGGWYRGRHDGFDI | 1214 | IGKV1-5*01 | IGKJ2*01 | QTIGTY | 1215 | EAS | QEYNSYSYT | 1216 | | | | | | | | |
| 69 | IGHV4-61*08 | IGHD6-19*01 | IGHJ3*02 | RGSVSNGGYY | 1217 | VYYTGSS | 1218 | ARLTSYKQRGGWYRGRHDAFDI | 1219 | IGKV1-5*01 | IGKJ2*01 | QSISTL | 1220 | DGS | QEYSSYSYT | 1221 | | | | | | | | |
| 9 | IGHV5-51*01 | IGHD3-22*01 | IGHJ4*02 | GYSFTSYW | 1222 | IQSGDYNT | 1223 | ARRARNVGNYGTSDFYPYFDH | 1224 | | | | | | | | IGLV2-14*01 | IGLJ3*02 | SSDVGRYNY | 1225 | DVT | | SSYISSNTLWV | 1226 |
| 60 | IGHV5-51*01 | IGHD1-14*01 | IGHJ3*02 | GYTFASYW | 1227 | INPPNSDT | 1228 | ARRRVSVTGTDAFDI | 1229 | | | | | | | | IGLV2-8*01 | IGLJ2*01 | SSDVGGYNY | 1230 | EVN | | SSYAGTNTFVV | 1231 |
| 60 | IGHV5-51*01 | IGHD1-14*01 | IGHJ3*02 | GYTFASYW | 1232 | INPPNSDT | 1233 | ARRRVSVTGTDAFDI | 1234 | | | | | | | | IGLV2-8*01 | IGLJ2*01 | SSDVGGYNY | 1235 | EVN | | SSYAGTNTFVV | 1236 |
| 69 | IGHV5- | IGHD1- | IGHJ4*02 | GDTFGN | 1237 | ILLSDSDT | 1238 | ARATPG | 1239 | | | | | | | | IGLV2- | IGLJ1* | SSDVGA | 1240 | DVT | | SSYTDS | 1241 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| | 51*01 | 1*01 | | YW | | | | NYYFDS | | | | | | | | | 14*01 | 01 | YNY | | | | SPNCV | |
| 99 | IGHV5-51*01 | IGHD2-2*01 | IGHJ1*01 | GYSFSNFW | 1242 | IYPGDSDT | 1243 | ARPSRSRDINKWYLSTSEYFHY | 1244 | IGKV3-20*01 | IGKJ4*01 | QSVSSRS | 1245 | GAS | QQYANSPLT | 1246 | | | | | | | | |
| 9 | IGHV6-1*01 | IGHD1-1*01 | IGHJ4*02 | GDSVSNNTAV | 1247 | TYYRSKWFN | 1248 | AVGHHWHFKY | 1249 | | | | | | | | IGLV2-8*01 | IGLJ1*01 | SSDVGGYSH | 1250 | EVS | | SSHAGSNYGV | 1251 |
| 9 | IGHV6-1*01 | IGHD1-1*01 | IGHJ4*02 | GDSVSNNTAV | 1252 | TYYRSKWFN | 1253 | AVGHHWHFKY | 1254 | | | | | | | | IGLV2-8*01 | IGLJ1*01 | SSDVGGYSH | 1255 | EVS | | SSHAGSNYGV | 1256 |
| 55 | IGHV6-1*01 | IGHD3-10*01 | IGHJ4*02 | GSSIFTNSAG | 1257 | TYYRSKWYN | 1258 | ARDTYYYTSASYYNVDY | 1259 | IGKV1-39*01 | IGKJ5*01 | ESIRSN | 1260 | AAS | QQSYRTPIT | 1261 | | | | | | | | |
| 55 | IGHV7-4-1*02 | IGHD1-7*01 | IGHJ4*02 | GYTFTSYG | 1262 | INTDTGNP | 1263 | ARLGEYSWNSIGYFDY | 1264 | | | | | | | | IGLV1-40*01 | IGLJ2*01 | SSNIGAGYD | 1265 | GNN | | QSYDRSLILVV | 1266 |

SUPPLEMENTAL TABLE S2-continued

Detailed information about cloned antibodies with paired heavy and light chains, Related to FIG. 2. Variable (V), diversity (D) and joining (J) genes, mutation on the variable gene (V MUT), and CDR3 amino acid sequences of cloned immunoglobulin heavy, kappa light and lambda light chains are listed. These antibodies are grouped by their IGHV genes, with our 5 selected H001-H020 antibodies indicated. H021 antibody used for sequence alignment in FIG. 2D is also indicated. The amino acid length of IGH CDR3 was between 5 and 27 amino acids, with the highest peak at 16 amino acids and the average around 15 amino acids. There are 16 of IGH CDR3 containing cysteines.

| | HEAVY CHAIN | | | | | | | | | KAPPA LIGHT CHAIN | | | | | | | LAMBDA LIGHT CHAIN | | | | | | | |
|---|---|---|---|---|---|---|---|---|---|---|---|---|---|---|---|---|---|---|---|---|---|---|---|---|
| DONOR ID | V | D | J | CDR 1 | SEQ ID NO: | CDR 2 | SEQ ID NO: | CDR 3 | SEQ ID NO: | V | J | CDR 1 | SEQ ID NO: | CDR 2 | CDR 3 | SEQ ID NO: | V | J | CDR 1 | SEQ ID NO: | CDR 2 | SEQ ID NO: | CDR 3 | SEQ ID NO: |
| 99 | IGHV7-4-1*02 | IGHD3-10*01 | IGHJ4*02 | GYVFTNYA | 1267 | INTNTGNP | 1268 | ARSYAYGDF | 1269 | IGKV1-39*01 | IGKJ1*01 | QNIAIR | 1270 | EAS | QQSDTLPWT | 1271 | | | | | | | | |
| 99 | IGHV7-4-1*02 | IGHD3-22*01 | IGHJ4*02 | GYTFSNYA | 1272 | INTNTGNP | 1273 | ARGARSYYDSSGYYSWSDY | 1274 | IGKV4-1*01 | IGKJ1*01 | QSVLYRSNNKNY | 1275 | WAS | QQYYNTLTWA | 1276 | | | | | | | | |

TABLE S3

| Primers and synthesized nucleotide sequences. | | |
|---|---|---|
| Single-Cell Antibody Cloning Primers A2 | | SEQ ID NO: |
| F1-HC | 5'-ACAGGTGCCCACTCCCAGGTGCAG | 1277 |
| F2-HC | 5'-AAGGTGTCCAGTGTGARGTGCAG | 1278 |
| F3-HC | 5'-CCCAGATGGGTCCTGTCCCAGGTGCAG | 1279 |
| F4-HC | 5'-CAAGGAGTCTGTTCCGAGGTGCAG | 1280 |
| R-1st-HC | 5'-GGAAGGTGTGCACGCCGCTGGTC | 1281 |
| R-2nd-HC | 5'-GTTCGGGGAAGTAGTCCTTGAC | 1282 |
| F1-Kappa | 5'-ATGAGGSTCCCYGCTCAGCTGCTGG | 1283 |
| F2-Kappa | 5'-CTCTTCCTCCTGCTACTCTGGCTCCCAG | 1284 |
| F3-Kappa | 5'-ATTTCTCTGTTGCTCTGGATCTCTG | 1285 |
| F4-Kappa | 5'-ATGACCCAGWCTCCABYCWCCCTG | 1286 |
| R-1st-Kappa | 5'-GTTTCTCGTAGTCTGCTTTGCTCA | 1287 |
| R-2nd-Kappa | 5'-GTGCTGTCCTTGCTGTCCTGCT | 1288 |
| F1-Lambda | 5'-GGTCCTGGGCCCAGTCTGTGCTG | 1289 |
| F2-Lambda | 5'-GGTCCTGGGCCCAGTCTGCCCTG | 1290 |
| F3-Lambda | 5'-GCTCTGTGACCTCCTATGAGCTG | 1291 |
| F4-Lambda | 5'-GGTCTCTCTCSCAGCYTGTGCTG | 1292 |
| F5-Lambda | 5'-GTTCTTGGGCCAATTTTATGCTG | 1293 |
| F6-Lambda | 5'-GGTCCAATTCYCAGGCTGTGGTG | 1294 |
| F7-Lambda | 5'-GAGTGGATTCTCAGACTGTGGTG | 1295 |
| R-1st-Lambda | T-CACCAGTGTGGCCTTGTTGGCTTG | 1296 |
| R-2nd-Lambda | 5'-CTCCTCACTCGAGGGYGGGAACAGAGTG | 1297 |
| F-Vector Seq Primer | 5'-GCTTCGTTAGAACGCGGCTAC | 1298 |
| Antibody Cloning Primers for Each Antibody | | |
| F-H001-HC | 5'-CTAGTAGCAACTGCAACCGGTGTACATTCT CAGGTCCAGCTTGTGCAGTCTGG | 1299 |
| R-H001-HC | 5'-CCGATGGGCCCTTGGTCGACGC TGAAGAGACGGTGACCATTGTCCCTT | 1300 |
| F-H001-Kappa | 5'-CTAGTAGCAACTGCAACCGGTGTACATTCT GACATCCAGATGA CCCAGTCTCCA | 1301 |
| R-H001-Kappa | 5'-GAAGACAGATGGTGCAGCCACCGTACG TTTGATCTCCACCTTG GTCCCTCC | 1302 |
| F-H002-HC | 5'-CTAGTAGCAACTGCAACCGGTGTACATTCT CAGGTCACCTTGAAGGAGTCTGG | 1303 |
| R-H002-HC | 5'-CCGATGGGCCCTTGGTCGACGC TGAGGAGACGGTGACCAGGGTG | 1304 |
| F-H002-Lambda | 5'-CTAGTAGCAACTGCAACCGGTTCCTGGGCC TCCTATGTGCTGA CCCAGGCGC | 1305 |
| F-H003-HC | 5'-CTAGTAGCAACTGCAACCGGTGTACATTCT GAGATGCAGCTGCTGGAGTCTGG | 1306 |

TABLE S3-continued

Primers and synthesized nucleotide sequences.

| Single-Cell Antibody Cloning Primers A2 | | SEQ ID NO: |
|---|---|---|
| R-H003-HC | 5'-CCGATGGGCCCTTGGTCGACGC TGAGGAGACAGTGACCAGGGTGC | 1307 |
| F-H003-Lambda | 5'-CTAGTAGCAACTGCAACCGGTTCCTGGGCC TCCTATATGCTGA CTCAGGCACCC | 1308 |
| F-H004-HC | 5'-CTAGTAGCAACTGCAACCGGTGTACATTCT GAGATGCAACTGGTGGAGTCTGG | 1309 |
| R-H004-HC | 5'-CCGATGGGCCCTTGGTCGACGC TGAGGAGACGATGACCGTGGTCC | 1310 |
| F-H004-Lambda | 5'-CTAGTAGCAACTGCAACCGGTTCCTGGGCC TCCTATGTGCTGA CTCAGCCACC | 1311 |
| F-H005-HC | 5'-CTAGTAGCAACTGCAACCGGTGTACATTCT CAGATGCGTCTGGTGGAATCTGG | 1312 |
| R-H005-HC | 5'-CCGATGGGCCCTTGGTCGACGC TGAGGAGACGGTGACCGGGGT | 1313 |
| F-H005-Lambda | 5'-CTAGTAGCAACTGCAACCGGTTCCTGGGCC TCCTATGTGCTGA CTCAGCCACC | 1314 |
| F-H006-HC | 5'-CTAGTAGCAACTGCAACCGGTGTACATTCT CAGATGCGTCTGGTGGAATCGGG | 1315 |
| R-H006-HC | 5'-CCGATGGGCCCTTGGTCGACGC TGAGGAGACGGTGACCGGGATC | 1316 |
| F-H006-Lambda | 5'-CTAGTAGCAACTGCAACCGGTTCCTGGGCC TCCTATGTGCTGA CTCAGCCACC | 1317 |
| F-H007-HC | 5'-CTAGTAGCAACTGCAACCGGTGTACATTCT CAGGTGCACCTGGTGGAGTCTG | 1318 |
| R-H007-HC | 5'-CCGATGGGCCCTTGGTCGACGC TGAGGAGACGGTGACCGTGGTC | 1319 |
| F-H007-Kappa | 5'-CTAGTAGCAACTGCAACCGGTGTACATTCT GAAATTGTGTTG ACGCAGTCTCCAG | 1320 |
| R-H007-Kappa | 5'-GAAGACAGATGGTGCAGCCACCGTACG TTTGATCTCCAACTTG GTCCCCTGG | 1321 |
| F-H008-HC | 5'-CTAGTAGCAACTGCAACCGGTGTACATTCT CAGATGCACCTATTGGAGTCTGGG | 1322 |
| R-H008-HC | 5'-CCGATGGGCCCTTGGTCGACGC TGACGAGACGGTGACCCTGGTC | 1323 |
| F-H008-Lambda | 5'-CTAGTAGCAACTGCAACCGGTTCCTGGGCC TCCTATGTGCTGA CTCAGCCACC | 1324 |
| F-H009-HC | 5'-CTAGTAGCAACTGCAACCGGTGTACATTCT CAGATGAAGTTGGTGGAGTCTGGG | 1325 |
| R-H009-HC | 5'-CCGATGGGCCCTTGGTCGACGC TGAGGAGACGGTGACCGTGGTC | 1326 |
| F-H009-Lambda | 5'-CTAGTAGCAACTGCAACCGGTTCCTGGGCC TCCTATGTGCTGA CTCAGCCACC | 1327 |
| F-H010-HC | 5'-CTAGTAGCAACTGCAACCGGTGTACATTCT CAGGTGCAGCTGGTGGAGTCTG | 1328 |
| R-H010-HC | 5'-CCGATGGGCCCTTGGTCGACGC TGAGGAGACGGTGACCAGGGTT | 1329 |
| F-H010-Lambda | 5'-CTAGTAGCAACTGCAACCGGTTCCTGGGCC TCCTATGTGCTGA CTCAGCCACC | 1330 |
| F-H011-HC | 5'-CTAGTAGCAACTGCAACCGGTGTACATTCT CAGGTTCACTTGGCGGAGTCTGG | 1331 |

TABLE S3-continued

Primers and synthesized nucleotide sequences.

Single-Cell Antibody Cloning Primers

| A2 | | SEQ ID NO: |
|---|---|---|
| R-H011-HC | 5'-CCGATGGGCCCTTGGTCGACGC TGAAGAGACGGTGACCAATGTCCC | 1332 |
| F-H011-Kappa | 5'-CTAGTAGCAACTGCAACCGGTGTACATTCT GAAGTTGTGTTGA CACAGTCTCCAGC | 1333 |
| R-H011-Kappa | 5'-GAAGACAGATGGTGCAGCCACCGTACG TTTGATCTCCAGCTTG GTCCCCTG | 1334 |
| F-H012-HC | 5'-CTAGTAGCAACTGCAACCGGTGTACATTCT CAGCTGCAGCTGGTGGAGTCTG | 1335 |
| R-H012-HC | 5'-CCGATGGGCCCTTGGTCGACGC TGAGGAGACGGTGACCAGGGTTC | 1336 |
| F-H012-Lambda | 5'-CTAGTAGCAACTGCAACCGGTTCCTGGGCC TCCTATGTGCTGA CTCAGCCACC | 1337 |
| F-H013-HC | 5'-CTAGTAGCAACTGCAACCGGTGTACATTCT CAGGTGCAGCTGGTGGAGTCTG | 1338 |
| R-H013-HC | 5'-CCGATGGGCCCTTGGTCGACGC TGAGGAGACGGTGACCAGGGCT | 1339 |
| F-H013-Lambda | 5'-CTAGTAGCAACTGCAACCGGTTCCTGGGCC TCCTATGTGCTGA CTCAGCCACC | 1340 |
| F-H014-HC | 5'-CTAGTAGCAACTGCAACCGGTGTACATTCT CAGGTACAACTGATGGAGTCTGGG | 1341 |
| R-H014-HC | 5'-CCGATGGGCCCTTGGTCGACGC TGAGGAGACGGTGACCAGGGCT | 1342 |
| F-H014-Lambda | 5'-CTAGTAGCAACTGCAACCGGTTCCTGGGCC TCCTATGTGCTGA CTCAGACACCC | 1343 |
| F-H015-HC | 5'-CTAGTAGCAACTGCAACCGGTGTACATTCT CAGGTGCAGCTGGTGGAGTCTG | 1344 |
| R-H015-HC | 5'-CCGATGGGCCCTTGGTCGACGC TGAGGAGACGGTGACCAGGGTTC | 1345 |
| F-H015-Kappa | 5'-CTAGTAGCAACTGCAACCGGTGTACATTCT GACATCCAGGTGA CCCAGTCAC | 1346 |
| R-H015-Kappa | 5'-GAAGACAGATGGTGCAGCCACCGTACG TTTGATGTCCACCTTG GTCCCTCC | 1347 |
| F-H016-HC | 5'-CTAGTAGCAACTGCAACCGGTGTACATTCT GAGATGCACCTGGTGGAGTCTGG | 1348 |
| R-H016-HC | 5'-CCGATGGGCCCTTGGTCGACGC TGAGGAGACAGTGACCAGGGTGC | 1349 |
| F-H016-Kappa | 5'-CTAGTAGCAACTGCAACCGGTGTACATTCT GAAATACTGCTGA CGCAGTCTCCAG | 1350 |
| R-H016-Kappa | 5'-GAAGACAGATGGTGCAGCCACCGTACG TTTGATCTCCACCTTG GTCCCTCC | 1351 |
| F-H017-HC | 5'-CTAGTAGCAACTGCAACCGGTGTACATTCT GAGGTGCAGCTGGTGGAGTCC | 1352 |
| R-H017-HC | 5'-CCGATGGGCCCTTGGTCGACGC TGAGGAGACGGTGACCAGGGTTC | 1353 |
| F-H017-Lambda | 5'-CTAGTAGCAACTGCAACCGGTTCCTGGGCC CAGTCTGCCCTGA CTCAGCCTG | 1354 |
| F-H018-HC | 5'-CTAGTAGCAACTGCAACCGGTGTACATTCT GAAGGACAGCTGGTGGAGTCTGG | 1355 |
| R-H018-HC | 5'-CCGATGGGCCCTTGGTCGACGC TGAGGAGACGGTGACCAGGGTTC | 1356 |

TABLE S3-continued

| Primers and synthesized nucleotide sequences. | | |
|---|---|---|
| Single-Cell Antibody Cloning Primers A2 | | SEQ ID NO: |
| F-H018-Lambda | 5'-CTAGTAGCAACTGCAACCGGTTCCTGGGCC CAGTCTGTGTTGA CGCAGCCGC | 1357 |
| F-H019-HC | 5'-CTAGTAGCAACTGCAACCGGTGTACATTCT CAGGTGGTGCTGCAGGAGTCG | 1358 |
| R-H019-HC | 5'-CCGATGGGCCCTTGGTCGACGC TGAAGAGACGGCGACCAGTGTCC | 1359 |
| F-H019-Kappa | 5'-CTAGTAGCAACTGCAACCGGTGTACATTCT GACATCCAGATGA CCCAGTCTCCG | 1360 |
| R-H19-Kappa | 5'-GAAGACAGATGGTGCAGCCACCGTACG TTTGATCTCCAGCTTG GTCCCCTG | 1361 |
| F-H020-HC | 5'-CTAGTAGCAACTGCAACCGGTGTACATTCT CAGGTGCAGCTGCAGGAGTCG | 1362 |
| R-H020-HC | 5'-CCGATGGGCCCTTGGTCGACGC TGAGGAGACGGTGACCAGGTTTCC | 1363 |
| F-H020-Kappa | 5'-CTAGTAGCAACTGCAACCGGTGTACATTCT GACATCCAGATGA CCCAGTCTCCA | 1364 |
| R-H020-Kappa | 5'-GAAGACAGATGGTGCAGCCACCGTACG TTTGAACTCCACCTTG GTCCCTCC | 1365 |
| R-Lambda | 5'-GGCTTGAAGCTCCTCACTCGAGGGYGGGAACAGAGTG | 1366 |
| gBlock Synthesis for Alanine Mutations | | |
| 101Q | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATGCAGGTATGTTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1367 |
| 102G | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGCAATGTTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1368 |
| 103M | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTGCATTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1369 |
| 104L | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT | 1370 |

TABLE S3-continued

Primers and synthesized nucleotide sequences.

| Single-Cell Antibody Cloning Primers A2 | | SEQ ID NO: |
|---|---|---|
| | TGGTTCTTCTGGATTATCAAGGTATGGCACCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | |
| 105P | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGGCAGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1371 |
| 106V | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGCATGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1372 |
| 108P | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTGCACT AATTCCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1373 |
| 109L | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTGC AATTCCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1374 |
| 110I | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AGCACCAGGATCAACAACAACCAGTACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1375 |
| 111P | 5'-ACAAGAATCCTCACAATACCGCAGAGTCTAGACTCGTGGTGGA CTTCTCTCAATTTTCTAGGGGGATCTCCCGTGTGTCTTGGCCA | 1376 |

TABLE S3-continued

| Primers and synthesized nucleotide sequences. | | |
|---|---|---|
| Single-Cell Antibody Cloning Primers<br>A2 | | SEQ ID NO: |
| | AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTGCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | |
| 112G | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGCATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1377 |
| 113S | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGAGCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1378 |
| 114T | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAGCAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1379 |
| 115T | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAGCAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1380 |
| 116T | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAGCAAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1381 |

TABLE S3-continued

Primers and synthesized nucleotide sequences.

| Single-Cell Antibody Cloning Primers A2 | | SEQ ID NO: |
|---|---|---|
| 117S | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCGCAACGGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1382 |
| 118T | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTGCAGGACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1383 |
| 119G | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGCACCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1384 |
| 120P | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGAGCATGCAAAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1385 |
| 122K | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCGCAACC TGCACGACTCCTGCTCAAGGCAACTCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1386 |
| 123T | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAGCA TGCACGACTCCTGCTCAAGGCAACTCTATGTTTCCCTCATGTT GCTGTACAAAACCTACGGATGGAAATTGCACCTGTATTCCCAT | 1387 |

TABLE S3-continued

Primers and synthesized nucleotide sequences.

| Single-Cell Antibody Cloning Primers<br>A2 | | SEQ ID NO: |
|---|---|---|
| | CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | |
| 125T | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCGCAACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1388 |
| 126T | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGGCACCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1389 |
| 127P | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTGCAGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1390 |
| 129Q | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTGCAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1391 |
| 130G | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGCAAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1392 |
| 131N | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT | 1393 |

TABLE S3-continued

Primers and synthesized nucleotide sequences.

| Single-Cell Antibody Cloning Primers A2 | | SEQ ID NO: |
|---|---|---|
| | AATTCCAGGATCAACAACAACCAGTACGGGACCATGCAAAACC TGCACGACTCCTGCTCAAGGCGCATCTATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | |
| 132S | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACGCAATGTTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1394 |
| 133M | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTGCATTTCCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1395 |
| 134F | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGGCACCCTCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1396 |
| 135P | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGTTTGCATCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1397 |
| 136S | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGTTTCCCGCATGTT GCTGTACAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1398 |
| 140T | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC | 1399 |

TABLE S3-continued

Primers and synthesized nucleotide sequences.

| Single-Cell Antibody Cloning Primers A2 | | SEQ ID NO: |
|---|---|---|
| | CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTGCAAAACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | |
| 141K | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAGCACCTACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1400 |
| 142P | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAAGCAACGGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1401 |
| 143T | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTGCAGATGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1402 |
| 144D | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTACGGCAGGAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1403 |
| 145G | 5'-ACAAGAATCCTCACAATACCGCAGAGTCTAGACTCGTGGTGGA CTTCTCTCAATTTTCTAGGGGGATCTCCCGTGTGTCTTGGCCA AAATTCGCAGTCCCCAACCTCCAATCACTCACCAACCTCCTGTC CTCCAATTTGTCCTGGTTATCGCTGGATGTGTCTGCGGCGTTT TATCATATTCCTCTTCATCCTGCTGCTATGCCTCATCTTCTTAT TGGTTCTTCTGGATTATCAAGGTATGTTGCCCGTTTGTCCTCT AATTCCAGGATCAACAACAACCAGTACGGGACCATGCAAAACC TGCACGACTCCTGCTCAAGGCAACTCTATGTTTCCCTCATGTT GCTGTACAAAACCTACGGATGCAAATTGCACCTGTATTCCCAT CCCATCGTCCTGGGCTTTCGCAAAATACCTATGGGAGTGGGCC TCAGTCCGTTTCTCTTGGCTCAGTTTACTAGTGCCATTTGTTC AGTGGTTCGTAGGG | 1404 |

TABLE S3-continued

Primers and synthesized nucleotide sequences.

| Single-Cell Antibody Cloning Primers<br>A2 | | SEQ ID NO: |
|---|---|---|
| 146N | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAGCATGCACCTGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1405 |
| 148T | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCGCATGTATTCCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1406 |
| 150I | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTGCACCCAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1407 |
| 151P | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTGCAAT<br>CCCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1408 |
| 152I | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCGC<br>ACCATCGTCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1409 |
| 153P | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CGCATCGTCCTGGGCTTTCGCAAAATACCTATGGGAGTGGGCC | 1410 |

TABLE S3-continued

| Primers and synthesized nucleotide sequences. | | |
|---|---|---|
| Single-Cell Antibody Cloning Primers<br>A2 | | SEQ ID NO: |
| | TCAGTCCGTTTCTCTTGGCTCAGTTTACTAGTGCCATTTGTTC<br>AGTGGTTCGTAGGG | |
| 154S | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCAGCATCCTGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1411 |
| 155S | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGGCATGGGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1412 |
| 156W | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCGCAGCTTTCGCAAAATACCTATGGGAGTGGGCC<br>TCAGTCCGTTTCTCTTGGCTCAGTTTACTAGTGCCATTTGTTC<br>AGTGGTTCGTAGGG | 1413 |
| 158F | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTGCAGCAAAATACCTATGGGAGTGGGCC<br>TCAGTCCGTTTCTCTTGGCTCAGTTTACTAGTGCCATTTGTTC<br>AGTGGTTCGTAGGG | 1414 |
| 160K | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAGCATACCTATGGGAGTGGGCC<br>TCAGTCCGTTTCTCTTGGCTCAGTTTACTAGTGCCATTTGTTC<br>AGTGGTTCGTAGGG | 1415 |
| 161Y | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC | 1416 |

TABLE S3-continued

Primers and synthesized nucleotide sequences.

| Single-Cell Antibody Cloning Primers A2 | | SEQ ID NO: |
|---|---|---|
| | TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAAGCACTATGGGAGTGGGCC<br>TCAGTCCGTTTCTCTTGGCTCAGTTTACTAGTGCCATTTGTTC<br>AGTGGTTCGTAGGG | |
| 162L | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACGCATGGGAGTGGGCC<br>TCAGTCCGTTTCTCTTGGCTCAGTTTACTAGTGCCATTTGTTC<br>AGTGGTTCGTAGGG | 1417 |
| 163W | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTAGCAGAGTGGGCC<br>TCAGTCCGTTTCTCTTGGCTCAGTTTACTAGTGCCATTTGTTC<br>AGTGGTTCGTAGGG | 1418 |
| 164E | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGCATGGGCC<br>TCAGTCCGTTTCTCTTGGCTCAGTTTACTAGTGCCATTTGTTC<br>AGTGGTTCGTAGGG | 1419 |
| 165W | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGGCAGCC<br>TCAGTCCGTTTCTCTTGGCTCAGTTTACTAGTGCCATTTGTTC<br>AGTGGTTCGTAGGG | 1420 |
| 167S | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>GCAGTCCGTTTCTCTTGGCTCAGTTTACTAGTGCCATTTGTTC<br>AGTGGTTCGTAGGG | 1421 |
| 168V | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT | 1422 |

TABLE S3-continued

| Primers and synthesized nucleotide sequences. | | |
|---|---|---|
| Single-Cell Antibody Cloning Primers<br>A2 | | SEQ ID NO: |
| | TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGCACGTTTCTCTTGGCTCAGTTTACTAGTGCCATTTGTTC<br>AGTGGTTCGTAGGG | |
| 169R | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCGCATTCTCTTGGCTCAGTTTACTAGTGCCATTTGTTC<br>AGTGGTTCGTAGGG | 1423 |
| 170F | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTGCATCTTGGCTCAGTTTACTAGTGCCATTTGTTC<br>AGTGGTTCGTAGGG | 1424 |
| 171S | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCGCATGGCTCAGTTTACTAGTGCCATTTGTTC<br>AGTGGTTCGTAGGG | 1425 |
| 172W | 5'-ACAAGAATCCTCACAATACCGCAGAGTCTAGACTCGTGGTGGA<br>CTTCTCTCAATTTTCTAGGGGGATCTCCCGTGTGTCTTGGCCA<br>AAATTCGCAGTCCCCAACCTCCAATCACTCACCAACCTCCTGTC<br>CTCCAATTTGTCCTGGTTATCGCTGGATGTGTCTGCGGCGTTT<br>TATCATATTCCTCTTCATCCTGCTGCTATGCCTCATCTTCTTAT<br>TGGTTCTTCTGGATTATCAAGGTATGTTGCCCGTTTGTCCTCT<br>AATTCCAGGATCAACAACAACCAGTACGGGACCATGCAAAACC<br>TGCACGACTCCTGCTCAAGGCAACTCTATGTTTCCCTCATGTT<br>GCTGTACAAAACCTACGGATGGAAATTGCACCTGTATTCCCAT<br>CCCATCGTCCTGGGCTTTCGCAAAATACCTATGGGAGTGGGCC<br>TCAGTCCGTTTCTCTGCACTCAGTTTACTAGTGCCATTTGTTC<br>AGTGGTTCGTAGGG | 1426 |
| gBlock Synthesis for Germline Antibodies | | |
| H006-<br>HC_GL | 5'-CTAGTAGCAACTGCAACCGGTGTACATTCTCAGGTGCAGCTGG<br>TGGAGTCTGGGGGAGGCGTGGTCCAGCCTGGGAGGTCCCTGAG<br>ACTCTCCTGTGCAGCCTCTGGATTCACCTTCAGTAGCTATGGC<br>ATGCACTGGGTCCGCCAGGCTCCAGGCAAGGGGCTGGAGTGGG<br>TGGCAGTTATATCATATGATGGAAGTAATAAATACTATGCAG<br>ACTCCGTGAAGGGCCGATTCACCATCTCCAGAGACAATTCCAA<br>GAACACGCTGTATCTGCAAATGAACAGCCTGAGAGCTGAGGAC<br>ACGGCTGTGTATTACTGTGCGAAAGATGCTTATCTTTCTGCAG<br>CGAGAGGATACGGTATGGACGTCTGGGGCCAAGGGACCACGGT<br>CACCGTCTCCTCAGCGTCGACCAAGGGCCCATCGG | 1427 |

TABLE S3-continued

| Primers and synthesized nucleotide sequences. | | |
|---|---|---|
| Single-Cell Antibody Cloning Primers<br>A2 | | SEQ ID NO: |
| H006-<br>Lambda_GL | 5'-CTAGTAGCAACTGCAACCGGTTCCTGGGCCTCCTATGTGCTGA<br>CTCAGCCACCCTCGGTGTCAGTGGCCCCAGGACAGACGGCCAG<br>GATTACCTGTGGGGGAAACAACATTGGAAGTAAAAGTGTGCAC<br>TGGTACCAGCAGAAGCCAGGCCAGGCCCCTGTGCTGGTCGTCT<br>ATGATGATAGCGACCGGCCCTCAGGGATCCCTGAGCGATTCTC<br>TGGCTCCAACTCTGGGAACACGGCCACCCTGACCATCAGCAGG<br>GTCGAAGCCGGGGATGAGGCCGACTATTACTGTCAGGTGTGGG<br>ATAGTAGTAGTGATCATGTGGTATTCGGCGGAGGGACCAAGCT<br>GACCGTCCTAGGTCAGCCCAAGGCTGCCCCCTCGGTCACTCTGT<br>TCCCACCCTCGAGTGAGGAGCTTCAAGCC | 1428 |
| H019-<br>HC_GL | 5'-CTAGTAGCAACTGCAACCGGTGTACATTCTCAGGTGCAGCTGC<br>AGGAGTCGGGCCCAGGACTGGTGAAGCCTTCACAGACCCTGTC<br>CCTCACCTGCACTGTCTCTGGTGGCTCCATCAGCAGTGGTGAT<br>TACTACTGGAGTTGGATCCGCCAGCCCCCAGGGAAGGGCCTGG<br>AGTGGATTGGGTACATCTATTACAGTGGGAGCACCTACTACAA<br>CCCGTCCCTCAAGAGTCGAGTTACCATATCAGTAGACACGTCC<br>AAGAACCAGTTCTCCCTGAAGCTGAGCTCTGTGACTGCCGCAG<br>ACACGGCCGTGTATTACTGTGCCATCTACATGGATGAGGCCTG<br>GGCTTTTGATATCTGGGGCCAAGGGACAATGGTCACCGTCTCT<br>TCAGCGTCGACCAAGGGCCCATCGG | 1429 |
| H019-<br>Kappa_GL | 5'-CTAGTAGCAACTGCAACCGGTGTACATTCTGACATCCAGATGA<br>CCCAGTCTCCATCCTCCCTGTCTGCATCTGTAGGAGACAGAGTC<br>ACCATCACTTGCCGGGCAAGTCAGAGCATTAGCAGCTATTTAA<br>ATTGGTATCAGCAGAAACCAGGGAAAGCCCCTAAGCTCCTGAT<br>CTATGCTGCATCCAGTTTGCAAAGTGGGGTCCCATCAAGGTTC<br>AGTGGCAGTGGATCTGGGACAGATTTCACTCTCACCATCAGCA<br>GTCTGCAACCTGAAGATTTTGCAACTTACTACTGTCAACAGAG<br>TTACAGTATTTCCTTATTCACTTTTGGCCAGGGGACCAAGCTG<br>GAGATCAAACGTACGGTGGCTGCACCATCTGTCTTC | 1430 |
| H020-<br>HC_GL | 5'-CTAGTAGCAACTGCAACCGGTGTACATTCTCAGGTGCAGCTGC<br>AGGAGTCGGGCCCAGGACTGGTGAAGCCTTCGGAGACCCTGTC<br>CCTCACCTGCACTGTCTCTGGTGGCTCCATCAGTAGTTACTACT<br>GGAGCTGGATCCGGCAGCCCCCAGGGAAGGGACTGGAGTGGAT<br>TGGGTATATCTATTACAGTGGGAGCACCAACTACAACCCCTCC<br>CTCAAGAGTCGAGTCACCATATCAGTAGACACGTCCAAGAACC<br>AGTTCTCCCTGAAGCTGAGCTCTGTGACCGCCGCAGACACGGC<br>CGTGTATTACTGTGCGAGACACCTTTATCGCTATGGTTATAGG<br>AACTACTTTGACTACTGGGGCCAGGGAACCCTGGTCACCGTCT<br>CCTCAGCGTCGACCAAGGGCCCATCGG | 1431 |
| H020-<br>Kappa_GL | 5'-CTAGTAGCAACTGCAACCGGTGTACATTCTGACATCCAGATGA<br>CCCAGTCTCCATCTTCCGTGTCTGCATCTGTAGGAGACAGAGT<br>CACCATCACTTGTCGGGCGAGTCAGGGTATTAGCAGCTGGTTA<br>GCCTGGTATCAGCAGAAACCAGGGAAAGCCCCTAAGCTCCTGA<br>TCTATGCTGCATCCAGTTTGCAAAGTGGGGTCCCATCAAGGTT<br>CAGCGGCAGTGGATCTGGGACAGATTTCACTCTCACCATCAGC<br>AGCCTGCAGCCTGAAGATTTTGCAACTTACTATTGTCAACAGG<br>CTAACAGTTTCCCGCTCACTTTCGGCGGAGGGACCAAGGTGGA<br>GATCAAACGTACGGTGGCTGCACCATCTGTCTTC | 1432 |
| | HBV TaqMan PCR | |
| F-sense | 5'-CCGTCTGTGCCTTCTCATCTG | 1433 |
| R-anti-<br>sense | 5'-AGTCCAAGAGTCCTCTTATGTAAGACCTT | 1434 |
| Probe | 5-/56 FAM/CCGTGTGCA/ZEN/CTTCGCTTC ACCTCT<br>GC/3IABkFQ/-3 | 1435 |
| | S-protein PCR | |
| F-S-protein | 5'-CCCTGCGCTGAACATGGAGAACA | 1436 |
| R-S-protein | 5'-AAATGTATACCCAAAGACAAAAGAAAA | 1437 |

It will be recognized from the foregoing that the present disclosure describes screening individuals who were either vaccinated or had spontaneously recovered from HBV infection. Antibody cloning from memory B cells revealed that all 5 of the top individuals produced clones of broadly neutralizing antibodies (bNAbs) that targeted 3 non-overlapping epitopes on the HBV S antigen (HBsAg). Clones with the same immunoglobulin variable, diversity and joining heavy and light chain genes were shared among elite neutralizers. Single bNAbs protected humanized mice against infection, but selected for resistance mutations in mice with established infection. In contrast, infection was controlled in the absence of detectable escape mutations by a combination of bNAbs targeting non-overlapping epitopes with complementary sensitivity to mutations that commonly emerge during human infection. The co-crystal structure of one of the bNAbs with a peptide epitope containing residues frequently mutated in human immune escape variants revealed a loop anchored by oppositely charged residues. The structure provides a molecular explanation for why immunotherapy for chronic HBV infection may require combinations of complementary bNAbs, as described herein.

While the disclosure has been described through specific embodiments, routine modifications will be apparent to those skilled in the art and such modifications are intended to be within the scope of the present disclosure.

What is claimed is:

1. A combination of recombinant or isolated antibodies or antigen binding fragments thereof, said combination comprising a first antibody (H019) comprising a heavy chain variable region that is IGHV4-30-4*01; a heavy chain diverse region that is IGHD2-2*03; a heavy chain joining region that is IGHJ3*02, a heavy chain CDR1 that comprises the sequence GGSITTGDYY (SEQ ID NO: 18), a heavy chain CDR2 that comprises the sequence IYYSGST (SEQ ID NO: 19), and a heavy chain CDR3 that comprises the sequence AIYMDEAWAFE (SEQ ID NO: 20); and a kappa light chain variable region that is IGKV1-39*01, a kappa light chain joining region that is IGKJ2*01, a light chain CDR1 that comprises the sequence QSVGNY (SEQ ID NO: 21), a light chain CDR2 that is AVS, and a light chain CDR3 that comprises the sequence QQSYTISLFT (SEQ ID NO: 22); and a second antibody (H017) comprising a heavy chain variable region that is IGHV3-74*01, a heavy chain diverse region that is IGHD3-10*01, a heavy chain joining region that is IGHJ4*02, a heavy chain CDR1 that comprises the sequence GFTFSNYW (SEQ ID NO: 13), a heavy chain CDR2 that comprises the sequence ISTDGSST (SEQ ID NO: 14), and a heavy chain CDR3 that comprises the sequence ARGSTYYFGSGSVDY (SEQ ID NO: 15); and a lambda light chain variable region that is IGLV2-14*01, a lambda light chain joining region that is IGLJ1*01, a light chain CDR1 that comprises the sequence SSDIGVYNY (SEQ ID NO: 16), a light chain CDR2 that is DVT, and a light chain CDR3 that comprises the sequence SSYRGSSTPYV (SEQ ID NO: 17).

2. The combination of recombinant or isolated antibodies of claim 1, wherein at least one of the antibodies comprises at least one modification of its constant region, wherein the modification increases in vivo half-life of the antibody, or alters the ability of the antibody to bind to Fc receptors, or inhibits aggregation of the antibodies, or a combination of said modifications, or wherein at least one of the antibodies is attached to a detectable label or a substrate.

3. The combination of recombinant or isolated antibodies of claim 2, wherein at least one antibody comprises the modification that increases in vivo half-life of the antibody.

4. The combination of recombinant or isolated antibodies claim 2, wherein at least one antibody comprises the modification that alters the ability of the antibody to bind to Fc receptors.

5. A pharmaceutical composition comprising the combination of antibodies or antigen binding fragment thereof, of claim 1.

6. A method for prophylaxis or therapy of a Hepatitis B virus infection comprising administering to an individual in need thereof an effective amount a combination of antibodies or antigen binding fragments thereof, wherein optionally least one antibody in the combination comprises at least one modification of its constant region, and wherein said combination comprises a first antibody (H019) comprising a heavy chain variable region that is IGHV4-30-4*01; a heavy chain diverse region that is IGHD2-2*03; a heavy chain joining region that is IGHJ3*02, a heavy chain CDR1 that comprises the sequence GGSITTGDYY (SEQ ID NO: 18), a heavy chain CDR2 that comprises the sequence IYYSGST (SEQ ID NO: 19), and a heavy chain CDR3 that comprises the sequence AIYMDEAWAFE (SEQ ID NO: 20); and a kappa light chain variable region that is IGKV1-39*01, a kappa light chain joining region that is IGKJ2*01, a light chain CDR1 that comprises the sequence QSVGNY (SEQ ID NO: 21), a light chain CDR2 that is AVS, and a light chain CDR3 that comprises the sequence QQSYTISLFT (SEQ ID NO: 22); and a second antibody (H017) comprising a heavy chain variable region that is IGHV3-74*01, a heavy chain diverse region that is IGHD3-10*01, a heavy chain joining region that is IGHJ4*02, a heavy chain CDR1 that comprises the sequence GFTFSNYW (SEQ ID NO: 13), a heavy chain CDR2 that comprises the sequence ISTDGSST (SEQ ID NO: 14), and a heavy chain CDR3 that comprises the sequence ARGSTYYFGSGSVDY (SEQ ID NO: 15); and a lambda light chain variable region that is IGLV2-14*01, a lambda light chain joining region that is IGLJ1*01, a light chain CDR1 that comprises the sequence SSDIGVYNY (SEQ ID NO: 16), a light chain CDR2 that is DVT, and a light chain CDR3 that comprises the sequence SSYRGSSTPYV (SEQ ID NO: 17).

7. The method of claim 6, wherein administering the combination of antibodies provides a therapeutic and/or prophylactic effect against infection by a hepatitis B virus that comprises one or more escape mutations in at least one of the HBsAg or the S-protein of the hepatitis B virus.

8. One or more recombinant expression vectors encoding the heavy chain and the light chain of one or both of the combination of the antibodies or antigen binding fragments thereof of claim 1, wherein the antibody or the antigen binding fragment thereof comprises six CDRs of the H017 or the H019 antibody.

9. Cells comprising one or more recombinant expression vectors of claim 8.

10. A kit comprising one or more expression vectors encoding according to claim 8.

11. A method for detecting Hepatitis B virus comprising: contacting a biological sample from an individual with an antibody of the combination of antibodies of claim 1, and detecting the presence of a complex comprising the antibody and a Hepatitis B virus protein, wherein the antibody comprises six CDRs of the H017 or the H019 antibody.

12. A method comprising testing one or more candidate drug agents for the capability to target an antigenic loop region of the hepatitis B virus S-protein by interfering with a complex formed by the peptide and an antibody of the combination of antibodies of claim 1, wherein the antibody comprises six CDRs of the H017 or the H019 antibody.

* * * * *

SEQUENCE LISTING

```
<160> NUMBER OF SEQ ID NOS: 1488

<210> SEQ ID NO 1
<211> LENGTH: 6
<212> TYPE: PRT
<213> ORGANISM: Hepatitis B virus

<400> SEQUENCE: 1

Lys Pro Ser Asp Gly Asn
1               5


<210> SEQ ID NO 2
<211> LENGTH: 400
<212> TYPE: PRT
<213> ORGANISM: Hepatitis B virus

<400> SEQUENCE: 2

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Val Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255
```

```
Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
        275                 280                 285

Thr Thr Ser Thr Gly Pro Cys Lys Thr Cys Thr Ser Pro Ala Gln Gly
    290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Tyr Trp Gly Pro Cys Leu Tyr Asn Ile Leu Ser
    370                 375                 380

Pro Phe Leu Pro Leu Leu Pro Ile Phe Phe Cys Leu Trp Val Tyr Ile
385                 390                 395                 400


<210> SEQ ID NO 3
<211> LENGTH: 226
<212> TYPE: PRT
<213> ORGANISM: Hepatitis B virus

<400> SEQUENCE: 3

Met Glu Asn Thr Ala Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr His Gly Met Leu Pro Val Cys Pro Leu Leu Pro Gly
            100                 105                 110

Thr Ser Thr Thr Ser Thr Gly Pro Cys Lys Thr Cys Thr Ile Pro Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Leu Pro Leu Leu Pro Ile Phe Phe Cys Leu Trp Val
    210                 215                 220

Tyr Ile
225
```

225

<210> SEQ ID NO 4
<211> LENGTH: 681
<212> TYPE: DNA
<213> ORGANISM: Hepatitis B virus

<400> SEQUENCE: 4
atggagaaca tcacatcagg attcctagga cccctgctcg tgttacaggc ggggtttttc 60
ttgttgacaa gaatcctcac aataccgcag agtctagact cgtggtggac ttctctcaat 120
tttctagggg gatctcccgt gtgtcttggc caaaattcgc agtccccaac ctccaatcac 180
tcaccaacct cctgtcctcc aatttgtcct ggttatcgct ggatgtgtct gcggcgtttt 240
atcatattcc tcttcatcct gctgctatgc ctcatcttct tattggttct tctggattat 300
caaggtatgt tgcccgtttg tcctctaatt ccaggatcaa caacaaccag tacgggacca 360
tgcaaaacct gcacgactcc tgctcaaggc aactctatgt ttccctcatg ttgctgtaca 420
aaacctacgg atggaaattg cacctgtatt cccatcccat cgtcctgggc tttcgcaaaa 480
tacctatggg agtgggcctc agtccgtttc tcttggctca gtttactagt gccatttgtt 540
cagtggttcg tagggctttc ccccactgtt tggctttcag ctatatggat gatgtggtat 600
tgggggccaa gtctgtacag catcgtgagt ccctttatac cgctgttacc aattttcttt 660
tgtctctggg tatacattta a 681

<210> SEQ ID NO 5
<211> LENGTH: 226
<212> TYPE: PRT
<213> ORGANISM: Hepatitis B virus

<400> SEQUENCE: 5

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile

```
        195                 200                 205

Val Ser Pro Phe Ile Pro Leu Leu Pro Ile Phe Phe Cys Leu Trp Val
    210                 215                 220

Tyr Ile
225


<210> SEQ ID NO 6
<211> LENGTH: 5
<212> TYPE: PRT
<213> ORGANISM: Hepatitis B virus

<400> SEQUENCE: 6

Lys Pro Ser Asp Gly
1               5


<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Ser Ser Ser Ser Thr Lys Pro Ser Asp Gly Asn Ser Thr Ser
1               5                   10                  15


<210> SEQ ID NO 8
<211> LENGTH: 8
<212> TYPE: PRT
<213> ORGANISM: Homo sapiens

<400> SEQUENCE: 8

Gly Phe Thr Phe Pro Ser His Thr
1               5


<210> SEQ ID NO 9
<211> LENGTH: 8
<212> TYPE: PRT
<213> ORGANISM: Homo sapiens

<400> SEQUENCE: 9

Ile Ser Thr Thr Ser Glu Ala Ile
1               5


<210> SEQ ID NO 10
<211> LENGTH: 17
<212> TYPE: PRT
<213> ORGANISM: Homo sapiens

<400> SEQUENCE: 10

Ala Arg Val Gly Leu Ala Leu Thr Ile Ser Gly Tyr Trp Tyr Phe Asp
1               5                   10                  15

Leu


<210> SEQ ID NO 11
<211> LENGTH: 6
<212> TYPE: PRT
<213> ORGANISM: Homo sapiens

<400> SEQUENCE: 11

Gln Ser Ile Ser Ser Asn
1               5
```

<210> SEQ ID NO 12
<211> LENGTH: 9
<212> TYPE: PRT
<213> ORGANISM: Homo sapiens

<400> SEQUENCE: 12

Gln Gln Tyr Asp His Trp Pro Leu Thr
1 5

<210> SEQ ID NO 13
<211> LENGTH: 8
<212> TYPE: PRT
<213> ORGANISM: Homo sapiens

<400> SEQUENCE: 13

Gly Phe Thr Phe Ser Asn Tyr Trp
1 5

<210> SEQ ID NO 14
<211> LENGTH: 8
<212> TYPE: PRT
<213> ORGANISM: Homo sapiens

<400> SEQUENCE: 14

Ile Ser Thr Asp Gly Ser Ser Thr
1 5

<210> SEQ ID NO 15
<211> LENGTH: 15
<212> TYPE: PRT
<213> ORGANISM: Homo sapiens

<400> SEQUENCE: 15

Ala Arg Gly Ser Thr Tyr Tyr Phe Gly Ser Gly Ser Val Asp Tyr
1 5 10 15

<210> SEQ ID NO 16
<211> LENGTH: 9
<212> TYPE: PRT
<213> ORGANISM: Homo sapiens

<400> SEQUENCE: 16

Ser Ser Asp Ile Gly Val Tyr Asn Tyr
1 5

<210> SEQ ID NO 17
<211> LENGTH: 11
<212> TYPE: PRT
<213> ORGANISM: Homo sapiens

<400> SEQUENCE: 17

Ser Ser Tyr Arg Gly Ser Ser Thr Pro Tyr Val
1 5 10

<210> SEQ ID NO 18
<211> LENGTH: 10
<212> TYPE: PRT
<213> ORGANISM: Homo sapiens

<400> SEQUENCE: 18

Gly Gly Ser Ile Thr Thr Gly Asp Tyr Tyr
1 5 10

<210> SEQ ID NO 19

<211> LENGTH: 7
<212> TYPE: PRT
<213> ORGANISM: Homo sapiens

<400> SEQUENCE: 19

Ile Tyr Tyr Ser Gly Ser Thr
1 5

<210> SEQ ID NO 20
<211> LENGTH: 11
<212> TYPE: PRT
<213> ORGANISM: Homo sapiens

<400> SEQUENCE: 20

Ala Ile Tyr Met Asp Glu Ala Trp Ala Phe Glu
1 5 10

<210> SEQ ID NO 21
<211> LENGTH: 6
<212> TYPE: PRT
<213> ORGANISM: Homo sapiens

<400> SEQUENCE: 21

Gln Ser Ile Gly Asn Tyr
1 5

<210> SEQ ID NO 22
<211> LENGTH: 10
<212> TYPE: PRT
<213> ORGANISM: Homo sapiens

<400> SEQUENCE: 22

Gln Gln Ser Tyr Thr Ile Ser Leu Phe Thr
1 5 10

<210> SEQ ID NO 23
<211> LENGTH: 6
<212> TYPE: PRT
<213> ORGANISM: Hepatitis B virus

<400> SEQUENCE: 23

Lys Pro Ser Asp Gly Asn
1 5

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Pro Ser Ser Ser Ser Thr Lys Pro Ser Asp Gly Asn Ser Thr Ser
1 5 10 15

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Ser Thr Lys Pro Ser Asp Gly Asn Ser Thr 1 5 10

<210> SEQ ID NO 26
<211> LENGTH: 8
<212> TYPE: PRT
<213> ORGANISM: Homo sapiens

<400> SEQUENCE: 26

Gly Tyr Thr Phe Thr Thr Tyr Gly
1 5

<210> SEQ ID NO 27
<211> LENGTH: 8
<212> TYPE: PRT
<213> ORGANISM: Homo sapiens

<400> SEQUENCE: 27

Ile Ser Thr Tyr Asn Arg Asn Thr
1 5

<210> SEQ ID NO 28
<211> LENGTH: 22
<212> TYPE: PRT
<213> ORGANISM: Homo sapiens

<400> SEQUENCE: 28

Ala Arg Asn Gly Tyr Ser Ser Ser Trp His Gly Gly Thr His Tyr Tyr
1 5 10 15

Tyr Tyr Ala Leu Asp Phe
20

<210> SEQ ID NO 29
<211> LENGTH: 6
<212> TYPE: PRT
<213> ORGANISM: Homo sapiens

<400> SEQUENCE: 29

Gln Ser Ile Thr Asn Trp
1 5

<210> SEQ ID NO 30
<211> LENGTH: 9
<212> TYPE: PRT
<213> ORGANISM: Homo sapiens

<400> SEQUENCE: 30

Gln Gln Tyr Tyr Ser Tyr Pro Trp Thr
1 5

<210> SEQ ID NO 31
<211> LENGTH: 8
<212> TYPE: PRT
<213> ORGANISM: Homo sapiens

<400> SEQUENCE: 31

Gly Tyr Ser Phe Asn Thr Tyr Gly
1 5

<210> SEQ ID NO 32
<211> LENGTH: 8
<212> TYPE: PRT
<213> ORGANISM: Homo sapiens

<400> SEQUENCE: 32

Ile Ser Thr Tyr Asn Gly Lys Thr
1 5

<210> SEQ ID NO 33
<211> LENGTH: 22
<212> TYPE: PRT
<213> ORGANISM: Homo sapiens

<400> SEQUENCE: 33

Ala Arg Asp Ser Val Ser Trp Trp Asn Leu Leu Phe Lys Ser Leu Glu
1 5 10 15

Lys Leu Thr Leu Asp Tyr
20

<210> SEQ ID NO 34
<211> LENGTH: 9
<212> TYPE: PRT
<213> ORGANISM: Homo sapiens

<400> SEQUENCE: 34

Ser Ser Asp Val Gly Ser Tyr Asp Leu
1 5

<210> SEQ ID NO 35
<211> LENGTH: 10
<212> TYPE: PRT
<213> ORGANISM: Homo sapiens

<400> SEQUENCE: 35

Cys Ser Tyr Ser Gly Ser Thr Thr Cys Val
1 5 10

<210> SEQ ID NO 36
<211> LENGTH: 8
<212> TYPE: PRT
<213> ORGANISM: Homo sapiens

<400> SEQUENCE: 36

Gly Tyr Ser Phe Asn Thr Tyr Gly
1 5

<210> SEQ ID NO 37
<211> LENGTH: 8
<212> TYPE: PRT
<213> ORGANISM: Homo sapiens

<400> SEQUENCE: 37

Ile Ser Thr Tyr Asn Gly Lys Thr
1 5

<210> SEQ ID NO 38
<211> LENGTH: 22
<212> TYPE: PRT
<213> ORGANISM: Homo sapiens

<400> SEQUENCE: 38

Ala Arg Asp Ser Val Ser Trp Trp Asn Leu Leu Phe Lys Ser Leu Glu
1 5 10 15

Lys Leu Thr Leu Asp Tyr
20

<210> SEQ ID NO 39
<211> LENGTH: 7
<212> TYPE: PRT

<213> ORGANISM: Homo sapiens

<400> SEQUENCE: 39

Gln Ser Val Ser Asn Ser Tyr
1 5

<210> SEQ ID NO 40
<211> LENGTH: 9
<212> TYPE: PRT
<213> ORGANISM: Homo sapiens

<400> SEQUENCE: 40

Gln Gln Phe Gly Ser Ser Pro Leu Thr
1 5

<210> SEQ ID NO 41
<211> LENGTH: 9
<212> TYPE: PRT
<213> ORGANISM: Homo sapiens

<400> SEQUENCE: 41

Ser Ser Asp Ile Gly Gly Tyr Asn Tyr
1 5

<210> SEQ ID NO 42
<211> LENGTH: 10
<212> TYPE: PRT
<213> ORGANISM: Homo sapiens

<400> SEQUENCE: 42

Asn Ser Tyr Ala Gly Asn Asn Asn Phe Val
1 5 10

<210> SEQ ID NO 43
<211> LENGTH: 8
<212> TYPE: PRT
<213> ORGANISM: Homo sapiens

<400> SEQUENCE: 43

Gly Tyr Ser Phe Asn Thr Tyr Gly
1 5

<210> SEQ ID NO 44
<211> LENGTH: 8
<212> TYPE: PRT
<213> ORGANISM: Homo sapiens

<400> SEQUENCE: 44

Ile Ser Thr Tyr Asn Gly Lys Thr
1 5

<210> SEQ ID NO 45
<211> LENGTH: 22
<212> TYPE: PRT
<213> ORGANISM: Homo sapiens

<400> SEQUENCE: 45

Ala Arg Asp Ser Val Ser Trp Trp Asn Leu Leu Phe Lys Ser Leu Glu
1 5 10 15

Lys Leu Thr Leu Asp Tyr
20

<210> SEQ ID NO 46
<211> LENGTH: 6

<212> TYPE: PRT
<213> ORGANISM: Homo sapiens

<400> SEQUENCE: 46

Gln Ser Val Ser Ser Tyr
1               5

<210> SEQ ID NO 47
<211> LENGTH: 8
<212> TYPE: PRT
<213> ORGANISM: Homo sapiens

<400> SEQUENCE: 47

Gln His Arg Ser Asn Ser Trp Thr
1               5

<210> SEQ ID NO 48
<211> LENGTH: 8
<212> TYPE: PRT
<213> ORGANISM: Homo sapiens

<400> SEQUENCE: 48

Gly Tyr Thr Phe Ser Ser Tyr Gly
1               5

<210> SEQ ID NO 49
<211> LENGTH: 8
<212> TYPE: PRT
<213> ORGANISM: Homo sapiens

<400> SEQUENCE: 49

Ile Ser Ala His Ser Gly Asn Thr
1               5

<210> SEQ ID NO 50
<211> LENGTH: 16
<212> TYPE: PRT
<213> ORGANISM: Homo sapiens

<400> SEQUENCE: 50

Ala Arg Asp Pro Asp Phe Gly Asp Tyr Gly Ser Asp Ile Val Asp Tyr
1               5                   10                  15

<210> SEQ ID NO 51
<211> LENGTH: 6
<212> TYPE: PRT
<213> ORGANISM: Homo sapiens

<400> SEQUENCE: 51

Ala Leu Pro Val Gln Phe
1               5

<210> SEQ ID NO 52
<211> LENGTH: 11
<212> TYPE: PRT
<213> ORGANISM: Homo sapiens

<400> SEQUENCE: 52

Gln Ser Ala Asp Ser Thr Ala Thr Tyr Trp Val
1               5                   10

<210> SEQ ID NO 53
<211> LENGTH: 8
<212> TYPE: PRT
<213> ORGANISM: Homo sapiens

<400> SEQUENCE: 53

Gly Tyr Ser Phe Ser Ser Tyr Gly
1               5

<210> SEQ ID NO 54
<211> LENGTH: 8
<212> TYPE: PRT
<213> ORGANISM: Homo sapiens

<400> SEQUENCE: 54

Ile Ser Ala Tyr Asn Gly Asp Thr
1               5

<210> SEQ ID NO 55
<211> LENGTH: 18
<212> TYPE: PRT
<213> ORGANISM: Homo sapiens

<400> SEQUENCE: 55

Ala Arg Trp Gly Val Gly Met Thr Phe Ser Tyr His Tyr His Tyr Met
1               5                   10                  15

Asp Val

<210> SEQ ID NO 56
<211> LENGTH: 6
<212> TYPE: PRT
<213> ORGANISM: Homo sapiens

<400> SEQUENCE: 56

Ser Leu Arg Thr Tyr Tyr
1               5

<210> SEQ ID NO 57
<211> LENGTH: 9
<212> TYPE: PRT
<213> ORGANISM: Homo sapiens

<400> SEQUENCE: 57

Gly Ser Arg Asp Asn Ser Gly Tyr Ser
1               5

<210> SEQ ID NO 58
<211> LENGTH: 8
<212> TYPE: PRT
<213> ORGANISM: Homo sapiens

<400> SEQUENCE: 58

Gly Tyr Thr Phe Gly Ser Phe Gly
1               5

<210> SEQ ID NO 59
<211> LENGTH: 8
<212> TYPE: PRT
<213> ORGANISM: Homo sapiens

<400> SEQUENCE: 59

Ile Ser Gly Tyr Ser Gly Lys Thr
1               5

<210> SEQ ID NO 60
<211> LENGTH: 14
<212> TYPE: PRT
<213> ORGANISM: Homo sapiens

<400> SEQUENCE: 60

Ala Arg Gly Arg Gly Asp Ser Ser Thr Trp Tyr Ser Leu Tyr
1 5 10

<210> SEQ ID NO 61
<211> LENGTH: 6
<212> TYPE: PRT
<213> ORGANISM: Homo sapiens

<400> SEQUENCE: 61

Gln Ser Val Gly Ser Tyr
1 5

<210> SEQ ID NO 62
<211> LENGTH: 8
<212> TYPE: PRT
<213> ORGANISM: Homo sapiens

<400> SEQUENCE: 62

Gln Gln Tyr Asn Asp Trp Leu Thr
1 5

<210> SEQ ID NO 63
<211> LENGTH: 8
<212> TYPE: PRT
<213> ORGANISM: Homo sapiens

<400> SEQUENCE: 63

Asp Tyr Arg Ser Ile Asn Ser Gly
1 5

<210> SEQ ID NO 64
<211> LENGTH: 8
<212> TYPE: PRT
<213> ORGANISM: Homo sapiens

<400> SEQUENCE: 64

Ile Ser Pro Phe Asn Gly Asn Thr
1 5

<210> SEQ ID NO 65
<211> LENGTH: 12
<212> TYPE: PRT
<213> ORGANISM: Homo sapiens

<400> SEQUENCE: 65

Ala Gly Asp Thr Thr Ser Ser Ala Ala Leu Thr Phe
1 5 10

<210> SEQ ID NO 66
<211> LENGTH: 12
<212> TYPE: PRT
<213> ORGANISM: Homo sapiens

<400> SEQUENCE: 66

Glu Ser Val Phe Phe Ser Pro His Asn Arg Asn Tyr
1 5 10

<210> SEQ ID NO 67
<211> LENGTH: 8
<212> TYPE: PRT
<213> ORGANISM: Homo sapiens

<400> SEQUENCE: 67

Gln Gln Tyr Tyr Thr Thr Pro Ser
1 5

<210> SEQ ID NO 68
<211> LENGTH: 8
<212> TYPE: PRT
<213> ORGANISM: Homo sapiens

<400> SEQUENCE: 68

Gly Tyr Asn Phe Ile Ser Tyr Ala
1 5

<210> SEQ ID NO 69
<211> LENGTH: 8
<212> TYPE: PRT
<213> ORGANISM: Homo sapiens

<400> SEQUENCE: 69

Ile Ser Pro Tyr Asn Gly Lys Lys
1 5

<210> SEQ ID NO 70
<211> LENGTH: 18
<212> TYPE: PRT
<213> ORGANISM: Homo sapiens

<400> SEQUENCE: 70

Ala Arg Phe Phe Gly Gly Ala Thr Met Thr Val Tyr Phe Tyr Gly Leu
1 5 10 15

Asp Val

<210> SEQ ID NO 71
<211> LENGTH: 6
<212> TYPE: PRT
<213> ORGANISM: Homo sapiens

<400> SEQUENCE: 71

Gln Ser Ile Lys Thr Trp
1 5

<210> SEQ ID NO 72
<211> LENGTH: 10
<212> TYPE: PRT
<213> ORGANISM: Homo sapiens

<400> SEQUENCE: 72

Gln Gln Tyr Asn Ser Tyr Ser Gly Trp Thr
1 5 10

<210> SEQ ID NO 73
<211> LENGTH: 8
<212> TYPE: PRT
<213> ORGANISM: Homo sapiens

<400> SEQUENCE: 73

Gly Tyr Lys Phe Thr Asn Tyr Gly
1 5

<210> SEQ ID NO 74
<211> LENGTH: 8
<212> TYPE: PRT
<213> ORGANISM: Homo sapiens

<400> SEQUENCE: 74

Ile Asn Ala Tyr Asn Gly His Thr
1 5

<210> SEQ ID NO 75
<211> LENGTH: 12
<212> TYPE: PRT
<213> ORGANISM: Homo sapiens

<400> SEQUENCE: 75

Thr Arg Ser Glu Gln Trp Arg Ser Arg Gly Glu Tyr
1 5 10

<210> SEQ ID NO 76
<211> LENGTH: 8
<212> TYPE: PRT
<213> ORGANISM: Homo sapiens

<400> SEQUENCE: 76

Asn Ser Asn Val Gly Asn Asn Val
1 5

<210> SEQ ID NO 77
<211> LENGTH: 12
<212> TYPE: PRT
<213> ORGANISM: Homo sapiens

<400> SEQUENCE: 77

Ala Ser Trp Asp Asp Ser Leu Ser Gly Ser Trp Val
1 5 10

<210> SEQ ID NO 78
<211> LENGTH: 8
<212> TYPE: PRT
<213> ORGANISM: Homo sapiens

<400> SEQUENCE: 78

Gly Tyr Thr Phe Ser Asn Tyr Gly
1 5

<210> SEQ ID NO 79
<211> LENGTH: 8
<212> TYPE: PRT
<213> ORGANISM: Homo sapiens

<400> SEQUENCE: 79

Ile Ser Ala Ser Ser Gly Asn Thr
1 5

<210> SEQ ID NO 80
<211> LENGTH: 12
<212> TYPE: PRT
<213> ORGANISM: Homo sapiens

<400> SEQUENCE: 80

Gly Arg Asp Asp Ser Gly Ser Tyr Pro Met Ser Pro
1 5 10

<210> SEQ ID NO 81
<211> LENGTH: 7
<212> TYPE: PRT
<213> ORGANISM: Homo sapiens

<400> SEQUENCE: 81

Gln Ser Val Ser Gly Ser Tyr 1 5

<210> SEQ ID NO 82
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Any amino acid

<400> SEQUENCE: 82

Gln Gln Tyr Xaa Ser Ser Pro Leu Ala
1 5

<210> SEQ ID NO 83
<211> LENGTH: 8
<212> TYPE: PRT
<213> ORGANISM: Homo sapiens

<400> SEQUENCE: 83

Gly Tyr Thr Phe Arg Asn Tyr Gly
1 5

<210> SEQ ID NO 84
<211> LENGTH: 8
<212> TYPE: PRT
<213> ORGANISM: Homo sapiens

<400> SEQUENCE: 84

Ile Asn Ala His Asn Gly Asp Thr
1 5

<210> SEQ ID NO 85
<211> LENGTH: 10
<212> TYPE: PRT
<213> ORGANISM: Homo sapiens

<400> SEQUENCE: 85

Val Arg Asp Ile Asn Phe Ile Phe Asp Tyr
1 5 10

<210> SEQ ID NO 86
<211> LENGTH: 9
<212> TYPE: PRT
<213> ORGANISM: Homo sapiens

<400> SEQUENCE: 86

Thr Gly Ala Val Thr Ser Ser Tyr Tyr
1 5

<210> SEQ ID NO 87
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Any amino acid

<400> SEQUENCE: 87

Leu Leu Tyr Xaa Trp Ser Ser Ser Ala Leu Gly
1 5 10

<210> SEQ ID NO 88
<211> LENGTH: 8

<212> TYPE: PRT
<213> ORGANISM: Homo sapiens

<400> SEQUENCE: 88

Gly Tyr Ser Phe Thr Ser Tyr Gly
1 5

<210> SEQ ID NO 89
<211> LENGTH: 8
<212> TYPE: PRT
<213> ORGANISM: Homo sapiens

<400> SEQUENCE: 89

Ile Asn Val Tyr Asn Ala Asn Thr
1 5

<210> SEQ ID NO 90
<211> LENGTH: 21
<212> TYPE: PRT
<213> ORGANISM: Homo sapiens

<400> SEQUENCE: 90

Ala Arg Glu Gly Trp Phe Gly Glu Phe Arg Arg Asn Tyr Asn Tyr Asn
1 5 10 15

Tyr Tyr Met Asp Val
20

<210> SEQ ID NO 91
<211> LENGTH: 6
<212> TYPE: PRT
<213> ORGANISM: Homo sapiens

<400> SEQUENCE: 91

Leu Ser Val Ser Ser Asn
1 5

<210> SEQ ID NO 92
<211> LENGTH: 9
<212> TYPE: PRT
<213> ORGANISM: Homo sapiens

<400> SEQUENCE: 92

Gln Gln Tyr His Glu Trp Pro Arg Thr
1 5

<210> SEQ ID NO 93
<211> LENGTH: 8
<212> TYPE: PRT
<213> ORGANISM: Homo sapiens

<400> SEQUENCE: 93

Gly Tyr Thr Leu Thr Glu Leu Ser
1 5

<210> SEQ ID NO 94
<211> LENGTH: 8
<212> TYPE: PRT
<213> ORGANISM: Homo sapiens

<400> SEQUENCE: 94

Phe Asp Pro Asp Glu Gly Glu Val
1 5

<210> SEQ ID NO 95

<211> LENGTH: 11
<212> TYPE: PRT
<213> ORGANISM: Homo sapiens

<400> SEQUENCE: 95

Thr Leu Val Thr Arg Val Asp Ala Phe Asp Val
1 5 10

<210> SEQ ID NO 96
<211> LENGTH: 6
<212> TYPE: PRT
<213> ORGANISM: Homo sapiens

<400> SEQUENCE: 96

Gln Ser Val Arg Thr Tyr
1 5

<210> SEQ ID NO 97
<211> LENGTH: 9
<212> TYPE: PRT
<213> ORGANISM: Homo sapiens

<400> SEQUENCE: 97

Gln Gln Ser Tyr Phe Ala Pro Tyr Thr
1 5

<210> SEQ ID NO 98
<211> LENGTH: 8
<212> TYPE: PRT
<213> ORGANISM: Homo sapiens

<400> SEQUENCE: 98

Gly Tyr Ser His Thr Glu Leu Pro
1 5

<210> SEQ ID NO 99
<211> LENGTH: 8
<212> TYPE: PRT
<213> ORGANISM: Homo sapiens

<400> SEQUENCE: 99

Phe Asp Pro Asp Glu Gly Glu Thr
1 5

<210> SEQ ID NO 100
<211> LENGTH: 11
<212> TYPE: PRT
<213> ORGANISM: Homo sapiens

<400> SEQUENCE: 100

Thr Leu Val Thr Arg Val Asp Ala Phe Glu Val
1 5 10

<210> SEQ ID NO 101
<211> LENGTH: 6
<212> TYPE: PRT
<213> ORGANISM: Homo sapiens

<400> SEQUENCE: 101

Gln Asn Ile Arg Asn Tyr
1 5

<210> SEQ ID NO 102
<211> LENGTH: 9
<212> TYPE: PRT

<213> ORGANISM: Homo sapiens

<400> SEQUENCE: 102

Gln Gln Ser Tyr Phe Ala Pro Tyr Thr
1 5

<210> SEQ ID NO 103
<211> LENGTH: 8
<212> TYPE: PRT
<213> ORGANISM: Homo sapiens

<400> SEQUENCE: 103

Gly Tyr Thr Leu Thr Glu Leu Pro
1 5

<210> SEQ ID NO 104
<211> LENGTH: 8
<212> TYPE: PRT
<213> ORGANISM: Homo sapiens

<400> SEQUENCE: 104

Phe Asp Pro Asp Glu Gly Glu Thr
1 5

<210> SEQ ID NO 105
<211> LENGTH: 11
<212> TYPE: PRT
<213> ORGANISM: Homo sapiens

<400> SEQUENCE: 105

Thr Leu Val Thr Gly Val Asp Ala Phe Ala Val
1 5 10

<210> SEQ ID NO 106
<211> LENGTH: 6
<212> TYPE: PRT
<213> ORGANISM: Homo sapiens

<400> SEQUENCE: 106

Gln Asn Ile Arg Thr Tyr
1 5

<210> SEQ ID NO 107
<211> LENGTH: 9
<212> TYPE: PRT
<213> ORGANISM: Homo sapiens

<400> SEQUENCE: 107

Gln Gln Ser Tyr Phe Ala Pro Tyr Thr
1 5

<210> SEQ ID NO 108
<211> LENGTH: 8
<212> TYPE: PRT
<213> ORGANISM: Homo sapiens

<400> SEQUENCE: 108

Gly Tyr Ile Phe Ser Glu Leu Ser
1 5

<210> SEQ ID NO 109
<211> LENGTH: 8
<212> TYPE: PRT
<213> ORGANISM: Homo sapiens

<400> SEQUENCE: 109

Phe Asp Pro Asp Glu Gly Glu Thr
1               5

<210> SEQ ID NO 110
<211> LENGTH: 11
<212> TYPE: PRT
<213> ORGANISM: Homo sapiens

<400> SEQUENCE: 110

Thr Ser Val Ile Lys Ala Asp Ala Phe Glu Val
1               5                   10

<210> SEQ ID NO 111
<211> LENGTH: 6
<212> TYPE: PRT
<213> ORGANISM: Homo sapiens

<400> SEQUENCE: 111

Gln Asn Ile Arg Thr Tyr
1               5

<210> SEQ ID NO 112
<211> LENGTH: 9
<212> TYPE: PRT
<213> ORGANISM: Homo sapiens

<400> SEQUENCE: 112

Gln Gln Ser Tyr Phe Ala Pro Tyr Thr
1               5

<210> SEQ ID NO 113
<211> LENGTH: 8
<212> TYPE: PRT
<213> ORGANISM: Homo sapiens

<400> SEQUENCE: 113

Gly Tyr Thr Phe Thr His Tyr Ala
1               5

<210> SEQ ID NO 114
<211> LENGTH: 8
<212> TYPE: PRT
<213> ORGANISM: Homo sapiens

<400> SEQUENCE: 114

Leu Asn Gly Gly Asn Asp Asp Arg
1               5

<210> SEQ ID NO 115
<211> LENGTH: 20
<212> TYPE: PRT
<213> ORGANISM: Homo sapiens

<400> SEQUENCE: 115

Ala Arg Gly Gly Trp Ile Ile Gln Asn Gly Gly Ala Arg Tyr Tyr His
1               5                   10                  15

Gly Met Asp Val
            20

<210> SEQ ID NO 116
<211> LENGTH: 7
<212> TYPE: PRT
<213> ORGANISM: Homo sapiens

<400> SEQUENCE: 116

Gln Ser Val Ser Ser Ser Gln
1 5

<210> SEQ ID NO 117
<211> LENGTH: 8
<212> TYPE: PRT
<213> ORGANISM: Homo sapiens

<400> SEQUENCE: 117

Gln His Tyr Asn Asn Pro Val Ala
1 5

<210> SEQ ID NO 118
<211> LENGTH: 6
<212> TYPE: PRT
<213> ORGANISM: Homo sapiens

<400> SEQUENCE: 118

Asn Ile Arg Asn Lys Asn
1 5

<210> SEQ ID NO 119
<211> LENGTH: 11
<212> TYPE: PRT
<213> ORGANISM: Homo sapiens

<400> SEQUENCE: 119

Gln Val Trp Asp Gly Gly Ser Tyr His Val Ile
1 5 10

<210> SEQ ID NO 120
<211> LENGTH: 8
<212> TYPE: PRT
<213> ORGANISM: Homo sapiens

<400> SEQUENCE: 120

Gly Tyr Thr Phe Thr Arg Tyr Pro
1 5

<210> SEQ ID NO 121
<211> LENGTH: 8
<212> TYPE: PRT
<213> ORGANISM: Homo sapiens

<400> SEQUENCE: 121

Ile Asn Ala Ala Asn Gly Asp Thr
1 5

<210> SEQ ID NO 122
<211> LENGTH: 15
<212> TYPE: PRT
<213> ORGANISM: Homo sapiens

<400> SEQUENCE: 122

Ala Arg Lys Asp Tyr Tyr Gly Ser Gly Ser Tyr Glu Phe Asp Asn
1 5 10 15

<210> SEQ ID NO 123
<211> LENGTH: 9
<212> TYPE: PRT
<213> ORGANISM: Homo sapiens

<400> SEQUENCE: 123

Ser Ser Asp Val Gly Gly Tyr Asn Tyr
1 5

<210> SEQ ID NO 124
<211> LENGTH: 10
<212> TYPE: PRT
<213> ORGANISM: Homo sapiens

<400> SEQUENCE: 124

Cys Ser Tyr Ala Gly Asn Tyr Ile Leu Val
1 5 10

<210> SEQ ID NO 125
<211> LENGTH: 8
<212> TYPE: PRT
<213> ORGANISM: Homo sapiens

<400> SEQUENCE: 125

Gly Tyr Asn Phe Gln Arg Ser Ala
1 5

<210> SEQ ID NO 126
<211> LENGTH: 8
<212> TYPE: PRT
<213> ORGANISM: Homo sapiens

<400> SEQUENCE: 126

Ile Asn Val Gly Asn Gly Asn Thr
1 5

<210> SEQ ID NO 127
<211> LENGTH: 15
<212> TYPE: PRT
<213> ORGANISM: Homo sapiens

<400> SEQUENCE: 127

Ala Lys Gly Arg Ser Ser His Asp Leu Tyr Asp Pro Phe Asp Phe
1 5 10 15

<210> SEQ ID NO 128
<211> LENGTH: 6
<212> TYPE: PRT
<213> ORGANISM: Homo sapiens

<400> SEQUENCE: 128

Glu Asn Ile Gly Gly Trp
1 5

<210> SEQ ID NO 129
<211> LENGTH: 10
<212> TYPE: PRT
<213> ORGANISM: Homo sapiens

<400> SEQUENCE: 129

Gln Gln Tyr Asn Ser Tyr Ser Arg Tyr Thr
1 5 10

<210> SEQ ID NO 130
<211> LENGTH: 8
<212> TYPE: PRT
<213> ORGANISM: Homo sapiens

<400> SEQUENCE: 130

Gly Tyr Thr Phe Thr Ser Tyr Pro 1 5

<210> SEQ ID NO 131
<211> LENGTH: 8
<212> TYPE: PRT
<213> ORGANISM: Homo sapiens

<400> SEQUENCE: 131

Ile Asn Pro Ala Asn Gly Asp Thr
1 5

<210> SEQ ID NO 132
<211> LENGTH: 15
<212> TYPE: PRT
<213> ORGANISM: Homo sapiens

<400> SEQUENCE: 132

Ala Arg Lys Asn Tyr Tyr Ala Ser Gly Ser Tyr His Phe Asp Leu
1 5 10 15

<210> SEQ ID NO 133
<211> LENGTH: 9
<212> TYPE: PRT
<213> ORGANISM: Homo sapiens

<400> SEQUENCE: 133

Asn Ser Asp Val Gly Gly Tyr Asn Tyr
1 5

<210> SEQ ID NO 134
<211> LENGTH: 10
<212> TYPE: PRT
<213> ORGANISM: Homo sapiens

<400> SEQUENCE: 134

Ser Ser Tyr Ala Gly Lys Tyr Thr Leu Val
1 5 10

<210> SEQ ID NO 135
<211> LENGTH: 8
<212> TYPE: PRT
<213> ORGANISM: Homo sapiens

<400> SEQUENCE: 135

Gly Tyr Thr Leu Thr Ser Tyr Ala
1 5

<210> SEQ ID NO 136
<211> LENGTH: 8
<212> TYPE: PRT
<213> ORGANISM: Homo sapiens

<400> SEQUENCE: 136

Ile Asn Ala Gly Ser Gly Leu Thr
1 5

<210> SEQ ID NO 137
<211> LENGTH: 17
<212> TYPE: PRT
<213> ORGANISM: Homo sapiens

<400> SEQUENCE: 137

Ala Arg Val Gly Ile Pro Leu Arg Gly Ala Gly Gly Ser Pro Phe Asp
1 5 10 15

Ile

<210> SEQ ID NO 138
<211> LENGTH: 6
<212> TYPE: PRT
<213> ORGANISM: Homo sapiens

<400> SEQUENCE: 138

Gln Ser Val Ser Thr Tyr
1 5

<210> SEQ ID NO 139
<211> LENGTH: 9
<212> TYPE: PRT
<213> ORGANISM: Homo sapiens

<400> SEQUENCE: 139

Gln Gln Ser Ser Ser Val Pro Leu Thr
1 5

<210> SEQ ID NO 140
<211> LENGTH: 8
<212> TYPE: PRT
<213> ORGANISM: Homo sapiens

<400> SEQUENCE: 140

Gly Tyr Thr Phe Thr Thr Tyr Ala
1 5

<210> SEQ ID NO 141
<211> LENGTH: 8
<212> TYPE: PRT
<213> ORGANISM: Homo sapiens

<400> SEQUENCE: 141

Ile Asn Ala Gly Asn Gly Ile Thr
1 5

<210> SEQ ID NO 142
<211> LENGTH: 17
<212> TYPE: PRT
<213> ORGANISM: Homo sapiens

<400> SEQUENCE: 142

Ala Arg Val Gly Ile Leu Val Arg Gly Ala Gly Gly Ser Pro Phe Asp
1 5 10 15

Ile

<210> SEQ ID NO 143
<211> LENGTH: 6
<212> TYPE: PRT
<213> ORGANISM: Homo sapiens

<400> SEQUENCE: 143

Gln Ser Ile Ser Thr Tyr
1 5

<210> SEQ ID NO 144
<211> LENGTH: 9
<212> TYPE: PRT
<213> ORGANISM: Homo sapiens

<400> SEQUENCE: 144

Gln Gln Ser Tyr Ser Thr Pro Leu Thr 1 5

<210> SEQ ID NO 145
<211> LENGTH: 8
<212> TYPE: PRT
<213> ORGANISM: Homo sapiens

<400> SEQUENCE: 145

Gly Tyr Thr Phe Thr Thr Tyr Ala
1 5

<210> SEQ ID NO 146
<211> LENGTH: 8
<212> TYPE: PRT
<213> ORGANISM: Homo sapiens

<400> SEQUENCE: 146

Ile Asn Ala Gly Asn Gly Ile Thr
1 5

<210> SEQ ID NO 147
<211> LENGTH: 17
<212> TYPE: PRT
<213> ORGANISM: Homo sapiens

<400> SEQUENCE: 147

Ala Arg Val Gly Ile Leu Val Arg Gly Ala Gly Gly Ser Pro Phe Asp
1 5 10 15

Ile

<210> SEQ ID NO 148
<211> LENGTH: 6
<212> TYPE: PRT
<213> ORGANISM: Homo sapiens

<400> SEQUENCE: 148

Gln Ser Ile Ser Thr Tyr
1 5

<210> SEQ ID NO 149
<211> LENGTH: 9
<212> TYPE: PRT
<213> ORGANISM: Homo sapiens

<400> SEQUENCE: 149

Gln Gln Ser Tyr Ser Thr Pro Leu Thr
1 5

<210> SEQ ID NO 150
<211> LENGTH: 8
<212> TYPE: PRT
<213> ORGANISM: Homo sapiens

<400> SEQUENCE: 150

Gly Tyr Thr Phe Ser Arg His Ala
1 5

<210> SEQ ID NO 151
<211> LENGTH: 8
<212> TYPE: PRT
<213> ORGANISM: Homo sapiens

<400> SEQUENCE: 151

Ile Asn Ile Gly Asn Gly Asn Thr 1 5

<210> SEQ ID NO 152
<211> LENGTH: 15
<212> TYPE: PRT
<213> ORGANISM: Homo sapiens

<400> SEQUENCE: 152

Ala Arg Glu Asp Tyr Thr Gly Asn Tyr Tyr Asp Ala Phe Asp Phe
1 5 10 15

<210> SEQ ID NO 153
<211> LENGTH: 6
<212> TYPE: PRT
<213> ORGANISM: Homo sapiens

<400> SEQUENCE: 153

Gln Ser Val Ser Thr Trp
1 5

<210> SEQ ID NO 154
<211> LENGTH: 10
<212> TYPE: PRT
<213> ORGANISM: Homo sapiens

<400> SEQUENCE: 154

Gln Leu Tyr Asn Ser Tyr Ser Gly Thr Thr
1 5 10

<210> SEQ ID NO 155
<211> LENGTH: 8
<212> TYPE: PRT
<213> ORGANISM: Homo sapiens

<400> SEQUENCE: 155

Gly Tyr Ser Phe Ser Asn Tyr Ala
1 5

<210> SEQ ID NO 156
<211> LENGTH: 8
<212> TYPE: PRT
<213> ORGANISM: Homo sapiens

<400> SEQUENCE: 156

Ile Asn Ala Ala Tyr Gly Asn Thr
1 5

<210> SEQ ID NO 157
<211> LENGTH: 18
<212> TYPE: PRT
<213> ORGANISM: Homo sapiens

<400> SEQUENCE: 157

Ala Arg Asp Gly Val Lys Glu Gln Leu Val Tyr Tyr Tyr Phe Gly Met
1 5 10 15

Asp Val

<210> SEQ ID NO 158
<211> LENGTH: 9
<212> TYPE: PRT
<213> ORGANISM: Homo sapiens

<400> SEQUENCE: 158

Ser Ser Asn Ile Gly Lys Asn Tyr Asp 1 5

<210> SEQ ID NO 159
<211> LENGTH: 12
<212> TYPE: PRT
<213> ORGANISM: Homo sapiens

<400> SEQUENCE: 159

Gln Ser Tyr Asp Ser Asn Leu Ser Gly Ser Val Val
1 5 10

<210> SEQ ID NO 160
<211> LENGTH: 8
<212> TYPE: PRT
<213> ORGANISM: Homo sapiens

<400> SEQUENCE: 160

Thr Tyr Val Phe Thr Ala Tyr Ala
1 5

<210> SEQ ID NO 161
<211> LENGTH: 8
<212> TYPE: PRT
<213> ORGANISM: Homo sapiens

<400> SEQUENCE: 161

Ile Asn Ala Gly Asn Gly Asp Thr
1 5

<210> SEQ ID NO 162
<211> LENGTH: 14
<212> TYPE: PRT
<213> ORGANISM: Homo sapiens

<400> SEQUENCE: 162

Ala Arg Gly Ala Leu Leu Trp Phe Arg Asp Asp Phe Asp Phe
1 5 10

<210> SEQ ID NO 163
<211> LENGTH: 6
<212> TYPE: PRT
<213> ORGANISM: Homo sapiens

<400> SEQUENCE: 163

Gln Gly Ile Ser Asn Tyr
1 5

<210> SEQ ID NO 164
<211> LENGTH: 9
<212> TYPE: PRT
<213> ORGANISM: Homo sapiens

<400> SEQUENCE: 164

Gln Lys Tyr Asp Ser Ala Pro Tyr Thr
1 5

<210> SEQ ID NO 165
<211> LENGTH: 8
<212> TYPE: PRT
<213> ORGANISM: Homo sapiens

<400> SEQUENCE: 165

Ser Ser Asn Ile Gly Asn Thr Tyr
1 5

<210> SEQ ID NO 166
<211> LENGTH: 12
<212> TYPE: PRT
<213> ORGANISM: Homo sapiens

<400> SEQUENCE: 166

Gly Ser Trp Asp Ser Ser Leu Tyr Ser Phe Tyr Val
1               5                   10

<210> SEQ ID NO 167
<211> LENGTH: 8
<212> TYPE: PRT
<213> ORGANISM: Homo sapiens

<400> SEQUENCE: 167

Gly Tyr Thr Phe Ser Asn Tyr His
1               5

<210> SEQ ID NO 168
<211> LENGTH: 8
<212> TYPE: PRT
<213> ORGANISM: Homo sapiens

<400> SEQUENCE: 168

Ile Asn Pro Ser Gly Asp Ser Thr
1               5

<210> SEQ ID NO 169
<211> LENGTH: 11
<212> TYPE: PRT
<213> ORGANISM: Homo sapiens

<400> SEQUENCE: 169

Ala Ser Arg Leu Asp Ala Ile Pro Phe Gln Val
1               5                   10

<210> SEQ ID NO 170
<211> LENGTH: 7
<212> TYPE: PRT
<213> ORGANISM: Homo sapiens

<400> SEQUENCE: 170

Pro Asn Ala Asn Ser Gly Ser
1               5

<210> SEQ ID NO 171
<211> LENGTH: 9
<212> TYPE: PRT
<213> ORGANISM: Homo sapiens

<400> SEQUENCE: 171

Gln Gln Tyr Gly Gly Leu Pro Phe Thr
1               5

<210> SEQ ID NO 172
<211> LENGTH: 8
<212> TYPE: PRT
<213> ORGANISM: Homo sapiens

<400> SEQUENCE: 172

Gly Tyr Ile Val Thr Ser Tyr Arg
1               5

<210> SEQ ID NO 173

<211> LENGTH: 8
<212> TYPE: PRT
<213> ORGANISM: Homo sapiens

<400> SEQUENCE: 173

Ile Asp Pro Ser Asp Thr Tyr Thr
1 5

<210> SEQ ID NO 174
<211> LENGTH: 16
<212> TYPE: PRT
<213> ORGANISM: Homo sapiens

<400> SEQUENCE: 174

Ala Arg Lys Gly Asn Tyr Gly Ser Arg Tyr Asp Trp Tyr Phe Asp Val
1 5 10 15

<210> SEQ ID NO 175
<211> LENGTH: 9
<212> TYPE: PRT
<213> ORGANISM: Homo sapiens

<400> SEQUENCE: 175

Ser Ser Asp Val Gly Asp Tyr Ser Tyr
1 5

<210> SEQ ID NO 176
<211> LENGTH: 10
<212> TYPE: PRT
<213> ORGANISM: Homo sapiens

<400> SEQUENCE: 176

Ser Ser Tyr Thr Ser Ser Ser Thr Gly Val
1 5 10

<210> SEQ ID NO 177
<211> LENGTH: 8
<212> TYPE: PRT
<213> ORGANISM: Homo sapiens

<400> SEQUENCE: 177

Gly Tyr Thr Phe Thr Asn Phe Asn
1 5

<210> SEQ ID NO 178
<211> LENGTH: 8
<212> TYPE: PRT
<213> ORGANISM: Homo sapiens

<400> SEQUENCE: 178

Ile Asn Pro Gly Ala Gly Thr Thr
1 5

<210> SEQ ID NO 179
<211> LENGTH: 19
<212> TYPE: PRT
<213> ORGANISM: Homo sapiens

<400> SEQUENCE: 179

Thr Arg Asp Pro Ile Leu Arg Tyr Phe Asp Trp Gln Ser Arg Asp Ala
1 5 10 15

Phe Asp Val

<210> SEQ ID NO 180

<211> LENGTH: 6
<212> TYPE: PRT
<213> ORGANISM: Homo sapiens

<400> SEQUENCE: 180

Gln Gly Ile Arg Asn Asp
1 5

<210> SEQ ID NO 181
<211> LENGTH: 9
<212> TYPE: PRT
<213> ORGANISM: Homo sapiens

<400> SEQUENCE: 181

Leu Gln His Asn Gly Tyr Pro Ile Thr
1 5

<210> SEQ ID NO 182
<211> LENGTH: 8
<212> TYPE: PRT
<213> ORGANISM: Homo sapiens

<400> SEQUENCE: 182

Gly Gly Thr Phe Ser Ser Tyr Ser
1 5

<210> SEQ ID NO 183
<211> LENGTH: 8
<212> TYPE: PRT
<213> ORGANISM: Homo sapiens

<400> SEQUENCE: 183

Ile Val Pro Ile Phe Gly Ile Pro
1 5

<210> SEQ ID NO 184
<211> LENGTH: 19
<212> TYPE: PRT
<213> ORGANISM: Homo sapiens

<400> SEQUENCE: 184

Ala Arg Val Pro Ser Val Ala Thr Cys Asn Phe Gly Cys Tyr Ser Ala
1 5 10 15

Met Asp Val

<210> SEQ ID NO 185
<211> LENGTH: 6
<212> TYPE: PRT
<213> ORGANISM: Homo sapiens

<400> SEQUENCE: 185

Gln Ser Ile Ser Asn Tyr
1 5

<210> SEQ ID NO 186
<211> LENGTH: 9
<212> TYPE: PRT
<213> ORGANISM: Homo sapiens

<400> SEQUENCE: 186

Gln Gln Ser Tyr Ser Thr Leu Phe Ser
1 5

<210> SEQ ID NO 187

<211> LENGTH: 9
<212> TYPE: PRT
<213> ORGANISM: Homo sapiens

<400> SEQUENCE: 187

Ser Ser Asp Val Gly Gly Tyr Lys Tyr
1 5

<210> SEQ ID NO 188
<211> LENGTH: 11
<212> TYPE: PRT
<213> ORGANISM: Homo sapiens

<400> SEQUENCE: 188

Ser Ser Tyr Thr Gly Ser Ser Thr Arg Tyr Val
1 5 10

<210> SEQ ID NO 189
<211> LENGTH: 8
<212> TYPE: PRT
<213> ORGANISM: Homo sapiens

<400> SEQUENCE: 189

Gly Gly Lys Phe Ile Ala Tyr Gly
1 5

<210> SEQ ID NO 190
<211> LENGTH: 8
<212> TYPE: PRT
<213> ORGANISM: Homo sapiens

<400> SEQUENCE: 190

Thr Ile Pro Ile Tyr Gly Thr Ala
1 5

<210> SEQ ID NO 191
<211> LENGTH: 19
<212> TYPE: PRT
<213> ORGANISM: Homo sapiens

<400> SEQUENCE: 191

Ala Arg Ala Ser Phe Gly Asp Leu Trp Ser Gly Tyr Pro Asn Gln Phe
1 5 10 15

Phe Asp His

<210> SEQ ID NO 192
<211> LENGTH: 6
<212> TYPE: PRT
<213> ORGANISM: Homo sapiens

<400> SEQUENCE: 192

Gln Gly Ile Ser Asn Ser
1 5

<210> SEQ ID NO 193
<211> LENGTH: 9
<212> TYPE: PRT
<213> ORGANISM: Homo sapiens

<400> SEQUENCE: 193

Leu Gln His Asn Thr Tyr Pro Trp Thr
1 5

<210> SEQ ID NO 194

<211> LENGTH: 10
<212> TYPE: PRT
<213> ORGANISM: Homo sapiens

<400> SEQUENCE: 194

Gly Phe Ser Phe Ser Thr Gly Gly Val Gly
1 5 10

<210> SEQ ID NO 195
<211> LENGTH: 7
<212> TYPE: PRT
<213> ORGANISM: Homo sapiens

<400> SEQUENCE: 195

Ile Tyr Gly Asp Gly Asp Glu
1 5

<210> SEQ ID NO 196
<211> LENGTH: 11
<212> TYPE: PRT
<213> ORGANISM: Homo sapiens

<400> SEQUENCE: 196

Ala His Arg Leu Leu Thr Ala Tyr Tyr Asp His
1 5 10

<210> SEQ ID NO 197
<211> LENGTH: 6
<212> TYPE: PRT
<213> ORGANISM: Homo sapiens

<400> SEQUENCE: 197

Gln Ser Ile Ser Arg Trp
1 5

<210> SEQ ID NO 198
<211> LENGTH: 9
<212> TYPE: PRT
<213> ORGANISM: Homo sapiens

<400> SEQUENCE: 198

Gln Gln Tyr Asn Ser Tyr Ser Trp Ala
1 5

<210> SEQ ID NO 199
<211> LENGTH: 10
<212> TYPE: PRT
<213> ORGANISM: Homo sapiens

<400> SEQUENCE: 199

Gly Phe Ser Leu Ser Thr Phe Gly Val Gly
1 5 10

<210> SEQ ID NO 200
<211> LENGTH: 7
<212> TYPE: PRT
<213> ORGANISM: Homo sapiens

<400> SEQUENCE: 200

Ile Tyr Trp Asp Asp Asp Lys
1 5

<210> SEQ ID NO 201
<211> LENGTH: 14
<212> TYPE: PRT

<213> ORGANISM: Homo sapiens

<400> SEQUENCE: 201

Ala His Thr Val Ala Ala Ala Ala Thr Phe Trp Phe Asp Pro
1 5 10

<210> SEQ ID NO 202
<211> LENGTH: 8
<212> TYPE: PRT
<213> ORGANISM: Homo sapiens

<400> SEQUENCE: 202

Ser Ser Asn Ile Gly Ser Asn Thr
1 5

<210> SEQ ID NO 203
<211> LENGTH: 11
<212> TYPE: PRT
<213> ORGANISM: Homo sapiens

<400> SEQUENCE: 203

Ala Thr Trp Asp Asp Ser Leu Asn Gly Leu Val
1 5 10

<210> SEQ ID NO 204
<211> LENGTH: 10
<212> TYPE: PRT
<213> ORGANISM: Homo sapiens

<400> SEQUENCE: 204

Gly Phe Ser Leu Ser Thr Thr Ala Val Gly
1 5 10

<210> SEQ ID NO 205
<211> LENGTH: 7
<212> TYPE: PRT
<213> ORGANISM: Homo sapiens

<400> SEQUENCE: 205

Ile Tyr Gly Asp Asp Asp Lys
1 5

<210> SEQ ID NO 206
<211> LENGTH: 19
<212> TYPE: PRT
<213> ORGANISM: Homo sapiens

<400> SEQUENCE: 206

Ala His Ser Ser Tyr Phe Asp Cys Gly Gly Asp Cys Ser Asp Val Ala
1 5 10 15

Phe Asp Ile

<210> SEQ ID NO 207
<211> LENGTH: 6
<212> TYPE: PRT
<213> ORGANISM: Homo sapiens

<400> SEQUENCE: 207

Ala Leu Pro Arg Lys Tyr
1 5

<210> SEQ ID NO 208
<211> LENGTH: 10
<212> TYPE: PRT

<213> ORGANISM: Homo sapiens

<400> SEQUENCE: 208

Tyr Ser Thr Asp Ser Ser Gly Asp Pro Val
1 5 10

<210> SEQ ID NO 209
<211> LENGTH: 10
<212> TYPE: PRT
<213> ORGANISM: Homo sapiens

<400> SEQUENCE: 209

Gly Phe Ser Leu Thr Thr Asn Gly Met Gly
1 5 10

<210> SEQ ID NO 210
<211> LENGTH: 7
<212> TYPE: PRT
<213> ORGANISM: Homo sapiens

<400> SEQUENCE: 210

Ile Tyr Trp Asp Asp Asp Lys
1 5

<210> SEQ ID NO 211
<211> LENGTH: 17
<212> TYPE: PRT
<213> ORGANISM: Homo sapiens

<400> SEQUENCE: 211

Ala Arg Ser Tyr Cys Arg Gly Gly Asn Cys Tyr Ser Thr Ala Phe Asn
1 5 10 15

Val

<210> SEQ ID NO 212
<211> LENGTH: 9
<212> TYPE: PRT
<213> ORGANISM: Homo sapiens

<400> SEQUENCE: 212

Ser Ser Asp Val Gly Gly Tyr Asp Tyr
1 5

<210> SEQ ID NO 213
<211> LENGTH: 11
<212> TYPE: PRT
<213> ORGANISM: Homo sapiens

<400> SEQUENCE: 213

Cys Ser Tyr Ala Gly Ala Tyr Thr Tyr Val Ala
1 5 10

<210> SEQ ID NO 214
<211> LENGTH: 10
<212> TYPE: PRT
<213> ORGANISM: Homo sapiens

<400> SEQUENCE: 214

Gly Phe Ser Leu Ser Thr Asn Thr Met Arg
1 5 10

<210> SEQ ID NO 215
<211> LENGTH: 7
<212> TYPE: PRT

<213> ORGANISM: Homo sapiens

<400> SEQUENCE: 215

Ile Asp Trp Asp Asp Glu Lys
1 5

<210> SEQ ID NO 216
<211> LENGTH: 12
<212> TYPE: PRT
<213> ORGANISM: Homo sapiens

<400> SEQUENCE: 216

Ala Arg Ser Asn His Trp Gly Ser His Phe Asp Tyr
1 5 10

<210> SEQ ID NO 217
<211> LENGTH: 6
<212> TYPE: PRT
<213> ORGANISM: Homo sapiens

<400> SEQUENCE: 217

Asn Ile Gly Gly Lys Thr
1 5

<210> SEQ ID NO 218
<211> LENGTH: 12
<212> TYPE: PRT
<213> ORGANISM: Homo sapiens

<400> SEQUENCE: 218

Gln Val Trp Asp Thr Ser Gly Asp His Leu Tyr Val
1 5 10

<210> SEQ ID NO 219
<211> LENGTH: 8
<212> TYPE: PRT
<213> ORGANISM: Homo sapiens

<400> SEQUENCE: 219

Gly Phe Thr Phe Ser Asp Tyr Tyr
1 5

<210> SEQ ID NO 220
<211> LENGTH: 8
<212> TYPE: PRT
<213> ORGANISM: Homo sapiens

<400> SEQUENCE: 220

Ile Arg Gly Ser His Ser Ser Val
1 5

<210> SEQ ID NO 221
<211> LENGTH: 15
<212> TYPE: PRT
<213> ORGANISM: Homo sapiens

<400> SEQUENCE: 221

Ala Arg Asp Leu Pro Gly Asp Glu Tyr Leu Asp Ala Phe Asp Leu
1 5 10 15

<210> SEQ ID NO 222
<211> LENGTH: 12
<212> TYPE: PRT
<213> ORGANISM: Homo sapiens

<400> SEQUENCE: 222

Gln Ser Leu Leu Tyr Ser Ser Asn Asn Lys Asn Tyr
1 5 10

<210> SEQ ID NO 223
<211> LENGTH: 9
<212> TYPE: PRT
<213> ORGANISM: Homo sapiens

<400> SEQUENCE: 223

Gln Gln Phe Tyr Thr Ala Pro Leu Thr
1 5

<210> SEQ ID NO 224
<211> LENGTH: 8
<212> TYPE: PRT
<213> ORGANISM: Homo sapiens

<400> SEQUENCE: 224

Gly Leu Thr Leu Ser Asp Tyr Tyr
1 5

<210> SEQ ID NO 225
<211> LENGTH: 8
<212> TYPE: PRT
<213> ORGANISM: Homo sapiens

<400> SEQUENCE: 225

Ile Ser His Asp Gly Ser Thr Ile
1 5

<210> SEQ ID NO 226
<211> LENGTH: 15
<212> TYPE: PRT
<213> ORGANISM: Homo sapiens

<400> SEQUENCE: 226

Ala Ser Gly Ala Ala Val Pro Tyr Phe Tyr Tyr Gly Val Asp Val
1 5 10 15

<210> SEQ ID NO 227
<211> LENGTH: 6
<212> TYPE: PRT
<213> ORGANISM: Homo sapiens

<400> SEQUENCE: 227

Lys Leu Gly Asp Ala Tyr
1 5

<210> SEQ ID NO 228
<211> LENGTH: 10
<212> TYPE: PRT
<213> ORGANISM: Homo sapiens

<400> SEQUENCE: 228

Gln Ala Trp Gly Ser Ser Pro Ala Lys Val
1 5 10

<210> SEQ ID NO 229
<211> LENGTH: 8
<212> TYPE: PRT
<213> ORGANISM: Homo sapiens

<400> SEQUENCE: 229

Gly Phe Thr Phe Ser Ser Tyr Asp
1 5

<210> SEQ ID NO 230
<211> LENGTH: 7
<212> TYPE: PRT
<213> ORGANISM: Homo sapiens

<400> SEQUENCE: 230

Ile Gly Ala Ala Thr Asp Thr
1 5

<210> SEQ ID NO 231
<211> LENGTH: 20
<212> TYPE: PRT
<213> ORGANISM: Homo sapiens

<400> SEQUENCE: 231

Ala Arg Ala Val His Tyr Tyr Asp Ser Ser Gly His Tyr Ser Gly Tyr
1 5 10 15

Tyr Phe Asp Tyr
20

<210> SEQ ID NO 232
<211> LENGTH: 8
<212> TYPE: PRT
<213> ORGANISM: Homo sapiens

<400> SEQUENCE: 232

Ser Ser Asn Ile Gly Ser Asn Thr
1 5

<210> SEQ ID NO 233
<211> LENGTH: 11
<212> TYPE: PRT
<213> ORGANISM: Homo sapiens

<400> SEQUENCE: 233

Ala Thr Trp Asp Ala Ser Leu Lys Gly Val Val
1 5 10

<210> SEQ ID NO 234
<211> LENGTH: 8
<212> TYPE: PRT
<213> ORGANISM: Homo sapiens

<400> SEQUENCE: 234

Gly Phe Thr Phe Ser Asn Ala Trp
1 5

<210> SEQ ID NO 235
<211> LENGTH: 10
<212> TYPE: PRT
<213> ORGANISM: Homo sapiens

<400> SEQUENCE: 235

Ile Arg Ser Lys Thr Asp Gly Gly Thr Ala
1 5 10

<210> SEQ ID NO 236
<211> LENGTH: 8
<212> TYPE: PRT
<213> ORGANISM: Homo sapiens

<400> SEQUENCE: 236

Thr Thr Gln Asn Ala Phe Glu Ser
1 5

<210> SEQ ID NO 237
<211> LENGTH: 6
<212> TYPE: PRT
<213> ORGANISM: Homo sapiens

<400> SEQUENCE: 237

Asn Ile Gly Ser Lys Ser
1 5

<210> SEQ ID NO 238
<211> LENGTH: 11
<212> TYPE: PRT
<213> ORGANISM: Homo sapiens

<400> SEQUENCE: 238

Gln Val Trp Asp Ser Ser Ser Asp His Tyr Val
1 5 10

<210> SEQ ID NO 239
<211> LENGTH: 8
<212> TYPE: PRT
<213> ORGANISM: Homo sapiens

<400> SEQUENCE: 239

Gly Phe Thr Phe Ser Asn Ala Tyr
1 5

<210> SEQ ID NO 240
<211> LENGTH: 10
<212> TYPE: PRT
<213> ORGANISM: Homo sapiens

<400> SEQUENCE: 240

Ile Lys Ser Ile Thr Asp Gly Gly Thr Ile
1 5 10

<210> SEQ ID NO 241
<211> LENGTH: 13
<212> TYPE: PRT
<213> ORGANISM: Homo sapiens

<400> SEQUENCE: 241

His Thr Leu Ser Thr Thr His Tyr Tyr Gly Met Asp Val
1 5 10

<210> SEQ ID NO 242
<211> LENGTH: 7
<212> TYPE: PRT
<213> ORGANISM: Homo sapiens

<400> SEQUENCE: 242

Gln Ser Val Thr Ser Asn Tyr
1 5

<210> SEQ ID NO 243
<211> LENGTH: 9
<212> TYPE: PRT
<213> ORGANISM: Homo sapiens

<400> SEQUENCE: 243

Gln Gln Tyr Ile Asn Ser Pro Leu Thr 1 5

<210> SEQ ID NO 244
<211> LENGTH: 8
<212> TYPE: PRT
<213> ORGANISM: Homo sapiens

<400> SEQUENCE: 244

Gly Phe Thr Phe Ser Asn Thr Tyr
1 5

<210> SEQ ID NO 245
<211> LENGTH: 10
<212> TYPE: PRT
<213> ORGANISM: Homo sapiens

<400> SEQUENCE: 245

Ile Gln Arg Lys Thr Asp Gly Gly Thr Ala
1 5 10

<210> SEQ ID NO 246
<211> LENGTH: 8
<212> TYPE: PRT
<213> ORGANISM: Homo sapiens

<400> SEQUENCE: 246

Ala Ala His Asn Arg Ala Ala Tyr
1 5

<210> SEQ ID NO 247
<211> LENGTH: 6
<212> TYPE: PRT
<213> ORGANISM: Homo sapiens

<400> SEQUENCE: 247

Gln Ser Ile Ser Asn Trp
1 5

<210> SEQ ID NO 248
<211> LENGTH: 9
<212> TYPE: PRT
<213> ORGANISM: Homo sapiens

<400> SEQUENCE: 248

Gln Gln Tyr Tyr Ser Tyr Pro Leu Thr
1 5

<210> SEQ ID NO 249
<211> LENGTH: 8
<212> TYPE: PRT
<213> ORGANISM: Homo sapiens

<400> SEQUENCE: 249

Gly Leu Thr Phe Ser Thr His Ser
1 5

<210> SEQ ID NO 250
<211> LENGTH: 8
<212> TYPE: PRT
<213> ORGANISM: Homo sapiens

<400> SEQUENCE: 250

Ile Ser Gly Ser Ser Asp Tyr Ile
1 5

<210> SEQ ID NO 251
<211> LENGTH: 14
<212> TYPE: PRT
<213> ORGANISM: Homo sapiens

<400> SEQUENCE: 251

Ala Arg Ala Arg Pro Pro Gly Thr Ala Phe Gly Phe Asp His
1               5                   10

<210> SEQ ID NO 252
<211> LENGTH: 9
<212> TYPE: PRT
<213> ORGANISM: Homo sapiens

<400> SEQUENCE: 252

Ser Ser Asn Ile Gly Ala Gly Tyr Asp
1               5

<210> SEQ ID NO 253
<211> LENGTH: 11
<212> TYPE: PRT
<213> ORGANISM: Homo sapiens

<400> SEQUENCE: 253

Gln Ser Tyr Asp Ser Ser Leu Ser Gly Ala Leu
1               5                   10

<210> SEQ ID NO 254
<211> LENGTH: 8
<212> TYPE: PRT
<213> ORGANISM: Homo sapiens

<400> SEQUENCE: 254

Gly Phe Thr Phe Ser Ser Tyr Val
1               5

<210> SEQ ID NO 255
<211> LENGTH: 8
<212> TYPE: PRT
<213> ORGANISM: Homo sapiens

<400> SEQUENCE: 255

Val Ser Ser Ser Ser Tyr Ser Ile
1               5

<210> SEQ ID NO 256
<211> LENGTH: 8
<212> TYPE: PRT
<213> ORGANISM: Homo sapiens

<400> SEQUENCE: 256

Val Arg Thr Phe Tyr Phe Asp Tyr
1               5

<210> SEQ ID NO 257
<211> LENGTH: 6
<212> TYPE: PRT
<213> ORGANISM: Homo sapiens

<400> SEQUENCE: 257

Gln Ser Val Arg Thr Asn
1               5

<210> SEQ ID NO 258

<211> LENGTH: 10
<212> TYPE: PRT
<213> ORGANISM: Homo sapiens

<400> SEQUENCE: 258

Gln Gln Tyr Asp Ile Trp Pro Pro Arg Thr
1 5 10

<210> SEQ ID NO 259
<211> LENGTH: 8
<212> TYPE: PRT
<213> ORGANISM: Homo sapiens

<400> SEQUENCE: 259

Gly Phe Thr Phe Ser Ser Phe Ser
1 5

<210> SEQ ID NO 260
<211> LENGTH: 8
<212> TYPE: PRT
<213> ORGANISM: Homo sapiens

<400> SEQUENCE: 260

Ile Ser Ser Ser Ser Arg Tyr Ile
1 5

<210> SEQ ID NO 261
<211> LENGTH: 14
<212> TYPE: PRT
<213> ORGANISM: Homo sapiens
<220> FEATURE:
<221> NAME/KEY: MOD_RES
<222> LOCATION: (11)..(12)
<223> OTHER INFORMATION: Any amino acid

<400> SEQUENCE: 261

Val Arg Asp Met Thr Thr Val Thr Thr Cys Xaa Xaa Gln His
1 5 10

<210> SEQ ID NO 262
<211> LENGTH: 8
<212> TYPE: PRT
<213> ORGANISM: Homo sapiens

<400> SEQUENCE: 262

Ser Ser Asn Ile Gly Ser His Thr
1 5

<210> SEQ ID NO 263
<211> LENGTH: 11
<212> TYPE: PRT
<213> ORGANISM: Homo sapiens

<400> SEQUENCE: 263

Ala Ala Trp Asp Asp Ser Leu Asn Gly Leu Val
1 5 10

<210> SEQ ID NO 264
<211> LENGTH: 8
<212> TYPE: PRT
<213> ORGANISM: Homo sapiens

<400> SEQUENCE: 264

Gly Phe Thr Phe Ser Ser Phe Ser
1 5

<210> SEQ ID NO 265
<211> LENGTH: 8
<212> TYPE: PRT
<213> ORGANISM: Homo sapiens

<400> SEQUENCE: 265

Ile Ser Ser Ser Ser Arg Tyr Ile
1 5

<210> SEQ ID NO 266
<211> LENGTH: 14
<212> TYPE: PRT
<213> ORGANISM: Homo sapiens

<400> SEQUENCE: 266

Val Arg Asp Met Thr Thr Val Thr Thr Cys Tyr Leu Gln His
1 5 10

<210> SEQ ID NO 267
<211> LENGTH: 8
<212> TYPE: PRT
<213> ORGANISM: Homo sapiens

<400> SEQUENCE: 267

Ser Ser Asn Ile Gly Ser His Thr
1 5

<210> SEQ ID NO 268
<211> LENGTH: 11
<212> TYPE: PRT
<213> ORGANISM: Homo sapiens

<400> SEQUENCE: 268

Ala Ala Trp Asp Asp Ser Leu Asn Gly Leu Val
1 5 10

<210> SEQ ID NO 269
<211> LENGTH: 8
<212> TYPE: PRT
<213> ORGANISM: Homo sapiens

<400> SEQUENCE: 269

Gly Phe Ser Phe Ser Ile Tyr Ser
1 5

<210> SEQ ID NO 270
<211> LENGTH: 8
<212> TYPE: PRT
<213> ORGANISM: Homo sapiens

<400> SEQUENCE: 270

Ile Gly Asn Arg Gly Asn Pro Lys
1 5

<210> SEQ ID NO 271
<211> LENGTH: 10
<212> TYPE: PRT
<213> ORGANISM: Homo sapiens

<400> SEQUENCE: 271

Ala Arg Gly Arg Thr Tyr Gly Asp Ser Asn
1 5 10

<210> SEQ ID NO 272

<211> LENGTH: 6
<212> TYPE: PRT
<213> ORGANISM: Homo sapiens

<400> SEQUENCE: 272

Arg Ser Ile Ser Ser Asn
1               5

<210> SEQ ID NO 273
<211> LENGTH: 8
<212> TYPE: PRT
<213> ORGANISM: Homo sapiens

<400> SEQUENCE: 273

Gln Gln Tyr Asp Asn Trp His Thr
1               5

<210> SEQ ID NO 274
<211> LENGTH: 8
<212> TYPE: PRT
<213> ORGANISM: Homo sapiens

<400> SEQUENCE: 274

Gly Phe Ser Phe Asn Ala Tyr Ser
1               5

<210> SEQ ID NO 275
<211> LENGTH: 8
<212> TYPE: PRT
<213> ORGANISM: Homo sapiens

<400> SEQUENCE: 275

Ile Ser Ser Ser Ser Ser Tyr Ile
1               5

<210> SEQ ID NO 276
<211> LENGTH: 16
<212> TYPE: PRT
<213> ORGANISM: Homo sapiens

<400> SEQUENCE: 276

Ala Arg Val Pro Ile Leu Leu Ala Gln Gly Val Pro Thr Phe Asp Leu
1               5                   10                  15

<210> SEQ ID NO 277
<211> LENGTH: 6
<212> TYPE: PRT
<213> ORGANISM: Homo sapiens

<400> SEQUENCE: 277

Gln Ser Val Asn Ser Asn
1               5

<210> SEQ ID NO 278
<211> LENGTH: 10
<212> TYPE: PRT
<213> ORGANISM: Homo sapiens

<400> SEQUENCE: 278

Gln Gln Tyr Ser Asp Trp Pro Arg Tyr Thr
1               5                   10

<210> SEQ ID NO 279
<211> LENGTH: 8
<212> TYPE: PRT

<213> ORGANISM: Homo sapiens

<400> SEQUENCE: 279

Gly Phe Thr Phe Thr Arg Tyr Thr
1 5

<210> SEQ ID NO 280
<211> LENGTH: 8
<212> TYPE: PRT
<213> ORGANISM: Homo sapiens

<400> SEQUENCE: 280

Val Ser Gly Ser Gly Ser Ser Thr
1 5

<210> SEQ ID NO 281
<211> LENGTH: 15
<212> TYPE: PRT
<213> ORGANISM: Homo sapiens

<400> SEQUENCE: 281

Ala Lys Ala Ala Ile Leu Gly Asn Tyr Asn Tyr Tyr Met Asp Val
1 5 10 15

<210> SEQ ID NO 282
<211> LENGTH: 6
<212> TYPE: PRT
<213> ORGANISM: Homo sapiens

<400> SEQUENCE: 282

Asn Ile Ala Ser Lys Ser
1 5

<210> SEQ ID NO 283
<211> LENGTH: 12
<212> TYPE: PRT
<213> ORGANISM: Homo sapiens

<400> SEQUENCE: 283

Gln Val Trp Asp Ser Ser Ala Asp His Leu Val Val
1 5 10

<210> SEQ ID NO 284
<211> LENGTH: 8
<212> TYPE: PRT
<213> ORGANISM: Homo sapiens

<400> SEQUENCE: 284

Glu Phe Arg Phe Gly Ser Tyr Ala
1 5

<210> SEQ ID NO 285
<211> LENGTH: 8
<212> TYPE: PRT
<213> ORGANISM: Homo sapiens

<400> SEQUENCE: 285

Ile Ile Ala Thr Gly Ala Lys Thr
1 5

<210> SEQ ID NO 286
<211> LENGTH: 16
<212> TYPE: PRT
<213> ORGANISM: Homo sapiens

<400> SEQUENCE: 286

Val Lys Asp Ala Ile Tyr Met Ser Asn Trp Pro Trp Tyr Phe Asp Tyr
1 5 10 15

<210> SEQ ID NO 287
<211> LENGTH: 6
<212> TYPE: PRT
<213> ORGANISM: Homo sapiens

<400> SEQUENCE: 287

Asn Ile Gly Ser Lys Ser
1 5

<210> SEQ ID NO 288
<211> LENGTH: 8
<212> TYPE: PRT
<213> ORGANISM: Homo sapiens

<400> SEQUENCE: 288

Gly Phe Thr Phe Thr Asn Tyr Ala
1 5

<210> SEQ ID NO 289
<211> LENGTH: 8
<212> TYPE: PRT
<213> ORGANISM: Homo sapiens

<400> SEQUENCE: 289

Ile Ser Gly Ser Gly Gly Ser Thr
1 5

<210> SEQ ID NO 290
<211> LENGTH: 16
<212> TYPE: PRT
<213> ORGANISM: Homo sapiens

<400> SEQUENCE: 290

Ala Lys Asp Pro Ile Tyr Ser Ser Ser Trp Pro Tyr Tyr Phe Asp Tyr
1 5 10 15

<210> SEQ ID NO 291
<211> LENGTH: 6
<212> TYPE: PRT
<213> ORGANISM: Homo sapiens

<400> SEQUENCE: 291

Asn Ile Gly Ser Arg Gly
1 5

<210> SEQ ID NO 292
<211> LENGTH: 13
<212> TYPE: PRT
<213> ORGANISM: Homo sapiens

<400> SEQUENCE: 292

Gln Val Trp Asp Ser Ser Ser Asp His Pro Glu Val Val
1 5 10

<210> SEQ ID NO 293
<211> LENGTH: 8
<212> TYPE: PRT
<213> ORGANISM: Homo sapiens

<400> SEQUENCE: 293

Gly Phe Arg Phe Ser Ser Tyr Ala
1 5

<210> SEQ ID NO 294
<211> LENGTH: 8
<212> TYPE: PRT
<213> ORGANISM: Homo sapiens

<400> SEQUENCE: 294

Ile Ser Gly Ser Gly Gly Ser Thr
1 5

<210> SEQ ID NO 295
<211> LENGTH: 16
<212> TYPE: PRT
<213> ORGANISM: Homo sapiens

<400> SEQUENCE: 295

Ala Lys Asp Pro Ile Tyr Thr Ser Arg Trp Pro Tyr Tyr Phe Asp Tyr
1 5 10 15

<210> SEQ ID NO 296
<211> LENGTH: 6
<212> TYPE: PRT
<213> ORGANISM: Homo sapiens

<400> SEQUENCE: 296

Gln Ser Ile Ser Ser Tyr
1 5

<210> SEQ ID NO 297
<211> LENGTH: 8
<212> TYPE: PRT
<213> ORGANISM: Homo sapiens

<400> SEQUENCE: 297

Gln Gln Ser Tyr Ser Leu Tyr Ser
1 5

<210> SEQ ID NO 298
<211> LENGTH: 6
<212> TYPE: PRT
<213> ORGANISM: Homo sapiens

<400> SEQUENCE: 298

Asn Ile Gly Ser Lys Ser
1 5

<210> SEQ ID NO 299
<211> LENGTH: 13
<212> TYPE: PRT
<213> ORGANISM: Homo sapiens

<400> SEQUENCE: 299

Gln Val Trp His Ser Ser Ser Asp His Ser Glu Val Ile
1 5 10

<210> SEQ ID NO 300
<211> LENGTH: 8
<212> TYPE: PRT
<213> ORGANISM: Homo sapiens

<400> SEQUENCE: 300

Gly Phe Arg Phe Ser Ser Tyr Ala
1 5

<210> SEQ ID NO 301
<211> LENGTH: 8
<212> TYPE: PRT
<213> ORGANISM: Homo sapiens

<400> SEQUENCE: 301

Ile Ser Gly Arg Asp Ala Ser Thr
1 5

<210> SEQ ID NO 302
<211> LENGTH: 16
<212> TYPE: PRT
<213> ORGANISM: Homo sapiens

<400> SEQUENCE: 302

Ala Lys Asp Gly Val Leu Gly Ser Tyr His Gln Tyr Tyr Phe Gln Tyr
1 5 10 15

<210> SEQ ID NO 303
<211> LENGTH: 6
<212> TYPE: PRT
<213> ORGANISM: Homo sapiens

<400> SEQUENCE: 303

Asn Ile Gly Ser Lys Ser
1 5

<210> SEQ ID NO 304
<211> LENGTH: 13
<212> TYPE: PRT
<213> ORGANISM: Homo sapiens

<400> SEQUENCE: 304

Gln Val Trp Asp Asn Ser Ser Asp His Pro Gly Val Val
1 5 10

<210> SEQ ID NO 305
<211> LENGTH: 8
<212> TYPE: PRT
<213> ORGANISM: Homo sapiens

<400> SEQUENCE: 305

Gly Phe Thr Phe Ser Ser Tyr Ala
1 5

<210> SEQ ID NO 306
<211> LENGTH: 8
<212> TYPE: PRT
<213> ORGANISM: Homo sapiens

<400> SEQUENCE: 306

Ile Ser Gly Ser Gly Gly Ser Thr
1 5

<210> SEQ ID NO 307
<211> LENGTH: 18
<212> TYPE: PRT
<213> ORGANISM: Homo sapiens

<400> SEQUENCE: 307

Ala Lys Gly Ser Arg Asn Gly Pro Tyr Ile Val Ala Thr Leu His Phe
1 5 10 15

Asp Tyr

<210> SEQ ID NO 308
<211> LENGTH: 6
<212> TYPE: PRT
<213> ORGANISM: Homo sapiens

<400> SEQUENCE: 308

Gln Ser Val Ser Ser Asn
1 5

<210> SEQ ID NO 309
<211> LENGTH: 9
<212> TYPE: PRT
<213> ORGANISM: Homo sapiens

<400> SEQUENCE: 309

Gln His Tyr Asn His Trp Ser Leu Thr
1 5

<210> SEQ ID NO 310
<211> LENGTH: 8
<212> TYPE: PRT
<213> ORGANISM: Homo sapiens

<400> SEQUENCE: 310

Gly Phe Thr Phe Asn Asn Tyr Ala
1 5

<210> SEQ ID NO 311
<211> LENGTH: 8
<212> TYPE: PRT
<213> ORGANISM: Homo sapiens

<400> SEQUENCE: 311

Val Ser Gly Asn Gly Gly Ser Thr
1 5

<210> SEQ ID NO 312
<211> LENGTH: 13
<212> TYPE: PRT
<213> ORGANISM: Homo sapiens

<400> SEQUENCE: 312

Val Leu Ser Ser Ser Trp Met Asp Asn Pro Phe Asp Phe
1 5 10

<210> SEQ ID NO 313
<211> LENGTH: 9
<212> TYPE: PRT
<213> ORGANISM: Homo sapiens

<400> SEQUENCE: 313

Ser Gly Ile Asn Val Gly Thr Tyr Arg
1 5

<210> SEQ ID NO 314
<211> LENGTH: 7
<212> TYPE: PRT
<213> ORGANISM: Homo sapiens

<400> SEQUENCE: 314

Tyr Lys Ser Asp Ser Asp Lys
1 5

<210> SEQ ID NO 315
<211> LENGTH: 9
<212> TYPE: PRT
<213> ORGANISM: Homo sapiens

<400> SEQUENCE: 315

Met Ile Trp His Ser Ser Ala Trp Val
1 5

<210> SEQ ID NO 316
<211> LENGTH: 8
<212> TYPE: PRT
<213> ORGANISM: Homo sapiens

<400> SEQUENCE: 316

Gly Phe Thr Phe Ser Ser Tyr Ala
1 5

<210> SEQ ID NO 317
<211> LENGTH: 8
<212> TYPE: PRT
<213> ORGANISM: Homo sapiens

<400> SEQUENCE: 317

Ala Ser Ala Ser Gly Arg Asn Thr
1 5

<210> SEQ ID NO 318
<211> LENGTH: 12
<212> TYPE: PRT
<213> ORGANISM: Homo sapiens

<400> SEQUENCE: 318

Ala Gly Phe Pro Ser Gly Thr His Phe Phe Asp Tyr
1 5 10

<210> SEQ ID NO 319
<211> LENGTH: 6
<212> TYPE: PRT
<213> ORGANISM: Homo sapiens

<400> SEQUENCE: 319

Gln Ser Val Ser Asn His
1 5

<210> SEQ ID NO 320
<211> LENGTH: 8
<212> TYPE: PRT
<213> ORGANISM: Homo sapiens

<400> SEQUENCE: 320

Gln Gln Arg Ser Asn Trp Trp Thr
1 5

<210> SEQ ID NO 321
<211> LENGTH: 8
<212> TYPE: PRT
<213> ORGANISM: Homo sapiens

<400> SEQUENCE: 321

Gly Phe Thr Phe Ser Ser Tyr Ala
1 5

<210> SEQ ID NO 322
<211> LENGTH: 8

<212> TYPE: PRT
<213> ORGANISM: Homo sapiens

<400> SEQUENCE: 322

Ala Ser Ala Ser Gly Arg Asn Thr
1 5

<210> SEQ ID NO 323
<211> LENGTH: 12
<212> TYPE: PRT
<213> ORGANISM: Homo sapiens

<400> SEQUENCE: 323

Ala Gly Phe Pro Ser Gly Thr His Phe Phe Asp Tyr
1 5 10

<210> SEQ ID NO 324
<211> LENGTH: 7
<212> TYPE: PRT
<213> ORGANISM: Homo sapiens

<400> SEQUENCE: 324

Gln Ser Val Ser Asn Ser Tyr
1 5

<210> SEQ ID NO 325
<211> LENGTH: 9
<212> TYPE: PRT
<213> ORGANISM: Homo sapiens

<400> SEQUENCE: 325

Gln Gln Phe Gly Ser Ser Pro Leu Thr
1 5

<210> SEQ ID NO 326
<211> LENGTH: 9
<212> TYPE: PRT
<213> ORGANISM: Homo sapiens

<400> SEQUENCE: 326

Ser Ser Asp Ile Gly Gly Tyr Asn Tyr
1 5

<210> SEQ ID NO 327
<211> LENGTH: 10
<212> TYPE: PRT
<213> ORGANISM: Homo sapiens

<400> SEQUENCE: 327

Asn Ser Tyr Ala Gly Asn Asn Asn Phe Val
1 5 10

<210> SEQ ID NO 328
<211> LENGTH: 8
<212> TYPE: PRT
<213> ORGANISM: Homo sapiens

<400> SEQUENCE: 328

Glu Phe Thr Phe Ser Ser Tyr Ala
1 5

<210> SEQ ID NO 329
<211> LENGTH: 8
<212> TYPE: PRT
<213> ORGANISM: Homo sapiens

<400> SEQUENCE: 329

Ile Ser Gly Ser Gly Asp Thr Thr
1 5

<210> SEQ ID NO 330
<211> LENGTH: 27
<212> TYPE: PRT
<213> ORGANISM: Homo sapiens

<400> SEQUENCE: 330

Ala Arg Pro Asp Ala Leu His Cys Ser Ser Ile Thr Ser Cys Ser Leu
1 5 10 15

Tyr Gly Leu Ala Tyr Tyr Tyr Gly Met Asp Val
20 25

<210> SEQ ID NO 331
<211> LENGTH: 8
<212> TYPE: PRT
<213> ORGANISM: Homo sapiens

<400> SEQUENCE: 331

Ser Ser Asn Ile Gly Thr Asn Thr
1 5

<210> SEQ ID NO 332
<211> LENGTH: 11
<212> TYPE: PRT
<213> ORGANISM: Homo sapiens

<400> SEQUENCE: 332

Ala Ala Trp Asp Asp Arg Leu Ile Gly Trp Val
1 5 10

<210> SEQ ID NO 333
<211> LENGTH: 8
<212> TYPE: PRT
<213> ORGANISM: Homo sapiens

<400> SEQUENCE: 333

Gly Phe Thr Phe Ser Ser His Gly
1 5

<210> SEQ ID NO 334
<211> LENGTH: 8
<212> TYPE: PRT
<213> ORGANISM: Homo sapiens

<400> SEQUENCE: 334

Ile Ser Gly Asn Gly Gly Phe Thr
1 5

<210> SEQ ID NO 335
<211> LENGTH: 14
<212> TYPE: PRT
<213> ORGANISM: Homo sapiens

<400> SEQUENCE: 335

Ala Lys Arg Met Val Glu Ala Thr Asn Arg Tyr Phe Asp Tyr
1 5 10

<210> SEQ ID NO 336
<211> LENGTH: 7
<212> TYPE: PRT

<213> ORGANISM: Homo sapiens

<400> SEQUENCE: 336

Gln Ser Val Ser Asn Ser Tyr
1               5

<210> SEQ ID NO 337
<211> LENGTH: 10
<212> TYPE: PRT
<213> ORGANISM: Homo sapiens

<400> SEQUENCE: 337

Gln Gln Tyr Gly Ser Ser Pro Pro Tyr Thr
1               5                   10

<210> SEQ ID NO 338
<211> LENGTH: 8
<212> TYPE: PRT
<213> ORGANISM: Homo sapiens

<400> SEQUENCE: 338

Gly Phe Thr Phe Ile Asn Tyr Ala
1               5

<210> SEQ ID NO 339
<211> LENGTH: 8
<212> TYPE: PRT
<213> ORGANISM: Homo sapiens

<400> SEQUENCE: 339

Ile Ser Ala Asn Gly Ile Tyr Thr
1               5

<210> SEQ ID NO 340
<211> LENGTH: 13
<212> TYPE: PRT
<213> ORGANISM: Homo sapiens

<400> SEQUENCE: 340

Ala Arg Asp Ser Ser Glu Trp Val Leu Gly Ile Asp Phe
1               5                   10

<210> SEQ ID NO 341
<211> LENGTH: 9
<212> TYPE: PRT
<213> ORGANISM: Homo sapiens

<400> SEQUENCE: 341

Ser Ser Asp Val Gly Gly Tyr Asn Tyr
1               5

<210> SEQ ID NO 342
<211> LENGTH: 10
<212> TYPE: PRT
<213> ORGANISM: Homo sapiens

<400> SEQUENCE: 342

Cys Ser Tyr Ala Gly Ser Tyr Thr Val Val
1               5                   10

<210> SEQ ID NO 343
<211> LENGTH: 8
<212> TYPE: PRT
<213> ORGANISM: Homo sapiens

<400> SEQUENCE: 343

Gly Phe Thr Phe Ser Ser Tyr Ala
1               5

<210> SEQ ID NO 344
<211> LENGTH: 8
<212> TYPE: PRT
<213> ORGANISM: Homo sapiens

<400> SEQUENCE: 344

Ile Thr Gly Ser Gly Gly Ser Thr
1               5

<210> SEQ ID NO 345
<211> LENGTH: 16
<212> TYPE: PRT
<213> ORGANISM: Homo sapiens

<400> SEQUENCE: 345

Ala Lys Asp Ala Val Arg Ser Ala Asn His Ala Trp Tyr Phe Asp Phe
1               5                   10                  15

<210> SEQ ID NO 346
<211> LENGTH: 6
<212> TYPE: PRT
<213> ORGANISM: Homo sapiens

<400> SEQUENCE: 346

Asn Ile Gly Ile Lys Ser
1               5

<210> SEQ ID NO 347
<211> LENGTH: 13
<212> TYPE: PRT
<213> ORGANISM: Homo sapiens

<400> SEQUENCE: 347

Gln Val Trp Asp Ser Asn Ser Asp His Pro Lys Val Val
1               5                   10

<210> SEQ ID NO 348
<211> LENGTH: 8
<212> TYPE: PRT
<213> ORGANISM: Homo sapiens

<400> SEQUENCE: 348

Gly Phe Thr Phe Ser Ser Thr Ala
1               5

<210> SEQ ID NO 349
<211> LENGTH: 8
<212> TYPE: PRT
<213> ORGANISM: Homo sapiens

<400> SEQUENCE: 349

Ile Ser Ser Asn Gly Ala Gly Thr
1               5

<210> SEQ ID NO 350
<211> LENGTH: 9
<212> TYPE: PRT
<213> ORGANISM: Homo sapiens

<400> SEQUENCE: 350

Ala Lys Gly Tyr Gly Leu Phe Asp Ser
1               5

<210> SEQ ID NO 351
<211> LENGTH: 6
<212> TYPE: PRT
<213> ORGANISM: Homo sapiens

<400> SEQUENCE: 351

Gln Ser Leu Val Thr Asn
1               5

<210> SEQ ID NO 352
<211> LENGTH: 10
<212> TYPE: PRT
<213> ORGANISM: Homo sapiens

<400> SEQUENCE: 352

Gln Gln Tyr Ile Asn Trp Pro Pro Trp Ser
1               5                   10

<210> SEQ ID NO 353
<211> LENGTH: 8
<212> TYPE: PRT
<213> ORGANISM: Homo sapiens

<400> SEQUENCE: 353

Gly Phe Thr Phe Ser Ser Tyr Ala
1               5

<210> SEQ ID NO 354
<211> LENGTH: 8
<212> TYPE: PRT
<213> ORGANISM: Homo sapiens

<400> SEQUENCE: 354

Leu Thr Ala Thr Gly Gly Asn Thr
1               5

<210> SEQ ID NO 355
<211> LENGTH: 16
<212> TYPE: PRT
<213> ORGANISM: Homo sapiens

<400> SEQUENCE: 355

Ala Lys Asp Ala Ile Arg Asn Ser Asn His Ala Trp Tyr Phe Asp Val
1               5                   10                  15

<210> SEQ ID NO 356
<211> LENGTH: 6
<212> TYPE: PRT
<213> ORGANISM: Homo sapiens

<400> SEQUENCE: 356

Asn Ile Gly Ser Lys Ser
1               5

<210> SEQ ID NO 357
<211> LENGTH: 10
<212> TYPE: PRT
<213> ORGANISM: Homo sapiens

<400> SEQUENCE: 357

Gln Val Trp Asp Pro Thr Ser Asp Gln Val
1               5                   10

<210> SEQ ID NO 358
<211> LENGTH: 8
<212> TYPE: PRT
<213> ORGANISM: Homo sapiens

<400> SEQUENCE: 358

Gly Phe Thr Phe Ser Ser Tyr Gly
1               5

<210> SEQ ID NO 359
<211> LENGTH: 8
<212> TYPE: PRT
<213> ORGANISM: Homo sapiens

<400> SEQUENCE: 359

Ile Ser Gly Arg Gly Asp Glu Thr
1               5

<210> SEQ ID NO 360
<211> LENGTH: 13
<212> TYPE: PRT
<213> ORGANISM: Homo sapiens

<400> SEQUENCE: 360

Ala Lys Ser Arg Val Thr Asn Ser Gly Ser Ile Asp His
1               5                   10

<210> SEQ ID NO 361
<211> LENGTH: 6
<212> TYPE: PRT
<213> ORGANISM: Homo sapiens

<400> SEQUENCE: 361

Gln Thr Ile Gly Thr Tyr
1               5

<210> SEQ ID NO 362
<211> LENGTH: 9
<212> TYPE: PRT
<213> ORGANISM: Homo sapiens

<400> SEQUENCE: 362

Gln Gln Ser Tyr Ser Thr Ser Ile Thr
1               5

<210> SEQ ID NO 363
<211> LENGTH: 8
<212> TYPE: PRT
<213> ORGANISM: Homo sapiens

<400> SEQUENCE: 363

Gly Phe Arg Phe Asn Asn Tyr Ala
1               5

<210> SEQ ID NO 364
<211> LENGTH: 8
<212> TYPE: PRT
<213> ORGANISM: Homo sapiens

<400> SEQUENCE: 364

Ile Ser Gly Gly Asp Gly Tyr Thr
1               5

<210> SEQ ID NO 365
<211> LENGTH: 16
<212> TYPE: PRT
<213> ORGANISM: Homo sapiens

<400> SEQUENCE: 365

Ala Lys Asp Ala Ile Leu Ser Ala Asn His Pro Trp Tyr Phe Asp Phe
1 5 10 15

<210> SEQ ID NO 366
<211> LENGTH: 12
<212> TYPE: PRT
<213> ORGANISM: Homo sapiens

<400> SEQUENCE: 366

Gln Ser Val Leu Tyr Ser Ser Asn Asn Lys Asn Tyr
1 5 10

<210> SEQ ID NO 367
<211> LENGTH: 9
<212> TYPE: PRT
<213> ORGANISM: Homo sapiens

<400> SEQUENCE: 367

Gln Gln Tyr Tyr Ser Thr Pro Leu Thr
1 5

<210> SEQ ID NO 368
<211> LENGTH: 6
<212> TYPE: PRT
<213> ORGANISM: Homo sapiens

<400> SEQUENCE: 368

Asn Ile Gly Thr Asn Ser
1 5

<210> SEQ ID NO 369
<211> LENGTH: 13
<212> TYPE: PRT
<213> ORGANISM: Homo sapiens

<400> SEQUENCE: 369

Gln Val Trp Asp Ser Ser Ser Asp His Pro Lys Val Val
1 5 10

<210> SEQ ID NO 370
<211> LENGTH: 8
<212> TYPE: PRT
<213> ORGANISM: Homo sapiens

<400> SEQUENCE: 370

Gly Phe Thr Phe Ser Ser Tyr Ala
1 5

<210> SEQ ID NO 371
<211> LENGTH: 8
<212> TYPE: PRT
<213> ORGANISM: Homo sapiens

<400> SEQUENCE: 371

Ile Val Asn Ser Gly Gly Ser Thr
1 5

<210> SEQ ID NO 372
<211> LENGTH: 16

<212> TYPE: PRT
<213> ORGANISM: Homo sapiens

<400> SEQUENCE: 372

Ala Lys Asp Ala Ile Arg Ser Ser Asn His Pro Trp Tyr Phe His Val
1 5 10 15

<210> SEQ ID NO 373
<211> LENGTH: 6
<212> TYPE: PRT
<213> ORGANISM: Homo sapiens

<400> SEQUENCE: 373

Asn Ile Gly Ser Glu Ser
1 5

<210> SEQ ID NO 374
<211> LENGTH: 13
<212> TYPE: PRT
<213> ORGANISM: Homo sapiens

<400> SEQUENCE: 374

Gln Val Trp Asp Gly Ser Ser Asp His Pro Lys Val Leu
1 5 10

<210> SEQ ID NO 375
<211> LENGTH: 8
<212> TYPE: PRT
<213> ORGANISM: Homo sapiens

<400> SEQUENCE: 375

Gly Phe Arg Phe Asn Asn Tyr Ala
1 5

<210> SEQ ID NO 376
<211> LENGTH: 8
<212> TYPE: PRT
<213> ORGANISM: Homo sapiens

<400> SEQUENCE: 376

Ile Thr Gly Gly Glu Gly Tyr Thr
1 5

<210> SEQ ID NO 377
<211> LENGTH: 16
<212> TYPE: PRT
<213> ORGANISM: Homo sapiens

<400> SEQUENCE: 377

Ala Lys Asp Ala Ile Leu Ser Ala Asn His Pro Trp Tyr Phe Asp Phe
1 5 10 15

<210> SEQ ID NO 378
<211> LENGTH: 6
<212> TYPE: PRT
<213> ORGANISM: Homo sapiens

<400> SEQUENCE: 378

Asn Ile Gly Thr Asn Ser
1 5

<210> SEQ ID NO 379
<211> LENGTH: 13
<212> TYPE: PRT
<213> ORGANISM: Homo sapiens

<400> SEQUENCE: 379

Gln Val Trp Asp Arg Ser Ser Asp Gln Ser Lys Val Val
1 5 10

<210> SEQ ID NO 380
<211> LENGTH: 8
<212> TYPE: PRT
<213> ORGANISM: Homo sapiens

<400> SEQUENCE: 380

Gly Phe Thr Phe Ser Thr His Ala
1 5

<210> SEQ ID NO 381
<211> LENGTH: 8
<212> TYPE: PRT
<213> ORGANISM: Homo sapiens

<400> SEQUENCE: 381

Ile Ser Gly Gly Ser Glu Trp Ser
1 5

<210> SEQ ID NO 382
<211> LENGTH: 9
<212> TYPE: PRT
<213> ORGANISM: Homo sapiens

<400> SEQUENCE: 382

Ala Lys Gly Tyr Gly Leu Phe Asp Phe
1 5

<210> SEQ ID NO 383
<211> LENGTH: 6
<212> TYPE: PRT
<213> ORGANISM: Homo sapiens

<400> SEQUENCE: 383

Gln Ser Val Ser Ser Asn
1 5

<210> SEQ ID NO 384
<211> LENGTH: 10
<212> TYPE: PRT
<213> ORGANISM: Homo sapiens

<400> SEQUENCE: 384

Gln Gln Tyr Ile Asn Arg Pro Pro Trp Thr
1 5 10

<210> SEQ ID NO 385
<211> LENGTH: 8
<212> TYPE: PRT
<213> ORGANISM: Homo sapiens

<400> SEQUENCE: 385

Gly Phe Thr Phe Ser Asn Tyr Ala
1 5

<210> SEQ ID NO 386
<211> LENGTH: 8
<212> TYPE: PRT
<213> ORGANISM: Homo sapiens

<400> SEQUENCE: 386

Ile Tyr Thr Gly Gly Ser Lys Thr
1 5

<210> SEQ ID NO 387
<211> LENGTH: 14
<212> TYPE: PRT
<213> ORGANISM: Homo sapiens

<400> SEQUENCE: 387

Ala Lys Val Leu Leu Gly Gly Trp Asn Gly Val Phe Asp His
1 5 10

<210> SEQ ID NO 388
<211> LENGTH: 6
<212> TYPE: PRT
<213> ORGANISM: Homo sapiens

<400> SEQUENCE: 388

Gln Ser Val Asp Ser Tyr
1 5

<210> SEQ ID NO 389
<211> LENGTH: 9
<212> TYPE: PRT
<213> ORGANISM: Homo sapiens

<400> SEQUENCE: 389

Gln Gln Arg Ser Thr Trp Pro Pro Ser
1 5

<210> SEQ ID NO 390
<211> LENGTH: 8
<212> TYPE: PRT
<213> ORGANISM: Homo sapiens

<400> SEQUENCE: 390

Gly Phe Arg Phe Asn Asn Tyr Gly
1 5

<210> SEQ ID NO 391
<211> LENGTH: 8
<212> TYPE: PRT
<213> ORGANISM: Homo sapiens

<400> SEQUENCE: 391

Phe Ser Gly Ser Gly Ser Asn Ile
1 5

<210> SEQ ID NO 392
<211> LENGTH: 16
<212> TYPE: PRT
<213> ORGANISM: Homo sapiens

<400> SEQUENCE: 392

Ala Lys Asp Gly Tyr Phe Gly Ser Gly Ser Leu Tyr Gly Ile Asp Val
1 5 10 15

<210> SEQ ID NO 393
<211> LENGTH: 6
<212> TYPE: PRT
<213> ORGANISM: Homo sapiens

<400> SEQUENCE: 393

Asn Ile Gly Ser Lys Ser 1 5

<210> SEQ ID NO 394
<211> LENGTH: 13
<212> TYPE: PRT
<213> ORGANISM: Homo sapiens

<400> SEQUENCE: 394

Gln Val Trp Asp Ser Asn His Asp His Pro Gly Val Val
1 5 10

<210> SEQ ID NO 395
<211> LENGTH: 8
<212> TYPE: PRT
<213> ORGANISM: Homo sapiens

<400> SEQUENCE: 395

Gly Phe Thr Phe Thr Ser Tyr Ala
1 5

<210> SEQ ID NO 396
<211> LENGTH: 8
<212> TYPE: PRT
<213> ORGANISM: Homo sapiens

<400> SEQUENCE: 396

Ile Ser Gly Ser Gly Gly Ser Thr
1 5

<210> SEQ ID NO 397
<211> LENGTH: 16
<212> TYPE: PRT
<213> ORGANISM: Homo sapiens

<400> SEQUENCE: 397

Ala Lys Asp Gly Tyr Tyr Gly Ser Gly Ser Leu Tyr Gly Met Asp Val
1 5 10 15

<210> SEQ ID NO 398
<211> LENGTH: 6
<212> TYPE: PRT
<213> ORGANISM: Homo sapiens

<400> SEQUENCE: 398

Asn Ile Gly Ser Lys Ser
1 5

<210> SEQ ID NO 399
<211> LENGTH: 13
<212> TYPE: PRT
<213> ORGANISM: Homo sapiens

<400> SEQUENCE: 399

Gln Val Trp Asp Ser Thr Ser Asp His Pro Gly Val Val
1 5 10

<210> SEQ ID NO 400
<211> LENGTH: 8
<212> TYPE: PRT
<213> ORGANISM: Homo sapiens

<400> SEQUENCE: 400

Gly Phe Thr Phe Ser Ser Tyr Ala
1 5

<210> SEQ ID NO 401
<211> LENGTH: 8
<212> TYPE: PRT
<213> ORGANISM: Homo sapiens

<400> SEQUENCE: 401

Phe Ser Gly Ser Gly Ser Ser Thr
1 5

<210> SEQ ID NO 402
<211> LENGTH: 17
<212> TYPE: PRT
<213> ORGANISM: Homo sapiens

<400> SEQUENCE: 402

Ala Lys Val Ile Gln Tyr Pro Arg Gly Phe Trp Phe Tyr Gly Met Asp
1 5 10 15

Val

<210> SEQ ID NO 403
<211> LENGTH: 8
<212> TYPE: PRT
<213> ORGANISM: Homo sapiens

<400> SEQUENCE: 403

Ser Ser Asn Ile Gly Asn Asn Tyr
1 5

<210> SEQ ID NO 404
<211> LENGTH: 11
<212> TYPE: PRT
<213> ORGANISM: Homo sapiens

<400> SEQUENCE: 404

Gly Thr Trp Asp Ser Ser Leu Asn Asn Cys Val
1 5 10

<210> SEQ ID NO 405
<211> LENGTH: 8
<212> TYPE: PRT
<213> ORGANISM: Homo sapiens

<400> SEQUENCE: 405

Gly Phe Thr Phe Thr Ser Tyr Ala
1 5

<210> SEQ ID NO 406
<211> LENGTH: 8
<212> TYPE: PRT
<213> ORGANISM: Homo sapiens

<400> SEQUENCE: 406

Ile Ser Tyr Asp Gly Ser Thr His
1 5

<210> SEQ ID NO 407
<211> LENGTH: 15
<212> TYPE: PRT
<213> ORGANISM: Homo sapiens

<400> SEQUENCE: 407

Ala Arg Asp Pro Gly Val Pro Tyr Tyr His Tyr Ala Met Asp Val
1 5 10 15

<210> SEQ ID NO 408
<211> LENGTH: 9
<212> TYPE: PRT
<213> ORGANISM: Homo sapiens

<400> SEQUENCE: 408

Ser Ser Asp Val Gly Gly Tyr His Tyr
1 5

<210> SEQ ID NO 409
<211> LENGTH: 11
<212> TYPE: PRT
<213> ORGANISM: Homo sapiens

<400> SEQUENCE: 409

Ser Ser Tyr Ala Gly Ser Asn Asn Tyr Ile Leu
1 5 10

<210> SEQ ID NO 410
<211> LENGTH: 8
<212> TYPE: PRT
<213> ORGANISM: Homo sapiens

<400> SEQUENCE: 410

Glu Phe Thr Phe Ser Thr Tyr Ala
1 5

<210> SEQ ID NO 411
<211> LENGTH: 8
<212> TYPE: PRT
<213> ORGANISM: Homo sapiens

<400> SEQUENCE: 411

Ile Ser Ala Asp Gly Asn Asn Arg
1 5

<210> SEQ ID NO 412
<211> LENGTH: 20
<212> TYPE: PRT
<213> ORGANISM: Homo sapiens

<400> SEQUENCE: 412

Val Arg Asp Glu Thr Asp Trp Glu Ile Gly Val Val Val Ala Thr Pro
1 5 10 15

Glu Phe Asp Tyr
20

<210> SEQ ID NO 413
<211> LENGTH: 6
<212> TYPE: PRT
<213> ORGANISM: Homo sapiens

<400> SEQUENCE: 413

Gln Gly Ile Arg Asn Asp
1 5

<210> SEQ ID NO 414
<211> LENGTH: 9
<212> TYPE: PRT
<213> ORGANISM: Homo sapiens

<400> SEQUENCE: 414

Leu Gln His Asn Ser Tyr Pro Arg Thr
1 5

<210> SEQ ID NO 415
<211> LENGTH: 8
<212> TYPE: PRT
<213> ORGANISM: Homo sapiens

<400> SEQUENCE: 415

Gly Ser Asn Val Gly Gly Asn Thr
1 5

<210> SEQ ID NO 416
<211> LENGTH: 11
<212> TYPE: PRT
<213> ORGANISM: Homo sapiens

<400> SEQUENCE: 416

Ser Thr Trp Asp Asp Ser Leu Asn Gly Val Val
1 5 10

<210> SEQ ID NO 417
<211> LENGTH: 8
<212> TYPE: PRT
<213> ORGANISM: Homo sapiens

<400> SEQUENCE: 417

Gly Phe Pro Phe Ser Ser His Ala
1 5

<210> SEQ ID NO 418
<211> LENGTH: 8
<212> TYPE: PRT
<213> ORGANISM: Homo sapiens

<400> SEQUENCE: 418

Leu Ser Phe Asn Gly Asp Tyr Ile
1 5

<210> SEQ ID NO 419
<211> LENGTH: 16
<212> TYPE: PRT
<213> ORGANISM: Homo sapiens

<400> SEQUENCE: 419

Val Thr Gly Ile Arg Ala Arg Asp Tyr Gly Gly Ser Thr Phe Asp Leu
1 5 10 15

<210> SEQ ID NO 420
<211> LENGTH: 8
<212> TYPE: PRT
<213> ORGANISM: Homo sapiens

<400> SEQUENCE: 420

Asn Lys Asn Val Gly Asn Glu Gly
1 5

<210> SEQ ID NO 421
<211> LENGTH: 11
<212> TYPE: PRT
<213> ORGANISM: Homo sapiens

<400> SEQUENCE: 421

Ala Ala Trp Asp Ser Ser Leu Ser Ala Met Ile
1 5 10

<210> SEQ ID NO 422
<211> LENGTH: 8
<212> TYPE: PRT
<213> ORGANISM: Homo sapiens

<400> SEQUENCE: 422

Gly Phe Arg Phe Thr Asn Tyr Gly
1               5

<210> SEQ ID NO 423
<211> LENGTH: 8
<212> TYPE: PRT
<213> ORGANISM: Homo sapiens

<400> SEQUENCE: 423

Ile Arg Tyr Asp Gly Ser Lys Lys
1               5

<210> SEQ ID NO 424
<211> LENGTH: 15
<212> TYPE: PRT
<213> ORGANISM: Homo sapiens

<400> SEQUENCE: 424

Ala Lys Asp Gly Arg Trp Phe Gly Glu Ser Gly Gly Phe Asp Val
1               5                   10                  15

<210> SEQ ID NO 425
<211> LENGTH: 6
<212> TYPE: PRT
<213> ORGANISM: Homo sapiens

<400> SEQUENCE: 425

Asn Ile Gly Asn Thr Val
1               5

<210> SEQ ID NO 426
<211> LENGTH: 11
<212> TYPE: PRT
<213> ORGANISM: Homo sapiens

<400> SEQUENCE: 426

Gln Val Trp Glu Ser Ser Thr Asp Pro Val Val
1               5                   10

<210> SEQ ID NO 427
<211> LENGTH: 8
<212> TYPE: PRT
<213> ORGANISM: Homo sapiens

<400> SEQUENCE: 427

Gly Phe Thr Phe Thr Ser Tyr Ser
1               5

<210> SEQ ID NO 428
<211> LENGTH: 8
<212> TYPE: PRT
<213> ORGANISM: Homo sapiens

<400> SEQUENCE: 428

Met Ser Tyr Asp Gly Ser Tyr Glu
1               5

<210> SEQ ID NO 429
<211> LENGTH: 17

<212> TYPE: PRT
<213> ORGANISM: Homo sapiens

<400> SEQUENCE: 429

Ala Arg Asp Tyr Cys Ser Arg Thr Asn Cys Ile Asn Trp Ile Phe Asp
1 5 10 15

Leu

<210> SEQ ID NO 430
<211> LENGTH: 7
<212> TYPE: PRT
<213> ORGANISM: Homo sapiens

<400> SEQUENCE: 430

Pro Ser Val Ser Ser Ser Tyr
1 5

<210> SEQ ID NO 431
<211> LENGTH: 9
<212> TYPE: PRT
<213> ORGANISM: Homo sapiens

<400> SEQUENCE: 431

Gln Gln Tyr Gly Ser Ser Pro Leu Thr
1 5

<210> SEQ ID NO 432
<211> LENGTH: 8
<212> TYPE: PRT
<213> ORGANISM: Homo sapiens

<400> SEQUENCE: 432

Gly Phe Arg Phe Thr Gly Tyr Gly
1 5

<210> SEQ ID NO 433
<211> LENGTH: 8
<212> TYPE: PRT
<213> ORGANISM: Homo sapiens

<400> SEQUENCE: 433

Ile Ser Asn Asp Gly Ser Lys Lys
1 5

<210> SEQ ID NO 434
<211> LENGTH: 16
<212> TYPE: PRT
<213> ORGANISM: Homo sapiens

<400> SEQUENCE: 434

Ala Lys Asp Gly Tyr Leu Ser Ala Ala Arg Gly Tyr Gly Met Asp Val
1 5 10 15

<210> SEQ ID NO 435
<211> LENGTH: 6
<212> TYPE: PRT
<213> ORGANISM: Homo sapiens

<400> SEQUENCE: 435

Asn Ile Gly Gly Lys Ser
1 5

<210> SEQ ID NO 436
<211> LENGTH: 11

<212> TYPE: PRT
<213> ORGANISM: Homo sapiens

<400> SEQUENCE: 436

Gln Val Trp Glu Thr Thr Ser Asp Gln Leu Val
1 5 10

<210> SEQ ID NO 437
<211> LENGTH: 8
<212> TYPE: PRT
<213> ORGANISM: Homo sapiens

<400> SEQUENCE: 437

Gly Phe Thr Phe Ser Asn Tyr Asp
1 5

<210> SEQ ID NO 438
<211> LENGTH: 8
<212> TYPE: PRT
<213> ORGANISM: Homo sapiens

<400> SEQUENCE: 438

Ile Ser Tyr Asp Gly Ser Asn Lys
1 5

<210> SEQ ID NO 439
<211> LENGTH: 12
<212> TYPE: PRT
<213> ORGANISM: Homo sapiens

<400> SEQUENCE: 439

Ala Arg Asp Thr Phe Gly Asp Tyr Tyr Phe Asp Tyr
1 5 10

<210> SEQ ID NO 440
<211> LENGTH: 9
<212> TYPE: PRT
<213> ORGANISM: Homo sapiens

<400> SEQUENCE: 440

Asn Ser Asn Ile Gly Ala Gly Tyr Asp
1 5

<210> SEQ ID NO 441
<211> LENGTH: 12
<212> TYPE: PRT
<213> ORGANISM: Homo sapiens

<400> SEQUENCE: 441

Gln Ser Tyr Asp Ser Arg Leu Ser Val Pro Tyr Val
1 5 10

<210> SEQ ID NO 442
<211> LENGTH: 8
<212> TYPE: PRT
<213> ORGANISM: Homo sapiens

<400> SEQUENCE: 442

Lys Phe Thr Phe Ser Lys Tyr Ala
1 5

<210> SEQ ID NO 443
<211> LENGTH: 8
<212> TYPE: PRT
<213> ORGANISM: Homo sapiens

<400> SEQUENCE: 443

Thr Ser Tyr Asn Gly Gly Ser Lys
1 5

<210> SEQ ID NO 444
<211> LENGTH: 17
<212> TYPE: PRT
<213> ORGANISM: Homo sapiens

<400> SEQUENCE: 444

Ala Arg Gly Gly Gly Tyr Thr Tyr Gly Ser Tyr Tyr Tyr Ser Met Asp
1 5 10 15

Val

<210> SEQ ID NO 445
<211> LENGTH: 12
<212> TYPE: PRT
<213> ORGANISM: Homo sapiens

<400> SEQUENCE: 445

Gln Ser Val Leu Tyr Ser Ser Asn Asn Lys Asn Tyr
1 5 10

<210> SEQ ID NO 446
<211> LENGTH: 9
<212> TYPE: PRT
<213> ORGANISM: Homo sapiens

<400> SEQUENCE: 446

Gln Gln Tyr Tyr Ser Thr Pro Phe Thr
1 5

<210> SEQ ID NO 447
<211> LENGTH: 8
<212> TYPE: PRT
<213> ORGANISM: Homo sapiens

<400> SEQUENCE: 447

Arg Phe Thr Phe Ser Lys Tyr Ala
1 5

<210> SEQ ID NO 448
<211> LENGTH: 8
<212> TYPE: PRT
<213> ORGANISM: Homo sapiens

<400> SEQUENCE: 448

Ile Ser Tyr Asp Gly Ser Ser Lys
1 5

<210> SEQ ID NO 449
<211> LENGTH: 17
<212> TYPE: PRT
<213> ORGANISM: Homo sapiens

<400> SEQUENCE: 449

Ala Arg Gly Gly Gly Tyr Thr Tyr Gly Ser Tyr Tyr Tyr Ala Met Asp
1 5 10 15

Val

<210> SEQ ID NO 450
<211> LENGTH: 12

<212> TYPE: PRT
<213> ORGANISM: Homo sapiens

<400> SEQUENCE: 450

Gln Ser Leu Leu Tyr Ser Ser Asn Asn Lys Asn Tyr
1 5 10

<210> SEQ ID NO 451
<211> LENGTH: 9
<212> TYPE: PRT
<213> ORGANISM: Homo sapiens

<400> SEQUENCE: 451

Gln Gln Tyr Tyr Ser Thr Pro Phe Thr
1 5

<210> SEQ ID NO 452
<211> LENGTH: 8
<212> TYPE: PRT
<213> ORGANISM: Homo sapiens

<400> SEQUENCE: 452

Gly Phe Thr Phe Ser Ser Tyr Ser
1 5

<210> SEQ ID NO 453
<211> LENGTH: 8
<212> TYPE: PRT
<213> ORGANISM: Homo sapiens

<400> SEQUENCE: 453

Met Ser Asn Thr Gly Ser Thr Lys
1 5

<210> SEQ ID NO 454
<211> LENGTH: 17
<212> TYPE: PRT
<213> ORGANISM: Homo sapiens

<400> SEQUENCE: 454

Ala Arg Ala Leu Leu Ser Val Val Gly Ser Lys Ser Tyr Tyr Phe Asp
1 5 10 15

Phe

<210> SEQ ID NO 455
<211> LENGTH: 6
<212> TYPE: PRT
<213> ORGANISM: Homo sapiens

<400> SEQUENCE: 455

Gln Ser Val Ser Ser Tyr
1 5

<210> SEQ ID NO 456
<211> LENGTH: 8
<212> TYPE: PRT
<213> ORGANISM: Homo sapiens

<400> SEQUENCE: 456

Gln His Arg Ser Asn Ser Trp Thr
1 5

<210> SEQ ID NO 457
<211> LENGTH: 8

<212> TYPE: PRT
<213> ORGANISM: Homo sapiens

<400> SEQUENCE: 457

Gly Phe Thr Phe Ser Ser Tyr Ser
1               5

<210> SEQ ID NO 458
<211> LENGTH: 8
<212> TYPE: PRT
<213> ORGANISM: Homo sapiens

<400> SEQUENCE: 458

Met Ser Asn Thr Gly Ser Thr Lys
1               5

<210> SEQ ID NO 459
<211> LENGTH: 17
<212> TYPE: PRT
<213> ORGANISM: Homo sapiens

<400> SEQUENCE: 459

Ala Arg Ala Leu Leu Ser Val Val Gly Ser Lys Ser Tyr Tyr Phe Asp
1               5                   10                  15

Phe

<210> SEQ ID NO 460
<211> LENGTH: 6
<212> TYPE: PRT
<213> ORGANISM: Homo sapiens

<400> SEQUENCE: 460

Gln Ser Val Ser Ser Tyr
1               5

<210> SEQ ID NO 461
<211> LENGTH: 8
<212> TYPE: PRT
<213> ORGANISM: Homo sapiens

<400> SEQUENCE: 461

Gln His Arg Ser Asn Ser Trp Thr
1               5

<210> SEQ ID NO 462
<211> LENGTH: 8
<212> TYPE: PRT
<213> ORGANISM: Homo sapiens

<400> SEQUENCE: 462

Gly Phe Asn Phe Asn Val Tyr Ala
1               5

<210> SEQ ID NO 463
<211> LENGTH: 8
<212> TYPE: PRT
<213> ORGANISM: Homo sapiens

<400> SEQUENCE: 463

Ile Ser Tyr Asp Gly Ser Lys Lys
1               5

<210> SEQ ID NO 464
<211> LENGTH: 23

<212> TYPE: PRT
<213> ORGANISM: Homo sapiens

<400> SEQUENCE: 464

Ala Arg Asp Glu Lys Tyr Ser Gly Leu Tyr Ser Gly Arg Thr Gly Asp
1 5 10 15

Tyr Tyr Tyr Gly Met Asp Val
20

<210> SEQ ID NO 465
<211> LENGTH: 8
<212> TYPE: PRT
<213> ORGANISM: Homo sapiens

<400> SEQUENCE: 465

Asn Ser Asn Ile Gly Asn Asn Phe
1 5

<210> SEQ ID NO 466
<211> LENGTH: 11
<212> TYPE: PRT
<213> ORGANISM: Homo sapiens

<400> SEQUENCE: 466

Gly Thr Trp Asp Ser Ser Leu Ser Leu Gly Val
1 5 10

<210> SEQ ID NO 467
<211> LENGTH: 8
<212> TYPE: PRT
<213> ORGANISM: Homo sapiens

<400> SEQUENCE: 467

Gly Phe Thr Phe Ser Ala Tyr Ser
1 5

<210> SEQ ID NO 468
<211> LENGTH: 8
<212> TYPE: PRT
<213> ORGANISM: Homo sapiens

<400> SEQUENCE: 468

Ile Ser Tyr Asp Gly Ser Asn Arg
1 5

<210> SEQ ID NO 469
<211> LENGTH: 23
<212> TYPE: PRT
<213> ORGANISM: Homo sapiens

<400> SEQUENCE: 469

Ala Arg Asp Gly Lys Leu Gly Arg Thr Tyr His Asp Ser Arg Gln Ser
1 5 10 15

Tyr Phe Tyr Ile Met Asp Val
20

<210> SEQ ID NO 470
<211> LENGTH: 9
<212> TYPE: PRT
<213> ORGANISM: Homo sapiens

<400> SEQUENCE: 470

Ser Ser Asp Val Gly Gly Tyr Asn Tyr
1 5

<210> SEQ ID NO 471
<211> LENGTH: 10
<212> TYPE: PRT
<213> ORGANISM: Homo sapiens

<400> SEQUENCE: 471

Ser Ser Tyr Thr Ser Ser Thr Ser Leu Val
1 5 10

<210> SEQ ID NO 472
<211> LENGTH: 8
<212> TYPE: PRT
<213> ORGANISM: Homo sapiens

<400> SEQUENCE: 472

Gly Phe Arg Phe Ser Ser Tyr Gly
1 5

<210> SEQ ID NO 473
<211> LENGTH: 8
<212> TYPE: PRT
<213> ORGANISM: Homo sapiens

<400> SEQUENCE: 473

Thr Ser Phe Asp Gly Ser Lys Thr
1 5

<210> SEQ ID NO 474
<211> LENGTH: 17
<212> TYPE: PRT
<213> ORGANISM: Homo sapiens

<400> SEQUENCE: 474

Ala Lys Asp Ala Tyr Tyr Phe Ala Ser Gly Ser Phe Phe Gly Met Asp
1 5 10 15

Val

<210> SEQ ID NO 475
<211> LENGTH: 6
<212> TYPE: PRT
<213> ORGANISM: Homo sapiens

<400> SEQUENCE: 475

Asn Ile Gly Ser Lys Ser
1 5

<210> SEQ ID NO 476
<211> LENGTH: 9
<212> TYPE: PRT
<213> ORGANISM: Homo sapiens

<400> SEQUENCE: 476

Gln Val Trp Gly Ser Gly Gly Val Ile
1 5

<210> SEQ ID NO 477
<211> LENGTH: 8
<212> TYPE: PRT
<213> ORGANISM: Homo sapiens

<400> SEQUENCE: 477

Gly Phe Thr Phe Ser Arg Tyr Gly
1 5

<210> SEQ ID NO 478
<211> LENGTH: 8
<212> TYPE: PRT
<213> ORGANISM: Homo sapiens

<400> SEQUENCE: 478

Ile Ser Tyr Asp Gly Ser Asn Lys
1               5

<210> SEQ ID NO 479
<211> LENGTH: 15
<212> TYPE: PRT
<213> ORGANISM: Homo sapiens

<400> SEQUENCE: 479

Ala Lys Asp Ala Tyr Tyr Tyr Gly Ser Gly Tyr Gly Met Asp Val
1               5                   10                  15

<210> SEQ ID NO 480
<211> LENGTH: 6
<212> TYPE: PRT
<213> ORGANISM: Homo sapiens

<400> SEQUENCE: 480

Gln Ser Ile Ser Val Trp
1               5

<210> SEQ ID NO 481
<211> LENGTH: 8
<212> TYPE: PRT
<213> ORGANISM: Homo sapiens

<400> SEQUENCE: 481

Gln Gln Tyr Thr Ser Phe Ser Thr
1               5

<210> SEQ ID NO 482
<211> LENGTH: 8
<212> TYPE: PRT
<213> ORGANISM: Homo sapiens

<400> SEQUENCE: 482

Ser Ser Asn Ile Gly Ser Asp Tyr
1               5

<210> SEQ ID NO 483
<211> LENGTH: 11
<212> TYPE: PRT
<213> ORGANISM: Homo sapiens

<400> SEQUENCE: 483

Ala Ala Trp Asp Asp Arg Leu Ser Gly Tyr Val
1               5                   10

<210> SEQ ID NO 484
<211> LENGTH: 8
<212> TYPE: PRT
<213> ORGANISM: Homo sapiens

<400> SEQUENCE: 484

Gly Phe Thr Phe Arg Ser Tyr Gly
1               5

<210> SEQ ID NO 485
<211> LENGTH: 8
<212> TYPE: PRT
<213> ORGANISM: Homo sapiens

<400> SEQUENCE: 485

Ile Ser Ser Asp Gly Ser Lys Lys
1 5

<210> SEQ ID NO 486
<211> LENGTH: 16
<212> TYPE: PRT
<213> ORGANISM: Homo sapiens

<400> SEQUENCE: 486

Ala Lys Asp Gly Tyr Val Val Ser Gly Ser Gly Tyr Gly Met Asp Val
1 5 10 15

<210> SEQ ID NO 487
<211> LENGTH: 6
<212> TYPE: PRT
<213> ORGANISM: Homo sapiens

<400> SEQUENCE: 487

Asn Ile Gly Ser Lys Ser
1 5

<210> SEQ ID NO 488
<211> LENGTH: 11
<212> TYPE: PRT
<213> ORGANISM: Homo sapiens

<400> SEQUENCE: 488

Gln Val Trp Asp Ser Ser Ser Asp His Val Val
1 5 10

<210> SEQ ID NO 489
<211> LENGTH: 8
<212> TYPE: PRT
<213> ORGANISM: Homo sapiens

<400> SEQUENCE: 489

Arg Phe Ser Phe Asn Thr Tyr Gly
1 5

<210> SEQ ID NO 490
<211> LENGTH: 8
<212> TYPE: PRT
<213> ORGANISM: Homo sapiens

<400> SEQUENCE: 490

Ile Ser Tyr Asp Gly Ser His Glu
1 5

<210> SEQ ID NO 491
<211> LENGTH: 16
<212> TYPE: PRT
<213> ORGANISM: Homo sapiens

<400> SEQUENCE: 491

Ala Lys Thr Asp Ile Lys Trp Gly Ala Thr Asn Tyr Gly Met Asp Val
1 5 10 15

<210> SEQ ID NO 492
<211> LENGTH: 6

<212> TYPE: PRT
<213> ORGANISM: Homo sapiens

<400> SEQUENCE: 492

Asn Ile Gly Arg Lys Ser
1 5

<210> SEQ ID NO 493
<211> LENGTH: 12
<212> TYPE: PRT
<213> ORGANISM: Homo sapiens

<400> SEQUENCE: 493

Gln Val Trp Asp Gly Thr Arg Asp His Leu Val Val
1 5 10

<210> SEQ ID NO 494
<211> LENGTH: 8
<212> TYPE: PRT
<213> ORGANISM: Homo sapiens

<400> SEQUENCE: 494

Gly Phe Thr Phe Ser Asn Tyr Ala
1 5

<210> SEQ ID NO 495
<211> LENGTH: 8
<212> TYPE: PRT
<213> ORGANISM: Homo sapiens

<400> SEQUENCE: 495

Thr Leu Tyr Asp Gly Ser His Ser
1 5

<210> SEQ ID NO 496
<211> LENGTH: 11
<212> TYPE: PRT
<213> ORGANISM: Homo sapiens

<400> SEQUENCE: 496

Ala Lys Asp Ser Ala Gly Tyr Gly Leu His Tyr
1 5 10

<210> SEQ ID NO 497
<211> LENGTH: 6
<212> TYPE: PRT
<213> ORGANISM: Homo sapiens

<400> SEQUENCE: 497

Gln Gly Ile Arg Thr Asp
1 5

<210> SEQ ID NO 498
<211> LENGTH: 9
<212> TYPE: PRT
<213> ORGANISM: Homo sapiens

<400> SEQUENCE: 498

Leu Gln His Asn Ser Tyr Pro Trp Thr
1 5

<210> SEQ ID NO 499
<211> LENGTH: 6
<212> TYPE: PRT
<213> ORGANISM: Homo sapiens

<400> SEQUENCE: 499

Ser Leu Arg Ser Phe Tyr
1 5

<210> SEQ ID NO 500
<211> LENGTH: 11
<212> TYPE: PRT
<213> ORGANISM: Homo sapiens

<400> SEQUENCE: 500

Asn Ser Arg Asp Ser Ile Gly Asn His Val Val
1 5 10

<210> SEQ ID NO 501
<211> LENGTH: 8
<212> TYPE: PRT
<213> ORGANISM: Homo sapiens

<400> SEQUENCE: 501

Gly Phe Arg Phe Thr Gly Tyr Gly
1 5

<210> SEQ ID NO 502
<211> LENGTH: 8
<212> TYPE: PRT
<213> ORGANISM: Homo sapiens

<400> SEQUENCE: 502

Ile Ser Asn Asp Gly Ser Lys Lys
1 5

<210> SEQ ID NO 503
<211> LENGTH: 16
<212> TYPE: PRT
<213> ORGANISM: Homo sapiens

<400> SEQUENCE: 503

Ala Lys Asp Gly Tyr Leu Ser Ala Ala Arg Gly Tyr Gly Met Asp Val
1 5 10 15

<210> SEQ ID NO 504
<211> LENGTH: 6
<212> TYPE: PRT
<213> ORGANISM: Homo sapiens

<400> SEQUENCE: 504

Asn Val Gly Ser Lys Ser
1 5

<210> SEQ ID NO 505
<211> LENGTH: 11
<212> TYPE: PRT
<213> ORGANISM: Homo sapiens

<400> SEQUENCE: 505

Gln Val Trp Asp Thr Thr Thr Asp Gln Leu Val
1 5 10

<210> SEQ ID NO 506
<211> LENGTH: 8
<212> TYPE: PRT
<213> ORGANISM: Homo sapiens

<400> SEQUENCE: 506

Gly Phe Arg Phe Thr Gly Tyr Gly
1 5

<210> SEQ ID NO 507
<211> LENGTH: 8
<212> TYPE: PRT
<213> ORGANISM: Homo sapiens

<400> SEQUENCE: 507

Ile Ser Asn Asp Gly Ser Lys Thr
1 5

<210> SEQ ID NO 508
<211> LENGTH: 16
<212> TYPE: PRT
<213> ORGANISM: Homo sapiens

<400> SEQUENCE: 508

Ala Lys Asp Gly Tyr Leu Ser Ala Ala Arg Gly Tyr Gly Met Asp Val
1 5 10 15

<210> SEQ ID NO 509
<211> LENGTH: 6
<212> TYPE: PRT
<213> ORGANISM: Homo sapiens

<400> SEQUENCE: 509

Asn Ile Gly Gly Lys Ser
1 5

<210> SEQ ID NO 510
<211> LENGTH: 11
<212> TYPE: PRT
<213> ORGANISM: Homo sapiens

<400> SEQUENCE: 510

Gln Val Trp Asp Thr Thr Ser Asp Gln Leu Val
1 5 10

<210> SEQ ID NO 511
<211> LENGTH: 8
<212> TYPE: PRT
<213> ORGANISM: Homo sapiens

<400> SEQUENCE: 511

Gly Phe Arg Phe Thr Gly Tyr Gly
1 5

<210> SEQ ID NO 512
<211> LENGTH: 8
<212> TYPE: PRT
<213> ORGANISM: Homo sapiens

<400> SEQUENCE: 512

Ile Ser Asn Asp Gly Ser Lys Lys
1 5

<210> SEQ ID NO 513
<211> LENGTH: 16
<212> TYPE: PRT
<213> ORGANISM: Homo sapiens

<400> SEQUENCE: 513

Ala Lys Asp Gly Tyr Leu Ser Ala Ala Arg Gly Tyr Gly Met Asp Val 1 5 10 15

<210> SEQ ID NO 514
<211> LENGTH: 6
<212> TYPE: PRT
<213> ORGANISM: Homo sapiens

<400> SEQUENCE: 514

Asn Ile Gly Ala Leu Ser
1 5

<210> SEQ ID NO 515
<211> LENGTH: 11
<212> TYPE: PRT
<213> ORGANISM: Homo sapiens

<400> SEQUENCE: 515

Gln Val Trp Asp Thr Ser Ser Asp Gln Leu Val
1 5 10

<210> SEQ ID NO 516
<211> LENGTH: 8
<212> TYPE: PRT
<213> ORGANISM: Homo sapiens

<400> SEQUENCE: 516

Gly Phe Arg Phe Thr Gly Tyr Gly
1 5

<210> SEQ ID NO 517
<211> LENGTH: 8
<212> TYPE: PRT
<213> ORGANISM: Homo sapiens

<400> SEQUENCE: 517

Ile Ser Asn Asp Gly Ser Lys Lys
1 5

<210> SEQ ID NO 518
<211> LENGTH: 16
<212> TYPE: PRT
<213> ORGANISM: Homo sapiens

<400> SEQUENCE: 518

Ala Lys Asp Ala Tyr Leu Ser Ala Ala Arg Gly Tyr Gly Met His Val
1 5 10 15

<210> SEQ ID NO 519
<211> LENGTH: 6
<212> TYPE: PRT
<213> ORGANISM: Homo sapiens

<400> SEQUENCE: 519

Asn Ile Gly Gly Lys Ser
1 5

<210> SEQ ID NO 520
<211> LENGTH: 11
<212> TYPE: PRT
<213> ORGANISM: Homo sapiens

<400> SEQUENCE: 520

Gln Val Trp Asp Thr Ala Ser Asp Gln Leu Val
1 5 10

<210> SEQ ID NO 521
<211> LENGTH: 8
<212> TYPE: PRT
<213> ORGANISM: Homo sapiens

<400> SEQUENCE: 521

Gly Phe Arg Phe Thr Gly Tyr Gly
1 5

<210> SEQ ID NO 522
<211> LENGTH: 8
<212> TYPE: PRT
<213> ORGANISM: Homo sapiens

<400> SEQUENCE: 522

Ile Ser Asn Asp Gly Ser Lys Lys
1 5

<210> SEQ ID NO 523
<211> LENGTH: 16
<212> TYPE: PRT
<213> ORGANISM: Homo sapiens

<400> SEQUENCE: 523

Ala Lys Asp Gly Tyr Leu Ser Ala Ala Arg Gly Tyr Gly Met Asp Val
1 5 10 15

<210> SEQ ID NO 524
<211> LENGTH: 6
<212> TYPE: PRT
<213> ORGANISM: Homo sapiens

<400> SEQUENCE: 524

Asn Ile Gly Gly Lys Ser
1 5

<210> SEQ ID NO 525
<211> LENGTH: 11
<212> TYPE: PRT
<213> ORGANISM: Homo sapiens

<400> SEQUENCE: 525

Gln Val Trp Asp Thr Thr Ser Asp Gln Leu Val
1 5 10

<210> SEQ ID NO 526
<211> LENGTH: 8
<212> TYPE: PRT
<213> ORGANISM: Homo sapiens

<400> SEQUENCE: 526

Gly Phe Arg Phe Thr Gly Tyr Gly
1 5

<210> SEQ ID NO 527
<211> LENGTH: 8
<212> TYPE: PRT
<213> ORGANISM: Homo sapiens

<400> SEQUENCE: 527

Ile Ser Asn Asp Gly Ser Lys Lys
1 5

<210> SEQ ID NO 528

<211> LENGTH: 16
<212> TYPE: PRT
<213> ORGANISM: Homo sapiens

<400> SEQUENCE: 528

Ala Lys Asp Gly Tyr Leu Ser Ala Ala Arg Gly Tyr Gly Met Asp Val
1 5 10 15

<210> SEQ ID NO 529
<211> LENGTH: 6
<212> TYPE: PRT
<213> ORGANISM: Homo sapiens

<400> SEQUENCE: 529

Asn Ile Gly Gly Lys Ser
1 5

<210> SEQ ID NO 530
<211> LENGTH: 11
<212> TYPE: PRT
<213> ORGANISM: Homo sapiens

<400> SEQUENCE: 530

Gln Val Trp Asp Thr Thr Ser Asp Gln Leu Val
1 5 10

<210> SEQ ID NO 531
<211> LENGTH: 8
<212> TYPE: PRT
<213> ORGANISM: Homo sapiens

<400> SEQUENCE: 531

Gly Phe Arg Phe Thr Gly Tyr Gly
1 5

<210> SEQ ID NO 532
<211> LENGTH: 8
<212> TYPE: PRT
<213> ORGANISM: Homo sapiens

<400> SEQUENCE: 532

Ile Ser Asn Asp Gly Ser Lys Lys
1 5

<210> SEQ ID NO 533
<211> LENGTH: 16
<212> TYPE: PRT
<213> ORGANISM: Homo sapiens

<400> SEQUENCE: 533

Ala Lys Asp Gly Tyr Leu Ser Ala Ala Arg Gly Tyr Gly Met Asp Val
1 5 10 15

<210> SEQ ID NO 534
<211> LENGTH: 6
<212> TYPE: PRT
<213> ORGANISM: Homo sapiens

<400> SEQUENCE: 534

Asn Ile Gly Gly Lys Ser
1 5

<210> SEQ ID NO 535
<211> LENGTH: 11
<212> TYPE: PRT

<213> ORGANISM: Homo sapiens

<400> SEQUENCE: 535

Gln Val Trp Asp Thr Thr Ser Asp Gln Leu Val
1 5 10

<210> SEQ ID NO 536
<211> LENGTH: 8
<212> TYPE: PRT
<213> ORGANISM: Homo sapiens

<400> SEQUENCE: 536

Gly Phe Thr Phe Asn Thr Tyr Ala
1 5

<210> SEQ ID NO 537
<211> LENGTH: 8
<212> TYPE: PRT
<213> ORGANISM: Homo sapiens

<400> SEQUENCE: 537

Ile Ser Tyr Asp Gly Ser Asn Lys
1 5

<210> SEQ ID NO 538
<211> LENGTH: 16
<212> TYPE: PRT
<213> ORGANISM: Homo sapiens

<400> SEQUENCE: 538

Ala Lys Thr Asp Ile Arg Trp Gly Ala Thr Asn Tyr Gly Met Asp Val
1 5 10 15

<210> SEQ ID NO 539
<211> LENGTH: 6
<212> TYPE: PRT
<213> ORGANISM: Homo sapiens

<400> SEQUENCE: 539

Asn Ile Gly Ser Lys Ser
1 5

<210> SEQ ID NO 540
<211> LENGTH: 12
<212> TYPE: PRT
<213> ORGANISM: Homo sapiens

<400> SEQUENCE: 540

Gln Val Trp Asp Gly Ser Ser Asp His Leu Val Val
1 5 10

<210> SEQ ID NO 541
<211> LENGTH: 8
<212> TYPE: PRT
<213> ORGANISM: Homo sapiens

<400> SEQUENCE: 541

Gly Phe Ser Phe Ser Thr Tyr Gly
1 5

<210> SEQ ID NO 542
<211> LENGTH: 8
<212> TYPE: PRT
<213> ORGANISM: Homo sapiens

<400> SEQUENCE: 542

Ile Ser Tyr Asp Gly Met Ile Lys
1 5

<210> SEQ ID NO 543
<211> LENGTH: 13
<212> TYPE: PRT
<213> ORGANISM: Homo sapiens

<400> SEQUENCE: 543

Ala Lys Gly Pro Leu Phe Gly Leu Phe Ser Phe Asp Gln
1 5 10

<210> SEQ ID NO 544
<211> LENGTH: 6
<212> TYPE: PRT
<213> ORGANISM: Homo sapiens

<400> SEQUENCE: 544

Asn Ile Gly Asp Met Ser
1 5

<210> SEQ ID NO 545
<211> LENGTH: 11
<212> TYPE: PRT
<213> ORGANISM: Homo sapiens

<400> SEQUENCE: 545

Gln Val Trp Asp Asn Ser Arg Asn Arg Gly Ile
1 5 10

<210> SEQ ID NO 546
<211> LENGTH: 8
<212> TYPE: PRT
<213> ORGANISM: Homo sapiens

<400> SEQUENCE: 546

Gly Phe Arg Phe Thr Gly Tyr Gly
1 5

<210> SEQ ID NO 547
<211> LENGTH: 8
<212> TYPE: PRT
<213> ORGANISM: Homo sapiens

<400> SEQUENCE: 547

Ile Ser Asn Asp Gly Ser Lys Lys
1 5

<210> SEQ ID NO 548
<211> LENGTH: 16
<212> TYPE: PRT
<213> ORGANISM: Homo sapiens

<400> SEQUENCE: 548

Ala Lys Asp Gly Tyr Leu Ser Ala Ala Arg Gly Tyr Gly Met Asp Val
1 5 10 15

<210> SEQ ID NO 549
<211> LENGTH: 6
<212> TYPE: PRT
<213> ORGANISM: Homo sapiens

<400> SEQUENCE: 549

Asn Ile Gly Gly Lys Ser
1               5

<210> SEQ ID NO 550
<211> LENGTH: 11
<212> TYPE: PRT
<213> ORGANISM: Homo sapiens

<400> SEQUENCE: 550

Gln Val Trp Asp Thr Thr Ser Asp Gln Leu Val
1               5                   10

<210> SEQ ID NO 551
<211> LENGTH: 8
<212> TYPE: PRT
<213> ORGANISM: Homo sapiens

<400> SEQUENCE: 551

Gly Phe Arg Phe Thr Gly Tyr Ser
1               5

<210> SEQ ID NO 552
<211> LENGTH: 8
<212> TYPE: PRT
<213> ORGANISM: Homo sapiens

<400> SEQUENCE: 552

Ile Ser Asn Asp Gly Ser Lys Arg
1               5

<210> SEQ ID NO 553
<211> LENGTH: 16
<212> TYPE: PRT
<213> ORGANISM: Homo sapiens

<400> SEQUENCE: 553

Ala Lys Asp Gly Tyr Leu Ser Ala Ala Arg Gly Tyr Gly Met Asp Val
1               5                   10                  15

<210> SEQ ID NO 554
<211> LENGTH: 11
<212> TYPE: PRT
<213> ORGANISM: Homo sapiens

<400> SEQUENCE: 554

Gln Ser Leu Val Tyr Ser Asp Gly Asn Thr Tyr
1               5                   10

<210> SEQ ID NO 555
<211> LENGTH: 10
<212> TYPE: PRT
<213> ORGANISM: Homo sapiens

<400> SEQUENCE: 555

Thr Gln Val Thr Leu Trp Pro Pro Trp Thr
1               5                   10

<210> SEQ ID NO 556
<211> LENGTH: 8
<212> TYPE: PRT
<213> ORGANISM: Homo sapiens

<400> SEQUENCE: 556

Gly Phe Arg Phe Thr Gly Tyr Gly
1               5

<210> SEQ ID NO 557
<211> LENGTH: 8
<212> TYPE: PRT
<213> ORGANISM: Homo sapiens

<400> SEQUENCE: 557

Ile Ser Asn Asp Gly Ser Lys Lys
1 5

<210> SEQ ID NO 558
<211> LENGTH: 16
<212> TYPE: PRT
<213> ORGANISM: Homo sapiens

<400> SEQUENCE: 558

Ala Lys Asp Gly Tyr Leu Ser Ala Ala Arg Gly Tyr Gly Met Asp Val
1 5 10 15

<210> SEQ ID NO 559
<211> LENGTH: 6
<212> TYPE: PRT
<213> ORGANISM: Homo sapiens

<400> SEQUENCE: 559

Asn Ile Gly Gly Lys Ser
1 5

<210> SEQ ID NO 560
<211> LENGTH: 11
<212> TYPE: PRT
<213> ORGANISM: Homo sapiens

<400> SEQUENCE: 560

Gln Val Trp Asp Thr Thr Ser Asp Gln Leu Val
1 5 10

<210> SEQ ID NO 561
<211> LENGTH: 8
<212> TYPE: PRT
<213> ORGANISM: Homo sapiens

<400> SEQUENCE: 561

Gly Phe Arg Phe Thr Gly Tyr Gly
1 5

<210> SEQ ID NO 562
<211> LENGTH: 8
<212> TYPE: PRT
<213> ORGANISM: Homo sapiens

<400> SEQUENCE: 562

Ile Ser Asn Asp Gly Ser Lys Lys
1 5

<210> SEQ ID NO 563
<211> LENGTH: 16
<212> TYPE: PRT
<213> ORGANISM: Homo sapiens

<400> SEQUENCE: 563

Ala Lys Asp Gly Tyr Leu Ser Ala Ala Arg Gly Tyr Gly Met Asp Val
1 5 10 15

<210> SEQ ID NO 564
<211> LENGTH: 9
<212> TYPE: PRT
<213> ORGANISM: Homo sapiens

<400> SEQUENCE: 564

Ser Ser Asp Val Gly Ser Tyr Asn Arg
1 5

<210> SEQ ID NO 565
<211> LENGTH: 10
<212> TYPE: PRT
<213> ORGANISM: Homo sapiens

<400> SEQUENCE: 565

Ser Ser Tyr Thr Ser Ser Ser Thr Leu Val
1 5 10

<210> SEQ ID NO 566
<211> LENGTH: 8
<212> TYPE: PRT
<213> ORGANISM: Homo sapiens

<400> SEQUENCE: 566

Gly Phe Thr Phe Arg Ser Tyr Gly
1 5

<210> SEQ ID NO 567
<211> LENGTH: 8
<212> TYPE: PRT
<213> ORGANISM: Homo sapiens

<400> SEQUENCE: 567

Ile Ser Ser Asp Gly Ser Lys Lys
1 5

<210> SEQ ID NO 568
<211> LENGTH: 16
<212> TYPE: PRT
<213> ORGANISM: Homo sapiens

<400> SEQUENCE: 568

Ala Lys Asp Pro Ile Lys Val Ser Ala Asn Gly Trp Gly Phe Asp Tyr
1 5 10 15

<210> SEQ ID NO 569
<211> LENGTH: 6
<212> TYPE: PRT
<213> ORGANISM: Homo sapiens

<400> SEQUENCE: 569

Asn Ile Gly Ser Lys Ser
1 5

<210> SEQ ID NO 570
<211> LENGTH: 11
<212> TYPE: PRT
<213> ORGANISM: Homo sapiens

<400> SEQUENCE: 570

Gln Val Trp Asp Ser Asn Ser Asp His Val Val
1 5 10

<210> SEQ ID NO 571
<211> LENGTH: 8

<212> TYPE: PRT
<213> ORGANISM: Homo sapiens

<400> SEQUENCE: 571

Gly Phe Arg Phe Thr Gly Tyr Gly
1 5

<210> SEQ ID NO 572
<211> LENGTH: 8
<212> TYPE: PRT
<213> ORGANISM: Homo sapiens

<400> SEQUENCE: 572

Ile Ser Asn Asp Gly Ser Arg Lys
1 5

<210> SEQ ID NO 573
<211> LENGTH: 16
<212> TYPE: PRT
<213> ORGANISM: Homo sapiens

<400> SEQUENCE: 573

Ala Lys Asp Gly Tyr Leu Ser Ala Ala Arg Gly Phe Gly Met Asp Val
1 5 10 15

<210> SEQ ID NO 574
<211> LENGTH: 6
<212> TYPE: PRT
<213> ORGANISM: Homo sapiens

<400> SEQUENCE: 574

Asn Ile Gly Gly Lys Ser
1 5

<210> SEQ ID NO 575
<211> LENGTH: 11
<212> TYPE: PRT
<213> ORGANISM: Homo sapiens

<400> SEQUENCE: 575

Gln Val Trp Asp Thr Thr Ser Asp Gln Leu Val
1 5 10

<210> SEQ ID NO 576
<211> LENGTH: 8
<212> TYPE: PRT
<213> ORGANISM: Homo sapiens

<400> SEQUENCE: 576

Arg Phe Ser Phe Ser Thr Tyr Gly
1 5

<210> SEQ ID NO 577
<211> LENGTH: 8
<212> TYPE: PRT
<213> ORGANISM: Homo sapiens

<400> SEQUENCE: 577

Ile Ser Tyr Asp Gly Ser Glu Lys
1 5

<210> SEQ ID NO 578
<211> LENGTH: 16
<212> TYPE: PRT
<213> ORGANISM: Homo sapiens

<400> SEQUENCE: 578

Ala Lys Thr Asp Ile Met Trp Arg Ala Val Asn Tyr Gly Met Asp Val
1 5 10 15

<210> SEQ ID NO 579
<211> LENGTH: 6
<212> TYPE: PRT
<213> ORGANISM: Homo sapiens

<400> SEQUENCE: 579

Asn Ile Gly Ser Lys Ser
1 5

<210> SEQ ID NO 580
<211> LENGTH: 12
<212> TYPE: PRT
<213> ORGANISM: Homo sapiens

<400> SEQUENCE: 580

Gln Val Trp Asp Asp Ser Arg Asp His Leu Val Ile
1 5 10

<210> SEQ ID NO 581
<211> LENGTH: 8
<212> TYPE: PRT
<213> ORGANISM: Homo sapiens

<400> SEQUENCE: 581

Arg Phe Ser Phe Ser Thr Tyr Gly
1 5

<210> SEQ ID NO 582
<211> LENGTH: 8
<212> TYPE: PRT
<213> ORGANISM: Homo sapiens

<400> SEQUENCE: 582

Ile Ser Tyr Asp Gly Ser Glu Lys
1 5

<210> SEQ ID NO 583
<211> LENGTH: 16
<212> TYPE: PRT
<213> ORGANISM: Homo sapiens

<400> SEQUENCE: 583

Ala Lys Thr Asp Ile Met Trp Arg Ala Val Asn Tyr Gly Met Asp Val
1 5 10 15

<210> SEQ ID NO 584
<211> LENGTH: 6
<212> TYPE: PRT
<213> ORGANISM: Homo sapiens

<400> SEQUENCE: 584

Asn Ile Gly Ser Lys Ser
1 5

<210> SEQ ID NO 585
<211> LENGTH: 12
<212> TYPE: PRT
<213> ORGANISM: Homo sapiens

<400> SEQUENCE: 585

Gln Val Trp Asp Asp Ser Arg Asp His Leu Val Ile
1 5 10

<210> SEQ ID NO 586
<211> LENGTH: 8
<212> TYPE: PRT
<213> ORGANISM: Homo sapiens

<400> SEQUENCE: 586

Gly Phe Ser Phe Ser Thr Tyr Gly
1 5

<210> SEQ ID NO 587
<211> LENGTH: 8
<212> TYPE: PRT
<213> ORGANISM: Homo sapiens

<400> SEQUENCE: 587

Ile Ser Tyr Asp Gly Ser Ser Lys
1 5

<210> SEQ ID NO 588
<211> LENGTH: 16
<212> TYPE: PRT
<213> ORGANISM: Homo sapiens

<400> SEQUENCE: 588

Ala Lys Thr Asp Ile Met Trp Gln Ala Val Asn Tyr Gly Met Asp Val
1 5 10 15

<210> SEQ ID NO 589
<211> LENGTH: 6
<212> TYPE: PRT
<213> ORGANISM: Homo sapiens

<400> SEQUENCE: 589

Asn Ile Gly Ser Lys Ser
1 5

<210> SEQ ID NO 590
<211> LENGTH: 12
<212> TYPE: PRT
<213> ORGANISM: Homo sapiens

<400> SEQUENCE: 590

Gln Val Trp Asp Asp Ser Arg Asp His Leu Val Ile
1 5 10

<210> SEQ ID NO 591
<211> LENGTH: 8
<212> TYPE: PRT
<213> ORGANISM: Homo sapiens

<400> SEQUENCE: 591

Gly Phe Arg Phe Thr Gly Tyr Gly
1 5

<210> SEQ ID NO 592
<211> LENGTH: 8
<212> TYPE: PRT
<213> ORGANISM: Homo sapiens

<400> SEQUENCE: 592

Ile Ser Asn Asp Gly Ser Lys Lys 1 5

<210> SEQ ID NO 593
<211> LENGTH: 16
<212> TYPE: PRT
<213> ORGANISM: Homo sapiens

<400> SEQUENCE: 593

Ala Lys Asp Gly Tyr Leu Ser Ala Ala Arg Gly Tyr Gly Met Asp Val
1 5 10 15

<210> SEQ ID NO 594
<211> LENGTH: 6
<212> TYPE: PRT
<213> ORGANISM: Homo sapiens

<400> SEQUENCE: 594

Asn Ile Gly Gly Lys Ser
1 5

<210> SEQ ID NO 595
<211> LENGTH: 11
<212> TYPE: PRT
<213> ORGANISM: Homo sapiens

<400> SEQUENCE: 595

Gln Val Trp Asp Thr Thr Ser Asp Gln Leu Val
1 5 10

<210> SEQ ID NO 596
<211> LENGTH: 8
<212> TYPE: PRT
<213> ORGANISM: Homo sapiens

<400> SEQUENCE: 596

Arg Phe Ser Phe Ser Thr Tyr Gly
1 5

<210> SEQ ID NO 597
<211> LENGTH: 8
<212> TYPE: PRT
<213> ORGANISM: Homo sapiens

<400> SEQUENCE: 597

Ile Ser Tyr Asp Gly Ser Glu Lys
1 5

<210> SEQ ID NO 598
<211> LENGTH: 16
<212> TYPE: PRT
<213> ORGANISM: Homo sapiens

<400> SEQUENCE: 598

Ala Lys Thr Asp Ile Met Trp Arg Ala Val Asn Tyr Gly Met Asp Val
1 5 10 15

<210> SEQ ID NO 599
<211> LENGTH: 6
<212> TYPE: PRT
<213> ORGANISM: Homo sapiens

<400> SEQUENCE: 599

Asn Ile Gly Ser Lys Ser
1 5

<210> SEQ ID NO 600
<211> LENGTH: 12
<212> TYPE: PRT
<213> ORGANISM: Homo sapiens

<400> SEQUENCE: 600

Gln Val Trp Asp Glu Ser Arg Asp His Leu Val Ile
1 5 10

<210> SEQ ID NO 601
<211> LENGTH: 8
<212> TYPE: PRT
<213> ORGANISM: Homo sapiens

<400> SEQUENCE: 601

Gly Phe Arg Phe Thr Gly Tyr Gly
1 5

<210> SEQ ID NO 602
<211> LENGTH: 8
<212> TYPE: PRT
<213> ORGANISM: Homo sapiens

<400> SEQUENCE: 602

Ile Ser Asn Asp Gly Ser Lys Lys
1 5

<210> SEQ ID NO 603
<211> LENGTH: 16
<212> TYPE: PRT
<213> ORGANISM: Homo sapiens

<400> SEQUENCE: 603

Ala Lys Asp Gly Tyr Leu Ser Ala Ala Arg Gly Tyr Gly Met Asp Val
1 5 10 15

<210> SEQ ID NO 604
<211> LENGTH: 6
<212> TYPE: PRT
<213> ORGANISM: Homo sapiens

<400> SEQUENCE: 604

Asn Ile Gly Gly Lys Ser
1 5

<210> SEQ ID NO 605
<211> LENGTH: 11
<212> TYPE: PRT
<213> ORGANISM: Homo sapiens

<400> SEQUENCE: 605

Gln Val Trp Asp Thr Thr Ser Asp Gln Leu Val
1 5 10

<210> SEQ ID NO 606
<211> LENGTH: 8
<212> TYPE: PRT
<213> ORGANISM: Homo sapiens

<400> SEQUENCE: 606

Gly Phe Arg Phe Thr Met Tyr Gly
1 5

<210> SEQ ID NO 607

<211> LENGTH: 8
<212> TYPE: PRT
<213> ORGANISM: Homo sapiens

<400> SEQUENCE: 607

Ile Pro Phe Asp Gly Arg Thr Gln
1               5

<210> SEQ ID NO 608
<211> LENGTH: 17
<212> TYPE: PRT
<213> ORGANISM: Homo sapiens

<400> SEQUENCE: 608

Ala Lys Asp Gly Ile Leu Gly Ala Arg Arg Gly Leu Tyr Gly Ile Asp
1               5                   10                  15

Val

<210> SEQ ID NO 609
<211> LENGTH: 6
<212> TYPE: PRT
<213> ORGANISM: Homo sapiens

<400> SEQUENCE: 609

Asp Val Gly Ser Lys Ser
1               5

<210> SEQ ID NO 610
<211> LENGTH: 11
<212> TYPE: PRT
<213> ORGANISM: Homo sapiens

<400> SEQUENCE: 610

Gln Val Trp Asp Ser Ser Ser Asp His Val Val
1               5                   10

<210> SEQ ID NO 611
<211> LENGTH: 8
<212> TYPE: PRT
<213> ORGANISM: Homo sapiens

<400> SEQUENCE: 611

Gly Phe Thr Phe Asn Asn Tyr Ala
1               5

<210> SEQ ID NO 612
<211> LENGTH: 8
<212> TYPE: PRT
<213> ORGANISM: Homo sapiens

<400> SEQUENCE: 612

Ile Ser Tyr Asp Gly Ser Asn Lys
1               5

<210> SEQ ID NO 613
<211> LENGTH: 24
<212> TYPE: PRT
<213> ORGANISM: Homo sapiens

<400> SEQUENCE: 613

Ala Lys Glu Ile Gly Gly Phe Asp Phe Arg Ser Gly Ser Gln Arg Ser
1               5                   10                  15

Tyr Tyr Tyr Tyr Gly Val Asp Val
            20

<210> SEQ ID NO 614
<211> LENGTH: 7
<212> TYPE: PRT
<213> ORGANISM: Homo sapiens

<400> SEQUENCE: 614

Gln Thr Ile Tyr Thr Thr Tyr
1 5

<210> SEQ ID NO 615
<211> LENGTH: 11
<212> TYPE: PRT
<213> ORGANISM: Homo sapiens

<400> SEQUENCE: 615

Gln Gln Tyr Ser Ser Ser Pro Pro Gly Tyr Thr
1 5 10

<210> SEQ ID NO 616
<211> LENGTH: 8
<212> TYPE: PRT
<213> ORGANISM: Homo sapiens

<400> SEQUENCE: 616

Gly Phe Thr Phe Ser Arg His Gly
1 5

<210> SEQ ID NO 617
<211> LENGTH: 8
<212> TYPE: PRT
<213> ORGANISM: Homo sapiens

<400> SEQUENCE: 617

Ile Ser Tyr Asp Gly Gly Asn Lys
1 5

<210> SEQ ID NO 618
<211> LENGTH: 24
<212> TYPE: PRT
<213> ORGANISM: Homo sapiens

<400> SEQUENCE: 618

Ala Lys Glu Ile Gly Gly Phe Asp Phe Arg Ser Gly Asp Gln Leu Thr
1 5 10 15

Tyr Tyr Tyr Tyr Gly Met Asp Val
20

<210> SEQ ID NO 619
<211> LENGTH: 7
<212> TYPE: PRT
<213> ORGANISM: Homo sapiens

<400> SEQUENCE: 619

Gln Ser Val Tyr Ser Thr Tyr
1 5

<210> SEQ ID NO 620
<211> LENGTH: 11
<212> TYPE: PRT
<213> ORGANISM: Homo sapiens

<400> SEQUENCE: 620

His Gln Tyr Val Thr Ser Pro Pro Gly Tyr Thr 1 5 10

<210> SEQ ID NO 621
<211> LENGTH: 8
<212> TYPE: PRT
<213> ORGANISM: Homo sapiens

<400> SEQUENCE: 621

Gly Phe Ser Phe Ser Asn Tyr Gly
1 5

<210> SEQ ID NO 622
<211> LENGTH: 8
<212> TYPE: PRT
<213> ORGANISM: Homo sapiens

<400> SEQUENCE: 622

Ile Ser Tyr Asp Gly Ser Asn Lys
1 5

<210> SEQ ID NO 623
<211> LENGTH: 17
<212> TYPE: PRT
<213> ORGANISM: Homo sapiens

<400> SEQUENCE: 623

Ala Lys Asp Ala Tyr Ile Tyr Ala Arg Gly Ser Tyr Tyr Gly Met Asp
1 5 10 15

Val

<210> SEQ ID NO 624
<211> LENGTH: 6
<212> TYPE: PRT
<213> ORGANISM: Homo sapiens

<400> SEQUENCE: 624

Asn Ile Ala Ser Lys Ser
1 5

<210> SEQ ID NO 625
<211> LENGTH: 12
<212> TYPE: PRT
<213> ORGANISM: Homo sapiens

<400> SEQUENCE: 625

Gln Val Trp Asp Ser Ser Ser Asn Asp Pro Val Val
1 5 10

<210> SEQ ID NO 626
<211> LENGTH: 8
<212> TYPE: PRT
<213> ORGANISM: Homo sapiens

<400> SEQUENCE: 626

Gly Phe Arg Phe Thr Lys Tyr Gly
1 5

<210> SEQ ID NO 627
<211> LENGTH: 8
<212> TYPE: PRT
<213> ORGANISM: Homo sapiens

<400> SEQUENCE: 627

Ile Ser Phe Asp Gly Ser Thr Gln 1               5

<210> SEQ ID NO 628
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Any amino acid

<400> SEQUENCE: 628

Ala Lys Asp Gly Ile Leu Gly Ala Arg Arg Gly Xaa Tyr Gly Ile Asp
1               5                   10                  15

Val

<210> SEQ ID NO 629
<211> LENGTH: 6
<212> TYPE: PRT
<213> ORGANISM: Homo sapiens

<400> SEQUENCE: 629

Asn Ile Arg Ser Lys Asn
1               5

<210> SEQ ID NO 630
<211> LENGTH: 11
<212> TYPE: PRT
<213> ORGANISM: Homo sapiens

<400> SEQUENCE: 630

Gln Val Trp Asp Ser Tyr Ser Asp His Val Val
1               5                   10

<210> SEQ ID NO 631
<211> LENGTH: 8
<212> TYPE: PRT
<213> ORGANISM: Homo sapiens

<400> SEQUENCE: 631

Gly Phe Thr Phe Ser Asn Tyr Ala
1               5

<210> SEQ ID NO 632
<211> LENGTH: 8
<212> TYPE: PRT
<213> ORGANISM: Homo sapiens

<400> SEQUENCE: 632

Ile Ser Phe Asp Gly Ser Asn Lys
1               5

<210> SEQ ID NO 633
<211> LENGTH: 24
<212> TYPE: PRT
<213> ORGANISM: Homo sapiens

<400> SEQUENCE: 633

Ala Lys Glu Ile Gly Gly Phe Asp Phe Arg Ser Gly Lys Gln Arg Ser
1               5                   10                  15

Tyr Tyr Tyr Tyr Gly Val Asp Val
            20

<210> SEQ ID NO 634

<211> LENGTH: 7
<212> TYPE: PRT
<213> ORGANISM: Homo sapiens

<400> SEQUENCE: 634

Gln Thr Val Tyr Asn Thr Tyr
1 5

<210> SEQ ID NO 635
<211> LENGTH: 11
<212> TYPE: PRT
<213> ORGANISM: Homo sapiens

<400> SEQUENCE: 635

Gln Gln Tyr Gly Asn Ser Pro Pro Gly Tyr Thr
1 5 10

<210> SEQ ID NO 636
<211> LENGTH: 8
<212> TYPE: PRT
<213> ORGANISM: Homo sapiens

<400> SEQUENCE: 636

Gly Phe Arg Phe Thr Ile Tyr Gly
1 5

<210> SEQ ID NO 637
<211> LENGTH: 8
<212> TYPE: PRT
<213> ORGANISM: Homo sapiens

<400> SEQUENCE: 637

Val Ser Tyr Asp Gly Ser Lys Gln
1 5

<210> SEQ ID NO 638
<211> LENGTH: 17
<212> TYPE: PRT
<213> ORGANISM: Homo sapiens

<400> SEQUENCE: 638

Ala Lys Asp Ala Tyr Tyr Tyr Gly Ser Gly Ser His Asn Asn Pro Asp
1 5 10 15

Tyr

<210> SEQ ID NO 639
<211> LENGTH: 6
<212> TYPE: PRT
<213> ORGANISM: Homo sapiens

<400> SEQUENCE: 639

Asn Ile Gly Ser Gln Ser
1 5

<210> SEQ ID NO 640
<211> LENGTH: 10
<212> TYPE: PRT
<213> ORGANISM: Homo sapiens

<400> SEQUENCE: 640

Gln Val Trp Asp Ser Ser Ser Met Gly Val
1 5 10

<210> SEQ ID NO 641

<211> LENGTH: 8
<212> TYPE: PRT
<213> ORGANISM: Homo sapiens

<400> SEQUENCE: 641

Gly Phe Thr Phe Ser Asn Tyr Gly
1 5

<210> SEQ ID NO 642
<211> LENGTH: 8
<212> TYPE: PRT
<213> ORGANISM: Homo sapiens

<400> SEQUENCE: 642

Ile Ser Tyr Asp Gly Arg Asp Lys
1 5

<210> SEQ ID NO 643
<211> LENGTH: 19
<212> TYPE: PRT
<213> ORGANISM: Homo sapiens

<400> SEQUENCE: 643

Ala Lys Gly Tyr Asp Tyr Ile Trp Gly Thr Tyr Arg Pro Arg Pro Asp
1 5 10 15

Leu Asp Ser

<210> SEQ ID NO 644
<211> LENGTH: 8
<212> TYPE: PRT
<213> ORGANISM: Homo sapiens

<400> SEQUENCE: 644

Asn Ser Asn Val Gly Asn Asn Val
1 5

<210> SEQ ID NO 645
<211> LENGTH: 12
<212> TYPE: PRT
<213> ORGANISM: Homo sapiens

<400> SEQUENCE: 645

Ala Ser Trp Asp Asp Ser Leu Ser Gly Ser Trp Val
1 5 10

<210> SEQ ID NO 646
<211> LENGTH: 8
<212> TYPE: PRT
<213> ORGANISM: Homo sapiens

<400> SEQUENCE: 646

Gly Phe Thr Phe Ser Asp Tyr Gly
1 5

<210> SEQ ID NO 647
<211> LENGTH: 8
<212> TYPE: PRT
<213> ORGANISM: Homo sapiens

<400> SEQUENCE: 647

Val Ser Tyr Asp Gly Thr Ser Glu
1 5

<210> SEQ ID NO 648

<211> LENGTH: 15
<212> TYPE: PRT
<213> ORGANISM: Homo sapiens

<400> SEQUENCE: 648

Ala Lys Asp Pro Val Gln Arg Ser Asn Trp Tyr Tyr Phe Asp Tyr
1 5 10 15

<210> SEQ ID NO 649
<211> LENGTH: 6
<212> TYPE: PRT
<213> ORGANISM: Homo sapiens

<400> SEQUENCE: 649

Asn Ile Gly Ser Lys Thr
1 5

<210> SEQ ID NO 650
<211> LENGTH: 11
<212> TYPE: PRT
<213> ORGANISM: Homo sapiens

<400> SEQUENCE: 650

Gln Val Trp His Ser Thr Thr Glu Pro Val Val
1 5 10

<210> SEQ ID NO 651
<211> LENGTH: 8
<212> TYPE: PRT
<213> ORGANISM: Homo sapiens

<400> SEQUENCE: 651

Gly Phe Thr Phe Ser Asn Tyr Gly
1 5

<210> SEQ ID NO 652
<211> LENGTH: 8
<212> TYPE: PRT
<213> ORGANISM: Homo sapiens

<400> SEQUENCE: 652

Thr Ser Tyr Asp Gly Ile Asn Lys
1 5

<210> SEQ ID NO 653
<211> LENGTH: 15
<212> TYPE: PRT
<213> ORGANISM: Homo sapiens

<400> SEQUENCE: 653

Ala Lys Asp Pro Val His Arg Ser Asn Trp Phe Tyr Phe Asp His
1 5 10 15

<210> SEQ ID NO 654
<211> LENGTH: 6
<212> TYPE: PRT
<213> ORGANISM: Homo sapiens

<400> SEQUENCE: 654

Tyr Ile Gly Ser Lys Thr
1 5

<210> SEQ ID NO 655
<211> LENGTH: 11
<212> TYPE: PRT

<213> ORGANISM: Homo sapiens

<400> SEQUENCE: 655

Gln Val Trp Tyr Ser Asn Ser Glu Pro Val Val
1 5 10

<210> SEQ ID NO 656
<211> LENGTH: 8
<212> TYPE: PRT
<213> ORGANISM: Homo sapiens

<400> SEQUENCE: 656

Gly Thr Ser Phe Ser Thr Ser Gly
1 5

<210> SEQ ID NO 657
<211> LENGTH: 8
<212> TYPE: PRT
<213> ORGANISM: Homo sapiens

<400> SEQUENCE: 657

Ile Ser Pro Asn Ala Phe Asp Lys
1 5

<210> SEQ ID NO 658
<211> LENGTH: 14
<212> TYPE: PRT
<213> ORGANISM: Homo sapiens

<400> SEQUENCE: 658

Ala Lys Gly Ser Pro Ile Ile Arg Phe Leu Met Met Asp Val
1 5 10

<210> SEQ ID NO 659
<211> LENGTH: 6
<212> TYPE: PRT
<213> ORGANISM: Homo sapiens

<400> SEQUENCE: 659

Gln Ser Ile Asp Thr Trp
1 5

<210> SEQ ID NO 660
<211> LENGTH: 8
<212> TYPE: PRT
<213> ORGANISM: Homo sapiens

<400> SEQUENCE: 660

Gln Tyr Tyr Ser Val Tyr Ser Thr
1 5

<210> SEQ ID NO 661
<211> LENGTH: 6
<212> TYPE: PRT
<213> ORGANISM: Homo sapiens

<400> SEQUENCE: 661

Asn Ile Gly Ser Lys Asn
1 5

<210> SEQ ID NO 662
<211> LENGTH: 11
<212> TYPE: PRT
<213> ORGANISM: Homo sapiens

<400> SEQUENCE: 662

Gln Val Trp Asp Asn Asn Ser Asp His Val Val
1 5 10

<210> SEQ ID NO 663
<211> LENGTH: 8
<212> TYPE: PRT
<213> ORGANISM: Homo sapiens

<400> SEQUENCE: 663

Gly Phe Thr Phe Ser Ser Tyr Gly
1 5

<210> SEQ ID NO 664
<211> LENGTH: 8
<212> TYPE: PRT
<213> ORGANISM: Homo sapiens

<400> SEQUENCE: 664

Ile Trp Ser Asp Gly Ser Asn Lys
1 5

<210> SEQ ID NO 665
<211> LENGTH: 14
<212> TYPE: PRT
<213> ORGANISM: Homo sapiens

<400> SEQUENCE: 665

Ala Arg Glu Ala Gly Ile Ala Ala Pro Ala Ser Leu Asp Phe
1 5 10

<210> SEQ ID NO 666
<211> LENGTH: 6
<212> TYPE: PRT
<213> ORGANISM: Homo sapiens

<400> SEQUENCE: 666

Asn Ile Arg Gly Lys Ser
1 5

<210> SEQ ID NO 667
<211> LENGTH: 11
<212> TYPE: PRT
<213> ORGANISM: Homo sapiens

<400> SEQUENCE: 667

Gln Val Trp Asp Ser Ser Ser Asp His Val Val
1 5 10

<210> SEQ ID NO 668
<211> LENGTH: 8
<212> TYPE: PRT
<213> ORGANISM: Homo sapiens

<400> SEQUENCE: 668

Gly Phe Thr Phe Ser Asn Tyr Gly
1 5

<210> SEQ ID NO 669
<211> LENGTH: 8
<212> TYPE: PRT
<213> ORGANISM: Homo sapiens

<400> SEQUENCE: 669

Ile Trp Ser Asp Gly Thr Asn Lys
1 5

<210> SEQ ID NO 670
<211> LENGTH: 14
<212> TYPE: PRT
<213> ORGANISM: Homo sapiens

<400> SEQUENCE: 670

Thr Arg Glu Ala Gly Ile Ala Ala Pro Ala Ala Leu Asp Tyr
1 5 10

<210> SEQ ID NO 671
<211> LENGTH: 6
<212> TYPE: PRT
<213> ORGANISM: Homo sapiens

<400> SEQUENCE: 671

Asn Ile Gly Asn Lys Asn
1 5

<210> SEQ ID NO 672
<211> LENGTH: 11
<212> TYPE: PRT
<213> ORGANISM: Homo sapiens

<400> SEQUENCE: 672

Gln Val Trp Asp Ser Ser Ser Tyr His Val Val
1 5 10

<210> SEQ ID NO 673
<211> LENGTH: 8
<212> TYPE: PRT
<213> ORGANISM: Homo sapiens

<400> SEQUENCE: 673

Gly Phe Thr Phe Ser Asn Tyr Gly
1 5

<210> SEQ ID NO 674
<211> LENGTH: 8
<212> TYPE: PRT
<213> ORGANISM: Homo sapiens

<400> SEQUENCE: 674

Val Trp Tyr Asp Gly Ser Tyr Lys
1 5

<210> SEQ ID NO 675
<211> LENGTH: 12
<212> TYPE: PRT
<213> ORGANISM: Homo sapiens

<400> SEQUENCE: 675

Val Arg Asp Asn Trp Ser Tyr Asn Ala Phe Asp Val
1 5 10

<210> SEQ ID NO 676
<211> LENGTH: 6
<212> TYPE: PRT
<213> ORGANISM: Homo sapiens

<400> SEQUENCE: 676

Gln Ser Ile Ser Ser Tyr
1 5

<210> SEQ ID NO 677
<211> LENGTH: 9
<212> TYPE: PRT
<213> ORGANISM: Homo sapiens

<400> SEQUENCE: 677

Gln His Arg Asn Ser Trp Pro Tyr Ser
1               5

<210> SEQ ID NO 678
<211> LENGTH: 8
<212> TYPE: PRT
<213> ORGANISM: Homo sapiens

<400> SEQUENCE: 678

Gly Phe Ile Phe Ser Asp Tyr Gly
1               5

<210> SEQ ID NO 679
<211> LENGTH: 8
<212> TYPE: PRT
<213> ORGANISM: Homo sapiens

<400> SEQUENCE: 679

Ile Trp Lys Asp Gly Ser Asn Lys
1               5

<210> SEQ ID NO 680
<211> LENGTH: 12
<212> TYPE: PRT
<213> ORGANISM: Homo sapiens

<400> SEQUENCE: 680

Val Arg Glu Asn Ser Gly Trp Tyr Tyr Phe Asp Tyr
1               5                   10

<210> SEQ ID NO 681
<211> LENGTH: 6
<212> TYPE: PRT
<213> ORGANISM: Homo sapiens

<400> SEQUENCE: 681

Gln Gly Ile Arg Asn Asn
1               5

<210> SEQ ID NO 682
<211> LENGTH: 9
<212> TYPE: PRT
<213> ORGANISM: Homo sapiens

<400> SEQUENCE: 682

Leu Gln His Asp Ser Tyr Pro Phe Thr
1               5

<210> SEQ ID NO 683
<211> LENGTH: 8
<212> TYPE: PRT
<213> ORGANISM: Homo sapiens

<400> SEQUENCE: 683

Gly Phe Ala Phe Arg Ser Tyr Gly
1               5

<210> SEQ ID NO 684
<211> LENGTH: 8
<212> TYPE: PRT
<213> ORGANISM: Homo sapiens

<400> SEQUENCE: 684

Ile Trp His Asp Gly Ser Asn Lys
1 5

<210> SEQ ID NO 685
<211> LENGTH: 14
<212> TYPE: PRT
<213> ORGANISM: Homo sapiens

<400> SEQUENCE: 685

Ala Arg Glu Gly Ala Ile Ala Ala Pro Ala Ser Leu Asp Val
1 5 10

<210> SEQ ID NO 686
<211> LENGTH: 6
<212> TYPE: PRT
<213> ORGANISM: Homo sapiens

<400> SEQUENCE: 686

Asn Ile Arg Ser Arg Asn
1 5

<210> SEQ ID NO 687
<211> LENGTH: 11
<212> TYPE: PRT
<213> ORGANISM: Homo sapiens

<400> SEQUENCE: 687

Gln Val Trp Asp Ser Gly Thr Asp His Val Ile
1 5 10

<210> SEQ ID NO 688
<211> LENGTH: 8
<212> TYPE: PRT
<213> ORGANISM: Homo sapiens

<400> SEQUENCE: 688

Gly Phe Thr Phe Ser Ser Phe Gly
1 5

<210> SEQ ID NO 689
<211> LENGTH: 8
<212> TYPE: PRT
<213> ORGANISM: Homo sapiens

<400> SEQUENCE: 689

Ile Trp Ser Asp Gly Ser Asn Gln
1 5

<210> SEQ ID NO 690
<211> LENGTH: 14
<212> TYPE: PRT
<213> ORGANISM: Homo sapiens

<400> SEQUENCE: 690

Ala Arg Glu Gly Gly Ile Ala Ala Pro Ala Ala Leu Asp Phe
1 5 10

<210> SEQ ID NO 691
<211> LENGTH: 6

<212> TYPE: PRT
<213> ORGANISM: Homo sapiens

<400> SEQUENCE: 691

Asn Ile Arg Asn Lys Asn
1 5

<210> SEQ ID NO 692
<211> LENGTH: 11
<212> TYPE: PRT
<213> ORGANISM: Homo sapiens

<400> SEQUENCE: 692

Gln Val Trp Asp Gly Gly Ser Tyr His Val Ile
1 5 10

<210> SEQ ID NO 693
<211> LENGTH: 8
<212> TYPE: PRT
<213> ORGANISM: Homo sapiens

<400> SEQUENCE: 693

Gly Val Thr Phe Asn Ser Tyr Gly
1 5

<210> SEQ ID NO 694
<211> LENGTH: 8
<212> TYPE: PRT
<213> ORGANISM: Homo sapiens

<400> SEQUENCE: 694

Ile Trp Tyr Asp Gly Thr Asn Lys
1 5

<210> SEQ ID NO 695
<211> LENGTH: 13
<212> TYPE: PRT
<213> ORGANISM: Homo sapiens

<400> SEQUENCE: 695

Ala Arg Glu Ser Lys Ala Tyr Pro Tyr Tyr Phe Asp Tyr
1 5 10

<210> SEQ ID NO 696
<211> LENGTH: 6
<212> TYPE: PRT
<213> ORGANISM: Homo sapiens

<400> SEQUENCE: 696

Gln Asn Ile Ser Ile Phe
1 5

<210> SEQ ID NO 697
<211> LENGTH: 10
<212> TYPE: PRT
<213> ORGANISM: Homo sapiens

<400> SEQUENCE: 697

Gln His Ser Ser Phe Pro Pro Gln Asp Ser
1 5 10

<210> SEQ ID NO 698
<211> LENGTH: 8
<212> TYPE: PRT
<213> ORGANISM: Homo sapiens

<400> SEQUENCE: 698

Gly Phe Thr Phe Ser Asn Tyr Ala
1               5

<210> SEQ ID NO 699
<211> LENGTH: 8
<212> TYPE: PRT
<213> ORGANISM: Homo sapiens

<400> SEQUENCE: 699

Ile Trp Tyr Asp Gly Thr Tyr Lys
1               5

<210> SEQ ID NO 700
<211> LENGTH: 11
<212> TYPE: PRT
<213> ORGANISM: Homo sapiens

<400> SEQUENCE: 700

Ala Arg Glu Ser Asn Gly Phe Gly Ser Asp Phe
1               5                   10

<210> SEQ ID NO 701
<211> LENGTH: 6
<212> TYPE: PRT
<213> ORGANISM: Homo sapiens

<400> SEQUENCE: 701

Gln Gly Ile Arg Asn Asn
1               5

<210> SEQ ID NO 702
<211> LENGTH: 9
<212> TYPE: PRT
<213> ORGANISM: Homo sapiens

<400> SEQUENCE: 702

Leu Gln His Asn Ser Phe Pro Arg Thr
1               5

<210> SEQ ID NO 703
<211> LENGTH: 8
<212> TYPE: PRT
<213> ORGANISM: Homo sapiens

<400> SEQUENCE: 703

Gly Phe Val Phe Ser Ser Tyr Gly
1               5

<210> SEQ ID NO 704
<211> LENGTH: 8
<212> TYPE: PRT
<213> ORGANISM: Homo sapiens

<400> SEQUENCE: 704

Val Trp Tyr Asp Gly Ser Tyr Lys
1               5

<210> SEQ ID NO 705
<211> LENGTH: 12
<212> TYPE: PRT
<213> ORGANISM: Homo sapiens

<400> SEQUENCE: 705

```
Val Arg Asp Asn Trp Ser Tyr Asn Ala Phe Asp Ile
1               5                   10


<210> SEQ ID NO 706
<211> LENGTH: 6
<212> TYPE: PRT
<213> ORGANISM: Homo sapiens

<400> SEQUENCE: 706

Gln Ser Ile Ser Ser Tyr
1               5


<210> SEQ ID NO 707
<211> LENGTH: 9
<212> TYPE: PRT
<213> ORGANISM: Homo sapiens

<400> SEQUENCE: 707

Gln His Arg Asn Ser Trp Pro Tyr Ser
1               5


<210> SEQ ID NO 708
<211> LENGTH: 8
<212> TYPE: PRT
<213> ORGANISM: Homo sapiens

<400> SEQUENCE: 708

Gly Phe Thr Phe Ser Asn Tyr Gly
1               5


<210> SEQ ID NO 709
<211> LENGTH: 8
<212> TYPE: PRT
<213> ORGANISM: Homo sapiens

<400> SEQUENCE: 709

Ile Trp Tyr Asp Gly Ser Tyr Lys
1               5


<210> SEQ ID NO 710
<211> LENGTH: 12
<212> TYPE: PRT
<213> ORGANISM: Homo sapiens

<400> SEQUENCE: 710

Ala Arg Asp Asn Trp Lys Tyr Asn Ala Phe Asp Ile
1               5                   10


<210> SEQ ID NO 711
<211> LENGTH: 6
<212> TYPE: PRT
<213> ORGANISM: Homo sapiens

<400> SEQUENCE: 711

Gln Ser Val Ser Ser Tyr
1               5


<210> SEQ ID NO 712
<211> LENGTH: 9
<212> TYPE: PRT
<213> ORGANISM: Homo sapiens

<400> SEQUENCE: 712

Gln His Arg Ser Asn Trp Pro Tyr Ser
```

1 5

<210> SEQ ID NO 713
<211> LENGTH: 8
<212> TYPE: PRT
<213> ORGANISM: Homo sapiens

<400> SEQUENCE: 713

Gly Phe Thr Phe Ser Arg Tyr Gly
1 5

<210> SEQ ID NO 714
<211> LENGTH: 8
<212> TYPE: PRT
<213> ORGANISM: Homo sapiens

<400> SEQUENCE: 714

Ile Trp Ser Asp Gly Ser Asn Gln
1 5

<210> SEQ ID NO 715
<211> LENGTH: 12
<212> TYPE: PRT
<213> ORGANISM: Homo sapiens

<400> SEQUENCE: 715

Ala Arg Glu Ser Ser Gly Trp Tyr Tyr Phe Asp Tyr
1 5 10

<210> SEQ ID NO 716
<211> LENGTH: 9
<212> TYPE: PRT
<213> ORGANISM: Homo sapiens

<400> SEQUENCE: 716

Ser Ser Asp Val Gly Asn Tyr Asn Phe
1 5

<210> SEQ ID NO 717
<211> LENGTH: 11
<212> TYPE: PRT
<213> ORGANISM: Homo sapiens

<400> SEQUENCE: 717

Cys Leu Tyr Ala Gly Ser Ser Ile Ser Tyr Val
1 5 10

<210> SEQ ID NO 718
<211> LENGTH: 8
<212> TYPE: PRT
<213> ORGANISM: Homo sapiens

<400> SEQUENCE: 718

Gly Phe Thr Phe Ser Ser Phe Gly
1 5

<210> SEQ ID NO 719
<211> LENGTH: 8
<212> TYPE: PRT
<213> ORGANISM: Homo sapiens

<400> SEQUENCE: 719

Ile Trp Tyr Asp Gly Ser Asn Glu
1 5

<210> SEQ ID NO 720
<211> LENGTH: 14
<212> TYPE: PRT
<213> ORGANISM: Homo sapiens

<400> SEQUENCE: 720

Ala Arg Glu Glu Arg Ile Ala Ala Pro Ala Ser Leu Asp Leu
1 5 10

<210> SEQ ID NO 721
<211> LENGTH: 6
<212> TYPE: PRT
<213> ORGANISM: Homo sapiens

<400> SEQUENCE: 721

Asn Ile Gly Arg Lys Asn
1 5

<210> SEQ ID NO 722
<211> LENGTH: 11
<212> TYPE: PRT
<213> ORGANISM: Homo sapiens

<400> SEQUENCE: 722

Gln Val Trp Asp Ser Ser Thr Tyr His Val Val
1 5 10

<210> SEQ ID NO 723
<211> LENGTH: 8
<212> TYPE: PRT
<213> ORGANISM: Homo sapiens

<400> SEQUENCE: 723

Gly Phe Thr Phe Ser Ser Tyr Gly
1 5

<210> SEQ ID NO 724
<211> LENGTH: 8
<212> TYPE: PRT
<213> ORGANISM: Homo sapiens

<400> SEQUENCE: 724

Ile Trp His Asp Gly Thr Asn Gln
1 5

<210> SEQ ID NO 725
<211> LENGTH: 14
<212> TYPE: PRT
<213> ORGANISM: Homo sapiens

<400> SEQUENCE: 725

Ala Arg Glu Leu Arg Ile Ala Ala Pro Ala Ala Leu Asp Tyr
1 5 10

<210> SEQ ID NO 726
<211> LENGTH: 6
<212> TYPE: PRT
<213> ORGANISM: Homo sapiens

<400> SEQUENCE: 726

Asn Ile Ala Asn Lys Asn
1 5

<210> SEQ ID NO 727

<211> LENGTH: 11
<212> TYPE: PRT
<213> ORGANISM: Homo sapiens

<400> SEQUENCE: 727

Gln Val Trp Asp Ser Gly Ser Asp His Val Leu
1 5 10

<210> SEQ ID NO 728
<211> LENGTH: 8
<212> TYPE: PRT
<213> ORGANISM: Homo sapiens

<400> SEQUENCE: 728

Gly Phe Thr Phe Ser Ser Phe Asn
1 5

<210> SEQ ID NO 729
<211> LENGTH: 8
<212> TYPE: PRT
<213> ORGANISM: Homo sapiens

<400> SEQUENCE: 729

Ile Trp Tyr Asp Gly Ser His Lys
1 5

<210> SEQ ID NO 730
<211> LENGTH: 11
<212> TYPE: PRT
<213> ORGANISM: Homo sapiens

<400> SEQUENCE: 730

Ala Arg Gln Met Phe Thr Gly His Phe Asp Tyr
1 5 10

<210> SEQ ID NO 731
<211> LENGTH: 6
<212> TYPE: PRT
<213> ORGANISM: Homo sapiens

<400> SEQUENCE: 731

Gln Gly Val Ser Ser Asn
1 5

<210> SEQ ID NO 732
<211> LENGTH: 9
<212> TYPE: PRT
<213> ORGANISM: Homo sapiens

<400> SEQUENCE: 732

Gln His Tyr Asn Asn Trp Pro Arg Thr
1 5

<210> SEQ ID NO 733
<211> LENGTH: 8
<212> TYPE: PRT
<213> ORGANISM: Homo sapiens

<400> SEQUENCE: 733

Gly Phe Thr Phe Ser Gly Tyr Gly
1 5

<210> SEQ ID NO 734
<211> LENGTH: 8
<212> TYPE: PRT

<213> ORGANISM: Homo sapiens

<400> SEQUENCE: 734

Ile Trp Asn Asp Gly Ser Phe Lys
1 5

<210> SEQ ID NO 735
<211> LENGTH: 15
<212> TYPE: PRT
<213> ORGANISM: Homo sapiens

<400> SEQUENCE: 735

Ala Arg Glu Gly Arg Gly Gln Leu Leu Phe His Gly Met Asp Val
1 5 10 15

<210> SEQ ID NO 736
<211> LENGTH: 7
<212> TYPE: PRT
<213> ORGANISM: Homo sapiens

<400> SEQUENCE: 736

Gln Ser Val Ser Ser Ser Tyr
1 5

<210> SEQ ID NO 737
<211> LENGTH: 10
<212> TYPE: PRT
<213> ORGANISM: Homo sapiens

<400> SEQUENCE: 737

Gln Gln Tyr Gly Arg Ser Gln Gly Phe Thr
1 5 10

<210> SEQ ID NO 738
<211> LENGTH: 8
<212> TYPE: PRT
<213> ORGANISM: Homo sapiens

<400> SEQUENCE: 738

Gly Phe Thr Phe Ser Gly His Gly
1 5

<210> SEQ ID NO 739
<211> LENGTH: 8
<212> TYPE: PRT
<213> ORGANISM: Homo sapiens

<400> SEQUENCE: 739

Ile Trp Ser Ser Gly Ser Lys Thr
1 5

<210> SEQ ID NO 740
<211> LENGTH: 17
<212> TYPE: PRT
<213> ORGANISM: Homo sapiens

<400> SEQUENCE: 740

Ala Arg Asp Gly His Cys Asp Gly Gly Cys Tyr Ser Ala Leu Tyr Asp
1 5 10 15

Tyr

<210> SEQ ID NO 741
<211> LENGTH: 9
<212> TYPE: PRT

<213> ORGANISM: Homo sapiens

<400> SEQUENCE: 741

Ser Ser Asp Val Gly Asn Tyr Asn Leu
1 5

<210> SEQ ID NO 742
<211> LENGTH: 9
<212> TYPE: PRT
<213> ORGANISM: Homo sapiens

<400> SEQUENCE: 742

Cys Ser Phe Ala Gly Ser Arg Trp Val
1 5

<210> SEQ ID NO 743
<211> LENGTH: 8
<212> TYPE: PRT
<213> ORGANISM: Homo sapiens

<400> SEQUENCE: 743

Gly Phe Ser Phe Ser Arg His Gly
1 5

<210> SEQ ID NO 744
<211> LENGTH: 8
<212> TYPE: PRT
<213> ORGANISM: Homo sapiens

<400> SEQUENCE: 744

Ile Trp Phe Asp Gly Thr Asn Asp
1 5

<210> SEQ ID NO 745
<211> LENGTH: 14
<212> TYPE: PRT
<213> ORGANISM: Homo sapiens

<400> SEQUENCE: 745

Ala Arg Glu Asp Pro His Leu Leu Ile Ala Thr Leu Asp Leu
1 5 10

<210> SEQ ID NO 746
<211> LENGTH: 6
<212> TYPE: PRT
<213> ORGANISM: Homo sapiens

<400> SEQUENCE: 746

Gln Gly Leu Thr Ser Phe
1 5

<210> SEQ ID NO 747
<211> LENGTH: 10
<212> TYPE: PRT
<213> ORGANISM: Homo sapiens

<400> SEQUENCE: 747

Gln Gln Ser Tyr Gly Thr Pro Ala Leu Ala
1 5 10

<210> SEQ ID NO 748
<211> LENGTH: 8
<212> TYPE: PRT
<213> ORGANISM: Homo sapiens

<400> SEQUENCE: 748

Gly Phe Thr Phe Arg Ser Tyr Gly
1 5

<210> SEQ ID NO 749
<211> LENGTH: 8
<212> TYPE: PRT
<213> ORGANISM: Homo sapiens

<400> SEQUENCE: 749

Ile Trp Ala Asp Gly Thr Lys Gln
1 5

<210> SEQ ID NO 750
<211> LENGTH: 13
<212> TYPE: PRT
<213> ORGANISM: Homo sapiens

<400> SEQUENCE: 750

Ala Arg Glu Thr Thr Ile Phe Asn Trp Tyr Phe Asp Leu
1 5 10

<210> SEQ ID NO 751
<211> LENGTH: 6
<212> TYPE: PRT
<213> ORGANISM: Homo sapiens

<400> SEQUENCE: 751

Gln Ser Ile Asn Lys Tyr
1 5

<210> SEQ ID NO 752
<211> LENGTH: 9
<212> TYPE: PRT
<213> ORGANISM: Homo sapiens

<400> SEQUENCE: 752

Gln Gln Ser Phe Ser Ile Pro Pro Thr
1 5

<210> SEQ ID NO 753
<211> LENGTH: 8
<212> TYPE: PRT
<213> ORGANISM: Homo sapiens

<400> SEQUENCE: 753

Gly Phe Thr Phe Ser Asp Tyr Gly
1 5

<210> SEQ ID NO 754
<211> LENGTH: 8
<212> TYPE: PRT
<213> ORGANISM: Homo sapiens

<400> SEQUENCE: 754

Ile Trp Ser Asp Gly Ser Asn Lys
1 5

<210> SEQ ID NO 755
<211> LENGTH: 14
<212> TYPE: PRT
<213> ORGANISM: Homo sapiens

<400> SEQUENCE: 755

Ala Arg Glu Arg Arg Gly Phe Ser Tyr Gly Leu Asp Asp Asn
1 5 10

<210> SEQ ID NO 756
<211> LENGTH: 9
<212> TYPE: PRT
<213> ORGANISM: Homo sapiens

<400> SEQUENCE: 756

Ser Ser Asp Val Gly Gly Tyr Asn Ser
1 5

<210> SEQ ID NO 757
<211> LENGTH: 11
<212> TYPE: PRT
<213> ORGANISM: Homo sapiens

<400> SEQUENCE: 757

Cys Ser Tyr Ala Gly Arg Tyr Thr Phe Val Val
1 5 10

<210> SEQ ID NO 758
<211> LENGTH: 8
<212> TYPE: PRT
<213> ORGANISM: Homo sapiens

<400> SEQUENCE: 758

Gly Phe Thr Phe Ser Arg Tyr Gly
1 5

<210> SEQ ID NO 759
<211> LENGTH: 8
<212> TYPE: PRT
<213> ORGANISM: Homo sapiens

<400> SEQUENCE: 759

Ile Trp Lys Asp Gly Thr Asn Asp
1 5

<210> SEQ ID NO 760
<211> LENGTH: 14
<212> TYPE: PRT
<213> ORGANISM: Homo sapiens

<400> SEQUENCE: 760

Ala Arg Glu Gln Ala Glu Ile Ala Val Ala Ser Phe Asp Phe
1 5 10

<210> SEQ ID NO 761
<211> LENGTH: 6
<212> TYPE: PRT
<213> ORGANISM: Homo sapiens

<400> SEQUENCE: 761

Gln Arg Ile Gly Asp Phe
1 5

<210> SEQ ID NO 762
<211> LENGTH: 10
<212> TYPE: PRT
<213> ORGANISM: Homo sapiens

<400> SEQUENCE: 762

Gln Gln Ala Tyr Asn Ala Pro Pro Leu Thr
1 5 10

<210> SEQ ID NO 763
<211> LENGTH: 8
<212> TYPE: PRT
<213> ORGANISM: Homo sapiens

<400> SEQUENCE: 763

Gly Phe Thr Phe Ser Asn Tyr Gly
1               5

<210> SEQ ID NO 764
<211> LENGTH: 8
<212> TYPE: PRT
<213> ORGANISM: Homo sapiens

<400> SEQUENCE: 764

Ile Trp Lys Asp Gly Thr Asn Lys
1               5

<210> SEQ ID NO 765
<211> LENGTH: 14
<212> TYPE: PRT
<213> ORGANISM: Homo sapiens

<400> SEQUENCE: 765

Ala Arg Glu Ser His Tyr Ser Ala Trp Tyr Val Leu Asp Tyr
1               5                   10

<210> SEQ ID NO 766
<211> LENGTH: 8
<212> TYPE: PRT
<213> ORGANISM: Homo sapiens

<400> SEQUENCE: 766

Arg Ser Asn Ile Gly Ser Asn Tyr
1               5

<210> SEQ ID NO 767
<211> LENGTH: 11
<212> TYPE: PRT
<213> ORGANISM: Homo sapiens

<400> SEQUENCE: 767

Gly Ser Trp Asp Gly Ser Leu Ser Val Gly Val
1               5                   10

<210> SEQ ID NO 768
<211> LENGTH: 8
<212> TYPE: PRT
<213> ORGANISM: Homo sapiens

<400> SEQUENCE: 768

Gly Phe Thr Phe Ser Arg His Gly
1               5

<210> SEQ ID NO 769
<211> LENGTH: 8
<212> TYPE: PRT
<213> ORGANISM: Homo sapiens

<400> SEQUENCE: 769

Ile Trp Tyr Asp Gly Ser Asn Lys
1               5

<210> SEQ ID NO 770
<211> LENGTH: 14
<212> TYPE: PRT
<213> ORGANISM: Homo sapiens

<400> SEQUENCE: 770

Ala Arg Glu Asp Pro Asn Val Phe Ile Ala Thr Leu Asp Leu
1               5                   10

<210> SEQ ID NO 771
<211> LENGTH: 6
<212> TYPE: PRT
<213> ORGANISM: Homo sapiens

<400> SEQUENCE: 771

Gln Thr Ile Thr Arg Ser
1               5

<210> SEQ ID NO 772
<211> LENGTH: 10
<212> TYPE: PRT
<213> ORGANISM: Homo sapiens

<400> SEQUENCE: 772

Gln Gln Ser Asp Ser Thr Pro Ala Leu Ala
1               5                   10

<210> SEQ ID NO 773
<211> LENGTH: 8
<212> TYPE: PRT
<213> ORGANISM: Homo sapiens

<400> SEQUENCE: 773

Gly Phe Thr Phe Ser Arg Tyr Gly
1               5

<210> SEQ ID NO 774
<211> LENGTH: 8
<212> TYPE: PRT
<213> ORGANISM: Homo sapiens

<400> SEQUENCE: 774

Ile Trp Asn Asp Gly Ser Thr Lys
1               5

<210> SEQ ID NO 775
<211> LENGTH: 14
<212> TYPE: PRT
<213> ORGANISM: Homo sapiens

<400> SEQUENCE: 775

Ala Arg Glu Asp Pro Tyr Val Phe Met Ala Thr Leu Asp Ser
1               5                   10

<210> SEQ ID NO 776
<211> LENGTH: 9
<212> TYPE: PRT
<213> ORGANISM: Homo sapiens

<400> SEQUENCE: 776

Ser Ser Asp Val Gly Gly Tyr Asn Tyr
1               5

<210> SEQ ID NO 777
<211> LENGTH: 10

<212> TYPE: PRT
<213> ORGANISM: Homo sapiens

<400> SEQUENCE: 777

Cys Ser Tyr Ala Gly Ser Tyr Thr Trp Val
1               5                   10

<210> SEQ ID NO 778
<211> LENGTH: 8
<212> TYPE: PRT
<213> ORGANISM: Homo sapiens

<400> SEQUENCE: 778

Gly Phe Thr Phe Arg Asn Tyr Gly
1               5

<210> SEQ ID NO 779
<211> LENGTH: 8
<212> TYPE: PRT
<213> ORGANISM: Homo sapiens

<400> SEQUENCE: 779

Ile Trp Ala Asp Gly Thr Asn Gln
1               5

<210> SEQ ID NO 780
<211> LENGTH: 13
<212> TYPE: PRT
<213> ORGANISM: Homo sapiens

<400> SEQUENCE: 780

Ala Arg Glu Thr Thr Ile Phe Gln Trp Tyr Phe Asp Leu
1               5                   10

<210> SEQ ID NO 781
<211> LENGTH: 6
<212> TYPE: PRT
<213> ORGANISM: Homo sapiens

<400> SEQUENCE: 781

Gln Ser Ile Asn Asn Tyr
1               5

<210> SEQ ID NO 782
<211> LENGTH: 9
<212> TYPE: PRT
<213> ORGANISM: Homo sapiens

<400> SEQUENCE: 782

Gln Gln Ser Phe Ser Ile Pro Pro Thr
1               5

<210> SEQ ID NO 783
<211> LENGTH: 8
<212> TYPE: PRT
<213> ORGANISM: Homo sapiens

<400> SEQUENCE: 783

Gly Phe Thr Phe Ser Ser Tyr Gly
1               5

<210> SEQ ID NO 784
<211> LENGTH: 8
<212> TYPE: PRT
<213> ORGANISM: Homo sapiens

<400> SEQUENCE: 784

Ile Trp Tyr Asp Gly Ser Leu Lys
1 5

<210> SEQ ID NO 785
<211> LENGTH: 25
<212> TYPE: PRT
<213> ORGANISM: Homo sapiens

<400> SEQUENCE: 785

Ala Arg Glu Thr Thr Phe Gly Arg Phe Cys Ser Gly Gly Ser Cys Tyr
1 5 10 15

Ser Asp Tyr Tyr Tyr Gly Met Asp Val
20 25

<210> SEQ ID NO 786
<211> LENGTH: 11
<212> TYPE: PRT
<213> ORGANISM: Homo sapiens

<400> SEQUENCE: 786

Gln Ser Leu Val His Ser Asp Gly Asn Thr Tyr
1 5 10

<210> SEQ ID NO 787
<211> LENGTH: 9
<212> TYPE: PRT
<213> ORGANISM: Homo sapiens

<400> SEQUENCE: 787

Met Gln Ala Ala Gln Phe Pro Trp Thr
1 5

<210> SEQ ID NO 788
<211> LENGTH: 8
<212> TYPE: PRT
<213> ORGANISM: Homo sapiens

<400> SEQUENCE: 788

Gly Phe Val Phe Ser Asn Tyr Gly
1 5

<210> SEQ ID NO 789
<211> LENGTH: 8
<212> TYPE: PRT
<213> ORGANISM: Homo sapiens

<400> SEQUENCE: 789

Ile Trp Ala Asp Gly Thr Asn Ser
1 5

<210> SEQ ID NO 790
<211> LENGTH: 11
<212> TYPE: PRT
<213> ORGANISM: Homo sapiens

<400> SEQUENCE: 790

Ala Arg Glu Gly Gly Ile Val Ala Ala Asp Lys
1 5 10

<210> SEQ ID NO 791
<211> LENGTH: 8
<212> TYPE: PRT

<213> ORGANISM: Homo sapiens

<400> SEQUENCE: 791

Ser Ser Asn Ile Gly Asn Asn Tyr
1               5

<210> SEQ ID NO 792
<211> LENGTH: 8
<212> TYPE: PRT
<213> ORGANISM: Homo sapiens

<400> SEQUENCE: 792

Gly Phe Ser Phe Ser Asp Tyr Gly
1               5

<210> SEQ ID NO 793
<211> LENGTH: 8
<212> TYPE: PRT
<213> ORGANISM: Homo sapiens

<400> SEQUENCE: 793

Ile Trp Arg Asp Gly Ser Asn Ser
1               5

<210> SEQ ID NO 794
<211> LENGTH: 14
<212> TYPE: PRT
<213> ORGANISM: Homo sapiens

<400> SEQUENCE: 794

Ala Arg Glu Ala Arg Val Ala Ala Pro Ala Ser Tyr Asp Tyr
1               5                   10

<210> SEQ ID NO 795
<211> LENGTH: 6
<212> TYPE: PRT
<213> ORGANISM: Homo sapiens

<400> SEQUENCE: 795

Lys Ile Val Asn Lys Asn
1               5

<210> SEQ ID NO 796
<211> LENGTH: 11
<212> TYPE: PRT
<213> ORGANISM: Homo sapiens

<400> SEQUENCE: 796

Gln Val Trp Asp Asn Gly Ser Asn His Val Val
1               5                   10

<210> SEQ ID NO 797
<211> LENGTH: 8
<212> TYPE: PRT
<213> ORGANISM: Homo sapiens

<400> SEQUENCE: 797

Gly Phe Thr Phe Ser Ser Cys Gly
1               5

<210> SEQ ID NO 798
<211> LENGTH: 8
<212> TYPE: PRT
<213> ORGANISM: Homo sapiens

<400> SEQUENCE: 798

Ile Trp Ala Asp Gly Thr Asn Lys
1 5

<210> SEQ ID NO 799
<211> LENGTH: 14
<212> TYPE: PRT
<213> ORGANISM: Homo sapiens

<400> SEQUENCE: 799

Ala Arg Glu Ala Leu Ile Ala Ala Pro Ala Thr Phe Asp Tyr
1 5 10

<210> SEQ ID NO 800
<211> LENGTH: 6
<212> TYPE: PRT
<213> ORGANISM: Homo sapiens

<400> SEQUENCE: 800

Asn Ile Arg Ser Lys Asn
1 5

<210> SEQ ID NO 801
<211> LENGTH: 11
<212> TYPE: PRT
<213> ORGANISM: Homo sapiens

<400> SEQUENCE: 801

Gln Val Trp Asp Asn Asn Ser Arg His Val Val
1 5 10

<210> SEQ ID NO 802
<211> LENGTH: 8
<212> TYPE: PRT
<213> ORGANISM: Homo sapiens

<400> SEQUENCE: 802

Gly Phe Thr Phe Arg Asn Tyr Gly
1 5

<210> SEQ ID NO 803
<211> LENGTH: 8
<212> TYPE: PRT
<213> ORGANISM: Homo sapiens

<400> SEQUENCE: 803

Ile Trp Ala Asp Gly Ser Asn Lys
1 5

<210> SEQ ID NO 804
<211> LENGTH: 14
<212> TYPE: PRT
<213> ORGANISM: Homo sapiens

<400> SEQUENCE: 804

Ala Arg Glu Gly His Ile Ala Ala Pro Ala Ala Leu Asp Leu
1 5 10

<210> SEQ ID NO 805
<211> LENGTH: 6
<212> TYPE: PRT
<213> ORGANISM: Homo sapiens

<400> SEQUENCE: 805

Asn Ile Arg Asn Lys Asn
1               5

<210> SEQ ID NO 806
<211> LENGTH: 11
<212> TYPE: PRT
<213> ORGANISM: Homo sapiens

<400> SEQUENCE: 806

Gln Val Trp Asp Ser Ser Ser Glu His Val Val
1               5                   10

<210> SEQ ID NO 807
<211> LENGTH: 8
<212> TYPE: PRT
<213> ORGANISM: Homo sapiens

<400> SEQUENCE: 807

Gly Phe Thr Phe Ser Gly Asn Gly
1               5

<210> SEQ ID NO 808
<211> LENGTH: 8
<212> TYPE: PRT
<213> ORGANISM: Homo sapiens

<400> SEQUENCE: 808

Ile Trp Ser Asp Gly Ser Asn Lys
1               5

<210> SEQ ID NO 809
<211> LENGTH: 14
<212> TYPE: PRT
<213> ORGANISM: Homo sapiens

<400> SEQUENCE: 809

Ala Arg Glu Ala Asn Ile Ala Ala Pro Ala Ile Tyr Asp His
1               5                   10

<210> SEQ ID NO 810
<211> LENGTH: 6
<212> TYPE: PRT
<213> ORGANISM: Homo sapiens

<400> SEQUENCE: 810

Asn Ile Arg Ser Lys Asn
1               5

<210> SEQ ID NO 811
<211> LENGTH: 11
<212> TYPE: PRT
<213> ORGANISM: Homo sapiens

<400> SEQUENCE: 811

Gln Val Trp Asp Ser Tyr Ser Asp His Val Val
1               5                   10

<210> SEQ ID NO 812
<211> LENGTH: 8
<212> TYPE: PRT
<213> ORGANISM: Homo sapiens

<400> SEQUENCE: 812

Gly Phe Thr Phe Thr Thr Tyr Gly
1               5

<210> SEQ ID NO 813
<211> LENGTH: 8
<212> TYPE: PRT
<213> ORGANISM: Homo sapiens

<400> SEQUENCE: 813

Ile Trp Ala Asp Gly Ser Asn Gln
1 5

<210> SEQ ID NO 814
<211> LENGTH: 13
<212> TYPE: PRT
<213> ORGANISM: Homo sapiens

<400> SEQUENCE: 814

Ala Arg Glu Gly His Val Ala Thr Pro Ile Leu Asp Leu
1 5 10

<210> SEQ ID NO 815
<211> LENGTH: 6
<212> TYPE: PRT
<213> ORGANISM: Homo sapiens

<400> SEQUENCE: 815

Gln Ser Ile Ala Asn Tyr
1 5

<210> SEQ ID NO 816
<211> LENGTH: 10
<212> TYPE: PRT
<213> ORGANISM: Homo sapiens

<400> SEQUENCE: 816

Gln Gln Ser Tyr Ser Met Pro Thr Leu Thr
1 5 10

<210> SEQ ID NO 817
<211> LENGTH: 8
<212> TYPE: PRT
<213> ORGANISM: Homo sapiens

<400> SEQUENCE: 817

Gly Phe Thr Phe Ser Ser Tyr Gly
1 5

<210> SEQ ID NO 818
<211> LENGTH: 8
<212> TYPE: PRT
<213> ORGANISM: Homo sapiens

<400> SEQUENCE: 818

Ile Trp Tyr Asp Gly Ser Ile Lys
1 5

<210> SEQ ID NO 819
<211> LENGTH: 12
<212> TYPE: PRT
<213> ORGANISM: Homo sapiens

<400> SEQUENCE: 819

Val Arg Asp Asn Phe Gly Leu Asn Ala Phe Asp Val
1 5 10

<210> SEQ ID NO 820
<211> LENGTH: 6
<212> TYPE: PRT
<213> ORGANISM: Homo sapiens

<400> SEQUENCE: 820

Gln Ser Val Thr Arg Tyr
1 5

<210> SEQ ID NO 821
<211> LENGTH: 9
<212> TYPE: PRT
<213> ORGANISM: Homo sapiens

<400> SEQUENCE: 821

Gln His Arg Ser Asn Trp Pro Tyr Thr
1 5

<210> SEQ ID NO 822
<211> LENGTH: 8
<212> TYPE: PRT
<213> ORGANISM: Homo sapiens

<400> SEQUENCE: 822

Gly Phe Thr Phe Ser Asn Tyr Gly
1 5

<210> SEQ ID NO 823
<211> LENGTH: 8
<212> TYPE: PRT
<213> ORGANISM: Homo sapiens

<400> SEQUENCE: 823

Ile Trp His Asp Gly Ser Asn Gln
1 5

<210> SEQ ID NO 824
<211> LENGTH: 14
<212> TYPE: PRT
<213> ORGANISM: Homo sapiens

<400> SEQUENCE: 824

Ala Thr Glu Arg Arg Ile Ala Ala Pro Gly Cys Leu Asp Tyr
1 5 10

<210> SEQ ID NO 825
<211> LENGTH: 9
<212> TYPE: PRT
<213> ORGANISM: Homo sapiens

<400> SEQUENCE: 825

Ser Gly Ile Ser Val Asp Arg Ser Arg
1 5

<210> SEQ ID NO 826
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Any amino acid

<400> SEQUENCE: 826

Ser Xaa Ser Asp Lys
1 5

<210> SEQ ID NO 827
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Any amino acid

<400> SEQUENCE: 827

Met Ile Xaa His Ser Ser Ala Met Trp
1               5

<210> SEQ ID NO 828
<211> LENGTH: 8
<212> TYPE: PRT
<213> ORGANISM: Homo sapiens

<400> SEQUENCE: 828

Gly Phe Thr Phe Ser Ser His Gly
1               5

<210> SEQ ID NO 829
<211> LENGTH: 8
<212> TYPE: PRT
<213> ORGANISM: Homo sapiens

<400> SEQUENCE: 829

Ile Trp Tyr Asp Gly Ser Thr Lys
1               5

<210> SEQ ID NO 830
<211> LENGTH: 14
<212> TYPE: PRT
<213> ORGANISM: Homo sapiens

<400> SEQUENCE: 830

Ala Arg Glu Ala Leu Ile Ala Ala Pro Ala Thr Phe Asp Tyr
1               5                   10

<210> SEQ ID NO 831
<211> LENGTH: 6
<212> TYPE: PRT
<213> ORGANISM: Homo sapiens

<400> SEQUENCE: 831

Gln Ser Ile Asp Thr Trp
1               5

<210> SEQ ID NO 832
<211> LENGTH: 8
<212> TYPE: PRT
<213> ORGANISM: Homo sapiens

<400> SEQUENCE: 832

Gln Tyr Tyr Ser Val Tyr Ser Thr
1               5

<210> SEQ ID NO 833
<211> LENGTH: 6
<212> TYPE: PRT
<213> ORGANISM: Homo sapiens

<400> SEQUENCE: 833

```
Asn Ile Gly Ser Lys Asn
1               5


<210> SEQ ID NO 834
<211> LENGTH: 11
<212> TYPE: PRT
<213> ORGANISM: Homo sapiens

<400> SEQUENCE: 834

Gln Val Trp Asp Asn Asn Ser Asp His Val Val
1               5                   10


<210> SEQ ID NO 835
<211> LENGTH: 8
<212> TYPE: PRT
<213> ORGANISM: Homo sapiens

<400> SEQUENCE: 835

Gly Phe Ser Phe Ser Arg Tyr Gly
1               5


<210> SEQ ID NO 836
<211> LENGTH: 8
<212> TYPE: PRT
<213> ORGANISM: Homo sapiens

<400> SEQUENCE: 836

Ile Trp Tyr Asp Gly Ser Thr Arg
1               5


<210> SEQ ID NO 837
<211> LENGTH: 17
<212> TYPE: PRT
<213> ORGANISM: Homo sapiens

<400> SEQUENCE: 837

Ala Gly Gly Gly Tyr Ser Ser Arg Gly Tyr Tyr Asn Tyr Gly Leu Asp
1               5                   10                  15

Val


<210> SEQ ID NO 838
<211> LENGTH: 6
<212> TYPE: PRT
<213> ORGANISM: Homo sapiens

<400> SEQUENCE: 838

Gln Asp Ile Ser Asn Tyr
1               5


<210> SEQ ID NO 839
<211> LENGTH: 10
<212> TYPE: PRT
<213> ORGANISM: Homo sapiens

<400> SEQUENCE: 839

Gln Gln Tyr Asp Asn Leu Pro Pro Leu Thr
1               5                   10


<210> SEQ ID NO 840
<211> LENGTH: 11
<212> TYPE: PRT
<213> ORGANISM: Homo sapiens

<400> SEQUENCE: 840
```

Tyr Ser Thr Asp Arg Ser Gly Asp Gln Arg Val
1 5 10

<210> SEQ ID NO 841
<211> LENGTH: 8
<212> TYPE: PRT
<213> ORGANISM: Homo sapiens

<400> SEQUENCE: 841

Gly Phe Thr Phe Ser Arg Tyr Gly
1 5

<210> SEQ ID NO 842
<211> LENGTH: 8
<212> TYPE: PRT
<213> ORGANISM: Homo sapiens

<400> SEQUENCE: 842

Ile Trp Ser Asp Gly Ser Asn Lys
1 5

<210> SEQ ID NO 843
<211> LENGTH: 17
<212> TYPE: PRT
<213> ORGANISM: Homo sapiens

<400> SEQUENCE: 843

Ala Lys Ala Thr Cys Gly Asp Gly Ser Cys Gly Leu Tyr Tyr Phe Asp
1 5 10 15

Tyr

<210> SEQ ID NO 844
<211> LENGTH: 9
<212> TYPE: PRT
<213> ORGANISM: Homo sapiens

<400> SEQUENCE: 844

Ser Ser Asn Ile Gly Ala Gly Tyr Asp
1 5

<210> SEQ ID NO 845
<211> LENGTH: 11
<212> TYPE: PRT
<213> ORGANISM: Homo sapiens

<400> SEQUENCE: 845

Gln Ser Tyr Asp Ser Asn Leu Ser Gly Trp Val
1 5 10

<210> SEQ ID NO 846
<211> LENGTH: 8
<212> TYPE: PRT
<213> ORGANISM: Homo sapiens

<400> SEQUENCE: 846

Ile Asn Gly Asn Gly Arg Asp Thr
1 5

<210> SEQ ID NO 847
<211> LENGTH: 19
<212> TYPE: PRT
<213> ORGANISM: Homo sapiens

<400> SEQUENCE: 847

```
Ala Lys Asp Ile Trp Ile Phe Asp Gly Arg Arg Trp Ile Ala Gly Ser
1               5                   10                  15

Pro Asp Ala


<210> SEQ ID NO 848
<211> LENGTH: 11
<212> TYPE: PRT
<213> ORGANISM: Homo sapiens

<400> SEQUENCE: 848

Gln Ser Leu Val Tyr Ser Asp Gly Asn Thr Tyr
1               5                   10


<210> SEQ ID NO 849
<211> LENGTH: 9
<212> TYPE: PRT
<213> ORGANISM: Homo sapiens

<400> SEQUENCE: 849

Met Gln Gln Thr His Trp Pro Trp Ala
1               5


<210> SEQ ID NO 850
<211> LENGTH: 8
<212> TYPE: PRT
<213> ORGANISM: Homo sapiens

<400> SEQUENCE: 850

Gly Phe Ser Phe Ser Ser Tyr Ser
1               5


<210> SEQ ID NO 851
<211> LENGTH: 8
<212> TYPE: PRT
<213> ORGANISM: Homo sapiens

<400> SEQUENCE: 851

Ile Thr Ser Asn Ser Ala Thr Ile
1               5


<210> SEQ ID NO 852
<211> LENGTH: 15
<212> TYPE: PRT
<213> ORGANISM: Homo sapiens

<400> SEQUENCE: 852

Ala Arg Ala Gly Pro Pro Ser Pro Pro Asn Tyr Gly Met Asp Val
1               5                   10                  15


<210> SEQ ID NO 853
<211> LENGTH: 12
<212> TYPE: PRT
<213> ORGANISM: Homo sapiens

<400> SEQUENCE: 853

Gln Ser Leu Leu Tyr Arg Ser Asn Asn Lys Asn Tyr
1               5                   10


<210> SEQ ID NO 854
<211> LENGTH: 9
<212> TYPE: PRT
<213> ORGANISM: Homo sapiens

<400> SEQUENCE: 854
```

Gln Gln Tyr Tyr Thr Ala Pro Leu Leu
1 5

<210> SEQ ID NO 855
<211> LENGTH: 8
<212> TYPE: PRT
<213> ORGANISM: Homo sapiens

<400> SEQUENCE: 855

Gly Phe Thr Phe Pro Ser His Thr
1 5

<210> SEQ ID NO 856
<211> LENGTH: 8
<212> TYPE: PRT
<213> ORGANISM: Homo sapiens

<400> SEQUENCE: 856

Ile Ser Thr Thr Ser Glu Ala Ile
1 5

<210> SEQ ID NO 857
<211> LENGTH: 17
<212> TYPE: PRT
<213> ORGANISM: Homo sapiens

<400> SEQUENCE: 857

Ala Ser Val Gly Leu Asp Ser Lys Ile Ser Gly Tyr Trp Tyr Phe Asp
1 5 10 15

Leu

<210> SEQ ID NO 858
<211> LENGTH: 6
<212> TYPE: PRT
<213> ORGANISM: Homo sapiens

<400> SEQUENCE: 858

Gln Ser Ile Ser Ser Asn
1 5

<210> SEQ ID NO 859
<211> LENGTH: 9
<212> TYPE: PRT
<213> ORGANISM: Homo sapiens

<400> SEQUENCE: 859

Gln Gln Tyr Asp His Trp Pro Leu Thr
1 5

<210> SEQ ID NO 860
<211> LENGTH: 8
<212> TYPE: PRT
<213> ORGANISM: Homo sapiens

<400> SEQUENCE: 860

Gly Phe Thr Phe Ser Thr Tyr Thr
1 5

<210> SEQ ID NO 861
<211> LENGTH: 8
<212> TYPE: PRT
<213> ORGANISM: Homo sapiens

<400> SEQUENCE: 861

Ile Ser Ser Ser Gly Asp Thr Ile
1 5

<210> SEQ ID NO 862
<211> LENGTH: 17
<212> TYPE: PRT
<213> ORGANISM: Homo sapiens

<400> SEQUENCE: 862

Ala Arg Val Gly Leu Ala Leu Thr Ile Ser Gly Tyr Trp Tyr Phe Asp
1 5 10 15

Leu

<210> SEQ ID NO 863
<211> LENGTH: 6
<212> TYPE: PRT
<213> ORGANISM: Homo sapiens

<400> SEQUENCE: 863

Gln Ser Val Ser Ser Asn
1 5

<210> SEQ ID NO 864
<211> LENGTH: 9
<212> TYPE: PRT
<213> ORGANISM: Homo sapiens

<400> SEQUENCE: 864

Gln Gln Tyr Asn Asp Trp Pro Leu Thr
1 5

<210> SEQ ID NO 865
<211> LENGTH: 8
<212> TYPE: PRT
<213> ORGANISM: Homo sapiens

<400> SEQUENCE: 865

Gly Phe Thr Phe Ser Ser Ser Val
1 5

<210> SEQ ID NO 866
<211> LENGTH: 8
<212> TYPE: PRT
<213> ORGANISM: Homo sapiens

<400> SEQUENCE: 866

Ile Ser Thr Thr Ser Ala Ala Ile
1 5

<210> SEQ ID NO 867
<211> LENGTH: 15
<212> TYPE: PRT
<213> ORGANISM: Homo sapiens

<400> SEQUENCE: 867

Ala Arg Ala Lys Leu Gly Ser Gly Ser Tyr Trp Tyr Phe Asp Leu
1 5 10 15

<210> SEQ ID NO 868
<211> LENGTH: 6
<212> TYPE: PRT
<213> ORGANISM: Homo sapiens

<400> SEQUENCE: 868

Gln Ser Val Gly Ser Asn
1 5

<210> SEQ ID NO 869
<211> LENGTH: 9
<212> TYPE: PRT
<213> ORGANISM: Homo sapiens

<400> SEQUENCE: 869

Gln Gln Tyr Asn Asn Trp Pro Leu Thr
1 5

<210> SEQ ID NO 870
<211> LENGTH: 8
<212> TYPE: PRT
<213> ORGANISM: Homo sapiens

<400> SEQUENCE: 870

Gly Ile Thr Leu Arg Thr Tyr Lys
1 5

<210> SEQ ID NO 871
<211> LENGTH: 8
<212> TYPE: PRT
<213> ORGANISM: Homo sapiens

<400> SEQUENCE: 871

Ile Ser Ser Asp Asp Lys Thr Ile
1 5

<210> SEQ ID NO 872
<211> LENGTH: 16
<212> TYPE: PRT
<213> ORGANISM: Homo sapiens

<400> SEQUENCE: 872

Ala Arg Asp Thr Gly Ile Trp Asn Gly Ala Tyr Asp Ala Phe Asp Ile
1 5 10 15

<210> SEQ ID NO 873
<211> LENGTH: 9
<212> TYPE: PRT
<213> ORGANISM: Homo sapiens

<400> SEQUENCE: 873

Ser Gly Ile Asn Val Gly Thr Tyr Arg
1 5

<210> SEQ ID NO 874
<211> LENGTH: 7
<212> TYPE: PRT
<213> ORGANISM: Homo sapiens

<400> SEQUENCE: 874

Tyr Arg Ser Asp Ser Asp Met
1 5

<210> SEQ ID NO 875
<211> LENGTH: 9
<212> TYPE: PRT
<213> ORGANISM: Homo sapiens

<400> SEQUENCE: 875

Met Ile Trp His Ser Thr Ala Tyr Val
1 5

<210> SEQ ID NO 876
<211> LENGTH: 8
<212> TYPE: PRT
<213> ORGANISM: Homo sapiens

<400> SEQUENCE: 876

Gly Phe Thr Phe Ser Ser Tyr Glu
1 5

<210> SEQ ID NO 877
<211> LENGTH: 8
<212> TYPE: PRT
<213> ORGANISM: Homo sapiens

<400> SEQUENCE: 877

Ile Ser Asn Ser Gly Asn Thr Ile
1 5

<210> SEQ ID NO 878
<211> LENGTH: 5
<212> TYPE: PRT
<213> ORGANISM: Homo sapiens

<400> SEQUENCE: 878

Val Gly Phe Asp His
1 5

<210> SEQ ID NO 879
<211> LENGTH: 12
<212> TYPE: PRT
<213> ORGANISM: Homo sapiens

<400> SEQUENCE: 879

Arg Ser Leu Leu Tyr Thr Ser Val Asn Lys Asn His
1 5 10

<210> SEQ ID NO 880
<211> LENGTH: 9
<212> TYPE: PRT
<213> ORGANISM: Homo sapiens

<400> SEQUENCE: 880

Gln Gln Tyr Tyr Ser Pro Pro Ile Thr
1 5

<210> SEQ ID NO 881
<211> LENGTH: 8
<212> TYPE: PRT
<213> ORGANISM: Homo sapiens

<400> SEQUENCE: 881

Gly Phe Thr Phe Ser Asn Asn Glu
1 5

<210> SEQ ID NO 882
<211> LENGTH: 8
<212> TYPE: PRT
<213> ORGANISM: Homo sapiens

<400> SEQUENCE: 882

Ile Ser Ser Ser Gly Ser Val Met
1 5

<210> SEQ ID NO 883
<211> LENGTH: 12
<212> TYPE: PRT
<213> ORGANISM: Homo sapiens

<400> SEQUENCE: 883

Ala Gly His Cys Ser Ser Asn Lys Cys Tyr Lys Tyr
1 5 10

<210> SEQ ID NO 884
<211> LENGTH: 9
<212> TYPE: PRT
<213> ORGANISM: Homo sapiens

<400> SEQUENCE: 884

Ser Ser Asn Ile Gly Ala Gly Tyr Asp
1 5

<210> SEQ ID NO 885
<211> LENGTH: 11
<212> TYPE: PRT
<213> ORGANISM: Homo sapiens

<400> SEQUENCE: 885

Gln Ser Tyr Asp Ser Ser Leu Ser Gly Ser Ile
1 5 10

<210> SEQ ID NO 886
<211> LENGTH: 8
<212> TYPE: PRT
<213> ORGANISM: Homo sapiens

<400> SEQUENCE: 886

Gly Phe Thr Phe Gly Asp Tyr Gly
1 5

<210> SEQ ID NO 887
<211> LENGTH: 10
<212> TYPE: PRT
<213> ORGANISM: Homo sapiens

<400> SEQUENCE: 887

Ile Lys Pro Lys Ala Tyr Gly Gly Ala Thr
1 5 10

<210> SEQ ID NO 888
<211> LENGTH: 15
<212> TYPE: PRT
<213> ORGANISM: Homo sapiens

<400> SEQUENCE: 888

Ala Arg Asp Leu Thr Ile Asn Lys Ile Ile Val Ala Asn Asp Phe
1 5 10 15

<210> SEQ ID NO 889
<211> LENGTH: 12
<212> TYPE: PRT
<213> ORGANISM: Homo sapiens

<400> SEQUENCE: 889

Gln Ser Leu Leu Tyr Ser Ser Asn Asn Lys Asn Tyr
1 5 10

<210> SEQ ID NO 890
<211> LENGTH: 9

<212> TYPE: PRT
<213> ORGANISM: Homo sapiens

<400> SEQUENCE: 890

Gln Gln Tyr Tyr Ser Thr Pro Ile Thr
1               5

<210> SEQ ID NO 891
<211> LENGTH: 8
<212> TYPE: PRT
<213> ORGANISM: Homo sapiens

<400> SEQUENCE: 891

Gly Phe Thr Phe Gly Asp Tyr Ala
1               5

<210> SEQ ID NO 892
<211> LENGTH: 10
<212> TYPE: PRT
<213> ORGANISM: Homo sapiens

<400> SEQUENCE: 892

Ile Arg Ser Lys Gly Tyr Gly Gly Thr Arg
1               5                   10

<210> SEQ ID NO 893
<211> LENGTH: 16
<212> TYPE: PRT
<213> ORGANISM: Homo sapiens

<400> SEQUENCE: 893

Ala Arg Val Pro Tyr Ser Ser Ser Trp Tyr Val Ala Trp Ala Asp Tyr
1               5                   10                  15

<210> SEQ ID NO 894
<211> LENGTH: 12
<212> TYPE: PRT
<213> ORGANISM: Homo sapiens

<400> SEQUENCE: 894

Gln Ser Val Leu Tyr Ser Phe Asn Asn Lys Asn Tyr
1               5                   10

<210> SEQ ID NO 895
<211> LENGTH: 9
<212> TYPE: PRT
<213> ORGANISM: Homo sapiens

<400> SEQUENCE: 895

Gln Gln Tyr Tyr Ser Thr Pro Leu Thr
1               5

<210> SEQ ID NO 896
<211> LENGTH: 8
<212> TYPE: PRT
<213> ORGANISM: Homo sapiens

<400> SEQUENCE: 896

Gly Phe Thr Phe Gly Asp Tyr Gly
1               5

<210> SEQ ID NO 897
<211> LENGTH: 10
<212> TYPE: PRT
<213> ORGANISM: Homo sapiens

<400> SEQUENCE: 897

Ile Arg Arg Lys Ala Asn Arg Gly Thr Thr
1 5 10

<210> SEQ ID NO 898
<211> LENGTH: 18
<212> TYPE: PRT
<213> ORGANISM: Homo sapiens

<400> SEQUENCE: 898

Thr Arg Gly Asp Tyr Tyr Gly Ser Arg Asn Ser Tyr Phe Trp Leu Phe
1 5 10 15

Asp Tyr

<210> SEQ ID NO 899
<211> LENGTH: 11
<212> TYPE: PRT
<213> ORGANISM: Homo sapiens

<400> SEQUENCE: 899

Gln Ser Leu Leu Tyr Ser Asp Gly Lys Thr Tyr
1 5 10

<210> SEQ ID NO 900
<211> LENGTH: 8
<212> TYPE: PRT
<213> ORGANISM: Homo sapiens

<400> SEQUENCE: 900

Met Gln Ser Ile Gln Leu Arg Thr
1 5

<210> SEQ ID NO 901
<211> LENGTH: 8
<212> TYPE: PRT
<213> ORGANISM: Homo sapiens

<400> SEQUENCE: 901

Gly Phe Thr Val Ile Ser Asn Tyr
1 5

<210> SEQ ID NO 902
<211> LENGTH: 7
<212> TYPE: PRT
<213> ORGANISM: Homo sapiens

<400> SEQUENCE: 902

Ile Tyr Ser Gly Val Asn Thr
1 5

<210> SEQ ID NO 903
<211> LENGTH: 24
<212> TYPE: PRT
<213> ORGANISM: Homo sapiens

<400> SEQUENCE: 903

Ala Arg Val Ile Ala Val Ala Gly Thr Asn Arg Gly Gly Pro Arg Trp
1 5 10 15

Arg Ser Thr Tyr Tyr Phe Asp Tyr
20

<210> SEQ ID NO 904

<211> LENGTH: 9
<212> TYPE: PRT
<213> ORGANISM: Homo sapiens

<400> SEQUENCE: 904

Ser Gly Thr Val Thr Thr Ala Asn Tyr
1 5

<210> SEQ ID NO 905
<211> LENGTH: 9
<212> TYPE: PRT
<213> ORGANISM: Homo sapiens

<400> SEQUENCE: 905

Leu Leu Tyr Cys Ser Gly Val Arg Val
1 5

<210> SEQ ID NO 906
<211> LENGTH: 8
<212> TYPE: PRT
<213> ORGANISM: Homo sapiens

<400> SEQUENCE: 906

Gly Leu Thr Phe Ser Arg Tyr Trp
1 5

<210> SEQ ID NO 907
<211> LENGTH: 8
<212> TYPE: PRT
<213> ORGANISM: Homo sapiens

<400> SEQUENCE: 907

Ile Asn Glu Glu Gly Ser His Ser
1 5

<210> SEQ ID NO 908
<211> LENGTH: 18
<212> TYPE: PRT
<213> ORGANISM: Homo sapiens

<400> SEQUENCE: 908

Ala Ser Glu Leu Trp Thr Ala Phe Asn Lys Asp Trp Ser Gly Tyr Asn
1 5 10 15

Asp Tyr

<210> SEQ ID NO 909
<211> LENGTH: 8
<212> TYPE: PRT
<213> ORGANISM: Homo sapiens

<400> SEQUENCE: 909

Ser Ser Asn Val Gly Lys Asn Tyr
1 5

<210> SEQ ID NO 910
<211> LENGTH: 11
<212> TYPE: PRT
<213> ORGANISM: Homo sapiens

<400> SEQUENCE: 910

Gly Thr Trp Asp Ser Ser Leu Lys Val Val Val
1 5 10

<210> SEQ ID NO 911

<211> LENGTH: 8
<212> TYPE: PRT
<213> ORGANISM: Homo sapiens

<400> SEQUENCE: 911

Gly Phe Thr Phe Thr Asn Phe Lys
1               5

<210> SEQ ID NO 912
<211> LENGTH: 8
<212> TYPE: PRT
<213> ORGANISM: Homo sapiens

<400> SEQUENCE: 912

Ile Lys Gln Asp Gly Ser Glu Lys
1               5

<210> SEQ ID NO 913
<211> LENGTH: 8
<212> TYPE: PRT
<213> ORGANISM: Homo sapiens

<400> SEQUENCE: 913

Thr Arg Asp Thr Trp Val Asp Ser
1               5

<210> SEQ ID NO 914
<211> LENGTH: 6
<212> TYPE: PRT
<213> ORGANISM: Homo sapiens

<400> SEQUENCE: 914

Gln Gly Ile Ser Lys Tyr
1               5

<210> SEQ ID NO 915
<211> LENGTH: 9
<212> TYPE: PRT
<213> ORGANISM: Homo sapiens

<400> SEQUENCE: 915

Leu Gln His Gln Ser Tyr Pro Phe Thr
1               5

<210> SEQ ID NO 916
<211> LENGTH: 8
<212> TYPE: PRT
<213> ORGANISM: Homo sapiens

<400> SEQUENCE: 916

Gly Phe Ser Phe Ser Asn Tyr Trp
1               5

<210> SEQ ID NO 917
<211> LENGTH: 8
<212> TYPE: PRT
<213> ORGANISM: Homo sapiens

<400> SEQUENCE: 917

Ile Lys Glu Asp Gly Ser Glu Lys
1               5

<210> SEQ ID NO 918
<211> LENGTH: 16
<212> TYPE: PRT

<213> ORGANISM: Homo sapiens

<400> SEQUENCE: 918

Ala Ser Ser His Tyr Ser Ala Gly Asp Val Ser Tyr Asn Phe Asp Tyr
1 5 10 15

<210> SEQ ID NO 919
<211> LENGTH: 8
<212> TYPE: PRT
<213> ORGANISM: Homo sapiens

<400> SEQUENCE: 919

Asn Lys Asn Val Gly Asn Lys Gly
1 5

<210> SEQ ID NO 920
<211> LENGTH: 11
<212> TYPE: PRT
<213> ORGANISM: Homo sapiens

<400> SEQUENCE: 920

Ser Ala Trp Asp Phe Ser Leu Arg Ala Trp Val
1 5 10

<210> SEQ ID NO 921
<211> LENGTH: 8
<212> TYPE: PRT
<213> ORGANISM: Homo sapiens

<400> SEQUENCE: 921

Gly Phe Ile Phe Ser Ser Ser Trp
1 5

<210> SEQ ID NO 922
<211> LENGTH: 8
<212> TYPE: PRT
<213> ORGANISM: Homo sapiens

<400> SEQUENCE: 922

Ile Lys Gln Asp Gly Ser Asp Lys
1 5

<210> SEQ ID NO 923
<211> LENGTH: 15
<212> TYPE: PRT
<213> ORGANISM: Homo sapiens

<400> SEQUENCE: 923

Ala Arg Ser His Val Ala Ala Gly Val Thr Arg Trp Phe Asp Pro
1 5 10 15

<210> SEQ ID NO 924
<211> LENGTH: 6
<212> TYPE: PRT
<213> ORGANISM: Homo sapiens

<400> SEQUENCE: 924

Gln Ser Val Ser Ser Tyr
1 5

<210> SEQ ID NO 925
<211> LENGTH: 5
<212> TYPE: PRT
<213> ORGANISM: Homo sapiens

<400> SEQUENCE: 925

Gln His Arg Ser Lys
1 5

<210> SEQ ID NO 926
<211> LENGTH: 8
<212> TYPE: PRT
<213> ORGANISM: Homo sapiens

<400> SEQUENCE: 926

Ser Phe Thr Phe Ser Thr Ser Trp
1 5

<210> SEQ ID NO 927
<211> LENGTH: 8
<212> TYPE: PRT
<213> ORGANISM: Homo sapiens

<400> SEQUENCE: 927

Ile Asn Gln Asp Gly Ser Glu Arg
1 5

<210> SEQ ID NO 928
<211> LENGTH: 15
<212> TYPE: PRT
<213> ORGANISM: Homo sapiens

<400> SEQUENCE: 928

Ala Arg Ser His Val Ala Ala Gly Gly Thr Arg Trp Ile Asp Ser
1 5 10 15

<210> SEQ ID NO 929
<211> LENGTH: 6
<212> TYPE: PRT
<213> ORGANISM: Homo sapiens

<400> SEQUENCE: 929

Gln Asn Ile Asn Ser Gln
1 5

<210> SEQ ID NO 930
<211> LENGTH: 5
<212> TYPE: PRT
<213> ORGANISM: Homo sapiens

<400> SEQUENCE: 930

His His Arg Ile Asn
1 5

<210> SEQ ID NO 931
<211> LENGTH: 8
<212> TYPE: PRT
<213> ORGANISM: Homo sapiens

<400> SEQUENCE: 931

Gly Phe Thr Phe Ser Asp Tyr Trp
1 5

<210> SEQ ID NO 932
<211> LENGTH: 8
<212> TYPE: PRT
<213> ORGANISM: Homo sapiens

<400> SEQUENCE: 932

Ile Asn Gln Asp Gly Ser Glu Tyr
1 5

<210> SEQ ID NO 933
<211> LENGTH: 17
<212> TYPE: PRT
<213> ORGANISM: Homo sapiens

<400> SEQUENCE: 933

Ala Arg Leu Asp Arg Gly Thr Gly Glu Ser Gly Tyr Arg Ser Ser Asp
1 5 10 15

Val

<210> SEQ ID NO 934
<211> LENGTH: 8
<212> TYPE: PRT
<213> ORGANISM: Homo sapiens

<400> SEQUENCE: 934

Ser Ser Asn Ile Gly Ser Arg Ser
1 5

<210> SEQ ID NO 935
<211> LENGTH: 11
<212> TYPE: PRT
<213> ORGANISM: Homo sapiens

<400> SEQUENCE: 935

Ala Ala Trp Asp Asp Ser Leu Asn Gly Val Val
1 5 10

<210> SEQ ID NO 936
<211> LENGTH: 8
<212> TYPE: PRT
<213> ORGANISM: Homo sapiens

<400> SEQUENCE: 936

Gly Phe Ile Phe Ser Ser Asn Trp
1 5

<210> SEQ ID NO 937
<211> LENGTH: 8
<212> TYPE: PRT
<213> ORGANISM: Homo sapiens

<400> SEQUENCE: 937

Ile Asn Gln Asp Gly Ser Asp Ile
1 5

<210> SEQ ID NO 938
<211> LENGTH: 15
<212> TYPE: PRT
<213> ORGANISM: Homo sapiens

<400> SEQUENCE: 938

Ala Arg Ser His Val Ala Ala Ser Gly Thr Arg Trp Phe Asp Pro
1 5 10 15

<210> SEQ ID NO 939
<211> LENGTH: 6
<212> TYPE: PRT
<213> ORGANISM: Homo sapiens

<400> SEQUENCE: 939

Gln Ser Val Ser Ser Tyr
1 5

<210> SEQ ID NO 940
<211> LENGTH: 5
<212> TYPE: PRT
<213> ORGANISM: Homo sapiens

<400> SEQUENCE: 940

Gln His Arg Ser Tyr
1 5

<210> SEQ ID NO 941
<211> LENGTH: 8
<212> TYPE: PRT
<213> ORGANISM: Homo sapiens

<400> SEQUENCE: 941

Gly Phe Thr Phe Ser Asp His Phe
1 5

<210> SEQ ID NO 942
<211> LENGTH: 10
<212> TYPE: PRT
<213> ORGANISM: Homo sapiens

<400> SEQUENCE: 942

Thr Arg Asn Lys Ala Asn Ser Tyr Thr Thr
1 5 10

<210> SEQ ID NO 943
<211> LENGTH: 16
<212> TYPE: PRT
<213> ORGANISM: Homo sapiens

<400> SEQUENCE: 943

Ala Arg Asp Gly Tyr Asp Ile Leu Asn His Phe Val Arg Phe Asp Phe
1 5 10 15

<210> SEQ ID NO 944
<211> LENGTH: 6
<212> TYPE: PRT
<213> ORGANISM: Homo sapiens

<400> SEQUENCE: 944

Gln Ser Val Ser Ser Tyr
1 5

<210> SEQ ID NO 945
<211> LENGTH: 5
<212> TYPE: PRT
<213> ORGANISM: Homo sapiens

<400> SEQUENCE: 945

Gln His Arg Ser Tyr
1 5

<210> SEQ ID NO 946
<211> LENGTH: 8
<212> TYPE: PRT
<213> ORGANISM: Homo sapiens

<400> SEQUENCE: 946

Gly Phe Thr Phe Ser Asp His Tyr
1 5

<210> SEQ ID NO 947
<211> LENGTH: 10
<212> TYPE: PRT
<213> ORGANISM: Homo sapiens

<400> SEQUENCE: 947

Ile Arg Asn Lys Ala Lys Ser Tyr Thr Thr
1 5 10

<210> SEQ ID NO 948
<211> LENGTH: 15
<212> TYPE: PRT
<213> ORGANISM: Homo sapiens

<400> SEQUENCE: 948

Ala Arg Glu Gly Leu Gly Ser Pro Thr Ser Asp Ala Phe Asp Ile
1 5 10 15

<210> SEQ ID NO 949
<211> LENGTH: 9
<212> TYPE: PRT
<213> ORGANISM: Homo sapiens

<400> SEQUENCE: 949

Ser Ser Asp Val Gly Gly Tyr Asn Tyr
1 5

<210> SEQ ID NO 950
<211> LENGTH: 10
<212> TYPE: PRT
<213> ORGANISM: Homo sapiens

<400> SEQUENCE: 950

Ser Ser Tyr Thr Thr Ser Ser Thr Leu Val
1 5 10

<210> SEQ ID NO 951
<211> LENGTH: 8
<212> TYPE: PRT
<213> ORGANISM: Homo sapiens

<400> SEQUENCE: 951

Gly Phe Thr Leu Ser Gly Ser Ala
1 5

<210> SEQ ID NO 952
<211> LENGTH: 10
<212> TYPE: PRT
<213> ORGANISM: Homo sapiens

<400> SEQUENCE: 952

Ile Arg Ser Lys Ala Asn Asn Tyr Ala Thr
1 5 10

<210> SEQ ID NO 953
<211> LENGTH: 14
<212> TYPE: PRT
<213> ORGANISM: Homo sapiens

<400> SEQUENCE: 953

Thr Ser Gln Tyr Gly Asp Gly Tyr Tyr Tyr Ala Met Asp Val
1 5 10

<210> SEQ ID NO 954
<211> LENGTH: 6
<212> TYPE: PRT
<213> ORGANISM: Homo sapiens

<400> SEQUENCE: 954

Gln Asn Ile Arg Asn Asn
1               5

<210> SEQ ID NO 955
<211> LENGTH: 10
<212> TYPE: PRT
<213> ORGANISM: Homo sapiens

<400> SEQUENCE: 955

Gln His Tyr Asn Asn Trp Pro Leu Phe Thr
1               5                   10

<210> SEQ ID NO 956
<211> LENGTH: 8
<212> TYPE: PRT
<213> ORGANISM: Homo sapiens

<400> SEQUENCE: 956

Ile Ser Asp Asp Glu Arg Ser Thr
1               5

<210> SEQ ID NO 957
<211> LENGTH: 10
<212> TYPE: PRT
<213> ORGANISM: Homo sapiens

<400> SEQUENCE: 957

Val Arg Gly Leu Asn His Ala Met Asp Val
1               5                   10

<210> SEQ ID NO 958
<211> LENGTH: 9
<212> TYPE: PRT
<213> ORGANISM: Homo sapiens

<400> SEQUENCE: 958

Asn Ser Asp Val Gly Gly Tyr Asn Phe
1               5

<210> SEQ ID NO 959
<211> LENGTH: 10
<212> TYPE: PRT
<213> ORGANISM: Homo sapiens

<400> SEQUENCE: 959

Cys Ser Phe Thr Thr Arg Asn Thr Trp Val
1               5                   10

<210> SEQ ID NO 960
<211> LENGTH: 8
<212> TYPE: PRT
<213> ORGANISM: Homo sapiens

<400> SEQUENCE: 960

Gly Phe Thr Phe Ser Thr Tyr Arg
1               5

<210> SEQ ID NO 961
<211> LENGTH: 8

<212> TYPE: PRT
<213> ORGANISM: Homo sapiens

<400> SEQUENCE: 961

Ile Lys Tyr Asp Gly Ser Ser Thr
1               5

<210> SEQ ID NO 962
<211> LENGTH: 18
<212> TYPE: PRT
<213> ORGANISM: Homo sapiens

<400> SEQUENCE: 962

Ala Arg Val Tyr Arg Asp Ser Arg Asp Gly Ser Asp Phe Arg His Phe
1               5                   10                  15

Asp Ser

<210> SEQ ID NO 963
<211> LENGTH: 12
<212> TYPE: PRT
<213> ORGANISM: Homo sapiens

<400> SEQUENCE: 963

Gln Ser Leu Leu Tyr Ser Ser Asn Lys Lys Asn Tyr
1               5                   10

<210> SEQ ID NO 964
<211> LENGTH: 9
<212> TYPE: PRT
<213> ORGANISM: Homo sapiens

<400> SEQUENCE: 964

Gln Gln Tyr Tyr Asp Ile Pro Tyr Thr
1               5

<210> SEQ ID NO 965
<211> LENGTH: 8
<212> TYPE: PRT
<213> ORGANISM: Homo sapiens

<400> SEQUENCE: 965

Gly Phe Thr Phe Ser Asn Tyr Trp
1               5

<210> SEQ ID NO 966
<211> LENGTH: 8
<212> TYPE: PRT
<213> ORGANISM: Homo sapiens

<400> SEQUENCE: 966

Ile Ser Thr Asp Gly Ser Ser Thr
1               5

<210> SEQ ID NO 967
<211> LENGTH: 15
<212> TYPE: PRT
<213> ORGANISM: Homo sapiens

<400> SEQUENCE: 967

Ala Arg Gly Ser Thr Tyr Tyr Phe Gly Ser Gly Ser Val Asp Tyr
1               5                   10                  15

<210> SEQ ID NO 968
<211> LENGTH: 9

<212> TYPE: PRT
<213> ORGANISM: Homo sapiens

<400> SEQUENCE: 968

Ser Ser Asp Ile Gly Val Tyr Asn Tyr
1 5

<210> SEQ ID NO 969
<211> LENGTH: 11
<212> TYPE: PRT
<213> ORGANISM: Homo sapiens

<400> SEQUENCE: 969

Ser Ser Tyr Arg Gly Ser Ser Thr Pro Tyr Val
1 5 10

<210> SEQ ID NO 970
<211> LENGTH: 8
<212> TYPE: PRT
<213> ORGANISM: Homo sapiens

<400> SEQUENCE: 970

Gly Phe Thr Phe Ser Asp Tyr Trp
1 5

<210> SEQ ID NO 971
<211> LENGTH: 8
<212> TYPE: PRT
<213> ORGANISM: Homo sapiens

<400> SEQUENCE: 971

Ile Glu Ser Asp Gly Ser Gly Thr
1 5

<210> SEQ ID NO 972
<211> LENGTH: 7
<212> TYPE: PRT
<213> ORGANISM: Homo sapiens

<400> SEQUENCE: 972

Ala Arg Gly Ser Leu Asp Phe
1 5

<210> SEQ ID NO 973
<211> LENGTH: 9
<212> TYPE: PRT
<213> ORGANISM: Homo sapiens

<400> SEQUENCE: 973

Arg Ser Asp Val Gly Ala Tyr Asn Tyr
1 5

<210> SEQ ID NO 974
<211> LENGTH: 10
<212> TYPE: PRT
<213> ORGANISM: Homo sapiens

<400> SEQUENCE: 974

Tyr Ser Tyr Thr Thr Ser Asn Thr Leu Val
1 5 10

<210> SEQ ID NO 975
<211> LENGTH: 8
<212> TYPE: PRT
<213> ORGANISM: Homo sapiens

<400> SEQUENCE: 975

Gly Phe Thr Phe Ser Asp Tyr Trp
1               5

<210> SEQ ID NO 976
<211> LENGTH: 8
<212> TYPE: PRT
<213> ORGANISM: Homo sapiens

<400> SEQUENCE: 976

Ile Asp Asp Gly Gly Ser Ala Thr
1               5

<210> SEQ ID NO 977
<211> LENGTH: 7
<212> TYPE: PRT
<213> ORGANISM: Homo sapiens

<400> SEQUENCE: 977

Ser Arg Gly Ser Leu Asp Tyr
1               5

<210> SEQ ID NO 978
<211> LENGTH: 9
<212> TYPE: PRT
<213> ORGANISM: Homo sapiens

<400> SEQUENCE: 978

Arg Ser Asp Val Gly Ala Tyr Asn Tyr
1               5

<210> SEQ ID NO 979
<211> LENGTH: 10
<212> TYPE: PRT
<213> ORGANISM: Homo sapiens

<400> SEQUENCE: 979

Tyr Ser Tyr Thr Thr Ser Asn Thr Leu Val
1               5                   10

<210> SEQ ID NO 980
<211> LENGTH: 8
<212> TYPE: PRT
<213> ORGANISM: Homo sapiens

<400> SEQUENCE: 980

Gly Phe Thr Phe Ser Asn Tyr Trp
1               5

<210> SEQ ID NO 981
<211> LENGTH: 8
<212> TYPE: PRT
<213> ORGANISM: Homo sapiens

<400> SEQUENCE: 981

Ile Asn Ser Asp Gly Thr Asn Thr
1               5

<210> SEQ ID NO 982
<211> LENGTH: 9
<212> TYPE: PRT
<213> ORGANISM: Homo sapiens

<400> SEQUENCE: 982

Ala Cys Leu Arg Val Pro Asp Arg Asn
1 5

<210> SEQ ID NO 983
<211> LENGTH: 9
<212> TYPE: PRT
<213> ORGANISM: Homo sapiens

<400> SEQUENCE: 983

Thr Gly Ala Val Thr Ser Gly His Tyr
1 5

<210> SEQ ID NO 984
<211> LENGTH: 9
<212> TYPE: PRT
<213> ORGANISM: Homo sapiens

<400> SEQUENCE: 984

Leu Leu Ser Tyr Ser Gly Ala Gln Val
1 5

<210> SEQ ID NO 985
<211> LENGTH: 8
<212> TYPE: PRT
<213> ORGANISM: Homo sapiens

<400> SEQUENCE: 985

Gly Phe Ile Phe Asp Asp Tyr Ser
1 5

<210> SEQ ID NO 986
<211> LENGTH: 8
<212> TYPE: PRT
<213> ORGANISM: Homo sapiens

<400> SEQUENCE: 986

Ile Ser Trp Asn Ser Glu Phe Met
1 5

<210> SEQ ID NO 987
<211> LENGTH: 15
<212> TYPE: PRT
<213> ORGANISM: Homo sapiens

<400> SEQUENCE: 987

Val Lys Ala Asn Val Lys Lys Gly Ser Thr Ser Cys Phe Asp Tyr
1 5 10 15

<210> SEQ ID NO 988
<211> LENGTH: 7
<212> TYPE: PRT
<213> ORGANISM: Homo sapiens

<400> SEQUENCE: 988

Gln Ser Val Ser Ser Ser Tyr
1 5

<210> SEQ ID NO 989
<211> LENGTH: 10
<212> TYPE: PRT
<213> ORGANISM: Homo sapiens

<400> SEQUENCE: 989

Gln Gln Tyr Ser Gly Ser Ser Pro Arg Thr 1 5 10

<210> SEQ ID NO 990
<211> LENGTH: 8
<212> TYPE: PRT
<213> ORGANISM: Homo sapiens

<400> SEQUENCE: 990

Gly Phe Asn Phe Asn Met Tyr Ala
1 5

<210> SEQ ID NO 991
<211> LENGTH: 8
<212> TYPE: PRT
<213> ORGANISM: Homo sapiens

<400> SEQUENCE: 991

Ile Ser Tyr Asn Gly Gly Ala Arg
1 5

<210> SEQ ID NO 992
<211> LENGTH: 15
<212> TYPE: PRT
<213> ORGANISM: Homo sapiens

<400> SEQUENCE: 992

Val Lys Asp Lys Ser Gln Gly Ile Pro Val Ala Gly Leu Glu Tyr
1 5 10 15

<210> SEQ ID NO 993
<211> LENGTH: 8
<212> TYPE: PRT
<213> ORGANISM: Homo sapiens

<400> SEQUENCE: 993

Asn Ser Asn Ile Gly Asn Asn Tyr
1 5

<210> SEQ ID NO 994
<211> LENGTH: 10
<212> TYPE: PRT
<213> ORGANISM: Homo sapiens

<400> SEQUENCE: 994

Gly Thr Trp Asp Ser Ser Leu Ser Ala Ala
1 5 10

<210> SEQ ID NO 995
<211> LENGTH: 8
<212> TYPE: PRT
<213> ORGANISM: Homo sapiens

<400> SEQUENCE: 995

Gly Phe Thr Phe Asn Met Tyr Ala
1 5

<210> SEQ ID NO 996
<211> LENGTH: 8
<212> TYPE: PRT
<213> ORGANISM: Homo sapiens

<400> SEQUENCE: 996

Ile Ser Phe Asn Gly Gly Ala Arg
1 5

<210> SEQ ID NO 997
<211> LENGTH: 15
<212> TYPE: PRT
<213> ORGANISM: Homo sapiens

<400> SEQUENCE: 997

Val Lys Asp Lys Ser Gln Gly Ile Pro Leu Ala Gly Leu Glu Tyr
1 5 10 15

<210> SEQ ID NO 998
<211> LENGTH: 8
<212> TYPE: PRT
<213> ORGANISM: Homo sapiens

<400> SEQUENCE: 998

Ser Ser Asn Ile Gly Asn Asn Tyr
1 5

<210> SEQ ID NO 999
<211> LENGTH: 10
<212> TYPE: PRT
<213> ORGANISM: Homo sapiens

<400> SEQUENCE: 999

Ala Thr Trp Asp Ser Ser Leu Thr Ala Ala
1 5 10

<210> SEQ ID NO 1000
<211> LENGTH: 8
<212> TYPE: PRT
<213> ORGANISM: Homo sapiens

<400> SEQUENCE: 1000

Gly Phe Asn Phe Asn Met Tyr Ala
1 5

<210> SEQ ID NO 1001
<211> LENGTH: 8
<212> TYPE: PRT
<213> ORGANISM: Homo sapiens

<400> SEQUENCE: 1001

Ile Ser Tyr Asn Gly Gly Ala Arg
1 5

<210> SEQ ID NO 1002
<211> LENGTH: 15
<212> TYPE: PRT
<213> ORGANISM: Homo sapiens

<400> SEQUENCE: 1002

Val Lys Asp Lys Ser Gln Gly Ile Pro Val Ala Gly Leu Glu Tyr
1 5 10 15

<210> SEQ ID NO 1003
<211> LENGTH: 8
<212> TYPE: PRT
<213> ORGANISM: Homo sapiens

<400> SEQUENCE: 1003

Asn Ser Asn Ile Gly Asn Asn Phe
1 5

<210> SEQ ID NO 1004

<211> LENGTH: 10
<212> TYPE: PRT
<213> ORGANISM: Homo sapiens

<400> SEQUENCE: 1004

Gly Thr Trp Asp Ser Ser Leu Ser Ala Ala
1               5                   10

<210> SEQ ID NO 1005
<211> LENGTH: 10
<212> TYPE: PRT
<213> ORGANISM: Homo sapiens

<400> SEQUENCE: 1005

Gly Gly Ser Ile Thr Thr Gly Asp Tyr Tyr
1               5                   10

<210> SEQ ID NO 1006
<211> LENGTH: 7
<212> TYPE: PRT
<213> ORGANISM: Homo sapiens

<400> SEQUENCE: 1006

Ile Tyr Tyr Ser Gly Ser Thr
1               5

<210> SEQ ID NO 1007
<211> LENGTH: 12
<212> TYPE: PRT
<213> ORGANISM: Homo sapiens

<400> SEQUENCE: 1007

Ala Ile Tyr Met Asp Glu Ala Trp Ala Phe Glu Ile
1               5                   10

<210> SEQ ID NO 1008
<211> LENGTH: 6
<212> TYPE: PRT
<213> ORGANISM: Homo sapiens

<400> SEQUENCE: 1008

Gln Ser Ile Gly Asn Tyr
1               5

<210> SEQ ID NO 1009
<211> LENGTH: 10
<212> TYPE: PRT
<213> ORGANISM: Homo sapiens

<400> SEQUENCE: 1009

Gln Gln Ser Tyr Thr Ile Ser Leu Phe Thr
1               5                   10

<210> SEQ ID NO 1010
<211> LENGTH: 10
<212> TYPE: PRT
<213> ORGANISM: Homo sapiens

<400> SEQUENCE: 1010

Gly Gly Ser Ile Thr Thr Gly Asp Tyr Tyr
1               5                   10

<210> SEQ ID NO 1011
<211> LENGTH: 7
<212> TYPE: PRT

<213> ORGANISM: Homo sapiens

<400> SEQUENCE: 1011

Ile Tyr Tyr Ser Gly Ser Thr
1 5

<210> SEQ ID NO 1012
<211> LENGTH: 12
<212> TYPE: PRT
<213> ORGANISM: Homo sapiens

<400> SEQUENCE: 1012

Ala Ile Tyr Met Asp Glu Ala Trp Ala Phe Glu Ile
1 5 10

<210> SEQ ID NO 1013
<211> LENGTH: 6
<212> TYPE: PRT
<213> ORGANISM: Homo sapiens

<400> SEQUENCE: 1013

Gln Ser Val Gly Asn Tyr
1 5

<210> SEQ ID NO 1014
<211> LENGTH: 10
<212> TYPE: PRT
<213> ORGANISM: Homo sapiens

<400> SEQUENCE: 1014

Gln Gln Ser Tyr Thr Ile Ser Leu Phe Thr
1 5 10

<210> SEQ ID NO 1015
<211> LENGTH: 10
<212> TYPE: PRT
<213> ORGANISM: Homo sapiens

<400> SEQUENCE: 1015

Gly Gly Ser Ile Ser Gly Gly Asp Tyr Tyr
1 5 10

<210> SEQ ID NO 1016
<211> LENGTH: 7
<212> TYPE: PRT
<213> ORGANISM: Homo sapiens

<400> SEQUENCE: 1016

Ile Tyr Tyr Ser Gly Asn Thr
1 5

<210> SEQ ID NO 1017
<211> LENGTH: 12
<212> TYPE: PRT
<213> ORGANISM: Homo sapiens

<400> SEQUENCE: 1017

Val Arg Glu Asn Tyr Ile Thr Ser Pro Leu Ser Arg
1 5 10

<210> SEQ ID NO 1018
<211> LENGTH: 9
<212> TYPE: PRT
<213> ORGANISM: Homo sapiens

<400> SEQUENCE: 1018

Ser Ser Asp Val Gly Gly Tyr Asn Tyr
1 5

<210> SEQ ID NO 1019
<211> LENGTH: 10
<212> TYPE: PRT
<213> ORGANISM: Homo sapiens

<400> SEQUENCE: 1019

Ser Ser Tyr Ala Gly Ser Asn Asp Val Val
1 5 10

<210> SEQ ID NO 1020
<211> LENGTH: 10
<212> TYPE: PRT
<213> ORGANISM: Homo sapiens

<400> SEQUENCE: 1020

Gly Gly Ser Ile Asn Ser Gly Asp Tyr Tyr
1 5 10

<210> SEQ ID NO 1021
<211> LENGTH: 7
<212> TYPE: PRT
<213> ORGANISM: Homo sapiens

<400> SEQUENCE: 1021

Val Tyr Ser Ser Gly Ser Thr
1 5

<210> SEQ ID NO 1022
<211> LENGTH: 13
<212> TYPE: PRT
<213> ORGANISM: Homo sapiens

<400> SEQUENCE: 1022

Ala Ser Tyr Thr Val Thr Thr Trp Gly Gly Phe Asp Tyr
1 5 10

<210> SEQ ID NO 1023
<211> LENGTH: 6
<212> TYPE: PRT
<213> ORGANISM: Homo sapiens

<400> SEQUENCE: 1023

Ala Leu Pro Lys Lys Tyr
1 5

<210> SEQ ID NO 1024
<211> LENGTH: 11
<212> TYPE: PRT
<213> ORGANISM: Homo sapiens

<400> SEQUENCE: 1024

Tyr Ser Thr Asp Ser Ser Gly Asn Tyr Arg Val
1 5 10

<210> SEQ ID NO 1025
<211> LENGTH: 10
<212> TYPE: PRT
<213> ORGANISM: Homo sapiens

<400> SEQUENCE: 1025

Gly Gly Ser Ile Ser Ser Gly Asn Tyr Tyr
1 5 10

<210> SEQ ID NO 1026
<211> LENGTH: 7
<212> TYPE: PRT
<213> ORGANISM: Homo sapiens

<400> SEQUENCE: 1026

Ile His Tyr Ser Gly Ser Thr
1 5

<210> SEQ ID NO 1027
<211> LENGTH: 6
<212> TYPE: PRT
<213> ORGANISM: Homo sapiens

<400> SEQUENCE: 1027

Ala Arg Gly Val Leu His
1 5

<210> SEQ ID NO 1028
<211> LENGTH: 7
<212> TYPE: PRT
<213> ORGANISM: Homo sapiens

<400> SEQUENCE: 1028

Gln Ser Val Ser Ser Ser Tyr
1 5

<210> SEQ ID NO 1029
<211> LENGTH: 9
<212> TYPE: PRT
<213> ORGANISM: Homo sapiens

<400> SEQUENCE: 1029

Gln Gln Tyr Gly Ser Ser Pro Tyr Thr
1 5

<210> SEQ ID NO 1030
<211> LENGTH: 10
<212> TYPE: PRT
<213> ORGANISM: Homo sapiens

<400> SEQUENCE: 1030

Gly Gly Ser Ile Ser Ser Gly Gly Tyr Tyr
1 5 10

<210> SEQ ID NO 1031
<211> LENGTH: 13
<212> TYPE: PRT
<213> ORGANISM: Homo sapiens

<400> SEQUENCE: 1031

Ile Tyr Tyr Ser Asp Thr Thr Tyr Tyr Ser Gly Ser Thr
1 5 10

<210> SEQ ID NO 1032
<211> LENGTH: 15
<212> TYPE: PRT
<213> ORGANISM: Homo sapiens

<400> SEQUENCE: 1032

Ala Arg Val Val Ser Ser Gly His Arg His Tyr Tyr Phe Asp Tyr
1 5 10 15

<210> SEQ ID NO 1033
<211> LENGTH: 6
<212> TYPE: PRT
<213> ORGANISM: Homo sapiens

<400> SEQUENCE: 1033

Gln Gly Ile Ser Asn Tyr
1 5

<210> SEQ ID NO 1034
<211> LENGTH: 5
<212> TYPE: PRT
<213> ORGANISM: Homo sapiens

<400> SEQUENCE: 1034

Gln Lys Tyr Trp Thr
1 5

<210> SEQ ID NO 1035
<211> LENGTH: 10
<212> TYPE: PRT
<213> ORGANISM: Homo sapiens

<400> SEQUENCE: 1035

Arg Gly Ser Val Gly Trp Gly Glu Asn Phe
1 5 10

<210> SEQ ID NO 1036
<211> LENGTH: 7
<212> TYPE: PRT
<213> ORGANISM: Homo sapiens

<400> SEQUENCE: 1036

Ile Leu Asn Thr Gly Ile Asp
1 5

<210> SEQ ID NO 1037
<211> LENGTH: 12
<212> TYPE: PRT
<213> ORGANISM: Homo sapiens

<400> SEQUENCE: 1037

Ala Gln Ser Arg Arg Leu Val Gly Pro Phe Val Ser
1 5 10

<210> SEQ ID NO 1038
<211> LENGTH: 5
<212> TYPE: PRT
<213> ORGANISM: Homo sapiens

<400> SEQUENCE: 1038

Ser Ile Asn Ile Asn
1 5

<210> SEQ ID NO 1039
<211> LENGTH: 9
<212> TYPE: PRT
<213> ORGANISM: Homo sapiens

<400> SEQUENCE: 1039

Gln Gln Tyr Asp Lys Trp Pro Arg Ser
1 5

<210> SEQ ID NO 1040
<211> LENGTH: 8
<212> TYPE: PRT
<213> ORGANISM: Homo sapiens

<400> SEQUENCE: 1040

Ser Gly Ser Ile Ala Ser Asn Tyr
1 5

<210> SEQ ID NO 1041
<211> LENGTH: 10
<212> TYPE: PRT
<213> ORGANISM: Homo sapiens

<400> SEQUENCE: 1041

Gln Ser Tyr Asp Ser Ser Asn His Gly Val
1 5 10

<210> SEQ ID NO 1042
<211> LENGTH: 10
<212> TYPE: PRT
<213> ORGANISM: Homo sapiens

<400> SEQUENCE: 1042

Gly Gly Ser Ile Ser Ser Gly Gly Tyr Tyr
1 5 10

<210> SEQ ID NO 1043
<211> LENGTH: 7
<212> TYPE: PRT
<213> ORGANISM: Homo sapiens

<400> SEQUENCE: 1043

Ile Ser Tyr Ser Gly Ser Thr
1 5

<210> SEQ ID NO 1044
<211> LENGTH: 6
<212> TYPE: PRT
<213> ORGANISM: Homo sapiens

<400> SEQUENCE: 1044

Ala Arg Gly Val Leu Val
1 5

<210> SEQ ID NO 1045
<211> LENGTH: 7
<212> TYPE: PRT
<213> ORGANISM: Homo sapiens

<400> SEQUENCE: 1045

Gln Ser Val Ser Arg Ala Tyr
1 5

<210> SEQ ID NO 1046
<211> LENGTH: 9
<212> TYPE: PRT
<213> ORGANISM: Homo sapiens

<400> SEQUENCE: 1046

Gln Gln Tyr Asp Ser Ser Pro Tyr Thr
1 5

<210> SEQ ID NO 1047
<211> LENGTH: 10

<212> TYPE: PRT
<213> ORGANISM: Homo sapiens

<400> SEQUENCE: 1047

Gly Gly Ser Ile Asn Ser Asp Asp Tyr Tyr
1 5 10

<210> SEQ ID NO 1048
<211> LENGTH: 7
<212> TYPE: PRT
<213> ORGANISM: Homo sapiens

<400> SEQUENCE: 1048

Ile Tyr Tyr Asp Gly Ser Ala
1 5

<210> SEQ ID NO 1049
<211> LENGTH: 13
<212> TYPE: PRT
<213> ORGANISM: Homo sapiens

<400> SEQUENCE: 1049

Ala Arg Val Val His Ala Ser Ala Asn Ala Phe Asp Val
1 5 10

<210> SEQ ID NO 1050
<211> LENGTH: 6
<212> TYPE: PRT
<213> ORGANISM: Homo sapiens

<400> SEQUENCE: 1050

Gln Gly Ile Arg Asn Asp
1 5

<210> SEQ ID NO 1051
<211> LENGTH: 9
<212> TYPE: PRT
<213> ORGANISM: Homo sapiens

<400> SEQUENCE: 1051

Leu Gln Asp Tyr Asn Tyr Pro Leu Thr
1 5

<210> SEQ ID NO 1052
<211> LENGTH: 8
<212> TYPE: PRT
<213> ORGANISM: Homo sapiens

<400> SEQUENCE: 1052

Ser Ser Asn Ile Gly Asn Thr Phe
1 5

<210> SEQ ID NO 1053
<211> LENGTH: 11
<212> TYPE: PRT
<213> ORGANISM: Homo sapiens

<400> SEQUENCE: 1053

Gly Thr Trp Asp Ser Ser Leu Asn Gly Trp Val
1 5 10

<210> SEQ ID NO 1054
<211> LENGTH: 10
<212> TYPE: PRT
<213> ORGANISM: Homo sapiens

<400> SEQUENCE: 1054

Gly Gly Ser Ile Ser Asn Asp Asn Tyr Tyr
1 5 10

<210> SEQ ID NO 1055
<211> LENGTH: 7
<212> TYPE: PRT
<213> ORGANISM: Homo sapiens

<400> SEQUENCE: 1055

Ile Tyr Tyr Asp Gly Ser Ala
1 5

<210> SEQ ID NO 1056
<211> LENGTH: 13
<212> TYPE: PRT
<213> ORGANISM: Homo sapiens

<400> SEQUENCE: 1056

Ala Arg Val Val His Ala Ser Ala Asn Ala Phe Asp Val
1 5 10

<210> SEQ ID NO 1057
<211> LENGTH: 6
<212> TYPE: PRT
<213> ORGANISM: Homo sapiens

<400> SEQUENCE: 1057

Gln Ser Ile Asn Lys Phe
1 5

<210> SEQ ID NO 1058
<211> LENGTH: 8
<212> TYPE: PRT
<213> ORGANISM: Homo sapiens

<400> SEQUENCE: 1058

Gln Gln Thr Tyr Ser Thr Pro Thr
1 5

<210> SEQ ID NO 1059
<211> LENGTH: 10
<212> TYPE: PRT
<213> ORGANISM: Homo sapiens

<400> SEQUENCE: 1059

Gly Val Pro Ile Asn Asn Ala Gly Phe Tyr
1 5 10

<210> SEQ ID NO 1060
<211> LENGTH: 7
<212> TYPE: PRT
<213> ORGANISM: Homo sapiens

<400> SEQUENCE: 1060

Ile His Ala Ser Gly Ala Thr
1 5

<210> SEQ ID NO 1061
<211> LENGTH: 19
<212> TYPE: PRT
<213> ORGANISM: Homo sapiens

<400> SEQUENCE: 1061

Ala Arg Val Pro Leu Arg Asp Phe Tyr Ser Asn Tyr Ser Pro Ser Ala
1 5 10 15

Phe Asp Ile

<210> SEQ ID NO 1062
<211> LENGTH: 6
<212> TYPE: PRT
<213> ORGANISM: Homo sapiens

<400> SEQUENCE: 1062

Gln Ser Val Ser Ser Asp
1 5

<210> SEQ ID NO 1063
<211> LENGTH: 10
<212> TYPE: PRT
<213> ORGANISM: Homo sapiens

<400> SEQUENCE: 1063

Gln Gln Tyr Lys Asn Trp Pro Pro Leu Thr
1 5 10

<210> SEQ ID NO 1064
<211> LENGTH: 8
<212> TYPE: PRT
<213> ORGANISM: Homo sapiens

<400> SEQUENCE: 1064

Arg Gly Ser Phe Ser Asp Tyr Tyr
1 5

<210> SEQ ID NO 1065
<211> LENGTH: 7
<212> TYPE: PRT
<213> ORGANISM: Homo sapiens

<400> SEQUENCE: 1065

Ile Asn His Ser Gly Ser Thr
1 5

<210> SEQ ID NO 1066
<211> LENGTH: 18
<212> TYPE: PRT
<213> ORGANISM: Homo sapiens

<400> SEQUENCE: 1066

Ala Gly Gly Arg Phe Thr Asn Asp Phe Val Trp Gly Ser Tyr Arg Tyr
1 5 10 15

Glu Ser

<210> SEQ ID NO 1067
<211> LENGTH: 11
<212> TYPE: PRT
<213> ORGANISM: Homo sapiens

<400> SEQUENCE: 1067

Gln Ser Leu Leu His Ser Asn Gly Tyr Asn Tyr
1 5 10

<210> SEQ ID NO 1068
<211> LENGTH: 10
<212> TYPE: PRT
<213> ORGANISM: Homo sapiens

<400> SEQUENCE: 1068

Met Gln Ala Leu Gln Thr Leu Leu Leu Thr
1 5 10

<210> SEQ ID NO 1069
<211> LENGTH: 8
<212> TYPE: PRT
<213> ORGANISM: Homo sapiens

<400> SEQUENCE: 1069

Gly Gly Ser Phe Ile Gly His Tyr
1 5

<210> SEQ ID NO 1070
<211> LENGTH: 7
<212> TYPE: PRT
<213> ORGANISM: Homo sapiens

<400> SEQUENCE: 1070

Ile Ser His Ser Gly Ser Ala
1 5

<210> SEQ ID NO 1071
<211> LENGTH: 16
<212> TYPE: PRT
<213> ORGANISM: Homo sapiens

<400> SEQUENCE: 1071

Val Arg Gly Gly Tyr Ser Ser Ala Pro Tyr Pro Arg Glu Trp Arg Tyr
1 5 10 15

<210> SEQ ID NO 1072
<211> LENGTH: 8
<212> TYPE: PRT
<213> ORGANISM: Homo sapiens

<400> SEQUENCE: 1072

Ser Ser Asn Ile Gly Ser Asn Thr
1 5

<210> SEQ ID NO 1073
<211> LENGTH: 11
<212> TYPE: PRT
<213> ORGANISM: Homo sapiens

<400> SEQUENCE: 1073

Ala Ala Trp Asp Asp Ser Leu Asn Gly Trp Val
1 5 10

<210> SEQ ID NO 1074
<211> LENGTH: 8
<212> TYPE: PRT
<213> ORGANISM: Homo sapiens

<400> SEQUENCE: 1074

Gly Gly Ser Phe Ser Gly Asp Phe
1 5

<210> SEQ ID NO 1075
<211> LENGTH: 7
<212> TYPE: PRT
<213> ORGANISM: Homo sapiens

<400> SEQUENCE: 1075

Ile Asn Gln Ser Gly Ser Thr
1 5

<210> SEQ ID NO 1076
<211> LENGTH: 20
<212> TYPE: PRT
<213> ORGANISM: Homo sapiens

<400> SEQUENCE: 1076

Ala Arg Gly Arg Asp Gly Tyr Asn Tyr Val Gly Tyr Tyr Tyr Tyr Tyr
1 5 10 15

Tyr Met Asp Val
20

<210> SEQ ID NO 1077
<211> LENGTH: 6
<212> TYPE: PRT
<213> ORGANISM: Homo sapiens

<400> SEQUENCE: 1077

Gln Ser Val Thr Asn Tyr
1 5

<210> SEQ ID NO 1078
<211> LENGTH: 9
<212> TYPE: PRT
<213> ORGANISM: Homo sapiens

<400> SEQUENCE: 1078

Gln Gln Arg Ser Asn Trp Gln Trp Thr
1 5

<210> SEQ ID NO 1079
<211> LENGTH: 8
<212> TYPE: PRT
<213> ORGANISM: Homo sapiens

<400> SEQUENCE: 1079

Gly Gly Thr Phe Ser Gly Tyr Tyr
1 5

<210> SEQ ID NO 1080
<211> LENGTH: 7
<212> TYPE: PRT
<213> ORGANISM: Homo sapiens

<400> SEQUENCE: 1080

Ile Asp His Ser Gly Gly Thr
1 5

<210> SEQ ID NO 1081
<211> LENGTH: 19
<212> TYPE: PRT
<213> ORGANISM: Homo sapiens

<400> SEQUENCE: 1081

Ala Arg Gly Ile Phe Glu Val Val Ile Ile Pro Tyr Tyr Ser Tyr Arg
1 5 10 15

Val Asp Val

<210> SEQ ID NO 1082
<211> LENGTH: 6
<212> TYPE: PRT

<213> ORGANISM: Homo sapiens

<400> SEQUENCE: 1082

Gln Thr Ile Ser Asn Asn
1               5

<210> SEQ ID NO 1083
<211> LENGTH: 10
<212> TYPE: PRT
<213> ORGANISM: Homo sapiens

<400> SEQUENCE: 1083

Gln Gln Tyr Asn Asn Trp Pro Pro Phe Thr
1               5                   10

<210> SEQ ID NO 1084
<211> LENGTH: 6
<212> TYPE: PRT
<213> ORGANISM: Homo sapiens

<400> SEQUENCE: 1084

Ser Leu Arg Ser Tyr Tyr
1               5

<210> SEQ ID NO 1085
<211> LENGTH: 9
<212> TYPE: PRT
<213> ORGANISM: Homo sapiens

<400> SEQUENCE: 1085

Ser Ser Arg Ser Gly Asn Arg Leu Val
1               5

<210> SEQ ID NO 1086
<211> LENGTH: 8
<212> TYPE: PRT
<213> ORGANISM: Homo sapiens

<400> SEQUENCE: 1086

Gly Gly Pro Phe Ser Gly Tyr Tyr
1               5

<210> SEQ ID NO 1087
<211> LENGTH: 7
<212> TYPE: PRT
<213> ORGANISM: Homo sapiens

<400> SEQUENCE: 1087

Ile Asn His Ser Gly Ser Thr
1               5

<210> SEQ ID NO 1088
<211> LENGTH: 20
<212> TYPE: PRT
<213> ORGANISM: Homo sapiens

<400> SEQUENCE: 1088

Gly Arg Gly Leu Gly Arg Glu Tyr Ser Ser Ser Trp Tyr Gly Gly Arg
1               5                   10                  15

Arg Phe Asp Pro
            20

<210> SEQ ID NO 1089
<211> LENGTH: 8

<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Any amino acid

<400> SEQUENCE: 1089

Ser Arg Gln Asp Gly Arg Tyr Xaa
1 5

<210> SEQ ID NO 1090
<211> LENGTH: 11
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: Any amino acid

<400> SEQUENCE: 1090

Arg Ser Tyr Ile Ser Asn Asn Xaa Xaa Trp Val
1 5 10

<210> SEQ ID NO 1091
<211> LENGTH: 9
<212> TYPE: PRT
<213> ORGANISM: Homo sapiens

<400> SEQUENCE: 1091

Gly Tyr Ser Ile Arg Asn Arg Tyr Tyr
1 5

<210> SEQ ID NO 1092
<211> LENGTH: 7
<212> TYPE: PRT
<213> ORGANISM: Homo sapiens

<400> SEQUENCE: 1092

Met Tyr His Ser Gly Ser Thr
1 5

<210> SEQ ID NO 1093
<211> LENGTH: 16
<212> TYPE: PRT
<213> ORGANISM: Homo sapiens

<400> SEQUENCE: 1093

Ala Arg Asp Arg Ser Gly Tyr Val Phe Phe Tyr Asp Ala Phe Asp Ile
1 5 10 15

<210> SEQ ID NO 1094
<211> LENGTH: 7
<212> TYPE: PRT
<213> ORGANISM: Homo sapiens

<400> SEQUENCE: 1094

Gln Ser Val Ser Ser Ser Tyr
1 5

<210> SEQ ID NO 1095
<211> LENGTH: 9
<212> TYPE: PRT
<213> ORGANISM: Homo sapiens

<400> SEQUENCE: 1095

Gln Gln Tyr Gly Ser Ser Pro Leu Thr
1 5

<210> SEQ ID NO 1096
<211> LENGTH: 9
<212> TYPE: PRT
<213> ORGANISM: Homo sapiens

<400> SEQUENCE: 1096

Gly Tyr Ser Ile Ser Arg Asp Tyr Tyr
1 5

<210> SEQ ID NO 1097
<211> LENGTH: 7
<212> TYPE: PRT
<213> ORGANISM: Homo sapiens

<400> SEQUENCE: 1097

Phe Ser His Ser Gly Thr Thr
1 5

<210> SEQ ID NO 1098
<211> LENGTH: 9
<212> TYPE: PRT
<213> ORGANISM: Homo sapiens

<400> SEQUENCE: 1098

Gly Gly Gly Val Thr Arg Ala Asp Tyr
1 5

<210> SEQ ID NO 1099
<211> LENGTH: 8
<212> TYPE: PRT
<213> ORGANISM: Homo sapiens

<400> SEQUENCE: 1099

Ser Ser Asn Ile Gly Lys Asn Tyr
1 5

<210> SEQ ID NO 1100
<211> LENGTH: 11
<212> TYPE: PRT
<213> ORGANISM: Homo sapiens

<400> SEQUENCE: 1100

Ala Val Trp Asp Asp Asn Leu Ser Ala Trp Glu
1 5 10

<210> SEQ ID NO 1101
<211> LENGTH: 10
<212> TYPE: PRT
<213> ORGANISM: Homo sapiens

<400> SEQUENCE: 1101

Gly Gly Ser Ile Ser Ser Ser Ser Tyr Tyr
1 5 10

<210> SEQ ID NO 1102
<211> LENGTH: 7
<212> TYPE: PRT
<213> ORGANISM: Homo sapiens

<400> SEQUENCE: 1102

Ile Asp Tyr Tyr Gly Ser Thr
1 5

<210> SEQ ID NO 1103
<211> LENGTH: 11
<212> TYPE: PRT
<213> ORGANISM: Homo sapiens

<400> SEQUENCE: 1103

Ala Arg Arg Ile Gln Leu Met Val Phe Asp Phe
1 5 10

<210> SEQ ID NO 1104
<211> LENGTH: 6
<212> TYPE: PRT
<213> ORGANISM: Homo sapiens

<400> SEQUENCE: 1104

Gln Ser Ile Ser Ser Trp
1 5

<210> SEQ ID NO 1105
<211> LENGTH: 9
<212> TYPE: PRT
<213> ORGANISM: Homo sapiens

<400> SEQUENCE: 1105

His Gln Tyr Asn Thr Tyr Pro Trp Thr
1 5

<210> SEQ ID NO 1106
<211> LENGTH: 10
<212> TYPE: PRT
<213> ORGANISM: Homo sapiens

<400> SEQUENCE: 1106

Gly Gly Ser Ile Ser Asn Ser Asn Tyr Tyr
1 5 10

<210> SEQ ID NO 1107
<211> LENGTH: 7
<212> TYPE: PRT
<213> ORGANISM: Homo sapiens

<400> SEQUENCE: 1107

Ile Tyr Tyr Ser Gly Ser Thr
1 5

<210> SEQ ID NO 1108
<211> LENGTH: 16
<212> TYPE: PRT
<213> ORGANISM: Homo sapiens

<400> SEQUENCE: 1108

Ala Arg His Pro Tyr Tyr Asn Phe Trp Ile Tyr Trp Tyr Phe Asp Leu
1 5 10 15

<210> SEQ ID NO 1109
<211> LENGTH: 8
<212> TYPE: PRT
<213> ORGANISM: Homo sapiens

<400> SEQUENCE: 1109

Ser Ser Thr Ile Gly Ser Asn Thr
1 5

<210> SEQ ID NO 1110
<211> LENGTH: 12
<212> TYPE: PRT
<213> ORGANISM: Homo sapiens

<400> SEQUENCE: 1110

Ala Ser Trp Asp Asp Ser Leu Asn Gly Leu Val Val
1               5                   10

<210> SEQ ID NO 1111
<211> LENGTH: 10
<212> TYPE: PRT
<213> ORGANISM: Homo sapiens

<400> SEQUENCE: 1111

Gly Gly Ser Ile Arg Ser Ser Gly Tyr Phe
1               5                   10

<210> SEQ ID NO 1112
<211> LENGTH: 7
<212> TYPE: PRT
<213> ORGANISM: Homo sapiens

<400> SEQUENCE: 1112

Val Ser Ser Lys Gly Lys Thr
1               5

<210> SEQ ID NO 1113
<211> LENGTH: 18
<212> TYPE: PRT
<213> ORGANISM: Homo sapiens

<400> SEQUENCE: 1113

Thr Arg His Trp Leu Gly Gly Asp Lys Trp Ser Gln Ser Pro Phe Leu
1               5                   10                  15

Ala Val

<210> SEQ ID NO 1114
<211> LENGTH: 8
<212> TYPE: PRT
<213> ORGANISM: Homo sapiens

<400> SEQUENCE: 1114

Ser Ser Asn Ile Gly Val Asn Thr
1               5

<210> SEQ ID NO 1115
<211> LENGTH: 11
<212> TYPE: PRT
<213> ORGANISM: Homo sapiens

<400> SEQUENCE: 1115

Ala Val Trp Asp Asp Ser Leu Asn Thr Trp Val
1               5                   10

<210> SEQ ID NO 1116
<211> LENGTH: 10
<212> TYPE: PRT
<213> ORGANISM: Homo sapiens

<400> SEQUENCE: 1116

Gly Gly Ser Ile Ser Thr Ser Asn Tyr Tyr
1               5                   10

<210> SEQ ID NO 1117
<211> LENGTH: 7
<212> TYPE: PRT
<213> ORGANISM: Homo sapiens

<400> SEQUENCE: 1117

Ile Tyr Tyr Gly Gly Ser Thr
1 5

<210> SEQ ID NO 1118
<211> LENGTH: 16
<212> TYPE: PRT
<213> ORGANISM: Homo sapiens

<400> SEQUENCE: 1118

Ala Lys Gly Arg Tyr Ser Gly Tyr Asn Asp Tyr Asn Ala Phe Asp Ile
1 5 10 15

<210> SEQ ID NO 1119
<211> LENGTH: 11
<212> TYPE: PRT
<213> ORGANISM: Homo sapiens

<400> SEQUENCE: 1119

Ala Ala Trp Asp Asp Ser Pro Glu Trp Leu Gly
1 5 10

<210> SEQ ID NO 1120
<211> LENGTH: 10
<212> TYPE: PRT
<213> ORGANISM: Homo sapiens

<400> SEQUENCE: 1120

Gly Gly Ser Ile Ser Ser Met Ser Tyr Tyr
1 5 10

<210> SEQ ID NO 1121
<211> LENGTH: 7
<212> TYPE: PRT
<213> ORGANISM: Homo sapiens

<400> SEQUENCE: 1121

Ile Tyr Tyr Ser Gly Thr Thr
1 5

<210> SEQ ID NO 1122
<211> LENGTH: 24
<212> TYPE: PRT
<213> ORGANISM: Homo sapiens

<400> SEQUENCE: 1122

Thr Arg Pro Ala Ser Gly Ala His Asp Tyr Val Ser Arg Ser Tyr Tyr
1 5 10 15

Pro Gly Gln Gly Ala Phe Gly Val
20

<210> SEQ ID NO 1123
<211> LENGTH: 7
<212> TYPE: PRT
<213> ORGANISM: Homo sapiens

<400> SEQUENCE: 1123

Gln Ser Val Ser Ser Ser Tyr
1 5

<210> SEQ ID NO 1124
<211> LENGTH: 9
<212> TYPE: PRT
<213> ORGANISM: Homo sapiens

<400> SEQUENCE: 1124

Gln Gln Tyr Gly Ser Ser Ser Ile Thr
1 5

<210> SEQ ID NO 1125
<211> LENGTH: 10
<212> TYPE: PRT
<213> ORGANISM: Homo sapiens

<400> SEQUENCE: 1125

Gly Gly Ser Ile Ile Ser Tyr Thr Tyr Tyr
1 5 10

<210> SEQ ID NO 1126
<211> LENGTH: 7
<212> TYPE: PRT
<213> ORGANISM: Homo sapiens

<400> SEQUENCE: 1126

Leu Tyr Tyr Thr Gly Ile Thr
1 5

<210> SEQ ID NO 1127
<211> LENGTH: 14
<212> TYPE: PRT
<213> ORGANISM: Homo sapiens

<400> SEQUENCE: 1127

Ala Arg Leu Leu Gly Ile Ala Ala Thr Gly His Phe Asp Ser
1 5 10

<210> SEQ ID NO 1128
<211> LENGTH: 8
<212> TYPE: PRT
<213> ORGANISM: Homo sapiens

<400> SEQUENCE: 1128

Ser Asn Asn Ile Asp Asn Gln Gly
1 5

<210> SEQ ID NO 1129
<211> LENGTH: 11
<212> TYPE: PRT
<213> ORGANISM: Homo sapiens

<400> SEQUENCE: 1129

Ser Thr Trp Asp Ser Ser Leu Ser Thr Trp Leu
1 5 10

<210> SEQ ID NO 1130
<211> LENGTH: 10
<212> TYPE: PRT
<213> ORGANISM: Homo sapiens

<400> SEQUENCE: 1130

Gly Gly Ser Ile Ser Ser Ile Ser Tyr Tyr
1 5 10

<210> SEQ ID NO 1131

<211> LENGTH: 7
<212> TYPE: PRT
<213> ORGANISM: Homo sapiens

<400> SEQUENCE: 1131

Ile Tyr Tyr Ser Gly Thr Pro
1 5

<210> SEQ ID NO 1132
<211> LENGTH: 24
<212> TYPE: PRT
<213> ORGANISM: Homo sapiens

<400> SEQUENCE: 1132

Thr Arg Pro Ala Ser Gly Ala His Asp Tyr Ala Ser Arg Ser Tyr Tyr
1 5 10 15

Pro Gly Leu Gly Ala Phe Gly Ile
20

<210> SEQ ID NO 1133
<211> LENGTH: 7
<212> TYPE: PRT
<213> ORGANISM: Homo sapiens

<400> SEQUENCE: 1133

Gln Ser Val Ser Thr Thr Tyr
1 5

<210> SEQ ID NO 1134
<211> LENGTH: 9
<212> TYPE: PRT
<213> ORGANISM: Homo sapiens

<400> SEQUENCE: 1134

Gln Gln Tyr Gly Ser Ser Ser Thr Thr
1 5

<210> SEQ ID NO 1135
<211> LENGTH: 10
<212> TYPE: PRT
<213> ORGANISM: Homo sapiens

<400> SEQUENCE: 1135

Gly Gly Ser Ile Thr Ser Leu Ser Tyr Trp
1 5 10

<210> SEQ ID NO 1136
<211> LENGTH: 7
<212> TYPE: PRT
<213> ORGANISM: Homo sapiens

<400> SEQUENCE: 1136

Ile Tyr Tyr Ser Gly Thr Thr
1 5

<210> SEQ ID NO 1137
<211> LENGTH: 22
<212> TYPE: PRT
<213> ORGANISM: Homo sapiens

<400> SEQUENCE: 1137

Ala Arg Pro Leu Leu Asn Pro Met Thr Leu Tyr Gly Val Thr Pro Gly
1 5 10 15

Ile Gly Pro Phe Glu Ile

20

<210> SEQ ID NO 1138
<211> LENGTH: 7
<212> TYPE: PRT
<213> ORGANISM: Homo sapiens

<400> SEQUENCE: 1138

Gln Ser Val Ser Ser Lys Cys
1               5

<210> SEQ ID NO 1139
<211> LENGTH: 8
<212> TYPE: PRT
<213> ORGANISM: Homo sapiens

<400> SEQUENCE: 1139

Gln Gln His Asp Asn Ser Leu Ser
1               5

<210> SEQ ID NO 1140
<211> LENGTH: 10
<212> TYPE: PRT
<213> ORGANISM: Homo sapiens

<400> SEQUENCE: 1140

Gly Asp Ser Met Ser Arg Asn Ser Phe Tyr
1               5                   10

<210> SEQ ID NO 1141
<211> LENGTH: 7
<212> TYPE: PRT
<213> ORGANISM: Homo sapiens

<400> SEQUENCE: 1141

Ile Asn Tyr Asn Gly Ile Thr
1               5

<210> SEQ ID NO 1142
<211> LENGTH: 13
<212> TYPE: PRT
<213> ORGANISM: Homo sapiens

<400> SEQUENCE: 1142

Ala Ala His Arg Val Ser Ser Ser Tyr Pro Ala Asp Tyr
1               5                   10

<210> SEQ ID NO 1143
<211> LENGTH: 6
<212> TYPE: PRT
<213> ORGANISM: Homo sapiens

<400> SEQUENCE: 1143

Gln Asn Ile Asp Asp Tyr
1               5

<210> SEQ ID NO 1144
<211> LENGTH: 8
<212> TYPE: PRT
<213> ORGANISM: Homo sapiens

<400> SEQUENCE: 1144

Gln Gln Ser Tyr Asn Thr Pro Thr
1               5

<210> SEQ ID NO 1145
<211> LENGTH: 10
<212> TYPE: PRT
<213> ORGANISM: Homo sapiens

<400> SEQUENCE: 1145

Gly Gly Ser Ile Ser Ser Leu Ser Tyr Tyr
1               5                   10

<210> SEQ ID NO 1146
<211> LENGTH: 7
<212> TYPE: PRT
<213> ORGANISM: Homo sapiens

<400> SEQUENCE: 1146

Ile Tyr Tyr Ser Gly Thr Ala
1               5

<210> SEQ ID NO 1147
<211> LENGTH: 22
<212> TYPE: PRT
<213> ORGANISM: Homo sapiens

<400> SEQUENCE: 1147

Ala Arg Pro Leu Leu Asn Pro Ser Thr Ile Tyr Gly Val Thr Pro Gly
1               5                   10                  15

Ile Gly Pro Phe Glu Met
            20

<210> SEQ ID NO 1148
<211> LENGTH: 6
<212> TYPE: PRT
<213> ORGANISM: Homo sapiens

<400> SEQUENCE: 1148

Gln Ser Ile Arg Ser Asn
1               5

<210> SEQ ID NO 1149
<211> LENGTH: 10
<212> TYPE: PRT
<213> ORGANISM: Homo sapiens

<400> SEQUENCE: 1149

Gln Gln Tyr Ile Asn Trp Pro Pro Trp Thr
1               5                   10

<210> SEQ ID NO 1150
<211> LENGTH: 9
<212> TYPE: PRT
<213> ORGANISM: Homo sapiens

<400> SEQUENCE: 1150

Gly Tyr Ser Val Ser Thr Ser Asn Trp
1               5

<210> SEQ ID NO 1151
<211> LENGTH: 7
<212> TYPE: PRT
<213> ORGANISM: Homo sapiens

<400> SEQUENCE: 1151

Ile Tyr His Ile Gly Ser Thr
1               5

<210> SEQ ID NO 1152
<211> LENGTH: 22
<212> TYPE: PRT
<213> ORGANISM: Homo sapiens

<400> SEQUENCE: 1152

Ala Arg Gly Asn Tyr Asp Tyr Val Trp Gly Ser Tyr Arg Ser Asp Gln
1 5 10 15

Gly Tyr Gly Leu Asp Val
20

<210> SEQ ID NO 1153
<211> LENGTH: 6
<212> TYPE: PRT
<213> ORGANISM: Homo sapiens

<400> SEQUENCE: 1153

Gln Ser Ile Asp Asn Tyr
1 5

<210> SEQ ID NO 1154
<211> LENGTH: 9
<212> TYPE: PRT
<213> ORGANISM: Homo sapiens

<400> SEQUENCE: 1154

Gln Arg Ser Tyr Ser Thr Pro Tyr Thr
1 5

<210> SEQ ID NO 1155
<211> LENGTH: 8
<212> TYPE: PRT
<213> ORGANISM: Homo sapiens

<400> SEQUENCE: 1155

Gly Ala Ser Ile Arg Ser His Tyr
1 5

<210> SEQ ID NO 1156
<211> LENGTH: 7
<212> TYPE: PRT
<213> ORGANISM: Homo sapiens

<400> SEQUENCE: 1156

Val His Ser Ser Gly Gly Thr
1 5

<210> SEQ ID NO 1157
<211> LENGTH: 16
<212> TYPE: PRT
<213> ORGANISM: Homo sapiens

<400> SEQUENCE: 1157

Ala Arg Glu Gly Gly Ser Ser Tyr Tyr Tyr Tyr Tyr Tyr Met Asp Val
1 5 10 15

<210> SEQ ID NO 1158
<211> LENGTH: 9
<212> TYPE: PRT
<213> ORGANISM: Homo sapiens

<400> SEQUENCE: 1158

Ser Ser Asp Val Gly Ser Tyr Asn Tyr 1 5

<210> SEQ ID NO 1159
<211> LENGTH: 11
<212> TYPE: PRT
<213> ORGANISM: Homo sapiens

<400> SEQUENCE: 1159

Ser Ser Tyr Ala Gly Ile Asn Ser Tyr Val Ile
1 5 10

<210> SEQ ID NO 1160
<211> LENGTH: 8
<212> TYPE: PRT
<213> ORGANISM: Homo sapiens

<400> SEQUENCE: 1160

Gly Gly Ser Ile Ser Thr Tyr Phe
1 5

<210> SEQ ID NO 1161
<211> LENGTH: 7
<212> TYPE: PRT
<213> ORGANISM: Homo sapiens

<400> SEQUENCE: 1161

Ile Tyr Tyr Asn Gly Gly Thr
1 5

<210> SEQ ID NO 1162
<211> LENGTH: 12
<212> TYPE: PRT
<213> ORGANISM: Homo sapiens

<400> SEQUENCE: 1162

Ala Arg Ser Lys Asn Gln Leu Leu Leu Phe Asp Pro
1 5 10

<210> SEQ ID NO 1163
<211> LENGTH: 6
<212> TYPE: PRT
<213> ORGANISM: Homo sapiens

<400> SEQUENCE: 1163

Gln Ser Val Gly Ser Asp
1 5

<210> SEQ ID NO 1164
<211> LENGTH: 10
<212> TYPE: PRT
<213> ORGANISM: Homo sapiens

<400> SEQUENCE: 1164

Gln Gln Tyr Asn Asp Trp Pro Pro Leu Thr
1 5 10

<210> SEQ ID NO 1165
<211> LENGTH: 8
<212> TYPE: PRT
<213> ORGANISM: Homo sapiens

<400> SEQUENCE: 1165

Gly Asp Ser Ile Gly Thr Tyr Phe
1 5

<210> SEQ ID NO 1166
<211> LENGTH: 7
<212> TYPE: PRT
<213> ORGANISM: Homo sapiens

<400> SEQUENCE: 1166

Val Tyr His Thr Gly Gly Thr
1 5

<210> SEQ ID NO 1167
<211> LENGTH: 12
<212> TYPE: PRT
<213> ORGANISM: Homo sapiens

<400> SEQUENCE: 1167

Ala Arg Ser Lys Asn Gln Leu Leu Leu Phe Glu Phe
1 5 10

<210> SEQ ID NO 1168
<211> LENGTH: 6
<212> TYPE: PRT
<213> ORGANISM: Homo sapiens

<400> SEQUENCE: 1168

Gln Asp Ile Ser Asn Tyr
1 5

<210> SEQ ID NO 1169
<211> LENGTH: 9
<212> TYPE: PRT
<213> ORGANISM: Homo sapiens

<400> SEQUENCE: 1169

Gln Gln Tyr Asp Asn Leu Pro Leu Thr
1 5

<210> SEQ ID NO 1170
<211> LENGTH: 8
<212> TYPE: PRT
<213> ORGANISM: Homo sapiens

<400> SEQUENCE: 1170

Gly Ala Ser Ile Ser Ser Asn Tyr
1 5

<210> SEQ ID NO 1171
<211> LENGTH: 7
<212> TYPE: PRT
<213> ORGANISM: Homo sapiens

<400> SEQUENCE: 1171

Met Tyr Ser Ser Gly Ser Val
1 5

<210> SEQ ID NO 1172
<211> LENGTH: 12
<212> TYPE: PRT
<213> ORGANISM: Homo sapiens

<400> SEQUENCE: 1172

Ala Arg Thr Asn Trp Ala Tyr Asp Pro Phe Asn Val
1 5 10

<210> SEQ ID NO 1173

<211> LENGTH: 6
<212> TYPE: PRT
<213> ORGANISM: Homo sapiens

<400> SEQUENCE: 1173

Gln Asn Ile Asn Ser Trp
1               5

<210> SEQ ID NO 1174
<211> LENGTH: 8
<212> TYPE: PRT
<213> ORGANISM: Homo sapiens

<400> SEQUENCE: 1174

Gln Gln Tyr Tyr Ser Tyr Ser Thr
1               5

<210> SEQ ID NO 1175
<211> LENGTH: 8
<212> TYPE: PRT
<213> ORGANISM: Homo sapiens

<400> SEQUENCE: 1175

Asn Asn Asn Ile Gly Arg Ser Ala
1               5

<210> SEQ ID NO 1176
<211> LENGTH: 11
<212> TYPE: PRT
<213> ORGANISM: Homo sapiens

<400> SEQUENCE: 1176

Ser Ala Trp Asp Phe Ser Leu Ser Val Gln Val
1               5                   10

<210> SEQ ID NO 1177
<211> LENGTH: 8
<212> TYPE: PRT
<213> ORGANISM: Homo sapiens

<400> SEQUENCE: 1177

Gly Gly Ser Ile Ser Ser Tyr Tyr
1               5

<210> SEQ ID NO 1178
<211> LENGTH: 7
<212> TYPE: PRT
<213> ORGANISM: Homo sapiens

<400> SEQUENCE: 1178

Ile Tyr Asp Ser Gly Ser Thr
1               5

<210> SEQ ID NO 1179
<211> LENGTH: 18
<212> TYPE: PRT
<213> ORGANISM: Homo sapiens

<400> SEQUENCE: 1179

Ala Arg Asp Arg Gly Tyr Cys Ser Gly Gly Ser Cys Leu Gly Gly Met
1               5                   10                  15

Asp Val

<210> SEQ ID NO 1180

<211> LENGTH: 6
<212> TYPE: PRT
<213> ORGANISM: Homo sapiens

<400> SEQUENCE: 1180

Gln Ser Ile Ser Arg Trp
1 5

<210> SEQ ID NO 1181
<211> LENGTH: 10
<212> TYPE: PRT
<213> ORGANISM: Homo sapiens

<400> SEQUENCE: 1181

Gln Gln Tyr Asn Ser Tyr Phe Pro Leu Thr
1 5 10

<210> SEQ ID NO 1182
<211> LENGTH: 8
<212> TYPE: PRT
<213> ORGANISM: Homo sapiens

<400> SEQUENCE: 1182

Gly Gly Ser Ile Ser Gly Ser Tyr
1 5

<210> SEQ ID NO 1183
<211> LENGTH: 7
<212> TYPE: PRT
<213> ORGANISM: Homo sapiens

<400> SEQUENCE: 1183

Ile Tyr Asp Ser Gly Asn Thr
1 5

<210> SEQ ID NO 1184
<211> LENGTH: 18
<212> TYPE: PRT
<213> ORGANISM: Homo sapiens

<400> SEQUENCE: 1184

Val Arg Asp Arg Gly Phe Cys Thr Gly Lys Ser Cys Leu Gly Gly Met
1 5 10 15

Asp Val

<210> SEQ ID NO 1185
<211> LENGTH: 6
<212> TYPE: PRT
<213> ORGANISM: Homo sapiens

<400> SEQUENCE: 1185

Gln Ser Ile Ser Ser Trp
1 5

<210> SEQ ID NO 1186
<211> LENGTH: 8
<212> TYPE: PRT
<213> ORGANISM: Homo sapiens

<400> SEQUENCE: 1186

Gln Gln Tyr Asn Ser Tyr Arg Thr
1 5

<210> SEQ ID NO 1187

<211> LENGTH: 8
<212> TYPE: PRT
<213> ORGANISM: Homo sapiens

<400> SEQUENCE: 1187

Gly Gly Ser Ile Ser Asn Tyr Phe
1               5

<210> SEQ ID NO 1188
<211> LENGTH: 7
<212> TYPE: PRT
<213> ORGANISM: Homo sapiens

<400> SEQUENCE: 1188

Val Tyr Ser Ser Gly Thr Thr
1               5

<210> SEQ ID NO 1189
<211> LENGTH: 15
<212> TYPE: PRT
<213> ORGANISM: Homo sapiens

<400> SEQUENCE: 1189

Ala Arg Leu Arg Arg Arg Gly Leu Thr Gly Thr Asp Phe Asp Tyr
1               5                   10                  15

<210> SEQ ID NO 1190
<211> LENGTH: 8
<212> TYPE: PRT
<213> ORGANISM: Homo sapiens

<400> SEQUENCE: 1190

Thr Ser Asn Ile Gly Asp Asn Asn
1               5

<210> SEQ ID NO 1191
<211> LENGTH: 13
<212> TYPE: PRT
<213> ORGANISM: Homo sapiens

<400> SEQUENCE: 1191

Ala Ala Trp Asp Asp Ser Leu Asn Gly Pro Asn Val Val
1               5                   10

<210> SEQ ID NO 1192
<211> LENGTH: 8
<212> TYPE: PRT
<213> ORGANISM: Homo sapiens

<400> SEQUENCE: 1192

Gly Gly Ser Ile Arg Ser Tyr Tyr
1               5

<210> SEQ ID NO 1193
<211> LENGTH: 7
<212> TYPE: PRT
<213> ORGANISM: Homo sapiens

<400> SEQUENCE: 1193

Ile Tyr Tyr Ser Gly Ser Thr
1               5

<210> SEQ ID NO 1194
<211> LENGTH: 22
<212> TYPE: PRT

<213> ORGANISM: Homo sapiens

<400> SEQUENCE: 1194

Ala Arg Ser Tyr Tyr Tyr Asp Ser Ser Gly Tyr Arg Pro Ser Phe Tyr
1 5 10 15

Tyr Tyr Tyr Met Asp Val
20

<210> SEQ ID NO 1195
<211> LENGTH: 6
<212> TYPE: PRT
<213> ORGANISM: Homo sapiens

<400> SEQUENCE: 1195

Lys Leu Gly Asp Lys Tyr
1 5

<210> SEQ ID NO 1196
<211> LENGTH: 8
<212> TYPE: PRT
<213> ORGANISM: Homo sapiens

<400> SEQUENCE: 1196

Gln Ala Trp Asp Ser Ser Val Val
1 5

<210> SEQ ID NO 1197
<211> LENGTH: 8
<212> TYPE: PRT
<213> ORGANISM: Homo sapiens

<400> SEQUENCE: 1197

Gly Gly Ser Ile Ser Gly Tyr Tyr
1 5

<210> SEQ ID NO 1198
<211> LENGTH: 7
<212> TYPE: PRT
<213> ORGANISM: Homo sapiens

<400> SEQUENCE: 1198

Ile Tyr Tyr Ser Gly Thr Thr
1 5

<210> SEQ ID NO 1199
<211> LENGTH: 17
<212> TYPE: PRT
<213> ORGANISM: Homo sapiens

<400> SEQUENCE: 1199

Ala Arg Gly Ile Leu Gly Ser Thr Trp Tyr Tyr Tyr Tyr Gly Leu Asp
1 5 10 15

Val

<210> SEQ ID NO 1200
<211> LENGTH: 6
<212> TYPE: PRT
<213> ORGANISM: Homo sapiens

<400> SEQUENCE: 1200

Gln Ser Ile Ser Ser Tyr
1 5

<210> SEQ ID NO 1201
<211> LENGTH: 9
<212> TYPE: PRT
<213> ORGANISM: Homo sapiens

<400> SEQUENCE: 1201

His Gln Ser Tyr Ser Ser Pro Tyr Thr
1 5

<210> SEQ ID NO 1202
<211> LENGTH: 8
<212> TYPE: PRT
<213> ORGANISM: Homo sapiens

<400> SEQUENCE: 1202

Gly Gly Ser Ile Ser Asn Asp Tyr
1 5

<210> SEQ ID NO 1203
<211> LENGTH: 7
<212> TYPE: PRT
<213> ORGANISM: Homo sapiens

<400> SEQUENCE: 1203

Ile His Ser Lys Gly Asp Thr
1 5

<210> SEQ ID NO 1204
<211> LENGTH: 15
<212> TYPE: PRT
<213> ORGANISM: Homo sapiens

<400> SEQUENCE: 1204

Ala Arg His Leu Tyr Arg Tyr Gly Tyr Arg Asn Tyr Phe Asp Tyr
1 5 10 15

<210> SEQ ID NO 1205
<211> LENGTH: 6
<212> TYPE: PRT
<213> ORGANISM: Homo sapiens

<400> SEQUENCE: 1205

Gln Gly Ile Ser Ser Gly
1 5

<210> SEQ ID NO 1206
<211> LENGTH: 9
<212> TYPE: PRT
<213> ORGANISM: Homo sapiens

<400> SEQUENCE: 1206

Gln Gln Ala Asn Ser Phe Pro Leu Thr
1 5

<210> SEQ ID NO 1207
<211> LENGTH: 8
<212> TYPE: PRT
<213> ORGANISM: Homo sapiens

<400> SEQUENCE: 1207

Gly Gly Ser Ile Ser Asn Asp Tyr
1 5

<210> SEQ ID NO 1208
<211> LENGTH: 7

<212> TYPE: PRT
<213> ORGANISM: Homo sapiens

<400> SEQUENCE: 1208

Ile His Ser Lys Gly Asp Thr
1 5

<210> SEQ ID NO 1209
<211> LENGTH: 15
<212> TYPE: PRT
<213> ORGANISM: Homo sapiens

<400> SEQUENCE: 1209

Ala Arg His Leu Tyr Arg Tyr Gly Tyr Arg Asn Tyr Phe Asp Tyr
1 5 10 15

<210> SEQ ID NO 1210
<211> LENGTH: 6
<212> TYPE: PRT
<213> ORGANISM: Homo sapiens

<400> SEQUENCE: 1210

Gln Gly Ile Ser Ser Gly
1 5

<210> SEQ ID NO 1211
<211> LENGTH: 9
<212> TYPE: PRT
<213> ORGANISM: Homo sapiens

<400> SEQUENCE: 1211

Gln Gln Ala Asn Ser Phe Pro Leu Thr
1 5

<210> SEQ ID NO 1212
<211> LENGTH: 10
<212> TYPE: PRT
<213> ORGANISM: Homo sapiens

<400> SEQUENCE: 1212

Gly Gly Ser Val Arg Ser Thr Gly Tyr Phe
1 5 10

<210> SEQ ID NO 1213
<211> LENGTH: 7
<212> TYPE: PRT
<213> ORGANISM: Homo sapiens

<400> SEQUENCE: 1213

Ile Tyr Thr Gly Gly Ala Thr
1 5

<210> SEQ ID NO 1214
<211> LENGTH: 22
<212> TYPE: PRT
<213> ORGANISM: Homo sapiens

<400> SEQUENCE: 1214

Ala Arg Met Thr Ser Phe Lys Gln Ser Gly Gly Trp Tyr Arg Gly Arg
1 5 10 15

His Asp Gly Phe Asp Ile
20

<210> SEQ ID NO 1215

<211> LENGTH: 6
<212> TYPE: PRT
<213> ORGANISM: Homo sapiens

<400> SEQUENCE: 1215

Gln Thr Ile Gly Thr Tyr
1 5

<210> SEQ ID NO 1216
<211> LENGTH: 9
<212> TYPE: PRT
<213> ORGANISM: Homo sapiens

<400> SEQUENCE: 1216

Gln Glu Tyr Asn Ser Tyr Ser Tyr Thr
1 5

<210> SEQ ID NO 1217
<211> LENGTH: 10
<212> TYPE: PRT
<213> ORGANISM: Homo sapiens

<400> SEQUENCE: 1217

Arg Gly Ser Val Ser Asn Gly Gly Tyr Tyr
1 5 10

<210> SEQ ID NO 1218
<211> LENGTH: 7
<212> TYPE: PRT
<213> ORGANISM: Homo sapiens

<400> SEQUENCE: 1218

Val Tyr Tyr Thr Gly Ser Ser
1 5

<210> SEQ ID NO 1219
<211> LENGTH: 22
<212> TYPE: PRT
<213> ORGANISM: Homo sapiens

<400> SEQUENCE: 1219

Ala Arg Leu Thr Ser Tyr Lys Gln Arg Gly Gly Trp Tyr Arg Gly Arg
1 5 10 15

His Asp Ala Phe Asp Ile
20

<210> SEQ ID NO 1220
<211> LENGTH: 6
<212> TYPE: PRT
<213> ORGANISM: Homo sapiens

<400> SEQUENCE: 1220

Gln Ser Ile Ser Thr Leu
1 5

<210> SEQ ID NO 1221
<211> LENGTH: 9
<212> TYPE: PRT
<213> ORGANISM: Homo sapiens

<400> SEQUENCE: 1221

Gln Glu Tyr Ser Ser Tyr Ser Tyr Thr
1 5

<210> SEQ ID NO 1222
<211> LENGTH: 8
<212> TYPE: PRT
<213> ORGANISM: Homo sapiens

<400> SEQUENCE: 1222

Gly Tyr Ser Phe Thr Ser Tyr Trp
1               5

<210> SEQ ID NO 1223
<211> LENGTH: 8
<212> TYPE: PRT
<213> ORGANISM: Homo sapiens

<400> SEQUENCE: 1223

Ile Gln Ser Gly Asp Tyr Asn Thr
1               5

<210> SEQ ID NO 1224
<211> LENGTH: 21
<212> TYPE: PRT
<213> ORGANISM: Homo sapiens

<400> SEQUENCE: 1224

Ala Arg Arg Ala Arg Asn Val Gly Asn Tyr Gly Thr Ser Asp Phe Tyr
1               5                   10                  15

Pro Tyr Phe Asp His
            20

<210> SEQ ID NO 1225
<211> LENGTH: 9
<212> TYPE: PRT
<213> ORGANISM: Homo sapiens

<400> SEQUENCE: 1225

Ser Ser Asp Val Gly Arg Tyr Asn Tyr
1               5

<210> SEQ ID NO 1226
<211> LENGTH: 11
<212> TYPE: PRT
<213> ORGANISM: Homo sapiens

<400> SEQUENCE: 1226

Ser Ser Tyr Ile Ser Ser Asn Thr Leu Trp Val
1               5                   10

<210> SEQ ID NO 1227
<211> LENGTH: 8
<212> TYPE: PRT
<213> ORGANISM: Homo sapiens

<400> SEQUENCE: 1227

Gly Tyr Thr Phe Ala Ser Tyr Trp
1               5

<210> SEQ ID NO 1228
<211> LENGTH: 8
<212> TYPE: PRT
<213> ORGANISM: Homo sapiens

<400> SEQUENCE: 1228

Ile Asn Pro Pro Asn Ser Asp Thr
1               5

<210> SEQ ID NO 1229
<211> LENGTH: 15
<212> TYPE: PRT
<213> ORGANISM: Homo sapiens

<400> SEQUENCE: 1229

Ala Arg Arg Arg Val Ser Val Thr Gly Thr Asp Ala Phe Asp Ile
1 5 10 15

<210> SEQ ID NO 1230
<211> LENGTH: 9
<212> TYPE: PRT
<213> ORGANISM: Homo sapiens

<400> SEQUENCE: 1230

Ser Ser Asp Val Gly Gly Tyr Asn Tyr
1 5

<210> SEQ ID NO 1231
<211> LENGTH: 11
<212> TYPE: PRT
<213> ORGANISM: Homo sapiens

<400> SEQUENCE: 1231

Ser Ser Tyr Ala Gly Thr Asn Thr Phe Val Val
1 5 10

<210> SEQ ID NO 1232
<211> LENGTH: 8
<212> TYPE: PRT
<213> ORGANISM: Homo sapiens

<400> SEQUENCE: 1232

Gly Tyr Thr Phe Ala Ser Tyr Trp
1 5

<210> SEQ ID NO 1233
<211> LENGTH: 8
<212> TYPE: PRT
<213> ORGANISM: Homo sapiens

<400> SEQUENCE: 1233

Ile Asn Pro Pro Asn Ser Asp Thr
1 5

<210> SEQ ID NO 1234
<211> LENGTH: 15
<212> TYPE: PRT
<213> ORGANISM: Homo sapiens

<400> SEQUENCE: 1234

Ala Arg Arg Arg Val Ser Val Thr Gly Thr Asp Ala Phe Asp Ile
1 5 10 15

<210> SEQ ID NO 1235
<211> LENGTH: 9
<212> TYPE: PRT
<213> ORGANISM: Homo sapiens

<400> SEQUENCE: 1235

Ser Ser Asp Val Gly Gly Tyr Asn Tyr
1 5

<210> SEQ ID NO 1236

<211> LENGTH: 11
<212> TYPE: PRT
<213> ORGANISM: Homo sapiens

<400> SEQUENCE: 1236

Ser Ser Tyr Ala Gly Thr Asn Thr Phe Val Val
1 5 10

<210> SEQ ID NO 1237
<211> LENGTH: 8
<212> TYPE: PRT
<213> ORGANISM: Homo sapiens

<400> SEQUENCE: 1237

Gly Asp Thr Phe Gly Asn Tyr Trp
1 5

<210> SEQ ID NO 1238
<211> LENGTH: 8
<212> TYPE: PRT
<213> ORGANISM: Homo sapiens

<400> SEQUENCE: 1238

Ile Leu Leu Ser Asp Ser Asp Thr
1 5

<210> SEQ ID NO 1239
<211> LENGTH: 12
<212> TYPE: PRT
<213> ORGANISM: Homo sapiens

<400> SEQUENCE: 1239

Ala Arg Ala Thr Pro Gly Asn Tyr Tyr Phe Asp Ser
1 5 10

<210> SEQ ID NO 1240
<211> LENGTH: 9
<212> TYPE: PRT
<213> ORGANISM: Homo sapiens

<400> SEQUENCE: 1240

Ser Ser Asp Val Gly Ala Tyr Asn Tyr
1 5

<210> SEQ ID NO 1241
<211> LENGTH: 11
<212> TYPE: PRT
<213> ORGANISM: Homo sapiens

<400> SEQUENCE: 1241

Ser Ser Tyr Thr Asp Ser Ser Pro Asn Cys Val
1 5 10

<210> SEQ ID NO 1242
<211> LENGTH: 8
<212> TYPE: PRT
<213> ORGANISM: Homo sapiens

<400> SEQUENCE: 1242

Gly Tyr Ser Phe Ser Asn Phe Trp
1 5

<210> SEQ ID NO 1243
<211> LENGTH: 8
<212> TYPE: PRT

<213> ORGANISM: Homo sapiens

<400> SEQUENCE: 1243

Ile Tyr Pro Gly Asp Ser Asp Thr
1 5

<210> SEQ ID NO 1244
<211> LENGTH: 22
<212> TYPE: PRT
<213> ORGANISM: Homo sapiens

<400> SEQUENCE: 1244

Ala Arg Pro Ser Arg Ser Arg Asp Ile Asn Lys Trp Tyr Leu Ser Thr
1 5 10 15

Ser Glu Tyr Phe His Tyr
20

<210> SEQ ID NO 1245
<211> LENGTH: 7
<212> TYPE: PRT
<213> ORGANISM: Homo sapiens

<400> SEQUENCE: 1245

Gln Ser Val Ser Ser Arg Ser
1 5

<210> SEQ ID NO 1246
<211> LENGTH: 9
<212> TYPE: PRT
<213> ORGANISM: Homo sapiens

<400> SEQUENCE: 1246

Gln Gln Tyr Ala Asn Ser Pro Leu Thr
1 5

<210> SEQ ID NO 1247
<211> LENGTH: 10
<212> TYPE: PRT
<213> ORGANISM: Homo sapiens

<400> SEQUENCE: 1247

Gly Asp Ser Val Ser Asn Asn Thr Ala Val
1 5 10

<210> SEQ ID NO 1248
<211> LENGTH: 9
<212> TYPE: PRT
<213> ORGANISM: Homo sapiens

<400> SEQUENCE: 1248

Thr Tyr Tyr Arg Ser Lys Trp Phe Asn
1 5

<210> SEQ ID NO 1249
<211> LENGTH: 10
<212> TYPE: PRT
<213> ORGANISM: Homo sapiens

<400> SEQUENCE: 1249

Ala Val Gly His His Trp His Phe Lys Tyr
1 5 10

<210> SEQ ID NO 1250
<211> LENGTH: 9

<212> TYPE: PRT
<213> ORGANISM: Homo sapiens

<400> SEQUENCE: 1250

Ser Ser Asp Val Gly Gly Tyr Ser His
1               5

<210> SEQ ID NO 1251
<211> LENGTH: 10
<212> TYPE: PRT
<213> ORGANISM: Homo sapiens

<400> SEQUENCE: 1251

Ser Ser His Ala Gly Ser Asn Tyr Gly Val
1               5                   10

<210> SEQ ID NO 1252
<211> LENGTH: 10
<212> TYPE: PRT
<213> ORGANISM: Homo sapiens

<400> SEQUENCE: 1252

Gly Asp Ser Val Ser Asn Asn Thr Ala Val
1               5                   10

<210> SEQ ID NO 1253
<211> LENGTH: 9
<212> TYPE: PRT
<213> ORGANISM: Homo sapiens

<400> SEQUENCE: 1253

Thr Tyr Tyr Arg Ser Lys Trp Phe Asn
1               5

<210> SEQ ID NO 1254
<211> LENGTH: 10
<212> TYPE: PRT
<213> ORGANISM: Homo sapiens

<400> SEQUENCE: 1254

Ala Val Gly His His Trp His Phe Lys Tyr
1               5                   10

<210> SEQ ID NO 1255
<211> LENGTH: 9
<212> TYPE: PRT
<213> ORGANISM: Homo sapiens

<400> SEQUENCE: 1255

Ser Ser Asp Val Gly Gly Tyr Ser His
1               5

<210> SEQ ID NO 1256
<211> LENGTH: 10
<212> TYPE: PRT
<213> ORGANISM: Homo sapiens

<400> SEQUENCE: 1256

Ser Ser His Ala Gly Ser Asn Tyr Gly Val
1               5                   10

<210> SEQ ID NO 1257
<211> LENGTH: 10
<212> TYPE: PRT
<213> ORGANISM: Homo sapiens

<400> SEQUENCE: 1257

Gly Ser Ser Ile Phe Thr Asn Ser Ala Gly
1 5 10

<210> SEQ ID NO 1258
<211> LENGTH: 9
<212> TYPE: PRT
<213> ORGANISM: Homo sapiens

<400> SEQUENCE: 1258

Thr Tyr Tyr Arg Ser Lys Trp Tyr Asn
1 5

<210> SEQ ID NO 1259
<211> LENGTH: 17
<212> TYPE: PRT
<213> ORGANISM: Homo sapiens

<400> SEQUENCE: 1259

Ala Arg Asp Thr Tyr Tyr Tyr Thr Ser Ala Ser Tyr Tyr Asn Val Asp
1 5 10 15

Tyr

<210> SEQ ID NO 1260
<211> LENGTH: 6
<212> TYPE: PRT
<213> ORGANISM: Homo sapiens

<400> SEQUENCE: 1260

Glu Ser Ile Arg Ser Asn
1 5

<210> SEQ ID NO 1261
<211> LENGTH: 9
<212> TYPE: PRT
<213> ORGANISM: Homo sapiens

<400> SEQUENCE: 1261

Gln Gln Ser Tyr Arg Thr Pro Ile Thr
1 5

<210> SEQ ID NO 1262
<211> LENGTH: 8
<212> TYPE: PRT
<213> ORGANISM: Homo sapiens

<400> SEQUENCE: 1262

Gly Tyr Thr Phe Thr Ser Tyr Gly
1 5

<210> SEQ ID NO 1263
<211> LENGTH: 8
<212> TYPE: PRT
<213> ORGANISM: Homo sapiens

<400> SEQUENCE: 1263

Ile Asn Thr Asp Thr Gly Asn Pro
1 5

<210> SEQ ID NO 1264
<211> LENGTH: 16
<212> TYPE: PRT
<213> ORGANISM: Homo sapiens

<400> SEQUENCE: 1264

Ala Arg Leu Gly Glu Tyr Ser Trp Asn Ser Ile Gly Tyr Phe Asp Tyr
1               5                   10                  15

<210> SEQ ID NO 1265
<211> LENGTH: 9
<212> TYPE: PRT
<213> ORGANISM: Homo sapiens

<400> SEQUENCE: 1265

Ser Ser Asn Ile Gly Ala Gly Tyr Asp
1               5

<210> SEQ ID NO 1266
<211> LENGTH: 11
<212> TYPE: PRT
<213> ORGANISM: Homo sapiens

<400> SEQUENCE: 1266

Gln Ser Tyr Asp Arg Ser Leu Ile Leu Val Val
1               5                   10

<210> SEQ ID NO 1267
<211> LENGTH: 8
<212> TYPE: PRT
<213> ORGANISM: Homo sapiens

<400> SEQUENCE: 1267

Gly Tyr Val Phe Thr Asn Tyr Ala
1               5

<210> SEQ ID NO 1268
<211> LENGTH: 8
<212> TYPE: PRT
<213> ORGANISM: Homo sapiens

<400> SEQUENCE: 1268

Ile Asn Thr Asn Thr Gly Asn Pro
1               5

<210> SEQ ID NO 1269
<211> LENGTH: 9
<212> TYPE: PRT
<213> ORGANISM: Homo sapiens

<400> SEQUENCE: 1269

Ala Arg Ser Tyr Ala Tyr Gly Asp Phe
1               5

<210> SEQ ID NO 1270
<211> LENGTH: 6
<212> TYPE: PRT
<213> ORGANISM: Homo sapiens

<400> SEQUENCE: 1270

Gln Asn Ile Ala Ile Arg
1               5

<210> SEQ ID NO 1271
<211> LENGTH: 9
<212> TYPE: PRT
<213> ORGANISM: Homo sapiens

<400> SEQUENCE: 1271

Gln Gln Ser Asp Thr Leu Pro Trp Thr
1 5

<210> SEQ ID NO 1272
<211> LENGTH: 8
<212> TYPE: PRT
<213> ORGANISM: Homo sapiens

<400> SEQUENCE: 1272

Gly Tyr Thr Phe Ser Asn Tyr Ala
1 5

<210> SEQ ID NO 1273
<211> LENGTH: 8
<212> TYPE: PRT
<213> ORGANISM: Homo sapiens

<400> SEQUENCE: 1273

Ile Asn Thr Asn Thr Gly Asn Pro
1 5

<210> SEQ ID NO 1274
<211> LENGTH: 19
<212> TYPE: PRT
<213> ORGANISM: Homo sapiens

<400> SEQUENCE: 1274

Ala Arg Gly Ala Arg Ser Tyr Tyr Asp Ser Ser Gly Tyr Tyr Ser Trp
1 5 10 15

Ser Asp Tyr

<210> SEQ ID NO 1275
<211> LENGTH: 12
<212> TYPE: PRT
<213> ORGANISM: Homo sapiens

<400> SEQUENCE: 1275

Gln Ser Val Leu Tyr Arg Ser Asn Asn Lys Asn Tyr
1 5 10

<210> SEQ ID NO 1276
<211> LENGTH: 10
<212> TYPE: PRT
<213> ORGANISM: Homo sapiens

<400> SEQUENCE: 1276

Gln Gln Tyr Tyr Asn Thr Leu Thr Trp Ala
1 5 10

<210> SEQ ID NO 1277
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1277
acaggtgccc actcccaggt gcag 24

<210> SEQ ID NO 1278
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1278
aaggtgtcca gtgtgargtg cag 23

<210> SEQ ID NO 1279
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1279
cccagatggg tcctgtccca ggtgcag 27

<210> SEQ ID NO 1280
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1280
caaggagtct gttccgaggt gcag 24

<210> SEQ ID NO 1281
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1281
ggaaggtgtg cacgccgctg gtc 23

<210> SEQ ID NO 1282
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1282
gttcggggaa gtagtccttg ac 22

<210> SEQ ID NO 1283
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1283
atgaggstcc cygctcagct gctgg 25

<210> SEQ ID NO 1284
<211> LENGTH: 28
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 1284
ctcttcctcc tgctactctg gctcccag 28

<210> SEQ ID NO 1285
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1285
atttctctgt tgctctggat ctctg 25

<210> SEQ ID NO 1286
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1286
atgacccagw ctccabycwc cctg 24

<210> SEQ ID NO 1287
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1287
gtttctcgta gtctgctttg ctca 24

<210> SEQ ID NO 1288
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1288
gtgctgtcct tgctgtcctg ct 22

<210> SEQ ID NO 1289
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1289
ggtcctgggc ccagtctgtg ctg 23

<210> SEQ ID NO 1290
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1290
ggtcctgggc ccagtctgcc ctg 23

<210> SEQ ID NO 1291
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1291
gctctgtgac ctcctatgag ctg 23

<210> SEQ ID NO 1292
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1292
ggtctctctc scagcytgtg ctg 23

<210> SEQ ID NO 1293
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1293
gttcttgggc caattttatg ctg 23

<210> SEQ ID NO 1294
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1294
ggtccaattc ycaggctgtg gtg 23

<210> SEQ ID NO 1295
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1295
gagtggattc tcagactgtg gtg 23

<210> SEQ ID NO 1296
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1296
caccagtgtg gccttgttgg cttg 24

<210> SEQ ID NO 1297
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1297
ctcctcactc gagggyggga acagagtg 28

<210> SEQ ID NO 1298
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1298
gcttcgttag aacgcggcta c 21

<210> SEQ ID NO 1299
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1299
ctagtagcaa ctgcaaccgg tgtacattct caggtccagc ttgtgcagtc tgg 53

<210> SEQ ID NO 1300
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1300
ccgatgggcc cttggtcgac gctgaagaga cggtgaccat tgtccctt 48

<210> SEQ ID NO 1301
<211> LENGTH: 54
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1301
ctagtagcaa ctgcaaccgg tgtacattct gacatccaga tgacccagtc tcca 54

<210> SEQ ID NO 1302
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1302
gaagacagat ggtgcagcca ccgtacgttt gatctccacc ttggtccctc c 51

<210> SEQ ID NO 1303
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1303
ctagtagcaa ctgcaaccgg tgtacattct caggtcacct tgaaggagtc tgg 53

<210> SEQ ID NO 1304
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 1304
ccgatgggcc cttggtcgac gctgaggaga cggtgaccag ggtg 44

<210> SEQ ID NO 1305
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 1305
ctagtagcaa ctgcaaccgg ttcctgggcc tcctatgtgc tgacccaggc gc 52

<210> SEQ ID NO 1306
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1306
ctagtagcaa ctgcaaccgg tgtacattct gagatgcagc tgctggagtc tgg 53

<210> SEQ ID NO 1307
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 1307
ccgatgggcc cttggtcgac gctgaggaga cagtgaccag ggtgc 45

<210> SEQ ID NO 1308
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 1308
ctagtagcaa ctgcaaccgg ttcctgggcc tcctatatgc tgactcaggc accc 54

<210> SEQ ID NO 1309
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1309
ctagtagcaa ctgcaaccgg tgtacattct gagatgcaac tggtggagtc tgg 53

<210> SEQ ID NO 1310
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 1310
ccgatgggcc cttggtcgac gctgaggaga cgatgaccgt ggtcc 45

<210> SEQ ID NO 1311
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1311
ctagtagcaa ctgcaaccgg ttcctgggcc tcctatgtgc tgactcagcc acc 53

<210> SEQ ID NO 1312
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1312
ctagtagcaa ctgcaaccgg tgtacattct cagatgcgtc tggtggaatc tgg 53

<210> SEQ ID NO 1313
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 1313
ccgatgggcc cttggtcgac gctgaggaga cggtgaccgg ggt 43

<210> SEQ ID NO 1314
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1314
ctagtagcaa ctgcaaccgg ttcctgggcc tcctatgtgc tgactcagcc acc 53

<210> SEQ ID NO 1315
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1315
ctagtagcaa ctgcaaccgg tgtacattct cagatgcgtc tggtggaatc ggg 53

<210> SEQ ID NO 1316
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1316
ccgatgggcc cttggtcgac gctgaggaga cggtgaccgg gatc 44

<210> SEQ ID NO 1317
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1317
ctagtagcaa ctgcaaccgg ttcctgggcc tcctatgtgc tgactcagcc acc 53

<210> SEQ ID NO 1318
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1318
ctagtagcaa ctgcaaccgg tgtacattct caggtgcacc tggtggagtc tg 52

<210> SEQ ID NO 1319
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1319
ccgatgggcc cttggtcgac gctgaggaga cggtgaccgt ggtc 44

<210> SEQ ID NO 1320
<211> LENGTH: 55
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1320
ctagtagcaa ctgcaaccgg tgtacattct gaaattgtgt tgacgcagtc tccag 55

<210> SEQ ID NO 1321
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1321
gaagacagat ggtgcagcca ccgtacgttt gatctccaac ttggtcccct gg 52

<210> SEQ ID NO 1322
<211> LENGTH: 54
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1322
ctagtagcaa ctgcaaccgg tgtacattct cagatgcacc tattggagtc tggg 54

<210> SEQ ID NO 1323
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1323
ccgatgggcc cttggtcgac gctgacgaga cggtgaccct ggtc 44

<210> SEQ ID NO 1324
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1324
ctagtagcaa ctgcaaccgg ttcctgggcc tcctatgtgc tgactcagcc acc 53

<210> SEQ ID NO 1325
<211> LENGTH: 54
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1325
ctagtagcaa ctgcaaccgg tgtacattct cagatgaagt tggtggagtc tggg 54

<210> SEQ ID NO 1326
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1326
ccgatgggcc cttggtcgac gctgaggaga cggtgaccgt ggtc 44

<210> SEQ ID NO 1327
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1327
ctagtagcaa ctgcaaccgg ttcctgggcc tcctatgtgc tgactcagcc acc 53

<210> SEQ ID NO 1328
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1328
ctagtagcaa ctgcaaccgg tgtacattct caggtgcagc tggtggagtc tg 52

<210> SEQ ID NO 1329
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1329
ccgatgggcc cttggtcgac gctgaggaga cggtgaccag ggtt 44

<210> SEQ ID NO 1330
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1330
ctagtagcaa ctgcaaccgg ttcctgggcc tcctatgtgc tgactcagcc acc 53

<210> SEQ ID NO 1331
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1331
ctagtagcaa ctgcaaccgg tgtacattct caggttcact tggcggagtc tgg 53

<210> SEQ ID NO 1332
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1332
ccgatgggcc cttggtcgac gctgaagaga cggtgaccaa tgtccc 46

<210> SEQ ID NO 1333
<211> LENGTH: 56
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1333
ctagtagcaa ctgcaaccgg tgtacattct gaagttgtgt tgacacagtc tccagc 56

<210> SEQ ID NO 1334
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1334
gaagacagat ggtgcagcca ccgtacgttt gatctccagc ttggtcccct g 51

<210> SEQ ID NO 1335
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1335
ctagtagcaa ctgcaaccgg tgtacattct cagctgcagc tggtggagtc tg 52

<210> SEQ ID NO 1336
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1336
ccgatgggcc cttggtcgac gctgaggaga cggtgaccag ggttc 45

<210> SEQ ID NO 1337
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1337
ctagtagcaa ctgcaaccgg ttcctgggcc tcctatgtgc tgactcagcc acc 53

<210> SEQ ID NO 1338
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1338
ctagtagcaa ctgcaaccgg tgtacattct caggtgcagc tggtggagtc tg 52

<210> SEQ ID NO 1339

<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 1339
ccgatgggcc cttggtcgac gctgaggaga cggtgaccag ggct 44

<210> SEQ ID NO 1340
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1340
ctagtagcaa ctgcaaccgg ttcctgggcc tcctatgtgc tgactcagcc acc 53

<210> SEQ ID NO 1341
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 1341
ctagtagcaa ctgcaaccgg tgtacattct caggtacaac tgatggagtc tggg 54

<210> SEQ ID NO 1342
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 1342
ccgatgggcc cttggtcgac gctgaggaga cggtgaccag ggct 44

<210> SEQ ID NO 1343
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 1343
ctagtagcaa ctgcaaccgg ttcctgggcc tcctatgtgc tgactcagac accc 54

<210> SEQ ID NO 1344
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 1344
ctagtagcaa ctgcaaccgg tgtacattct caggtgcagc tggtggagtc tg 52

<210> SEQ ID NO 1345
<211> LENGTH: 45

<212> TYPE: DNA
<213> ORGANISM: Artificial Sequence
<220> FEATURE:
<223> OTHER INFORMATION: Description of Artificial Sequence: Synthetic primer

<400> SEQUENCE: 1345
ccgatgggcc cttggtcgac gctgaggaga cggtgaccag ggttc 45

<210> SEQ ID NO 1346
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 1346
ctagtagcaa ctgcaaccgg tgtacattct gacatccagg tgacccagtc ac 52

<210> SEQ ID NO 1347
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 1347
gaagacagat ggtgcagcca ccgtacgttt gatgtccacc ttggtccctc c 51

<210> SEQ ID NO 1348
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1348
ctagtagcaa ctgcaaccgg tgtacattct gagatgcacc tggtggagtc tgg 53

<210> SEQ ID NO 1349
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 1349
ccgatgggcc cttggtcgac gctgaggaga cagtgaccag ggtgc 45

<210> SEQ ID NO 1350
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 1350
ctagtagcaa ctgcaaccgg tgtacattct gaaatactgc tgacgcagtc tccag 55

<210> SEQ ID NO 1351
<211> LENGTH: 51
<212> TYPE: DNA

<213> ORGANISM: Artificial Sequence
<220> FEATURE:
<223> OTHER INFORMATION: Description of Artificial Sequence: Synthetic
primer

<400> SEQUENCE: 1351
gaagacagat ggtgcagcca ccgtacgttt gatctccacc ttggtccctc c 51

<210> SEQ ID NO 1352
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1352
ctagtagcaa ctgcaaccgg tgtacattct gaggtgcagc tggtggagtc c 51

<210> SEQ ID NO 1353
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1353
ccgatgggcc cttggtcgac gctgaggaga cggtgaccag ggttc 45

<210> SEQ ID NO 1354
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1354
ctagtagcaa ctgcaaccgg ttcctgggcc cagtctgccc tgactcagcc tg 52

<210> SEQ ID NO 1355
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1355
ctagtagcaa ctgcaaccgg tgtacattct gaaggacagc tggtggagtc tgg 53

<210> SEQ ID NO 1356
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1356
ccgatgggcc cttggtcgac gctgaggaga cggtgaccag ggttc 45

<210> SEQ ID NO 1357
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1357
ctagtagcaa ctgcaaccgg ttcctgggcc cagtctgtgt tgacgcagcc gc 52

<210> SEQ ID NO 1358
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1358
ctagtagcaa ctgcaaccgg tgtacattct caggtggtgc tgcaggagtc g 51

<210> SEQ ID NO 1359
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1359
ccgatgggcc cttggtcgac gctgaagaga cggcgaccag tgtcc 45

<210> SEQ ID NO 1360
<211> LENGTH: 54
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1360
ctagtagcaa ctgcaaccgg tgtacattct gacatccaga tgacccagtc tccg 54

<210> SEQ ID NO 1361
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1361
gaagacagat ggtgcagcca ccgtacgttt gatctccagc ttggtcccct g 51

<210> SEQ ID NO 1362
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1362
ctagtagcaa ctgcaaccgg tgtacattct caggtgcagc tgcaggagtc g 51

<210> SEQ ID NO 1363
<211> LENGTH: 46
<212> TYPE: DNA
<213> ORGANISM: Artificial Sequence
<220> FEATURE:

<223> OTHER INFORMATION: Description of Artificial Sequence: Synthetic
primer

<400> SEQUENCE: 1363
ccgatgggcc cttggtcgac gctgaggaga cggtgaccag gtttcc 46

<210> SEQ ID NO 1364
<211> LENGTH: 54
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1364
ctagtagcaa ctgcaaccgg tgtacattct gacatccaga tgacccagtc tcca 54

<210> SEQ ID NO 1365
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1365
gaagacagat ggtgcagcca ccgtacgttt gaactccacc ttggtccctc c 51

<210> SEQ ID NO 1366
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1366
ggcttgaagc tcctcactcg agggygggaa cagagtg 37

<210> SEQ ID NO 1367
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1367
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatgcaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1368
<211> LENGTH: 489
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 1368
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaagca 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1369
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1369
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
gcattgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1370
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1370
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atggcacccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1371
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1371
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttggcag tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1372
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1372
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg catgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1373
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1373
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtgcact aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1374
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1374
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctgc aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1375
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1375
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct agcaccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1376
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1376
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattgcagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1377
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1377
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagca tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1378
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1378
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga gcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1379
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1379
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcagcaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1380
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1380
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacagcaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1381
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1381
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacag caagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1382
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1382
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccgcaacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1383
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1383
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtgcagg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1384
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1384
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggc accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1385
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1385
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg agcatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1386
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1386
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcgca 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1387
<211> LENGTH: 489
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 1387
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
gcatgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1388
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1388
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcgcaa ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1389
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1389
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacgg cacctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1390
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1390
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctgcagctca aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1391
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1391
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctgc aggcaactct atgtttccct catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1392
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1392
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240

```
atgttgcccg tttgtcctct aattccagga tcaacaacaa ccagtacggg accatgcaaa    300

acctgcacga ctcctgctca agcaaactct atgtttccct catgttgctg tacaaaacct    360

acggatggaa attgcacctg tattcccatc ccatcgtcct gggctttcgc aaaataccta    420

tgggagtggg cctcagtccg tttctcttgg ctcagtttac tagtgccatt tgttcagtgg    480

ttcgtaggg                                                            489
```

<210> SEQ ID NO 1393
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1393

```
acaagaatcc tcacaatacc gcagagtcta gactcgtggt ggacttctct caattttcta     60

gggggatctc ccgtgtgtct tggccaaaat tcgcagtccc caacctccaa tcactcacca    120

acctcctgtc ctccaatttg tcctggttat cgctggatgt gtctgcggcg ttttatcata    180

ttcctcttca tcctgctgct atgcctcatc ttcttattgg ttcttctgga ttatcaaggt    240

atgttgcccg tttgtcctct aattccagga tcaacaacaa ccagtacggg accatgcaaa    300

acctgcacga ctcctgctca aggcgcatct atgtttccct catgttgctg tacaaaacct    360

acggatggaa attgcacctg tattcccatc ccatcgtcct gggctttcgc aaaataccta    420

tgggagtggg cctcagtccg tttctcttgg ctcagtttac tagtgccatt tgttcagtgg    480

ttcgtaggg                                                            489
```

<210> SEQ ID NO 1394
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1394

```
acaagaatcc tcacaatacc gcagagtcta gactcgtggt ggacttctct caattttcta     60

gggggatctc ccgtgtgtct tggccaaaat tcgcagtccc caacctccaa tcactcacca    120

acctcctgtc ctccaatttg tcctggttat cgctggatgt gtctgcggcg ttttatcata    180

ttcctcttca tcctgctgct atgcctcatc ttcttattgg ttcttctgga ttatcaaggt    240

atgttgcccg tttgtcctct aattccagga tcaacaacaa ccagtacggg accatgcaaa    300

acctgcacga ctcctgctca aggcaacgca atgtttccct catgttgctg tacaaaacct    360

acggatggaa attgcacctg tattcccatc ccatcgtcct gggctttcgc aaaataccta    420

tgggagtggg cctcagtccg tttctcttgg ctcagtttac tagtgccatt tgttcagtgg    480

ttcgtaggg                                                            489
```

<210> SEQ ID NO 1395
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1395

```
acaagaatcc tcacaatacc gcagagtcta gactcgtggt ggacttctct caattttcta     60

gggggatctc ccgtgtgtct tggccaaaat tcgcagtccc caacctccaa tcactcacca    120

acctcctgtc ctccaatttg tcctggttat cgctggatgt gtctgcggcg ttttatcata    180

ttcctcttca tcctgctgct atgcctcatc ttcttattgg ttcttctgga ttatcaaggt    240

atgttgcccg tttgtcctct aattccagga tcaacaacaa ccagtacggg accatgcaaa    300

acctgcacga ctcctgctca aggcaactct gcatttccct catgttgctg tacaaaacct    360

acggatggaa attgcacctg tattcccatc ccatcgtcct gggctttcgc aaaataccta    420

tgggagtggg cctcagtccg tttctcttgg ctcagtttac tagtgccatt tgttcagtgg    480

ttcgtaggg                                                            489
```

```
<210> SEQ ID NO 1396
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1396

acaagaatcc tcacaatacc gcagagtcta gactcgtggt ggacttctct caattttcta     60

gggggatctc ccgtgtgtct tggccaaaat tcgcagtccc caacctccaa tcactcacca    120

acctcctgtc ctccaatttg tcctggttat cgctggatgt gtctgcggcg ttttatcata    180

ttcctcttca tcctgctgct atgcctcatc ttcttattgg ttcttctgga ttatcaaggt    240

atgttgcccg tttgtcctct aattccagga tcaacaacaa ccagtacggg accatgcaaa    300

acctgcacga ctcctgctca aggcaactct atggcaccct catgttgctg tacaaaacct    360

acggatggaa attgcacctg tattcccatc ccatcgtcct gggctttcgc aaaataccta    420

tgggagtggg cctcagtccg tttctcttgg ctcagtttac tagtgccatt tgttcagtgg    480

ttcgtaggg                                                            489
```

```
<210> SEQ ID NO 1397
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1397

acaagaatcc tcacaatacc gcagagtcta gactcgtggt ggacttctct caattttcta     60

gggggatctc ccgtgtgtct tggccaaaat tcgcagtccc caacctccaa tcactcacca    120

acctcctgtc ctccaatttg tcctggttat cgctggatgt gtctgcggcg ttttatcata    180

ttcctcttca tcctgctgct atgcctcatc ttcttattgg ttcttctgga ttatcaaggt    240

atgttgcccg tttgtcctct aattccagga tcaacaacaa ccagtacggg accatgcaaa    300

acctgcacga ctcctgctca aggcaactct atgtttgcat catgttgctg tacaaaacct    360

acggatggaa attgcacctg tattcccatc ccatcgtcct gggctttcgc aaaataccta    420

tgggagtggg cctcagtccg tttctcttgg ctcagtttac tagtgccatt tgttcagtgg    480

ttcgtaggg                                                            489
```

```
<210> SEQ ID NO 1398
<211> LENGTH: 489
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1398
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttcccg catgttgctg tacaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1399
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1399
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tgcaaaacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1400
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1400
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacagcacct 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1401
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1401
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaagca 360
acggatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1402
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1402
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
gcagatggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1403
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1403
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggcaggaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1404
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1404
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatgcaa attgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1405
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1405
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggag catgcacctg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1406
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1406
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcgcatg tattcccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1407
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1407
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tgcacccatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1408
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1408
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattgcaatc ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1409
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1409
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccgca ccatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1410
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1410
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc gcatcgtcct gggctttcgc aaaataccta 420
tgggagtggg cctcagtccg tttctcttgg ctcagtttac tagtgccatt tgttcagtgg 480
ttcgtaggg 489

<210> SEQ ID NO 1411
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1411
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccagcatcct gggctttcgc aaaataccta 420
tgggagtggg cctcagtccg tttctcttgg ctcagtttac tagtgccatt tgttcagtgg 480
ttcgtaggg 489

<210> SEQ ID NO 1412
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1412
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcggcat gggctttcgc aaaataccta 420
tgggagtggg cctcagtccg tttctcttgg ctcagtttac tagtgccatt tgttcagtgg 480
ttcgtaggg 489

<210> SEQ ID NO 1413
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1413
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtccg cagctttcgc aaaataccta 420
tgggagtggg cctcagtccg tttctcttgg ctcagtttac tagtgccatt tgttcagtgg 480
ttcgtaggg 489

<210> SEQ ID NO 1414
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1414
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctgcagc aaaataccta 420
tgggagtggg cctcagtccg tttctcttgg ctcagtttac tagtgccatt tgttcagtgg 480
ttcgtaggg 489

<210> SEQ ID NO 1415
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1415
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc agcataccta 420
tgggagtggg cctcagtccg tttctcttgg ctcagtttac tagtgccatt tgttcagtgg 480
ttcgtaggg 489

<210> SEQ ID NO 1416
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1416
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaagcacta 420
tgggagtggg cctcagtccg tttctcttgg ctcagtttac tagtgccatt tgttcagtgg 480
ttcgtaggg 489

<210> SEQ ID NO 1417
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1417
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaatacgca 420
tgggagtggg cctcagtccg tttctcttgg ctcagtttac tagtgccatt tgttcagtgg 480
ttcgtaggg 489

<210> SEQ ID NO 1418
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1418
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
gcagagtggg cctcagtccg tttctcttgg ctcagtttac tagtgccatt tgttcagtgg 480
ttcgtaggg 489

<210> SEQ ID NO 1419
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1419
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggcatggg cctcagtccg tttctcttgg ctcagtttac tagtgccatt tgttcagtgg 480
ttcgtaggg 489

<210> SEQ ID NO 1420
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1420
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggaggcag cctcagtccg tttctcttgg ctcagtttac tagtgccatt tgttcagtgg 480
ttcgtaggg 489

<210> SEQ ID NO 1421
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1421
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg ccgcagtccg tttctcttgg ctcagtttac tagtgccatt tgttcagtgg 480
ttcgtaggg 489

<210> SEQ ID NO 1422
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1422
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagcacg tttctcttgg ctcagtttac tagtgccatt tgttcagtgg 480
ttcgtaggg 489

<210> SEQ ID NO 1423
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1423
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtcgc attctcttgg ctcagtttac tagtgccatt tgttcagtgg 480
ttcgtaggg 489

<210> SEQ ID NO 1424
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1424
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tgcatcttgg ctcagtttac tagtgccatt tgttcagtgg 480
ttcgtaggg 489

<210> SEQ ID NO 1425
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1425
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttcgcatgg ctcagtttac tagtgccatt tgttcagtgg 480
ttcgtaggg 489

<210> SEQ ID NO 1426
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1426
acaagaatcc tcacaatacc gcagagtcta gactcgtggt ggacttctct caattttcta 60
gggggatctc ccgtgtgtct tggccaaaat tcgcagtccc caacctccaa tcactcacca 120
acctcctgtc ctccaatttg tcctggttat cgctggatgt gtctgcggcg ttttatcata 180
ttcctcttca tcctgctgct atgcctcatc ttcttattgg ttcttctgga ttatcaaggt 240
atgttgcccg tttgtcctct aattccagga tcaacaacaa ccagtacggg accatgcaaa 300
acctgcacga ctcctgctca aggcaactct atgtttccct catgttgctg tacaaaacct 360
acggatggaa attgcacctg tattcccatc ccatcgtcct gggctttcgc aaaataccta 420
tgggagtggg cctcagtccg tttctctgca ctcagtttac tagtgccatt tgttcagtgg 480
ttcgtaggg 489

<210> SEQ ID NO 1427
<211> LENGTH: 421
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1427
ctagtagcaa ctgcaaccgg tgtacattct caggtgcagc tggtggagtc tgggggaggc 60
gtggtccagc ctgggaggtc cctgagactc tcctgtgcag cctctggatt caccttcagt 120
agctatggca tgcactgggt ccgccaggct ccaggcaagg ggctggagtg ggtggcagtt 180
atatcatatg atggaagtaa taaatactat gcagactccg tgaagggccg attcaccatc 240
tccagagaca attccaagaa cacgctgtat ctgcaaatga acagcctgag agctgaggac 300
acggctgtgt attactgtgc gaaagatgct tatctttctg cagcgagagg atacggtatg 360
gacgtctggg gccaagggac cacggtcacc gtctcctcag cgtcgaccaa gggcccatcg 420
g 421

<210> SEQ ID NO 1428
<211> LENGTH: 417
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 1428
ctagtagcaa ctgcaaccgg ttcctgggcc tcctatgtgc tgactcagcc accctcggtg 60
tcagtggccc caggacagac ggccaggatt acctgtgggg gaaacaacat tggaagtaaa 120
agtgtgcact ggtaccagca gaagccaggc caggcccctg tgctggtcgt ctatgatgat 180
agcgaccggc cctcagggat ccctgagcga ttctctggct ccaactctgg gaacacggcc 240
accctgacca tcagcagggt cgaagccggg gatgaggccg actattactg tcaggtgtgg 300
gatagtagta gtgatcatgt ggtattcggc ggagggacca agctgaccgt cctaggtcag 360
cccaaggctg ccccctcggt cactctgttc ccaccctcga gtgaggagct tcaagcc 417

<210> SEQ ID NO 1429
<211> LENGTH: 412
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1429
ctagtagcaa ctgcaaccgg tgtacattct caggtgcagc tgcaggagtc gggcccagga 60
ctggtgaagc cttcacagac cctgtccctc acctgcactg tctctggtgg ctccatcagc 120
agtggtgatt actactggag ttggatccgc cagcccccag ggaagggcct ggagtggatt 180
gggtacatct attacagtgg gagcacctac tacaacccgt ccctcaagag tcgagttacc 240
atatcagtag acacgtccaa gaaccagttc tccctgaagc tgagctctgt gactgccgca 300
gacacggccg tgtattactg tgccatctac atggatgagg cctgggcttt tgatatctgg 360
ggccaaggga caatggtcac cgtctcttca gcgtcgacca agggcccatc gg 412

<210> SEQ ID NO 1430
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1430
ctagtagcaa ctgcaaccgg tgtacattct gacatccaga tgacccagtc tccatcctcc 60
ctgtctgcat ctgtaggaga cagagtcacc atcacttgcc gggcaagtca gagcattagc 120
agctatttaa attggtatca gcagaaacca gggaaagccc ctaagctcct gatctatgct 180
gcatccagtt tgcaaagtgg ggtcccatca aggttcagtg gcagtggatc tgggacagat 240
ttcactctca ccatcagcag tctgcaacct gaagattttg caacttacta ctgtcaacag 300
agttacagta tttccttatt cacttttggc caggggacca agctggagat caaacgtacg 360
gtggctgcac catctgtctt c 381

<210> SEQ ID NO 1431
<211> LENGTH: 415
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1431
ctagtagcaa ctgcaaccgg tgtacattct caggtgcagc tgcaggagtc gggcccagga 60
ctggtgaagc cttcggagac cctgtccctc acctgcactg tctctggtgg ctccatcagt 120
agttactact ggagctggat ccggcagccc ccagggaagg gactggagtg gattgggtat 180
atctattaca gtgggagcac caactacaac ccctccctca agagtcgagt caccatatca 240
gtagacacgt ccaagaacca gttctccctg aagctgagct ctgtgaccgc cgcagacacg 300
gccgtgtatt actgtgcgag acacctttat cgctatggtt ataggaacta ctttgactac 360
tggggccagg gaaccctggt caccgtctcc tcagcgtcga ccaagggccc atcgg 415

<210> SEQ ID NO 1432
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1432
ctagtagcaa ctgcaaccgg tgtacattct gacatccaga tgacccagtc tccatcttcc 60
gtgtctgcat ctgtaggaga cagagtcacc atcacttgtc gggcgagtca gggtattagc 120
agctggttag cctggtatca gcagaaacca gggaaagccc ctaagctcct gatctatgct 180
gcatccagtt tgcaaagtgg ggtcccatca aggttcagcg gcagtggatc tgggacagat 240
ttcactctca ccatcagcag cctgcagcct gaagattttg caacttacta ttgtcaacag 300
gctaacagtt tcccgctcac tttcggcgga gggaccaagg tggagatcaa acgtacggtg 360
gctgcaccat ctgtcttc 378

<210> SEQ ID NO 1433
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1433
ccgtctgtgc cttctcatct g 21

<210> SEQ ID NO 1434
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1434
agtccaagag tcctcttatg taagacctt 29

<210> SEQ ID NO 1435
<211> LENGTH: 17
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1435
cttcgcttca cctctgc 17

<210> SEQ ID NO 1436
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1436
ccctgcgctg aacatggaga aca 23

<210> SEQ ID NO 1437
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 1437
aaatgtatac ccaaagacaa aagaaaa 27

<210> SEQ ID NO 1438
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1438

Gln Met Arg Leu Val Glu Ser Gly Gly Gly Val Val Arg Pro Gly Gly
1 5 10 15

Ser Leu Arg Leu Ser Cys Ala Gly Ser Gly Phe Arg Phe Thr Gly Tyr
20 25 30

Gly Ile His Trp Val Arg Gln Ala Pro Gly Lys Gly Leu Glu Trp Leu
35 40 45

Ala Tyr Ile Ser Asn Asp Gly Ser Lys Lys Tyr His Thr Asp Ser Val
50 55 60

Lys Gly Arg Phe Thr Val Ser Arg Asp Asn Ala Lys Asn Thr Ala Tyr
65 70 75 80

Leu Gln Met Asn Ser Leu Arg Val Glu Glu Thr Ala Val Tyr Phe Cys
85 90 95

Ala Lys Asp Gly Tyr Leu Ser Ala Ala Arg Gly Tyr Gly Met Asp Val
100 105 110

Trp Gly Gln Gly Ile Pro Val Thr Val Ser Pro
115 120

<210> SEQ ID NO 1439
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1439

Gln Met His Leu Leu Glu Ser Gly Gly Gly Val Val Gln Pro Gly Arg
1 5 10 15

Ser Leu Arg Leu Ser Cys Ala Ala Ser Gly Phe Arg Phe Thr Met Tyr
20 25 30

```
Gly Ile Asn Trp Val Arg Gln Ala Pro Gly Lys Gly Leu Glu Trp Val
        35                  40                  45

Ala Gly Ile Pro Phe Asp Gly Arg Thr Gln Tyr Tyr Ala Asp Ser Val
    50                  55                  60

Lys Gly Arg Tyr Val Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
                85                  90                  95

Ala Lys Asp Gly Ile Leu Gly Ala Arg Arg Gly Leu Tyr Gly Ile Asp
            100                 105                 110

Val Trp Gly Gln Gly Thr Arg Val Thr Val Ser Ser
        115                 120


<210> SEQ ID NO 1440
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1440

Ser Tyr Val Leu Thr Gln Pro Pro Ser Val Ser Val Ala Pro Gly Gln
1               5                   10                  15

Thr Ala Thr Ile Thr Cys Gly Gly Asn Asn Ile Gly Gly Lys Ser Val
            20                  25                  30

His Trp Phe Gln Gln Lys Pro Gly Gln Ala Pro Leu Leu Ile Ile Ser
        35                  40                  45

Asp Asp Asn Asp Arg Pro Ser Gly Ile Pro Glu Arg Val Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Thr Ser Asp Gln
                85                  90                  95

Leu Val Phe Gly Gly Gly Thr Met Leu Thr Val Leu
            100                 105


<210> SEQ ID NO 1441
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1441

Ser Tyr Val Leu Thr Gln Pro Pro Ser Val Ala Val Ala Pro Gly Gln
1               5                   10                  15

Thr Ala Arg Ile Thr Cys Gly Gly Ile Asp Val Gly Ser Lys Ser Val
            20                  25                  30

Asn Trp Tyr Gln Gln Lys Pro Gly Gln Ala Pro Val Gln Val Val Asn
        35                  40                  45

Asp Asp Thr Glu Arg Pro Ser Gly Ile Pro Glu Arg Phe Ser Gly Ser
    50                  55                  60

Asn Ser Gly Asn Thr Ala Thr Leu Thr Val Ser Arg Val Glu Ala Gly
65                  70                  75                  80

Asp Glu Ala Asp Tyr Tyr Cys Gln Val Trp Asp Ser Ser Ser Asp His
                85                  90                  95
```

```
Val Val Phe Gly Gly Gly Thr Lys Leu Thr Val Leu
            100                 105


<210> SEQ ID NO 1442
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1442

Gln Val Gln Leu Met Glu Ser Gly Gly Gly Val Val Gln Pro Gly Gly
1               5                   10                  15

Ser Leu Arg Leu Ser Cys Thr Val Ser Gly Phe Ser Phe Ser Asp Tyr
            20                  25                  30

Gly Met His Trp Val Arg Gln Ala Pro Gly Lys Gly Leu Glu Trp Val
        35                  40                  45

Ala Leu Ile Trp Arg Asp Gly Ser Asn Ser His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Ser Ser Leu Gly Val Thr Asp Thr Ala Val Tyr Tyr Cys
                85                  90                  95

Ala Arg Glu Ala Arg Val Ala Ala Pro Ala Ser Tyr Asp Tyr Trp Gly
            100                 105                 110

Gln Gly Ala Leu Val Thr Val Ser Ser
        115                 120


<210> SEQ ID NO 1443
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1443

Gln Leu Gln Leu Val Glu Ser Gly Gly Gly Val Val Gln Pro Gly Lys
1               5                   10                  15

Ser Leu Arg Leu Ser Cys Ala Ala Ser Gly Phe Ala Phe Arg Ser Tyr
            20                  25                  30

Gly Met His Trp Val Arg Gln Ala Pro Gly Lys Gly Leu Glu Trp Val
        35                  40                  45

Ala Leu Ile Trp His Asp Gly Ser Asn Lys Lys Tyr Ala Asp Ser Val
    50                  55                  60

Lys Gly Arg Phe Thr Val Ser Arg Asp Asn Ser Lys Asn Thr Val Ser
65                  70                  75                  80

Leu Gln Met Asn Ser Leu Arg Ala Asp Asp Thr Ala Leu Tyr Tyr Cys
                85                  90                  95

Ala Arg Glu Gly Ala Ile Ala Ala Pro Ala Ser Leu Asp Val Trp Gly
            100                 105                 110

Gln Gly Thr Leu Val Thr Val Ser Ser
        115                 120


<210> SEQ ID NO 1444
<211> LENGTH: 108
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 1444

Ser Tyr Val Leu Thr Gln Thr Pro Ser Val Ser Val Ala Pro Gly Gln
1 5 10 15

Thr Ala Arg Ile Thr Cys Gly Gly Asn Lys Ile Val Asn Lys Asn Val
20 25 30

His Trp Tyr Gln Gln Arg Pro Gly Gln Ala Pro Val Leu Val Leu Tyr
35 40 45

Asp Asp Asp Asp Arg Pro Ser Gly Ile Pro Ala Arg Phe Ser Gly Ser
50 55 60

Asn Ser Trp Asn Ala Ala Thr Leu Thr Ile Ser Arg Val Glu Ala Gly
65 70 75 80

Asp Glu Ala Asp Tyr Tyr Cys Gln Val Trp Asp Asn Gly Ser Asn His
85 90 95

Val Val Phe Gly Gly Gly Thr Lys Leu Thr Val Val
100 105

<210> SEQ ID NO 1445
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (38)..(39)
<223> OTHER INFORMATION: Any amino acid

<400> SEQUENCE: 1445

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Arg Ser Arg Asn Val
20 25 30

His Trp Tyr Gln Gln Xaa Xaa Gly Gln Thr Pro Leu Leu Val Val Tyr
35 40 45

Ala Asp Ser Ala Arg Pro Ser Gly Ile Pro Asp Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Gly Thr Asp His
85 90 95

Val Ile Phe Gly Gly Gly Thr Glu Leu Thr Val Leu
100 105

<210> SEQ ID NO 1446
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 1446

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Asn Tyr
20 25 30

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ile Tyr Ser Ser Ser Trp Pro Tyr Tyr Phe Asp Tyr
            100                 105                 110

Trp Gly Gln Gly Thr Leu Val Thr Val Ser Ser
        115                 120
```

<210> SEQ ID NO 1447
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1447

```
Glu Met Gln Leu Leu Glu Ser Gly Gly Gly Leu Val Gln Pro Gly Gly
1               5                   10                  15

Ser Leu Arg Leu Ser Cys Glu Val Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Leu Thr Ala Thr Gly Gly Asn Thr Tyr Tyr Ala Asp Ser Val
    50                  55                  60

Lys Gly Arg Phe Thr Ile Ser Arg Asp Asn Ser Asn Asn Ala Leu Tyr
65                  70                  75                  80

Leu Gln Met Asn Ser Leu Arg Ala Glu Asp Thr Ala Val Tyr Phe Cys
                85                  90                  95

Ala Lys Asp Ala Ile Arg Asn Ser Asn His Ala Trp Tyr Phe Asp Val
            100                 105                 110

Trp Gly Arg Gly Thr Leu Val Thr Val Ser Ser
        115                 120
```

<210> SEQ ID NO 1448
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1448

```
Glu Met Gln Leu Val Glu Ser Gly Gly Gly Leu Ala His Pro Gly Glu
1               5                   10                  15

Ser Leu Arg Leu Ser Cys Val Gly Ser Gly Phe Arg Phe Asn Asn Tyr
            20                  25                  30

Gly Ile Ser Trp Val Arg Gln Ala Pro Gly Arg Gly Leu Glu Trp Val
        35                  40                  45

Ser Gly Phe Ser Gly Ser Gly Ser Asn Ile Phe Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Asp Met Arg Gly Leu Arg Ala Glu Asp Thr Ala Val Tyr Tyr Cys
85 90 95

Ala Lys Asp Gly Tyr Phe Gly Ser Gly Ser Leu Tyr Gly Ile Asp Val
100 105 110

Trp Gly Gln Gly Thr Thr Val Ile Val Ser Ser
115 120

<210> SEQ ID NO 1449
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1449

Ser Tyr Val Leu Thr Gln Pro Pro Ser Val Ser Val Ala Pro Gly Gln
1 5 10 15

Thr Ala Arg Ile Thr Cys Gly Gly Asp Asn Ile Gly Ser Arg Gly Val
20 25 30

Glu Trp Tyr Gln Gln Lys Pro Gly Gln Ala Pro Val Leu Val Val Tyr
35 40 45

Glu Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Ala Ala Gly
65 70 75 80

Asp Glu Ala Asp Tyr Tyr Cys Gln Val Trp Asp Ser Ser Ser Asp His
85 90 95

Pro Glu Val Val Phe Gly Gly Gly Thr Lys Leu Thr Val Leu
100 105 110

<210> SEQ ID NO 1450
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1450

Ser Tyr Met Leu Thr Gln Ala Pro Ser Val Ser Val Ala Pro Gly His
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Val Tyr
35 40 45

Asp Asp Asn Glu Arg Pro Ser Gly Ile Pro Glu Arg Phe Ser Gly Ser
50 55 60

Asn Ser Gly Asn Thr Ala Thr Leu Thr Ile Ser Arg Val Glu Val Gly
65 70 75 80

Asp Glu Ala Asp Tyr Tyr Cys Gln Val Trp Asp Pro Thr Ser Asp Gln
85 90 95

Val Phe Gly Gly Gly Thr Ile Leu Ser Val Leu
100 105

<210> SEQ ID NO 1451
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 1451

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

Tyr Trp His Gln Gln Lys Ser Gly Gln Ala Pro Val Val Val Val Ser
35 40 45

Glu Asp Ser Ala Arg Pro Ser Gly Ile Pro Glu Arg Phe Ser Gly Ser
50 55 60

Asn Ser Gly Asn Thr Ala Thr Leu Thr Ile Ser Arg Val Glu Val Gly
65 70 75 80

Asp Glu Ala Asp Tyr Tyr Cys Gln Val Trp Asp Ser Asn His Asp His
85 90 95

Pro Gly Val Val Phe Gly Gly Gly Thr Lys Leu Thr Val Leu
100 105 110

<210> SEQ ID NO 1452
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1452

Thr Ser Met Phe Pro Ser Cys Cys Cys Thr Lys Pro Ser Asp Gly
1 5 10 15

<210> SEQ ID NO 1453
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1453

Pro Ser Cys Cys Cys Thr Lys Pro Ser Asp Gly Asn Cys Thr Cys
1 5 10 15

<210> SEQ ID NO 1454
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1454

Cys Thr Lys Pro Ser Asp Gly Asn Cys Thr Cys Ile Pro Ile Pro
1 5 10 15

<210> SEQ ID NO 1455
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1455

Ser Asp Gly Asn Cys Thr Cys Ile Pro Ile Pro Ser Ser Trp Ala
1 5 10 15

<210> SEQ ID NO 1456
<211> LENGTH: 72
<212> TYPE: PRT
<213> ORGANISM: Hepatitis B virus

<400> SEQUENCE: 1456

Gln Gly Met Leu Pro Val Cys Pro Leu Ile Pro Gly Ser Thr Thr Thr
1 5 10 15

Ser Thr Gly Pro Cys Lys Thr Cys Thr Thr Pro Ala Gln Gly Asn Ser
20 25 30

Met Phe Pro Ser Cys Cys Cys Thr Lys Pro Thr Asp Gly Asn Cys Thr
35 40 45

Cys Ile Pro Ile Pro Ser Ser Trp Ala Phe Ala Lys Tyr Leu Trp Glu
50 55 60

Trp Ala Ser Val Arg Phe Ser Trp
65 70

<210> SEQ ID NO 1457
<211> LENGTH: 72
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (10)..(10)
<223> OTHER INFORMATION: Ile or Ala
<220> FEATURE:
<221> NAME/KEY: MOD_RES
<222> LOCATION: (20)..(20)
<223> OTHER INFORMATION: Pro or Ala
<220> FEATURE:
<221> NAME/KEY: MOD_RES
<222> LOCATION: (23)..(23)
<223> OTHER INFORMATION: Thr or Ala
<220> FEATURE:
<221> NAME/KEY: MOD_RES
<222> LOCATION: (41)..(41)
<223> OTHER INFORMATION: Lys or Ala
<220> FEATURE:
<221> NAME/KEY: MOD_RES
<222> LOCATION: (42)..(42)
<223> OTHER INFORMATION: Pro or Ala
<220> FEATURE:
<221> NAME/KEY: MOD_RES
<222> LOCATION: (43)..(43)
<223> OTHER INFORMATION: Thr or Ala
<220> FEATURE:
<221> NAME/KEY: MOD_RES
<222> LOCATION: (44)..(44)
<223> OTHER INFORMATION: Asp or Ala
<220> FEATURE:
<221> NAME/KEY: MOD_RES
<222> LOCATION: (45)..(45)
<223> OTHER INFORMATION: Gly or Ala
<220> FEATURE:
<221> NAME/KEY: MOD_RES
<222> LOCATION: (48)..(48)
<223> OTHER INFORMATION: Thr or Ala
<220> FEATURE:
<223> OTHER INFORMATION: See specification as filed for detailed description of substitutions and preferred embodiments

<400> SEQUENCE: 1457

Gln Gly Met Leu Pro Val Cys Pro Leu Xaa Pro Gly Ser Thr Thr Thr
1 5 10 15

```
Ser Thr Gly Xaa Cys Lys Xaa Cys Thr Thr Pro Ala Gln Gly Asn Ser
            20                  25                  30

Met Phe Pro Ser Cys Cys Cys Thr Xaa Xaa Xaa Xaa Xaa Asn Cys Xaa
        35                  40                  45

Cys Ile Pro Ile Pro Ser Ser Trp Ala Phe Ala Lys Tyr Leu Trp Glu
    50                  55                  60

Trp Ala Ser Val Arg Phe Ser Trp
65                  70


<210> SEQ ID NO 1458
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1458

Leu Val Leu Leu Asp Tyr Gln Gly Met Leu Pro Val Cys Pro Leu Leu
1               5                   10                  15

Pro Gly Thr Ser Thr Thr Ser Thr Gly Pro Cys Lys Thr Cys Thr Ile
            20                  25                  30

Pro Ala Gln Gly Thr Ser Met Phe Pro Ser Cys Cys Cys Thr Lys Pro
        35                  40                  45

Ser Asp Gly Asn Cys Thr Cys Ile Pro Ile Pro Ser Ser Trp Ala Phe
    50                  55                  60

Ala Arg Phe Leu Trp Glu Trp Ala Ser Val Arg Phe Ser Trp Leu Ser
65                  70                  75                  80

Leu Leu Val


<210> SEQ ID NO 1459
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1459

Leu Val Leu Leu Asp Tyr Gln Gly Met Leu Pro Val Cys Pro Leu
1               5                   10                  15


<210> SEQ ID NO 1460
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1460

Asp Tyr Gln Gly Met Leu Pro Val Cys Pro Leu Leu Pro Gly Thr
1               5                   10                  15


<210> SEQ ID NO 1461
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1461
```

Met Leu Pro Val Cys Pro Leu Leu Pro Gly Thr Ser Thr Thr Ser
1 5 10 15

<210> SEQ ID NO 1462
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1462

Cys Pro Leu Leu Pro Gly Thr Ser Thr Thr Ser Thr Gly Pro Cys
1 5 10 15

<210> SEQ ID NO 1463
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1463

Pro Gly Thr Ser Thr Thr Ser Thr Gly Pro Cys Lys Thr Cys Thr
1 5 10 15

<210> SEQ ID NO 1464
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1464

Thr Thr Ser Thr Gly Pro Cys Lys Thr Cys Thr Ile Pro Ala Gln
1 5 10 15

<210> SEQ ID NO 1465
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1465

Gly Pro Cys Lys Thr Cys Thr Ile Pro Ala Gln Gly Thr Ser Met
1 5 10 15

<210> SEQ ID NO 1466
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1466

Thr Cys Thr Ile Pro Ala Gln Gly Thr Ser Met Phe Pro Ser Cys
1 5 10 15

<210> SEQ ID NO 1467
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1467

Pro Ala Gln Gly Thr Ser Met Phe Pro Ser Cys Cys Cys Thr Lys
1 5 10 15

<210> SEQ ID NO 1468
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1468

Thr Ser Met Phe Pro Ser Cys Cys Cys Thr Lys Pro Ser Asp Gly
1 5 10 15

<210> SEQ ID NO 1469
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1469

Pro Ser Cys Cys Cys Thr Lys Pro Ser Asp Gly Asn Cys Thr Cys
1 5 10 15

<210> SEQ ID NO 1470
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1470

Cys Thr Lys Pro Ser Asp Gly Asn Cys Thr Cys Ile Pro Ile Pro
1 5 10 15

<210> SEQ ID NO 1471
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1471

Ser Asp Gly Asn Cys Thr Cys Ile Pro Ile Pro Ser Ser Trp Ala
1 5 10 15

<210> SEQ ID NO 1472
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1472

Cys Thr Cys Ile Pro Ile Pro Ser Ser Trp Ala Phe Ala Arg Phe
1 5 10 15

<210> SEQ ID NO 1473
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1473

Pro Ile Pro Ser Ser Trp Ala Phe Ala Arg Phe Leu Trp Glu Trp
1 5 10 15

<210> SEQ ID NO 1474
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1474

Ser Trp Ala Phe Ala Arg Phe Leu Trp Glu Trp Ala Ser Val Arg
1 5 10 15

<210> SEQ ID NO 1475
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1475

Ala Arg Phe Leu Trp Glu Trp Ala Ser Val Arg Phe Ser Trp Leu
1 5 10 15

<210> SEQ ID NO 1476
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1476

Trp Glu Trp Ala Ser Val Arg Phe Ser Trp Leu Ser Leu Leu Val
1 5 10 15

<210> SEQ ID NO 1477
<211> LENGTH: 24
<212> TYPE: PRT
<213> ORGANISM: Hepatitis B virus

<400> SEQUENCE: 1477

Lys Thr Cys Thr Thr Pro Ala Gln Gly Thr Ser Thr Phe Pro Ser Cys
1 5 10 15

Cys Cys Thr Lys Pro Ser Asp Gly
20

<210> SEQ ID NO 1478
<211> LENGTH: 72
<212> TYPE: DNA
<213> ORGANISM: Hepatitis B virus

<400> SEQUENCE: 1478
aagacctgca cgactcctgc tcaagggacc tctacgtttc cctcttgttg ctgtacaaaa 60
ccttcggacg ga 72

<210> SEQ ID NO 1479
<211> LENGTH: 24
<212> TYPE: PRT
<213> ORGANISM: Hepatitis B virus

<400> SEQUENCE: 1479

Lys Thr Cys Thr Thr Pro Ala Gln Gly Thr Ser Thr Phe Pro Ser Cys
1 5 10 15

Cys Cys Thr Lys Pro Ser Asp Arg
20

<210> SEQ ID NO 1480
<211> LENGTH: 72
<212> TYPE: DNA
<213> ORGANISM: Hepatitis B virus

<400> SEQUENCE: 1480
aagacctgca cgactcctgc tcaagggacc tctacgtttc cctcttgttg ctgtacaaaa 60
ccttcggaca ga 72

<210> SEQ ID NO 1481
<211> LENGTH: 24
<212> TYPE: PRT
<213> ORGANISM: Hepatitis B virus

<400> SEQUENCE: 1481

Lys Thr Cys Thr Thr Pro Ala Gln Gly Thr Ser Thr Phe Pro Ser Cys
1 5 10 15

Cys Cys Thr Lys Pro Ser Asp Glu
20

<210> SEQ ID NO 1482
<211> LENGTH: 72
<212> TYPE: DNA
<213> ORGANISM: Hepatitis B virus

<400> SEQUENCE: 1482
aagacctgca cgactcctgc tcaagggacc tctacgtttc cctcttgttg ctgtacaaaa 60
ccttcggacg aa 72

<210> SEQ ID NO 1483
<211> LENGTH: 24
<212> TYPE: PRT
<213> ORGANISM: Hepatitis B virus

<400> SEQUENCE: 1483

Arg Thr Cys Thr Thr Pro Ala Gln Gly Thr Ser Thr Phe Pro Ser Cys
1 5 10 15

Cys Cys Thr Lys Pro Ser Asp Arg
20

<210> SEQ ID NO 1484
<211> LENGTH: 72
<212> TYPE: DNA
<213> ORGANISM: Hepatitis B virus

<400> SEQUENCE: 1484
aggacctgca cgactcctgc tcaagggacc tctacgtttc cctcttgttg ctgtacaaaa 60

-continued

```
ccttcggaca ga                                                      72


<210> SEQ ID NO 1485
<211> LENGTH: 24
<212> TYPE: PRT
<213> ORGANISM: Hepatitis B virus

<400> SEQUENCE: 1485

Lys Thr Cys Thr Thr Pro Ala Gln Gly Thr Ser Thr Phe Pro Ser Tyr
1               5                   10                  15

Cys Cys Thr Lys Pro Ser Asp Gly
            20


<210> SEQ ID NO 1486
<211> LENGTH: 72
<212> TYPE: DNA
<213> ORGANISM: Hepatitis B virus

<400> SEQUENCE: 1486

aagacctgca cgactcctgc tcaagggacc tctacgtttc cctcttattg ctgtacaaaa     60

ccttcggacg ga                                                      72


<210> SEQ ID NO 1487
<211> LENGTH: 24
<212> TYPE: PRT
<213> ORGANISM: Hepatitis B virus

<400> SEQUENCE: 1487

Lys Thr Cys Thr Thr Pro Ala Gln Gly Thr Ser Thr Phe Pro Ser Tyr
1               5                   10                  15

Cys Cys Thr Lys Pro Ser Val Gly
            20


<210> SEQ ID NO 1488
<211> LENGTH: 72
<212> TYPE: DNA
<213> ORGANISM: Hepatitis B virus

<400> SEQUENCE: 1488

aagacctgca cgactcctgc tcaagggacc tctacgtttc cctcttattg ctgtacaaaa     60

ccttcggtcg ga                                                      72
```